(12) United States Patent
Kurani et al.

(10) Patent No.: US 12,364,430 B2
(45) Date of Patent: **\*Jul. 22, 2025**

(54) WEARABLE DEVICE FOR CONTINUOUS MONITORING OF USER HEALTH FOR ACCURATE CLINICAL OUTCOMES AND WELLNESS PROGRAMS

(71) Applicants: Hetal B. Kurani, Sunnyvale, CA (US); Hemal B. Kurani, Sunnyvale, CA (US); Bharat C. Kurani, Sunnyvale, CA (US)

(72) Inventors: Hetal B. Kurani, Sunnyvale, CA (US); Hemal B. Kurani, Sunnyvale, CA (US); Bharat C. Kurani, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/388,495

(22) Filed: Nov. 9, 2023

(65) Prior Publication Data

US 2025/0157623 A1 May 15, 2025

Related U.S. Application Data

(63) Continuation of application No. 17/984,167, filed on Nov. 9, 2022, now Pat. No. 11,896,383, which is a
(Continued)

(51) Int. Cl.
*A61B 5/00* (2006.01)
*A61B 5/08* (2006.01)
(Continued)

(52) U.S. Cl.
CPC .......... *G16H 20/60* (2018.01); *A61B 5/0022* (2013.01); *A61B 5/082* (2013.01); *A61B 5/1112* (2013.01);
(Continued)

(58) Field of Classification Search
None
See application file for complete search history.

(56) References Cited

U.S. PATENT DOCUMENTS 11,490,852 B1 * 11/2022 Kurani ................... A61B 5/746
11,896,383 B2 * 2/2024 Kurani ................... A61B 5/411
(Continued)

*Primary Examiner* — Shirley X Jian

(57) ABSTRACT

A wearable device consists of a smart band and a display unit. The smart band comprises a microbial biosensor, a particulate matter sensor, an enviro sensor, a physiological sensor, a biofluid sensor, a biokinetics sensor, a lifestyle sensor, and a single board computer. The microbial biosensor detects, measures, and monitors microorganisms, and a sterilizer kills pathogens. The particulate matter sensor detects, measures, and monitors a set of suspended particles in the surrounding air. The enviro sensor monitors environmental conditions surrounding the user. The biofluid sensor detects, measures, and monitors biological fluid parameters of the user. The physiological sensor detects, measures, and monitors physiological parameters of the user. The biokinetics sensor detects, measures, and monitors physical activities of the user. The lifestyle sensor detects, measures, and monitors healthy lifestyle activities of the user. The wearable device allows for continuous monitoring of user health for accurate clinical outcomes and wellness programs.

18 Claims, 105 Drawing Sheets

Related U.S. Application Data continuation of application No. 17/397,798, filed on Aug. 9, 2021, now Pat. No. 11,490,852.

(51) Int. Cl.
  *A61B 5/11* (2006.01)
  *A61B 5/1171* (2016.01)
  *G16H 20/60* (2018.01)

(52) U.S. Cl.
  CPC ............ *A61B 5/1171* (2016.02); *A61B 5/681* (2013.01); *A61B 5/7275* (2013.01); *A61B 5/742* (2013.01); *A61B 5/746* (2013.01); *A61B 5/748* (2013.01); *A61B 2560/0242* (2013.01); *A61B 2562/06* (2013.01)

(56) References Cited

U.S. PATENT DOCUMENTS

| | | | | |
|---|---|---|---|---|
| 2015/0313542 | A1* | 11/2015 | Goldberg | G04B 47/063 368/282 |
| 2016/0062623 | A1* | 3/2016 | Howard | G06F 3/0488 715/788 |
| 2020/0309703 | A1* | 10/2020 | Luk | G08B 3/10 |
| 2021/0356771 | A1* | 11/2021 | Poteet | A61L 2/26 |
| 2022/0007763 | A1* | 1/2022 | Masna | A61B 5/7267 |

* cited by examiner

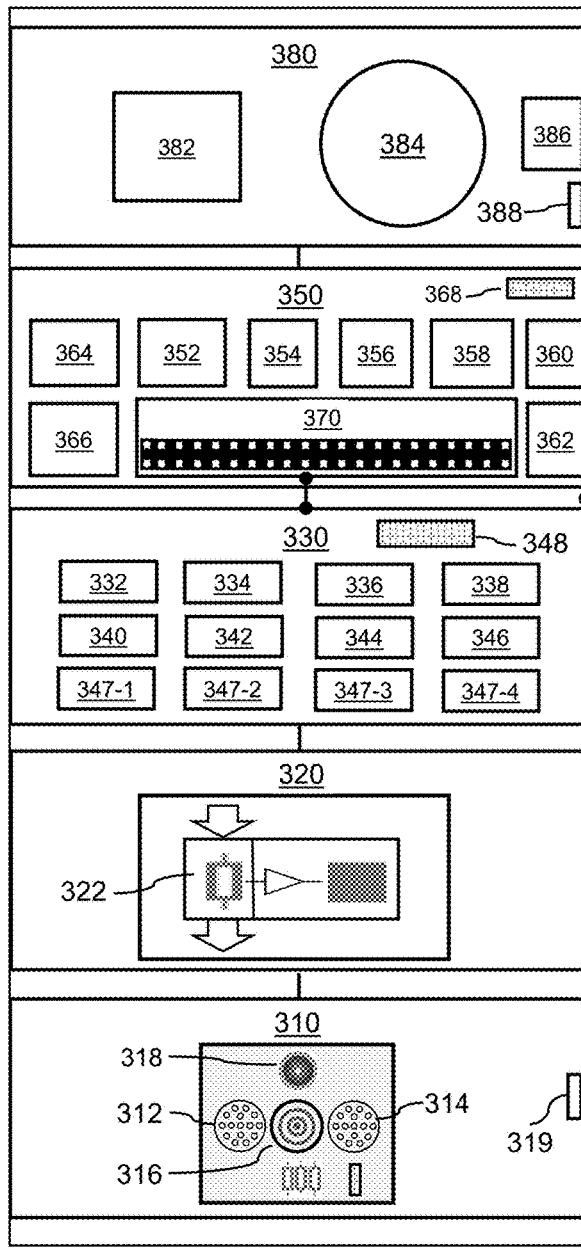
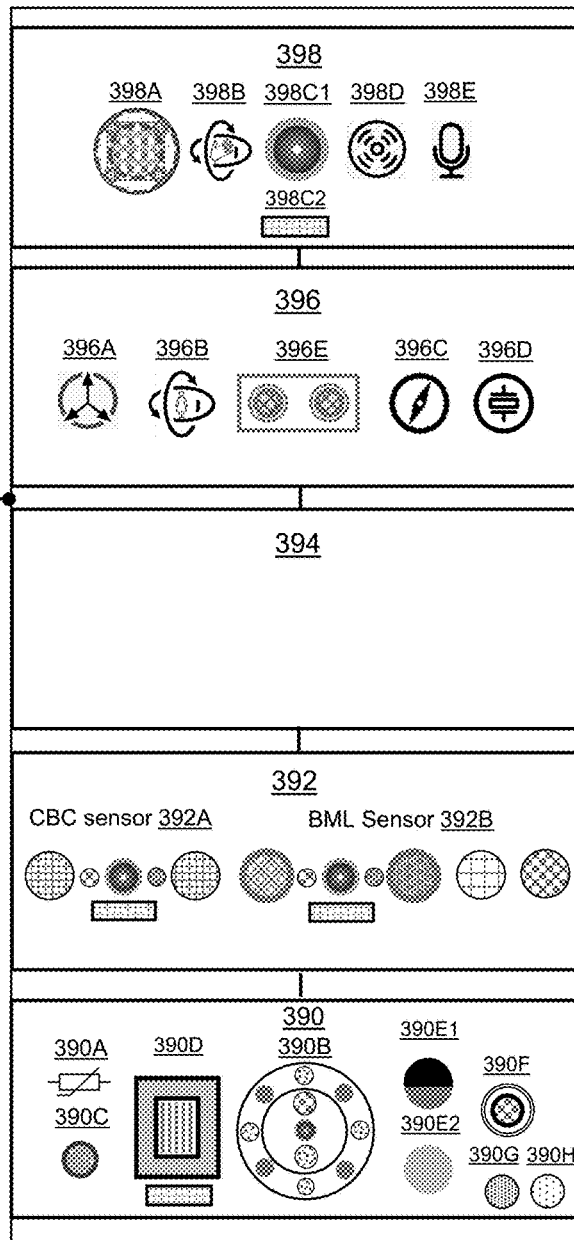
FIG. 3

General purpose input output pinout numbering diagram 410

| 1 | 3 | 5 | 7 | 9 | 11 | 13 | 15 | 17 | 19 | 21 | 23 | 25 | 27 | 29 | 31 | 33 | 35 | 37 | 39 | 41 |
|---|---|---|---|---|---|---|---|---|---|---|---|---|---|---|---|---|---|---|---|---|
| 2 | 4 | 6 | 8 | 10 | 12 | 14 | 16 | 18 | 20 | 22 | 24 | 26 | 28 | 30 | 32 | 34 | 36 | 38 | 40 | 42 |

| 3V3 and 5V power supply | Ground (GND) |

General purpose input output pinout function 450

| | | |
|---|---|---|
| GPIO 1 (3V3 power) ○— | 1 | 2 | —○ GPIO 2 (5V power) |
| GPIO 3 (SDA) ○— | 3 | 4 | —○ GPIO 4 (5V power) |
| GPIO 5 (SCL) ○— | 5 | 6 | —○ GPIO 6 Ground (GND) |
| GPIO 7 (GPCLK0) ○— | 7 | 8 | —○ GPIO 8 (TXD) |
| GPIO 9 Ground (GND) ○— | 9 | 10 | —○ GPIO 10 (RXD) |
| GPIO 11 ○— | 11 | 12 | —○ GPIO 12 (PCM_CLK) |
| GPIO 13 ○— | 13 | 14 | —○ Ground (GND) |
| GPIO 14 ○— | 15 | 16 | —○ GPIO 16 |
| GPIO 17 (3V3 power) ○— | 17 | 18 | —○ GPIO 18 |
| GPIO 19 (MOSI) ○— | 19 | 20 | —○ GPIO 20 Ground (GND) |
| GPIO 21 (MISO) ○— | 21 | 22 | —○ GPIO 22 |
| GPIO 23 (SCLK) ○— | 23 | 24 | —○ GPIO 24 (CE0) |
| GPIO 25 Ground (GND) ○— | 25 | 26 | —○ GPIO 26 (CE1) |
| GPIO 27 (ID_SD) ○— | 27 | 28 | —○ GPIO 28 (ID_SC) |
| GPIO 29 ○— | 29 | 30 | —○ Ground (GND) |
| GPIO 31 ○— | 31 | 32 | —○ GPIO 32 (PWM0) |
| GPIO 33 (PWMT) ○— | 33 | 34 | —○ Ground (GND) |
| GPIO (PCM_FS) ○— | 35 | 36 | —○ GPIO 36 |
| GPIO 37 ○— | 37 | 38 | —○ GPIO 38 (PCM_DIN) |
| GPIO 39 Ground (GND) ○— | 39 | 40 | —○ GPIO 40 (PCM_DOUT) |
| GPIO 41 (5V power) ○— | 41 | 42 | —○ GPIO 1 (3V3 power) |

FIG. 4

General purpose input output pinout function description table 500

| Voltage 502 <br> 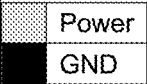 Power / GND | Three 5V pins and three 3V3 pins are present on the single board microcomputer, and there are eight ground pins (0V), which are not configurable. The remaining pins are all general purpose 3V3 pins, meaning outputs are set to 3V3 and inputs are 3V3 tolerant. <br> Almost all integrated circuits (ICs) sensors have at least two pins that connect to the power rails of the circuit in which they are installed. These are known as the power-supply pins. <br> A sensor component power supply pin Vcc = Collector supply voltage and VDD = Drain supply is connected to the single board microcomputer GPIO 5V or 3V pin per the specification. The other power-supply pin is referred to as ground (abbreviated "GND"). |
|---|---|
| Inputs 504 <br> 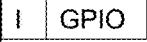 I / GPIO | A GPIO pin designated as an input pin can be read as high (3V3) or low (0V). This is done with internal pull-up or pull-down resistors. Pins GPIO3 and GPIO5 have fixed pull-up resistors, but for other pins this can be configured in software. A GPIO pin is assigned as an input pin through SBM software settings. |
| Outputs 506 <br>  O / GPIO | A GPIO pin designated as an output pin can be set to high (3V3) or low (0V). The GPIO pin is assigned as an output pin through SBM software settings. |
| Alternative functions | GPIO pins can be used with a variety of alternative functions, some are available on all pins, others on specific pins as follows: |
|  | Pulse-Width Modulation (PWM) 508 <br> Software PWM available on all pins. <br> Hardware PWM available on GPIO 32, GPIO 33, GPIO 12, and GPIO 35. |
| 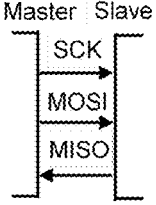 Master Slave SCK / MOSI / MISO | Serial Peripheral Interface (SPI) 510 <br> SPI0: MOSI (GPIO 19); MISO (GPIO 21); SCLK (GPIO 23); CE0 (GPIO 24), CE1 (GPIO 26) <br> SPI1: MOSI (GPIO 38); MISO (GPIO 35); SCLK (GPIO 40); CE0 (GPIO 12); CE1 (GPIO 11); CE2 (GPIO 36). <br> MOSI – Master Out Slave In, MISO – Master In Slave Out, SCLK – Serial CLocK Signal, CE – Chip Enable |
| 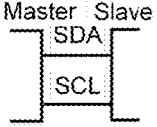 Master Slave SDA / SCL | Inter-Integrated Circuit (I2C) 512 <br> SDA Data (Serial Data): (GPIO 3); SCL Clock (GPIO 5) <br> EEPROM Data: (GPIO 27); EEPROM Clock (GPIO 28) <br> EEPROM - Electrically Erasable Programmable Read-Only Memory |
| 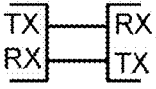 TX—RX / RX—TX | Serial Interface 514 <br> TX (GPIO 8); RX (GPIO 10) <br> TX – Transmit and RX – Receive |

FIG. 5

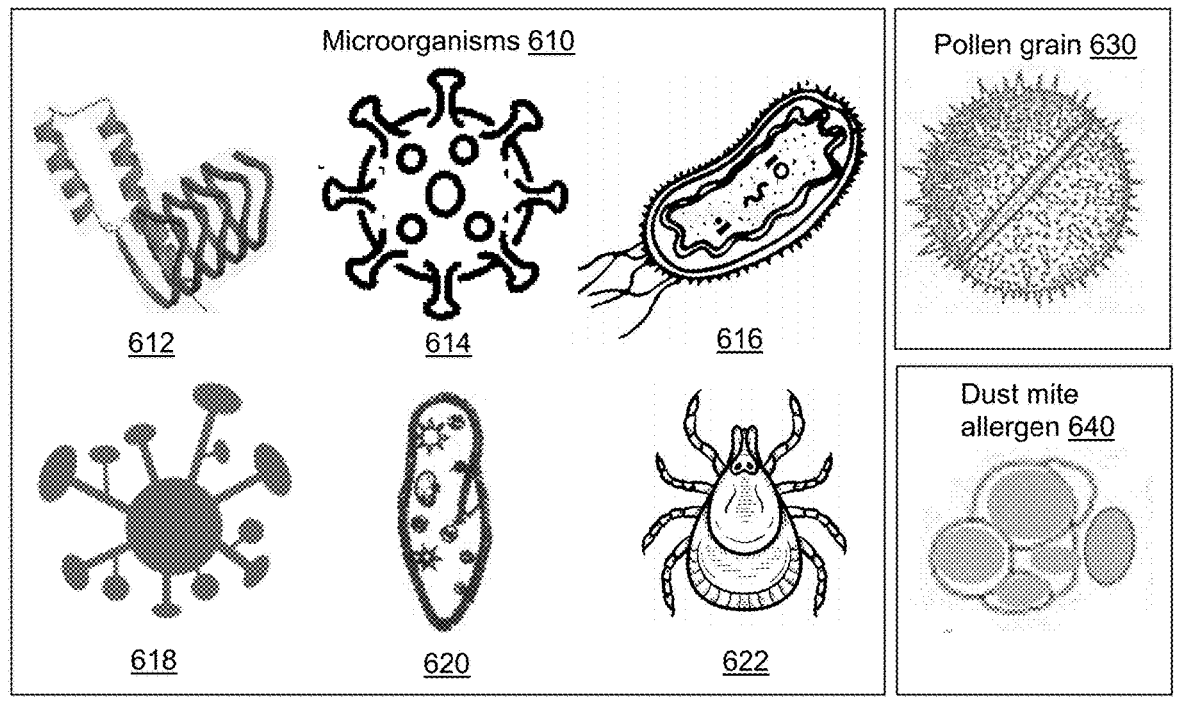
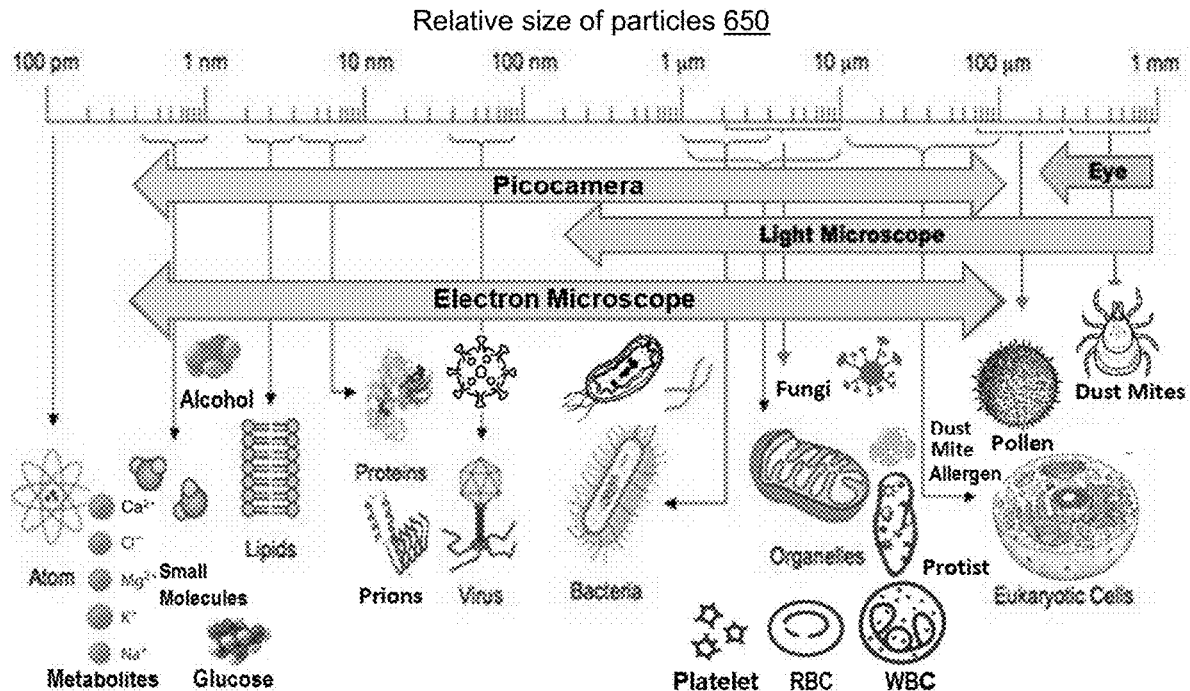
FIG. 6

Prion structure and components diagram 710

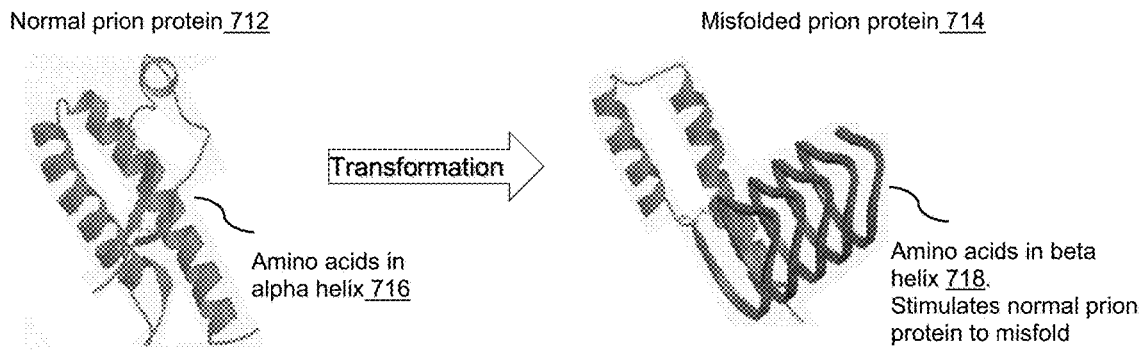

Prion structure components, function, and chemical composition list 730

| Component | Description of Primary Function(s) | Predominant chemical composition |
|---|---|---|
| Amino acids in alpha helix 716 | Normal cellular prion proteins (PrP$^C$) - tiny spherical shape | Amino acids<br>Alpha Helices – 43%<br>Beta Sheet – 3% |
| Amino acids in alpha helix 718 | Pathological Scrapie form of the prion proteins (PrP$^{Sc}$) - usually cube shape | Amino acids<br>Alpha Helices – 30%<br>Beta Sheet - - 43% |

Prion disease, status, and source list 750

| Prion Disease | Status | Source |
|---|---|---|
| Creutzfeldt-Jakob Disease (CJD) - Fatal neurodegenerative disorder due to abnormal isoform of a cellular glycoprotein known as the prion protein. | Noncontagious | Mutations |
| Variant Creutzfeldt-Jakob Disease (vCJD) - Prominent psychiatric/behavioral symptoms - The disease damages brain cells and the spinal cord. This is an infectious type of the disease that is related to "mad cow disease." Eating diseased meat may cause normal human prion protein to develop abnormally. | May be spread from person to person | Animals (Meat) |
| Gerstmann-Straussler-Scheinker Syndrome - Progressive loss of coordination | Noncontagious | Mutations |
| Fatal Familial Insomnia - Rare hereditary disorder causing difficulty in sleeping. There is also a sporadic form of the disease that is not inherited. | Noncontagious | Mutations |

Prion attributes and biosensor detector list 790

| Prion attributes | Amino acids and beta sheet shapes and concentration |
|---|---|
| Biosensor detector | Microbial biosensor, Particulate matter sensor |

FIG. 7

Virus structure and components diagram 810

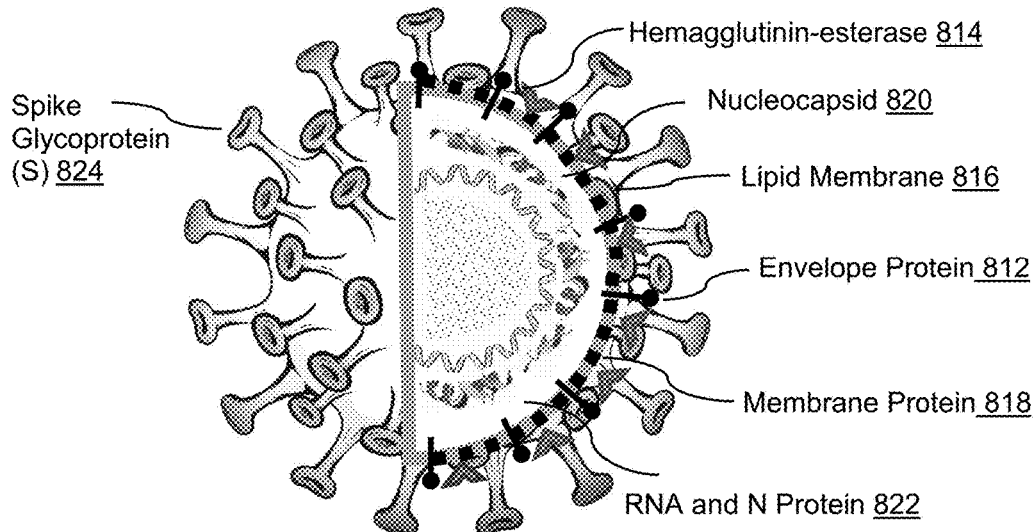

Virus structure components, function, and chemical composition list 830

| Component | Description of Primary Function(s) | Predominant chemical composition |
|---|---|---|
| Envelope Protein 812 | The viral envelope glycoproteins mediate the interaction of the virus with cell receptors and promote the fusion of the viral and cellular membranes during infection of susceptible cell | E-Protein |
| Hemagglutinin-esterase 814 | Glycoprotein that certain enveloped viruses possess and use as invading mechanism | H-Protein |
| Lipid Membrane 816 | Enveloped viruses acquire lipid membranes as their outer coat through interactions with cellular membranes during morphogenesis within, and egress from, infected cells | Phospholipids |
| Membrane Protein 818 | Purpose is to protect the genome-containing virus nucleocapsid from damage, and to facilitate entry of the nucleocapsid into a host cell. | M-Protein |
| Nucleocapsid 820 | Genome plus the protein coat of a virus. The genome is nucleic acid (RNA or DNA) of the virus. The protein coat is its capsid. | N-Protein |
| RNA 822 | The nucleic acid (RNA or DNA) of the virus genome | Mostly RNA |
| Spike Glycoprotein 824 | The S protein plays a role in penetrating host cells and initiating infection. S proteins gives rise to the spike-shaped protrusions found on their surface. | S-Protein |

Percent chemical composition of a virus list 850

| Primary Constituents | Percent of dry weight |
|---|---|
| Protein | 55.0 |
| Carbohydrate | 5 |
| Nucleic Acid / DNA or RNA | 20 |
| Lipid solvents | 15-25% |
| Ionic Environment and pH | Traces |
| Total % | 100% |

FIG. 8

Virus name, disease, status, source, shape, size, and nucleic acid list 1000

| Virus Name | Disease | Status | Source | Shape | Size (nm) | Nucleic Acid |
|---|---|---|---|---|---|---|
| Bacteriophage | Infects bacteria | Non | All | Complex | Head 80x100 L, tail 110 L | DNA or RNA |
| Rabies lyssavirus | Brain | Contagious | Rodents | Bullet | 180 L x 75W | RNA |
| Ebola and Marburg | Hemorrhagic fever | Contagious | Rodents | Filament-ous | 800 L x 80 W | RNA |
| Adenovirus | Colds | Contagious | Humans | Spherical | Polyhedral capsid 70-100 D | DNA |
| Dengue virus | Nausea, vomiting | Non | Mosquito | Spherical | 40-60 D | RNA |
| Hantavirus | Hantavirus | Non | Rodents | Spherical | 120-160 D | RNA |
| Hepatitis B | Liver infection, fever | Contagious | Humans | Spherical | 40-42 D | DNA |
| HIV Virus | AIDS | Contagious | Humans | Spherical | 100-120 D | RNA |
| Influenza A, B | Flu | Contagious | Humans | Spherical | 80-120 D | RNA |
| Norovirus | Vomiting, diarrhea | Contagious | Humans | Spherical | 0.040 D | RNA |
| Zika virus | Birth defects | Non | Mosquito | Spherical | 0,050 D | RNA |
| Rotavirus | Diarrhea, vomiting | Contagious | Humans | Spherical | 70-75 D | RNA |
| SARS-CoV-2 | COVID_19 | Contagious | Humans | Spherical | Polyhedral capsid 80-160 D | RNA |

Virus attributes and biosensor detector list 1090

| Virus attributes | Shape, Size, Structure, DNA/RNA, Chemical Composition |
|---|---|
| Biosensor detector | Microbial biosensor, Particulate matter sensor |

FIG. 10

Bacteria cell structure and components diagram 1110

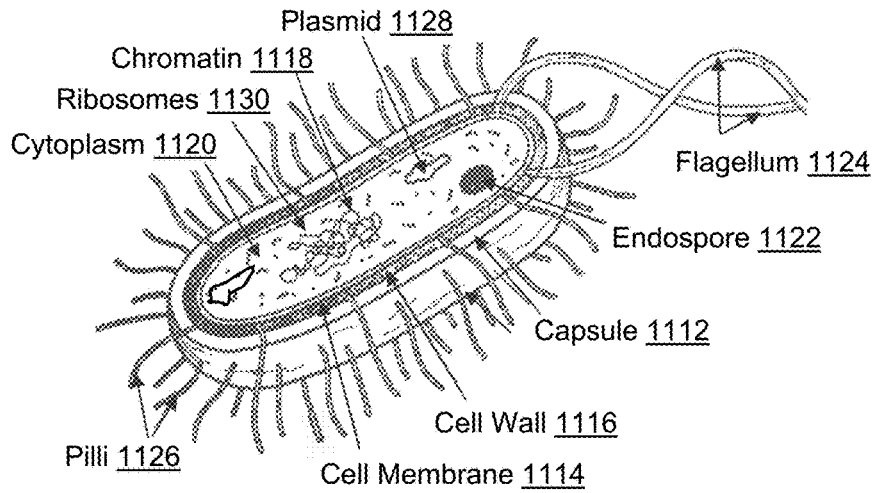

Bacteria cell structure components, function, and chemical composition list 1130

| Component | Description of Primary Function(s) | Predominant chemical composition |
|---|---|---|
| Capsule 1112 | Capsules protects a bacterial cell from ingestion and destruction | Polysaccharide |
| Cell membrane 1114 | Permeability barrier; transport of solutes; energy generation; location of numerous enzyme systems | Phospholipid and protein |
| Cell wall 1116 | Maintain bacterial cell integrity and shape as well as resisting internal turgor pressure | Peptidoglycan (murein) |
| Chromatin 1118 | Genetic material of cell. The DNA of most bacteria is contained in a single circular bacterial chromosome along with proteins & RNA molecules to form nucleoid. | DNA |
| Cytoplasm 1120 | Functions for cell growth, metabolism, and replication | Enzymes, nutrients |
| Endospore 1122 | Produce a dormant and highly resistant cell to preserve the cell's genetic material in times of extreme stress | Dipicolinic acid |
| Flagellum 1124 | Swimming movement | Protein |
| Pilli 1126 | Attachment to surfaces; protection against phagotrophic engulfment | Protein |
| Plasmid 1128 | Extrachromosomal genetic material | DNA |
| Ribosomes 1130 | Sites of translation (protein synthesis) | RNA and protein |

Percent chemical composition of a bacteria list 1150

| Primary Constituents | Percent of dry weight |
|---|---|
| Protein | 55.0 |
| Polysaccharide | 5.0 |
| Lipid | 9.1 |
| DNA | 3.1 |
| RNA | 20.5 |
| Others (sugars, amino acid) | 6.3 |
| Inorganic ions | 1.0 |
| Total % | 100% |
| Cell elements percentage – C (50), O(22), N (12), H (9), P (2), S(1), Na (1), and Traces of Ca, Mg, Cl, Fe elements | |

FIG. 11

Bacteria cell shapes diagram 1200

Spherical (Cocci) 1210

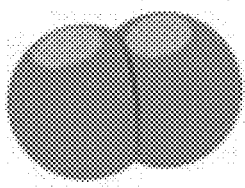

Streptococcus pneumoniae 1212

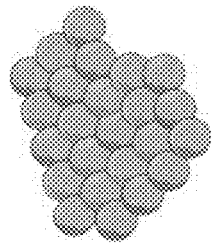

Staphylococcus aureus 1214

Spiral 1220

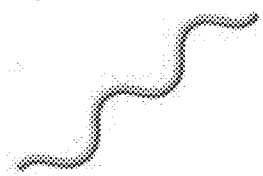

Treponema pallidum 1222

Rod (Bacillus) 1230

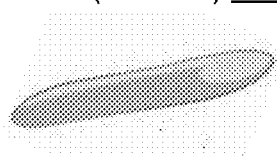

Legionella pneumophila 1232

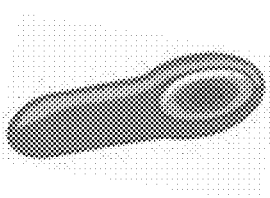

Clostridium botulinum 1234

Streptobacillus moniliformis 1236

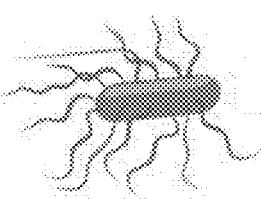

Salmonella typhi 1238

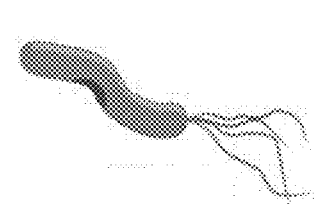

Helicobacter pylori 1240

Comma 1250

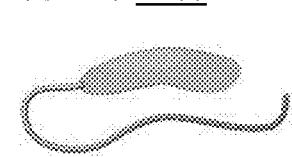

Vibrio cholerae 1252

Box 1260

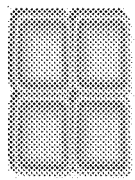

Halophilic 1262

Appendaged 1270

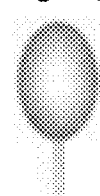

Hyphomicrobium 1272

Pleomorphic 1280

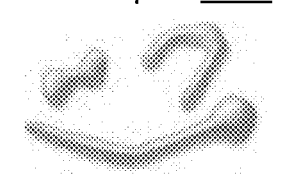

Corynebacterium diphtheria 1282

FIG. 12

Bacteria name, disease, status, source, shape, size, and nucleic acid list 1300

| Bacteria Name | Disease | Status | Source | Shape | Size (μm) | Nucleic Acid |
|---|---|---|---|---|---|---|
| Streptococcus pneumoniae | Pneumonia, otitis media | Contagious | Humans | Spherical (Cocci) | 0.5–1.25 D | DNA |
| Staphylococcus aureus | Opportunistic infections | Endogenous | Humans | Spherical (Cocci) | 0.5–1.5 D | DNA |
| Treponema pallidum | Syphilis | Contagious | Humans | Spiral | 6–20L x 0.2 D | DNA |
| Legionella pneumophila | Pneumonia, Pontiac fever | Non | Env | Rod (Bacillus) | 2–20L x 0.3–0.9 D | DNA |
| Clostridium botulinum | Botulism | Non | Humans | Rod (Bacillus) | 1.2–22 L x 0.5–2 D | DNA |
| Streptobacillus moniliformis | Rat bite fever | Contagious | Rodents | Rod (Bacillus) | 2–5 L x 0.1–0.5 D | DNA |
| Helicobacter pylori | Stomach ulcers or cancer | Contagious | Humans | Rod (Bacillus) | 2–4 L x 0.5–1 D | DNA |
| Salmonella typhi | Infect intestine, blood | Contagious | Humans | Rod (Bacillus) | 2–5 L x 0.5–1.5 D | DNA |
| Vibrio cholerae | Cholera - toxin in intestine | Contagious | Humans | Comma shaped | 2–3 L x 0.5–0.8 D | DNA |
| Halophilic | Biopolymers, biofertilizers | Contagious | Humans | Box | 2.500 | DNA |
| Hyphomicrobium | Drinking water | Contagious | Humans | Append aged | 1.0–3.0 L x 0.3–1.2 D | DNA |
| Corynebacterium diphtheria | Diphtheria | Contagious | Humans | Pleomorphic | 1.5–8.0 L x 0.3–0.6 D | DNA |
| Mycobacterium tuberculosis | Tuberculosis (TB) | Contagious | Humans | Rod (Bacillus) | 2–4 L x 0.2–0.5 D | DNA |
| Streptococcus salivarius | Bacterial meningitis | Contagious | Humans | Spherical (Cocci) | 0.5–2.0 D | DNA |

Bacteria attributes and biosensor detector list 1390

| Bacteria attributes | Shape, Size, Structure, DNA, Chemical Composition, Clusters |
|---|---|
| Biosensor detector | Microbial biosensor, Particulate matter sensor |

FIG. 13

Fungi cell structure and components diagram 1410

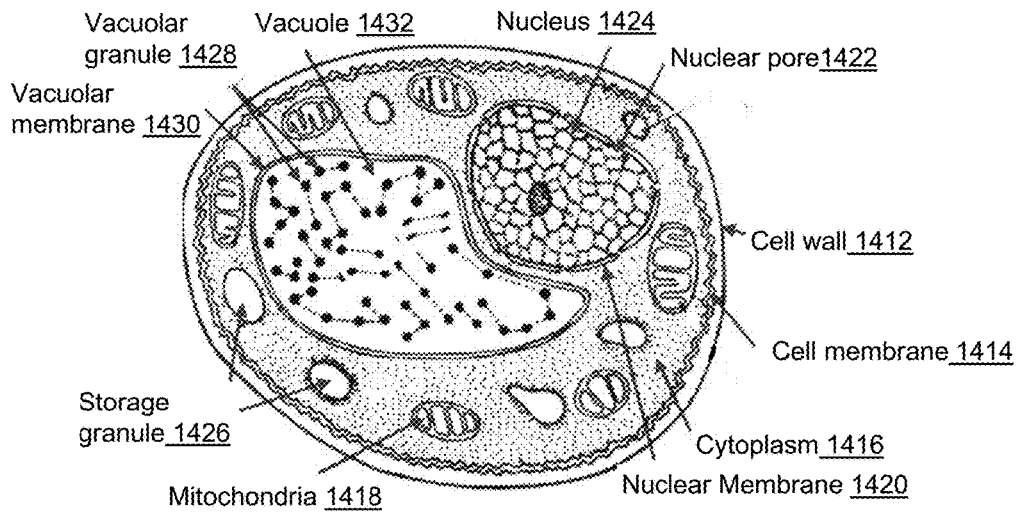

Fungi cell structure components, function, and chemical composition list 1440

| Component | Description of Primary Function(s) | Predominant chemical composition |
|---|---|---|
| Cell membrane 1412 | Allows gases and water to diffuse freely into and out of the cell. Controls the transport of other molecules | Sterols, sphingolipids glycerophospholipids |
| Cell wall 1414 | A layer around the cell membrane of fungi cells made largely of chitin | Chitin |
| Cytoplasm 1416 | Makes enzymes and other proteins | Water, ion, protein |
| Mitochondria 1418 | Contains enzymes for the reactions in aerobic respiration | Phospholipid & proteins |
| Nuclear membrane 1420 | Separates the contents of the nucleus from the rest of the cell. | Lipids |
| Nuclear pore 1422 | Allow the transport of molecules across the nuclear envelope | Nucleoporins |
| Nucleus 1424 | Contains DNA which carries the genetic code for making enzymes | DNA |
| Storage granule 1426 | Store cell energy reserve | Phosphorous & oxygen |
| Vacuolar granule 1428 | Primary storage site for certain small molecules | Polyphosphate |
| Vacuolar membrane 1430 | Separates the contents of the Vacuolar from the rest of the cell. | Lipids |
| Vacuole 1432 | Reservoir for the storage of small molecules (including polyphosphate, amino acids, several divalent cations (e.g., calcium), other ions, and other small molecules) as well as being the primary compartment for degradation | Closed sacs |

Percent chemical composition of a fungi list 1450

| Primary Constituents | Percent of dry weight |
|---|---|
| Fiber | 66–83% |
| Crude Protein | 5.5–13.4% |
| Sugar | 2—5.6% |
| Crude Fat | 0.9–.6% |
| Others | 8–10% |
| Total % | 100% |
| Cell elements – Carbon, hydrogen, and oxygen (as carbohydrates) collectively comprise ~ 45% grams dry weight of a typical yeast cell. | |

FIG. 14

Fungi cell shapes diagram 1510
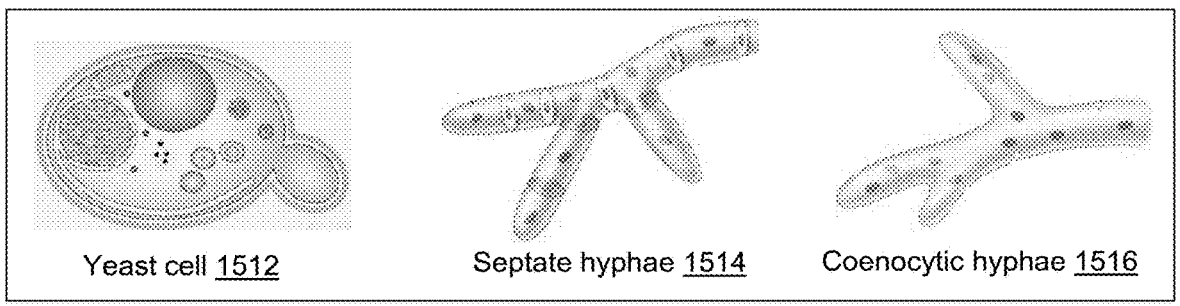
Yeast cell 1512     Septate hyphae 1514     Coenocytic hyphae 1516
Fungi cell shape in environment and shape shift in host diagram 1520
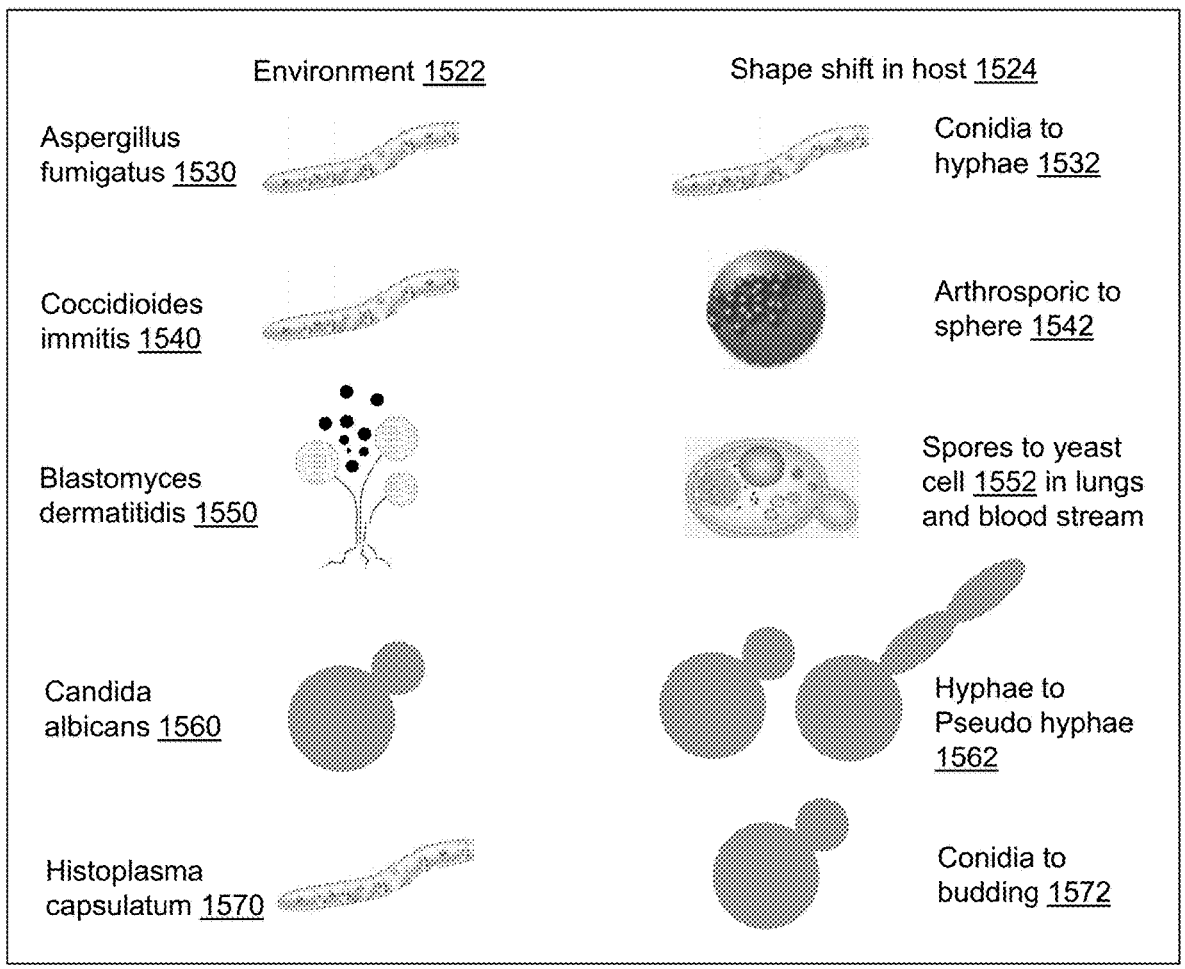
FIG. 15

Fungi name, disease, status, source, shape, size, and nucleic acid list 1600

| Fungi | Disease | Status | Source | Shape | Size (μm) | Nucleic Acid |
|---|---|---|---|---|---|---|
| Aspergillus flavus | Aspergillosis | Non | Env | Aspergillum Hyphae | 2.0–3.5 D | DNA |
| Aspergillus fumigatus | Aspergillosis | Non | Env | Aspergillum Hyphae | 2.0–3.5 D | DNA |
| Blastomyces dermatitidis | Blastomycosis | Non | Env | Spherical | 1.5–2.0 D | DNA |
| Coccidioides immitis | Coccidioido mycosis | Non | Env | Barrel shaped | 30–100 D | DNA |
| Candida albicans | Nonrespiratory | Non | Env | Spherical | 10–12 D | DNA |
| Cryptococcus albidus | Allergen | Non | Env | Spherical | Ovoid 2–5 x 3–7 | DNA |
| Cryptococcus laurentii | Allergen | Non | Env | Spherical | Ovoid 2–5 x 3–7 | DNA |
| Cryptococcus neoformans | Cryptococcosis | Non | Env | Spherical | Ovoid 2–5 x 3–7 | DNA |
| Histoplasma capsulatum | Histoplasmosis | Non | Env | Hyphae | 2–4 D | DNA |
| Stachybotris atra | Allergic alveolitis | Non | Env | Bottle shaped | 9–14 L | DNA |
| Stachybotris chartarum | Allergic alveolitis | Non | Env | Bottle shaped | 9–14 L | DNA |
| Trichophyton | Athlete's foot, mouth, throat, esophagus | Non | Env | Spherical | 8–50 L | DNA |
| Microsporum | Athlete's foot, mouth, throat, esophagus | Non | Env | Spherical | Obvate 7–20 x 30–160 | DNA |
| Epidermo phyton | Athlete's foot, mouth, throat, esophagus | Non | Env | Spherical | 20–40 L x 7–12 W | DNA |

Fungi attributes and biosensor detector list 1690

| Fungi attributes | Shape, Size, Structure, DNA, Chemical Composition in the environment and in the host |
|---|---|
| Biosensor detector | Microbial biosensor, Particulate matter sensor |

FIG. 16

Protist cell structure and components diagram 1710

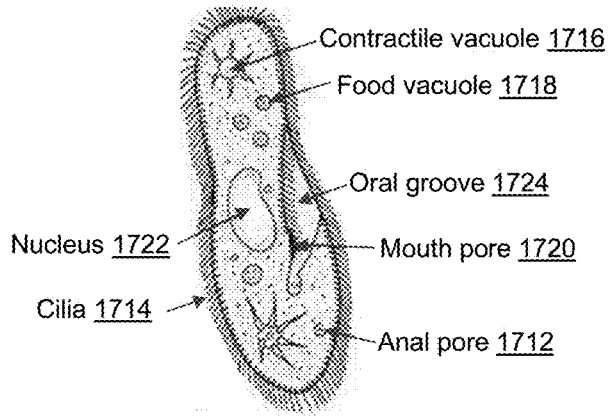

- Contractile vacuole 1716
- Food vacuole 1718
- Oral groove 1724
- Mouth pore 1720
- Anal pore 1712

Nucleus 1722

Cilia 1714

Protist cell structure components, function, and chemical composition list 1750

| Component | Description of Primary Function(s) | Predominant chemical composition |
|---|---|---|
| Anal pore 1712 | Ejection of waste is ejected after the nutrients from food have been absorbed | Piles of fibers, and microtubules |
| Cilia 1714 | Move water across the cell and contribute to both locomotion and food capture | Protein tubulin |
| Contractile vacuole 1716 | Controls the intracellular water balance by accumulating and expelling excess water out of the cell, allowing cells to survive under hypotonic stress. | Closed sacs |
| Food vacuole 1718 | Storing food which has been absorbed by the organism | Polyphosphate |
| Mouth pore 1720 | Draw and prey organisms inside the mouth opening using Celia | Oral groove protein |
| Nucleus 1722 | Protects DNA, which is the blueprint or code that runs every function of protist cell | DNA |
| Oral groove 1724 | It is used to capture and digest bacteria. | Protein |

Protists, disease, source, shape, size, and nucleic acid list 1780

| Protists | Disease | Status | Source | Shape | Size (μm) | Nucleic Acid |
|---|---|---|---|---|---|---|
| Paramecium | Ingest, kill the cells of the human pathogenic fungus Cryptococcus neoformans | Non | Water | Elongated | 50–300 L | DNA |
| Trypanosoma protozoa | Sleeping sickness | Non | Fly/Bug | Spindle | 16–42 L X 1–3 W | DNA |
| Plasmodium | Malaria spread by mosquito vector | Non | Mosquito | Crescent shaped | 1.5 L x 1 to 20 W | DNA |
| Giardia | Diarrhea and stomach cramps. Fecal /Oral Transfer | Contagious | Humans / Water | Pear Shaped | 12–15 L x 5–10 W | DNA |

Protist attributes and biosensor detector list 1790

| Protist attributes | Shape, Size, Structure, DNA, Chemical Composition |
|---|---|
| Biosensor detector | Microbial biosensor, Particulate matter sensor |

FIG. 17

Dust mite structure and components diagram 1810

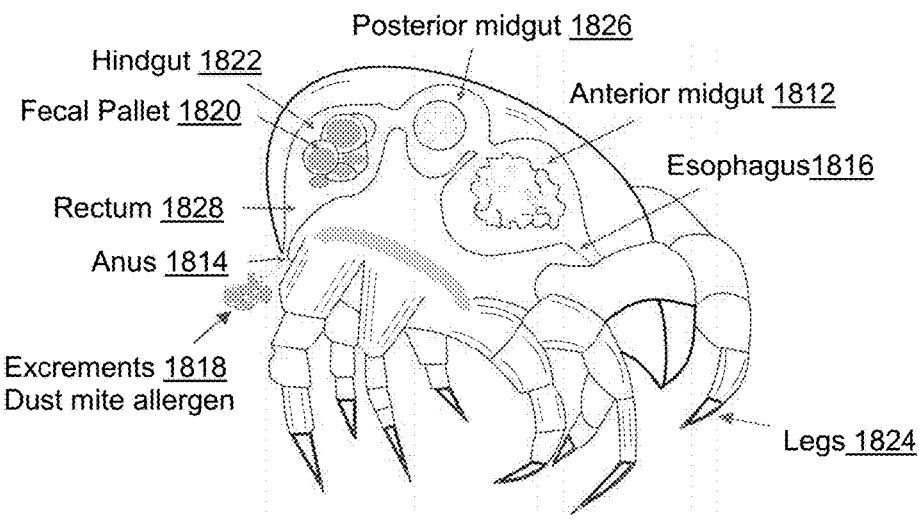

Dust mite structure components, function, and chemical composition list 1850

| Component | Description of Primary Function(s) |
|---|---|
| Anterior midgut 1812 | Products of digestion to pass through the gut |
| Anus 1814 | Discharge of excrements |
| Esophagus 1816 | Transport material from the mouth to anterior midgut |
| Excrements 1818 | Excrements are considered the main source of allergy. Consists of protein / digestive enzymes |
| Fecal Pallet 1820 | Reservoir containing excrements |
| Hindgut 1822 | The hindgut is the posterior part of the digestive system |
| Legs 1824 | There are eight legs for the movement |
| Posterior midgut 1826 | Part of the digestive track responsible for physiological regulation such as metabolism, |
| Rectum 1828 | Receive fecal pallet from the hindgut |

Dust mite attributes and biosensor detector list 1890

| Dust mite attributes | Shape, Size, Structure, DNA, Chemical Composition |
|---|---|
| Biosensor detector | Microbial biosensor, Particulate matter sensor |

FIG. 18

Virus, bacteria, and fungi attributes comparison list 1900

| Attributes | Virus | Bacteria | Fungi |
|---|---|---|---|
| Size | Small. Most viruses diameter is from 20 nm to 250–400 nm. Largest measure about 500 nm in diameter & are about 700–1,000 nm in length | Medium. Most common bacteria are about 1 to 2 μm in diameter and 5 to 10 μm long | Large. Most small fungi are 2-10 μm in diameter and several tenths of an inch in length. The average size of fungi hyphae is 5-50 μm in length |
| Organism Type | Non-Living - Intercellular organisms | Prokaryotic - Intercellular organisms | Eukaryotes - Either unicellular or multi-cellular |
| Shape | icosahedral or helical capsid. Usually rod & filament shape | Spherical or oval, rod, spiral | Mass of hyphae |
| Color | Smaller than light particles, using electron microscope it reveals grey color | Usually white, red, purple, yellow, and blue green | Usually red, purple, yellow, brown, orange, and green |
| Cell membrane | No cell membrane. Many viruses are surrounded by a continuous bilayer membrane studded with viral proteins | Cell membrane below the cell wall | Have a cell membrane |
| Genetic Material | DNA and RNA | DNA | DNA |
| Host | Needs a living host, like a plant or animal. | Can grow on non-living surfaces | Can live on its own |
| Mobility | Viruses do not have structures and thus cannot move on their own | There are several types of bacteria movements | Typically, fungi are non-mobile organisms |
| Reproduction | Virus enters the host cell, makes a copy of itself, and causes the cell to burst | Reproduce by splitting into two cells | Reproduction can take place in multiple ways |
| Living | Characteristics of both living and non-living | Yes | Yes |
| Energy Sources | Get materials and energy from host cells | Get energy from the same sources as humans | Use pre-existing carbon sources in their environment and energy from chemical reactions |
| Usefulness | Mostly are harmful | Some bacteria can be useful | Many fungi are beneficial |
| Transmission Mode | Airborne, touch, body fluid, contaminated objects, insects, animals | Air, water, food, touch, body fluid or living vector | Air and touch |
| Example Infection | Common cold, Influenza, COVID-19, food poisoning | Dental, post-surgery, food poisoning | Athlete's foot, vaginal yeast infection, ringworm |
| Treatment | Vaccines, antiviral drugs, and over the counter products to manage symptoms | Antibiotics and over the counter products to manage symptoms | Antifungal medication and over the counter products to manage symptoms |
| Prevention | Good hygiene, wear a mask, and vaccines | Good hygiene, keep wounds clean and covered | Good hygiene, keep the skin clean, and wear masks. |

FIG. 19

Platform dataset 2010

| No | Platform Dataset Resources |
|---|---|
| 1 | National Center for Biotechnology Information (NCBI) |
| 2 | European Molecular Biology Laboratory/ European Bioinformatics Institute (EMBL-EB) |
| 3 | MicrobeNet - Centers for Disease Control and Prevention (CDC) |
| 4 | Pathosystems Resource Integration Center (PATRIC) |
| 5 | Prion disease database – NCBI, CDC |
| 6 | Virus Pathogen Resources (ViPR) |
| 7 | Bacterial genomes – Wellcome Sanger Institute |
| 8 | Fungi Database (FungiDB) |
| 9 | Pathogenic Protist database, ,Dust mite database |
| 10 | Ensembl genome browser provides access to organized information from the analysis of biological data for virus, bacteria, and fungi |
| 11 | Pollen data from National Centers for Environmental Information and Global Pollen Project |
| 12 | Allergens and isoallergens/variants – CDC, WHO/IUIS-Allergen, Allergome, AllergenOnline, GenBank, GenPept, UniProtKB, PDB, PubMed, and others |

Microorganism taxonomy 2050

| Virus Taxonomy | | Kingdom | Orthornavirae –Domain - *Duplodnaviria,Monodnaviria.* | | |
|---|---|---|---|---|---|
| Phylum | Class | Order | Family | Genus | Species |
| *Pisuviricota* | *Pisoniviricetes* | *Nidovirales* | *Coronaviridae* | *Betacoronavirus* | *SARS-coronavirus* |
| *Negarnaviricota* | *Insthoviricetes* | *Articulavirales* | *Orthomyxoviridae* | *Alphainfluenzavirus* | *Influenza A virus* |

| Bacteria Taxonomy | | Kingdom | Bacteria /Eubacteria /Monera - Domain - *Prokaryotic* | | |
|---|---|---|---|---|---|
| Phylum | Class | Order | Family | Genus | Species |
| *Firmicutes* | *Bacilli* | *Bacillales* | *Staphylococcaceae* | *Staphylococcus* | *Staphylococcus aureus* |
| *Proteobacteria* | *Gammaproteo bacteria* | *Legionellales* | *Legionellaceae* | *Legionella* | *Legionella pneumophila* |

| Fungi Taxonomy | | Kingdom | Fungi - Domain - *Eukaryotic* | | |
|---|---|---|---|---|---|
| Phylum | Class | Order | Family | Genus | Species |
| *Ascomycota* | *Eurotiomycetes* | *Eurotiales* | *Trichocomaceae* | *Aspergillus* | *Aspergillus flavus* |
| *Ascomycota* | *Eurotiomycetes* | *Onygenales* | *Ajellomycetaceae* | *Blastomyces* | *Blastomyces dermatitidis* |

| Protist Taxonomy | | Kingdom | Protista - Domain - *Eukaryotic* | | |
|---|---|---|---|---|---|
| Phylum | Class | Order | Family | Genus | Species |
| *Paramecium aurelia* | *Oligohymenophorea* | *Peniculida* | *Parameciidae* | *Paramecium* | *Paramecium biaurelia* |

| Dust mite Taxonomy | | Kingdom | Animalia - Domain - *Uniramia, Crustacea, Chelicerata* | | |
|---|---|---|---|---|---|
| Phylum | Class | Order | Family | Genus | Species |
| *Arthropoda* | *Arachnida* | *Sarcoptiformes* | *Pyroglyphidae* | *Dermatophagoides* | *Dermatophagoides farinae* |

FIG. 20

Microorganism data 2110

| No | Data |
|---|---|
| 1 | Genome – Taxonomy, Organism name, organism groups, gene assembly, assembly level, length of genome assembly, GC%, host, protein coding genes, neighbor nucleotides, cell type, number of cells, size, microscopy, shape, cellular machinery, type of organism, structure, cell wall, cellular membrane, genome (DNA or RNA), strand type (single, double), nucleic acid, mRNA, ribosomes, living attributes, replication, cells infected, diseases/infections, duration of illness, treatment and so on |
| 2 | Annotation - Prokaryotic and Eukaryotic genome annotation and Structural RNA, tRNA, protein coding genes, pathogenic information. Classification as pathogenic, beneficial, or harmless. |
| 3 | Pathogen Safety Data Sheet - infections agent, hazard identification, dissemination, stability, and viability, first aid / medical, laboratory hazards, exposure controls / personal protection, handling and storage, and regulatory and other information |
| 4 | Attributes –Structure and morphology (shape, size, color, component), component function, chemical composition, constituent, or element, and other information |
| 5 | Unique Identifiers - Unique identification based on biosensor detection method |
| 6 | Microorganism parameters detected: a pathogen count, a pathogen type, a pathogen concentration, a pathogen biosafety, a beneficial microorganism count, a beneficial microorganism type, and a beneficial microorganism concentration, genome, annotation, attributes, unique identifiers and so on |

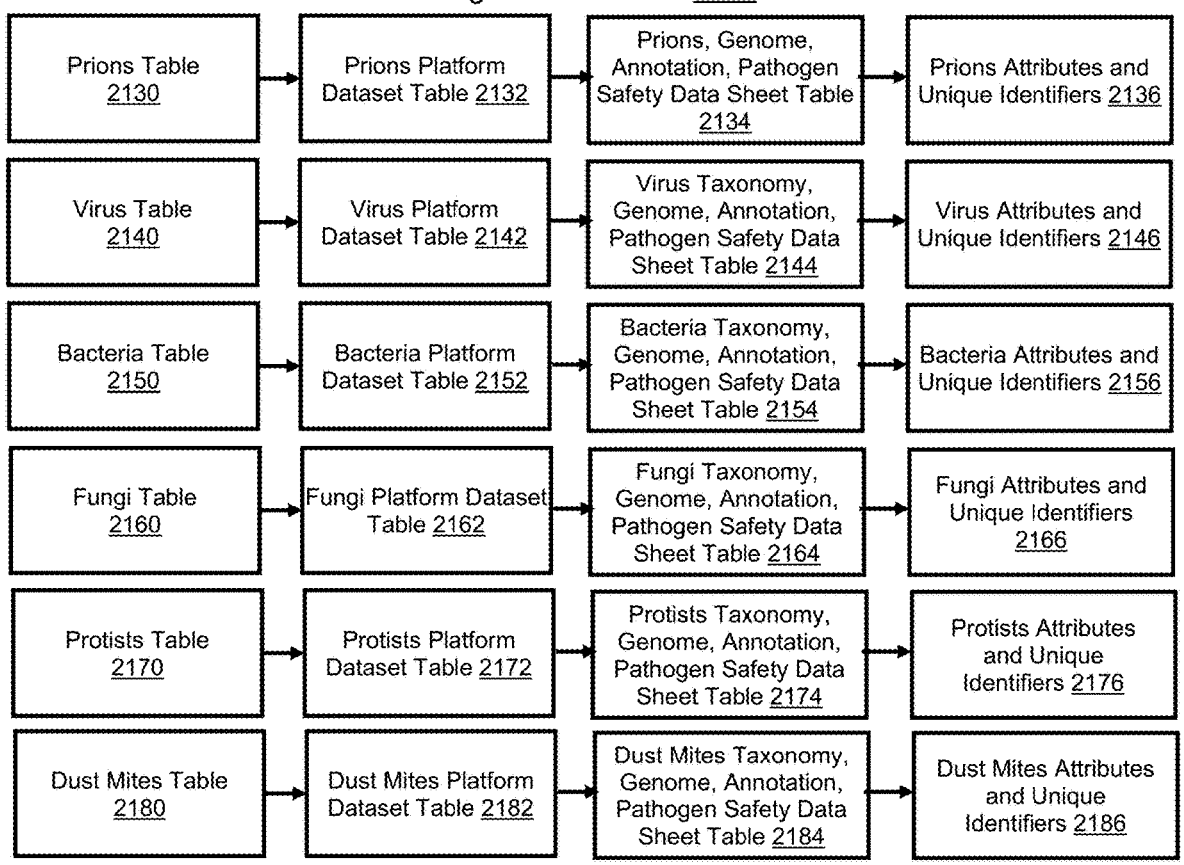

FIG. 21

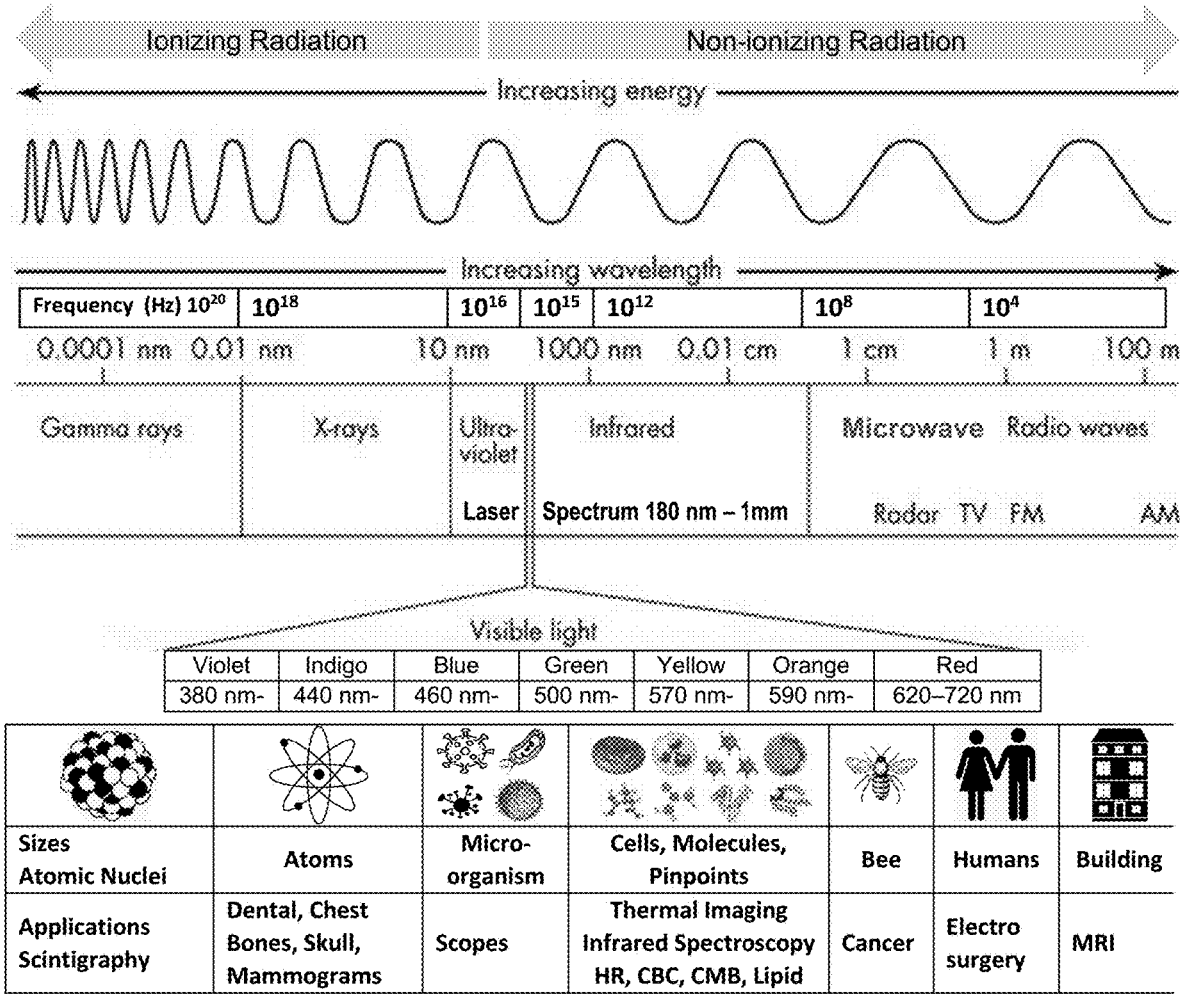
FIG. 23

Noninvasive biosensors for particle detection, and sterilization list 2410

| Microorganism Detected | Biosensor Detector | Type of Biosensor / Transducer | Measurement Condition | Particle Detection Method |
|---|---|---|---|---|
| Prions, viruses, bacteria, fungi, protists, dust mites | Microbial biosensor | Optical, Mass based, Ultrasound waves | Nasal cavity, Oral cavity, Surface | Optical – Infrared spectroscopy, Fluorescence Imaging, Particle Imaging Nucleic acid sequence identification Mass based – Electromagnetic waves Ultrasound waves – Acoustic waves |
| Prions, viruses, bacteria, fungi, protists, dust mites, pollen grains, dust mite allergens | Particulate matter sensor | Laser scattering and imaging | Environment air | Light scattering and imaging Particle Imaging Nucleic acid sequence identification |
| Prions, viruses, bacteria, fungi, protists, dust mites | Microbial biosensor sterilizer | Heat; Ultraviolet light; magnetic, Acoustic wave, amplitude; wavelength, and phase | Nasal cavity, Oral cavity, Surface | Heat, Ultrasound, Acoustic wave, Ultraviolet light to kill microorganism |

Picomaterials 2450

Picoparticle 2452    Picotube 2454    Picofiber 2456    Picorod 2458

  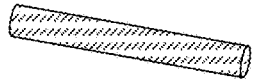 

Particle detection methods working principle list 2490

| No | Particle Detection Method | Microorganisms Attributes Unique Identifier |
|---|---|---|
| 1 | Infrared spectroscopy – Shining infrared light on the object and measuring infrared absorption, transmission, reflectance wavelength signal specific to microorganism cell chemicals | Cell structure components and chemical composition |
| 2 | Fluorescence imaging – Taking pictures of the radiation emitted by the microorganisms because of incident radiation of certain wavelength | Shape, size, color, cell structure components, chemical composition |
| 3 | Particle Imaging – High magnification and resolution images of microorganisms using picomaterials followed by pattern recognition and classification | Shape, size, color, cell structure components |
| 4 | Nucleic acid sequence identification – High resolution image of nucleic acid and identification of unique DNA and RNA sequence segments | Unique DNA and RNA sequence segments |
| 5 | Electromagnetic waves – Detects the changes in magnitude of a magnetic field of the microorganisms containing ferromagnetic materials using the Hall effect | Cell ferromagnetic materials composition |
| 6 | Light scattering and imaging – Analysis of reflection pattern of incident laser light from the outer surface of microorganism, pollen, and dust mite allergens | Cell structure components and chemical composition |
| 7 | Ultrasound waves and sound – Directing sound waves towards a surface and measuring the reflected echoes. Echoes are different depending on the density of the microorganism that the ultrasound waves hit. Acoustic reporter gene to scatter sound waves coupled with cell structure high resolution imaging technique. Listening to unique sound of one microorganism through picotube microphone. | Cell structure components and chemical composition, Gas filled nanostructure vesicles |

FIG. 24

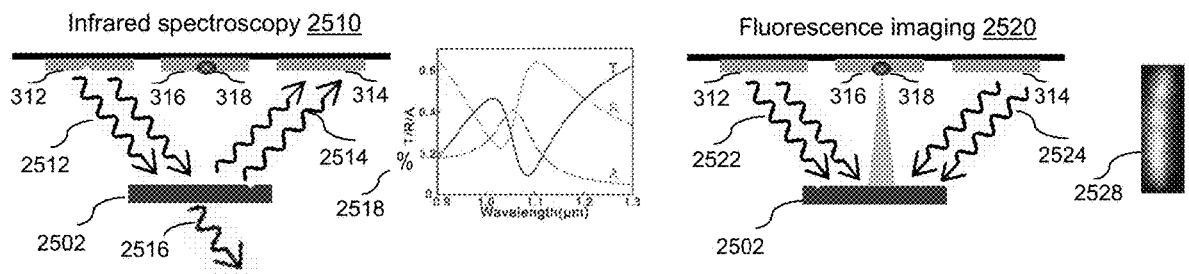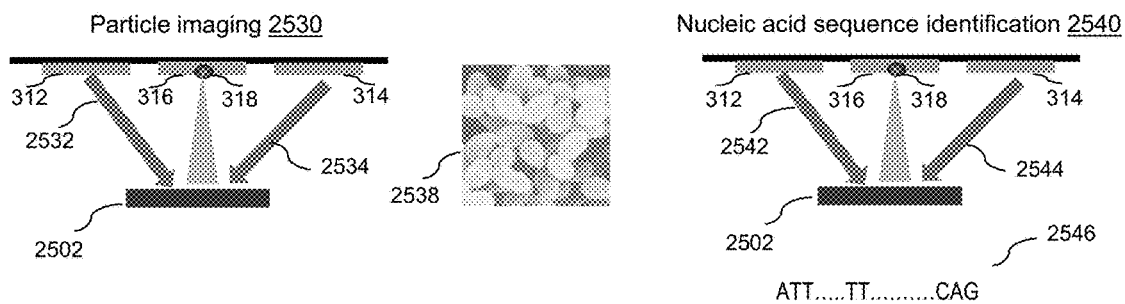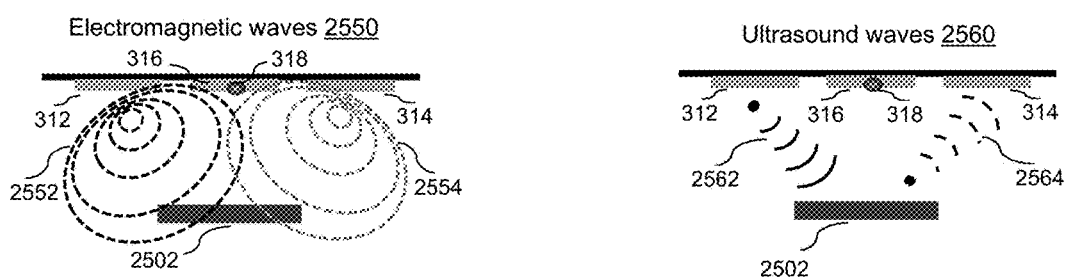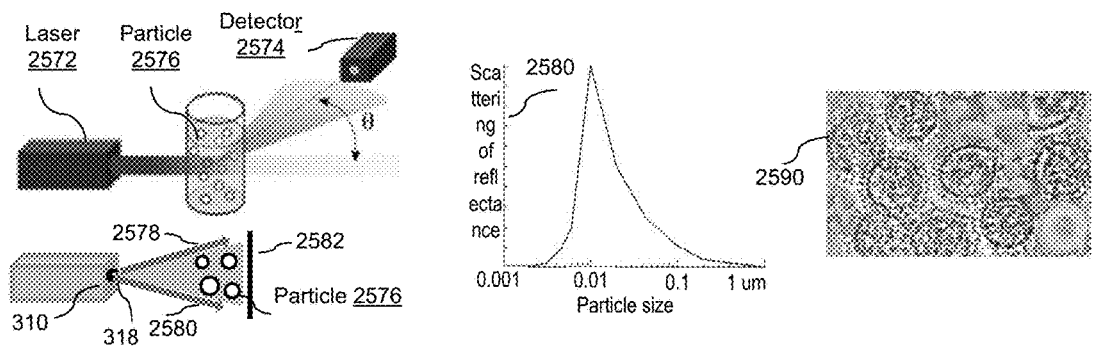
FIG. 25

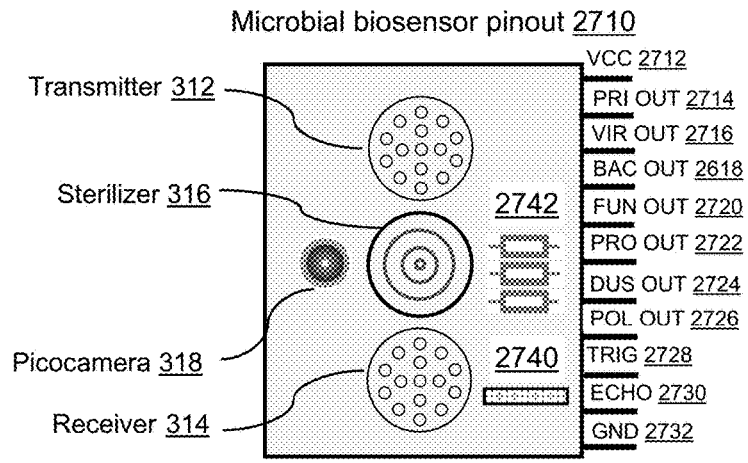

| Microbial biosensor pinout | Microbial biosensor pin function | Steps to wire a Microbial biosensor pin to the SBC GPIO pin |
|---|---|---|
| VCC 2712 | VCC 2712 pin is used as positive power supply. | Connect microbial biosensor VCC 2712 pin to the assigned SBC GPIO pinout 370 5V power pin. |
| PRI OUT 2714 | PRI OUT 2714 pin is used as output pin for pion. | Connect microbial biosensor PRI OUT 2714 pin to the assigned SBC GPIO pinout 370 pin. |
| VIR OUT 2716 | VIR OUT 2716 pin is used as output pin for virus. | Connect microbial biosensor VIR OUT 2716 pin to the assigned SBC GPIO pinout 370 pin. |
| BAC OUT 2718 | BAC OUT 2718 pin is used as output pin for bacteria. | Connect microbial biosensor BAC 2718 pin to the assigned SBC GPIO pinout 370 pin. |
| FUN OUT 2720 | FUN OUT 2720 pin is used as output pin for fungi. | Connect microbial biosensor FUN OUT 2720 pin to the assigned SBC GPIO pinout 370 pin. |
| PRO OUT 2722 | PRO OUT 2722 pin is used as output pin for protists. | Connect microbial biosensor PRO OUT 2722 pin to the assigned SBC GPIO pinout 370 pin. |
| DUS OUT 2724 | DUS OUT 2724 pin is used as output pin for dust mites. | Connect microbial biosensor DUS OUT 2724 pin to the assigned SBC GPIO pinout 370 pin. |
| POL OUT 2726 | POL OUT 2726 pin is used as output pin for pollen grains and dust mite allergens | Connect microbial biosensor POL OUT 2726 pin to the assigned SBC GPIO pinout 370 pin. |
| TRIG 2728 | TRIG 2728 pin is used to trigger the signal pulses such as light or sound | Connect microbial biosensor TRIG 2728 pin to the assigned SBC GPIO pinout 370 TRIG pin. |
| ECHO 2730 | ECHO 2730 pin produces a pulse when the reflected signal is received. | Connect microbial biosensor ECHO 2730 pin to the assigned SBC GPIO pinout 370 TRIG pin. |
| GND 2732 | GND 2732 pin is used as negative power ground. | Connect microbial biosensor GND 2732 pin to the assigned SBC GPIO pinout 370 GND pin. |
| Camera CSI port 2740 | Camera CSI port 2740 is used as an electrical bus. | Connect camera CSI port 2740 to the SBC Camera CSI port 368. |

FIG. 27

Microbial biosensor infrared spectroscopy sensing working principle diagram 2810
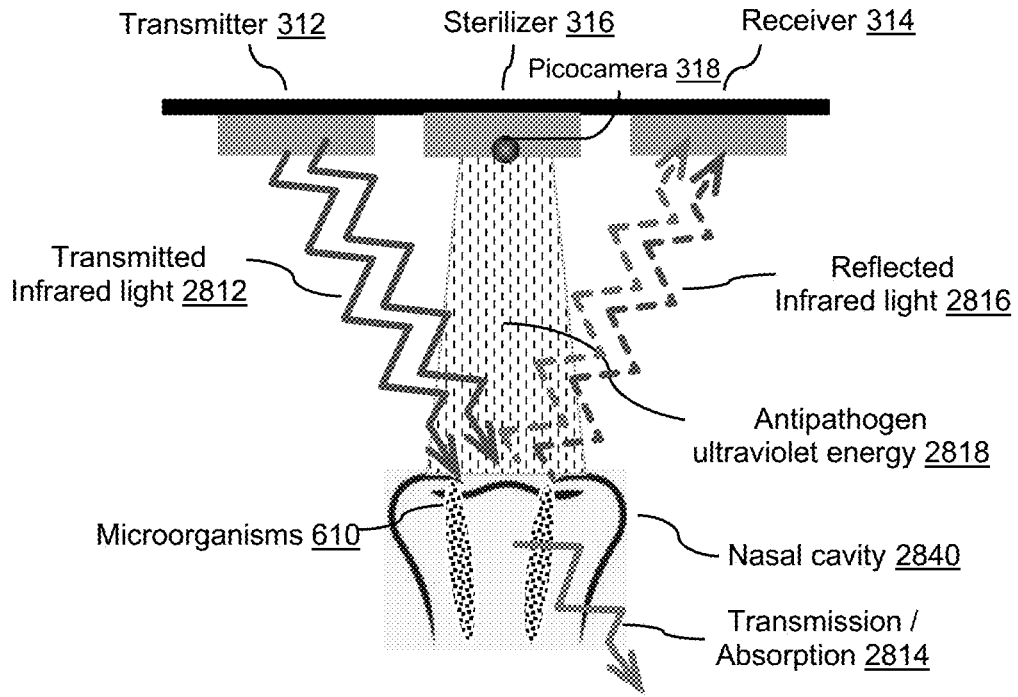
Microbial biosensor particle imaging working principle diagram 2850
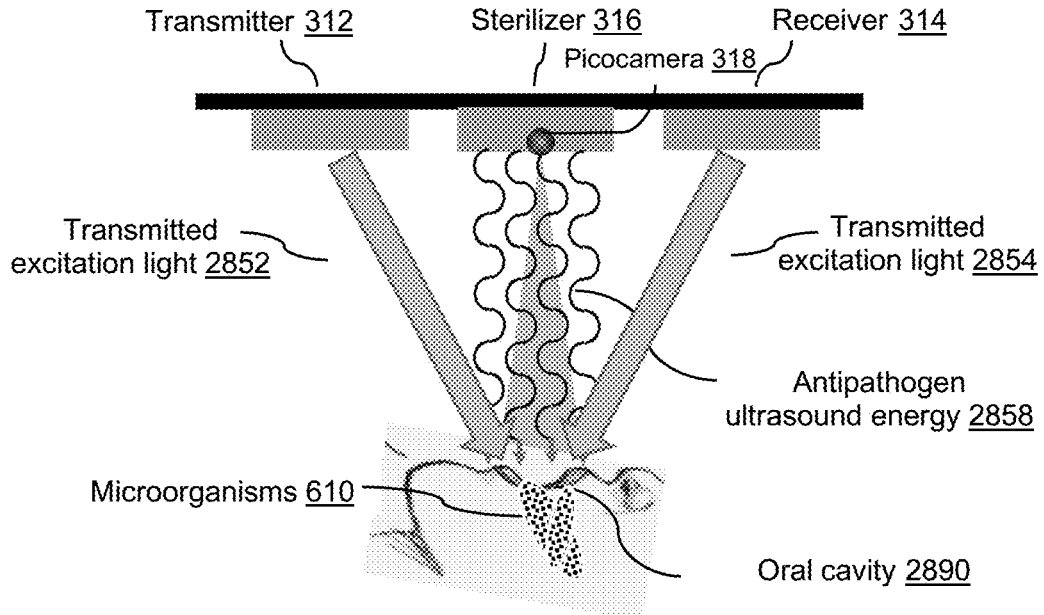
FIG. 28

Microbial biosensor nasal cavity test method diagram 2910
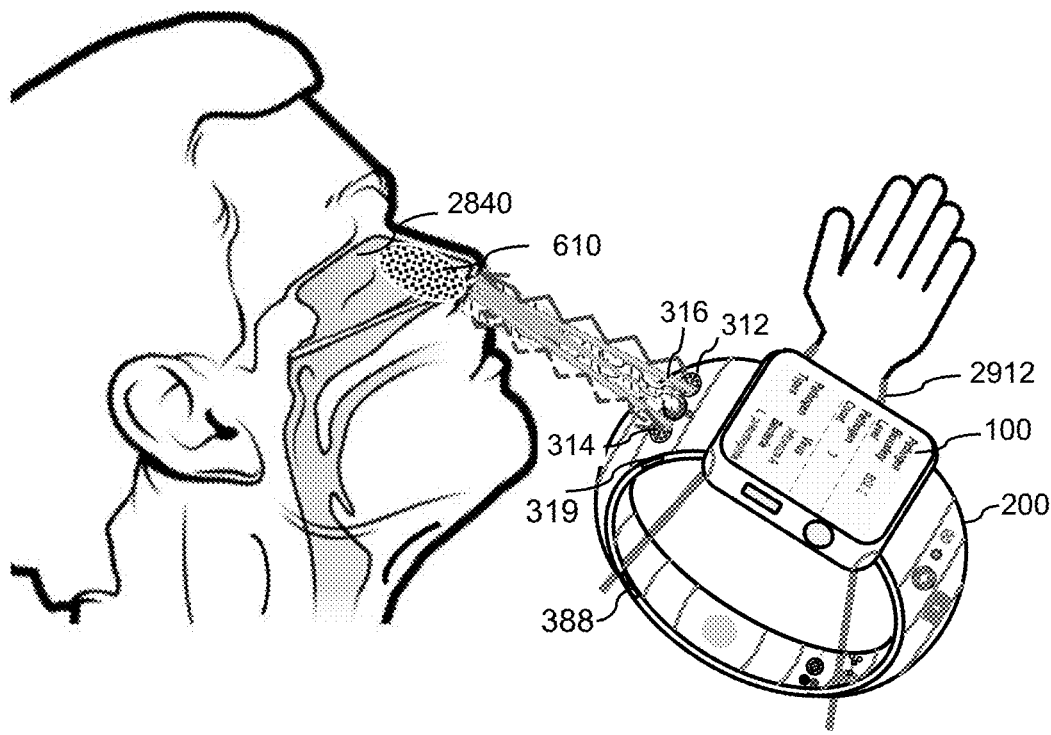
Microbial biosensor oral cavity test method diagram 2950
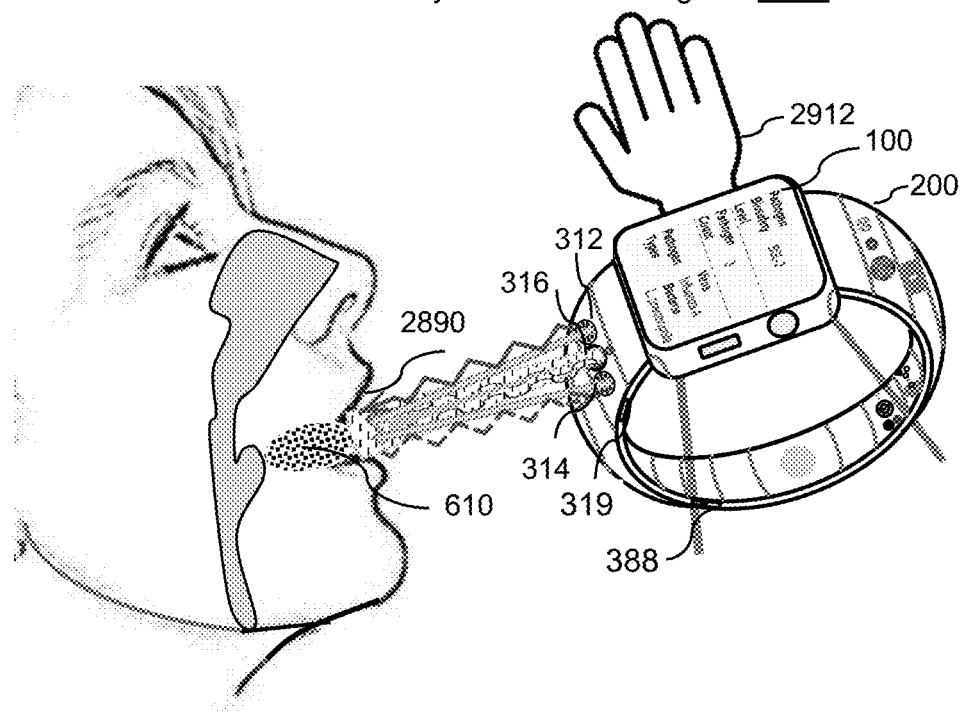
FIG. 29

Microbial biosensor surface test method diagram 3010
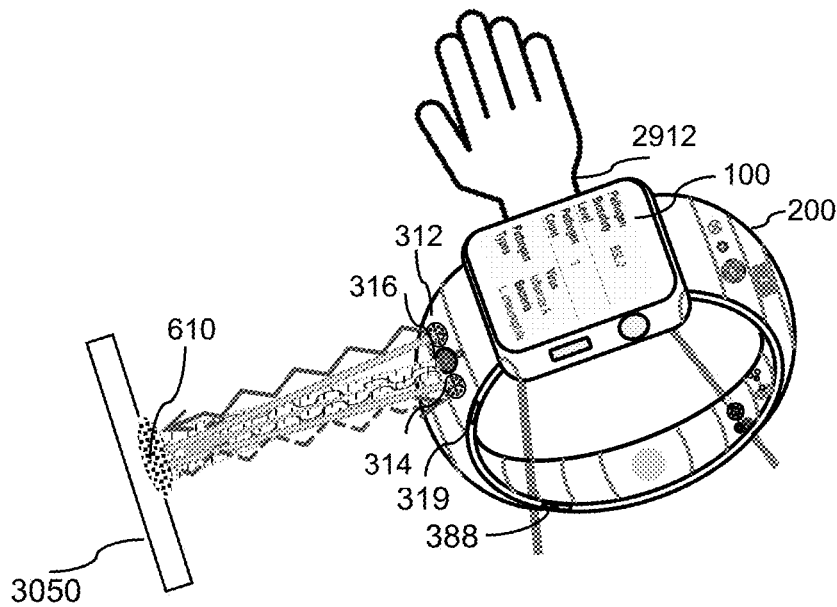
Surface 3050
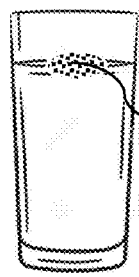
Drinks 3052
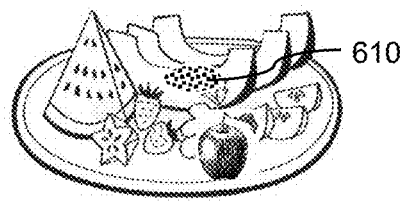
Food 3054
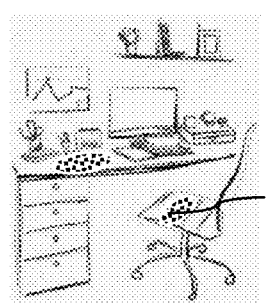
Furniture 3056
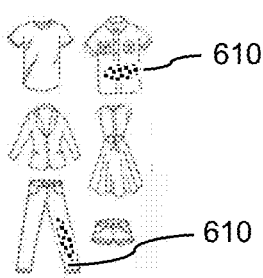
Clothes 3058
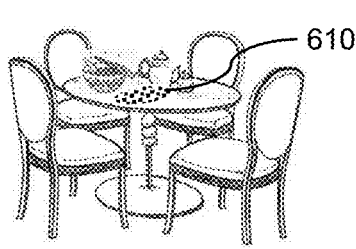
Dining Table 3060
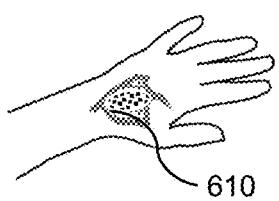
Skin Infection 3062
FIG. 30

Pollen grain diagram 3110      Pollen grain structure and components diagram 3150

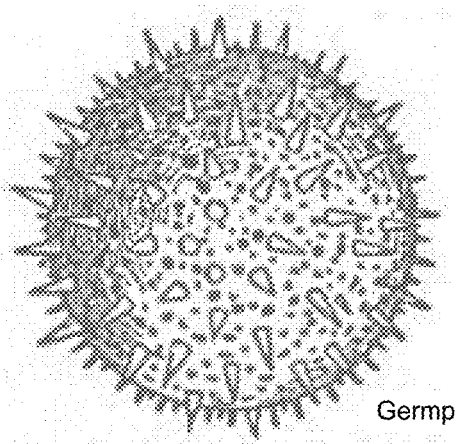
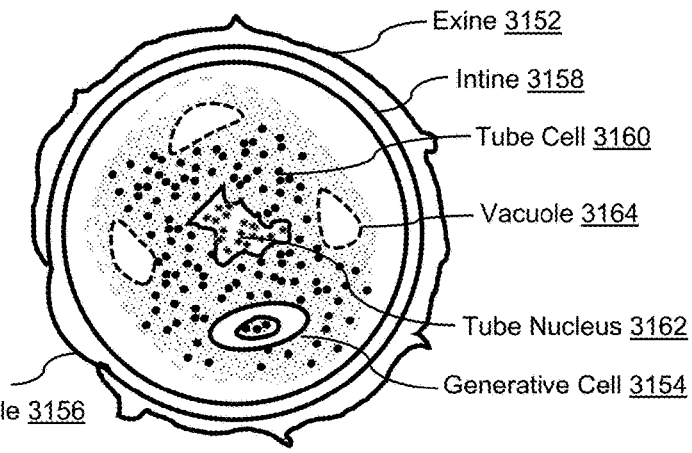

Pollen structure components, function, and chemical composition list 3170

| Component | Description of Primary Function(s) | Predominant chemical composition |
|---|---|---|
| Exine 3152 | Decay-resistant outer coating of a pollen grain or spore. It bears a characteristic surface pattern that is used in palynology | Cellulose and pectins. |
| Generative Cell 3154 | A reproductive cell, especially a cell of an angiosperm pollen grain that divides to produce two male gamete nuclei | Sperm nuclei |
| Germpole 3156 | A pore, pit, or thin area in the outer wall of a spore or pollen grain through which the germ tube or pollen tube makes its exit on germination | Cellulose and pectins |
| Intine 3158 | It is essential for the maturation of the pollen grain and pollen tube germination | Cellulose and pectins. |
| Tube Cell 3160 | The cell in the pollen grain that develops into the pollen tube (the tube which conveys the male gametes of seed-bearing plants to the ovule). | Cellulose and pectins |
| Tube Nucleus 3162 | Nuclei formed by mitotic division of a microspore during the formation of a pollen grain that is held to control subsequent growth of the pollen tube & that does not divide again | Cellulose and pectins |
| Vacuole 3164 | A space within a cell that is empty of cytoplasm, lined with a membrane filled with fluid | Water / inorganic and Organic molecule |

Percent chemical composition of an air-dried pollen list 3190

| Primary Constituents | Percent of dry weight |
|---|---|
| Proteins | 22.7 – 32.8% |
| Amino Acids | 10.4 – 11.5% |
| Reducing Sugars | 36.5 – 40.7% |
| Sucrose | 3.7% |
| Lipids | 7.3 – 12.8% |
| Others | 4.0% |
| Total % | 100% |

FIG. 31

Pollen grain shapes diagram 3200
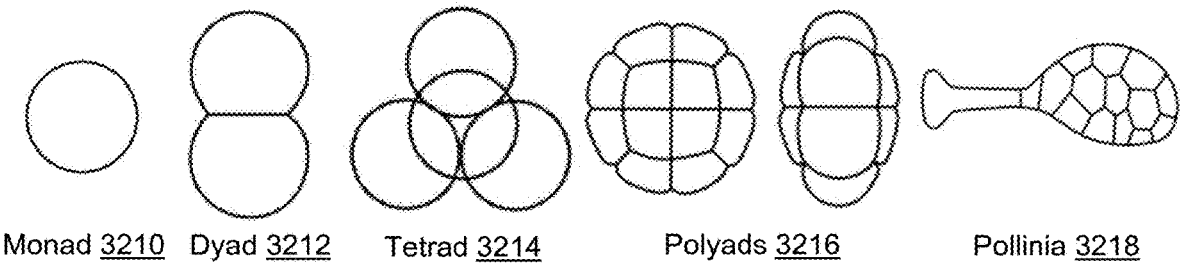
Monad 3210  Dyad 3212  Tetrad 3214  Polyads 3216  Pollinia 3218
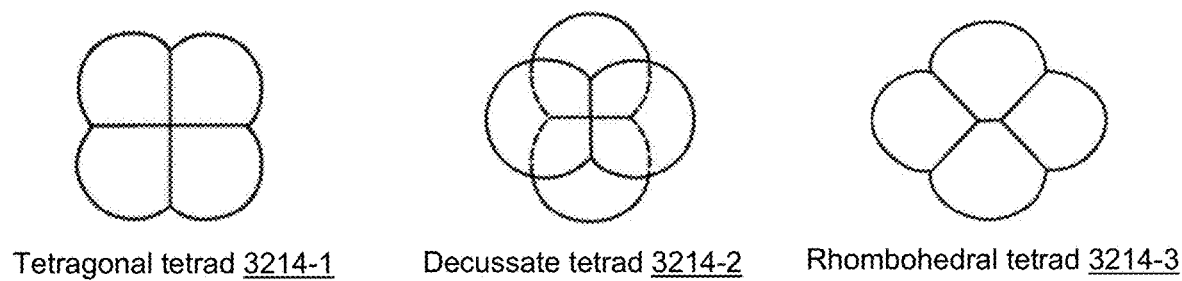
Tetragonal tetrad 3214-1  Decussate tetrad 3214-2  Rhombohedral tetrad 3214-3
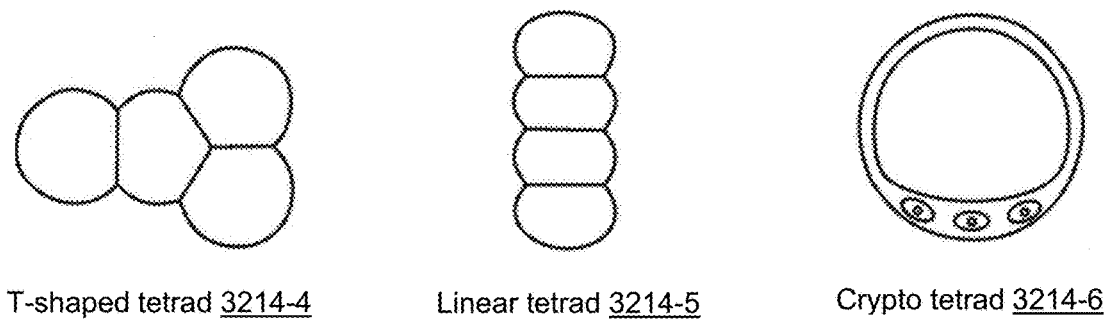
T-shaped tetrad 3214-4  Linear tetrad 3214-5  Crypto tetrad 3214-6
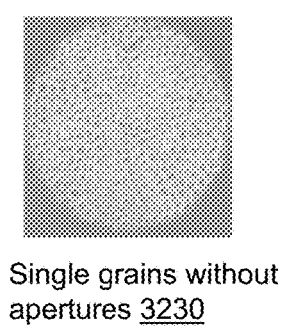 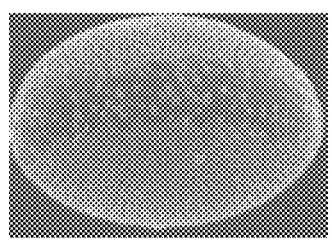 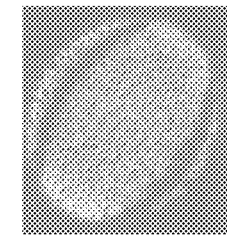
Single grains without apertures 3230  Single grains with furrows 3240  Single grains with apertures 3250
FIG. 32

Pollen type source, name, disease, source, shape, and size list 3300

| Order | Family | Type | General name | Genus Name | Disease / Allergy | Shape | Size (μm) |
|---|---|---|---|---|---|---|---|
| Fagales | Betulaceae | Tree | Birch | Betula verrucosa | Sneezing, Stuffy nose | Spheroidal | 10–25 D |
| Fagales | Fagaceae | Tree | Beech | Fagus engleriana | Rhinitis, Asthama | Ellipsoidal | 29–44 D |
| Salicales | Salicaceae | Tree | Willow | Salix caprea | Seneezing, Itchy eyes | Long and narrow | 28–34 x 20–21 D |
| Utricales | Ulmaceae | Tree | Elm | Ulmus americana | itching, sneezing, wheezing, headache, sinus pain, breathing problems, red or tearing eyes | Spheroidal | 25–36 D |
| Malvales | Moraceae | Tree | Mulberry | Morus alba | Asthma - acoughing and wheezing | Ellipsoidal | 13–22 D |
| Sapindales | Aceraceae | Tree | Maple | Olea europaea | Sneezing. Nasal congestion. Runny nose | Ellipsoidal | 22–28 D |
| Sapindales | Oleaceae | Tree | Olive | Olea europaea | Same as above | Ellipsoidal | 22–28 D |
| Pinales | Cupressaceae | Tree | Cypress | Cupressus arizonica | Same as above | Spheroidal | 20–29 D |
| Pinales | Pinaceae | Tree | Pine | Pinus densiflora | Same as above | Ellipsoidal | 40–85 D |
| Poales | Gramiceae | Grass | Orchard grass | Dactylis glomerata L. | Runny or stuffy nose. itchy throat, mouth, skin, or eyes. puffy eyes | Spheroidal to ovoidal | 22–122 D |
| Poales | Gramiceae | Grass | Sweet vernal grass | Anthoxantu odoratum | Same as above | Spheroidal to ovoidal | 22–122 D |
| Asterales | Asteraceae | Weed | Common ragweed | Ambrosia artemiiifolia L. | Itchy mouth, throat, tongue, or face | Spherical | 15–25 D |
| Caryophyllales | Amaranthaceae | Weed | Pigweed | A. retroflexus | Itchy mouth, throat, tongue, or face | Spherical | 18–31 D |

Pollen attributes and biosensor detector list 3390

| Pollen attributes | Shape, Size, Structure, Exine, Number of apertures |
|---|---|
| Biosensor detector | Particulate matter sensor |

FIG. 33

Pollen tree taxonomy 3410

| Pollen Taxonomy | | Kingdom | Plantae | | |
|---|---|---|---|---|---|
| Phylum | Class | Order | Family | Genus | Species |
| Angiospermatophyta | Dicotyledonouses | Asterales | Asteraceae | Ambrosia | Ambrosia artemisiifolia |
| Spermatophyta | Dicotyledonae | Urticales | Moraceae | Morus | Morus alba |

Pollen data 3430

| No | Data |
|---|---|
| 1 | Allergens of Pollen, Pollen Allergy |
| 2 | Annotation – Pollen grain and associated allergies |
| 3 | Pollen Safety Data Sheet – Pollen type, name, allergy identification, diagnosis, first aid / medical, and regulatory and other information |
| 4 | Attributes – Pollen grain size and shape, number, and arrangement of apertures, exine and intine thickness, exine sculpture, and internal texture. |
| 5 | Unique Identifiers – Unique identification of a pollen based on biosensor transducer used to detect pollen |
| 6. | Pollen parameters detected: pollen type, pollen count, pollen allergy level, annotation, pollen safety data sheet related parameters, attributes, unique identifiers and so on. |

Pollen database 3450

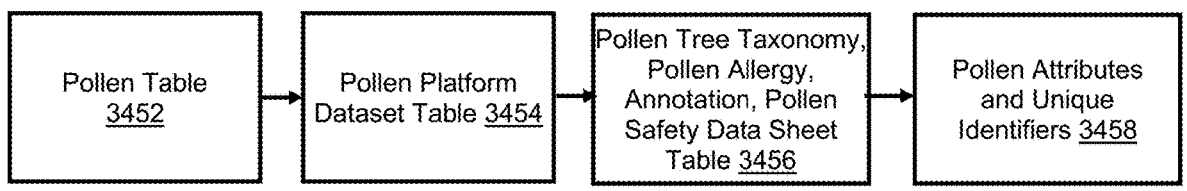

FIG. 34

Particulate matter sensor pinout 3510

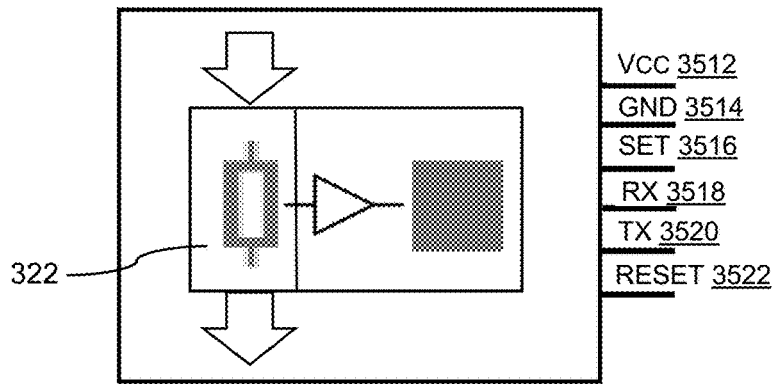

Particulate matter sensor wiring table 3550

| Particulate matter sensor pinout | Particulate matter sensor pin function | Steps to wire an particulate matter sensor pin to the SBC GPIO pin |
|---|---|---|
| Vcc 3512 | Vcc 3512 pin is used as positive power supply. | Connect particulate matter sensor Vcc 3512 pin to the assigned SBC GPIO pinout 370 5V power pin. |
| GND 3514 | GND 3514 pin is used as negative power ground. | Connect particulate matter sensor GND 3514 pin to the assigned SBC GPIO pinout 370 GND pin. |
| SET 3516 | SET 3516 pin is used as high level 3V3 or suspending normal working status, while low level is sleeping mode. | Connect particulate matter sensor SET 3516 pin to the assigned SBC GPIO pinout 370 pin. |
| RX 3518 | RX 3518 pin is used to configure and send data to the particulate matter control from the single board microcomputer. | Connect particulate matter sensor RX 3518 pin to the assigned SBC GPIO pinout 370 TXD pin. |
| TX 3520 | TX 3520 pin transmits data from the particulate matter control sensor to the single board microcomputer. | Connect particulate matter sensor TX 3520 pin to the assigned SBC GPIO pinout 370 RXD pin. |
| RESET 3522 | RESET 3522 pin is used to reset the particulate matter sensor. Reset signal is 3V3. | Connect particulate matter sensor RESET 3522 pin to the assigned SBC GPIO pinout 370 pin. |

FIG. 35

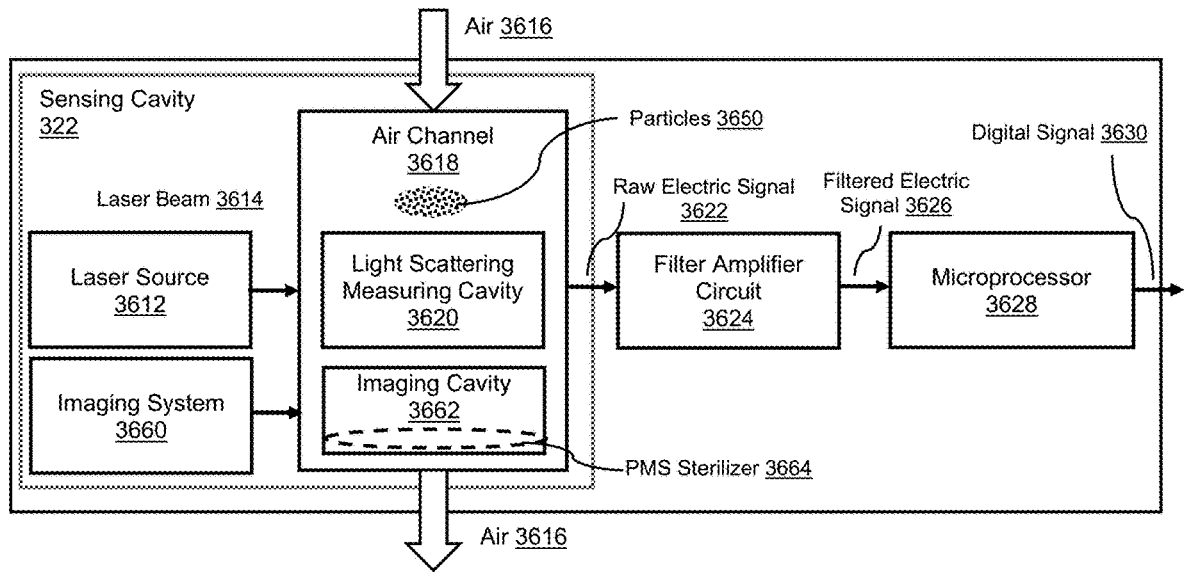

Particulate matter sensor working principle block diagram 3610

Air quality index level of concern table 3680

| AQI Color | Levels of Concern | Values of Index | Description of Air Quality |
|---|---|---|---|
| Green | Good | 0 to 50 | Air quality is satisfactory, and air pollution poses little or no risk. |
| Yellow | Moderate | 51 to 100 | Air quality is acceptable. However, there may be a risk for some people, particularly those who are unusually sensitive to air pollution. Some might require personal protective equipment (PPE) while going out. |
| Orange | Unhealthy for Sensitive Groups | 101 to 150 | Members of sensitive groups may experience health effects. The public is less likely to be affected. Sensitive groups might require PPE while going out. |
| Red | Unhealthy | 151 to 200 | Some members of the public may experience health effects; members of sensitive groups may experience more serious health effects. Wear PPE while going out. |
| Purple | Very Unhealthy | 201 to 300 | Health alert: the risk of health effects is increased for everyone. Wear PPE while going out. |
| Maroon | Hazardous | 301 and higher | Health warning of emergency conditions: everyone is more likely to be affected. Wear PPE while going out. |

FIG. 36

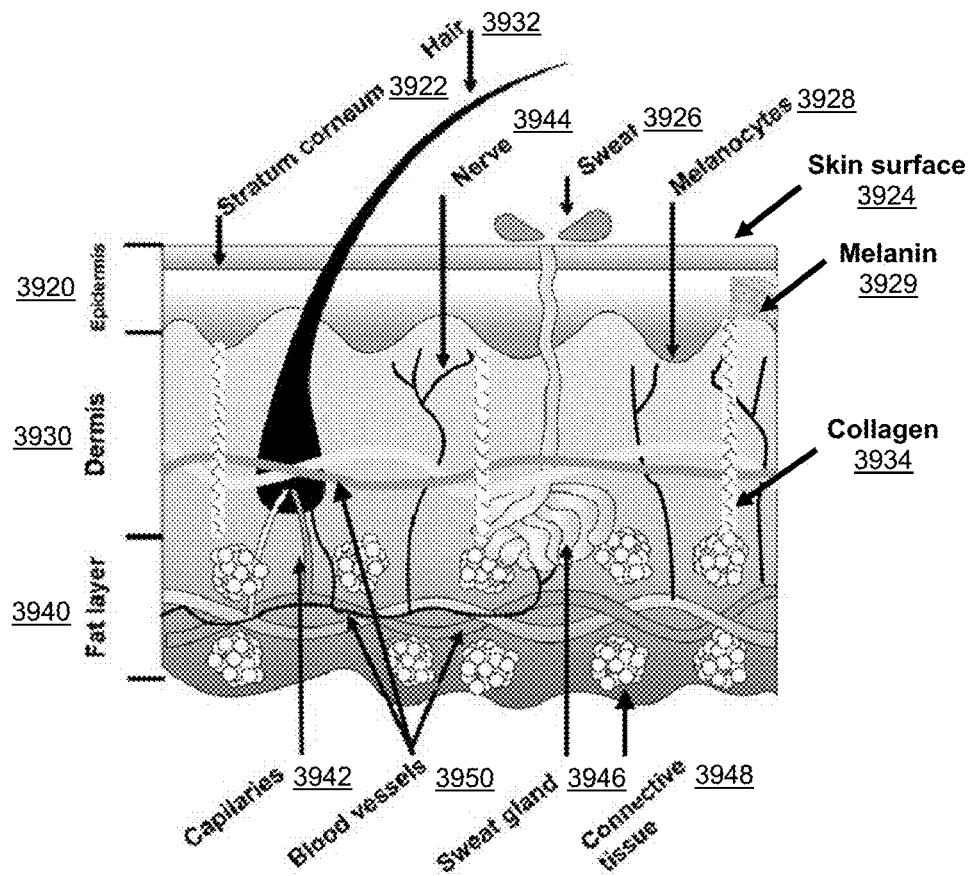
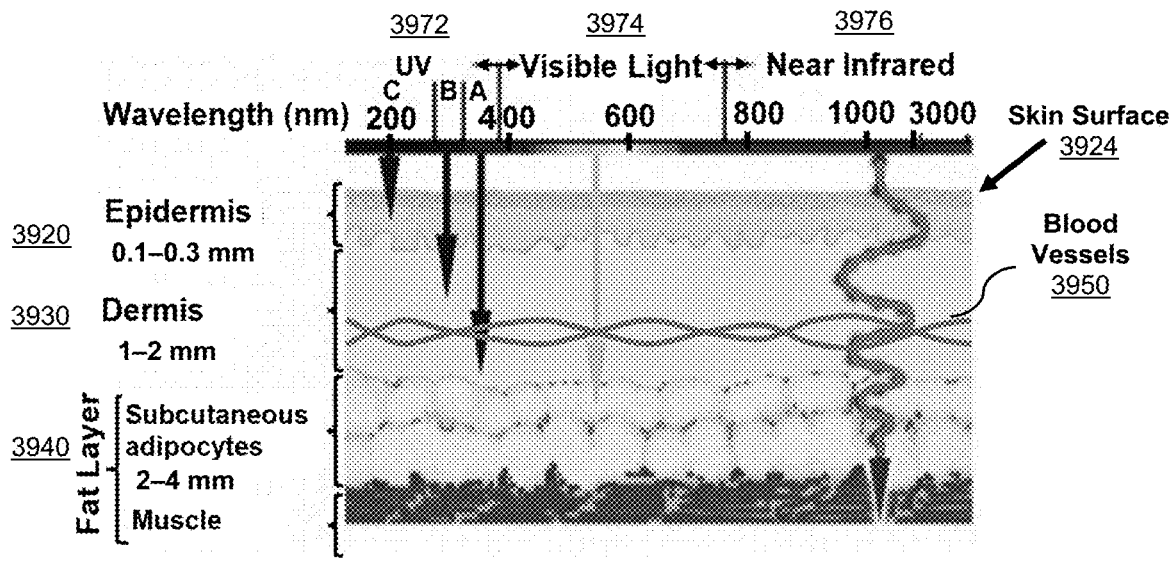
FIG. 39

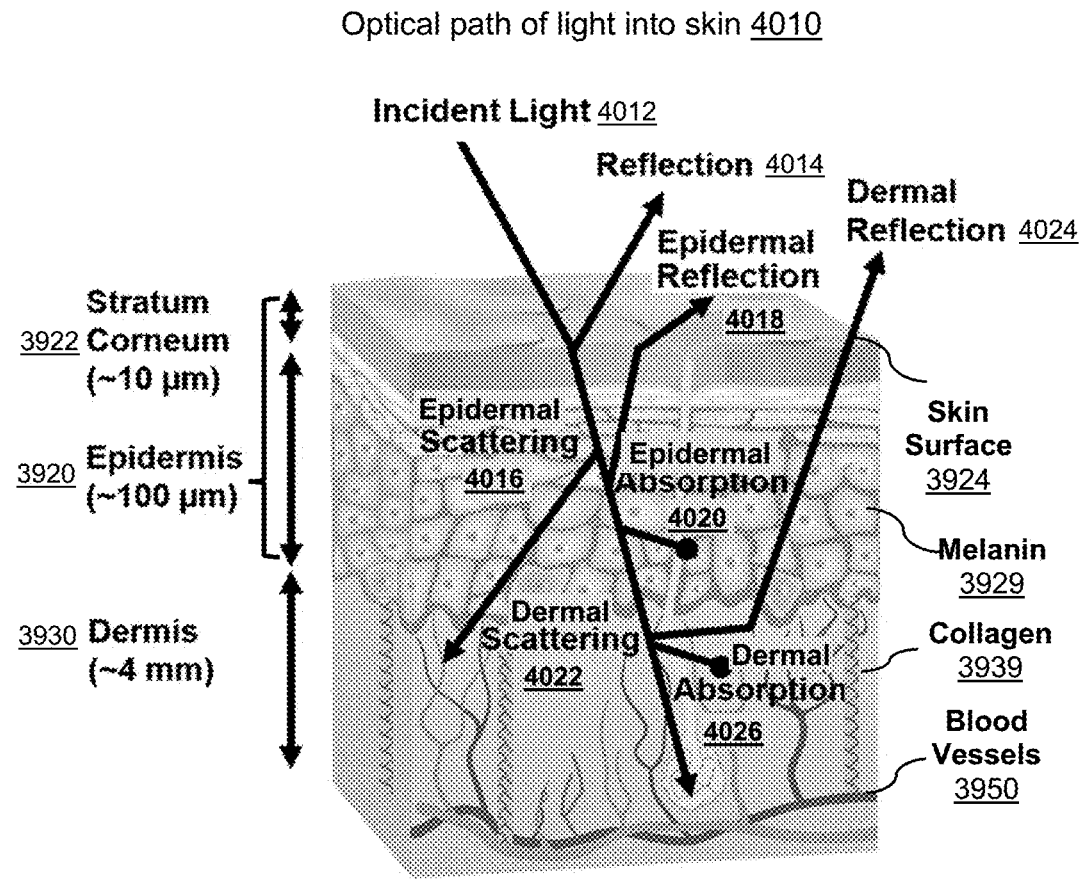
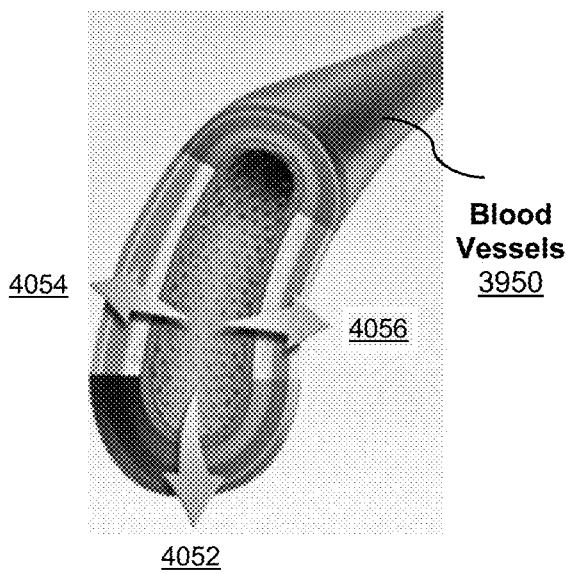
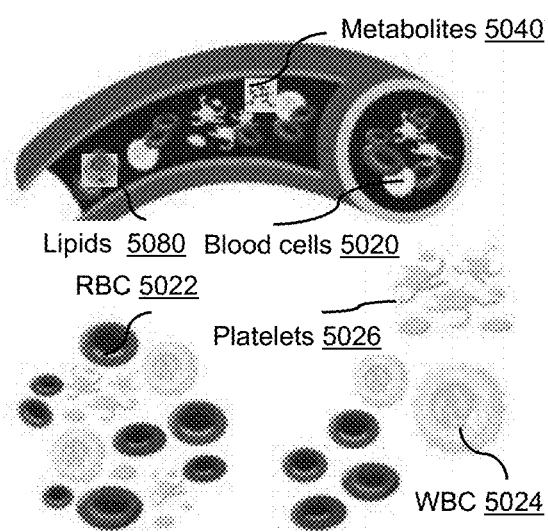
FIG. 40

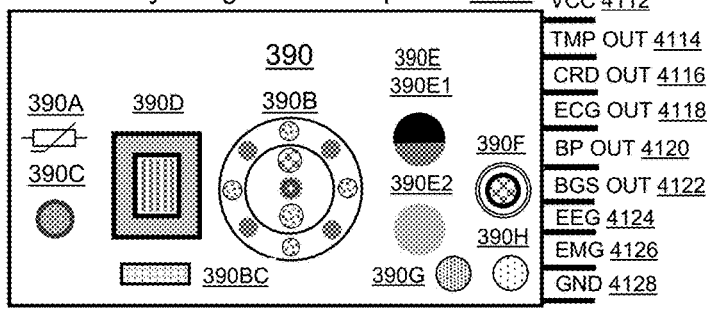

| Physiological sensor pinout | Physiological sensor pin function | Steps to wire a physiological sensor pin to the SBC GPIO pin |
|---|---|---|
| VCC 4112 | VCC 4112 pin is used as positive power supply. | Connect physiological sensor VCC 4112 pin to the assigned SBC GPIO pinout 370 5V power pin. |
| TMP OUT 4114 | TMP OUT 4114 pin is used as output pin for temperature. | Connect physiological sensor TMP OUT 4114 pin to the assigned SBC GPIO pinout 370 pin. |
| CRD OUT 4116 | CRD OUT 4116 pin is used as output pin for heart parameters. | Connect physiological sensor CRD OUT 4116 pin to the assigned SBC GPIO pinout 370 pin. |
| ECG OUT 4118 | ECG OUT 4118 pin is used as output pin for ECG parameters. | Connect physiological sensor ECG OUT 4118 pin to the assigned SBC GPIO pinout 370 pin. |
| BP OUT 4120 | BP OUT 4120 pin is used as output pin for blood pressure. | Connect physiological sensor BP OUT 4120 pin to the assigned SBC GPIO pinout 370 pin. |
| BGS OUT 4122 | BGS OUT 4122 pin is used as output pin for blood gases. | Connect physiological sensor BGS OUT 4122 pin to the assigned SBC GPIO pinout 370 pin. |
| EEG OUT 4124 | EEG OUT 4124 pin is used as output pin for EEG parameters. | Connect physiological sensor EEG OUT 4124 pin to the assigned SBC GPIO pinout 370 pin. |
| EMG OUT 4126 | EMG OUT 4126 pin is used as output pin for EMG parameters. | Connect physiological sensor EMG OUT 4126 pin to the assigned SBC GPIO pinout 370 pin. |
| GND 4128 | GND 4128 pin is used as negative power ground. | Connect physiological sensor GND 4128 pin to the assigned SBC GPIO pinout 370 GND pin. |
| Camera CSI port 390BC | Camera CSI port 390BC is used as an electrical bus. | Connect camera CSI port 390BC to the SBC Camera CSI port 368. |

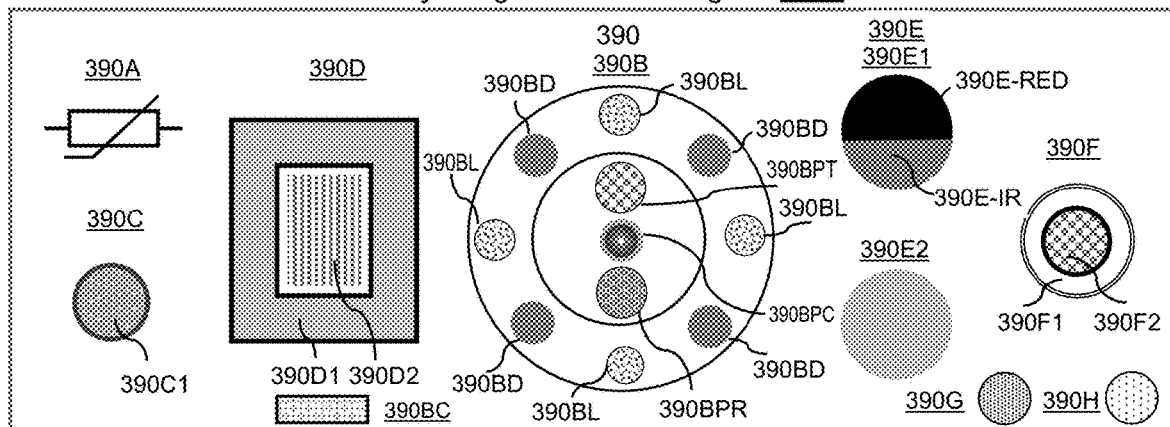

FIG. 41

Physiological parameters, detection sensor, and detected normal reference ranges 4200

| No | Physiological Parameter | Human Anatomy | Detection Sensor | Normal Reference Ranges |
|---|---|---|---|---|
| 1 | Skin Temperature 4212 and Body Temperature 4214 | Skin and Hypothalamus | Thermistor, Photoconductivity, Thermoelectric, Optical | 33.5—36.9 °C (Skin)<br>92.3— 98.4 °F (Skin)<br>36.1—37.2 °C (Body)<br>97.0—99.0 °F (Body)<br>Avg. body temperature - 37 °C (98.6 °F) |
| 2 | Heart Rate 4216 | Heart | Cardiac photoplethysmography sensor (PPG) | 0—1 month: 70—190<br>1—11 months: 80 —160 bpm<br>1—2 years: 80—130 bpm<br>3—4 years: 80—120 bpm<br>5—6 years: 75—115 bpm<br>7—9 years: 70—110 bpm<br>10—60 years: 70—100 bpm<br>60+ years: 70—120 bpm |
| 3 | Heart Rate Variability 4218 | Heart | Cardiac photoplethysmography (PPG) sensor, Accelerometer | HRV < 50 ms is unhealthy,<br>HRV 50—100 ms compromised health<br>HRV > 100 ms is healthy |
| 4 | Respiratory Rate 4220 | Lungs | Cardiac photoplethysmography (PPG) sensor, Green, Red, and Infrared LED, Photodiode | Age Rate (in breaths per minute)<br>0—1 year: 30—60<br>1—3 years: 24—40<br>3—6 years: 22—34<br>6—12 years: 18—30<br>12+ years: 12—16 |
| 5 | Electrocardiogram (ECG) 4222 | Heart | ECG sensor - Photoplethysmography (PPG) | PQRST sequence or one cardiac cycle<br>Sinus rhythm<br>Resting heart rate: 60—100<br>Walking heart rate: 110—120<br>Atrial fibrillation |
| 6 | Blood Pressure 4224<br>Systolic blood pressure 4224SBP<br>Diastolic blood pressure 4224DBP | Heart and Blood Vessels | Piezoelectric, Hall effect, Pressure Strain, Photoconductivity | Age:       Systolic Diastolic mmHg<br>14–18 years: 90–120 50–80<br>19–40 years: 95–135 60–80<br>41–60 years: 110–145 70–90<br>61+ :           95–145 70–90 |
| 7 | Blood Oxygen 5012 ($O_2$) | Blood | Blood oxygen sensor – RED, IR light and PD | > 95% |
| 8 | Blood Carbon Dioxide 5014 ($CO_2$) | Blood | Nondispersive Infrared Sensor (NDIR), Resistive, Piezoelectric, Electrochemical | 20—29 mmol/L |
| 9 | Electroencephalogram (EEG) 4230 | Brain | Noninvasive dry differential electrodes | EEG: 1—5 AU<br>EEG Bands: Delta, Theta, Alpha, Beta, Gama, and Mu waves |
| 10 | Elbow Electromyogram (EEMG) 4232 | Elbow | Noninvasive array of multiple dry electrodes including reference electrode | EEMG: 1—5 AU<br>Normal – Muscle at rest electrically inactive, Abnormal results – Disorders of muscle, disorders of the neuromuscular junction, disorders of nerves, |
| 11 | Knee Electromyogram (KEMG) 4234 | Knee | Noninvasive array of multiple dry electrodes including reference electrode | KEMG: 1—5 AU<br>Normal – Muscle at rest electrically inactive, Abnormal results – Disorders of muscle, disorders of the neuromuscular junction, disorders of nerves, |

FIG. 42

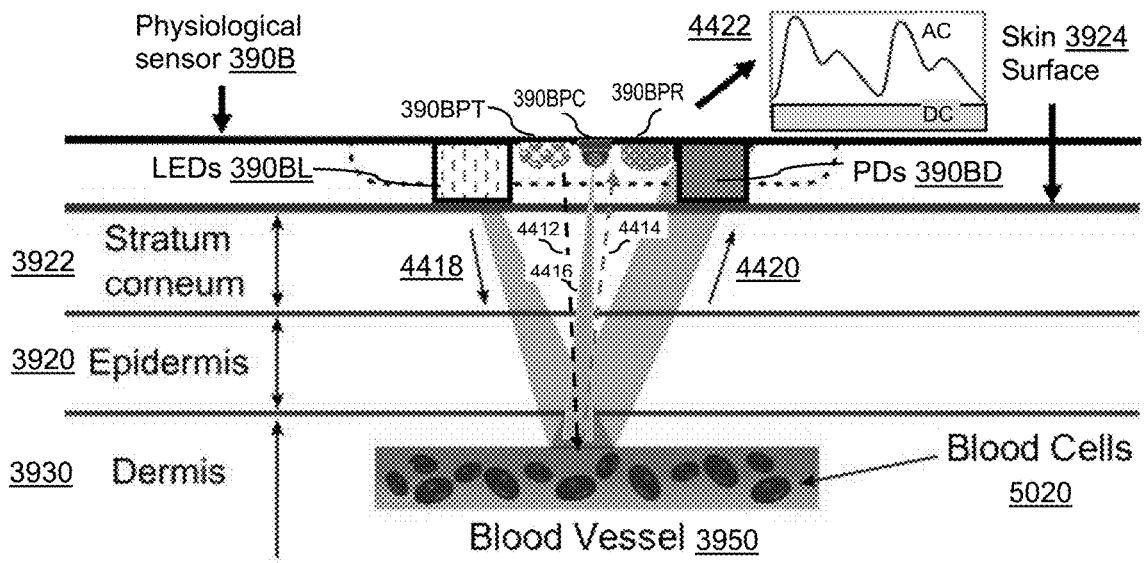
Cardiac photoplethysmography (PPG) sensor operating principle diagram 4410
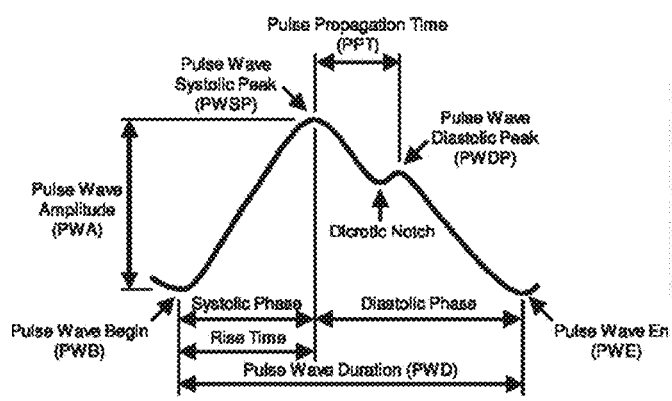
Pulse waveform PPG signal AC Part 4430
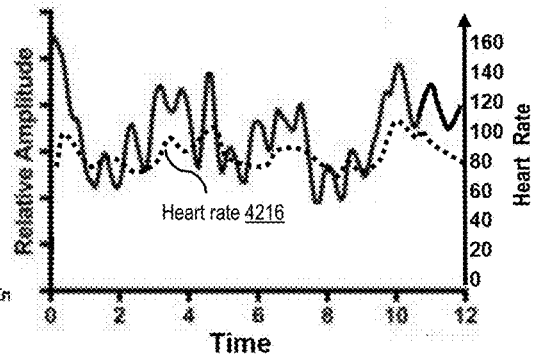
Heart rate PPG signal 4440
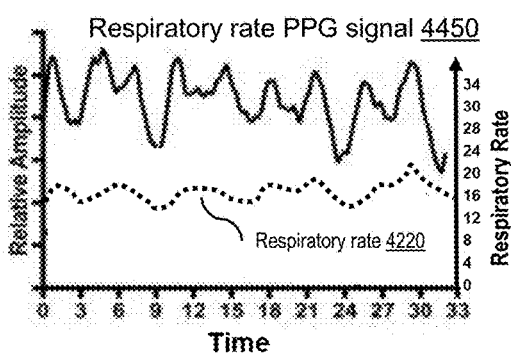
Respiratory rate PPG signal 4450
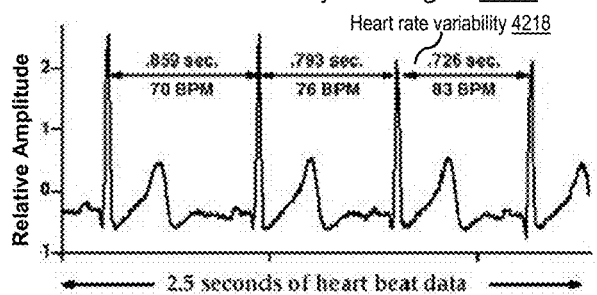
Heart rate variability PPG signal 4460
FIG. 44

ECG sensor operating principle diagram 4510
ECG sensor operation 4520
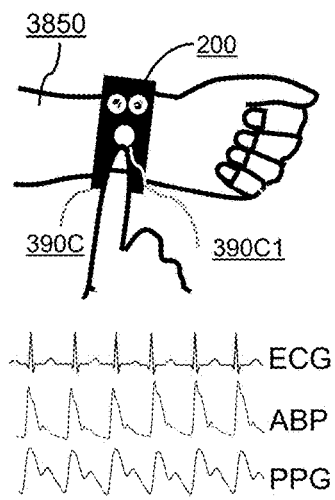
ECG and heart rhythm 4530
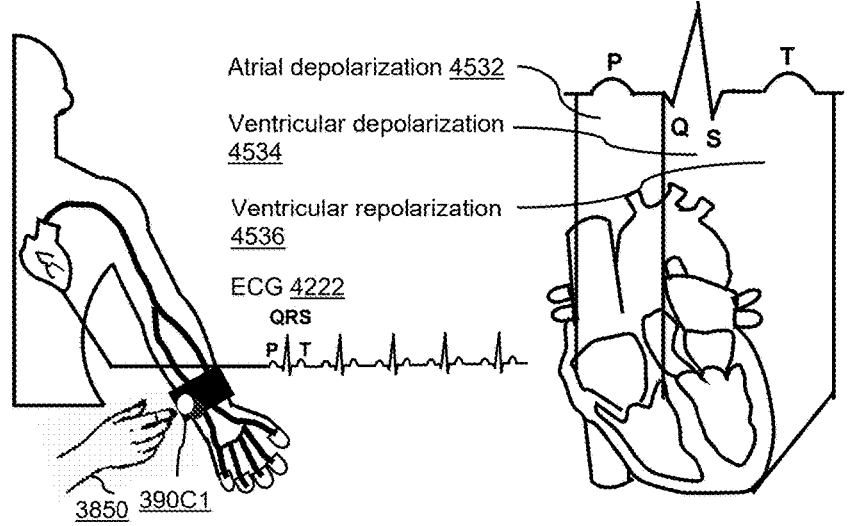
ECG signal 4550
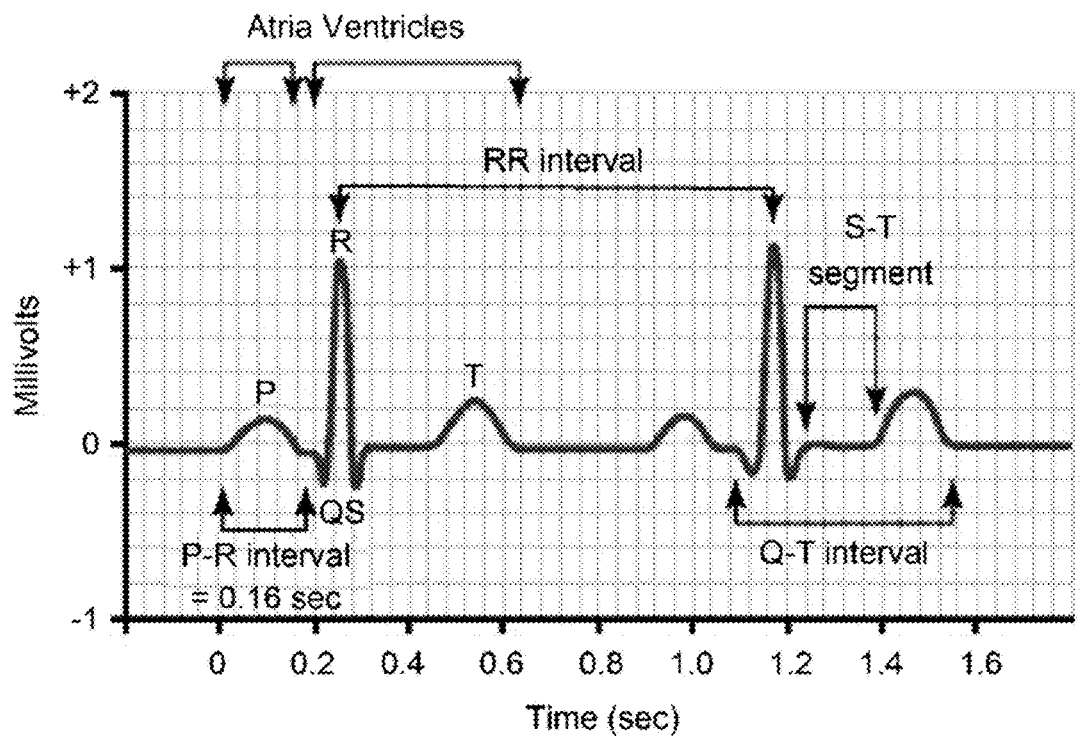
FIG. 45

Blood pressure sensor operating principle diagram 4600
Dilation 4620
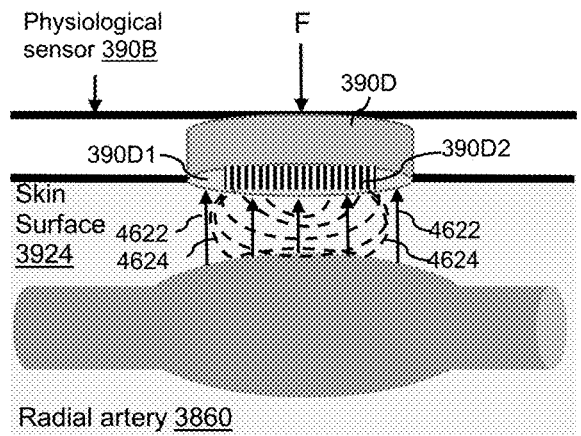
Coarctation 4630
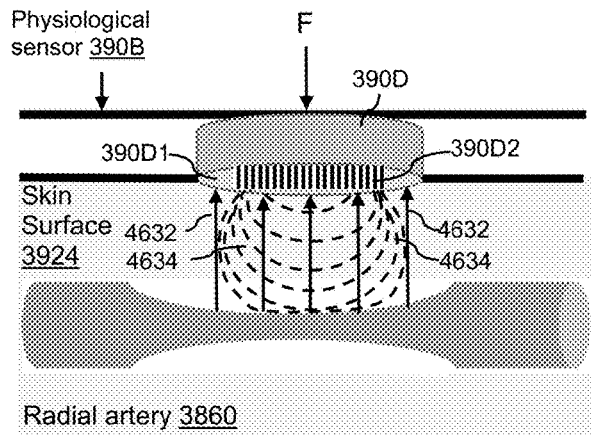
Piezoelectric sensor pressure conversion to an electric signal 4640
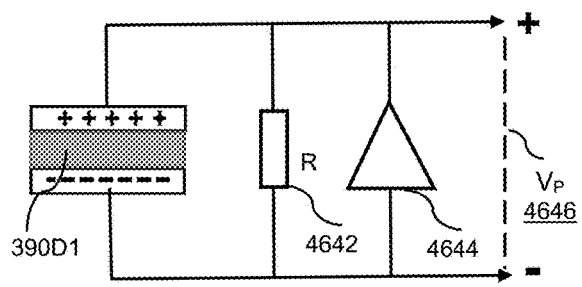
Hall effect sensor conversion to an electric signal 4660
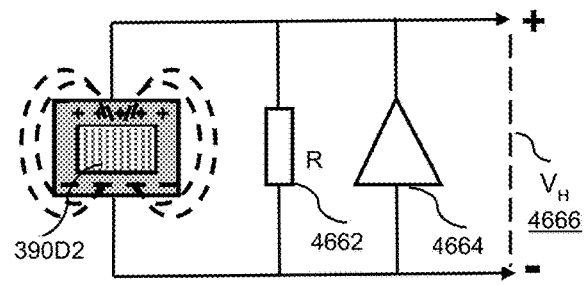
Blood pressure signal 4680
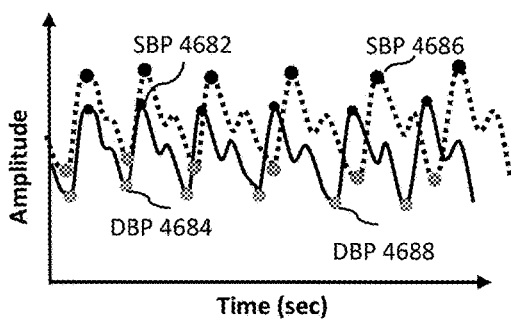
Systolic and diastolic blood pressure 4690
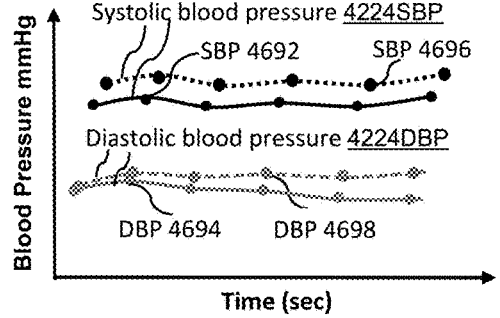
FIG. 46

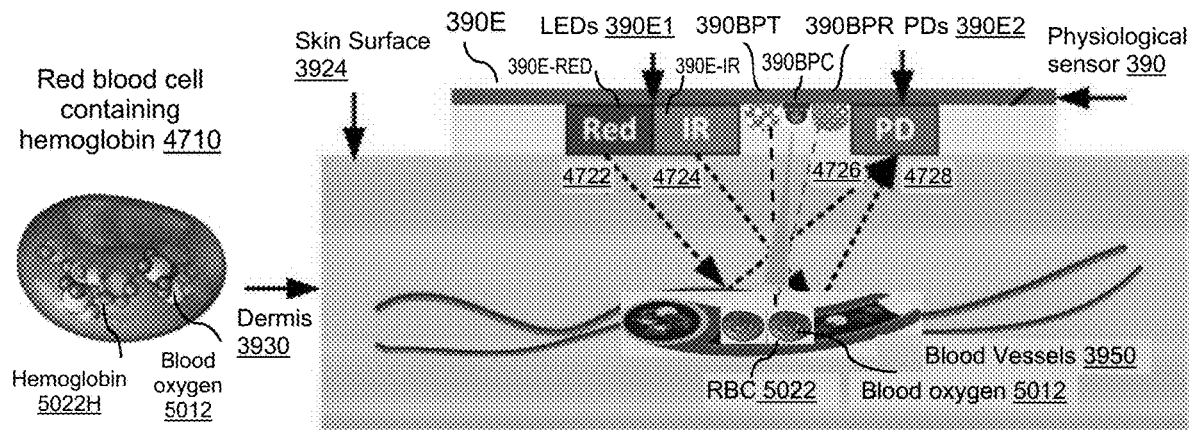
Blood oxygen sensor operating principle diagram 4720
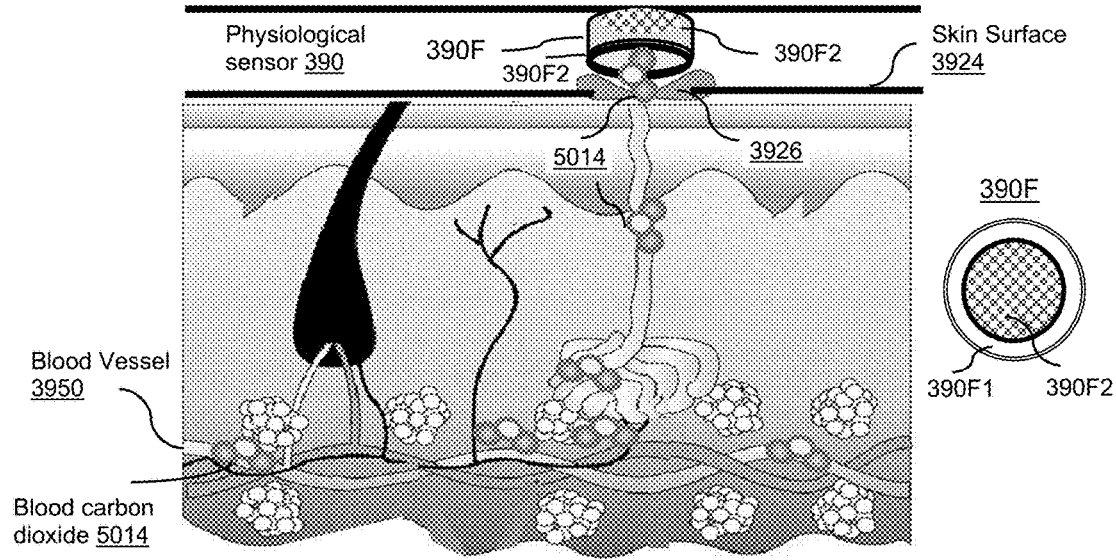
Blood carbon dioxide sensor operating principle diagram 4750
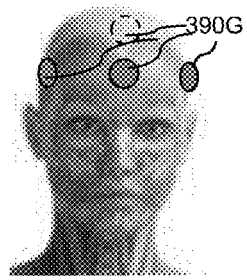
Brain EEG operating principle diagram 4770
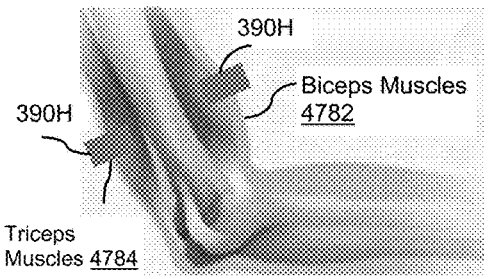
Elbow EMG operating principle diagram 4780
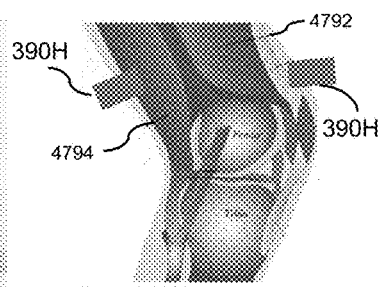
Knee EMG operating principle diagram 4790
FIG. 47

Biofluid sensors diagram 4910

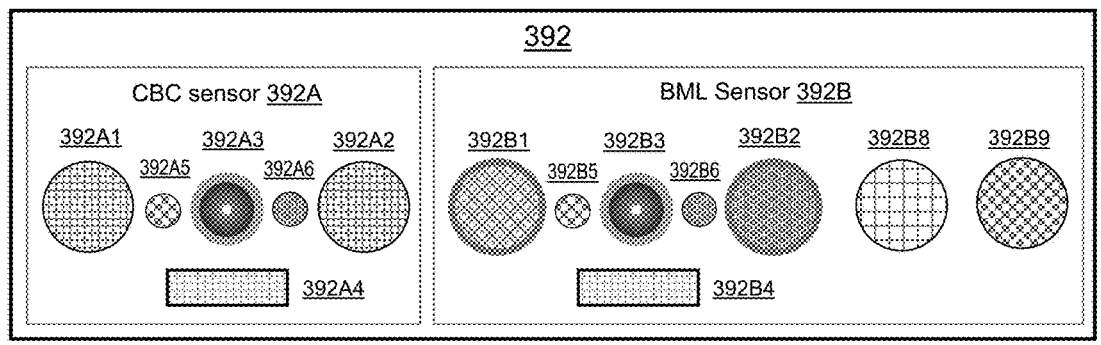

Schematic structure of pixelated LEDs array 4930

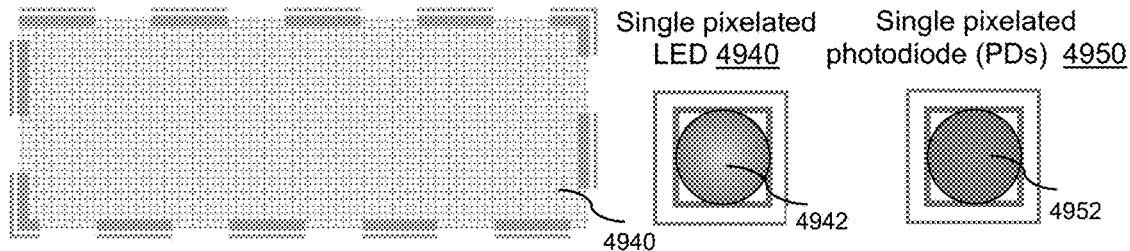

Morphology of blood cells diagram 4960

| RBC Morphology | | | | | | WBC | Platelet |
|---|---|---|---|---|---|---|---|
| Size variation | Shape variation | Hemoglobin distribution | Red cell distribution | Inclusions | | Morphology | Morphology |
| Normal | Acanthocyte | Bite cell | Hypochromia 1+ | Agglutination | Basophilic stippling | Basophil | Giant Platelets |
| Microcyte | Helmet cell | Ovalocyte | 2+ | | Cabot's ring | Eosinophil | Platelet Clumps |
| Macrocyte | Sickle cell | Schistocyte | 3+ | Rouleaux | Howell-Jolly | Neutrophil Segmented | Platelet Satellitism |
| Oval macrocyte | Spherocyte | Stomatocyte | 4+ | | Pappenheimer bodies | Lymphocyte Reactive | Erythrocyte with overlaying platelet |
| Hypochromic macrocyte | Target cell | Tear drop | Polychromasia | | Babesia | Monocyte Immature | Hypo granular platelet |

FIG. 49

Biofluid analytes detected structure 5000

Blood Gases 5010

Blood oxygen 5012    Blood carbon dioxide 5014

  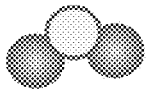

Blood Cells 5020

Red Blood Cell (RBC) 5022

White Blood Cell (WBC) 5024

| Monocyte 5024M | Lymphocyte 5024L | Neutrophil 5024N | Eosinophil 5024E | Basophil 5024B |

Platelet 5026

   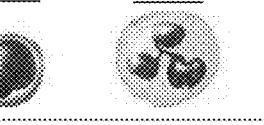  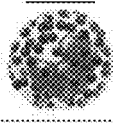 

Hemoglobin 5022H

Metabolites 5040

Albumin 5042    Bilirubin 5044    Blood Glucose 5046    Blood alcohol 5048    Blood Urea Nitrogen (BUN) 5050

 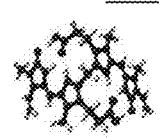 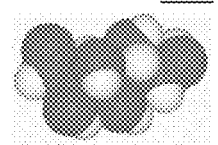 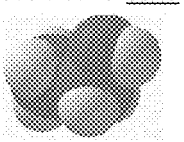 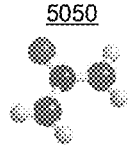

Cortisol 5052    Creatinine 5054    Electrolytes 5056

$Ca^{2+}$ 5056Ca  $Cl^{-}$ 5056Cl  $Mg^{2+}$ 5056Mg  $P^{-}$ 5056P  $K^{+}$ 5056K  $Na^{2+}$ 5056Na

 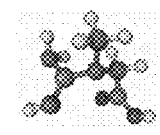 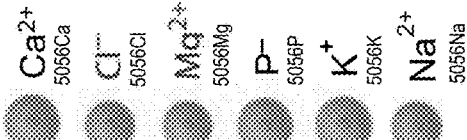

Alkaline Phosphatase (ALP) 5060    Alanine Aminotransferase (ALT) 5062    Aspartate Aminotransferase (AST) 5064

 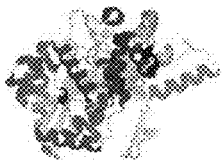 

Lipids 5080

High Density Lipoprotein (HDL) 5082    Low Density Lipoprotein (LDL) 5084    Triglyceride 5086

 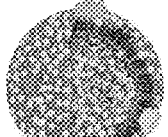 

FIG. 50

Biofluid complete blood count parameters, detection sensor, and detected normal reference ranges 5100

| No | Biofluid Parameter | Human Anatomy | Detection Sensor | Normal Reference Ranges |
|---|---|---|---|---|
| 1 | RBC 5022 | Blood (Carry oxygen) | Spectrally encoded flow cytometry (SEFC) imaging, hyperspectral (HS) imaging and label free autofluorescence using picocamera | 6 months—2 yrs: 3.7—5.4 x 10E6/uL<br>2—5 yrs: 3.9—5.3 x 10E6/uL<br>5—11 yrs: 4—5.2 x 10E6/uL<br>12—< 18 yrs: 4.1—6 x 10E6/uL<br>≥ 18 yrs: 4.63—6.08 x 10E6/uL |
| 2 | Hemoglobin (Hb) 5022Hb | Blood (Protein in RBC) | SEFC and HS imaging, label free autofluorescence using picocamera | 6 months—< 2 yrs: 10.5—13.g/dL<br>2—< 12 yrs: 11.5—13.5 g/dL<br>12—< 18 yrs: 11.7—15.7 g/dL<br>≥ 18 yrs: 11.2—15.7 g/dL |
| 3 | Hematocrit (HCT) 5022HCT | Blood | Mathematically calculated<br><br>HCT = (RBC x MCV)/10 or<br>HCT = RBC/Total Blood Volume | 6 months—< 2 yrs: 33—39 %<br>2—< 6 yrs: 34—40 %<br>6—< 12 yrs: 35—45 %<br>12—< 18 yrs: 35—47 %<br>≥ 18 yrs: 34.1—44.9 % |
| 4 | Mean Corpuscular Volume (MCV) 5022MCV | Blood | Mathematically calculated<br>MCV = HCT x 10/RBC | Male: 85—95 fL<br>Female 85—95 fL |
| 5 | Mean Corpuscular Hemoglobin (MCH) 5022MCH | Blood | Mathematically calculated<br>MCH = Hb (g/dL) × 10/RBC count (10E6/µL) | 6 months—< 2 yrs: 23—31 pg/cell<br>2 to < 18 yrs: 24—34 pg/cell<br>≥ 18 yrs: 25.6—32.2 pg/cell |
| 6 | Mean Corpuscular Hemoglobin Concentration(MCHC) 5022MCHC | Blood | Mathematically calculated<br>MCHC (g/dL) = Hemoglobin ÷ Hematocrit | 2 to 12 yrs: 31—37 g/dL<br>12 to < 18 yrs: 32—36 g/dL<br>≥ 18 yrs: 32.2—35.5 g/dL |
| 7 | WBC 5024 | Blood (Fight infection) | SEFC and HS imaging, label free autofluorescence using picocamera | Male: 3.9—11.7 x 10E3/uL<br>Female: 4.0—11.6 x 10E3/uL |
| 8 | WBC Differential 5024D<br>Neutrophils 5024N<br>Lymphocytes 5024L<br>Monocytes 5024M<br>Eosinophils 5024E<br>Basophils 5024B | Blood | Spectrally encoded flow cytometry (SEFC) imaging, hyperspectral (HS) imaging and label free autofluorescence using picocamera<br><br>Functions of cells<br>Neutrophils: They kill and digest bacteria and fungi. 40% to 60%<br>Lymphocytes: They create antibodies to fight against bacteria, viruses, and other invaders. 20% to 40%<br>Monocyte: Help to break down bacteria. 2% to 8%<br>Eosinophils: They attack and kill parasites and cancer cells. 1% to 4%<br>Basophils: Sound alarm when infectious agents invade. 0.5% to 1% | Neutrophil Count: x 10E3/µL<br>0 to < 12 yrs: 1.65—6.75<br>12 to < 18 yrs: 1.95—6.95<br>≥ 18 yrs: 1.56—6.13<br>Lymphocyte Count: x 10E3/µL<br>1 to < 2 yrs: 2.7—11.9<br>2 to < 18 : 1.1—6.9<br>≥ 18 yrs: 1.18—3.74<br>Monocyte Count: x 10E3/µL<br>0 to < 12 yrs: 0.3—0.95<br>12 to < 18 yrs: 0—0.9<br>≥ 18 yrs: 0.24—0.36<br>Eosinophil Count: x 10E3/µL<br>0 to < 12 yrs: 0.05—0.55<br>12 to < 18 yrs: 0—0.7<br>≥ 18 yrs: 0.04—0.36<br>Basophil Count: x 10E3/µL<br>0 to < 12 yrs: 0—0.25<br>12 to < 18 yrs: 0—0.2<br>≥ 18 yrs: 0.01—0.08 |
| 9 | Platelet 5026 | Blood (Blood clotting) | SEFC and HS imaging, label free autofluorescence using picocamera | 150—450 x10E3/uL |

FIG. 51

Blood cell components 5200

| Features | Red Blood Cell (RBC) 5022 | White Blood Cell (WBC) 5024 | Platelet 5026 |
|---|---|---|---|
| Scientific name | RBC are scientifically called erythrocytes. | WBC are called leukocytes. | Thrombocytes |
| Detection method | SEFC and HS imaging, label free autofluorescence using picocamera. | SEFC and HS imaging, label free autofluorescence using picocamera. | SEFC and HS imaging, label free autofluorescence using picocamera. |
| Appearance | RBC are anucleated, bi-concave, and disc-shaped. | WBC are nucleated and irregular in shape. | Their shape varies greatly, but they are usually round, oval, or rod-shaped. |
| Size | The size of RBC is roughly 6--8 µm and thickness of 1.7--2.7 µm. | The size of WBC is 12--15 µm. | 2--4 µm in greatest diameter |
| Production location | RBC are produced in the red bone marrow. | WBC are produced in the spleen, lymph nodes, etc. | Bone marrow |
| Production number | Almost 2 million RBC are produced in the body per second. | WBC are produced in a comparatively lower number than the RBC. | Production of 1,011 platelets daily to maintain levels of 150,000 to 400,000 platelets per microliter of blood |
| Formation process | The process of RBC formation is called erythropoiesis. | The process of WBC formation in the body is called leukopoiesis. | Platelets are produced during hematopoiesis in a sub-process called thrombopoiesis. |
| Motility | RBC are non-motile. | WBC are motile. | Platelets have no cell nucleus; they are fragments of cytoplasm. |
| Percentage in blood | RBC account for 36% to 50% of the blood in the body. This percentage, however, differs according to the height, weight, and age of the person. | In comparison, WBC constitute a 1% of the blood. Neutrophils: 40% to 60%, Lymphocytes: 20% to 40%, Monocytes: 2% to 8%, Eosinophils: 1% to 4%, Basophils: 0.5% to 1% | Platelets constitute less than 1% of the blood. |
| Types | Red blood cells are only of one type. | White blood cells are of multiple types: lymphocytes, monocytes, neutrophils, eosinophils, and basophils. | Platelets have different shapes such as round, oval or rod-shaped. |
| Life span | RBC can survive up to 120 days in the body. | WBC can survive anywhere between 13 and 20 days. | Platelets have a life span of 3 to 7 days. |
| Constitution | RBC are made up of hemoglobin. | WBC are made up of antibodies with MHC antigen cell markers. | Thrombocytes, or platelets, are not complete cells, but are small fragments of very large cells called megakaryocytes. |
| Color | The presence of hemoglobin lends a red color to the RBC. | The absence of hemoglobin makes WBC colorless. | Platelets are colorless. |
| Function | The primary function of the RBC is to carry oxygen to the various parts of the body. As a secondary function, they also carry waste materials and carbon dioxide to the lungs. | The primary function of WBC is to produce antibodies to strengthen the defense mechanism of the body and protect against attack by germs and provide immunity against infections. | Their primary function of platelets is to prevent and stop bleeding. Platelets get to the site of the injury, growing sticky tentacles that help them stick (adhere) to one another. |
| Circulation | The circulation system used is the cardiovascular system that is related to the blood vessels and the heart. | The circulation systems used are cardiovascular as well as lymphatic. | The circulation systems used are cardiovascular as well as lymphatic. |
| Low count effect | A low RBC count in the body can lead to anemia which can affect the body's ability to carry and supply oxygen to the tissues. | A low WBC count can lead to leukopenia that can hamper the immune system of the body. | People with thrombocytopenia have low platelet levels. Platelets aid blood clotting. When platelet levels are low, they may bruise and bleed excessively. |
| High count effect | A high RBC count is produced in the body during exercise or at high altitudes. | A high WBC count is an indication of infection present in the body or of a lower response rate of the bone marrow. | Primary thrombocythemia high platelet count can cause blood clots to develop spontaneously. |

FIG. 52

Biofluid complete metabolic panel analytes, detection sensor, and detected normal reference ranges 5300

| No | Biofluid Parameter | Human Anatomy | Detection Sensor | Normal Reference Ranges |
|---|---|---|---|---|
| 1 | Albumin 5042 ($C_{123}H_{193}N_{35}O_{37}$) | Liver function (Protein made in liver) | NIR diffuse reflectance spectra | 3.4—5.4 g/dL |
| 2 | Bilirubin 5044 ($C_{33}H_{36}N_4O$) | Liver function (Waste made by the liver) | NIR diffuse reflectance spectra | ≤1.2 mg/dL |
| 3 | Blood Glucose 5046 ($C_6H_{12}O_6$) | Blood (Source of energy) | NIR Spectroscopy, Photoconductivity, Raman Spectroscopy | Random: 70—100 mg/dL Fasting (8 hrs.): 90—110 mg/dL Fasting (2 hrs.): < 140 mg/dL Tolerance Test (2 hr.): < 140 mg/dL |
| 6 | Blood Alcohol 5048 ($C_2H_5OH$) | Blood (Causes blackouts, heart disease) | NIR Spectroscopy | Sober: 0.0 percent BAC Legally intoxicated: 0.08 percent BAC Very impaired: .08—0.40 percent BAC. Risk of death above 0.40 percent BAC. |
| 7 | Blood Urea Nitrogen (BUN) 5050 ($CO(NH_2)_2$) | Liver to blood (Waste products removed from your blood by kidneys) | NIR diffuse reflectance spectra | Males: 1—17 years: 7—20 mg/dL ≥18 years: 8—24 mg/dL. Females: 1—17 years: 7—20mg/dL ≥18 years: 6—21 mg/dL |
| 4 | Cortisol 5052 ($C_{21}H_{30}O_5$) | Adrenal glands | NIR diffuse reflectance spectra | 4.6—20.6 ul/dL evening 1.8—13.6 ul/dL evening |
| 5 | Creatinine 5054 ($C_4H_7N_3O$) | Kidney function Breakdown of creatine from muscle | NIR diffuse reflectance spectra | Male: 0.74—1.35 mg/dL Females: 0.59—1.04 mg/dL |
| 8 | Calcium 5056Ca ($Ca^{+2}$) | Bones and diet to blood (Proper functioning of nerves, muscles, and heart) | NIR with visible light absorption spectrum | <1 year: 8.7—11.0 mg/dL 1—17 years: 9.3—10.6 mg/dL 18—59 years: 8.6—10.0 mg/dL ≥60 years: 8.8—10.2 mg/dL |
| 9 | Chloride 5056Cl ($Cl^-$) | Electrolyte imbalance: Gastric secretion to blood | NIR with visible light absorption spectrum | 1—17 years: 102—112 mmol/L ≥18 years: 98—107 mmol/L |
| 10 | Magnesium 5056Mg ($Mg^{2-}$) | Electrolyte imbalance: Diet to blood | NIR with visible light absorption spectrum | 4.7—18.3 ng/mL |
| 11 | Phosphorus 5056P (P) | Diet to blood | NIR with visible light absorption spectrum | 2.8—4.5 mg/dL |
| 12 | Potassium 5056K ($K^+$) | Electrolyte imbalance: Diet to blood | NIR with visible light absorption spectrum | ≥1 year: 3.6—5.2 mmol/L |
| 13 | Sodium 5056Na ($Na^+$) | Electrolyte imbalance: Diet to blood | NIR with visible light absorption spectrum | ≥1 year: 135—145 mmol/L |
| 14 | Alkaline Phosphatase (ALP) 5060 | Liver function (Enzymes made by the liver. Homodimer protein enzyme) | NIR metabolite Picocamera imaging | 0—14 days: 83 – 248 U/L 15 days—1 yr: 122—469 U/L 1 yr—17 yrs: 57—335 U/L 17 yrs—19 yrs: 45—87 U/L >19 yrs: 35—104 U/L |
| 15 | Alanine Aminotransferase (ALT) 5062 | Liver function (enzyme) | NIR metabolite Picocamera imaging | 0—18 yrs: 9—52 U/L ≥18 yrs: ≤ 33 U/L |
| 16 | Aspartate Aminotransferase (AST) 5064 | Liver function (enzyme) | NIR metabolite Picocamera imaging | 0—18 yrs: ≤ 30 U/L ≥18 yrs: ≤ 32 U/L |

FIG. 53

Biofluid lipid panel parameters, detection sensor, and
detected normal reference ranges 5400

| No | Biofluid Parameter | Human Anatomy | Detection Sensor | Normal Reference Ranges |
|---|---|---|---|---|
| 1 | High Density Lipoprotein (HDL) 5082<br>Composed of lipid (80%) and protein (20%)<br>Size: 5–17 nm<br>Shape: Spherical & doughnut<br>(Cholesterol ($C_{27}H_{46}O$))<br>Cholesteryl ester ($C_{44}H_{78}O_2$)<br>Phospholipid ($CH_2OH-CHOH-CH_2OH$) | Liver and diet<br>(Acts as its antioxidant, anti-inflammatory, endothelial cell maintenance functions. Absorbs cholesterol and carries it back to the liver.) | NIR metabolite Picocamera imaging | Male $\geq$ 40 mg/dL<br>Female $\geq$ 50 mg/dL |
| 2 | High Density Lipoprotein (LDL) 5084<br>Composed of lipid (60%) and protein (40%)<br>Size: 22–29 nm<br>Shape: Spherical & doughnut<br>(Cholesterol ($C_{27}H_{46}O$))<br>Cholesteryl ester ($C_{44}H_{78}O_2$)<br>Phospholipid ($CH_2OH-CHOH-CH_2OH$) | Liver and diet<br>(Transports cholesterol from its site of synthesis in the liver to the various tissues and body cells. Collects in the walls of blood vessels.) | NIR metabolite Picocamera imaging | Less than 100 mg/dL Optimal<br>100—129 mg/dL Near optimal/above optimal<br>130—159 mg/dL Borderline high<br>160—189 mg/dL High |
| 3 | Triglycerides 5086<br>Composed of glycerol and three fatty acids<br>Size: 26–240 nm<br>($C_{55}H_{98}O_6$) | Liver and diet<br>(Store unused calories and provides body with energy.) | Calculated mathematically | Normal: 10—150 mg/dL<br>Borderline: 150—199 mg/dL<br>High: 200—499 mg/dL<br>Very High: 500+ mg/dL |
| 4 | Total Cholesterol 5080T | Liver and diet | NIR Diffuse reflectance spectra<br>Mathematical formula<br>(HDL + LDL+ 0.2xT) | Normal: < 200 mg/dL<br>Borderline High: 200—239 mg/dL<br>High: > 240 mg/dL |

Cholesterol in the blood plasma compartment exists in two forms, free cholesterol (Chol) and cholesteryl esters (CE), both of which are constituents of circulating lipoproteins. Lipoproteins are made of fat and proteins. Cholesterol moves through user body while inside lipoproteins. HDL is known as "good cholesterol" because it transports cholesterol to user liver to be released from your body. HDL helps rid body of excess cholesterol so it's less likely to end up in the arteries

|  | Diameter (nm) | Apolipoproteins | (% of total content) | | (% of total Lipid content) | | | |
|---|---|---|---|---|---|---|---|---|
|  |  |  | Protein | Lipid | Triacylglycerols | Cholesteryl esters | Phospholipids | Free fatty acids |
| HDL | 10-25 | AI, AII, CI | 40 | 60 | 12 | 40 | 47 | 1 |
| LDL | 20-25 | B100 | 20 | 80 | 12 | 59 | 28 | 1 |

FIG. 54

In vivo noninvasive imaging of blood flow in a single vessel diagram 5510
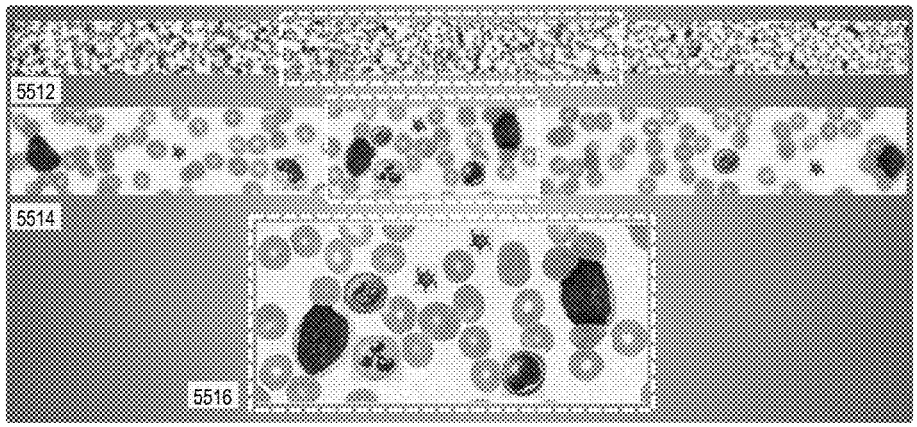
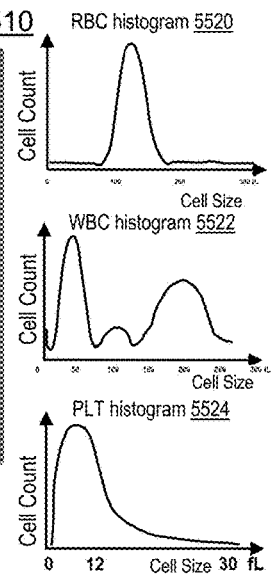
Spectrally encoded flow cytometry (SEFC) imaging of blood cells operating principle diagram 5530
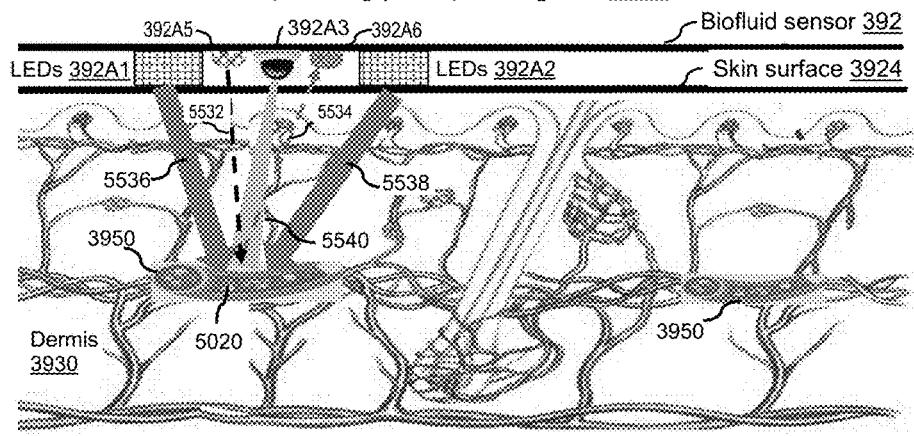
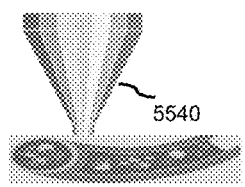
SEFC Image acquisition 5542
Single cell crossing spectral line 5544
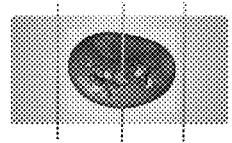
NIR hyperspectral (HS) imaging of blood cells operating principle diagram 5550
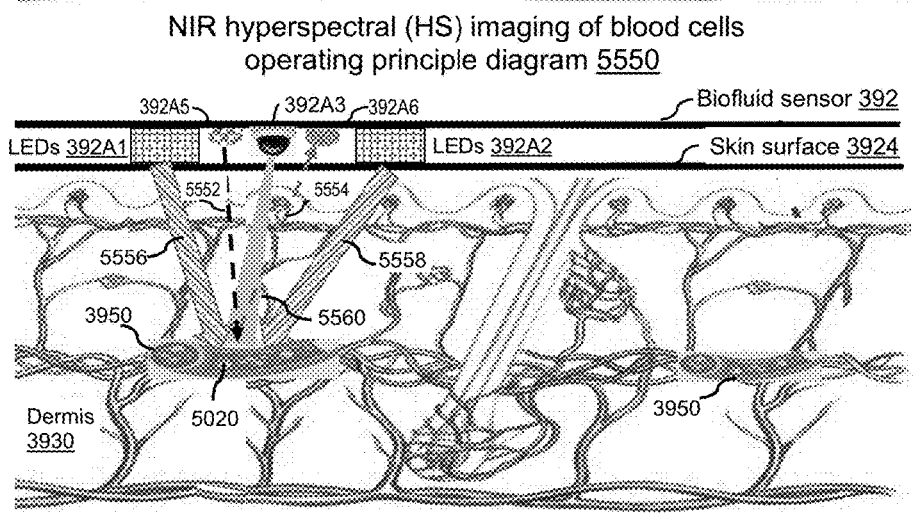
Snapshot imaging method 5562
FIG. 55

NIR spectroscopy fundamental equations 5710

Planck's Equation 5712

$$E = hf = hc/\lambda$$

Travelling wave equation 5714

$$v = f\lambda$$

Speed of light 5716

$$c = f\lambda$$

Wavenumber equation 5718

$$w = 1/\lambda$$

Absorbance 5720

$$A_\lambda = -\log_{10}(T_\lambda) = -\log_{10}(I/I_0) = \varepsilon_\lambda \cdot l \cdot c$$

Reflectance 5722

$$R = -\log_{10}(I_R/I_{R0})$$

Kubelka-Munk Function 5726

$$f(C) = (1-R)^2 / 2R$$

Energy conservation equation 5728

$$A + R + T + S = 1$$

A vibration of a diatomic molecule 5740

Equilibrium 5742 

Stretched 5744 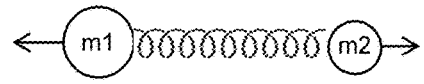

Vibrations of polyatomic molecules (AX2 group) 5760

Symmetric stretch 5762 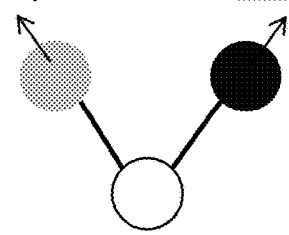

Asymmetric stretch 5764 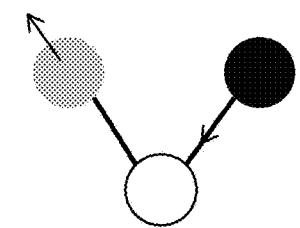

Rocking 5766 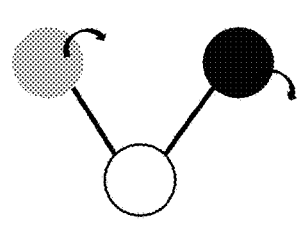

Scissoring 5768 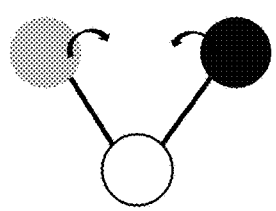

Wagging 5770 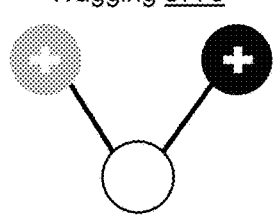

Twisting 5772 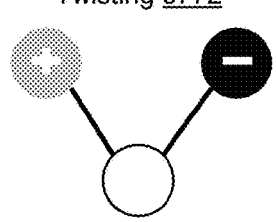

FIG. 57

Principal types of NIR absorption bands and their locations 5810

| Regions | Wavelength (nm) λ | Frequency (THz) f | Wavenumber (cm⁻¹) w | Vibration Bonds |
|---|---|---|---|---|
| IR | 15000 | | | |
| IR | 3030—2850 | | 3300—3500 | Amines $NH_2$, $NH_3$ |
| | 2500 | 120 | 4000 | |
| NIR | | | | C—H Combinations<br>$CH_2$ Combinations<br>C—C, C—N<br>C≡N Combinations |
| NIR | 2200 | 136 | 4545 | |
| NIR | | | | O—H Combinations<br>N—H, Combinations<br>C=O Combinations<br>C=C Combinations<br>C≡C Combinations |
| NIR | 1800 | 167 | 5556 | |
| NIR | | | | C—H 1st Overtone |
| NIR | 1600 | 187 | 6250 | |
| NIR | | | | O—H, N—H 1st Overtone |
| NIR | 1420 | 211 | 7042 | |
| NIR | | | | C—H Combinations,<br>O—H 1st Overtone |
| NIR | 1300 | 231 | 7692 | |
| NIR | | | | C—H 2nd Overtone<br>O—H Combination |
| NIR | 1100 | 273 | 9091 | |
| NIR | | | | N—H 2nd Overtone<br>O—H 2nd Overtone<br>C—H 3rd Overtone |
| Visible | 700 | 428 | 14286 | |
| Visible | 400 | | | |
| UV | 190 | | | |

Biofluid chemical NIR vibrational mode list 5850

| Wavenumber in nm | Vibrational mode |
|---|---|
| 900–1100 | 2nd overtone N—H and O—H, C—H 3rd overtone (e.g., alcohol, glucose) |
| 1200 | 3rd overtone C-H strong (C-H rich compounds, e.g., carbohydrates, lipids) |
| 1400 | 2nd overtone C-H strong, C-H def. (carbohydrates, lipids) combinations, $NH_3$ |
| 1600–1750 | 2nd overtone C-H strong (carbohydrates, lipids) |
| 2100 | O-H strong, O-H def. (alcohols, polyphenols) combinations |
| 2150 | Amide I, amide III (proteins) combinations |
| 2300 | N-H strong, CO strong (proteins) combinations |

FIG. 58

Metabolites molecular formula and chemical structure 5900
Albumin MF 5912
($C_{123}H_{193}N_{35}O_{37}$)
Bilirubin MF 5914
($C_{33}H_{36}N_4O$)
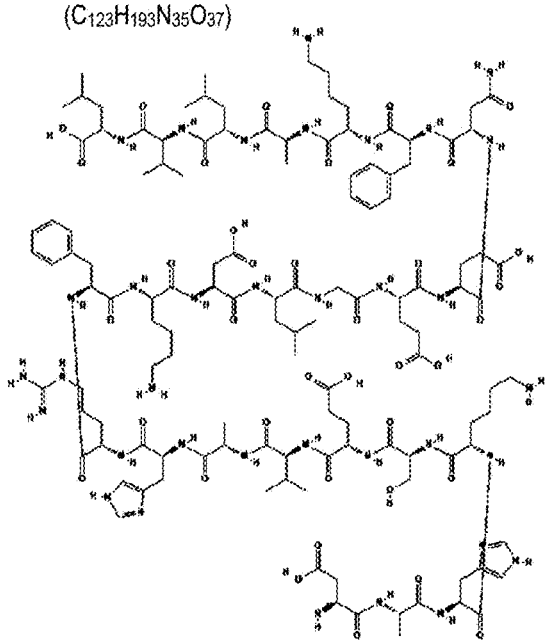
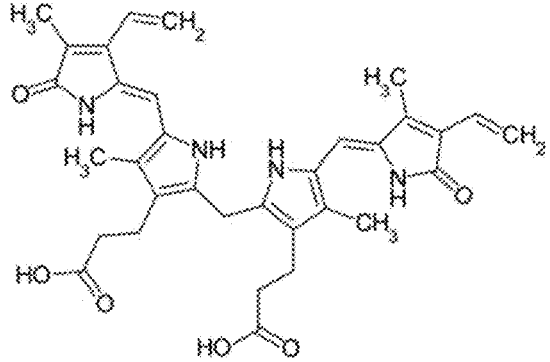
Blood Glucose MF 5916
($C_6H_{12}O_6$)
Blood Alcohol MF 5918
($C_2H_5OH$)
Blood Urea Nitrogen MF 5920
($CO(NH_2)_2$)
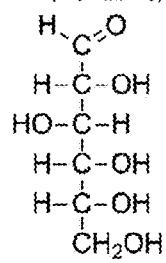
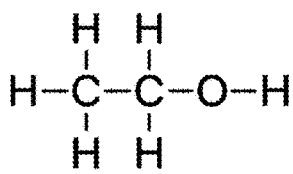
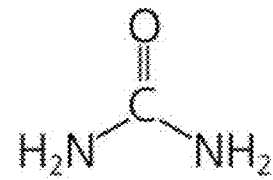
Cortisol MF 5922
($C_{21}H_{30}O_5$)
Creatinine MF 5924
($C_4H_7N_3O$)
Electrolyte MF 5926
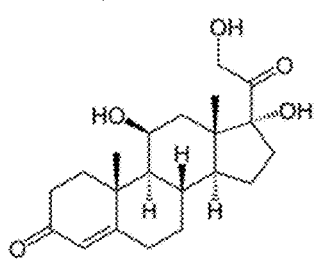
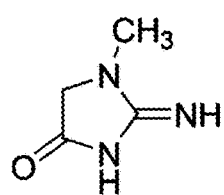
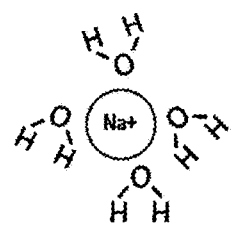
FIG. 59

Metabolites and lipids molecular formula and chemical structure 6000
ALP MF 6012
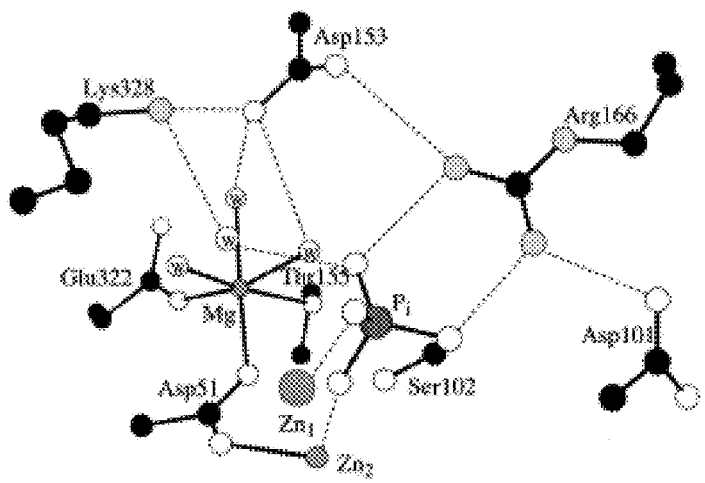
ALT MF 6014
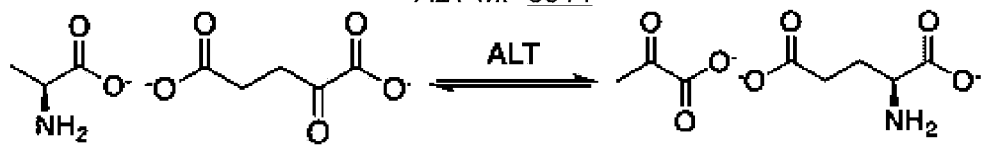
AST MF 6016
Cholesterol MF 6018
($C_{27}H_{46}O$)
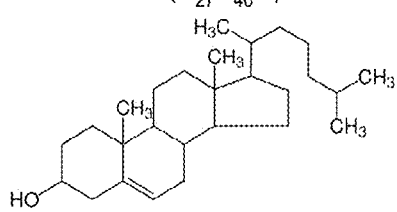
Cholesteryl ester MF 6020
($C_{44}H_{78}O_2$)
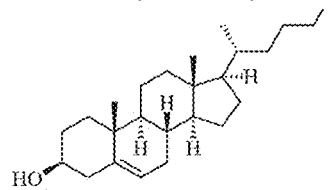
Phospholipids MF 6022
($CH_2OH-CHOH-CH_2OH$)
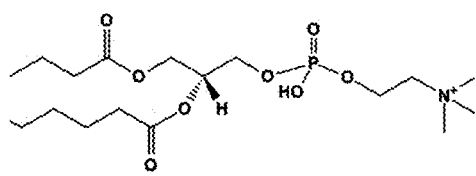
Triglycerides MF 6024
($C_{55}H_{98}O_6$)
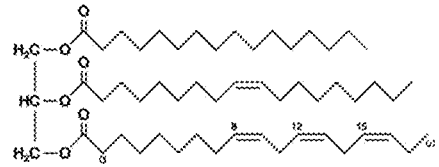
FIG. 60

BML sensor diffuse reflectance spectroscopy working principle diagram 6110
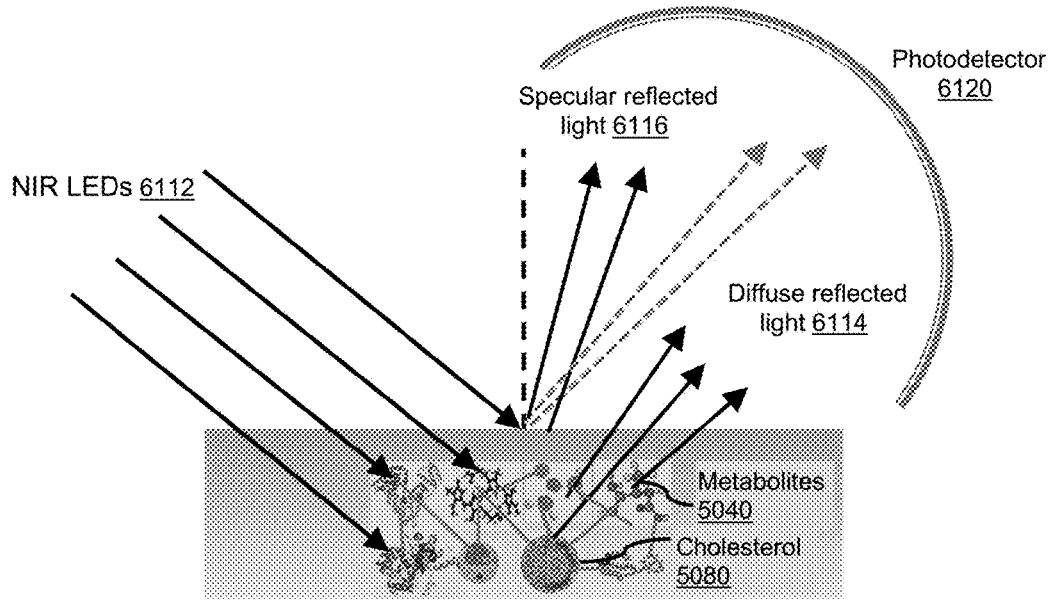
BML sensor NIR diffuse reflectance spectroscopy operating principle diagram 6150
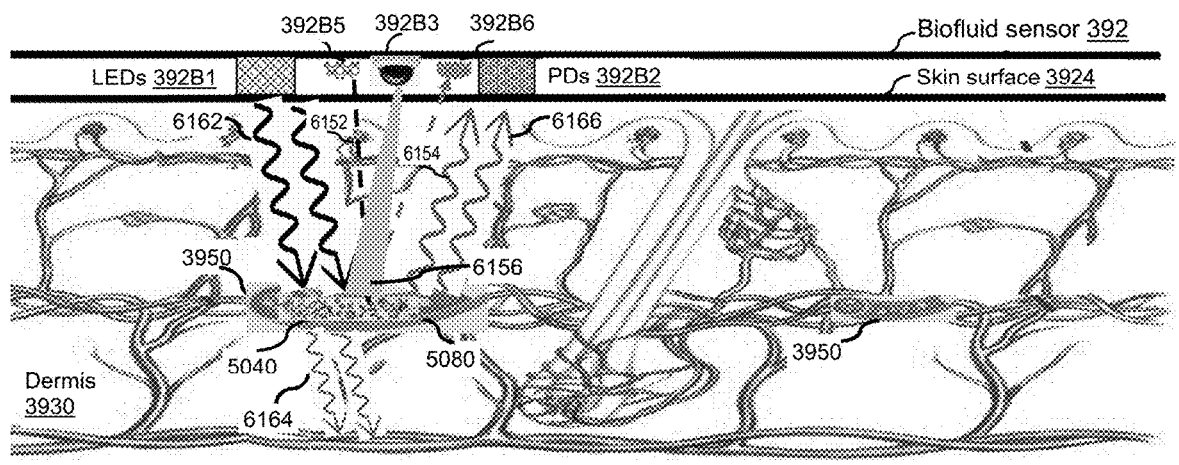
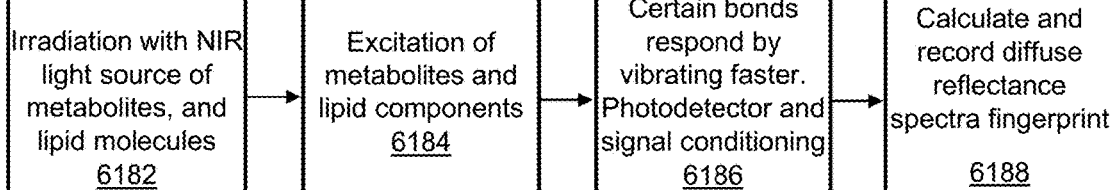
FIG. 61

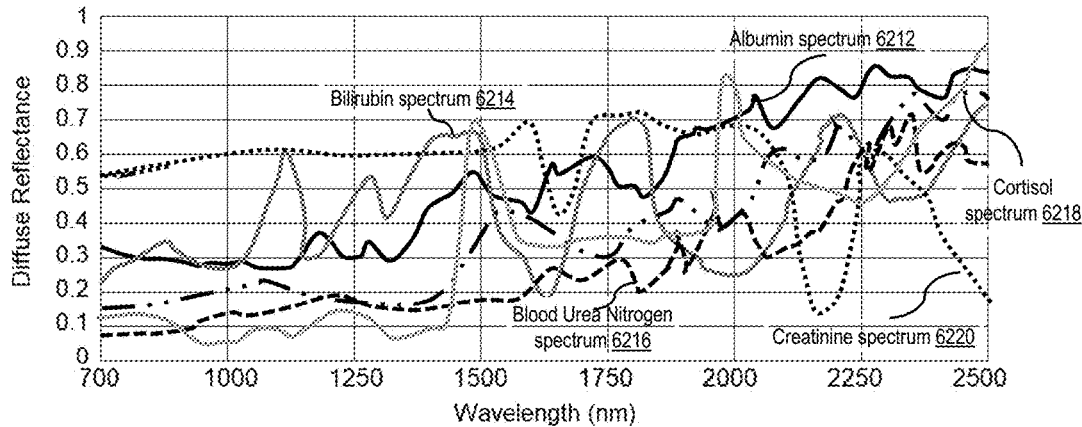

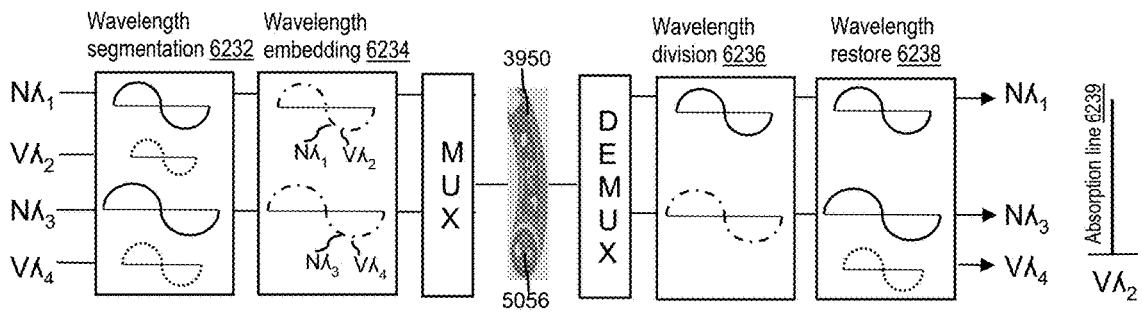

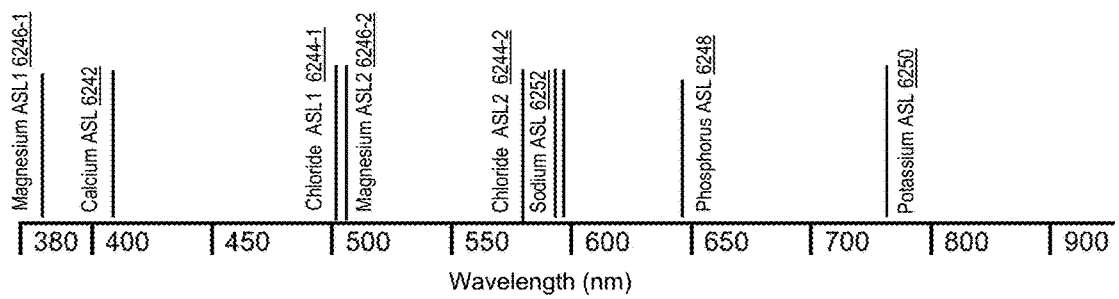

| Calcium (Ca+2) | Wavelength of 422.7 nm |
|---|---|
| Chloride (Cl-) | Wavelength range 509-570 nm |
| Magnesium (Mg2-) | Lines are found at wavelength of 383.8 and 518.4 nm. The most prominent line in the spectrum at wavelength of 285.2nm. |
| Phosphorus (P) | Wavelength of 645.9 nm |
| Potassium (K+) | Wavelength of 766.5 nm |
| Sodium (Na+) | The sodium spectrum is dominated by the bright doublet known as the Sodium D-lines at 588.99 and 589.59 nanometer |
| Zinc1,Zinc2 | Wavelength of 481, 589 |

FIG. 62

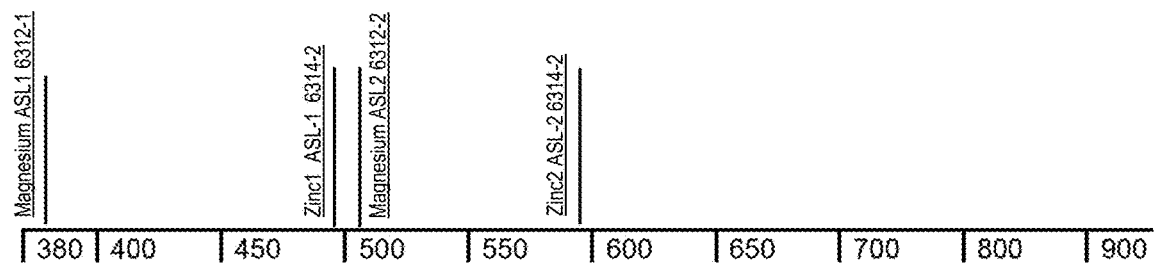
ALP ZnMg surrogate absorption line spectrum 6310
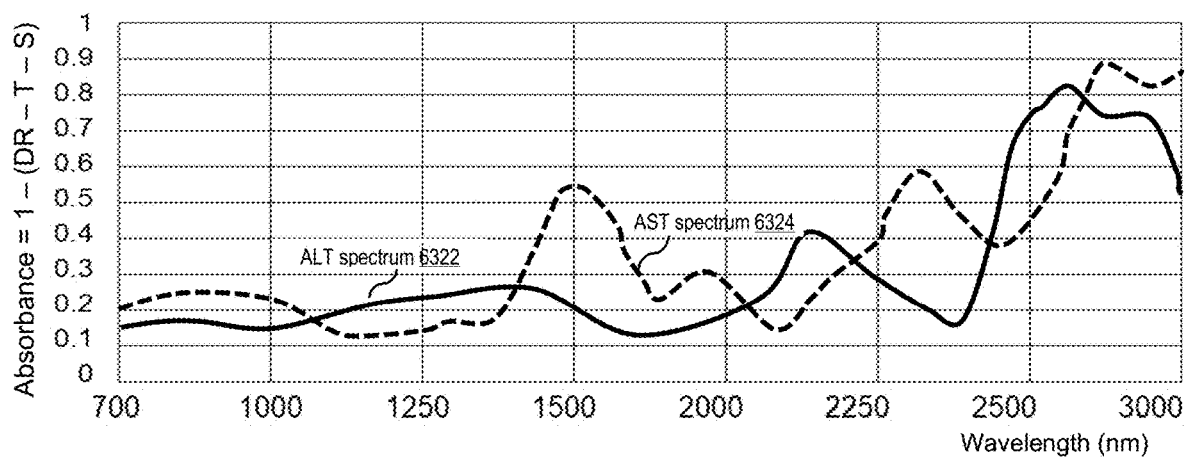
ALT NH2 and AST NH3 surrogate diffuse reflectance spectra 6320
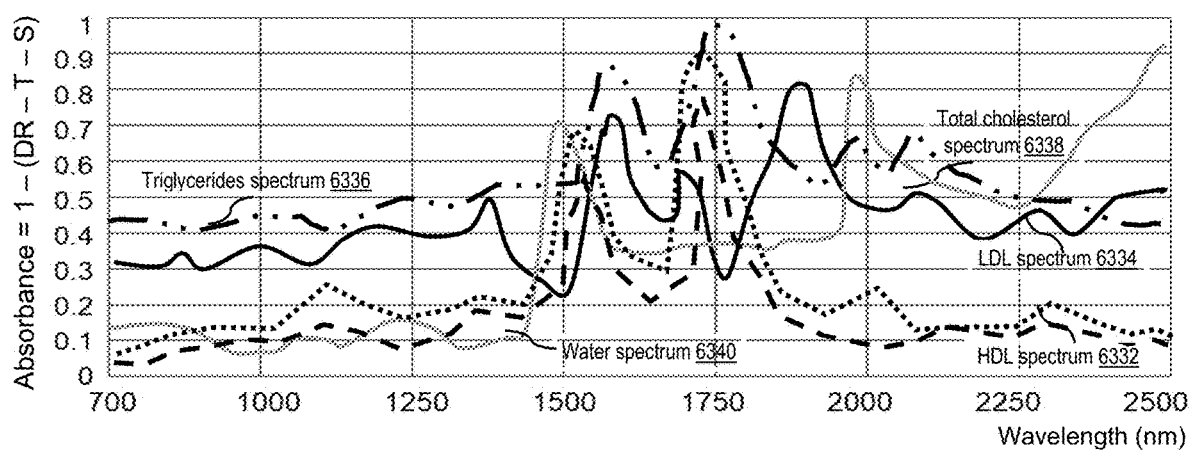
Lipids diffuse reflectance spectra 6330
FIG. 63

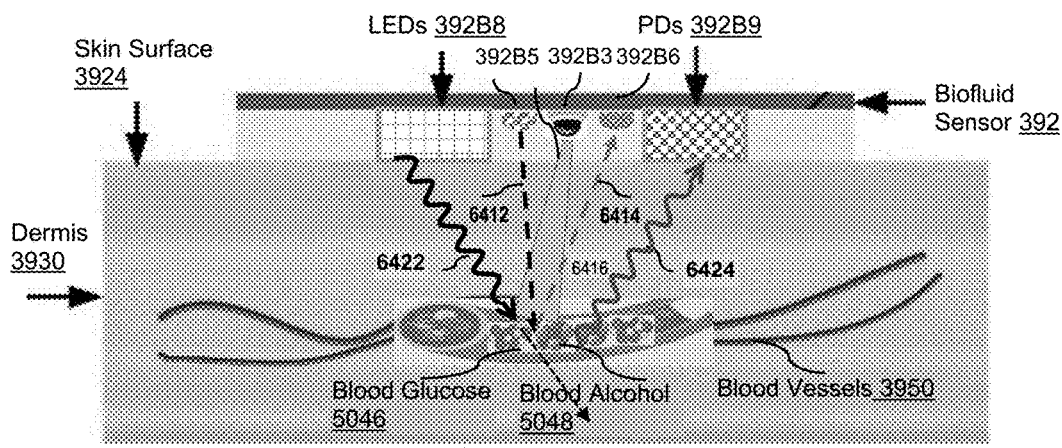
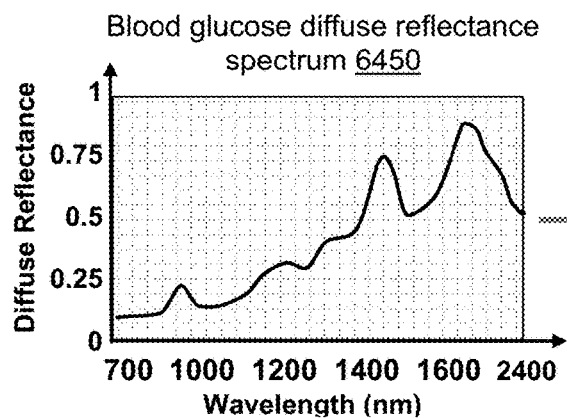
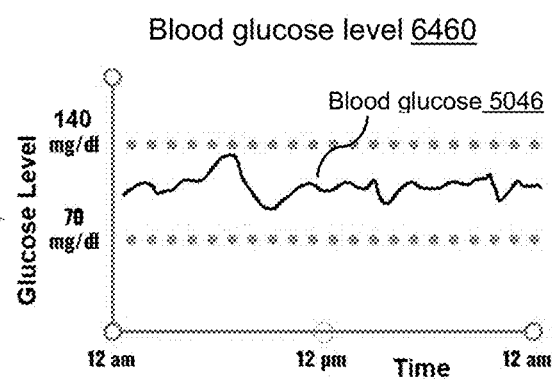
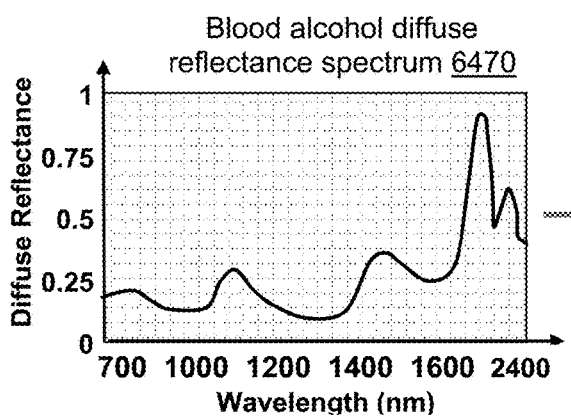
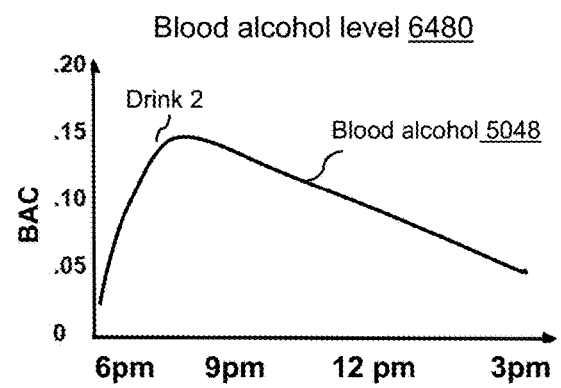
FIG. 64

Biokinetics sensor pinout 6510

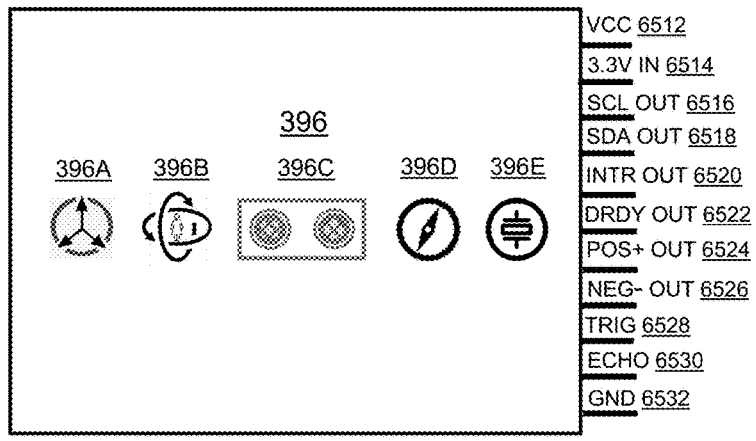

| Biokinetics sensor pinout | Biokinetics sensor pin function | Steps to wire biokinetics sensor pin to the SBC GPIO pin |
|---|---|---|
| VCC 6512 | VCC 6512 pin is used as positive power supply. | Connect biokinetics sensor VCC 6512 pin to the assigned SBC GPIO pinout 370 5V power pin. |
| 3.3V IN 6514 | 3.3V IN 6514 pin is used as input pin for logic supply voltage. | Connect biokinetics sensor 3.3V IN 6514 pin to the assigned SBC GPIO pinout 370 pin. Used to select between 3.3V and VCC 5V as the logic supply voltage. |
| SCL OUT 6516 | SCL OUT 6516 pin is for I2C bus interface Serial Clock Terminal. | Connect biokinetics sensor SCL OUT 6516 pin to the assigned SBM GPIO pinout 370 SCL pin. |
| SDA OUT 6518 | SDA OUT 6518 pin is for I2C bus interface Serial Data Terminal. | Connect biokinetics sensor SDA OUT 6518 pin to the assigned SBM GPIO pinout 370 SDA pin. |
| INTR OUT 6520 | INTR OUT 6520 pin is used as output pin for interrupts. | Connect biokinetics sensor INTR OUT 6520 pin to the assigned SBC GPIO pinout 370 pin. |
| DRDY OUT 6522 | DRDY OUT 6522 pin is used as output pin for digital x, y, z magnetometer. | Connect biokinetics sensor DRDY OUT 6522 pin to the assigned SBC GPIO pinout 370 pin. |
| POS+ OUT 6524 | POS+ OUT 6524 pin is used as output pin for piezoelectric positive pressure. | Connect biokinetics sensor POS+ OUT 6524 pin to the assigned SBC GPIO pinout 370 pin. |
| NEG- OUT 6526 | NEG- OUT 6526 pin is used as output pin for piezoelectric negative pressure. | Connect biokinetics sensor NEG- OUT 6526 pin to the assigned SBC GPIO pinout 370 TRIG pin. |
| TRIG 6528 | TRIG 6528 pin is used to trigger the signal pulses such as ultrasonic sound or infrared light. | Connect biokinetics sensor TRIG 6528 pin to the assigned SBM GPIO pinout 370 output pin. |
| ECHO 6530 | ECHO 6530 pin produces a pulse when the reflected signal is received. | Connect biokinetics sensor ECHO 6530 pin to the assigned SBM GPIO pinout 370 input pin. |
| GND 6532 | GND 6532 pin is used as negative power ground. | Connect biokinetics sensor GND 6532 pin to the assigned SBC GPIO pinout 370 GND pin. |

FIG. 65

Human musculoskeletal system diagram 6610
Woman muscles 6612
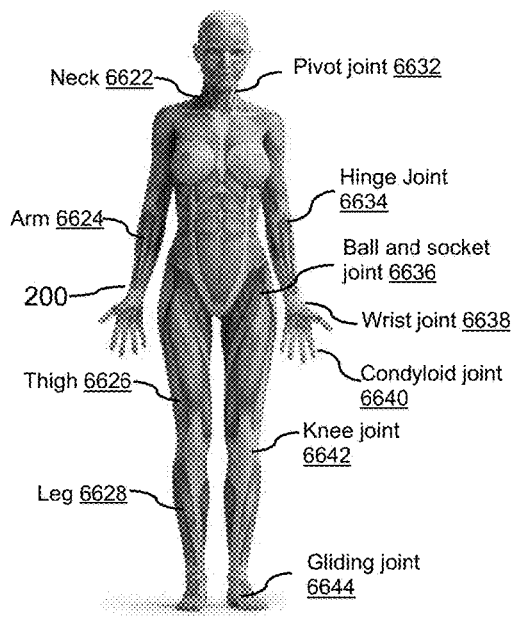
Man muscles 6614
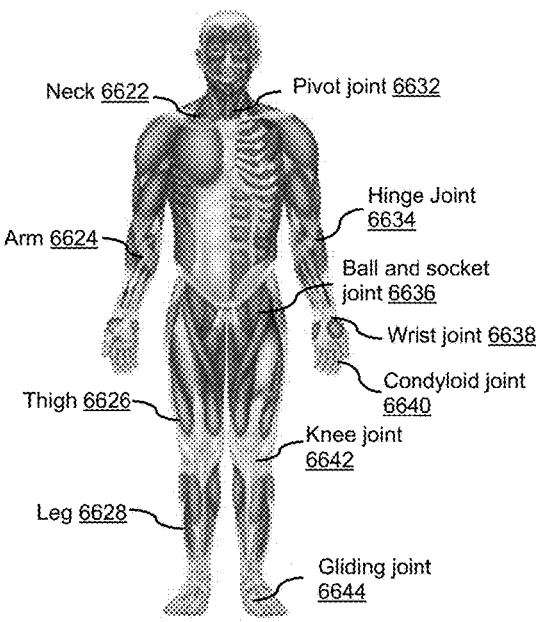
Biokinetics position diagram 6660
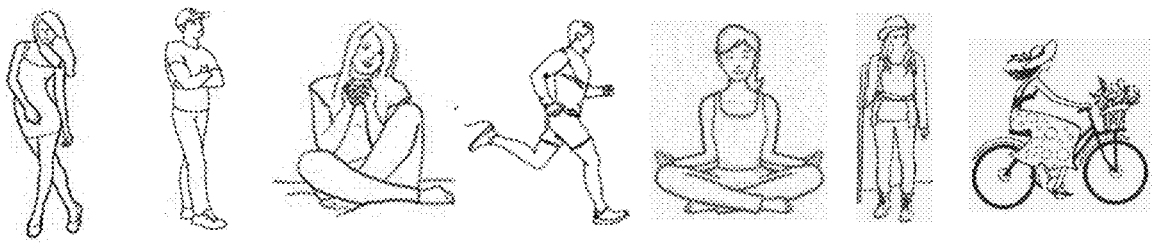
Walking 6662  Standing 6664  Sitting 6666  Running 6668  Yoga 6670  Hiking 6672  Cycling 6674
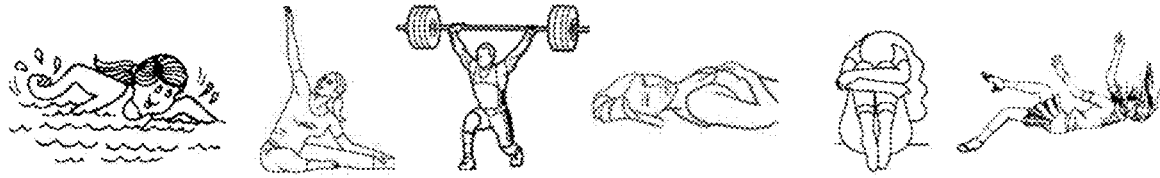
Swimming 6676  Movement 6678  Exercise 6680  Sleep 6682  Stress 6684  Fall 6686
FIG. 66

Biokinetics parameters, detection sensor, detected normal reference ranges 6700

| No | Biokinetics Parameter | Human Anatomy | Detection Sensor | Normal Reference Ranges |
|---|---|---|---|---|
| 1 | Walking 6662 | Whole body movement | Accelerometer, gyroscope, magnetometer, piezoelectric (AGMP) sensors | 30—60 minutes<br>6—11 years: 6,000—15,000 steps<br>12—18 years: 6,000—14,000 steps<br>19—65 years: 3,000—12,000 steps<br>65+ years: 3,000—11,000 steps<br>Around 8 km or 5 miles |
| 2 | Standing 6664 | Legs and back | AGMP sensors | 2—4 hours (intermittent) |
| 3 | Sitting 6666 | Lower body muscles | AGMP sensors | 4—5 hours (intermittent) |
| 4 | Running 6668 | Lower body muscles | AGMP sensors | 30—60 minutes |
| 5 | Yoga 6670 | Whole body movement | AGMP sensors | 15—30 minutes |
| 6 | Hiking 6672 | Lower body muscles | AGMP sensors | 30—60 minutes |
| 7 | Cycling 6674 | Lower body muscles | AGMP sensors | 30—60 minutes |
| 8 | Swimming 6676 | Whole body movement | AGMP sensors | 15—30 minutes |
| 9 | Movement 6678 | Whole body movement | AGMP sensors | ≥ 120 minutes of activity |
| 10 | Exercise 6680 | Whole body movement | AGMP sensors | 75—150 minutes vigorous-intensity activity |
| 11 | Sleep 6682 | Body at rest | Physiological, and AGMP sensors | 4—12 months: 12—16 hours (+ naps)<br>1—2 years: 11—14 hours (+ naps)<br>3—5 years: 10—13 hours (+ naps)<br>6—12 years: 9—12 hours<br>13—18 years: 8—10 hours<br>18—60 years: 7 or more hours / night |
| 12 | Stress 6684 | All systems of body | Cortisol, physiological sensors & AGMP sensors | 0—4 level |
| 13 | Fall 6686 | Whole body | AGMP sensors | Not Applicable |
| 14 | Proximity to an object 6688 | Hand/Object | Ultrasonic sensor | ≤ 1 foot |

FIG. 67

Biokinetics parameters detection methods 6800

BK accelerometer sensor operating diagram 6810

BK accelerometer sensor 396A
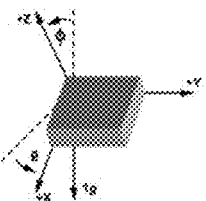
Walking motion 6812

BK gyroscope sensor operating diagram 6830

BK gyroscope sensor 396B
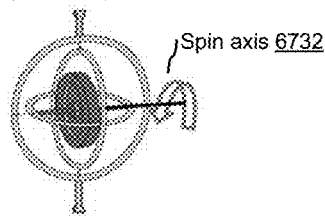
Spin axis 6732
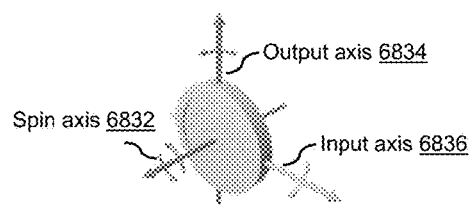
Output axis 6834
Spin axis 6832
Input axis 6836

BK ultrasound sensor operating diagram 6850

BK ultrasound sensor 396E
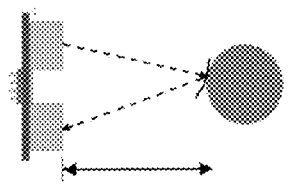
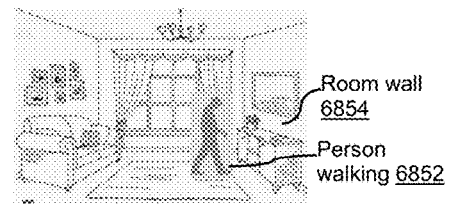
Room wall 6854
Person walking 6852

BK magnetometer sensor operating diagram 6860

BK magnetometer sensor 396C
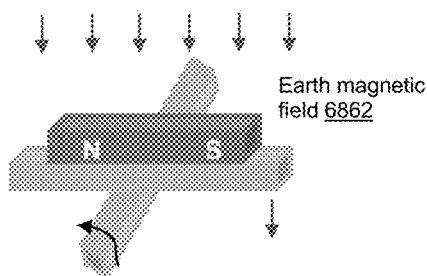
Earth magnetic field 6862
Directions 6864
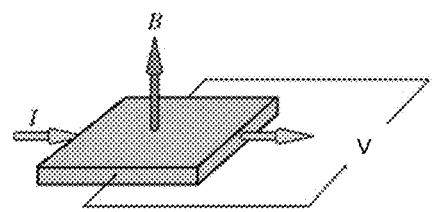

BK piezoelectric sensor operating diagram 6880

BK piezoelectric sensor 396D
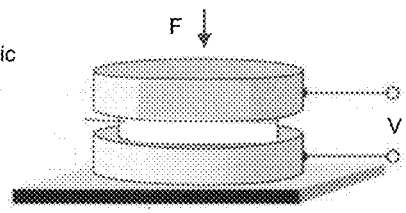
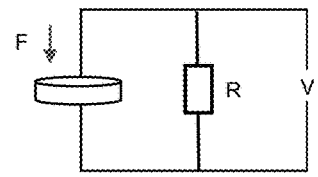

FIG. 68

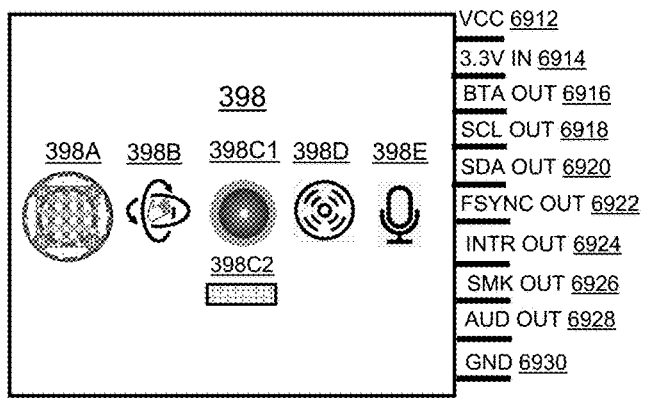

Lifestyle sensor pinout 6910

Lifestyle sensor wiring table 6950

| Lifestyle sensor pinout | Lifestyle sensor pin function | Steps to wire lifestyle sensor pin to the SBC GPIO pin |
|---|---|---|
| VCC 6912 | VCC 6912 pin is used as positive power supply. | Connect lifestyle sensor VCC 6912 pin to the assigned SBC GPIO pinout 370 5V power pin. |
| 3.3V IN 6914 | 3.3V IN 6914 pin is used as input pin for logic supply voltage. | Connect lifestyle sensor ACC OUT 6914 pin to the assigned SBC GPIO pinout 370 pin. Used to select between 3V and VCC 5V as the logic supply voltage. |
| BTA OUT 6916 | BTA OUT 6916 pin is used as output pin for breath analyzer signal. | Connect lifestyle sensor BTA OUT 6916 pin to the assigned SBC GPIO pinout 370 pin. |
| SCL OUT 6918 | SCL 6918 pin is for I2C bus interface Serial Clock Terminal. | Connect lifestyle sensor SCL 6918 pin to the assigned SBM GPIO pinout 370 SCL pin. |
| SDA OUT 6920 | SDA 6920 pin is for I2C bus interface Serial Data Terminal. | Connect lifestyle sensor SDA 6920 pin to the assigned SBM GPIO pinout 370 SDA pin. |
| FSYNC OUT 6922 | FSYNC OUT 6922 pin is used in a camera's image stabilization system. | Connect lifestyle sensor FSYNC OUT 6922 pin to the assigned SBC GPIO pinout 370 pin. |
| INTR OUT 6924 | INTR OUT 6924 pin is used as output pin for interrupts. | Connect lifestyle sensor INTR OUT 6924 pin to the assigned SBC GPIO pinout 370 pin. |
| SMK OUT 6926 | SMK OUT 6926 pin is used as output pin for digital smoke signal. | Connect lifestyle sensor SMK OUT 6926 pin to the assigned SBC GPIO pinout 370 pin. |
| AUD OUT 6928 | AUD OUT 6928 pin is used as output pin for digital audio out (noise). | Connect lifestyle sensor AUD OUT 6928 pin to the assigned SBC GPIO pinout 370 pin. |
| GND 6930 | GND 6930 pin is used as negative power ground. | Connect lifestyle sensor GND 6930 pin to the assigned SBC GPIO pinout 370 GND pin. |
| Camera CSI port 398C2 | Camera CSI port 398C2 is used as an electrical bus. | Connect camera CSI port 398C2 to the SBC Camera CSI port 368. |

FIG. 69

Lifestyle parameters, detection sensor, and detected normal reference ranges 7000

| No | Lifestyle Parameter | Human Anatomy | Detection Sensor | Reference Ranges |
|---|---|---|---|---|
| 1 | Alcohol 7012 (C2H5OH) | Blood pressure | Chemiresistor | Positive/Negative. Cut-Off (0.0—0.25%) |
| 2 | Amphetamine 7014 (C9H13N) | Talkative, excited | Chemiresistor | Positive/Negative. Cut-Off (500 ng/mL) |
| 3 | Benzoylecgonine 7016 (C16H19NO4) | Neurovascular | Chemiresistor | Positive/Negative. Cut-Off (200 ng/mL) |
| 4 | Cocaine 7018 (C17H21NO) | Neurovascular | Chemiresistor | Positive/Negative. Cut-Off (300 ng/mL) |
| 5 | Heroin (6-acetylmorphine) 7020 (C19H21NO4) | Whole body | Chemiresistor | Positive/Negative. Cut-Off (10 ng/mL) |
| 6 | Marijuana (Tetrahydrocannabinol) 7022 (C21H30O2) | Mind and body | Chemiresistor | Positive/Negative. Cut-Off (50 ng/mL) |
| 7 | Methamphetamine 7024 (C10H15N) | Whole body | Chemiresistor | Positive/Negative. Cut-Off (500 ng/mL) |
| 8 | Morphine 7026 ($C_{17}H_{19}NO_3$) | Nervous system | Chemiresistor | Positive/Negative. Cut-Off (300 ng/mL) |
| 9 | Number of meals 7050 | Whole body | Picocamera and Accelerometer | 3 balanced meals (350 to 600 calories each) 1 to 3 snacks per day (between 150 & 200 calories) |
| 10 | Set of food types 7052 | Whole body | Picocamera | Breakfast, lunch, dinner |
| 11 | Number of drinks 7054 | Whole body | Picocamera and Accelerometer | As needed |
| 12 | Set of drink types 7056 | Whole body | Picocamera | Recommendation ~ 15.5 cups (3.7 liters) of fluids a day for men. ~ 11.5 cups (2.7 liters) of fluids a day for women Covers fluids from water, other beverages, and food. About 20% of daily fluid intake usually comes from food and the rest from drinks |
| 13 | Number of bathroom visits 7058 | Reproductive organs | Microphone and Accelerometer | Urinate: 6—7 in a 24-hour period Poop: 3 times a day to 3 times a week |
| 14 | Number of smoking occurrences 7060 | Lung and body | Smoke sensor | 0 |
| 15 | Number of occupational interactions 7062 | Whole body | Microphone | 5—8 hours / day 5 days a week |
| 16 | Number of financial interactions 7064 | Nervous system | Microphone | 3—5 |
| 17 | Number of intellectual interactions 7066 | Nervous system | Microphone | 3—5 |
| 18 | Number of emotional Interactions 7068 | Nervous system | Microphone | 3—5 hours/day |
| 19 | Number of social interactions 7070 | Nervous system | Microphone | 1—2 hours/day |
| 20 | Number of spiritual interactions 7072 | Nervous system | Microphone | 1—2 hours/day |

FIG. 70

Breath analyzer sensor working principle 7110
Breath analyzer sensor 398A
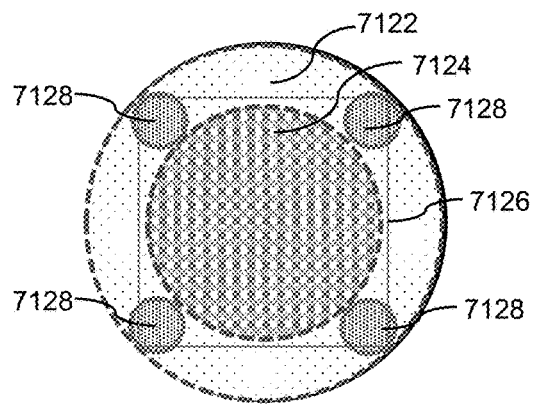
Chemiresistor sensor working principle 7130
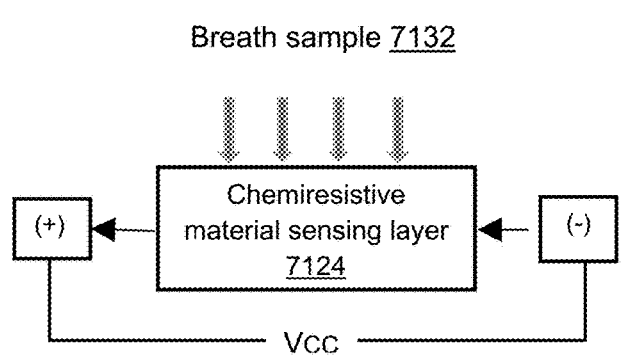
Breath analyzer sensor test method 7150
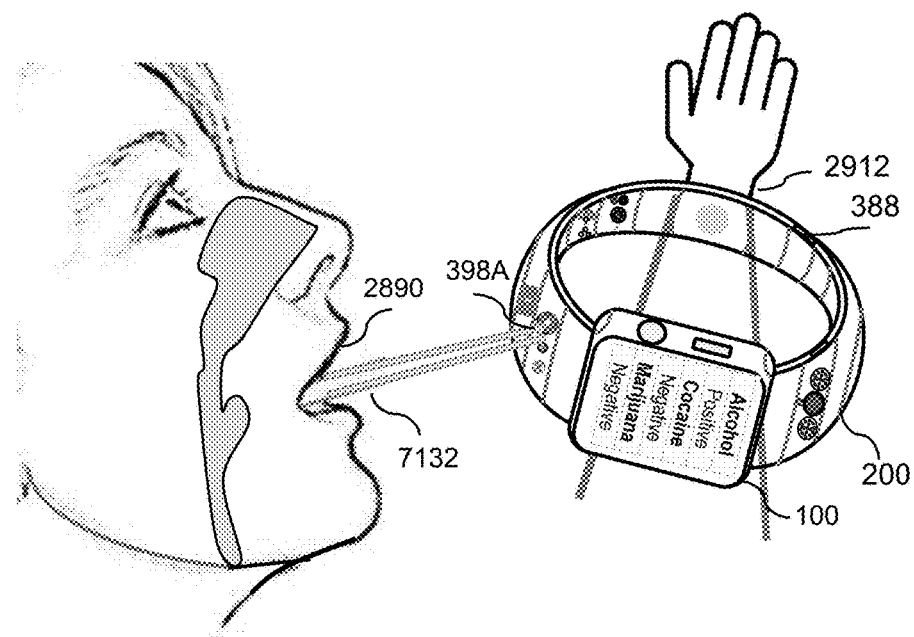
FIG. 71

Lifestyle parameters detection methods 7200
LS gyroscope operating diagram 7210
Grabbing 7212　　Holding 7214　　Twist 7216　　Roll 7218　　Eating 7220
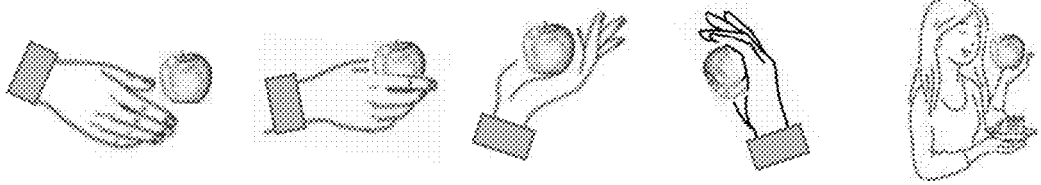
LS camera operating diagram 7230
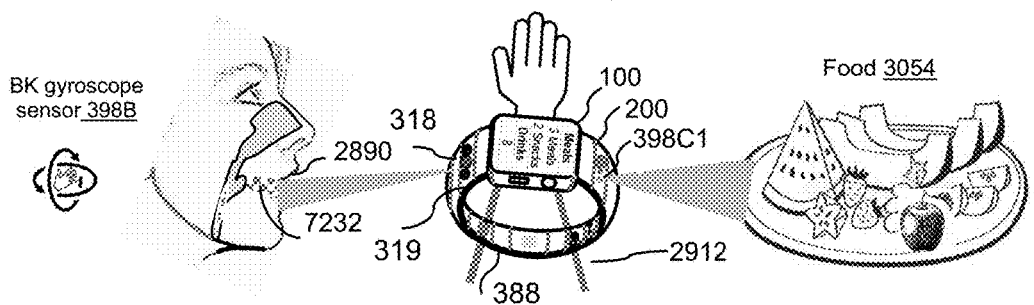
LS smoke sensor operating diagram 7240
Smoke sensing element schematic circuit 7242　　Man smoking 7244
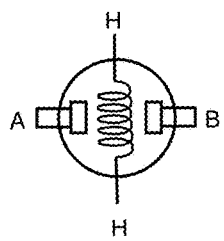 
LS sound sensor operating diagram 7260
Sound sensor unit 7262　　Sound waves 7264　　Interactions 7266　　Noise pollution 7268
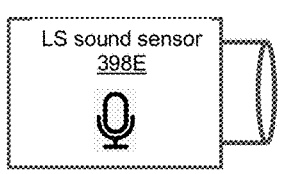   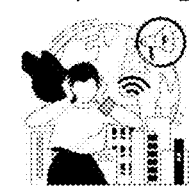
FIG. 72

Human wellness dimensions wheel 7310

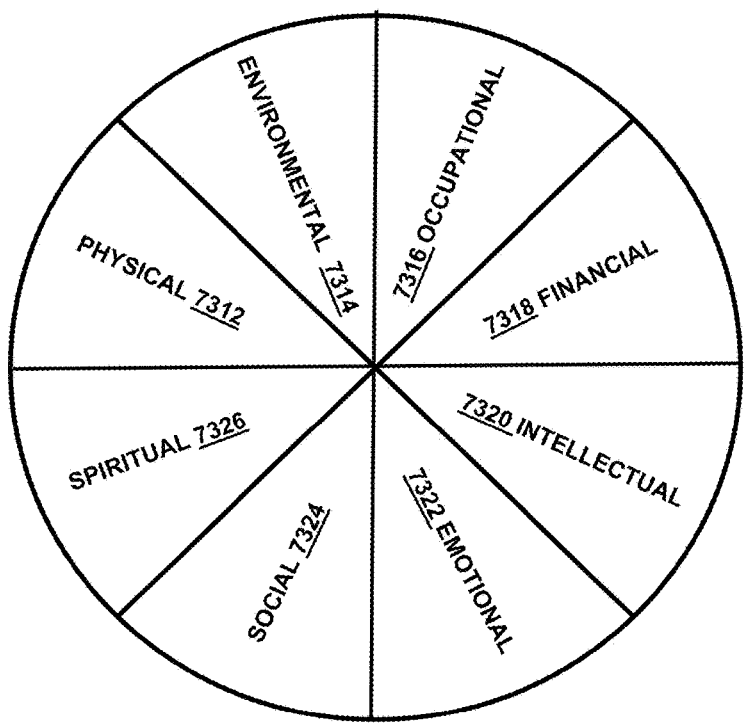

Human wellness dimensions description 7350

| No | Wellness dimension | Description |
|---|---|---|
| 1 | Physical | Physical wellness is the process of having a flexible, and aerobically fit body. |
| 2 | Environmental | Environmental wellness is the process of making choices to create sustainable human and ecological communities, improving qualities in air, water, land, and space. |
| 3 | Occupational | Occupational wellness is the process of making and maintaining choices that are meaningful and contributes to personal growth as well as work. |
| 4 | Financial | Financial wellness is the process of managing your resources to live within one's means, making informed financial decisions and investments, setting realistic goals, and preparing for short-term and long-term needs or emergencies. |
| 5 | Intellectual | Intellectual wellness is the process of using the mind to create a greater understanding of oneself and the universe. |
| 6 | Emotional | Emotional wellness is the process of creating and maintaining a positive realistic self-concept and enthusiasm about life. |
| 7 | Social | Social wellness is the process of creating and maintaining healthy relationships. |
| 8 | Spiritual | Spiritual wellness is the process of "experiencing life" while seeking meaning and purpose in human existence. Spirituality allows one to have consistency between values and behaviors. |

FIG. 73

Human wellness dimensions database 7410

| No | Data |
|---|---|
| 1 | User defined input forms containing quiz, test, questions, and worksheets. The input form is presented to the user and a score is calculated for each user quiz wellness dimension |
| 2 | The user quiz wellness dimension score is recalculated using wearable device sensor data. |
| 3 | The wellness dimension score is further refined using wellness dimension specific databases such as Nutrition.gov, NIH Dietary Supplement Fact Sheets, NIH Nutrient Databases, FoodData Central, Health.gov, CDC, meeting invite planners, credit card company ratings, and so on. |
| 4 | Annotation – Data specific annotation is based on wellness dimension ranking to improve score and quality of life. |

Human wellness dimensions reference ranges 7420

| Wellness Dimension Ranking | Definition | Description |
|---|---|---|
| 5 | Excellent | Fully content |
| 4 | Very Good | Very satisfied |
| 3 | Good | Satisfied |
| 2 | Fair | Less than adequate |
| 1 | Poor | Needs immediate improvement |

Human wellness dimensions detection methods 7450

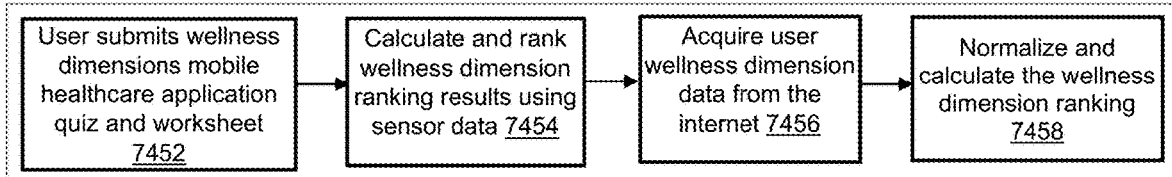

Example personalized wellness programs 7490

| No | Wellness dimension | Example personalized wellness programs |
|---|---|---|
| 1 | Physical | Programs to bring out of range microbial biosensor, physiological, biofluids, biokinetics sensor parameters result value to normal reference range. e.g., treatments, healthy eating, active lifestyle, dietary supplements, act on quiz response and so on |
| 2 | Environmental | Programs to bring out of range particulate matter, and enviro sensor parameters result value to normal reference range. e.g., treatments, reducing exposure to adverse environment etc. |
| 3 | Occupational | Programs to bring out of range particulate matter, enviro sensor, biokinetics, lifestyle sensor parameters value to normal reference range. e.g., ergonomic, personal growth etc. |
| 4 | Financial | Programs to bring out of range lifestyle sensor parameters result value to normal reference range. e.g., financial interactions and goals, act on quiz response etc. |
| 5 | Intellectual | Programs to bring out of range lifestyle sensor parameters result value to normal reference range. e.g., intellectual interactions, act on quiz response etc. |
| 6 | Emotional | Programs to bring out of range biofluids, and lifestyle sensor parameters result value to normal reference range. e.g., emotional interactions and goals, act on quiz response etc. |
| 7 | Social | Programs to bring out of range lifestyle sensor parameters result value to normal reference range. e.g., social interactions and goals, act on quiz response etc. |
| 8 | Spiritual | Programs to bring out of range lifestyle sensor parameters result value to normal reference range. e.g., spiritual interactions and goals, act on quiz response etc. |

FIG. 74

Clinical laboratory test discipline and test methods list 1 7700

| Discipline | Subdiscipline | Clinical laboratory test methods description |
|---|---|---|
| Anatomic Pathology | <ul><li>Anatomic Pathology</li><li>Processing</li><li>Autopsy Pathology</li><li>Circulating Tumor Cell Analysis</li><li>Digital Image Analysis</li><li>Electron Microscopy</li><li>Flow Cytometry Data Interpretation</li></ul> | <ul><li>Histology</li><li>Immunochemistry and immunofluorescence microscopy</li><li>In situ hybridization (ISH)</li><li>Predictive marker testing</li><li>Digital image analysis</li><li>Flow cytometry data interpretation</li><li>Circulating tumor cell analysis</li><li>Autopsy pathology</li><li>Forensic pathology</li><li>Electron microscopy</li><li>In vivo and ex vivo microscopy</li></ul> |
| Chemistry and Toxicology | <ul><li>Blood Gases</li><li>Chemistry</li><li>Special Chemistry</li><li>Toxicology</li></ul> | <ul><li>Automated chemistry procedures</li><li>Blood gas analysis</li><li>Therapeutic drug monitoring</li><li>Toxicology screening and confirmatory testing</li><li>Prenatal screening</li><li>Cystic fibrosis sweat testing</li><li>Tumor marker, immune system, and infectious disease immunoassays</li><li>Hemoglobin separation</li><li>Methods, such as thin layer chromatography (TLC), gas chromatography (GC), high performance liquid chromatography (HPLC), mass spectrometry (MS), imaging MS, atomic absorption, radioimmunoassay (RIA), and electrophoresis</li></ul> |
| Clinical Biochemical Genetics | <ul><li>Biochemical Genetics</li><li>Newborn Screening</li></ul> | <ul><li>Methods, such as enzyme assays, TLC, GC, HPLC, MS, electrophoresis.</li><li>Newborn screening</li></ul> |
| Cytogenetics | <ul><li>Conventional Cytogenetics</li><li>Genomic Copy Number</li><li>Microarray</li><li>In Situ Hybridization</li></ul> | <ul><li>Cytogenetic studies for constitutional and neoplastic disorders</li><li>ISH for constitutional and neoplastic disorders, including predictive marker testing</li><li>Digital image analysis</li><li>Genomic copy number analysis using arrays</li></ul> |
| Forensic Drug Testing | <ul><li>Drug Testing – Hair, Meconium, Nails, Oral Fluid, Umbilical Cord, Urine, Urine Screen Only, Whole Blood</li></ul> | <ul><li>Screening and confirmatory testing for different specimen types (urine, blood, oral fluid, hair, meconium, umbilical cord, and nails) using methods, such as immunoassays, LC, GC, and MS</li></ul> |
| Hematology and Coagulation | <ul><li>Body Fluid Analysis</li><li>Coagulation</li><li>Hematology</li></ul> | <ul><li>CBC and differentials, automated and manual</li><li>Reticulocytes, automated and manual</li><li>Bone marrow preparations</li><li>Abnormal hemoglobin detection</li><li>Blood film examination for microorganisms</li><li>Semen analysis, automated and manual</li><li>Routine coagulation assays</li></ul> |

FIG. 77

Clinical laboratory test discipline and test methods list 2 7800

| Discipline | Subdiscipline | Clinical laboratory test methods description |
|---|---|---|
| Immunology | • Immunology | • General immunology assays, manual and automated<br>• Immune system profiles<br>• Tumor marker and infectious disease immunoassays<br>• Microbial antigen testing<br>• Waived molecular-based microbiology tests<br>• ABO/Rh and antibody screening (non-transfusion related)<br>• Syphilis serology<br>• HIV primary diagnostic testing<br>• Western blot |
| Microbiology | • Bacteriology<br>• Molecular Microbiology<br>• Mycobacteriology<br>• Mycology<br>• Parasitology<br>• Virology | • Culture setup, staining, antigen typing, screening, identification, and susceptibility testing for bacteriology, mycology, mycobacteriology, and virology<br>• Parasitology, including stool for ova and parasites and blood films for microorganisms<br>• Molecular microbiology, including waived and non-waived FDA-cleared/approved methods, modified methods, and laboratory-developed methods<br>• Microbial identification, using methods such as MALDI-TOF MS, GC, HPLC, ISH, target and signal amplification, and sequencing |
| Molecular Pathology | • Inherited Genetics<br>• Molecular Oncology – Hematologic Diseases<br>• Molecular Oncology – Solid Tumor<br>• Molecular Pathology | • Clinical molecular genetics testing, including oncology, inherited disease, pharmacogenomics, HLA, forensic identity, and relationship testing applications<br>• Molecular assay validation<br>• ISH for constitutional and neoplastic disorders, including predictive marker testing<br>• Methods, such as electrophoresis, polymerase chain reaction (PCR), arrays, digital image analysis, and sequencing<br>• Next-generation sequencing, including non-invasive screening of maternal plasma to detect fetal trisomy<br>• Hematopoietic progenitor cell engraftment monitoring |
| Point-of-Care Testing (POC) | • POCT – Provider-Performed Microscopy and Limited | • Tests performed at or near the patient bedside<br>• Kit tests or hand-carried instruments<br>• Blood gas analysis<br>• D-dimer studies<br>• HIV primary diagnostic testing<br>• • Provider-performed microscopy |
| Urinalysis | Urinalysis | • Urinalysis dipstick, automated and manual methods<br>• Manual urine microscopy<br>• Automated microscopy systems |

FIG. 78

Commonly ordered clinical laboratory tests 7900

| Human anatomy | Sample type | Commonly ordered clinical laboratory tests |
|---|---|---|
| Complete Blood Test (Hematology) | Blood | Red Blood Cell Count, Hemoglobin Level, Hematocrit Level, Mean Corpuscular Volume (MCV), Mean Corpuscular Hemoglobin (MCH), Mean Corpuscular Hemoglobin Concentration (MCHC), White Blood Cell Count, White Cell Count Differential, and Platelet Count |
| Complete Metabolic Panel | Blood | Albumin, Bilirubin, Blood Glucose Level, Blood Alcohol Concentration Level, Blood Urea Nitrogen (BUN), Creatinine, Cortisol, Calcium, Chloride, Magnesium, Phosphorus, Potassium, Sodium, Total Bilirubin, Total Protein, Alanine Aminotransferase (ALT), Alkaline Phosphatase (ALP), and Aspartate Aminotransferase (AST) |
| Cholesterol Test (Cardiovascular System) | Blood | HDL Cholesterol, LDL Cholesterol, Total Cholesterol, Triglycerides, Troponins I and T |
| Drugs and Toxins | Blood, Urine, Saliva, and Hair | Amphetamine, Benzoylecgonine, Cocaine, Heroin (6-Acetylmorphine), Marijuana (Tetrahydrocannabinol), Methamphetamine, and Morphine Oxycodone – Oxycodone, Oxymorphone, Hydrocodon. |
| Endocrinology System | Blood | Hypothalamus, Pituitary, Thyroid, Parathyroid, Adrenal, Ovaries (females only), Testicles (males only), Endocrine Pancreas |
| Gastroenterology | Stool | Celiac, Irritable Bowel Syndrome (IBS), Lactose Intolerance, Gastrointestinal Pathogens |
| Oncology | Blood Tissue | Blood and solid tumor cancer test, liquid biopsy cancer tests for lung, breast, prostate, pancreas, colorectal, kidney etc. |
| Immunology | Blood | Immune system profiles tests<br>Tumor marker and infectious disease immunoassays, food and inhalant allergy tests<br>Microbial antigen testing |
| Musculoskeletal System | Blood Imaging | ANA, ENA, Rheumatoid arthritis, HLA-B27, X-rays, Arthrography, Bone Scanning, computed tomography (CT) and magnetic resonance imaging (MRI), nerve and muscle tests |
| Nephrology/ Kidney/Renal System | Blood Urine | Glucose, Creatinine, eGFR, Sodium, Potassium, Chloride, Carbon Dioxide, Calcium, Phosphorus, Albumin, Urea Nitrogen |
| Nervous System | CFA | Cerebrospinal fluid analysis – Meningitis, Encephalitis, Multiple Sclerosis, Alzheimer |
| Reproductive System | Male and Female | Prolactin, Semen Analysis, Testosterone, Prostate Specific Antigen (PSA), Progesterone, Estradiol, Estrogen, Bilirubin |
| Respiratory System | Blood Saliva Nasal Swab | Blood gases, Arterial Alveolar Oxygen Ratio<br>SARS-CoV-2, influenza A, influenza B, RSV, human metapneumovirus, human rhinovirus, and adenovirus. Detects and differentiates parainfluenza 1, 2, 3, and 4. |
| Vitamins and Trace Elements | Blood | Vitamin B12, Vitamin D, Vitamin E, Vitamin K, Copper, Iron, Zinc |

FIG. 79

Endocrinology ordered clinical laboratory tests 8000

| Endocrinology system | Human anatomy area | Commonly ordered clinical laboratory tests |
|---|---|---|
| Hypothalamus | Lower middle of the brain; communicates with both nervous and endocrine systems | Growth hormone-releasing hormone (GHRH) |
| | | Thyrotropin-releasing hormone (TRH) |
| | | Corticotropin-releasing hormone (CRH) |
| | | Gonadotropin-releasing hormone (GnRH) |
| | | Prolactin inhibitory hormone (PIH, dopamine) |
| | | Oxytocin; produced by the hypothalamus; stored and secreted by the pituitary |
| | | Arginine vasopressin (AVP), also called antidiuretic hormone (ADH); produced by the hypothalamus; stored and secreted by the pituitary |
| | | Somatostatin |
| Pituitary | Below hypothalamus, behind sinus cavity | Prolactin |
| | | Growth hormone (GH) |
| | | ACTH |
| | | TSH |
| | | LH, FSH |
| Thyroid | Butterfly-shaped; lies flat against windpipe in the throat | T4 (thyroxine), T3 (triiodothyronine) |
| | | Calcitonin |
| Parathyroid | 4 tiny glands located behind, next to, or below the thyroid | Parathyroid hormone (PTH) |
| Adrenal | 2 triangular organs, on top of each kidney | Epinephrine (adrenaline) Norepinephrine (catecholamines) |
| | | Aldosterone |
| | | Cortisol |
| | | DHEA-S |
| Ovaries (females only) | 2, located in the pelvis | Estrogen Progesterone |
| Testicles (males only) | 2, located in the groin | Testosterone |
| Endocrine Pancreas | Large, gourd-shaped gland, located behind the stomach | Insulin Glucagon Somatostatin |
| Pineal | Lower side of the brain | Melatonin |

FIG. 80

Example intelligent relationship interpretation table 1 between sensor parameters, 8100

| Parameter / Analyte | Body temperature 97.0—99.0 °F (Body) | Heart rate 70—100 bpm | Blood pressure Systolic < 120 mmHg Diastolic < 80 mmHg |
|---|---|---|---|
| Blood Glucose Level 70—100 mg/dL | High body temperatures can also cause blood vessels to dilate, which can enhance insulin absorption, potentially leading to low blood sugar. | Hyperinsulinemia and elevated blood glucose levels are both associated with a higher heart rate. | People with systolic blood pressure of equal or greater than 160 mmHg have significantly higher glucose concentrations. |
| RBC Count 3.92—5.13 x 10E6/μL | As the body temperature rises the red blood count decreases due to limiting cellular metabolism, resulting in body's efforts to reduce metabolic heat production. | High heart rates result in increased RBC count. | High blood pressure results in abnormalities in the functional and physicochemical properties of red blood cells (RBCs\). |
| Hemoglobin 13.2—16.6 g/dL | As the body temperature rises the red blood count decreases which results in decrease in amount of hemoglobin and oxygen. | Anemia or low RBC count can lead to a rapid or irregular heartbeat (arrhythmia). | Increase in systolic blood pressure (SBP) and diastolic blood pressure (DBP) may be due to increasing hemoglobin. |
| WBC Count 4.1—11.6 x 10E3/μL | The high body temperature results in higher count of WBC monocytes and lower count of lymphocytes. | High heart rate is associated with elevated WBC count. | Elevated WBC count is associated with incident hypertension or high blood pressure. |
| Platelet Count 135—317 x 10E3/μL | High body temperature or hyperthermia induces platelet apoptosis, thus resulting in lower platelet count in some patients with fever or hyperthermia. | High heart rate results in higher platelet counts. | An elevated platelet aggregation and activation results during hypertension or high blood pressure. |
| Blood Oxygen Saturation 95—100% | Low body temperatures cause blood vessels to narrow which restricts blood flow and reduces oxygen levels.<br><br>Increased body temperature and in turn blood temperature decreases the affinity of oxygen to hemoglobin, resulting in decrease in blood oxygen saturation. | High heart rate results in low blood oxygen saturation. | Low blood oxygen saturation results in high blood pressure. |

FIG. 81

Example intelligent relationship interpretation table 2 between sensor parameters, 8200

| Parameter / Analyte | Body temperature<br>97.0—99.0 °F (Body) | Heart rate<br>70—100 bpm | Blood pressure<br>Systolic < 120 mmHg<br>Diastolic < 80 mmHg |
|---|---|---|---|
| Carbon Dioxide<br><br>20—29 mm/L | Carbon dioxide (CO2) is produced by aerobic metabolism. Fever, and high carbohydrate intake increase carbon dioxide production. | The heart rate goes up with increasing carbon dioxide concentrations. | High carbon dioxide or hypocapnia induced by hyperventilation causes a drop in arterial blood pressure. |
| Calcium<br><br>8.6—11 mg/dL | High body temperature can result in lowered blood calcium level. | Hypercalcemia can affect the electrical impulses that regulate heartbeat, causing heart to beat irregularly. | Calcium intake is inversely associated with blood pressure. |
| Phosphorous<br><br>2.8—4.5 mg/dL | Phosphorus is correlated inversely with increase in body temperature. Increase in body temperature results in lower phosphorous. | Phosphorus is an electrolyte, and changes in electrolyte levels can cause irregular heart rate. | Increased phosphate intake, more specifically an increased serum phosphate level, activates the sympathetic nervous system, which accelerates cardiac activity and increases blood pressure. |
| Potassium<br><br>3.6—5.2 mmol/L | Hypokalemia is common in patients who have fever. Fever-induced hypokalemia may be due to low caloric intake, | Potassium is an electrolyte, and changes in electrolyte levels can cause irregular heart rate. | Dietary potassium Intake results in reduction of blood pressure. |
| Sodium<br><br>135—145 mmol/L | In hypernatremia, the level of sodium in blood is too high. Hypernatremia involves dehydration due to high body temperature and fever. | Sodium is an electrolyte, and changes in electrolyte levels can cause irregular heart rate. | Dietary sodium and salt intake results in reduction of blood pressure.<br><br>Signs of a serious electrolyte imbalance include blood pressure changes, and shortness of breath. A number of things can cause an electrolyte imbalance, including fluid loss from heavy exercise or physical activity. |

FIG. 82

Example intelligent relationship interpretation table 3 between sensor parameters, 8300

| Parameter / Analyte | Pollution / Air quality index AQI ≤ 50 | Altitude ≤ 5,000 feet | Ambient temperature 15 to 25 °C |
|---|---|---|---|
| Blood Glucose Level 70—100 mg/dL | Particulate matter exposures are positively associated with blood glucose measures in nondiabetic adults. | Hyperglycemia: High altitudes can increase body's production of stress-related hormones which can raise blood sugar levels. | Dehydration due to high ambient temperature can cause blood sugar to rise as the glucose in blood becomes more concentrated. |
| RBC Count 3.92—5.13 x 10E6/μL | Pollution exposure is negatively correlated with the RBC count and size, hemoglobin concentration, and monocyte count and positively correlated with the lymphocyte count. | High altitude has less oxygen and results in increased RBC count because of high heart rates. | Low ambient temperatures cause blood vessels and arteries to narrow, restricting blood flow and count and reducing oxygen to the heart. |
| Hemoglobin 13.2—16.6 g/dL | Pollution exposure is negatively correlated with the RBC count, hemoglobin concentration, and monocyte count and positively correlated with the lymphocyte count. | The amount of hemoglobin in blood increases at high altitude to increase the amount of oxygen that can be carried. | In hot weather the concentration of hemoglobin in the blood decreases, and this leads to a decrease in the level of oxygen in the blood due to a decrease in the affinity of hemoglobin to bind oxygen. |
| WBC Count 4.1—11.6 x 10E3/μL | Pollution exposure is negatively correlated with the RBC count, hemoglobin concentration, and monocyte count and positively correlated with the lymphocyte count. | People living above sea level have higher white blood cell counts than those living below sea level. | The higher ambient temperature can increase the WBC counts due to cells working harder. |
| Platelet count 135—317 X 10E3/μL | Pollution results in decrease in platelet count. Low platelets, or thrombocytopenia, are a common side effect of blood cancers. | High-altitude exposure decreases the platelet count. | Low ambient temperature results in decrease in platelet count. |
| Blood Oxygen Saturation 95—100% | Increased exposure to air pollution, including the nontraffic pollutant Sulphur oxide from industrial sources, leads to changes in blood oxygen saturation. | A drop in atmospheric pressure, as observed at high altitudes, leads to decreased blood oxygen saturation. | Low ambient temperature along with low body temperatures cause blood vessels to narrow which restricts blood flow and reduces oxygen levels. High ambient temperature increase body temperature and in turn blood temperature decreases the affinity of oxygen to hemoglobin, resulting in decrease in blood oxygen saturation. |

FIG. 83

Example intelligent relationship interpretation table 4 between sensor parameters, 8400

| Parameter / Analyte | Pollution/Air quality index AQI ≤ 50 | Altitude ≤ 5000 feet | Ambient temperature 15 to 25 °C |
|---|---|---|---|
| Carbon Dioxide 20—29 mm/L | Higher level of air pollution with increased carbon dioxide level causes high heart rate and respiratory rate. | Carbon dioxide is carried as a bicarbonate in the blood plasma. The carbon dioxide percentage increases and the oxygen percentage decrease progressively with increase in altitude. | Carbon dioxide is carried as a bicarbonate in the blood plasma. The carbon dioxide percentage increases and the oxygen percentage decrease progressively with increase in altitude. |
| Calcium 8.6—11 mg/dL | Polluted air exposure could adversely affect almost all cells of the body. This changes the calcium level. | There are changes in electrolytes during acclimatization at high altitude. It results in lower calcium levels. | Low altitude and pressure results in decreased serum bicarbonate due to hypocapnia. |
| Phosphorous 2.8—4.5 mg/dL | Exposure to phosphorous pollution results in elevated phosphorous levels. | There are changes in electrolytes during acclimatization at high altitude resulting in phosphorous levels changes. | High altitude with low pressure conditions influences anabolic and metabolic processes results in phosphorous level changes. |
| Potassium 3.6—5.2 mmol/L | High pollution results in slight elevation of calcium, magnesium, phosphorus, and ALP. | There are changes in electrolytes during acclimatization at high altitude. There is no significant change to potassium level. | High altitude with low pressure conditions influences anabolic and metabolic processes resulting in potassium levels changes. |
| Sodium 135—145 mmol/L | Exposure to high pollution results in changes to sodium levels. | There are changes in electrolytes during acclimatization at high altitude. They result in lower sodium levels. | High-altitude with low pressure conditions influences anabolic and metabolic processes resulting in sodium levels changes. |

FIG. 84

Clinical laboratory test critical results range 8500

| Chemistry test | | Toxicology test | |
|---|---|---|---|
| Biomarker / Analyte | Value | Biomarker / Analyte | Value |
| Bicarbonate (total CO2) | < 10 or > 42 mmol/L | Acetone | > 100 mg/dL |
| Bilirubin, Total | > 16 mg/dL | Caffeine (Neonate) | > 20 µg/mL |
| Calcium, Ionized | ≤ 0.78 or ≥ 1.58 mmol/L | Cyanide | > 100 µg/mL |
| Calcium, Total | < 6.0 or > 13.0 mg/dL | Ethanol | > 250 mg/dL |
| Glucose (birth to 30 days) | < 46 or > 200 mg/dL | Ethylene Glycol | > 20 mg/dL |
| Glucose (>30 days to adult) | < 55 or > 450 mg/dL | Isopropanol | > 50 mg/dL |
| Iron | > 500 µg/dL | Methanol | > 20 mg/dL |
| Glucose, WB POC | < 60 or > 452 mg/dL | Lithium | ≥ 1.6 mmol/L |
| Glucose, WB, neonatal POC | < 40 or > 200 mg/dL | Pentobarbital | > 10 µg/mL |
| Magnesium | < 1.0 or > 9.0 mg/dL | Salicylate | > 300 µg/mL or > 30 mg/dL |
| Phosphorus | < 1.0 or > 9.0 mg/dL | TCA Tricyclics | > 400 ng/mL |
| Potassium | < 3.0 or > 6.1 mmol/L | Lead (birth--18 years) | ≥ 45 µg/dL |
| Sodium | < 120 or > 162 mmol/L | Lead (≥ 19 years) | ≥ 70 µg/dL |
| Troponin I | ≥ 0.30 ng/mL | | |

| Hematology test | | Arterial blood gases test | |
|---|---|---|---|
| Biomarker / Analyte | Value | Biomarker / Analyte | Value |
| Hematocrit (birth to 6 days) | ≤ 35% or ≥ 65% | pH | ≤ 7.25 or ≥ 7.61 |
| Hematocrit (>6 days to adult) | ≤ 21% or ≥ 65% | PCO2 | ≤ 20 or ≥ 62 mmHg |
| Hemoglobin (birth to 6 days) | ≤12.0 or ≥ 22.0 g/dL | PO2 | ≤ 40 mmHg |
| Hemoglobin | ≤7 or > 21.0 g/dL | Virology test | |
| Platelet Count | ≤ 20 or ≥ 1000 x $10^3$/µL | Infectious agent test, Antigen test, culture, serology, or molecular test | Positive or suspicious for any pandemic (influenza or SARS-CoV-2 virus) or bioterrorism agents |
| White Blood Cell Count | ≤ 2.0 or ≥ 40 x $10^3$/µL | Any cerebrospinal fluid (CSF) Assay | Positive (including virus growth or molecular test) |

| Coagulation test | | | |
|---|---|---|---|
| Prothrombin Time | ≥ 45.0 seconds | Fibrinogen | <100 mg/dL (any age) |
| Factor 5 | ≤ 5% | Heparin, unfractionated | <0.1 or >0.7 IU/mL |

| Infectious Disease | | |
|---|---|---|
| Detection of infectious agent in | by | Comments |
| Blood | Positive culture, smear, rapid antigen, or nucleic acid test (NAT) detection (not speciation) | Acid-fast bacillus (AFB), bacterial, fungal, parasite |
| Eye/ocular | Positive culture, smear, or NAT | AFB, bacterial, fungal, viral, parasite |
| Tissue | Positive culture or smear | AFB, bacterial, fungal, viral, parasite |
| Detection of infectious agent | by | Comments |
| *Mycobacterium tuberculosis* | Identification, positive NAT, and resistance to primary anti-tuberculosis agents (INF and RIF) | Within the last 90 days |
| Any clinically significant mold | Positive culture or NAT from original specimen | BAL, wash, sinus, or any sterile site |
| *Histoplasma capsulatum, Blastomyces dermatitidis, Talaromyces (Penicillium) marneffei, Coccidioides immitis, Cryptococcus neoformans,* and *Cryptococcus gattii* | Identification by culture or NAT | |
| Highly pathogenic organisms such as: *Bacillus anthracis, Brucella spp.(B.abortus, B. melitensis, B. suis), Burkholderia mallei, Burkholderia pseudomallei, Francisella tularensis, Yersinia pestis,* and *Corynebacterium diphtheriae, Salmonella typhi, Vibrio cholera, Clostridium botulinum* etc. | Identification by validated method | |

FIG. 85

Personalized accurate user/patient clinical laboratory test results method 8810
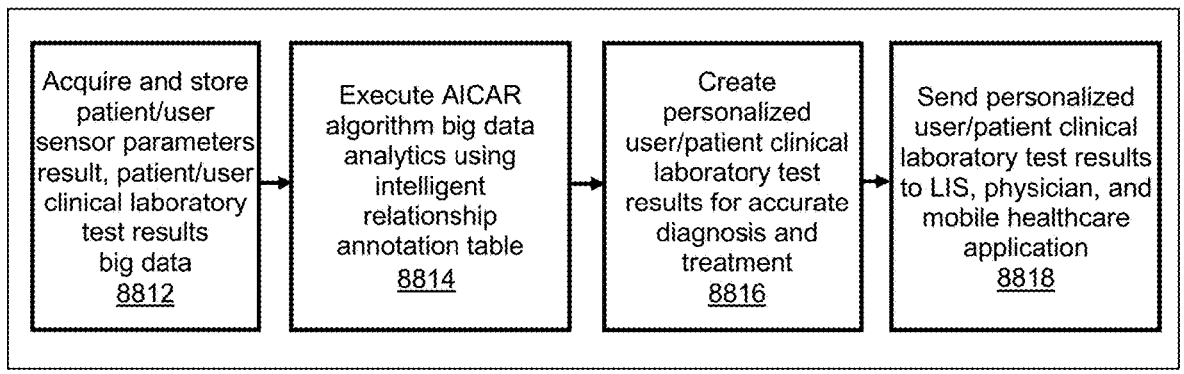
Personalized accurate user/patient clinical laboratory test critical results method 8850
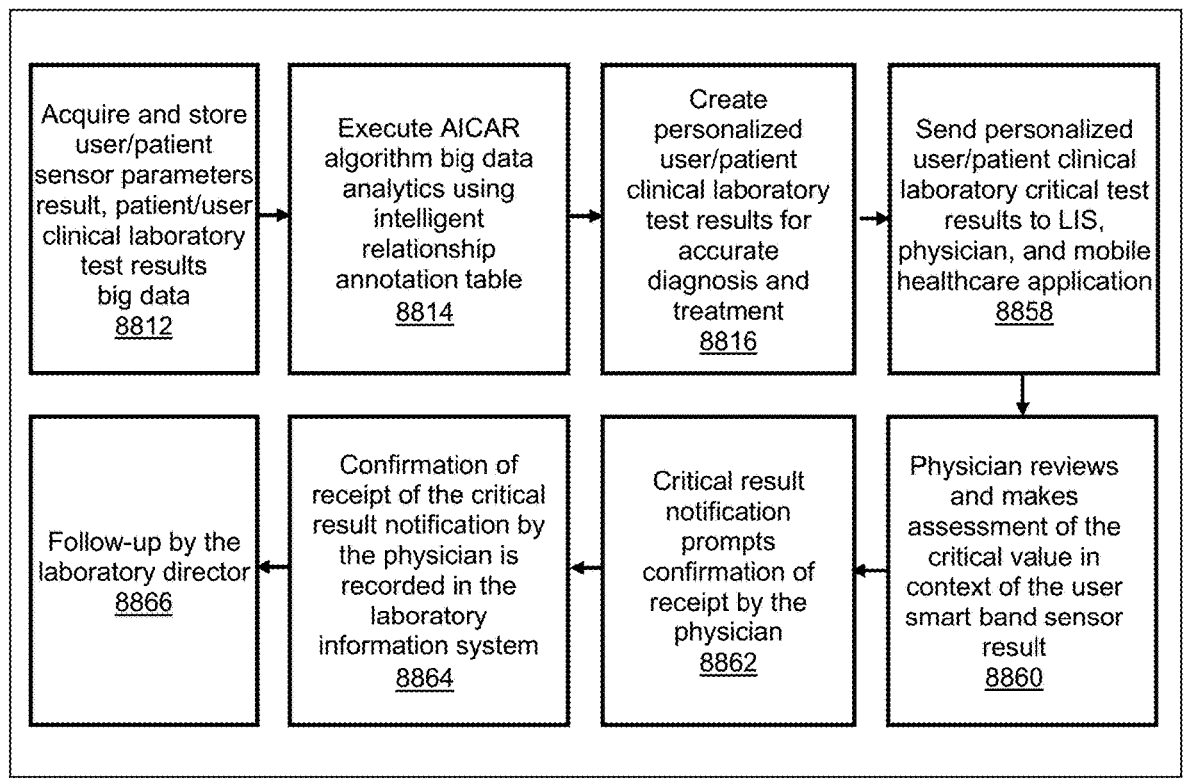
FIG. 88

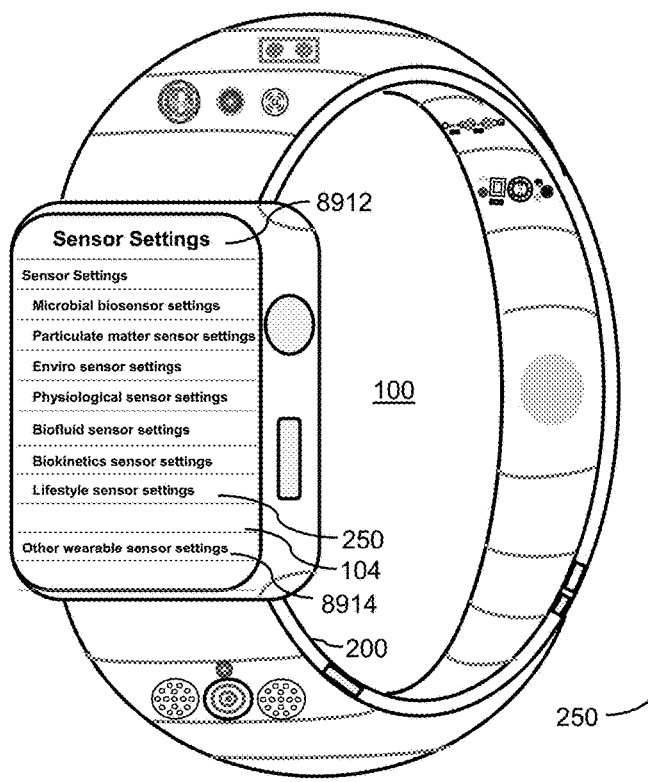
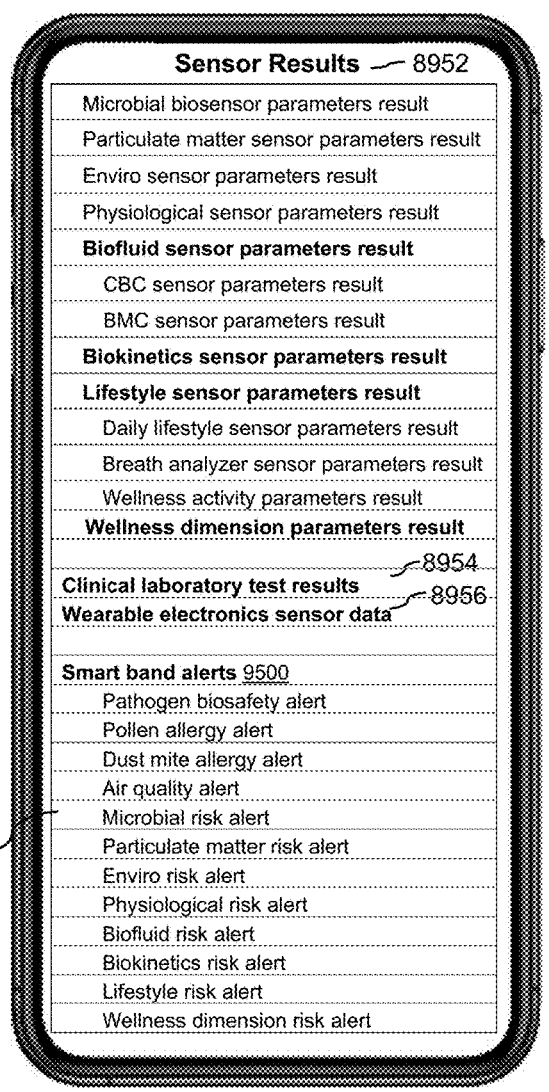
FIG. 89

Mobile healthcare application displaying microbial biosensor nasal cavity parameters result 9010
Mobile healthcare application displaying microbial biosensor oral cavity parameters result 9050
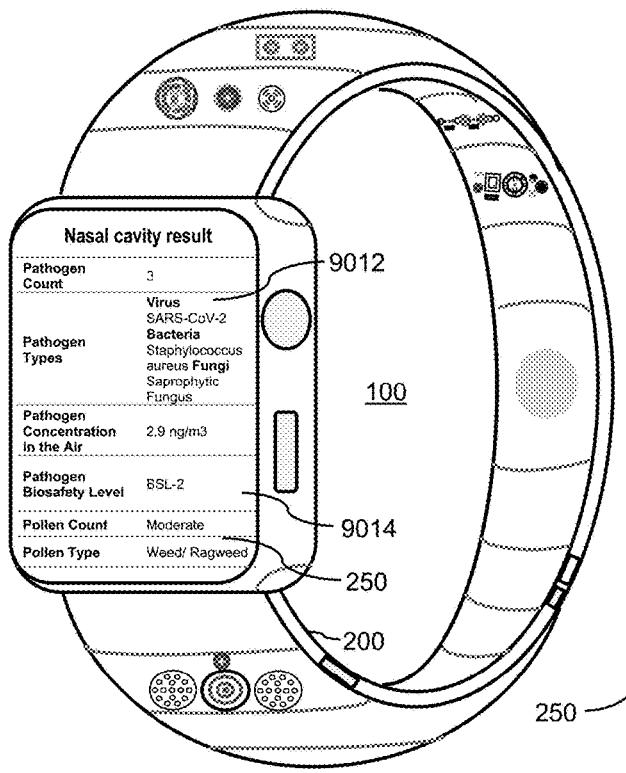
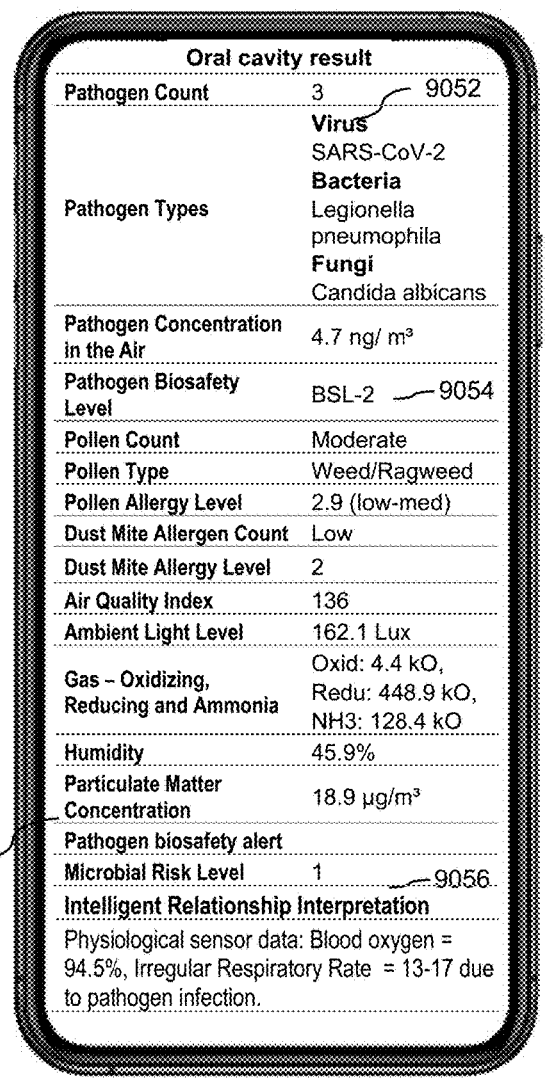
FIG. 90

Mobile healthcare application displaying physiological sensor parameter results 9210

| Physiological sensor parameters result | |
|---|---|
| Name: Jane Doe | |
| Age: 29 | |
| Sex: F | |
| Address: 123X Main Street, Stanford CA, 94305, USA | |
| Physiological parameter | Results _____ 9212 |
| Skin and Body Temperature | 94.9°F (Skin) 98.2°F (Body) |
| Heart Rate | 89 bpm |
| Heart Rate Variability | HRV = 125 ms |
| Respiratory Rate | 21 breaths per minute |
| Blood Pressure | Systolic = 114 mmHg Diastolic = 69 mmHg |
| Electrocardiogram | PQRST sequence and Atrial fibrillation |
| Blood Oxygen Saturation | 95.90% |
| Blood Carbon Dioxide | 23 mmol/L |
| Physiological Risk Level | 1 |
| Intelligent Relationship Interpretation —9214 | |
| Microbial biosensor data nasal cavity results Pathogen = SARS-CoV-2. High respiratory rate and low blood oxygen saturation might be due to viral infection. | |

Mobile healthcare application displaying biofluid sensor parameters CBC result 9250

| Biofluid sensor parameters result | |
|---|---|
| Biofluid parameter | |
| Complete Blood Count | Results ___9252 |
| RBC Count | 4.89 x 10E6/μL |
| Hemoglobin | 14.2 g/dL |
| Hematocrit | 39.90% |
| Mean Corpuscular Volume (MCV) | 89 fL |
| Mean Corpuscular Hemoglobin (MCH) | 27.2 pg |
| Mean Corpuscular Hemoglobin Concentration (MCHC) | 31.5 g/dL |
| WBC Count | 12.7 x 10E3/μL |
| WBC Differential | |
| Neutrophils | 4.13 x 10^3/μL |
| Lymphocytes | 2.74 x 10^3/μL |
| Monocytes. | 0.32 x 10^3/μL |
| Eosinophils. | 0.29 x 10^3/μL |
| Basophils | 0.06 x 10^3/μL |
| Platelet Count | 121 x 1-E3/uL |
| Biofluid Risk Level | 2 ___9254 |
| Intelligent Relationship Interpretation | |
| Enviro sensor data: Altitude = 6500 ft. High WBC count and low platelet count can be due to high altitude. | |

FIG. 92

Mobile healthcare application displaying complete metabolic panel parameters result 9310

Mobile healthcare application displaying biokinetics sensor parameters result 9350

| Biofluid sensor parameters result | |
|---|---|
| Biofluid Parameter | 9312 |
| Complete Metabolic Panel | Results |
| Albumin | 3.4 to 5.4 g/dL |
| Bilirubin | 0.8 mg/dL |
| Blood Glucose Level | Random: 189 mg/dL |
| Blood Alcohol Level | Sober: 0.04 percent |
| Blood Urea Nitrogen | 18 mg/dL |
| Cortisol | 10.6 mg/dL evening |
| Creatinine | 1.01 mg/dL |
| Calcium | 9.7 mg/dL |
| Chloride | 110 mmol/L |
| Magnesium | 12.5 ng/mL |
| Phosphorus | 3.7 mg/dL |
| Potassium | 4.2 mmol/L |
| Sodium | 139 mmol/L |
| Alkaline Phosphatase (ALP) | 148 U/L |
| Alanine Aminotransferase (ALT) | 29.7 U/L |
| Aspartate Aminotransferase (AST) | 18 U/L |
| Complete Cholesterol | Panel |
| HDL Cholesterol Level | ≥ 59 mg/dL |
| LDL Cholesterol Level | 79 mg/dL Optimal |
| Triglycerides Level | Normal: 120 mg/dL |
| Total Cholesterol | Normal: 170 mg/dL |
| Biofluid Risk Level | 2  9314 |
| Intelligent Relationship Interpretation | |
| Particulate matter sensor data: AQI = 149. High glucose can be due to pollution. | |

250

| Biokinetics sensor parameters result | |
|---|---|
| Biokinetics Parameter | Results  9352 |
| Walking | 30 minutes / 6000 steps |
| Standing | 3.5 hours (intermittent) |
| Sitting | 4.5 hours (intermittent) |
| Running | 30 minutes |
| Yoga | 15 minutes |
| Hiking | 30 minutes |
| Cycling | 30 minutes |
| Swimming | 15 minutes |
| Movement | 3.5 hours of activity |
| Exercise | 2.5 hours of vigorous-intensity activity |
| Sleep | 4.5 hours |
| Stress | 1 level |
| Fall | None |
| Proximity | 0 events, 1 foot too close to wall |
| Biokinetics Risk Level | 2 |
| Intelligent Relationship Interpretation | 9354 |
| Physiological sensor data: High blood pressure = 135/90 mmHg and Biofluid sensor data: High cortisol = 35 mg/dL might be due to lower sleep level | |

FIG. 93

Mobile healthcare application displaying lifestyle sensor parameters result 9410

| Lifestyle sensor parameters result | |
|---|---|
| Lifestyle Parameter | Results 9412 |
| Breath parameters | Positive for alcohol |
| Number of meals | 3 meals<br>2 snacks |
| Set of food types | Breakfast: pancake<br>Lunch: pasta, soup<br>Dinner: Thai curry and rice |
| Number of drinks | 4 times |
| Set of drink types | Water and soup |
| Number of bathroom visits | Urinate: 6<br>Poop: 2 |
| Number of smoking occurrences | 12 |
| Number of occupation interactions | 5 |
| Number of financial interactions | 2 |
| Number of intellectual interactions | 5 |
| Number of emotional interactions | 3 |
| Number of social interactions | 1.5 hours |
| Number of spiritual interactions | 30 minutes |
| Lifestyle Risk Level | 2 |
| Intelligent Relationship Interpretation 9414 | |
| Particulate matter sensor: AQI = 135, Enviro sensor data: Ambient Temperature = 42°C Humidity = 78%. Quality of air is too poor. It is also very hot and humid. | |

Mobile healthcare application displaying wellness dimension parameters result 9450

| Wellness dimension parameters result 9452 | |
|---|---|
| Name: Jane Doe | |
| Age: 29 | |
| Sex: F | |
| Address: 12X Main Street, Stanford | |
| CA, 94305, USA | |
| Wellness Dimension | Results 9454 |
| Physical | 3 |
| Environmental | 2 |
| Occupational | 3 |
| Financial | 3 |
| Intellectual | 4 |
| Emotional | 3 |
| Social | 3 |
| Spiritual | 3 |
| Average Total Score | 3 |
| Lifestyle Risk Level | 3 |
| Intelligent Relationship Interpretation 9454 | |
| Physiological sensor data: Heart Rate = 100, Number of smoking occurrences = 12. AQI = 135. Physical and Environmental wellness dimension needs to be improved. | |

Smart band alert 9510

|  9512 | \<Sensor\> Risk Alert<br>\<Sensor\> Risk Level is above a predetermined threshold level<br>\<Sensor\> Risk Level 48<br>Date: June 27, 2022<br>Location: 123X Campus Drive, Stanford 94309, California, USA |  9514 | \<Parameter\> Risk Alert<br>\<Parameter\> value is below normal reference range<br>\<Parameter\> Risk Level 24<br>Date: June 27, 2022<br>Location: 123X Campus Drive, Stanford 94309, California, USA |
|---|---|---|---|

Smart band sensor risk level and corrective action and preventive action table 9520

| Risk Level | Health hazard | Description |
|---|---|---|
| 45-125 | Intolerable (INT) | Risk in this category is not acceptable. Situation can result in death or critical illness. Risk mitigation through corrective actions and preventive actions required.<br>Example: Microbial biosensor<br>Microbial risk level 75 (5x3x5) is intolerable. SARS-CoV-2 virus was found in the nasal cavity.<br>Corrective action: Isolate from others in your home for 5 days.<br>Preventive action: Visit your physician for further treatment. Take multivitamins, analgesic.<br>Example: Biofluid sensor<br>Biofluid risk level 60 (5x3x5) is intolerable. Low RBC, High Sodium, and High LDL levels are outside normal reference range.<br>Corrective action: Eat iron rich food to increase RBC, Reduce intake of food with sodium. Reduce saturated fats.<br>Preventive action: Take iron-rich dietary supplements to increase RBC levels. Lower sodium meal and ensure there is no salt in the meal. To maintain right level of cholesterol. Avoid animal products such as cheese, fatty meat, and dairy desserts. |
| 16-44 | Investigate (INV) | Risk should be mitigated. Situation can result in serious or moderate illness. Additional mitigation should be investigated to reduce the risk through corrective actions and preventive actions to Broadly Acceptable Region.<br>Example: Physiological sensor<br>Physiological risk level is 24 (2x3x4) needs investigation. High body temperature. Low heart rate.<br>Corrective action: Take ibuprofen for reduce body temperature. Walk more often<br>Preventive action: Make sure surrounding temperature is ambient. Reduce stress and exercise daily to increase heart rate.<br>Example: Particulate matter sensor<br>Particulate matter risk level is 18 (3x2x3) needs investigation. Pollen count is too high.<br>Corrective Action: Stay indoors and make sure windows are shut.<br>Preventive Action: Avoid grassy areas, parks, and fields particularly in early morning & night. |
| 1-15 | Broadly Acceptable Region (BAR) | Risk is negligible compared to the risk of other health hazards. Situation may result in temporary discomfort or might not result in illness.<br>Example: Biokinetics sensor<br>Biokinetics risk level 12 (2x2x3) is in BAR. Continuously sitting for long hrs. Irregular sleep hrs.<br>Corrective action: Walk and stand more often. Set bedtime sleep alarm and sleep well.<br>Preventive action: Exercise daily for recommended hours. Eat healthy diet, avoid caffeine and alcohol before sleep.<br>Example: Lifestyle sensor<br>Lifestyle risk level 6 (1x2x3) is in BAR. Too many no. of meals. High no. of bathroom visits<br>Corrective action: Reduce number of meals, Reduce fluid intake.<br>Preventive action: Eat healthy meals at set time. Loose excess weight an exercise. |

FIG. 95

PATHOGEN SAFETY DATA SHEET – SARS-CoV-2

SECTION 1 – INFECTIOUS AGENT

NAME: Severe acute respiratory syndrome (SARS)-related coronavirus

SYNONYM OR CROSS REFERENCE: *SARS-CoV-2 may also be called 2019-nCoV, HCoV-19, and COVID-19*

CHARACTERISTICS: SARS-CoV-2 is a spherical enveloped virion measuring 80 to 160 nm in diameter with a single-stranded, linear, non-segmented, positive-sense RNA genome 27-30 kb in size.

SECTION 2 – HAZARD IDENTIFICATION INFORMATION

PATHOGENICITY/TOXICITY: Severe acute respiratory syndrome coronavirus 2 (SARS-CoV-2) is a member of the Coronaviridae family and genus beta coronavirus that causes COVID-19 infections in humans. Coronaviruses are enveloped viruses that contain a single strand of positive-sense RNA. The acute viral disease is characterized by fever (temperature 37.8°C or above), headache, myalgia, malaise, sore throat, cough, sneezing, and nasal discharge. After 2 to 7 days, this is followed by respiratory symptoms such as a dry cough, shortness of breath, difficulty breathing, or hypoxia. In some cases, the respiratory symptoms become increasingly severe, and patients require oxygen support and mechanical ventilation.

EPIDEMIOLOGY: SARS-CoV-2 caused approximately 5.86 million deaths with 420 million cases between 2019 and Feb 2022.

HOST RANGE: Humans, ferrets, cats, dogs, mink, and primates

INFECTIOUS DOSE: Estimations as low as 100 particles.

MODE OF TRANSMISSION: The primary transmission of SARS-CoV-2 is through close-contact, person-to-person spread. Transmission is driven by respiratory droplets. A person may sneeze or cough onto a surface leaving potentially infectious material.

INCUBATION PERIOD: 2-14 days.

COMMUNICABILITY: Highly communicable. Infected persons can shed detectable amounts of virus the day before symptoms begin. Adults usually shed the virus for 3 to 5 days.

SECTION 3 – DISSEMINATION/TRANSMISSION

RESERVOIR: Humans are the principal reservoir of virus. Animal reservoirs are suspected as sources of new human subtypes.

ZOONOSIS: SARS-CoV-2 has been implicated to be originated from animals, and associated with animal linkages, spillover events, cross-species barrier jumping and zoonosis.

VECTORS: None.

Page 1

FIG. 96

SECTION 4 – STABILITY AND VIABILITY

DRUG SUSCEPTIBILITY: .

DRUG RESISTANCE: The development of effective antiviral therapy for SARS-CoV-2 is critical for those awaiting vaccination, as well as for those who do not respond robustly to vaccination. Currently drug companies are working on developing anti-viral therapies for COVID-19.

SUSCEPTIBILITY TO DISINFECTANTS: SARS-CoV-2 is susceptible to disinfectants, including sodium hypochlorite (freshly made 1:10 dilution of bleach), 60 to 95% ethanol, 2% alkaline glutaraldehyde, 5 to 8% formalin, and 5% phenol.

PHYSICAL INACTIVATION: Physical inactivation can be performed using heat or exposure to UV. Heat inactivates the virus by denaturing the structure of the proteins, affecting the attachment and replication of the virus in the host cell. In recent studies SARS-CoV-2 was successfully inactivated with a temperature of 80°C.

SURVIVAL OUTSIDE HOST: Up to 3 hours on printer paper or tissue paper, up to 2 days on wood or cloth. Up to 4 days on glass and paper currency. Up to 7 days on stainless steel or plastic and surgical masks. Several research studies have demonstrated interdependence between the survival of SARS-CoV-2, surface or material composition, temperature, and relative humidity.

SECTION 5 – FIRST AID/MEDICAL

SURVEILLANCE: Monitor for symptoms of fever and breathing. Confirm diagnosis with RT-PCR (favored) or point-of-care testing and give appropriate antiviral treatment. Laboratory confirmation of the virus can be done using RT-PCR and antigen testing.

FIRST AID/TREATMENT: Fluids and rest. Vitamin C, D, Calcium, Magnesium, Zinc supplements are used to boost body immunity. Antiviral agents can be employed to treat SARS-CoV-2. Antibiotic treatment (in combination with antiviral treatment) may also be used to prevent or treat secondary bacterial pneumonia. To help lower a fever and get some relief for uncomfortable body aches, acetaminophen, naproxen, or ibuprofen is useful. Wear a face mask indoors in public.

IMMUNIZATION: The most effective strategy for reducing the effect of SARS-CoV-2 is through vaccination. There are several vaccines developed by various drug companies worldwide. For example, Pfizer-BioNTech, Moderna, Johnson & Johnson - Janssen, Covaxin, Oxford/AstraZeneca, Covishield, Sinovac, and so on.

PROPHYLAXIS: None

SECTION 6 – LABORATORY HAZARDS

LABORATORY-ACQUIRED INFECTIONS: There are confirmed cases of laboratory acquired infections.

SOURCES/SPECIMENS: Respiratory tissues, human secretions, nasal swab, and saliva. In addition, the virus may be present on surfaces.

Page 2

FIG. 97

PRIMARY HAZARDS: Splash/droplet-creating activities (shaking incubators, liquid culturing, mechanical pipetting), Equipment contamination.

SPECIAL HAZARDS: Natural genetic variants of virus have an unknown potential for altering host range, pathogenicity, and/or for introducing transmissible viruses with novel antigenic composition into humans.

SECTION 7 – EXPOSURE CONTROLS / PERSONAL PROTECTION

RISK GROUP CLASSIFICATION: Risk Group 2. This risk group applies to the species as a whole and may not apply to every strain.

CONTAINMENT REQUIREMENTS: Containment Biosafety Level 2/3 facilities, equipment, and operational practices for work involving infectious or potentially infectious materials and cultures.

PROTECTIVE CLOTHING: For diagnostic work: lab coat. Gloves when direct skin contact with infected materials or animals is unavoidable. Eye protection must be used where there is a known or potential risk of exposure to splashes.

OTHER PRECAUTIONS: All procedures that may produce aerosols or involve high concentrations or large volumes should be conducted in a biological safety cabinet (BSC). The use of needles, syringes, and other sharp objects should be strictly limited.

SECTION 8 – HANDLING AND STORAGE

SPILLS: Allow aerosols to settle and, wearing protective clothing, gently cover the spill with paper towels and apply suitable disinfectant, starting at the perimeter and working towards the center. Allow sufficient contact time (30 minutes) and then clean the area.

DISPOSAL: Decontaminate before disposal by steam sterilization, chemical disinfection, or incineration.

STORAGE: In sealed containers that are appropriately labelled.

SECTION 9 – EDUCATION AND TRAINING

Laboratory personnel should be trained on Biosafety Level 2 and 3 requirements.

SECTION 10 – REGULATORY AND OTHER INFORMATION

REGULATORY INFORMATION: The import, transport, and use of pathogens in the US is regulated under many regulatory bodies. If you are in country outside of the US. please check local regulations. Users are responsible for ensuring they are compliant with all relevant acts, regulations, guidelines, and standards.

Although the information, opinions and recommendations contained in this Pathogen Safety Data Sheet are compiled from sources believed to be reliable, there is no guarantee, and we accept no responsibility for the accuracy, sufficiency, or reliability or for any loss or injury resulting from the use of the information. All attempts are made to keep the information up to date. Newly discovered hazards are frequent, and this information may not be completely up to date. The information is provided for educational purpose only.

Page 3

FIG. 98

POLLEN SAFETY DATA SHEET – Ragweed

SECTION 1 – POLLEN TYPE

NAME: Ragweed/Weed

SYNONYM OR CROSS REFERENCE: *Family: Asteraceae, Scientific name: Ambrosia, Higher classification: Daisy family, Kingdom: Plantae, Order: Asterales, Rank: Genus.* Members of this plant family include Sage, Burweed marsh elder, Rabbit brush, Mugwort, Groundsel bush, Eupatorium.

CHARACTERISTICS: Ragweed is a weed that grows throughout the United States, especially in the Eastern and Midwestern states. Each plant lives only one season. But that one plant can produce up to 1 billion pollen grains. There are about 17 types of ragweed in North America, two species are the most abundant: Common ragweed (Ambrosia artemisiifolia) and Giant ragweed (Ambrosia trifida).

SECTION 2 – ALLERGY IDENTIFICATION

ALLERGY SYMPTOMS: Ragweed pollen inhaled from the air causes rhinitis (hay fever) symptoms. Rhinitis symptoms often include sneezing, stuffy or runny nose, Itchy nose, and throat, itchy or puffy eyes, mucus in the throat (postnasal drip).

HOST RANGE: Humans, and other mammalians.

MODE OF TRANSMISSION: Transmission of ragweed pollen in humans can occur via air or from contact transmission from contaminated surfaces with ragweed pollen.

SECTION 3 – DIAGNOSIS

Skin prick test to confirm allergy.

SECTION 4 – FIRST AID / MEDICAL

There is no cure for a ragweed pollen allergy but there are ways to treat and manage it such as:
Track the pollen count for area.
Stay indoors in central air conditioning.
Prevent pollen from being tracked into home.
Take anti-inflammatory or antihistamine medicines.

SECTION 5 – EDUCATION AND TRAINING

SECTION 6 – REGULATORY AND OTHER INFORMATION

REGULATORY INFORMATION:

Although the information, opinions and recommendations contained in this Pollen Safety Data Sheet are compiled from sources believed to be reliable, there is no guarantee, and we accept no responsibility for the accuracy, sufficiency, or reliability or for any loss or injury resulting from the use of the information. All attempts are made to keep the information up to date. Newly discovered hazards are frequent, and this information may not be completely up to date. The information is provided for educational purpose only.

FIG. 99

Predicted surrogate user CBC test result from the user smart band sensor result 10010

| No | Physiological Parameter | Physiological Parameter Normal Reference Ranges | Biofluid Parameter | Predicted surrogate user CBC test result Normal Reference Ranges |
|---|---|---|---|---|
| 1 | Skin Temperature 4212 and Body Temperature 4214 | 33.5—36.9 °C (Skin) 92.3—98.4 °F (Skin) 36.1—37.2 °C (Body) 97.0—99.0 °F (Body) | RBC 5022 | 0—1 month: 3.7—5.4 x 10E6/uL 1—3 years: 3.9—5.3 x 10E6/uL 3—6 years: 4—5.2 x 10E6/uL 6—12 years: 4.1—6 x 10E6/uL 12+ years: 4.63—6.08 x 10E6/uL |
| 2 | Heart Rate 4216 | 0—1 month: 70—190 1—3 years: 80—120 bpm 3—6 years: 75—115 bpm 6—12 years: 70—110 bpm 12+ years: 70—100 bpm | | |
| 3 | Heart Rate Variability 4218 | HRV < 50 ms is unhealthy, HRV 50—100 ms compromised health HRV > 100 ms is healthy | WBC 5024 | 0—1 month: 3.7—10.4 x 10E3/uL 1—3 years: 3.8—10.6 x 10E3/uL 3—6 years: 3.9—10.7 x 10E3/uL 6—12 years: 3.9—11.2 x 10E3/uL 12+ years: 4.0—11.6 x 10E3/uL |
| 4 | Respiratory Rate 4220 | Age Rate (in breaths per minute) 0—1 year: 30—60 1—3 years: 24—40 3—6 years: 22—34 6—12 years: 18—30 12+ years: 12—16 | | |
| 5 | Blood Pressure 4224 Systolic blood pressure 4224SBP Diastolic blood pressure 4224DBP | Age: Systolic Diastolic mmHg 0—1 month: 87–105 53–66 1—3 years: 95–105 53–66 3—6 years: 97–112 57–71 6—12 years: 112–128 66–88 12+ : 95–145 70–90 | Platelet 5026 | 0—1 month: 250—450 x10E3/uL 1—3 years: 200—450 x10E3/uL 3—6 years: 180—450 x10E3/uL L 6—12 years: 170—450 x10E3/uL 12+ years: 150—450 x10E3/uL |
| 6 | Blood Oxygen 5012 ($O_2$) Blood Carbon Dioxide 5014 ($CO_2$) | > 95% 20—29 mmol/L | | |

Method to predict a surrogate user CBC test result 10050

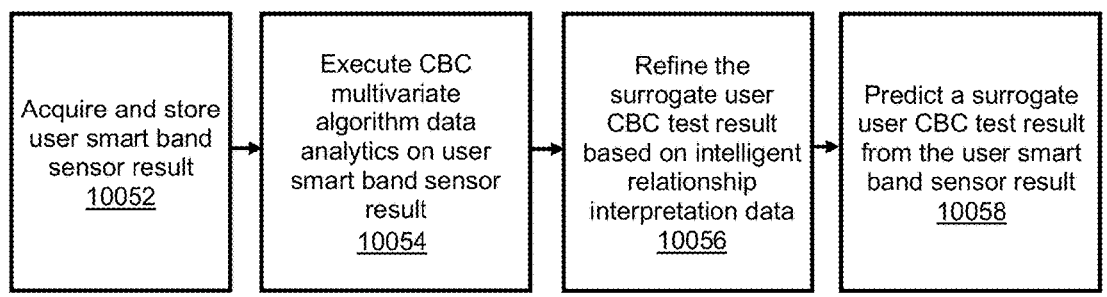

FIG. 100

Personalized accurate user/patient clinical laboratory test results report 1 10101

| Patient Report | Sample Report | Specimen ID | 202203271589 |
|---|---|---|---|
| Clinical Information | Abnormal Report | | |
| Patient Details | | Specimen Details | Physician Details |
| DOB: 1980-01-01 | | Date collected: 2022-10-27 | Name: Dr. Hetal Kurani |
| Age: 42 | | Date received: 2022-10-28 | Address: 123ABC Main Street, Stanford, CA 94309 |
| Gender: M | SSN: | Date entered: 2022-10-28 | ID: ABC12345 |
| Patient ID: 94087818 | | Date reported: 2022-10-29 | NPI: 123456789 |

| No | Parameter/Analyte | Result | Flag | Unit | Normal Reference Range | Intelligent Relationship Interpretation element 10110 |
|---|---|---|---|---|---|---|
| 1 | Blood Glucose Level | 135 | High | mg/dL | Random:70—100 | Hyperglycemia causes: Kidney disease, hyperthyroidism, pancreatitis, and pancreatic cancer. Physiological sensor parameters result: Blood pressure 10112 Systolic = 155 mmHg, Diastolic = 97 mmHg. Systolic blood pressures of ≥ 160 mmHg have significantly higher glucose concentrations. |
| 2 | Blood Alcohol Level | 0.01 | | % | 0.0—0.25 | |
| 3 | RBC Count | 3.6 | Low | x 10E6/μL | 4.35—5.65 | Anemia causes: Leukemia, a type of blood cancer, Malnutrition, a condition in which your body does not get the calories, vitamins, and/or minerals needed for good health, Multiple myeloma, a cancer of the bone marrow. Particulate matter sensor parameters result: AQI 10014 = 147. Pollution exposure is negatively correlated with the RBC count size. |
| 4 | Hemoglobin | 10.2 | Low | g/dL | 13.2—16.6 | Anemia causes: Thalassemia, iron deficiency, liver disease, cancer, and other diseases Particulate matter sensor parameters result: AQI 10014 = 147. Pollution exposure is negatively correlated with the hemoglobin concentration. |
| 5 | Hematocrit | 42.5 | | % | 38.3—48.6 | |
| 6 | MCV | 91 | | fL | 85—95 | |
| 7 | MCH | 28.6 | | pg | 25.6—32.2 | |
| 8 | MCHC | 34.2 | | g/dL | 32.2—35.5 | |
| 9 | WBC Count | 11.4 | High | x 10E3/μL | 3.98—10.04 | Leukopenia causes: Bone marrow damage. This may be caused by infection, disease, or treatments such as chemotherapy, cancers that affect the bone marrow, an autoimmune disorder like lupus Enviro sensor parameters result: Altitude 10016 = 6579 ft. People living above sea level have higher white blood cell counts than those living below sea level. |
| 10 | WBC Differential | | | | | |
| 11 | Neutrophils | 6.4 | High | x 10E3/μL | 1.56—6.13 | Microbial biosensor parameters result: Pathogen type virus 10018 = SARS-CoV-2. Elevated numbers of neutrophils have been observed in the nasopharyngeal epithelium and later in the more distal parts of the lung. |
| 12 | Lymphocytes. | 2.5 | | x 10E3/μL | 1.18—3.74 | |
| 13 | Monocytes. | 0.7 | | x 10E3/μL | 0.24—0.36 | |
| 14 | Eosinophils. | 0.2 | | x 10E3/μL | 0.04—0.36 | |
| 15 | Basophils | 1.3 | | x 10E3/μL | 0.01—0.08 | |
| 16 | Platelet count | 357 | High | x 10E3/μL | 135—317 | Thrombocytopenia causes: Trapping of platelets in the spleen, decreased platelet production or increased destruction of platelets. Biokinetics sensor parameters result: Exercise 10020 = 135 minutes. Strenuous exercise results in significant platelet activation. |

FIG. 101

Personalized accurate user/patient clinical laboratory test results report 2 10200

| Patient Report | Sample Report | Specimen ID | 202203271729 |
|---|---|---|---|
| Clinical Information | Abnormal Report | | |
| Patient Details | | Specimen Details | Physician Details |
| DOB: 1976-01-01 | | Date collected: 2022-10-27 | Name: Dr. Hemal Kurani |
| Age: 46 | | Date received: 2022-10-28 | Address: 123ABC Main Street, Stanford, CA 94309 |
| Gender: F | SSN: | Date entered: 2022-10-28 | ID: ABC12345 |
| Patient ID: 95051262 | | Date reported: 2022-10-29 | NPI: 123456789 |

| No | Parameter/Analyte | Result | Flag | Unit | Normal Reference Range | Intelligent Relationship Interpretation 10210 |
|---|---|---|---|---|---|---|
| 1 | Albumin | 2.5 | | g/dL | 3.4—5.4 | |
| 2 | Bilirubin | 1.1 | | mg/dL | ≤ 1.2 | |
| 3 | BUN | 18 | | mg/dL | 6—21 | |
| 4 | Calcium | 8.2 | Low | mg/dL | 8.8—10.2 | Hypocalcemia causes: Calcium imbalance is due to Kidney disease, Thyroid disease, Malnutrition, Certain types of cancer. Physiological sensor data: Body Temperature 10212 = 100.6 °F. High body temperature can result in lowered blood calcium level. |
| 5 | Chloride | 99 | | mmol/L | 98—107 | |
| 6 | Cortisol | 28.2 | High | µg/dL | 4.6—20.6 | Causes: Cushing disease, which occurs when the pituitary gland makes too much of the adrenocorticotrophic hormone (ACTH). Enviro sensor parameters result: Humidity 10214 = 74%. Very humid conditions induce a typical stress response resulting in elevated cortisol. Lifestyle sensor parameters result: number of smoking occurrences 10216 = 12. Cigarette smoking is associated acutely with elevated cortisol levels. |
| 7 | Creatinine | 1.09 | High | mg/dL | 0.59—1.04 | Causes: Blocked urinary tract, kidney problems, such as kidney damage or failure, infection, or reduced blood flow. Loss of body fluid. Physiological sensor parameters result: Body Temperature 10218 = 100.6 °F, Blood Pressure 10220: Systolic = 154 mmHg, Diastolic = 92 mmHg. Elevated serum creatinine has been associated with increased mortality in persons with high body temperatures and high blood pressure. |
| 8 | Magnesium | 12.4 | | ng/mL | 4.7—18.3 | |
| 9 | Phosphorus | 3.9 | | mg/dL | 2.8—4.5 | |
| 10 | Potassium | 4.2 | | mmol/L | 3.6—5.2 | |
| 11 | Sodium | 154 | High | mmol/L | 135—145 | Hypernatremia causes: Diarrhea, kidney disorder, adrenal gland disorder, certain medications. Physiological sensor parameters result: Body Temperature 10222 = 100.6 °F. In hypernatremia, the level of sodium in blood is too high. Hypernatremia involves dehydration due to high fever. |
| 12 | ALT | 44 | | U/L | ≤ 33 | |
| 13 | ALP | 42 | | U/L | 35—104 | |
| 14 | AST | 39 | | U/L | ≤ 32 | |
| 15 | HDL Cholesterol | 55 | | mg/dL | ≥ 50 | |
| 16 | LDL Cholesterol | 125 | High | mg/dL | ≤ 100 | Causes: Diet: Saturated fat and cholesterol in the food eat, excessive weight, less physical activity, and smoking. Physiological sensor parameters result: Blood Pressure 10224 : Systolic = 154 mmHg, Diastolic = 92 mmHg. High systolic and diastolic blood pressure are linked to high LDL which restricts blood flow through the arteries and damages blood vessels, which can make the heartbeat faster than normal to move blood through the body. |
| 17 | Triglycerides | 99 | | mg/dL | 10—150 | |
| 18 | Total Cholesterol | 160 | | mg/dL | < 200 | |

FIG. 102

Personalized daily nutritional goal comprising nutrient and daily reference intake 10300

| Daily Nutritional Goals Report | | | | Name: Urvashi Apsara, Age 34, Date: Oct 29, 2022 |
|---|---|---|---|---|
| Nutrient | Source of Goal | DRI Goal | Personal DRI | Intelligent Nutrient Required Recommendation |
| Macronutrients | | | | |
| Protein (% kcal) | AMDR | 10-35 | 10-35 | |
| Protein (g) | RDA | 46 | 38 | Protein Deficiency. Eat Oats, Amaranth, Quinoa, Pasta, and Rice |
| Carbohydrate (% kcal) | AMDR | 45-65 | 45-65 | |
| Carbohydrate (g) | RDA | 130 | 130 | |
| Fiber (g) - 1,000 kcal | 14g | 25 | 39 | Reduce fiber DRI. Drink plenty of water, stop using fiber supplements |
| Added Sugars (% kcal) | DGA | <10 | <10 | |
| Total lipid (% kcal) | AMDR | 20-35 | 20-35 | |
| Saturated Fatty Acids (% kcal) | DGA | <10 | <10 | |
| Minerals | | | | |
| Calcium (mg) | RDA | 1,000 | 850 | Calcium Deficiency. Increase Calcium DRI intake in form of supplements or Vegetables such as Collard Greens, Spinach, and Kale |
| Iron (mg) | RDA | 18 | 18 | |
| Magnesium (mg) | RDA | 320 | 320 | |
| Phosphorus (mg) | RDA | 700 | 700 | |
| Potassium (mg) | AI | 2,600 | 2,600 | |
| Sodium (mg) | CDRR | 2,300 | 2850 | High Sodium. Decrease salt intake and eat low sodium fruits e.g., Apples, apricots, papayas, and pears |
| Zinc (mg) | RDA | 8 | 8 | |
| Vitamins | | | | |
| Vitamin A (mcg RAE) | RDA | 700 | 700 | |
| Vitamin E (mg AT) | RDA | 15 | 15 | |
| Vitamin D (IU) | RDA | 600 | 450 | Low Vitamin C. Increase DRI in the form of supplements or orange juice |
| Vitamin C (mg) | RDA | 75 | 75 | |
| Thiamin (mg) | RDA | 1.1 | 1.1 | |
| Riboflavin (mg) | RDA | 1.1 | 1.1 | |
| Niacin (mg) | RDA | 14 | 14 | |
| Vitamin B-6 (mg) | RDA | 1.3 | 1.3 | |
| Vitamin B-12 (mcg) | RDA | 2.4 | 2.4 | |
| Choline (mg) | AI | 425 | 649 | High choline. Increase exercise, limit milk, and yogurt intake |
| Vitamin K (mcg) | AI | 90 | 90 | |
| Folate (mcg DFE) | RDA | 400 | 400 | |

| The Dietary Reference Intake (DRI) is a system of nutrition recommendations from the National Academy of Medicine (NAM)[a] of the National Academies (United States). DRI provides several different types of reference values | | |
|---|---|---|
| AMDR | Acceptable Macronutrient Distribution Ranges | Acceptable Macronutrient Distribution Ranges (AMDR) is a range of intake specified as a percentage of total energy intake. Used for sources of energy, such as proteins, carbohydrates, and lipids. |
| RDA | Recommended Dietary Allowances | The RDA is the average daily dietary intake level that is sufficient to meet the nutrient requirement of nearly 97.5% healthy individuals in a particular life-stage and gender group |
| AI | Adequate Intake | An adequate intake is the average nutrient level consumed daily by a typical healthy population that is assumed to be adequate for the population's needs. |

| Estimated Calorie Needs per Day, by Age, Sex, and Physical Activity Level | | | |
|---|---|---|---|
| Your Calorie Needs | Sedentary | Moderately Active | Active |
| 2050 | 1800 | 2000 | 2200 |

Sedentary means a lifestyle that includes only the physical activity.
Moderately Active means a lifestyle that includes physical activity equivalent to walking about 1.5 to 3 miles per day at 3 to 4 miles per hour.
Active means a lifestyle that includes physical activity equivalent to walking more than 3 miles per day at 3 to 4 miles per hour.

FIG. 103

Personalized dietary pattern comprising food and amount 10400

| Personalized Dietary Patterns Report | Name: Urvashi Apsara, Age 34, Date: Oct 29, 2022 | |
|---|---|---|
| Calorie Level Assessed | 2050 | |
| Food | Amount | Intelligent Food Required Recommendation |
| Vegetables (cup eq/day) – Daily Amount | 2 ½ | |
| Dark-Green Vegetables (cup eq/weekly) | 1 ½ | Amaranth leaves, basil, mustard green, and lettuce |
| Red and Orange Vegetables (cup eq/weekly) | 5 ½ | Carrots, orange bell peepers, sweet potatoes, and tomatoes |
| Beans, Peas, Lentils (cup eq/weekly) | 1 ½ | Black beans, peas, and mung beans |
| Starchy Vegetables (cup eq/weekly) | 5 | Corn and white potatoes |
| Other Vegetables (cup eq/weekly) | 4 | Avocado, cauliflower, okra, cucumber, eggplant |
| Fruits (cup eq/day) – Daily Amount | 1 ½ | Apples, bananas, orange, nectarine, strawberry, raspberry |
| Grains (ounce eq/day) – Daily Amount | 6 | |
| Whole Grains (ounce eq/day) | 3 | Quinoa, whole wheat chapati, cereals and rice |
| Refined Grains (ounce eq/day) | 3 | White bread, and pasta |
| Dairy (cup eq/day) – Daily Amount | 3 | Buttermilk, yogurt, soy, and milk |
| Protein Foods (ounce eq/day) – Daily Amount | 5 | Oats, buckwheat, millet |
| Meats, Poultry, Eggs (ounce eq/weekly) | 23 | Eggs |
| Seafood (ounce eq/weekly) | 8 | Salmon |
| Nuts, Seeds, Soy Products (ounce eq/weekly) | 4 | Cashew, almonds, pistachio |
| Oils (grams/day) | 24 | Peanut and olive oil |
| 1 cup size is equal to 250mm or 8.5 FL oz or size of tennis ball | | |

| Food | Examples |
|---|---|
| Dark-Green Vegetables | Amaranth leaves, basil, beet greens, bitter melon leaves, broccoli, chrysanthemum leaves, chard, cilantro, collards, cress, dandelion greens, kale, mustard greens, romaine lettuce, spinach, taro leaves, turnip greens |
| Red and Orange Vegetables | Calabaza, carrots, red chili peppers, red or orange bell peppers, pimento/pimiento, sweet potatoes, tomatoes, 100% tomato juice, and winter squash such as acorn, butternut, kabocha, and pumpkin |
| Beans, Peas, Lentils | Black beans, black-eyed peas, brown beans, chickpeas (garbanzo beans), fava beans, kidney beans, lentils, lima beans, mung beans, pigeon peas, pink beans, pinto beans, split peas, soybeans, and white beans. |
| Starchy Vegetables | cassava, corn, jicama, lotus root, lima beans, immature or raw (not dried) peas (e.g., cowpeas, black-eyed peas, green peas, pigeon peas), plantains, white potatoes, salsify, tapioca, taro root, water chestnuts, yam, and yucca |
| Other Vegetables | Artichoke, asparagus, avocado, bamboo shoots, bean sprouts, beets, bitter melon (bitter gourd, balsam pear), Brussels sprouts, cabbage (green, red, napa, savoy), cactus pads, cauliflower, celeriac, celery, chayote (mirliton), chives, cucumber, eggplant, fennel bulb, garlic, ginger root, green beans, iceberg lettuce, kohlrabi, leeks, luffa (Chinese okra), mushrooms, okra, onions, peppers (chili and bell types that are not red or orange in color), radicchio, sprouted beans (e.g. sprouted mung beans), radish, rutabaga, seaweed, snow peas, summer squash, tomatillos, turnips, and winter melons |
| Fruits | Apples, apricots, Asian pears, bananas, berries (e.g., blackberries, blueberries, cranberries, currants, dewberries, huckleberries, kiwifruit, loganberries, mulberries, raspberries, and strawberries); citrus fruit (e.g., calamondin, grapefruit, kumquats, lemons, limes, mandarin oranges, pomelos, tangerines, and tangelos); cherries, dates, figs, grapes, guava, jackfruit, lychee, mangoes, melons (e.g., cantaloupe, casaba, honeydew, and watermelon); nectarines, papaya, passion fruit, peaches, pears, persimmons, pineapple, plums, pomegranates, prunes, raisins, rhubarb, sapote, soursop, starfruit, and tamarind |
| Grains | Barley (not pearled), brown rice, buckwheat, bulgur, millet, oats, popcorn, quinoa, dark rye, triticale, whole-grain cornmeal, whole-wheat bread, whole-wheat chapati, whole-grain cereals and crackers, and wild rice. |
| Refined Grains | White breads, refined-grain cereals and crackers, corn grits, cream of rice, cream of wheat, barley, pasta, and white rice |
| Dairy | All fluid, dry, or evaporated milk, including lactose-free and lactose-reduced products and fortified soy beverages (soy milk), buttermilk, yogurt, kefir, frozen yogurt, dairy desserts, and cheeses |
| Nuts, Seeds, Soy Products | Nuts and seeds include all nuts (tree nuts, cashew, almonds, pistachio and peanuts), nut butters, seeds (e.g., chia, flax, pumpkin, sesame, and sunflower), and seed butters (e.g., sesame or tahini and sunflower). Soy includes tofu, tempeh, and products made from soy flour, soy protein isolate, and soy concentrate. Nuts should be unsalted |
| Oils | Peanut, Olive, Canola, Avocado, Sesame, Canola. |

FIG. 104

Personalized wellness program 10500

| No | Wellness dimension | Program Activity | Current Ranking |
|---|---|---|---|
| 1 | Physical | 1. Eat nutritional food (lifestyle sensor)<br>2. Exercise at least four times a week (biokinetics sensor)<br>3. Drink moderate amount of alcohol (lifestyle sensor)<br>4. Work on reducing weight (biokinetics sensor)<br>5. Monitor blood pressure (physiological sensor)<br>6. Ensure biofluid parameters are within normal reference range (biofluid sensor) | 3 |
| 2 | Environmental | 1. Set up your workspace to be efficient and comfortable (biokinetics sensor)<br>2. Conserve energy by switching off the lights in the computer when not in use (enviro sensor)<br>3. Reduce noise level and exposure to pollution (enviro sensor)<br>4. Reduce exposure to pathogens (microbial biosensor, particulate matter sensor) | 2 |
| 3 | Occupational | 1. Set realistic yearly and career goals (wellness worksheet)<br>2. Set tasks at work or school do you enjoy (wellness worksheet)<br>3. Ensure work environment parameters are in the normal range (enviro sensor)<br>4. Ensure number of occupational interactions are within normal reference range (lifestyle sensor)<br>5. Communicate well with co-workers or other students (wellness worksheet) | 3 |
| 4 | Financial | 1. Programs to bring number of financial interactions out of range lifestyle sensor parameter to normal reference range (lifestyle sensor)<br>2. Document a yearly budget and save money (wellness worksheet)<br>3. Document financial goals and plans (wellness worksheet)<br>4. Increase number of financial interactions (lifestyle sensor) | 3 |
| 5 | Intellectual | 1. Programs to bring number of intellectual interactions out of range lifestyle sensor parameter to normal reference range (lifestyle sensor)<br>2. Learn new skills and exercise brain (wellness worksheet)<br>3. Act on intellectual wellness quiz responses (wellness worksheet) | 4 |
| 6 | Emotional | 1. Programs to bring number of emotional interactions out of range lifestyle sensor parameters to normal reference range (lifestyle sensor)<br>2. Act on emotional wellness quiz responses (wellness worksheet) | 3 |
| 7 | Social | 1. Programs to bring number of social interactions out of range lifestyle sensor parameters to normal reference range (lifestyle sensor)<br>2. Act on social wellness quiz responses for conflicts and communication (wellness worksheet) | 3 |
| 8 | Spiritual | 1. Programs to bring number of social interactions out of range lifestyle sensor parameters to normal reference range (lifestyle sensor)<br>2. Act on spiritual wellness quiz responses for trusting others, forgive people, feeling of inner peace (wellness worksheet) | 3 |
| Wellness Dimension Ranking - Average | | | 3 |
| Wellness dimension ranking ( 1 (poor), 2 (fair), 3 (good), 4 (very good), 5 (excellent) | | | |

FIG. 105

WEARABLE DEVICE FOR CONTINUOUS MONITORING OF USER HEALTH FOR ACCURATE CLINICAL OUTCOMES AND WELLNESS PROGRAMS

CLAIM OF PRIORITY

This application is a continuation-in-part of U.S. patent Ser. No. 11/490,852 granted on 10-19-2022, and claims priority to U.S. patent application Ser. No. 17/397,798 filed on Aug. 9, 2021, and U.S. patent application Ser. No. 17/984,167 filed on Nov. 9, 2022. These patent applications are incorporated herein by reference in their entirety.

FIELD OF THE INVENTION

The present invention relates to the field of detection, measuring, and monitoring of microorganism, particulate matter, environment, physiological, biofluid, biokinetics, and lifestyle parameters, and more specifically to the wearable device comprising a smart band and a display for continuous monitoring of a user health for an accurate clinical outcome assessment and a wellness program for a healthy lifestyle.

DESCRIPTION OF THE PRIOR ART

There exist various types of wearable devices for measuring and monitoring user's or patient's health which allow for early detection of illnesses or disorders. The wearable sensors have recently seen a large increase in both research and commercialization. The noninvasive wearable devices are used for the continuous monitoring of physiological parameters, environment parameters, health, exercise activity, assessing performance, and other monitoring activities. The real-time information from these devices allows individuals to change their lifestyle, optimize exercises or training, prevent hazards, and optimize sleep patterns, among other use cases. Most of these devices are miniaturizations of existing mechanical and electrical machines. The laboratory based devices for microorganism, complete blood count, metabolites, and cholesterol detection require wet lab testing on an in vitro diagnostic instrument. There are no noninvasive in vivo wearable devices which can measure the microorganisms in nasal and oral cavities, microorganisms in surrounding air, complete blood count, metabolites, and cholesterol. In addition, the physiological, environmental, and exercise activity sensors do not measure all the parameters.

Current microorganism, complete blood count, metabolites, and cholesterol detection tests usually require a visit to a hospital for sample collection. This is followed by sending the sample to a clinical laboratory for testing and reporting of the results. Testing is expensive, resource intensive, and time consuming, and results are only available after a few days. Test methods are as follows:

The common microorganism laboratory tests methods are as follows:
1) RT-PCR, which is the synthesis of cDNA (complementary DNA) from RNA by reverse transcription (RT) and the amplification of a specific cDNA by the polymerase chain reaction (PCR) from a nasopharyngeal or oropharyngeal swab sample.
2) Antibody Test, which is based on binding of antibodies from a blood or serum or plasma sample to labeled antigens.
3) Antigen Test, which is based on binding of antigens from a nasopharyngeal or oropharyngeal swab sample to labeled antibodies.
4) Microscope based test, the working principle of which involves viewing of a labeled pathogen image under a microscope from a blood, saliva, or tissue sample.
5) Next-generation sequencing is a term that collectively refers to high-throughput DNA sequencing strategies that can produce large amounts of genomic data in a single reaction by diverse methodologies. Customized pathogens panels allow for detection of pathogens in a sample. Microbial profiling using 16S ribosomal RNA (rRNA) sequencing is a common method for studying bacterial phylogeny and taxonomy.
6) Microarray is a microchip-based testing platform that allows high-volume, automated analysis of many pieces of DNA at once, including pathogen arrays.
7) Mass Spectrometry is useful for measuring the mass-to-charge ratio (m/z) of one or more molecules present in a sample. These measurements can often be used to calculate the exact molecular weight of the sample components as well. The identification of pathogens by Mass Spectrometry can be done by cell enrichment, nucleic acid amplification, or direct sampling methods on microbial samples. The basic principle of mass spectrometry (MS) is to generate ions from either inorganic or organic compounds by a suitable method, to separate these ions by their mass-to-charge ratio (m/z), and to detect them qualitatively and quantitatively by their respective m/z and abundance.

The physiological sensor does not detect healthy blood vessels to accurately measure the physiological parameters, and lacks measurement of blood oxygen, blood carbon dioxide, and associated corrective actions and preventive actions.

The common complete blood count laboratory tests methods consist of a hemocytometer or the use of an automated cell counter.

The metabolites and cholesterol laboratory test methods consist of variety of methodologies to test the countless analytes that are of interest to the medical community. These laboratory methods are based on established scientific principles involving biology, chemistry, and physics.

The breath analyzer testing is based on a portable analyzer but does not provide a complete profile of the breath. The breath testing is usually limited to breath alcohol concentration (BAC).

The existing prior art exercise activity sensors do not measure the stress based on blood cortisol measurements. The normal reference ranges provided are general in nature and not based on the microorganism, particulate matter, environment, physiological, biofluid, and lifestyle sensor parameters result.

The existing prior art lacks lifestyle sensor parameter measurements to calculate and provide a wellness dimension ranking and wellness programs.

These test methods include clinical laboratory testing run on an in vitro diagnostic instrument. The manufacturer of the test must establish analytical and clinical performance. The total testing process in the laboratory is a cyclical process divided into three phases: preanalytical, analytical, and postanalytical. In the pre-analytical phase, the patient sample is collected and sent to a clinical laboratory, where is it accessioned. In the pre-analytical phase for certain methods, the sample must go through microbial culture of multiplying microorganisms by letting them reproduce in predetermined culture media under controlled laboratory conditions. The analytic phase begins when the patient specimen is prepared for testing and ends when the test result is interpreted and verified. The analytical phase includes moderate or high complexity testing on an in vitro diagnostic instrument, using reagents and consumables, by the clinical laboratory scientist. The post-analytic phase is the final phase of the laboratory process. This phase culminates in the creation and reporting of patient results by the laboratory director or laboratory operations. Along with laboratory testing, computed tomography of the chest, commonly known as CT scans, may be helpful to diagnose pathogens like SARS-CoV-2 in individuals with a high clinical suspicion of infection, especially in the lungs. For samples like wastewater, food, and crime scenes, the pathogen or microbial testing is done in specialized labs like water testing laboratories, food testing laboratories, and forensic laboratories, respectively. The above tests and instruments are not noninvasive point of care devices to detect microorganisms, sterilize pathogens, and monitor the surrounding air environment. The tests require specialized laboratories, trained resources, sample transportation, and specialized equipment and consumables.

The management of health and wellness programs and more particularly to a system and method for managing health and wellness programs are based on partial data which is unable to provide comprehensive a wellness program for a healthy lifestyle.

The prior art discussed below does not contain microorganism, particulate matter, environment, physiological, biofluid, biokinetics, and lifestyle sensors in a single ubiquitous wearable smart band. The prior art also does not provide information about the clinical outcome assessments, wellness dimensions ranking, and wellness programs for a healthy lifestyle based on the comprehensive set of sensors, systems, and methods.

European Patent No. EP2430461B2 to Ronnie J. Robinson, et al. discloses an automated instrument and method for rapidly characterizing and/or identifying a microbial agent in a sample, such as blood or other biological sample, stored in a specimen container. As an example, the instrument of this disclosure provides information as to Gram type (positive or negative), morphology, species, or other relevant clinical information of the microbial agent rapidly and automatically. The European Patent to Ronnie J. Robinson et al. does not teach or claim a noninvasive wearable device. The apparatus detection system is bulky and must be installed in a special testing facility. The test sample must be collected and loaded on the system. The patent does not claim multiplex detection of prions, viruses, fungi, protists, dust mites, and pollen using a noninvasive wearable device. It cannot detect many microorganisms, particulate matter, environmental, physiological, biofluid, biokinetics, and lifestyle parameters.

Japan Patent No. JP5707399B2 to Katsuran Lee, et al. discloses a microorganism method, a microorganism detection apparatus, and a program for inspecting an inspection object such as food by detecting bacteria such as *E. coli* and microorganisms such as eukaryotes. The test requires sample collection and laboratory testing. The patent does not support or claim a noninvasive wearable device and detection of prions, viruses, fungi, protists, dust mites, and pollen. The JP5707399B2 patent to Katsuran Lee et al. does not teach detection of many microorganisms, particulate matter, environmental, physiological, biofluid, biokinetics, and lifestyle parameters.

U.S. Patent No. 2016/U.S. Pat. No. 9,291,549 B2 to Eric Schwoebel, et al. discloses a pathogen detection biosensor, which provides methods for the detection of target particles, such as pathogens, soluble antigens, nucleic acids, toxins, chemicals, plant pathogens, blood borne pathogens, bacteria, viruses, and the like. The method for detecting an antigen in a sample comprises a spraying of emitter cells onto a sample. The emitter cell comprises a receptor and an emitter molecule that emits a photon in response to binding of a target antigen in the sample to the receptor. The photon emission is indicative of the antigen in the sample. The optoelectronic sensor device can detect a target particle in a liquid sample, or in an air or aerosol sample. The biosensor size is about 2 feet and bulky. The U.S. Patent to Eric Schwoebel, et al. does not teach or claim a wearable device. It does not test for beneficial microorganisms and pathogens in a nasal and an oral cavity. The technology involved is spraying of emitter cells. It does not have a built in sterilizer, which is very important for disinfection. The device is not portable and carried by the user.

U.S. Patent No. 2005/U.S. Pat. No. 6,996,472 B2 to Jon G. Wilkes, et al. discloses a method of compensating for drift in fingerprint spectra of microorganisms caused by changes in their environment. These methods of compensating for drift permit identification of microorganisms from their fingerprint spectra regardless of the environment from which the microorganisms are obtained. The disclosed methods use a coherent database of fingerprint spectra that may be expanded even though the standard database conditions are no longer experimentally achievable. Embodiments, methods of compensating for drift in pyrolysis mass spectra, constructing coherent pyrolysis mass spectral databases, and identifying bacteria from their pyrolysis mass spectra are disclosed. The U.S. Patent to Jon G. Wilkes, et al. does not teach or claim a wearable device with real time detection of beneficial microorganisms, pathogens, pollen, and environmental conditions. The disclosed method does not include sterilization. The method disclosed is culturing of microorganisms and involves wet laboratory testing. It does not cover the fingerprint spectra database and does not detect viruses and pollen.

U.S. Patent No. 2009/U.S. Pat. No. 7,542,137 B2 to Sangeeta Murugkar, et al. provides a system and method for automatic real-time monitoring for the presence of a pathogen in water using coherent anti-stokes Raman scattering (CARS) microscopy. A water sample trapped in a trapping medium is provided to a CARS imager. CARS images are provided to a processor for automatic analyzing for the presence of image artifacts having pre-determined features characteristic to the pathogen. If a match is found, a CARS spectrum is taken and compared to a stored library of reference pathogen-specific spectra for pathogen identification. The system enables automatic pathogen detection in flowing water in real time. The U.S. Patent to Sangeeta Murugkar, et al. does not teach or claim a wearable device to test for pathogens in a nasal cavity, an oral cavity, on a surface, or in surrounding air. The device is very bulky and cannot be carried by the user and tests for pathogens in water only.

U.S. Patent No. 2020/U.S. Pat. No. 10,724,068 B2 to Mansour Samadpour discloses methods for enrichment and detection of pathogens or other microbes in a food, water, wastewater, industrial, pharmaceutical, botanical, environmental samples, and other types of samples provided. In particular aspects, a sample is obtained and diluted at a first location and incubated at an optimal temperature and either tested locally or sent in a shipping incubator to a second location that may be a remote test location for testing with an assay suitable to detect the pathogen or other microbe.

The U.S. Patent to Mansour Samadpour does not teach or claim a wearable device providing a real time beneficial microorganism, pathogen, and pollen detection. It is liquid sample-based testing run in a laboratory environment.

U.S. Patent No. 2008/U.S. Pat. No. 7,430,046 B2 to Jian-Ping Jiang, et al. discloses a particle detector that has a sample area of cross section not in excess of about 2 mm for containing environmental fluid, a light source on one side of the sample area for directing a collimated or nearly collimated beam of light through the sample air or water so that part of the light beam will be scattered by any particles present in the air or water while the remainder remains unscattered, and a beam diverting device on the opposite side of the sample area for diverting or blocking at least the unscattered portion of the beam of light and directing at least part of the scattered light onto a detector. The detector produces output pulses in which each pulse has a height proportional to particle size, and a pulse height discriminator obtains the size distribution of airborne particles detected in the air or water sample at a given time from the detector output. The detector may also include a device for discriminating between biological agents and inorganic particles. The U.S. Patent to Jian-Ping Jiang, et al. does not teach or claim a wearable device to detect and sterilize pathogens. The detector cannot be worn by the user for rapid detection of the pathogens.

WO Patent No. WO 2017/136383 to Martin, et al. discloses embodiments that can provide a watchband with integrated electronics, a method for manufacturing a watchband with integrated electronics, a method of over molding electronics, and a flexible electronic strip, comprising one or more electronic modules; and one or more modular batteries. The flexible strip and/or watchband can have multiple sensors, electronics, batteries, vibration motors, and/or buttons. The over molding can be protective, waterproof, and flexible. A volume of protective material can be applied via a sleeve application or through over molding layer deposition. Martin, et al. does not teach a sensing cavity that can detect picometer, nanometer, and micrometer particle sizes and ensure the differentiation and identification of the suspended particles in the air in terms of pathogens, beneficial microorganisms, pollen, dust mite allergens, and so on. The WO Patent to Martin, et al. does not teach or claim a microbial biosensor and a particulate matter sensor, to detect microorganisms. Martin, et al. does not claim a physiological sensor, a biofluid sensor, a biokinetics sensor, and a lifestyle sensor. The WO Patent 136383 to Martin, et al. air quality sensor is only used to detect the ambient humidity and air quality. The air quality sensor can be chemical or electrical but cannot detect microorganisms. To detect microorganisms, the Martin specification should describe a microorganism database with detection size, unique identifiers, and associated detection method. Martin, et al. cannot detect the RFID tag, location, sound, and ultraviolet light. The location sensor has the position and elevation data of the user which allows for pollen, allergy, and dust mites risk levels information associated with the geolocation map. The Martin, et al. specification does not teach that risk factors allow the user to take appropriate corrective actions and protective actions to prevent exposure to unhealthy environmental conditions.

US Patent App. 2016/US 0062623 A1 to Howard, et al. discloses a system and method are described for delivering content to a mobile device using a companion device. The companion device acts as a proxy device to send and receive signals on behalf of other proxied devices. Once content is loaded onto the mobile device, a user can navigate through the content using a navigation path determined based on a user's item of focus. Various transitions and animations can be displayed along the navigation path. Moreover, a user can interact with the content when viewed in a specific layout using touch events or a rotation input device. The US Patent App to Howard, et al. does not teach or claim a microbial biosensor, a particulate matter sensor, an enviro sensor, a physiological sensor, a biofluid sensor, a biokinetics sensor, a lifestyle sensor, and a mobile healthcare application function/structure navigation to view the sensor results.

US Patent App. 2020/US 0152312 A1 to Connor discloses a system for nutritional monitoring and management which includes a camera, a spectroscopic sensor, a fiducial component, a wearable biometric sensor, a smart utensil or dish, a passive feedback mechanism which provides a person with information concerning food item types and/or quantities, and an active stimulus mechanism which modifies the person's food-related physiological processes. This system can help a person to improve their dietary habits and health. Connor does not teach a wearable device which can detect the microorganism, pollen, dust mite allergen, particulate matter concentration, and air quality in the surrounding air including the environment parameters. Connor [0453] states that "wearable device which emits light beams toward food and receives light beams after the light beams have been reflected from (or passed through) food" and "food are analyzed to identify chemicals and/or microbes in the food," but does not teach or claim a wearable smart band with detection of microorganisms in a nasal cavity, an oral cavity, or on a surface where the reflection pattern is based on anatomy of the oral cavity, nasal cavity, and object type. The reflection pattern is different from the nasal cavity anatomy consisting of nostrils, nasal mucosa, nasal vestibule, and the oral cavity anatomy consisting of tongue, retromolar trigone, soft plate, hard palate, uvula, tonsil, and buccal mucosa than the food surface due to epidermal and dermal absorption, scattering, and reflection. This includes the variety of skin surface, pigmentation, and presence of melanin and collagen. In addition, the microorganism detection in a nasal cavity, an oral cavity, or on a surface requires multiple methods such as nucleic acid sequence identification, fluorescence imaging, and electromagnetic waves, including a microorganism database containing unique identifiers. Connor [0453] and [0123] does not teach or claim use of a camera for identification of microorganisms. It uses a camera for recording images of food items, wherein the images are analyzed to help identify food item types and/or estimate food item quantities, whereas the present invention uses picocamera 318, which takes images and videos of the small particles such as small molecules, proteins, microorganisms, and, after image analysis identifies the microorganism type. Connor does not teach or claim a Microbial biosensor result, a particulate matter sensor result, an enviro sensor result, a physiological sensor result, a biofluid sensor result, and a biokinetics sensor result to help a person to improve their dietary habits and health.

US Patent App. 2022/US 0084650 A1 to Rakshit discloses an approach for a computer in a robotic arm device attached to a patient to receive data identifying at least one protected area of the patient from a computing device of a medical professional. The approach includes the computer receiving instructions for one or more actions by the robotic arm device associated with at least one protected area of the patient from the computing device of the medical professional. Additionally, the approach includes the computer receiving sensor data associated with one or more movements of the patient from one or more sensors in the robotic arm device and determining that a hand of the patient in the robotic arm device is entering at least one protected area. Furthermore, the approach includes the computer initiating one action of one or more actions by the robotic arm device that is associated with at least one protected area of the patient. Rakshit teaches a wrist band (22) is part of a robotic arm for patient protection particularly post-surgery to prevent the patient from contaminating specific surgical areas or surgical stitches specifically to clean their hands via UV light or chemical disinfectant. Rakshit does not teach a portable wearable device with a sterilizer to disinfect a nasal cavity, an oral cavity, or a surface. The wrist band (22) is attached to the robotic arm device (10), making it very difficult for a patient to sterilize the nasal cavity and an oral cavity. The chemical spray disinfection used for the hand is harmful to the nasal cavity, oral cavity, and potentially to a surface. Rakshit does not teach a wrist band (22) which can be used to detect pathogens to make sure that sterilization did indeed kill pathogens and the disinfection process was successful.

US Patent App. 2010/US 0217099 to LeBoeuf, et al. discloses a monitoring apparatus and methods provided for assessing a physiological condition of a subject. At least two types of physiological information are detected from a subject via a portable monitoring device associated with the subject, and an assessment of a physiological condition of the subject is made using the at least two types of physiological information, wherein each type of physiological information is individually insufficient to make the physiological condition assessment. Environmental information from a vicinity of a subject also may be detected, and an assessment of a physiological condition of the subject may be made using the environmental information in combination with the physiological information. Exemplary physiological information may include subject heart rate, subject activity level, subject tympanic membrane temperature, and subject breathing rate. Exemplary environmental information may include humidity level information in the vicinity of the subject. An exemplary physiological condition assessment may be subject hydration level. LeBoeuf, et al. claims a wearable device ([0137]) which is headset or earpiece monitoring apparatus for physiological and environmental information. As per the claim [6][27], the environmental information detected and claimed is ambient humidity level. LeBoeuf, et al. [0010-0011; 0076-0077] contains long list of physiological and environmental information that can be detected, including identity and/or concentration of viruses and/or bacteria without specification of detection such as microbial biosensors, cameras, databases, software, and methods. LeBoeuf, et al. [0010-0011] does not teach detection of prions, protists, fungi, dust mites, dust mite allergens, and sterilizer to kill pathogens. LeBoeuf, et al. merely lists physiological and environmental information that can be detected. The claim [6][7] is for ambient humidity level. LeBoeuf, et al. does not claim or provide specification of wrist wearable microbial sensors, cameras, databases, software, and methods.

US Patent App. 2017/US 0112434 to John A. Lane discloses aspects of the subject disclosure that may include, for example, detecting, by a substance delivery system coupled to a body part of an individual, an input signal not associated with a biological measurement of the individual, determining from the input signal, by the substance delivery system, whether delivering a dosage of a substance stored in the substance delivery system is needed and conforms to a dosage policy, and responsive to determining from the input signal that delivery of the dosage of the substance is needed and conforms to the dosage policy, initiating, by the substance delivery system, delivery of the dosage of the substance to the body part of the individual. Other embodiments are disclosed. Lane teaches a method and apparatus for delivering a dosage of a substance to an individual. Lane [0175] does not teach or claim pathogen and beneficial microorganism detection. Lane does not teach detection of a pollen type source, name, disease, source, shape, and size list [3300], and pollen tree taxonomy, pollen allergy, annotation, pollen safety data sheet information [3456]. Lane does not teach and provide information for dust mite taxonomy, genome annotation, and pathogen safety data sheet table [2184]. In order to detect additional particles related to allergy or asthma, Lane does not teach or list specifications containing unique identifiers, detection methods, and hardware.

US Patent App. 2008/US 0146890 to LeBoeuf, Tucker, et al. discloses a wearable apparatus for monitoring various physiological and environmental factors. Real-time, noninvasive health and environmental monitors include a plurality of compact sensors integrated within small, low-profile devices, such as earpiece modules. Physiological and environmental data is collected and wirelessly transmitted into a wireless network, where the data is stored and/or processed.

US Patent App. 2020/US 0345300 to Potyrailo, et al. discloses a sensor system that includes a first sensor to detect environmental conditions of an environment in operational contact with a subject, a second sensor to detect physiological parameters of the subject in operational contact with an asset, and a control unit comprising one or more processors communicatively coupled with the first sensor and the second sensor. The processors receive a first signal from the first sensor indicative of the environmental conditions and receive a second signal from the second sensor indicative of the physiological parameters of the subject and determine a relation between the environmental conditions and the physiological parameters based on the first signal and the second signal. The processors determine a responsive action of the asset based on the first signal indicative of the environmental conditions of the environment or the second signal indicative of the physiological parameters of the subject in operational contact with the asset. Potyrailo, et al. does not teach a wearable device with environmental sensors ([0040]) that sends the biosafety alert based on biosafety levels (BSLs) when pathogens are detected, dust mite allergens, location which is important for a national allergy map, ultraviolet light, high temperatures, humidity, and so on. Potyrailo, et al. does not teach or claim a microbial biosensor, a biofluid sensor, a biokinetics sensor, and a lifestyle sensor.

US Patent App. 2019/US 0117099 to Bardy, et al. discloses an electronic medical record (EMR) with the results of the monitoring that can be stored in a cloud-computing environment. All communications with the cloud-computing environment are performed via a secure connection. Each of the EMRs can be associated with an identifier that is provided with the results of the monitoring data. The EMRs can be created, viewed, and modified using a mobile application. The mobile application can use a scanner in the mobile device on which the application executes to obtain an identifier and uses the identifier to direct actions of the user towards the appropriate EMR. The mobile application can further provide additional user access verification. Alerts can further be provided through the mobile application. The data processed by the Bardy system is ECG physiological data received from the sensor. Bardy, et al. does not teach a wearable monitoring device system with a cloud server which can process microbial biosensor parameters result, particulate matter sensor parameters result, enviro sensor parameters result, and intelligent relationship interpretation data.

U.S. Patent No. 2003/U.S. Pat. No. 6,579,231 B1 to Eric T. Phipps discloses a portable unit worn by a subject, comprising a medical monitoring device and a data processing module with memory and transmitter for collecting, monitoring, and storing the subject's physiological data and issuing the subject's medical alarm conditions via wireless communications network to the appropriate location for expeditious dispatch of assistance. The unit also works in conjunction with a central reporting system for long term collection and storage of the subject's physiological data. The U.S. Patent to Eric T. Phipps does not teach or claim a wearable device that detects the healthy blood vessels for accurate physiological measurements based on age, problematic blood vessels, smaller or hidden blood vessels, genetic predisposition, and so on for monitoring parameters. The device does not include blood oxygen and blood carbon dioxide monitoring. The physiological data does not consider the pathogenic microbial information in the nasal cavity, oral cavity, or surrounding environment. Further it does not predict physiological risk levels including use of the physiological data for user wellness programs for early intervention to prevent illness. The portable unit alerts are based on physiological data and the alerts do not consider microorganism, particulate matter, environmental, biofluid, biokinetics, and lifestyle parameters results.

U.S. Patent No. 2020/U.S. Ser. No. 10/687,717 B1 to Peterson, et al. discloses wearable devices and methods for measuring a photoplethysmography (PPG) signal. The wearable devices and methods described can obtain PPG signals by employing a PPG sensor array configured to receive light at angles associated with a high perfusion index. Viewing components may be coupled to the PPG sensor array to effect transmission of light at these preferential angles. The scope of the patent is limited to a PPG sensor having light arrival angle control at detector. The U.S. Patent to Peterson, et al. does not disclose or claim a wearable device to detect microorganism, particulate matter, physiological, environmental, biofluid, biokinetics, and lifestyle parameters. The claim does not include alerts and prediction of risk levels for users to take appropriate preventive measures before health deteriorates.

U.S. Patent No. 2020/U.S. Ser. No. 10/694,960 B2 to Saponas, et al. discloses wearable pulse pressure wave sensing devices presented that generally provide a non-intrusive way to measure a pulse pressure wave traveling through an artery using a wearable device. In one implementation, the device includes an array of pressure sensors disposed on a mounting structure which is attachable to a user on an area proximate to an underlying artery. A pulse pressure wave is then measured using the pressure sensor of the array closest to the identified location. The U.S. Patent to Saponas, et al. does not teach a location of healthy blood vessels by NIR based on light scattering and absorption differences between RBC and surrounding tissues but relies on attachment on an area underlying the artery. The U.S. Patent to Saponas, et al. relies on a pulse pressure wave travelling through an artery instead of an NIR wavelength penetrating the skin and reaching the dermis to detect HbO2 and HbO in RBC to find the healthy blood vessels. The U.S. Patent to Saponas, et al. does not claim a wearable device to detect microorganism, particulate matter, environmental, biofluid, biokinetics, and lifestyle parameters.

U.S. Patent No. 2017/US 0340209 A1 to Klaassen, et al. describes non-invasive devices, methods, and systems for determining a pressure of blood within a cardiovascular system of a user, the cardiovascular system including a heart and the user having a wrist covered by skin. Approaches disclosed allow for absolute blood pressure values to be determined directly without the requirement for any periodic calibrations or for relative blood pressure values to be tracked to provide relative blood pressure indices. The U.S. Patent to Klaassen, et al. does not teach or claim physiological risk levels associated with the indices based on other parameters measured like heart rate, heart rate variability, blood oxygen level, blood carbon dioxide level, and environmental sensor data. It does not teach calculation of a risk level, providing proactive alerts to prevent deterioration of health. The patent to Klaassen, et al. does not detect microorganism, particulate matter, environmental, biofluid, biokinetics, and lifestyle parameters.

U.S. Patent No. 2019/U.S. Ser. No. 10/299,708 B1 to Poeze, et al. disclosure relates to noninvasive methods, devices, and systems for measuring various blood constituents or analytes, such as glucose. In an embodiment, a light source comprises LEDs and super-luminescent LEDs for measurement of oxygen, carbon monoxide, total hemoglobin, glucose, proteins, and lipids. U.S. Patent to Poeze, et al. is bulky and not a wearable device and cannot detect the complete human blood cells and comprehensive metabolites. The data exchange is through an ethernet port and USB interfaces. Poeze, et al. noninvasive system does not have a microbial biosensor, enviro sensor, biokinetics sensor, and lifestyle sensor.

U.S. Patent No. 2011/U.S. Pat. No. 8,086,301 B2 to Cho, et al. discloses a method of cufflessly and non-invasively measuring blood pressure in a wrist region of a patient in association with a communication device that relays the information being measured, which includes: detecting a magnitude difference between a plurality of pulse wave signals detected from a wrist of a user; detecting feature points from an electrocardiogram (ECG) and pulse wave signals detected from the user; extracting variables needed to calculate the highest blood pressure and the lowest blood pressure using the detected feature points; and calculating the highest blood pressure and the lowest blood pressure of the user by deducing a scatter diagram using the extracted variables. The U.S. Patent to Cho, et al. does not teach how to measure the blood pressure after detecting the healthy blood pressure. It also relies on an ECG measurement to detect the blood pressure. It also does not detect the blood pressure using two independent methods simultaneously to increase the accuracy of the results. The patent to Cho, et al. does not detect microorganism, particulate matter, environmental, biofluid, biokinetics, and lifestyle parameters.

U.S. Patent No. 2015/U.S. Pat. No. 8,945,017 B2 to Venkatraman, et al. discloses a wearable heart rate monitor to determine a user's heart rate by using a heartbeat waveform sensor and a motion detecting sensor. In some embodiments, the device collects concurrent output data from the heartbeat waveform sensor and output data from the motion detecting sensor, detects a periodic component of the output data from the motion detecting sensor, and uses the periodic component of the output data from the motion detecting sensor to remove a corresponding periodic component from the output data from the heartbeat waveform sensor. From this result, the device may determine and present the user's heart rate. It does not teach detection of the healthy blood vessels for accurate heart rate measurements, heart rate variability, and associated symptoms. The U.S. Patent to Venkatraman, et al. does not teach or claim simultaneous detection of the important physiological parameters such as respiratory rate, blood pressure, blood oxygen level, and blood carbon dioxide level and their association to the heart rate measured. The method focuses on detection of the heart rate. The U.S. Patent to Venkatraman, et al. does not disclose a wearable device to detect microorganism, particulate matter, environmental, biofluid, biokinetics, and lifestyle parameters.

U.S. Patent No. 2020/U.S. Ser. No. 10/624,550 B2 to Soli, et al. discloses user interfaces for health monitoring. Exemplary user interfaces for initial setup of health monitoring using a first electronic device and a second electronic device are described. Exemplary user interfaces for recording biometric information for use in health monitoring are described. Exemplary user interfaces for using an input device while recording biometric information for health monitoring are described. Exemplary user interfaces for viewing and managing aspects of health monitoring are described which include heart rhythm and heart rate evaluation. The U.S. Patent to Soli, et al. does not teach or disclose detection and user interfaces for monitoring of microorganism, particulate matter, environmental, biofluid, biokinetics, and lifestyle parameters. The U.S. Patent to Soli, et al. health monitoring does not include wellness dimensions monitoring.

U.S. Patent No. 2022/U.S. Ser. No. 10/561,321 B2 to Valys, et al. discloses devices, systems, methods, and platforms for continuously monitoring the health status of a user, for example the cardiac health status PPG signals, heart rate or blood pressure from a user device in combination with corresponding (in time) data related to factors that may impact the health indicator to determine whether a user has normal health as judged by or compared to a group of individuals impacted by similar other factors, or the user him/herself impacted by similar other factors. The U.S. Patent to Valys, et al. monitors part of physiological parameters. It does not monitor other physiological data such as skin temperature, body temperature, blood oxygen levels, and blood carbon dioxide levels that may impact the health. The comparison of the physiological data is based on comparison to a group of individuals impacted by similar other factors only, but does not include detection, monitoring, and comparison of other related vital parameters such as microorganism, particulate matter, environmental, biofluid, biokinetics, lifestyle, and wellness dimensions.

U.S. Patent No. 2018/U.S. Pat. No. 9,974,451 B2 to Robert Steven Newberry discloses a health care band that operably attaches a biosensor to a patient. The biosensor includes one or more sensors for collecting vitals of a patient and a wireless transmitter that is configured to communicate with an EMR network that stores and maintains an EMR of the patient. The sensors in the biosensor may include a temperature sensor and motion detector/accelerometer. In addition, one of the sensors includes a photoplethysmography (PPG) based sensor configured to measure a patient's vitals continuously or periodically, such as heart rate, pulse, blood oxygen levels, and nitric oxide concentration levels. The U.S. Patent to Newberry does not teach or claim a physiological sensor to detect healthy blood vessels for accurate measurements of heart rate, pulse, blood oxygen levels, and nitric oxide concentration levels and does not include measurement of skin temperature, body temperature, respiratory rate, blood pressure, and ECG. The U.S. Patent to Newberry does not teach a band to detect and measure microorganism, particulate matter, environmental, biofluid, biokinetics, and lifestyle parameters.

U.S. Patent No. 1993/U.S. Pat. No. 5,246,004 to Clarke, et al. discloses systems and methods for non-invasive blood analysis in which blood is illuminated at a plurality of discrete wavelengths selected from the near infrared spectrum. Measurements of the intensity of reflected or transmitted light at such wavelengths are taken, and an analysis of reflectance or transmittance ratios for various wavelengths is performed. Changes in the ratios can be correlated to concentration of cholesterol in a subject's circulatory system. The U.S. Patent to Clarke, et al. does not teach or claim a portable multisensor and multiparameter measurements device which detects a healthy blood vessel for accurate measurement of HDL cholesterol, LDL cholesterol, and triglycerides. The U.S. Patent to Clarke, et al. is based on measurement of only cholesterol.

U.S. Patent No. 2018/U.S. Pat. No. 9,870,716 B1 to Rao, et al. discloses a system for wearable devices including intelligent electronic devices, smart glasses, smart watches, and smart devices. A variety of sensors may be integrated into a wearable smart watch device for health management, voice commands, and lifestyle management. The glasses may continuously screen the food consumed by an individual and analyze the food content based on the size of the morsel, consistency, transparency, and other factors. The device may image various people and assess health factors including hydration rate, skin health such as skin rashes, and pulse rates. This may be determined using image recognition and shining a light source on the skin to determine the rate of blood flow and refractory of the light. The U.S. Patent to Rao, et al. does not teach or claim a ubiquitous simple wearable device which monitors multiple parameters. A person must use smart glasses, watches, and other multiple devices. The device does not detect microorganism, particulate matter, environmental, physiological, biofluid, biokinetics, and all lifestyle parameters. The lifestyle parameters are limited to monitoring of food intake and calorie consumption only. Wearable devices do not measure the breath content. They do not teach or cover the entire spectrum of personalized wellness dimensions such as physical, environmental, occupational, financial, intellectual, emotional, social, and spiritual.

U.S. Patent No. 2011/U.S. Pat. No. 7,967,731 B2 to David H. Kil discloses a system and method for motivating users to improve their wellness utilizing complex event processing on sensor and user-interaction data of the users collected over time using inference and predictive models to deliver personalized interactions to motivate the users toward their wellness goals. The U.S. Patent to Kil does not teach or disclose a wearable device with sensors to monitor microorganism, particulate matter, environmental, physiological, biofluid, biokinetics, and all lifestyle parameters. The method relies on user interactions and interfaces to other systems data instead of proactively collecting data and performing analytics and providing wellness programs. Wearable devices do not measure the user breath content. They do not cover the entire spectrum of personalized wellness dimensions such as physical, environmental, occupational, financial, intellectual, emotional, social, and spiritual and provide proactive recommendations to improve the health and well-being of the user.

U.S. Patent No. 2017/U.S. Pat. No. 9,536,449 B2 to Connor discloses a device and system for monitoring a person's food consumption comprising: a wearable sensor that automatically collects data to detect eating events; a smart food utensil, probe, or dish that collects data concerning the chemical composition of food which the person is prompted to use when an eating event is detected; and a data analysis component that analyzes chemical composition data to estimate the types and amounts of foods, ingredients, nutrients, and/or calories consumed by the person. In an example, the wearable sensor can be part of a smart watch or smart bracelet. In an example, the smart food utensil, probe, or dish can be a smart spoon with a chemical composition sensor. The integrated operation of the wearable sensor and the smart food utensil, probe, or dish disclosed in this invention offers accurate measurement of food consumption with low intrusion into the person's privacy. The U.S. Patent to Connor does not detect number of smoking occurrences, number of bathroom visits, breath content, and number of wellness interactions. The U.S. Patent to Connor also relies on smart utensils instead of a portable wrist wearable device detecting and measuring types and amount of foods. The U.S. Patent to Connor does not cover the entire spectrum of personalized wellness dimensions such as physical, environmental, occupational, financial, intellectual, emotional, social, and spiritual and provide recommended actions to provide proactive recommendations on type and time of food consumption. The U.S. Patent to Connor does not teach availability of microorganism, particulate matter, environmental, physiological, biofluid, biokinetics, and all lifestyle parameters data from the wearable device to provide wellness programs recommendations.

U.S. Patent No. 2011/U.S. Pat. No. 7,967,731 B2 to Kil discloses a system and method for motivating users to improve their wellness utilizing complex event processing on sensor and user-interaction data of the users collected over time using inference and predictive models to deliver personalized interactions to motive the users toward their wellness goals. The U.S. Patent to Kil does not teach a wearable device with sensors to monitor microorganism, particulate matter, environmental, physiological, biofluid, biokinetics, and all lifestyle parameters. The method does analysis on sensor data received from other wearable electronics. It does not categorize the wellness states to more personalized and focused wellness dimensions such as physical, environmental, occupational, financial, intellectual, emotional, social, and spiritual. The personalized intervention does not have real time data available from the wearable device to provide proactive recommendations to improve the health and well-being of the user based on user sensor data.

U.S. Patent No. 2014/US 0335469 A1 to Boyden, et al. discloses an oral illumination apparatus configured for placement in a mouth. The oral illumination apparatus includes a housing configured to be coupled to a structure in the mouth. The housing including a processing circuit. The oral illumination apparatus further includes a sensor coupled to the housing and configured to detect a characteristic from within the mouth. In one configuration the sensor detects bacteria, and based on the detected level of bacteria, the activated light may be an ultraviolet light (to kill the bacteria). The U.S. Patent to Boyden, et al. is a bulky user customized illuminated dental brace that must be placed in the mouth compared to a wrist wearable device which can be used by anyone. The U.S. Patent to Boyden, et al. does not claim a method of sterilization of the bacteria in the mouth. It cannot detect and sterilize pathogens such as prions, virus, fungi, protists, dust mites, and so on. The U.S. Patent to Boyden, et al. does not claim a method of sterilization using heat, wavelengths of certain type, and acoustic waves.

KR 2022 0003433A discloses a wearable device and a driving method thereof, and the wearable device driving method according to the present invention is a method of driving a wearable device having a non-contact body temperature detection unit, and when a nearby subject within a reference distance is detected, alarming the user, and notifying the user of the body temperature measurement result. KR 2022 0003433A states it is possible to have a UV sterilization function to sterilize objects when necessary. KR 2022 0003433A does not teach or claim detection of pathogens in the nasal cavity, oral cavity, and on a surface. KR 2022 0003433A does not teach sterilization of pathogens in the nasal and oral cavity. The sterilization of pathogens on the object is based on body temperature and fever and not on accurate detection using a microbial biosensor.

WO 2021/231287 to Poteet discloses an eyeglass device for inactivating a pathogen that includes an eyeglass frame connectable with a face of a person and a pair of lenses connected with the eyeglass frame. The pair of lenses includes a composition that blocks some wavelengths of beams of ultraviolet light. The eyeglass device includes a light affixed to the eyeglass frame and that emits an ultraviolet light beam where methods of inactivating a pathogen are also described. Inactivating the pathogen has a form of an aerosol droplet that is floating in front of the face of the person. The eyeglass device frame includes the light emission sources to inactivate the pathogens. WO 2021/231287 to Poteet does not teach or claim detection and sterilization of pathogens in the nasal and oral cavity. It does not provide information on the pathogen type, concentration, and safety information.

U.S. Patent App. No. 2017/US 0156597 A1 to Peter Whitehead discloses a detection systems and methods configured to scan and interpret a suspected infection at an in vivo biological target site, and then based at least in part on the sensed fluorescent light and the heat levels, determining a probability whether the target site comprises an infection and differentiation between viral and bacterial infections. U.S. Patent App. to Peter Whitehead differentiates virus and bacteria in infection based on the probability and cannot accurately detect the pathogens such as prions, fungi, and protists in the nasal cavity, oral cavity, and the surrounding air. The U.S. Patent App. to Peter Whitehead cannot sterilize the pathogens.

U.S. Patent App. No. 2010/US 0056873 to Allen, et al. discloses a systems and methods for configuring and using displays, speakers, or other output devices positioned by an article of clothing or other such structure wearable by a healthcare recipient, for example, in a clinic or residential care facility. U.S. Patent App. to Allen, et al. in [0057][0059] including application of existing technologies [0127] states that markers may be used for monitoring targeted physiological constituents and/or pathogens. Allen, et al. in [0058] lists receipt of chemical components, proteins and/or structures. U.S. Patent App. to Allen, et al. does not teach or claim a wearable device to detect beneficial microorganisms such as virus: bacteriophages, bacteria: *lactobacillus, micrococcus*, fungi: saprophytic, prototists, and other microbes in the nasal cavity, oral cavity, on the surface, and in the surrounding air that play a crucial role in health. Allen, et al. does not claim or teach a wearable device to detect beneficial microorganisms. Allen, et al. does not teach sterilization of the pathogens. Allen, et al. does not provide information about the safety data sheet with complete detail of infectious agent, hazardous, transmission mode, medical aid, exposure controls, and personal protection information. U.S. Patent App. to Allen does list transmission of data but does not teach, claim, and describe a specification or method to detect the microbial biosensor, biofluids, biokinetics, and lifestyle parameters.

U.S. Patent App. 2016/US 0022024 A1 to Vetter, et al. discloses a fastenable device for oral area position detection that is fastenable to oral care implements. In U.S. Patent App. to Vette,r et al. [0070], that device may comprise other sensors such as biological sensors (e.g., assessing bacteria types, and levels). Vetter, et al. does not teach the distinction between pathogenic and beneficial bacteria, and the fastenable device cannot selectively sterilize the pathogenic bacteria. U.S. Patent App. to Vetter, et al. does not teach a biological sensor to detect microorganisms such as prions, virus, fungi, protists, dust mites, and so on in the nasal cavity and on the surface of an object.

U.S. Patent App. 2016/US 0177366 to Auner, et al. discloses a hand-held micro-Raman based detection instrument and method of detection, where a Raman spectroscopy based system and method for examination and interrogation provides a method for rapid and cost effective screening of various protein-based compounds such as bacteria, virus, drugs, and tissue abnormalities. The Auner, et al. detection method is limited to a Raman spectroscopic instrument. Not all the microorganisms, pollen, dust mite allergens, and so on can be detected using the Raman spectroscopic instrument. Auner, et al. does not teach or claim a wearable device that can also detect beneficial microorganisms, pollen, and dust mite allergens. Auner, et al. does not teach detection of virus and bacteria in the surrounding air.

U.S. Patent 2010/US 0113892 to Kaput, et al. discloses a method for determining personalized nutrition and diet using nutrigenomics and physiological data. U.S. Patent to Kaput, et al. does not disclose or teach a wearable device with a smart band which can measure important CBC, metabolic, lipid, biokinetics, and lifestyle data to continuously determine the personalized diet and nutrition.

U.S. Patent 2015/US 0371553 to Michael T. Vento discloses a system and method for personalized nutrition. A system including a web-based application that creates a personalized diet and then communicates with a client (for example, by mobile phone) application to provide eating options, including telling a user what menu items will fit with his personalized diet at restaurants is disclosed. The U.S. Patent to Michael T. Vento does not disclose a proactive wearable device with a smart band to calculate and provide the nutrition and dietary supplement information.

There exist several beneficial microorganism and pathogen testing-based patents for RT-PCR, microarray, next generation sequencing (NGS), clustered regularly interspaced short palindromic repeats (CRISPR), mass spectrometer, and microscope enzyme-linked immunosorbent assay (ELISA), an analytical technique to detect the presence of an antigen or antibody in a given sample. There are microscope-based methods which involve identification of bacteria based on morphological features of the cells, which can be visualized via microscopic observation, staining to detect important cellular structure, hyperspectral imaging darkfield microscopy, and so on. There also exist self-test devices or point of care pathogen testing devices which require sample collection and testing. All these patents involve wet lab clinical laboratory-based testing. These methods are limited to testing few beneficial microorganisms and pathogen types and are time consuming. The test requires a clinical laboratory facility and skilled clinical laboratory scientist. The testing protocol consists of use of in vitro diagnostic instruments, reagents, consumables, software, and data intensive computers.

Clinical laboratory test results play an integral role in the identification, assessment, and treatment of patients with disease. While every effort is made to generate test results that accurately reflect the condition of the patient, error can occur at all stages of the testing process.

In summary, the scope and contents of the prior art of the above beneficial microorganisms, pathogen devices, and detectors for testing and sterilizing pathogens are limited because of size of the device, fixed location, laboratory-based testing, and not being wearable devices. The pathogen testing is limited to few pathogen types within each of the categories of viruses, bacteria, and fungi. As such there exists a need for an inexpensive wearable device which can noninvasively detect both beneficial microorganisms and pathogens such as prions, viruses, bacteria, fungi, dust mites, pollen, and so on in a nasal cavity, an oral cavity, on a surface, or in the air surrounding the user in a cost-effective manner. The wearable device should also allow for detection of the pollen in the air, allergy forecast, and environmental conditions. The wearable device allows the user to diagnose medical diseases and conditions associated with pathogens, allergens, and pollen, and predict treatment response or reactions and define or monitor therapeutic measures in consultation with their physician.

The innovative wearable device is suitable for testing beneficial microorganisms, pathogens, pollens, and dust mite allergens. Lately, due to spread of infectious diseases like COVID-19, Dengue, Ebola, ringworm, strep throat, food poisoning, and other diseases, it has become increasingly important to do real time testing for pathogens like prions, viruses, bacteria, fungi, protists, dust mites, and so on without collecting a sample. The wearable device can also sterilize the pathogens. The wearable device does not use substrates made of glass, paper, polymer, and silicon with nasal, oral, blood, serum, tissue, or surface samples as needed by traditional wet lab-based test.

In conclusion, compared to prior art, the present invention incorporates a wearable device which comprises innovative sensors, picometer sensing hardware, and particle detection methods. The set of picoprobes and a picocamera are configured to locate a healthy blood vessel for a noninvasive in vivo measurement of physiological and biofluid parameters. A wearable device consists of a smart band and a display unit. The smart band comprises a microbial biosensor, a particulate matter sensor, an enviro sensor, a physiological sensor, a biofluid sensor, a biokinetics sensor, and a lifestyle sensor. The microbial biosensor detects, measures, and monitors a beneficial microorganism count, a beneficial microorganism type, and a beneficial microorganism concentration, a pathogen count, a pathogen type, a pathogen concentration, and a pathogen biosafety level in a nasal cavity, an oral cavity, or on a surface. The microbial biosensor sterilizer kills pathogens. The particulate matter sensor detects, measures, and monitors a set of suspended particles in the surrounding air comprising a beneficial microorganism, a pathogen, a pollen, and an air quality index. The enviro sensor detects, monitors, and measures environmental conditions surrounding the user including the cosmic ray, solar flare, ozone, and a climate change level. The physiological sensor detects, measures, and monitors physiological parameters of the user. The biofluid sensor detects, measures, and monitors biological fluid parameters of the user. The biokinetics sensor detects, measures, and monitors physical activities of the user. The lifestyle sensor detects, measures, and monitors healthy lifestyle activities of the user. The agile sensor detection methods based on machine learning algorithms implement, operate, detect, measure, monitor, and store sensor data locally and transmit to the cloud server. The wearable device is a point of care (POC) device providing results while with the user or close to the user. Currently the total number of blood count, metabolic and cholesterol clinical laboratory tests performed in the USA alone is approximately 5 billion tests annually. A very high number of unnecessary tests are eliminated due to availability of intelligent relationship interpretation data resulting in billions of dollars in savings. The wearable device eliminates user/patient sample collection, transportation, laboratory testing, reporting of results, and associated biohazardous medical waste for the detection of microorganism, particulate matter, enviro, physiological, biofluid, biokinetics, and lifestyle parameters. The set of sensor parameters result comprises: a symptom, a cause, a treatment, and an intelligent relationship interpretation when the set of sensor parameters value falls outside a normal reference range. The smart band noninvasive in vivo measurement of the set of sensor parameters are configured for a reduced number of hospital visits, eliminates medical waste, and reduces healthcare cost. The smart band is configured for a continuous monitoring of a user health for an accurate clinical outcome assessment and a wellness program for a healthy lifestyle. The analytical and clinical performance of the wearable device is very high because of confirmation of results by multiple detection methods. The FDA, EU, and Rest of the world (ROW) regulatory agencies have spent considerable time on classifying the pathogenic diseases and associated devices. The wearable device with smart band fills the unmet needs as a self-testing and point of care device intended to be used by lay persons for detecting sensor parameters and associated diseases.

The applications of present wrist wearable invention are possible in different domains:

1) Aviation, firefighting, construction, and warehouses: To monitor a person's vital health parameters to prevent potential hazardous situations during work such as accidents and injuries and offer corrective actions or preventive actions to be undertaken to avoid further deterioration or risk.
2) Biological warfare agents or Bioterrorism agents: The wearable device smart band microbial biosensor and particulate matter sensor pathogen detection methods are much more rapid than traditional methods of identifying microorganisms through clinical laboratory testing. In cases of biological warfare or bioterrorism rapid detection and identification of biological warfare agents deliberately dispersed in an area will prevent disease outbreak, extinction of wildlife, and deaths.
3) Education: Monitoring student stress levels and wellness dimension rankings to offer personalized learning curriculum, scheduling, and development of classroom activities.
4) Environmental: Noninvasive detection of microorganism, particulate matter, physiological, biofluid, biokinetics, and lifestyle eliminates medical waste resulting in protecting the environment with no incineration or autoclaving required.
5) Energy: Amount of power required to run wearable device is minimal compared to performing the same test in clinical laboratory test which requires lot of electricity, human resources, space, and generated medical waste.
6) Medicine: Monitoring a patient's health to prevent injuries and allow for the early detection of symptoms, illnesses and/or disorders, causes as well as early interventions, and offer preventive actions to avoid the deterioration of a health condition. Noninvasive monitoring of vital parameters results in reduced visits to doctor's offices, hospitals, and eliminates medical waste.
7) Military: Monitoring of vital physiological and biological parameters of the soldiers is very important to provide appropriate nutrients and supplements. Taking corrective action and preventive action during bioterrorism, biological warfare, or germ warfare due to use of harmful microorganisms as weapons in war can save lives. Immediate detection of the intentional release of viruses, bacteria, or other germs that can sicken or kill people, livestock, or crops results in saving lives. *Bacillus anthracis*, the bacteria that causes anthrax, is one of the likely agents that can be used in a biological attack.
8) Office environment and industry: To monitor company employees' health parameters, especially monitoring stress levels to prevent the potential deterioration of health conditions caused by occupational and environmental stress resulting in poor job performance.
9) Pandemic: To monitor the pathogens in the nasal cavity, oral cavity, on the surface, and surrounding air to prevent exposure and transmission of pathogens. The wearable device is configured for a rapid identification of pathogenic microorganisms in outbreak situations at a given location.
10) Sports lifestyle: Monitoring physiological, biofluid, biokinetics, and lifestyle parameters and training activities to prevent potential injuries, to reach optimal fitness, help change lifestyle, assess sleep quality, and so on. Wearable device can quickly and sensitively detect body movements (changes of joint angle, frequency, and relative humidity during exercise) and physiological information.

SUMMARY OF THE INVENTION

A wearable device consists of a smart band, and a display unit. The smart band comprises a microbial biosensor, a particulate matter sensor, an enviro sensor, a physiological sensor, a biofluid sensor, a biokinetics sensor, a lifestyle sensor, a single board computer, a power supply unit, a band fastener, and a set of watch adapters. The microbial biosensor detects, measures, and monitors beneficial microorganisms and pathogens in a nasal cavity, an oral cavity, or on a surface. The microbial biosensor sterilizer kills pathogens. The particulate matter sensor detects, measures, and monitors a set of suspended particles in the surrounding air comprising beneficial microorganisms, pathogens, pollen grains, dust mite allergens, and an air quality index. The pathogen results comprise a pathogen count, a pathogen type, a pathogen concentration, and a pathogen biosafety level. The enviro sensor detects, monitors, and measures environmental conditions surrounding the user. The physiological sensor detects, measures, and monitors physiological parameters of the user. The biofluid sensor detects, measures, and monitors biological fluid parameters of the user. The biokinetics sensor detects, measures, and monitors physical activities of the user. The lifestyle sensor detects, measures, and monitors healthy lifestyle activities of the user. A computing system comprises a wearable device, a mobile healthcare application, a mobile device, a cloud server, a laboratory testing facility, a laboratory computer, a laboratory information system, an application programming interface, a user smart band sensor result, a user clinical laboratory test result. A patient/user is wearing the wearable device, a laboratory director can be laboratory operations, a physician can be a doctor or clinician network consisting of expert clinicians.

The application programming interface comprises a set of functions enabling a cloud application to access the sensor data of a set of wearable electronics. The user smart band sensor result comprises a microbial biosensor parameters result, a particulate matter sensor parameters result, an enviro sensor parameters result, a physiological sensor parameters result, a biofluid sensor parameters result, a biokinetics sensor parameters result, and a lifestyle sensor parameters result. The clinical laboratory test results are from various medical test disciplines.

The smart band sends and receives signals through a wireless network to the mobile healthcare application installed on the mobile device, and to the cloud server. The wearable device allows for continuous monitoring of user health for accurate clinical outcomes and wellness programs.

BRIEF DESCRIPTION OF THE DRAWINGS

FIG. 3 is an example smart band circuit block diagram, according to some embodiments.

FIG. 4 is an example schematic representation of a single board computer general purpose input output pin numbering diagram, and a general purpose input output pinout function that can be utilized to implement various embodiments.

FIG. 5 is an example single board computer general purpose input output pinout function description table that can be utilized to implement various embodiments.

FIG. 6 illustrates an example set of microorganisms, pollen grain, dust mite allergen, and relative size of particles that can be utilized to implement various embodiments.

FIG. 7 is an example prion structure and components diagram, a prion structure components, function, and chemical composition list, a prion disease, status, and source list, and a prion attributes and biosensor detector list, according to some embodiments.

FIG. 8 is an example virus structure and components diagram, a virus structure components, function, and chemical composition list, and a percent chemical composition of a virus list, according to some embodiments.

FIG. 10 is an example virus name, disease, status, source, shape, size, and nucleic acid list, and a virus attributes and biosensor detector list, according to some embodiments.

FIG. 11 is an example bacteria cell structure and components diagram, a bacteria cell structure components, function, and chemical composition list, and a percent chemical composition of a bacteria list, according to some embodiments.

FIG. 12 is an example bacterial cell shapes diagram, according to some embodiments.

FIG. 13 is an example bacteria name, disease, status, source, shape, size, and nucleic acid list, and a bacteria attributes and biosensor detector list, according to some embodiments.

FIG. 14 is an example fungi cell structure and components diagram, a fungi cell structure components, function, and chemical composition list, and a percent chemical composition of a fungi list, according to some embodiments.

FIG. 15 illustrates an example fungi cell shapes diagram, and a fungi cell shape in environment and shape shift in host diagram, according to some embodiments.

FIG. 16 is an example fungi name, disease, status, source, shape, size, and nucleic acid list, and a fungi attributes and biosensor detector list, according to some embodiments.

FIG. 17 is an example protist cell structure and components diagram, a protist cell structure components, function, and chemical composition list, a protist, disease, source, shape, size, and nucleic acid list, and a protist attributes and biosensor detector list, according to some embodiments.

FIG. 18 is an example dust mite structure and components diagram, a dust mite structure components, function, and chemical composition list, and a dust mite attributes and biosensor detector list, according to some embodiments.

FIG. 19 is an example virus, bacteria, and fungi attributes comparison list, according to some embodiments.

FIG. 20 is an example platform dataset, and a microorganism taxonomy, according to some embodiments.

FIG. 21 is an example microorganism data, and a microorganism database, according to some embodiments.

FIG. 23 illustrates an electromagnetic spectrum, and a spectrum of sound, according to some embodiments.

FIG. 24 illustrates noninvasive biosensors for microorganism detection, and sterilization list, picomaterials, and a microorganism detection method working principle list, according to some embodiments.

FIG. 25 illustrates particle detection methods, according to some embodiments.

FIG. 27 illustrates an example microbial biosensor pinout and a microbial biosensor wiring table describing the hardware wiring connection steps of a microbial biosensor pinout connected to the single board computer general purpose input output pinout that can be utilized to implement various embodiments.

FIG. 28 illustrates an example microbial biosensor infrared spectroscopy working principle diagram, and a microbial biosensor particle imaging working principle diagram that can be utilized to implement various embodiments.

FIG. 29 illustrates a microbial biosensor nasal cavity test method diagram, and microbial biosensor oral cavity test method diagram that can be utilized to implement various embodiments.

FIG. 30 illustrates a microbial biosensor surface test method diagram, and surface types that can be utilized to implement various embodiments.

FIG. 31 is an example pollen grain diagram, a pollen grain structure and components diagram, a pollen structure components, function, and chemical composition list, and a percent chemical composition of an air-dried pollen list, according to some embodiments.

FIG. 32 illustrates a pollen grain shapes diagram, according to some embodiments.

FIG. 33 is an example pollen type source, name, disease, shape, and size list, and a pollen attributes and biosensor detector list, according to some embodiments.

FIG. 34 is an example pollen tree taxonomy, pollen data, and a pollen database, according to some embodiments.

FIG. 35 illustrates an example particulate matter sensor pinout, and a particulate matter sensor wiring table describing the hardware wiring connection steps of a particulate matter sensor pinout connected to the single board computer general purpose input output pinout that can be utilized to implement various embodiments.

FIG. 36 illustrates an example particulate matter sensor working principle block diagram, and an air quality index level of concern table that can be utilized to implement various embodiments.

FIG. 39 illustrates anatomy of the skin, and light penetration into skin, according to some embodiments.

FIG. 40 illustrates an optical path of light into skin, blood vessel expansion, and blood vessel cross section, according to some embodiments.

FIG. 41 illustrates an example physiological sensor pinout, and a physiological sensor wiring table describing the hardware wiring connection steps of a physiological sensor pinout connected to the single board computer general purpose input output pinout that can be utilized to implement various embodiments. The physiological sensors diagram illustrates different components.

FIG. 42 lists physiological parameters, detection sensors, and detected normal reference ranges, according to some embodiments.

FIG. 44 illustrates a cardiac photoplethysmography (PPG) sensor operating principle diagram, pulse waveform PPG signal AC part, heart rate PPG signal, respiratory rate PPG signal, and heart rate variability PPG signal, according to some embodiments.

FIG. 45 illustrates an ECG sensor operating principle diagram, and ECG signal, according to some embodiments.

FIG. 46 illustrates a blood pressure sensor operating principle diagram, according to some embodiments.

FIG. 47 illustrates a red blood cell containing hemoglobin, blood oxygen sensor operating principle diagram, blood carbon dioxide sensor operating principle diagram, brain EEG operating principle diagram, elbow EMG operating principle diagram, and knee EMG operating principle diagram, according to some embodiments.

FIG. 49 illustrates a biofluid sensors diagram, schematic structure of pixelated LEDs array, single pixelated LED, and single pixelated photodetector, and morphology of blood cells diagram that can be utilized to implement various embodiments.

FIG. 50 illustrates biofluid analyte detected structure, according to some embodiments.

FIG. 51 lists biofluid complete blood count parameters, detection sensor, and detected normal reference ranges, according to some embodiments.

FIG. 52 lists blood cell components, according to some embodiments.

FIG. 53 lists biofluid complete metabolic panel analytes, detection sensor, and detected normal reference ranges, according to some embodiments.

FIG. 54 lists biofluid lipid panel parameters, detection sensor, and detected normal reference ranges, according to some embodiments.

FIG. 55 illustrates an in vivo noninvasive imaging of blood flow in a single vessel diagram, spectrally encoded flow cytometry (SEFC) imaging of blood cells operating principle diagram, and NIR hyperspectral (HS) imaging of blood cells operating principle diagram, according to some embodiments.

FIG. 57 illustrates NIR spectroscopy fundamental equations, a vibration of a diatomic molecule, and vibrations of polyatomic molecules (AX2 group) 5760 to detect metabolites, according to some embodiments.

FIG. 58 lists principal types of NIR absorption bands and their locations, and biofluid chemical NIR vibrational mode list, according to some embodiments.

FIG. 59 shows a metabolites molecular formula and chemical structure, according to some embodiments.

FIG. 60 shows a metabolites and lipids molecular formula and chemical structure, according to some embodiments.

FIG. 61 illustrates a Blood Metabolites and Lipid Panels (BML) sensor diffuse reflectance spectroscopy working principle diagram, BML sensor NIR diffuse reflectance spectroscopy operating principle diagram, and diffuse reflectance detection method, according to some embodiments.

FIG. 62 shows albumin, bilirubin, BUN, cortisol, creatinine diffuse reflectance spectra, NIR wavelength embedding method, electrolyte absorption line spectrum, and electrolytes absorption line wavelength locations, according to some embodiments.

FIG. 63 illustrates an ALP ZnMg surrogate absorption line spectrum, ALT NH2 and AST NH3 surrogate diffuse reflectance spectra, and lipids diffuse reflectance spectra, according to some embodiments.

FIG. 64 illustrates a blood glucose and alcohol sensor diffuse reflectance operating principle diagram, blood glucose diffuse reflectance spectrum, blood glucose level, blood alcohol diffuse reflectance spectrum, and blood alcohol level, according to some embodiments.

FIG. 65 illustrates an example biokinetics sensor pinout, and a biokinetics sensor wiring table describing the hardware wiring connection steps of a biokinetics sensor pinout connected to the single board computer general purpose input output pinout that can be utilized to implement various embodiments.

FIG. 66 illustrates a human musculoskeletal system diagram, and biokinetics position diagram, according to some embodiments.

FIG. 67 lists biokinetics parameters, detection sensor, and detected normal reference ranges, according to some embodiments.

FIG. 68 illustrates biokinetics parameters detection methods, according to some embodiments.

FIG. 69 illustrates an example lifestyle sensor pinout, and a lifestyle sensor wiring table describing the hardware wiring connection steps of a lifestyle sensor pinout connected to the single board computer general purpose input output pinout that can be utilized to implement various embodiments.

FIG. 70 lists lifestyle parameters, detection sensor, and detected normal reference ranges, according to some embodiments.

FIG. 71 illustrates a breath analyzer sensor working principle, and breath analyzer sensor test method, according to some embodiments.

FIG. 72 illustrates various lifestyle parameters detection methods, according to some embodiments.

FIG. 73 illustrates a human wellness dimensions wheel, and a human wellness dimensions description, according to some embodiments.

FIG. 74 lists a human wellness dimensions database, human wellness dimensions reference ranges, human wellness dimensions detection methods, and example personalized wellness programs, according to some embodiments.

FIG. 77 lists clinical laboratory test discipline and test methods list 1, according to some embodiments.

FIG. 78 lists clinical laboratory test discipline and test methods list 2, according to some embodiments.

FIG. 79 lists commonly ordered clinical laboratory tests, according to some embodiments.

FIG. 80 lists endocrinology ordered clinical laboratory tests, according to some embodiments.

FIG. 81 is an example intelligent relationship interpretation table 1 between sensor parameters, according to some embodiments.

FIG. 82 is an example intelligent relationship interpretation table 2 between sensor parameters, according to some embodiments.

FIG. 83 is an example intelligent relationship interpretation table 3 between sensor parameters, according to some embodiments.

FIG. 84 is an example intelligent relationship interpretation table 4 between sensor parameters, according to some embodiments.

FIG. 85 is an example clinical laboratory test critical results range, according to some embodiments.

FIG. 88 illustrates a personalized accurate user/patient clinical laboratory test results method, and personalized accurate user/patient clinical laboratory test critical results method, according to some embodiments.

FIG. 89 illustrates a mobile healthcare application displaying sensor settings interface, and a mobile healthcare application displaying smart band sensor results, according to some embodiments.

FIG. 90 illustrates an example mobile healthcare application displaying microbial biosensor nasal cavity parameters result, and a mobile healthcare application displaying microbial biosensor oral cavity parameters result, according to some embodiments.

FIG. 92 illustrates an example mobile healthcare application displaying physiological sensor parameters result, and a mobile healthcare application displaying biofluid sensor parameters CBC result, according to some embodiments.

FIG. 93 illustrates an example mobile healthcare application displaying complete metabolic panel results, and a mobile healthcare application displaying biokinetics sensor parameters result, according to some embodiments.

FIG. 94 illustrates an example mobile healthcare application displaying lifestyle sensor parameters result, and a mobile healthcare application displaying wellness dimension parameters result, according to some embodiments.

FIG. 95 illustrates an example smart band alert, smart band sensor risk level and corrective action and preventive action, according to some embodiments.

FIG. 96 is an example first page of a pathogen safety data sheet, according to some embodiments.

FIG. 97 is an example second page of a pathogen safety data sheet, according to some embodiments.

FIG. 98 is an example third page of a pathogen safety data sheet, according to some embodiments.

FIG. 99 is an example page of a pollen safety data sheet, according to some embodiments.

FIG. 100 illustrates an exemplary predicted surrogate user CBC test result from the user smart band sensor result, and method to predict a surrogate user CBC test result, according to some embodiments.

FIG. 101 is an example personalized accurate patient clinical laboratory test results report 1, according to some embodiments.

FIG. 102 is an example personalized accurate patient clinical laboratory test results report 2, according to some embodiments.

FIG. 103 is an example personalized daily nutritional goal comprising nutrient and daily reference intake, according to some embodiments.

FIG. 104 is an example personalized dietary pattern comprising food and amount, according to some embodiments.

FIG. 105 is an example personalized wellness program, according to some embodiments.

Figure 1:
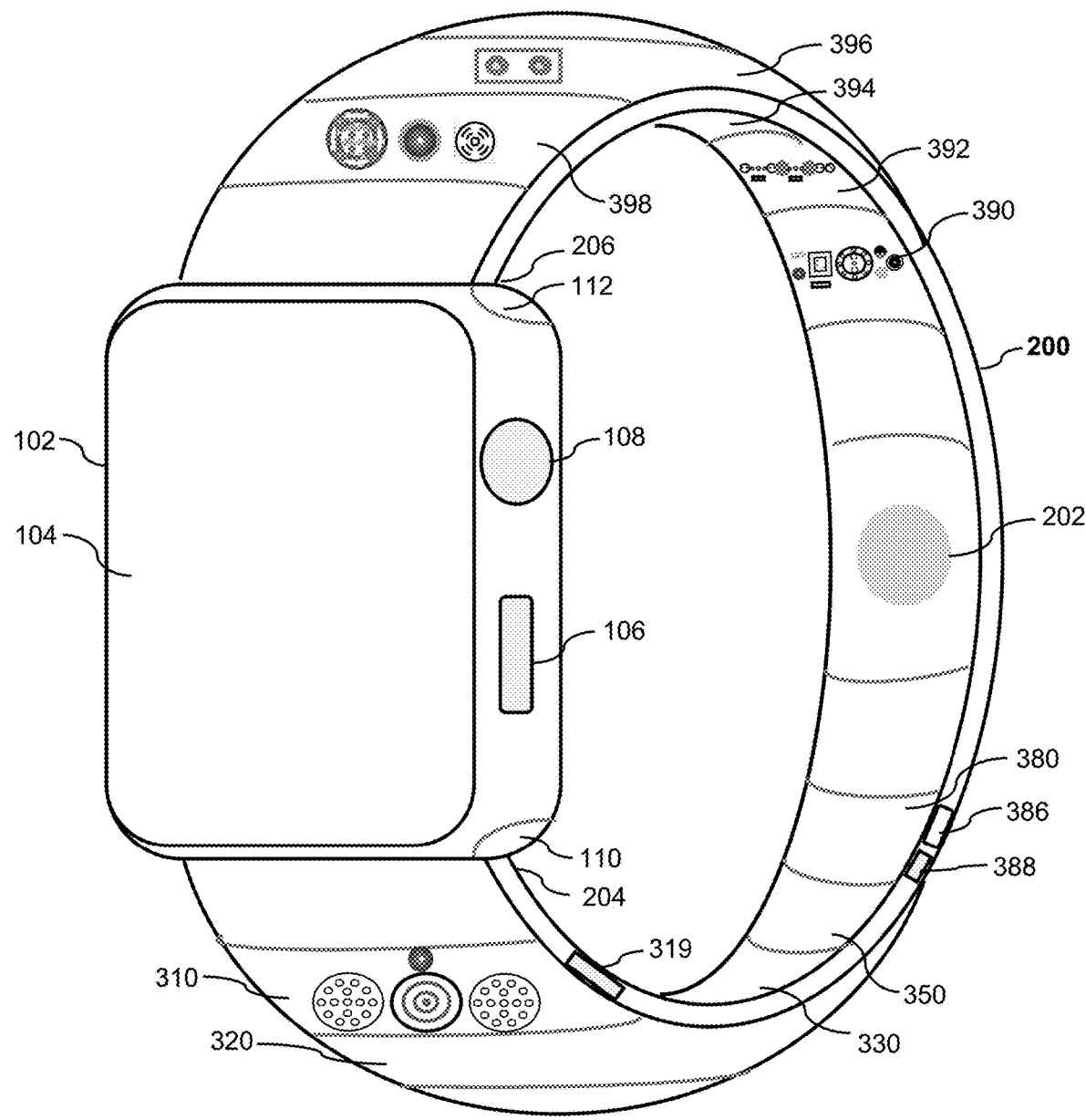
FIG. 1 is an example perspective view of an example wearable device design that can be utilized to implement various embodiments.

The Figures described above are a representative set and are not exhaustive with respect to embodying the invention.

DESCRIPTION

Disclosed are a system, method, and article of manufacture for methods and systems of a wearable device. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to "one embodiment," "an embodiment," "one example," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of how to operate, detect, measure, and monitor a beneficial microorganism count, a beneficial microorganism type, and a beneficial microorganism concentration, a pathogen count, a pathogen type, a pathogen concentration, and a pathogen biosafety level and environmental conditions surrounding the user using various sensors to provide a thorough understanding of embodiments of the invention. The physiological, biofluid, biokinetics, lifestyle sensor pinout diagram and wiring table allows complete understanding of the hardware, software drivers, and detection output. One who is skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The disclosed system consists of a wearable device, mobile healthcare application, and associated methods. A wearable device consists of a smart band, and a display unit. The smart band comprises a microbial biosensor, a particulate matter sensor, an enviro sensor, a single board computer, a power supply unit, a band fastener, and a set of watch adapters. The microbial biosensor detects, measures, and monitors beneficial microorganisms and pathogens in a nasal cavity, an oral cavity, or on a surface. The microbial biosensor sterilizer kills pathogens. The particulate matter sensor detects, measures, and monitors a set of suspended particles in the surrounding air comprising beneficial microorganisms, pathogens, pollen grains, dust mite allergens, and an air quality index. The pathogen results comprise a pathogen count, a pathogen type, a pathogen concentration, and a pathogen biosafety level. The enviro sensor detects, monitors, and measures environmental conditions surrounding the user. The physiological sensor detects, measures, and monitors physiological parameters of the user. The biofluid sensor detects, measures, and monitors biological fluid parameters of the user. The biokinetics sensor detects, measures, and monitors physical activities of the user. The lifestyle sensor detects, measures, and monitors healthy lifestyle activities of the user. A computing system comprises a wearable device, a mobile healthcare application, a user, a mobile device, a cloud server, a laboratory testing facility, a laboratory information system, a laboratory director, and a physician. The smart band sends and receives signals through a wireless network to the mobile healthcare application installed on the mobile device, and to the cloud server.

In one embodiment, the system is twofold, with a hardware and software system. The hardware includes smart band, and a display unit. The display unit is removable, and a user smartwatch or standard watch can be connected. The smart band comprises a microbial biosensor, a particulate matter sensor, an enviro sensor, a single board computer, and a power supply unit. The software consists of mobile healthcare application which is preinstalled in the wearable device and displays the sensor data on the display unit. The mobile healthcare application can also be installed on the smartwatch and mobile devices. The mobile healthcare application includes different interactive user interfaces such as, inter alia: wearable device details, a microbial biosensor parameters result, a particulate matter sensor parameters result, and an enviro sensor parameters result. The mobile healthcare application can connect to a laboratory information system through application programmer interfaces and transmit the user wearable device data.

The disclosed invention runs on an end-to-end application workflow consisting of collecting wearable device sensor data, performing big data analysis, providing detailed results, monitoring, trending, and reporting of health performance data.

The wearable device sends a pathogen biosafety alert to the mobile healthcare application when the pathogen biosafety level is above a predetermined threshold level in the nasal cavity, oral cavity, surface, or in the air surrounding and presents a corrective action and a preventive action to prevent exposure to the pathogen type. The system can send the pathogen biosafety alert to the physician and laboratory information system. The pathogen biosafety alert allows the user to take additional appropriate sterilization methods like heat treatment, ultraviolet light, acoustic wave, irradiation, thermal inactivation, and so on, to kill pathogens in a nasal cavity, an oral cavity, on a surface, or surrounding environment to ensure they are free of pathogens. The enviro sensor detects, monitors, and measures environmental conditions surrounding the user. The physiological sensor detects, measures, and monitors physiological parameters of the user. The biofluid sensor detects, measures, and monitors biological fluid parameters of the user. The biokinetics sensor detects, measures, and monitors physical activities of the user. The lifestyle sensor detects, measures, and monitors healthy lifestyle activities of the user.

The wearable device and mobile healthcare application are self-contained and are operated independently and do not need to be connected to the cloud server. The connection to the cloud server allows for sharing of data with other users, laboratory information system, physicians, and so on.

The schematic flow chart diagrams included herein are generally set forth as logical flow chart diagrams. As such, the depicted order and labeled steps are indicative of one embodiment.

EXEMPLARY DEFINITIONS

An accelerometer sensor can be used to measure the acceleration or deceleration of forces exerted upon the sensor. Such forces may be static, like the continuous force of gravity or, as is the case with many mobile or moving devices, dynamic, to sense movement or vibrations. The intended use of the accelerometer sensor is to measure the movement of the wearable device. The accelerometer sensor is used for centering the wearable device for nasal ID, open mouth ID, and surface ID recognition. The unit of measurement of the accelerometer sensor is the rate of change of velocity of an object expressed in meters per second squared ($m/s^2$). The accelerometer sensor sends real-time acceleration data to the mobile healthcare application and the cloud server. Accelerometers can measure acceleration in one, two, or three orthogonal axes. Accelerometer sensors are typically used in one of three modes: in the case of 1 dimension as an inertial measurement of velocity and position, as a sensor of inclination, tilt, or orientation in 2 or 3 dimensions, as referenced from the acceleration of gravity (1 $g=9.8$ $m/s^2$) and as a vibration or impact sensor. Most accelerometers are micro-electromechanical sensors (MEMS). The basic principle of operation of the MEMS accelerometer is the displacement of a small proof mass etched into the silicon surface of the integrated circuit and suspended by small beams. Per Newton's second law of motion ($F=ma$), as an acceleration is applied to the device, a force develops which displaces the mass. The support beams act as a spring and the air trapped inside integrated circuits (IC) as a damper. The common accelerometer sensor types can be capacitive sensing or use piezoelectric effect to sense the displacement of the proof mass proportional to the applied acceleration.

Air Quality Index (AQI) is an index for reporting air quality. The Air Quality Index is used to provide information about how polluted the air currently is or how polluted it is forecasted to become.

An algorithm is a precise, step-by-step plan or set of rules to be followed in calculations or computational procedures or other problem-solving operations, especially by a computer. An algorithm computational procedure begins with an input value and yields an output value in a finite number of steps. The microorganism and pathogen algorithms used are a computational procedure algorithm to calculate sensor data values, various cluster algorithms, a picocamera machine vision algorithm, a neural network algorithm, and so on. The algorithms implemented in the method can vary. Algorithms allow for rapid multiplex detection and characterization of microorganisms, pathogens, and pollen by calculating the unique identifiers.

An allergy is a damaging immune response by the body to a substance, especially pollen, a particular food, or dust, to which it has become hypersensitive. The substances that cause an allergic reaction are called allergens, which are proteins or glycoproteins. Usually they are harmless to most people. Allergy is an abnormal reaction to a very small amount of allergen. Allergens stimulate the production of allergic antibodies or sensitized cells. This response is mediated by immunoglobulin IgE antibody specific to the allergen. The basophils and mast cells are activated after IgE binding, starting a series of cellular and molecular events that results in clinical manifestation of allergic disease.

Alleviation is easing the severity of a pain or a disease without removing the cause. It also includes making pain or suffering more bearable. For example, a medicine alleviates the symptoms, a reduced smoking (lifestyle sensor parameter) reduces asthma symptoms and a condition involving constriction of the airways and difficulty or discomfort in breathing.

Aeroallergens are airborne particles that can cause respiratory or conjunctival allergy. Aeroallergens, to be clinically significant, must be buoyant, present in significant numbers, and allergenic, such as ragweed and grass. Wind pollinated plants produce significant amounts of allergen than can travel for miles. Fungal spores may be more numerous than pollen grains in the air. The house dust mite is also a very common indoor allergen.

An ambient light sensor (ALS) is an electronic component, also known as an illuminance or illumination sensor, optical sensor, brightness sensor, or simply light sensor, which is used to reduce the power consumption to provide the user with increased battery life. The intended use of the ambient light sensor is to detect, measure, and monitor ambient light inside or surrounding the wearable device to reduce power consumption and increase battery life. The wearable device can be programmed to go into power saving sleep mode when the device is turned off. The unit of measurement is lux, and it can be expressed in terms of ambient light level values of 1 to 5. The ambient light sensor sends real-time ambient light, i.e., illuminance data, to the mobile healthcare application and cloud server. Ambient light sensor technologies can be based on photo electric cell, photodiode, photo transistor, and photo integrated circuit (IC). Ambient light sensors contain a photodiode which can sense light wavelengths visible to the human eye in the 380-nm to 780-nm range and convert them into electricity. Light is measured depending upon its intensity.

Analytical performance means the ability of a device to correctly detect or measure a particular analyte. Analytical performance characteristics comprise parameters such as analytical sensitivity, analytical specificity, trueness (bias), precision (repeatability and reproducibility), accuracy (resulting from trueness and precision), limits of detection and measurement range, (information needed for the control of known relevant interferences, cross-reactions, and limitations of the method), measuring range, linearity.

An application programming interface (API) can specify how application software components of various systems interact with each other. APIs are source code-based specifications intended to be used as interfaces by application software components to communicate with each other. Microorganism and pathogen APIs allow connection and retrieval of data from public databases like National Center for Biotechnology (NCBI), European Pathogen databases, and other commercial pathogen databases. Pollen APIs allow for access to local pollen and allergy forecast data. Laboratory information system APIs are application programming interfaces that allow connection to patient health records, laboratory medical instruments, and a cloud server. Weather APIs are application programming interfaces that allow connection to large databases of weather forecast and historical information. For example, the mobile healthcare application and laboratory information system can connect to weather APIs such as OpenWeatherMap API, AccuWeather API, Dark Sky API, Air Quality API, and so on. The weather data imported from weather APIs can be used to display it on the mobile healthcare application and laboratory information system.

An audio port links the single board computer's sound hardware to speakers, microphone, headsets, or other equipment.

A bacterium is a member of a large group of unicellular microorganisms classified as prokaryotes, which have cell walls but lack organelles and an organized nucleus, including some that can cause disease. Bacteria are microorganisms made of a single cell, and those that cause infections are called pathogenic bacteria. Currently it is estimated that about 700 species of bacteria are found in the oral cavity, many which are still uncultivable and need to be identified. About 20 are known to be pathogenic. The most common bacteria sizes are about 1 to 2 µm in diameter and 5 to 10 µm long. The bacteria shapes are spherical bacteria (Coccus), rod-shaped bacteria (*Bacillus*), spiral bacteria, filamentous bacteria, box shaped bacteria, appendaged bacteria, pleomorphic bacteria, and so on. Bacteria are microscopic organisms not visible with the naked eye. Bacteria are everywhere, both inside and outside of our body. Bacteria can live in a variety of environments, from hot water to ice. Some bacteria are good for humans, while others can make us sick. These beneficial or good bacteria, also called probiotics, reside naturally in the body. Probiotics may be beneficial to health and are available in yogurt or in various dietary supplements. Some of the good bacteria are as follows: a) *Lactobacillus acidophilus* resides in the intestines where it helps in the digestion of food. b) Bifidobacteria make up most of the "good" bacteria living in the gut. They help to digest dietary fiber, prevent infection, and produce vitamins and other important chemicals. c) *Streptococcus thermophilus* is for relief of the abdominal cramps, diarrhea, nausea, and other gastrointestinal symptoms associated with lactose intolerance. d) *Saccharomyces boulardii* is most used for treating and preventing diarrhea, including infectious types such as rotaviral diarrhea in children. e) *Bacillus coagulans* may be useful in the treatment of gastrointestinal disorders such as diarrhea associated with an antibiotic regimen, inflammatory bowel disease, and irritable bowel syndrome. Many disease-causing bacteria produce toxins-powerful chemicals that damage cells and make a person ill. Other bacteria can directly invade and damage tissues. Common pathogenic bacterial infections are as follows: a) Strep throat caused by pathogenic Group A *Streptococcus*. b) Urinary tract infection usually caused by *Escherichia coli*. c) Food poisoning caused by Norovirus and *Salmonella*. d) Tuberculosis, a serious infectious disease that affects lungs and is caused by *Mycobacterium tuberculosis*. e) Lyme disease caused by *Borrelia* burgdorfer. It is transmitted to humans through the bite of infected blacklegged ticks. Typical symptoms include fever, headache, fatigue, and a characteristic skin rash called erythema migrans.

Bluetooth is a wireless technology standard for exchanging data over short distances for, e.g., using short-wavelength UHF radio waves in the ISM band from 2.4 to 2.485 GHz from fixed and mobile devices, and building personal area networks (PANs), etc. It is noted that other communication systems which transmit signals with messages from a user's device to recipients can be used as well. Wearable device Bluetooth can be used to connect to a mobile device, smartwatch, or other devices such as personal wellness, rooftop rain and wind weather stations, and so on.

A biofluid sensor is an electronic component which can be used to noninvasively detect the biofluid parameters or analytes in blood, serum, plasma, urine, saliva, sweat, and so on using optical properties of the light. The intended use of the biofluid sensor is to detect, measure, and monitor noninvasively in vivo complete blood count, blood metabolites, and blood cholesterol. The biofluid sensor contains specialized probes to detect best blood vessels for accurate measurement of blood parameters or analytes by discarding the small, hidden, or compromised blood vessels. The biofluid sensor measured analyte data is configured for a prediction of a biofluid risk level. The biofluid sensor analyte results are often shown as a set of numbers known as a reference range. A reference range may also be called "normal reference range" or "normal values." If the biofluid sensor measured parameter or analyte results fall outside the reference range, the user or patient can have health problems. The biofluid risk level is based on either individual lower or higher values of biofluid parameter result or relationship with other biofluid parameter or wearable device sensors data.

A biohazard is a risk to human health or the environment arising from biological work, especially with microorganisms. Biohazard materials are infectious agents or hazardous biologic materials that present a risk or potential risk to the health of humans, animals, or the environment. The risk can be direct through infection or indirect through damage to the environment.

A biohazardous waste or medical waste is waste that potentially contains biological agents that may pose risk to the population if released in the environment. Biohazardous waste also known as medical waste or healthcare waste is any kind of waste that contains infectious material or material that is potentially infectious. This definition includes waste generated by healthcare facilities like physician's offices, hospitals, dental practices, laboratories, medical research facilities, and veterinary clinics. Increasingly due to the COVID-19 pandemic, biohazardous waste is disposed of in private (residential), public, and commercial waste bins. Waste bins containing biohazard materials can pose risk to the waste collection vehicle driver or waste collection operator workers.

A biokinetics sensor is an electronic component which can be used to noninvasively detect the biokinetics parameters related to human musculoskeletal movements of or within body parts using accelerometer, gyroscope, magnetometer, surface electromyography, pressure/strain, ultrasonic, radio frequency, GPS, piezoelectric-based, and so on. The intended use of the biokinetics sensor is to detect, measure, and monitor noninvasively walking, standing, sitting, running, yoga, hiking, cycling, swimming, movement, exercise, sleep, stress, fall, and proximity to an object. The biokinetics sensor parameters result enables prediction of a biokinetics risk level. The biokinetics sensor parameters results are often shown as a set of numbers known as a reference range. A reference range may also be called "normal reference range" or "normal values." If the biokinetics sensor measured parameters result falls outside the reference range, the user or patient can have health problems. The biokinetics risk level is based on either individual lower or higher values of biokinetics parameter result or relationship with other biokinetics parameter or wearable device sensors data.

Biosafety is the application of safety precautions that reduce users' risk of exposure to a potentially infectious microbe or pathogen and limit contamination of the work environment and, ultimately, the community. Pathogens are mapped to biosafety level. The laboratory information system and mobile healthcare application allow for automated training and instruction on biosafety policies and procedures to minimize the occupational risk of exposure to infectious agents in the surrounding environment, in accordance with current local, county, state, and governmental recommendations regarding the biosafety levels for working with different organisms.

Biosafety levels (BSLs) or Biological Safety Levels: there are four biosafety levels. Each level has specific controls for containment of microbes or pathogens and biological agents. The primary risks that determine levels of containment are infectivity, severity of disease, transmissibility, and the nature of the work conducted. The origin of the pathogen or microbe, or the agent in question, and the route of exposure are also important. Each biosafety level has its own specific containment controls that are required for the following best waste collection practices, safety equipment, and facility construction. The biosafety level 1 (BSL-1) for sample organisms like nonpathogenic strains of *E. coli, Staphylococcus, Bacillus subtilis*, and *Saccharomyces cerevisiae* does not require containment and has pathogen type agents that present minimal potential hazard to the user and the environment and are unlikely to cause disease. The biosafety level 2 (BSL-2) for sample organisms like Influenza, HIV, Lyme disease, Equine Encephalitis, monkeypox, and COVID-19 requires containment and has pathogen type agents associated with human disease that pose moderate hazards to personnel and the environment but can cause severe illness in humans and are transmitted through direct contact with infected material. The biosafety level 3 (BSL-3) for sample organisms like Yellow Fever, West Nile Virus, and Tuberculosis requires high containment and has pathogen type agents that present a potential for aerosol transmission, and agents causing serious or potentially lethal disease. The biosafety level 4 (BSL-4) for sample organisms like Ebola Virus, Tick Borne Encephalitis, Marburg Virus, and Crimean-Congo hemorrhagic fever requires maximum containment and has pathogen type agents that pose a high risk of aerosol transmitted infections and life threating diseases. The biosafety levels 3 and 4 require the user to sterilize the nasal cavity, oral cavity, top of the surface, and environment. The detection and monitoring of pathogen biosafety level allows for implementation of appropriate sterilization and containment actions. The pathogen safety data sheet also provides the detail about the biosafety level. The biosafety information allows the user of the wearable device to take appropriate measures to reduce exposure to pathogens.

A biosensor is a device used to detect the presence or concentration of a biological analyte or element, such as a biomolecule, a biological structure, an antibody, a biomimetic, a cell, a DNA, an enzyme, a pathogen comprising a virus, a bacterium, and a fungus, a phage, a tissue, or a microorganism. It has a sensor that integrates a biological element with a physiochemical or optical transducer to produce an electronic signal proportional to a single analyte which is then conveyed to a detector. Biosensors consist of three parts: a component that recognizes the analyte and produces a signal, a signal transducer with an amplifier, and a reader device.

A camera serial interface (CSI) is a specification of the Mobile Industry Processor Interface (MIPI) Alliance. It defines an interface between a picocamera and a single board computer (SBC). The high-speed protocol primarily is intended for point-to-point image and video transmission between cameras and host devices. Usually, it is in the form of a ribbon cable. The picocamera is connected to the single board computer (SBC) through a CSI cable.

A cell is the basic smallest structural, functional, and biological unit of all organisms. Cells are the smallest units of life, and hence are often referred to as the "building blocks of life." All living things are composed of cells. New cells are produced from the existing cell. The cell is the basic membrane-bound unit that contains the fundamental molecules of life and of which all living things are composed. Organisms typically consist of a cell, which is either prokaryotic or eukaryotic. Prokaryotes have cell membranes and cytoplasm but do not contain nuclei. The cells of eukaryotes contain nuclei. Cells may also be classified based on the number of cells that make up an organism, i.e., "unicellular," "multicellular," or "acellular." Cells make up tissues, tissues make up organs, and organs make up organ systems. The study of cells is called cellular biology, cell biology, or cytology. The branch of science that deals with microorganisms is called microbiology.

A cholesterol is a waxy, fat-like substance that's found in all the cells in the body. The body needs some cholesterol to make hormones, vitamin D, and substances that help a person digest foods. The body makes all the cholesterol it needs. The two main type of cholesterol include low-density lipoprotein—LDL cholesterol (bad cholesterol), and high-density lipoprotein—HDL cholesterol (good cholesterol). The blood also includes triglycerides which are a type of fat. They are the most common type of fat in the body. Triglycerides come from foods, especially butter, oils, and other fats persons eat. Triglycerides can't float around in the blood on their own. They ride along with certain proteins, called "lipoproteins," such as LDL and HDL cholesterol. This way, they can move around the body until they are stored in body fat cells. Lipids are a broader group of biomolecules found in the body. Fats are the type of lipids necessary for a healthy body. Cholesterol in the blood plasma compartment exists in two forms, free cholesterol (Chol) and cholesteryl esters (CE), both of which are constituents of circulating lipoproteins.

Clinical performance is the ability of a device to yield results that are correlated with a particular clinical condition or a physiological or pathological process or state in accordance with the target population and intended user. The clinical performance comprises parameters such as diagnostic sensitivity, diagnostic specificity, positive predictive value, negative predictive value, likelihood ratio, and expected values in normal and affected populations.

A cloud server can involve deploying groups of remote servers and/or software networks that allow centralized data storage and online access to computer application software or resources. These groups of remote servers and/or software networks can be a collection of remote computing services. A cloud server can contain algorithms, methods, http web server, program logic, middleware stack, and databases. Wearable device data is stored locally in a secure digital card (SDC) and is also sent to the cloud server and stored in a database for further processing and can be accessed by the mobile healthcare application or laboratory information system.

Clustering is a machine learning technique that involves the grouping of data points. It usually involves the grouping of similar things or people positioned or occurring closely together. For example, microorganisms' data from same genus and species but different variant can be clustered. Wearable devices can be clustered based on zip code, location, content type, and so on. Wearable devices sensor data can be clustered to predict and forecast the environmental conditions surrounding the user.

Correlation is an establishment of agreement between two or more measured values. The agreement can be between wearable device sensor parameter values and clinical laboratory test results.

Cosmic rays are a form of high-energy radiation that originates from outside our solar system in our own galaxy and from distant galaxies. When they reach Earth, the rays collide with particles in the upper atmosphere to produce a "shower" of particles, including muons. Muons are unstable subatomic particles of the same class as an electron (a lepton), but with a mass around 200 times greater. Cosmic rays place astronauts at significant risk for radiation sickness and increased lifetime risk for cancer, alter the cardiovascular system, eliminate some of the cell's linings of the blood vessels, and cause central nervous system effects and degenerative diseases.

Critical results are defined as those results that may require rapid clinical attention to avert significant patient morbidity or mortality. Critical results are usually values which are beyond the abnormal lower and upper limits. In addition, for some infectious diseases, the critical results are usually positive results. Each laboratory can define the critical values and critical results that pertain to its patient population. The laboratory may establish different critical results for specific patient subpopulations (for example, age, sex, comorbidities, baseline disease risk, dialysis clinic patients, and so on). Critical results are usually defined by the laboratory director, in consultation with the clinicians served.

A database is a structured set of data held in a computer, especially one that is accessible in various ways. The software computing environment allows for various operations associated with wearable device data. Wearable device data is held in a structured manner in the database. The database includes tables and records for a wearable device, location, laboratory information system, laboratory testing facility, laboratory director, physician, system administration, external weather data, and so on. Predefined, agile models are created for which extra attributes can be added to the existing models. The program logic allows data definition operations like creating databases, files, groups, tables, views, and so on; data manipulation operations like creating, inserting, reading, updating, deleting data from objects; data control operations like grant, revoke, rollback, commit; and database maintenance operations like backup, restore, and rebuild. The program logic is responsible for getting the wearable device big data and performing standard database relational operations like select, project, join, product, union, intersect, difference, divide, and so on. The wearable device database consists of a microorganism database, pollen database, wearable device data, and user information data.

Diagnosis is concerned with identifying disease or illness or other problem. a distinctive symptom or characteristic. It involves process of identifying a disease, condition, or injury from its signs, and symptoms. A health history, physical exam, and test results, such as microorganism detection, particulate matter, biofluid, physiological, biokinetics, lifestyle, imaging, and biopsies are used to help make a diagnosis. The term diagnosis and diagnostic are used interchangeably.

Diffuse reflectance spectroscopy, or diffuse reflection spectroscopy, is a subset of absorption spectroscopy. It is sometimes called remission spectroscopy. Remission is the reflection or back-scattering of light by a material, while transmission is the passage of light through a material. Remission includes both specular and diffusely back-scattered light. The diffuse reflectance infrared Fourier transform spectroscopy (DRIFTS) and diffuse-reflectance ultraviolet-visible spectroscopy are the common technique to detect biomolecules. The diffuse reflectance spectroscopy (DRS) utilizes visible and near-infrared (NIR) light to determine the metabolites noninvasively. The DRS yields spectral plots of single point measurements of diffuse reflectance, the diffuse reflectance imaging (DRI) further extends DRS by yielding wide-field spectral images of diffuse reflectance. Both DRS and DRI are quantitative techniques that allow both optical absorption and optical scattering to be determined from images of diffuse reflectance.

Digital image analysis is a computer-assisted software detection or quantification of specific features in an image following enhancement and processing of that image, including analysis of blood vessels, blood components, microorganisms, particulate matter components, DNA analysis, morphometric analysis, and so on.

A display serial interface (DSI) specifies a high-speed differential signaling point-to-point serial bus. DSI is the hardware in the single board computer. The display serial interface defines a high-speed serial interface between a host processor and a display module. The display serial interface (DSI) standard allows for high-speed communication between Liquid Crystal Display (LCD) screens. DSI supports ultra-high definition such as 4K and 8K required by mobile displays. It specifies the physical link between the chip and display in devices such as smartphones, tablets, and connected cars. The DSI interface can be used to connect a capacitive touchscreen to the wearable device to display all the sensor data. It is usually in the form of connectors or ribbon cables. The DSI can be used to connect to the touchscreen for testing of the wearable device. The DSI port can connect to display unit. The DSI port connectors can be made available to connect to any smartwatch through a set of attachment slots in the smart band.

Deoxyribonucleic acid (DNA) is a self-replicating material that is present in nearly all living organisms as the main constituent of chromosomes. It is the carrier of genetic information. DNA is the molecule that contains within it all the instructions and information about an organism. It is the chemical name for the molecule that carries genetic instructions in all living things. DNA contains information regarding how the organism will develop, how it lives and reproduces, and is described as the blueprint of a living organism. The DNA molecule consists of two strands that wind around one another to form a shape known as a double helix. Each strand has a backbone made of alternating sugar (deoxyribose) and phosphate groups. Attached to each sugar is one of four bases: adenine (A), cytosine (C), guanine (G), and thymine (T). The two strands are held together by bonds between the bases: adenine bonds with thymine, and cytosine bonds with guanine. The sequence of the bases along the backbones serves as instructions for assembling protein and RNA molecules. Given that DNA molecules are found inside the cells, they are too small to be seen with the naked eye. A microscope is needed. It possible to see the nucleus (containing DNA) using a light microscope. DNA strands/threads can only be viewed using microscopes that allow for higher resolution. A picocamera is a component of a particle imaging system that allows for high-magnification and high-resolution pictures of microorganisms and small molecules. The particle imaging system allows for detection of microorganisms based on DNA segments.

A dust mite is a microscopic organism that is the primary cause of allergies related to house dust. Dust mites work their way into soft places like pillows, blankets, mattresses, and stuffed animals. Many people with asthma are allergic to dust, but it's the droppings produced by the mites in the dust, along with the body fragments of dead dust mites, that really cause allergic reactions. The term "dust mite allergy" is a misnomer because it is the fecal excretion of these mites to which people are allergic. Dust mites can therefore trigger allergic reactions even when dead. When breathed in, these can lead a person to develop allergy or asthma symptoms. Dust mites are 0.5-50 µm in size, and a high efficiency particulate air (HEPA) filter can filter contaminants as small as 0.3 µm.

An enviro sensor consists of an RFID tag sensor, a location sensor, an ambient light sensor, a gas sensor, a smoke sensor, a temperature, humidity, and pressure sensor, a sound sensor, and an ultraviolet light sensor. It detects, measures, and monitors the surrounding environment sensor parameters result. The enviro sensor measured parameters result enables prediction of an enviro risk level. The enviro sensor parameter results are often shown as a set of numbers known as a reference range. A reference range may also be called "normal reference range" or "normal values." If the enviro sensor measured parameters result falls outside the reference range, the user or patient can have health problems. The enviro risk level is based on either individual lower or higher values of the enviro parameter result or relationship with other enviro parameters or wearable device sensors data.

A eukaryote is an organism with cells that contain a nucleus. In addition to a nucleus, a cell membrane, and cytoplasm, most eukaryote cells contain dozens of other specialized structures, called organelles, which perform important cellular functions. These organelles are mitochondria, plastids, endoplasmic reticulum, and Golgi apparatus. These organelles are not present in prokaryotic cells. The wearable device picocamera and particle imaging system can take pictures of organelles.

Fluorescence imaging is the visualization of fluorescent proteins such as ALP, ALT, AST, LDL, and HDL as labels for molecular processes or structures. The processes involve using the fluorescence property of some atoms and molecules to absorb light at a particular wavelength and to subsequently emit light of longer wavelength. Fluorescence is the emission of light by a substance that has absorbed light or other electromagnetic radiation. It is a form of luminescence. A perceptible example of fluorescence occurs when the absorbed radiation is in the ultraviolet region of the spectrum (invisible to the human eye), while the emitted light is in the visible region; this gives the fluorescent substance a distinct color that can only be seen when exposed to UV light. Fluorescent materials cease to glow nearly immediately when the radiation source stops, unlike phosphorescent materials, which continue to emit light for some time after.

A fungus is a group of spore-producing single-celled or multinucleate organisms feeding on organic matter, including molds, yeast, mushrooms, and toadstools. A fungus is any member of the group of eukaryotic organisms which includes yeasts, rusts, smuts, mildews, molds, and mushrooms. Most microscopic or smaller fungi are 2 to 10 micrometers. The cell shapes include spherical, ellipsoidal, or cylindrical yeast cells or chains of highly polarized cylindrical cells which form pseudo hyphae or hyphae. There are lots of good or beneficial fungi to eat, like some mushrooms or foods made from yeast, like bread or soy sauce. Molds from fungi are used to make cheese, beer, and wine. Scientists use fungi to make antibiotics, which doctors sometimes use to treat bacterial infections. Fungi also help to decompose by releasing enzymes to break down the decaying material, after which they absorb the nutrients in the decaying material, from leaves to insects. Fungi can cause disease in many ways, for example: a) Replication of the fungus such that fungal cells can invade tissues and disrupt their function, b) Immune response by immune cells or antibodies, c) Competitive metabolism by which they consume energy and nutrients intended for the host, d) Toxic metabolites, for example, *Candida* species that can produce acetaldehyde, a carcinogenic substance, during metabolism. Fungi are linked to human ailments, such as allergic and asthmatic diseases that affect millions of people. Some fungi reproduce through tiny spores in the air. Inhaled spores result in fungal infections which often start in the lungs or on the skin. Fungi cause eye infections which can result in blindness. Fungi create harm by spoiling food, destroying timber, and by causing diseases of crops, livestock, and humans. Only a few of the fungi cause sickness and infection. Common fungal infections are as follows: a) Ringworm, which is a contagious fungal infection caused by common mold-like parasites that live on the cells in the outer layer of the skin. Types of fungi that cause ringworm are *Trichophyton, Microsporum*, and *Epidermophyton*. b) Fungal nail infections and athlete's foot (tinea pedis), a fungal infection that usually begins between the toes caused by dermatophytes. Athlete's foot is caused by several different fungi, including species of *Trichophyton, Microsporum*, and *Epidermophyton*. c) Mouth, throat, esophagus, and vaginal yeast infections caused by the yeast *Candida*. The biohazards associated with different fungi can be reported in the form of biosafety level. The biosafety level allows the user and physician to take appropriate preventive measures to sterilize the fungus.

A gas sensor is an electronic component that can be used to detect the presence or concentration of gases. The sensor has different sensitivities to different types of gases in the ambient air. The intended use of the gas sensor is to detect, measure, and monitor gas types such as reducing gases with low oxidation numbers, such as carbon monoxide (CO), ammonia ($NH_3$), ethanol ($C_2H_5OH$), hydrogen (H), methane ($CH_4$), propane ($C_3H_8$), and isobutane ($C_4H_{10}$). Oxidizing gases generally provide oxygen, cause, or contribute to the combustion of other material more than air does. They include nitrogen dioxide ($NO_2$), nitrogen oxide (NO), and hydrogen (H). Gases that react to ammonia include hydrogen (H), ethanol ($C_2H_5OH$), ammonia ($NH_3$), propane ($C_3H_8$), and isobutane ($C_4H_{10}$), either inside or surrounding the user. The gas type information can be used by the user or physician to take appropriate actions such as removal of toxic gases or evacuation based on set acceptance criteria. The gas type information surrounding the user can also be used by the user to take appropriate preventive measures by wearing appropriate personal protective equipment. The gas type can also provide information about potential fire hazards due to the presence of highly flammable gases like methane. Improperly managed harmful gases can serve as a rich source of disease and contribute to global climate change through the generation of greenhouse gases, and even promote urban violence with the degradation of urban environments. The detection of gas is expressed as a gas type present. The gas sensor sends real-time gas types surrounding the user data to the cloud server. The gas sensor working principle can be based on variation to the electrical resistance or capacitance in response to the concentration of the gas. In the case of electrical resistance type, the concentration of the gas near the sensor produces a corresponding potential difference by changing the resistance of the material inside the sensor, which can be measured as output voltage. Based on this voltage value, the type and concentration of the gas can be estimated. The gas type which the sensor can detect depends on the sensing material present inside the sensor. Gas sensors are typically classified based on the type of the sensing element they are built with (i.e., a metal oxide based gas sensor uses the measurement of change in resistance, a fluorescence gas sensor uses the detection of wavelength change of fluorescence, an optical gas sensor detects gas types based on spectral range, an electrochemical gas sensor is operated based on the diffusion of gas of interest into the sensor, a capacitance-based gas sensor uses changes in the capacitance value to detect gas types, and calorimetric gas sensors and acoustic based gas sensors are based on a change in the resonant frequency). The most common gases found in home or work areas are carbon monoxide, ammonia, chlorine, methane, carbon dioxide, nitrogen, hydrogen sulfide, and hydrogen.

General purpose input output pins, also known as GPIO pins, are uncommitted digital signal pins on an integrated circuit or electronic circuit board whose behavior—including whether they act as input or output—is controllable by the user at run time. GPIOs have no predefined purpose and are unused by default. Sensor software drivers are used to map and assign the GPIO to the sensor pinout. Microbial biosensor, particulate matter sensor, enviro sensor, and display unit pinouts are connected to single board computer GPIO pins.

A global positioning system (GPS) is a satellite-based navigation system made up of at least 24 satellites. GPS works in any weather condition, anywhere in the world, 24 hours a day, with no subscription fees or setup charges. A GPS measures elevation below the orbit of the satellites. To convert this to altitude, it subtracts the distance from the center of the earth (i.e., center of the satellites' orbits) from the average sea level. It provides geospatial position data which can be mapped to street addresses and altitudes. The geospatial position data allows for tracking of a wearable device location.

A graphics processing unit (GPU) is a specialized electronic circuit designed to rapidly manipulate and alter memory to accelerate the creation of images in a frame buffer intended for output on a display device. A GPU is one of the components of a system on chip of a single board computer. The GPU accelerates the processing of picocamera photos and videos for multiple functions, such as microorganism recognition, particulate matter size, object ID recognition, surface type recognition, and so on.

A gyroscope can be used for measuring or maintaining the orientation and angular velocity of the wearable device. The orientation allows centering of the wearable device to an object like a nasal cavity, an oral cavity, or a surface.

A haptic technology can interface with the user through the sense of touch. A wearable device touchscreen is touch sensitive.

A healthy diet is a diet that maintains or improves overall health. A healthy diet provides the body with essential nutrition: fluid, macronutrients such as protein, micronutrients such as vitamins, minerals, fiber, and food energy. A healthy diet is one in which macronutrients are consumed in appropriate proportions to support energetic and physiologic needs without excess intake while also providing sufficient micronutrients and hydration to meet the physiologic and lifestyle needs of the body.

A healthy lifestyle is a way of living that lowers the risk of being seriously ill or dying early. It helps a person to enjoy more aspects of their life through a balanced physical, environmental, occupational, financial, intellectual, emotional, social, and spiritual wellness dimension ranking. This also includes mindfulness.

A humidity sensor is an electronic component that detects and measures water vapors. The intended use of the humidity sensor is to detect, measure, and monitor the relative humidity surrounding the user. The wearable device humidity value can be used by the user of a wearable device to ensure that humidity is within set acceptance criteria. It is very important to reduce the high moisture content; otherwise, it can also result high microbial activity and could even facilitate growth of pathogens, foul odor, unpleasant smell, and infectious diseases. Dust mites thrive in temperatures of 20 to 25 degrees Celsius. Dust mites also like humidity levels of 70 to 80 percent. The unit of measurement of the results of the humidity sensor can be a percentage of relative humidity surrounding the user. The humidity is reported in the form of a percentage that runs from 0 to 100. The humidity sensor sends real-time humidity data surrounding the user to the cloud server. The humidity sensor detects the relative humidity of the immediate environments in which it is placed. It measures both the moisture and temperature in the air and expresses relative humidity as a percentage of the ratio of moisture in the air to the maximum amount that can be held in the air at the current temperature. The working principles of the humidity sensor can be based on capacitive humidity sensors, resistive humidity sensors, thermal conductive sensors, and such. A nano and MEMS relative humidity sensor is a differential capacitance type that consists of a layer sensitive to water vapor that is sandwiched between two electrodes acting as capacitor plates. The upper water vapor permeable electrode consists of a grid that allows water vapor to pass into the humidity sensitive polymer layer below, which is a backplate electrode, thus altering the capacitance between the two electrodes. The above units are on top of a base substrate. On-chip circuits carry out automatic calibration and signal processing to produce a relative humidity measurement.

Illuminance is the amount of luminous flux per unit area. The unit for the quantity of light flowing from a source in any one second or luminous flux is called the lumen. In a sensor, the unit of measurement is the lux, which is equal to one lumen per square meter.

An infrared radiation is that portion of the electromagnetic spectrum that extends from the long wavelength, or red, end of the visible-light range to the microwave range. Invisible to the eye, it can be detected as a sensation of warmth on the skin. The infrared range is usually divided into three regions: near infrared (nearest the visible spectrum), with wavelengths 700 nm to about 2,500 nm; middle infrared, with wavelengths 2,500 nm to about 5,000 nm; and far infrared, with wavelengths 5,000 nm to 1,000,000 nm. Most of the radiation emitted by a moderately heated surface is infrared; it forms a continuous spectrum. Molecular excitation also produces copious infrared radiation, but in a discrete spectrum of lines or bands.

An intelligent relationship interpretation defines how two entities relate to each other with a note of explanation or comment to make sense of information intelligently and easily. The intelligent relationship interpretation is a relationship of one of the smart band sensor parameters with another sensor parameter. For example, how the biofluid parameter is related to the physiological sensor, biokinetics sensor, or lifestyle sensor parameter. The explanation or description is based on the scientific validity of the relationship between sensor parameters and/or a clinical laboratory test result and a sensor parameter result (e.g., scientific test, piece of research, peer reviewed scientific publications, clinical studies, and so on). The intelligent relationship interpretation consists of a symptom, a cause, and a treatment. The cause and the treatment are accurately determined based on a related smart band sensor parameter result value. For example, a person with a smart band sensor glucose result of high blood glucose level of 150 mg/dL could be due to physiological parameters of systolic blood pressure of equal or greater than 180 mmHg, and/or environmental parameter of high ambient temperature. This is due to people with systolic blood pressure of 180 mmHg have significant higher glucose concentrations. The relationship is multivariate, involving more than one variable. The accurate cause of high glucose in this example is due to high systolic blood pressure. The accurate treatment is lisinopril, benazepril, captopril and others which help relax blood vessels by blocking the formation of a natural chemical that narrows blood vessels instead of insulin program or a supplement of short-acting insulin to help control hyperglycemia. If the person has been working in the high temperature of 40 degree Celsius for long period of time, the high glucose could be because of dehydration where high temperature can cause blood sugar to rise as the glucose in the blood become more concentrated. The treatment in this case could simply be working in cooler temperature areas and staying hydrated. The intelligent relationship interpretation also consists of a relationship between clinical laboratory test result and smart band sensor parameter result with explanation of the way in which they are connected.

An LED flash is an electronic component device that emits light when charged with electricity. LEDs come in white and many colors, including non-visible light such as infrared and ultraviolet. Bright white LEDs are commonly used for phone camera flashes and LCD display backlights. The LED flash is part of the picocamera.

A laboratory director is a person responsible for the overall operation and administration of the laboratory, including provision of timely, reliable, and clinically relevant test results and compliance with applicable regulations and accreditation requirements. The responsibility also includes employment of competent personnel, test validations, availability of equipment and consumables, safety, laboratory policies, quality assurance, proficiency testing, and test reports. The laboratory director reviews patient test result and determines the cause of disorders and reports out user test results. The laboratory director routes the critical value test results such as pathogen and abnormal patient test results to report to the physician and patient.

A laboratory information system (LIS) or laboratory information management system (LIMS) has a local or cloud system comprising of computer hardware and software serving the information needs of the laboratory. The laboratory database contains all the information for patient specimen accessioning, pre-analytical, analytical, and post analytical testing, and quality control information. A laboratory director reviews the patient result in the laboratory information system before reporting the results out to a physician. The laboratory information auto verification method allows for auto review of the patient test result to determine the cause of disorders and reports out user test results. The laboratory is also enabled to automatically send patient test results to the physician and patient.

A laboratory testing facility includes a clinical laboratory, biorepository, healthcare facility, water testing facility, food testing facility, forensic testing facility, and so on. A healthcare facility provides a wide range of laboratory procedures which aid the physicians in carrying out the diagnosis, treatment, and management of patients. The water and food testing facilities test for pathogens in water, liquids, and food. The forensic testing facility tests involve pathology tests associated with crime.

A lifestyle sensor is an electronic component which can be used to noninvasively detect the lifestyle parameters related to movements of or within body parts using chemiresistor, polyvinylidene fluoride (PVDF) film, alcohol or MQ3, camera, accelerometer, gyroscope, magnetometer, surface electromyography, pressure/strain, ultrasonic, proximity detectors, radio frequency, GPS, smoke detector, microphone, and so on. The intended use of the lifestyle sensor is to detect, measure, and monitor noninvasively walking, standing, sitting, running, yoga, hiking, cycling, swimming, movement, exercise, sleep, stress, fall, and proximity to an object. The lifestyle sensor detects and keeps track of the numbers of occupational, financial, intellectual, emotional, social, and spiritual interactions. The lifestyle sensor measured parameters result enables prediction of a lifestyle risk level. The lifestyle sensor parameter results are often shown as a set of numbers known as a reference range. A reference range may also be called "normal reference range" or "normal values." If the lifestyle sensor measured parameters result falls outside the reference range, the user or patient can have health problems. The lifestyle risk level is based on either individual lower or higher values of lifestyle parameter result or relationship with other lifestyle parameter or wearable device sensors data.

A location sensor is an electronic component that can determine and monitor the geospatial position which includes latitude, longitude, and altitude, or the street location of an object, and provide internet access. The intended use of the location sensor is to determine the geospatial location of a wearable device and provide internet access to a wearable device. The information can also include time and other data. The wearable device location value can be used to associate the sensor data with the location. It can consist of global positioning system (GPS) receivers and cellular adapter elements. The location sensor working principle can be based on GPS and cellular network internet connectivity. The GPS is a satellite-based navigation system that provides geolocation and time information to a GPS receiver anywhere on or near the Earth where there is an unobstructed line of sight to four or more GPS satellites. The GPS part of location sensors are receivers with antennas that use a satellite-based navigation system with a network of satellites in orbit around the Earth to provide position, velocity, and timing information. A cellular adapter part of the location sensor enables cellular internet connectivity. The location sensor sends real-time data to the cloud server. The wearable device location information can be used to track it through connected mobile devices.

Machine learning can be a method of data analysis that automates analytical model building. Machine learning is a branch of artificial intelligence that uses statistical techniques to give computer systems the ability to learn from data, without being explicitly programmed. Example machine learning techniques that can be used herein include, inter alia: decision tree learning, association rule learning, artificial neural networks, inductive logic programming, support vector machines, clustering, Bayesian networks, reinforcement learning, representation learning, similarity, metric learning, and/or sparse dictionary learning. Historical user sensor data sets can be used as training data sets. Machine learning, along with neural network algorithms, can continually learn to recognize new objects like food, liquids, paper, containers, cardboard boxes, and such, from different angles and in various ranges from the photos and videos taken by the picocamera. Machine learning can also learn and predict pathogens on surfaces of different type of objects. The more learning, the more accurate the prediction, thereby increasing the accuracy of the results. Machine learning algorithms of the wearable devices allow for identification of the microorganisms, pollens, and other particulate matter.

Magnetism can be a physical phenomenon produced by the motion of an electric charge, resulting in attractive and repulsive forces. A magnet can be piece of iron that has its component atoms so ordered that the material exhibits properties of magnetism, such as attracting other iron-containing ferromagnetic materials such as iron, cobalt, nickel, and gadolinium. A magnetic field is a vector field that describes the magnetic influence on moving electric charges, electric currents, and magnetic materials. Magnetic fields surround magnetized materials and are created by electric currents such as those used in electromagnets, and by electric fields varying in time. Since both the strength and direction of a magnetic field may vary with location, they are described as a map assigning a vector to each point of space. Magnetic fields are produced by moving electric charges and the intrinsic magnetic movements of elementary particles associated with a fundamental quantum property, their spin. The electromagnetic waves method uses a Hall sensor array to detect microorganisms containing ferromagnetic material. A Hall sensor is a type of sensor which detects the presence and magnitude of a magnetic field using the Hall effect. The output voltage of a Hall sensor is directly proportional to the strength of the field. The effect of Earth's electromagnetic waves is masked out to increase the accuracy of the results.

A metabolite is any substance produced during metabolism (digestion or other bodily chemical processes usually break down food or chemicals). The term metabolite may also refer to the product that remains after a drug is broken down (metabolized) by the body. Some of the important blood metabolites detected and measure are albumin, bilirubin, blood glucose level, blood alcohol concentration level, blood urea nitrogen (BUN), cortisol, creatinine, calcium, chloride, magnesium, phosphorus, potassium, sodium, alkaline phosphatase (ALP), alanine aminotransferase (ALT), and aspartate aminotransferase (AST).

Methane is a gas byproduct generated through the natural decomposition of solid waste in landfills. Methane is an odorless and flammable gas. When present in very high concentrations, it can be potentially explosive. Methane is nonreactive and not harmful to human health, but if there is excess methane in a room and it displaces the oxygen, one could die from suffocation. The user should leave the area immediately if there is excessive methane gas in the surrounding area. Excessive methane gas is linked to global warming. There is a type of beneficial bacteria, methanotrophs, which hold the key to dismantling methane gas. Methanotrophs survive extreme conditions by eating methane.

A method can be a particular procedure for accomplishing a task or activity. Wearable devices, various other sensors, and software computing environments use methods and algorithms to set specific acceptance criteria to detect and sterilize pathogens and monitor the environment. A method can implement many algorithms. A wearable device can have sensor methods to implement, operate, calculate, and monitor pathogens, pollens, and the environment. Software computing environments can contain pathogen detection and sterilization methods. Microorganisms can be detected through particle detection methods such as infrared spectroscopy, fluorescence imaging, particle imaging, nucleic acid sequence identification, electromagnetic waves, ultrasound waves, light scattering, and so on.

Micro-electromechanical systems (MEMS) devices contain tiny integrated devices or systems that combine mechanical and electrical components. They now also include nanomaterials and picomaterial based components. They are fabricated using integrated circuit (IC) batch processing techniques and can range in size from a few micrometers to millimeters. MEMS devices combine small mechanical and electronic components on a silicon chip. The fabrication techniques used for creating transistors, interconnects, and other components on an integrated circuit (IC) can also be used to construct mechanical components such as springs, deformable membranes, vibrating structures, valves, gears, and levers. This technology can be used to make a variety of sensors such as microbial biosensors, particulate matter sensors, enviro sensor comprising RIFD tag sensors, location, temperature, humidity, pressure, air quality, smoke, gas, ambient light, and so on. MEMS enables the combination of accurate sensors, powerful processing, and wireless communication (for example, Wi-Fi or Bluetooth) on a single integrated circuit. Large numbers of devices can be made at the same time, so they benefit from the same scaling advantages and cost efficiencies as traditional ICs. MEMS based sensors allow for the manufacturing of compact and power efficient wearable devices. The microbial biosensor, particulate matter sensor, and enviro sensor are very small MEMS devices that fit on a wrist smart band.

A microorganism, or microbe, is an organism that is microscopic or submicroscopic, which may exist in its single-celled form or a colony of cells. A microscopic organism is usually a prion, virus, bacterium, fungus, protist, or dust mite. The study of microorganisms is called microbiology. Prions and viruses are non-living but are usually considered part of microorganisms. The microorganisms can be beneficial or harmful to humans. The exact number is not known, but there are about one trillion species of microbes on Earth, and 99.999 percent of them have yet to be discovered. Viruses are considered neither prokaryotes nor eukaryotes because they lack the characteristics of living things, except the ability to replicate in a host cell. Bacteria are prokaryotes, i.e., microscopic single-celled organisms that have neither a distinct nucleus with a membrane nor other specialized organelles. In contrast, fungi and dust mites are eukaryote organisms consisting of a cell or cells in which the genetic material is DNA in the form of chromosomes contained within a distinct nucleus. Microorganisms can be good or beneficial for humans, such as microbes that contribute to digestion, produce vitamins, promote development of the immune system, and detoxify harmful chemicals. Microorganisms or microbes are essential to making many foods we enjoy, such as bread, cheese, and wine. Microorganisms or microbes that cause disease are called pathogens.

A microphone is a device that converts the air pressure variations of a sound wave to an electrical signal. The wearable device microphone and speaker allow users near the wearable device two-way communication with a person on the mobile device through the mobile healthcare application or laboratory information system. The microphone can be used as an input for voice activated commands.

A microprocessor is an integrated circuit that contains all the functions of a central processing unit of a computer.

A microscope is an optical instrument used for viewing very small objects, such as animal or plant cells, or large microorganisms, typically magnified several hundred times. The limit of resolution for a light microscope is 0.2 μm or 200 nm, and most viruses are smaller than that. As such, an electron microscope is needed. An electron microscope is a microscope with high magnification and resolution, employing electron beams in place of light and using electron lenses. The electron microscopes have a higher resolving power than light microscopes and can reveal the structure of smaller objects such as viruses, bacteria, and fungi. An electron microscope can have magnifications of up to about 10,000,000×, whereas most light microscopes are limited by diffraction to about 200-nm resolution and useful magnifications below 2,000. The electron microscope types usually are Transmission Electron Microscope (TEM), Scanning Electron Microscope (SEM), Reflection Electron Microscope (REM), Scanning Transmission Electron Microscope (STEM), and Scanning Tunneling Microscopy (STM). Atomic force microscopy (AFM) is a kind of scanning probe microscopy, where a probe or tip is used to map the contours of the sample. These instruments are bulky, costly, and require an experienced person to look at magnified images. To view the DNA, RNA, as well as a variety of other protein molecules, an electron microscope is used. Whereas the typical light microscope is only limited to a resolution of about 0.25 μm, the electron microscope is capable of resolutions of about 0.2 nanometers, which makes it possible to view smaller molecules. This is achieved because electron microscopes use electron beams rather than the visible light used for light microscopes. Existing microscopes require sample to be put on substrates like glass, are very bulky, and require a special room and light. The electron or e-beam is like X rays and gamma radiation and ionizes the material it strikes by stripping electrons from the atoms of the exposed surface, and is damaging to the humans and microorganisms. The wearable device picocamera instead uses MEMS and a picomaterials based specialized magnifying lens, aperture, and auto adjustment of the image or video and objective. The optical micro, nano, and picomaterials enable super high magnification and resolution biological imaging and video of microorganisms using visible light that is compressed and not harmful to humans or environment. Picomaterials have diameters in the picometer range. Picofibers have fibers with diameters in the picometer range, and nanofibers are fibers with diameters in the nanometer range. Picofibers and nanofibers can be generated from different polymers. The picocamera hardware uses picomaterials.

A microbial biosensor is a device that detects microorganisms. Microorganisms detected include both beneficial microorganisms and pathogenic microorganisms also known as pathogens. A microbial biosensor is an electronic component that utilizes optical, mass based, and acoustic sensors to detect microorganisms and kill pathogens. The intended use of the microbial biosensor is to detect, measure, and monitor pathogen types, concentrations, and biosafety levels, and kill pathogens in a nasal cavity, an oral cavity, or on a surface of the object. The microbial biosensor also detects, measures, and monitors a beneficial microorganism count, a beneficial microorganism type, and a beneficial microorganism concentration in a nasal cavity, an oral cavity, or on a surface of the object. The microorganisms detected can be prions, viruses, bacteria, fungi, protists, dust mites, and so on. Pathogens of all classes must have mechanisms for entering their host and for evading immediate destruction by the host immune system. Pathogens that are most contagious and cause the most severe symptoms are SARS-CoV-2, *E. coli*, Hepatitis A, Nontyphoidal *Salmonella, Norovirus, Shigella*, and *Salmonella Typhi*. Software computing environments can contain pathogen detection and sterilization methods. Microorganisms can be detected through particle detection methods such as infrared spectroscopy, fluorescence imaging, particle imaging, nucleic acid sequence identification, electromagnetic waves, ultrasound waves, light scattering, and so on. The microbial biosensor measured parameters result enables prediction of a microbial risk level. The microbial biosensor parameter results are shown as pathogen and beneficial microorganism count, type, concentration, and biosafety level. The microbial risk level is based on either individual lower or higher values of microbial biosensor parameter result or relationship with other microbial biosensor parameter or wearable device sensors data.

A mobile healthcare application is a computer program or software application, or an app designed to run on a wearable device to set up a wearable device and access the sensor data. The mobile healthcare application can also be installed on the smartwatch and mobile devices. The mobile healthcare application retrieves public, private, and commercial pathogen annotation information stored in a microorganism database and pollen database. The mobile healthcare application, microorganism database, and pollen database reside in the secure digital card of the single board computer. In a system software computing environment, they are also stored in the cloud server database for global access.

A microorganism database stores the platform dataset, genome, annotation, pathogen safety data sheet, attributes, and unique identifiers based on biosensor transducers and the microorganism detection method used. The taxonomy data comprises pathogen kingdom, phylum, class, order, family, genus, species, and so on. The genomic information contains organism name, organism groups, gene assembly, assembly level, length of genome assembly, GC %, host, protein coding genes, neighbor nucleotides, cell type, number of cells, size, microscopy, shape, cellular machinery, type of organism, structure, cell wall, cellular membrane, genome (DNA or RNA), strand type (single, double), nucleic acid, mRNA, ribosomes, living attributes, replication, cells infected, diseases/infections, duration of illness, treatment, and so on. The pathogen safety data sheet contains information such as infectious agent, hazard identification, dissemination, stability, and viability, first aid/medical, laboratory hazards, exposure controls/personal protection, handling and storage, and regulatory and other information. The microorganism attributes comprise structure, morphology, component, function, chemical composition, constituent or element, and so on.

A middleware stack is software that lies between an operating system and the applications running on it. A middleware stack functions as a hidden translation layer and enables communication and data management for distributed applications. It connects two applications together so data and databases can be easily passed between them. For example, middleware allows users to perform such requests, allowing the web server to return dynamic web pages based on a user's profile, or submitting forms on a web browser. The mobile healthcare application and laboratory information system dynamic web pages interface with the middleware stack to send and fetch the data and display it on the web browser.

A model can be a system or thing or procedure or a proposed structure used as an example to follow. Models are created for methods like clusters based on microorganism types, pathogen types, shape, size, composition, wearable device location, and zip codes. Models are also created for the wearable device database structure to contain all the wearable device information.

A molecular formula is a chemical formula that gives the total number of atoms of each element in each molecule of a substance or compound.

Monitoring In medicine is used to regularly watch and check a person or condition or health parameter to see if there is any change. Also refers to a device such as smart band that records and/or displays patient or user data, such as microorganism parameter, a particulate matter parameter, an enviro parameter, a physiological parameter, a biofluid parameter, a biokinetics parameter, and a lifestyle parameter. It also includes devices used for the measurement of the analyte (measurand) levels for the purpose of adjusting treatments/interventions as required. Devices for monitoring are used to assess whether an analyte remains within physiological levels or within an established therapeutic drug range. These types of devices are designed to evaluate a patient or a user current state. These are also used for serial measurement; whereby multiple determinations are taken over time. This is typically used for the detection/assessment of disease progression/regression, disease recurrence, minimum residual disease, response/resistance to therapy, and/or adverse effects due to therapy.

A nasal cavity is a large, air-filled space above and behind the nose in the middle of the face. The nasal septum divides the cavity into two cavities, also known as fossae. Each cavity is the continuation of one of the two nostrils. The origin of organisms that are introduced into the sinuses and may eventually cause sinusitis is the nasal cavity. The normal flora of that site includes *Staphylococcus aureus, Staphylococcus epidermidis*, Streptococci, *Propionibacterium acnes*, and aerobic diphtheroid. The most common aerobic bacteria are *Staphylococcus epidermidis*, diphtheroids, and *Staphylococcus aureus*. The wearable device nasal cavity detection can be based on the entire nasal cavity measurement area or can be programmed to look for microorganisms in a specific area within the nasal cavity. The individual user nasal cavity can be profiled and set up initially. This allows for masking the nasal cavity tissues for faster detection of microorganisms. The particle detection methods are programmed to first do the comparison of detected microorganisms with the commonly found microorganisms in the nasal cavity. Also, based on enviro sensor parameters result, some of the microorganisms are not present in the nasal cavity and can be ruled out during microorganism detection.

Normal reference ranges or reference ranges or reference interval is a range of test values expected for a designated population of individuals. The values below the lower limit or above the limit values are considered as abnormal values. The normal reference ranges help describe what is typical for a particular group of people based on age, sex, and other characteristics. In the case of clinical laboratory instruments, the reference ranges for the same methods or instruments may differ slightly between laboratories and geographic areas because of different operating conditions, different criteria for selection of healthy subjects, different patient populations, and so on.

Nucleobases, also known as nitrogenous bases or often simply bases, are nitrogen-containing biological compounds that form nucleosides, which, in turn, are components of nucleotides, with all these monomers constituting the basic building blocks of nucleic acids. The ability of nucleobases to form base pairs and to stack one upon another leads directly to long-chain helical structures such as ribonucleic acid (RNA) and deoxyribonucleic acid (DNA). Five nucleobases-adenine (A), cytosine (C), guanine (G), thymine (T), and uracil (U)—are called primary or canonical. They function as the fundamental units of the genetic code, with the bases A, G, C, and T being found in DNA while A, G, C, and U are found in RNA. Thymine and uracil are distinguished merely by the presence or absence of a methyl group on the fifth carbon (C5) of these heterocyclic six-membered rings. Adenine and guanine have a fused-ring skeletal structure derived of purine; hence they are called purine bases. The simple-ring structure of cytosine, uracil, and thymine is derived of pyrimidine, so those three bases are called the pyrimidine bases. Each of the base pairs in a typical double-helix DNA comprises a purine and a pyrimidine: either an A paired with a T or a C paired with a G. These purine-pyrimidine pairs, which are called base complements, connect the two strands of the helix and are often compared to the rungs of a ladder. The super sensitive picocamera based on picomaterials, capable of registering single electrons, is used to take high-resolution images of the DNA and RNA, which includes base molecules. Bases are identified based on the A, G, C, T, and U bond structures.

An oral cavity or open mouth cavity is the lining inside the cheeks and lips, the front two thirds of the tongue, the upper and lower gums, the floor of the mouth under the tongue, the bony roof of the mouth, and the small area behind the wisdom teeth. The oral cavity flora are home to many microorganisms. The presence of nutrients, epithelial debris, and secretions makes the mouth a favorable habitat for a great variety of bacteria, including both beneficial and pathogens. Oral bacteria include *streptococcus, granulicatella, gemella, veillonella, lactobacilli, staphylococci*, and corynebacteria, with a great number of anaerobes. Anaerobes such as *Treponema denticola* and *Porphyromonas gingivalisoral* cause diseases such as periodontitis. In addition, specific oral bacterial species have been implicated in several systemic diseases, such as bacterial endocarditis, aspiration pneumonia, osteomyelitis in children, preterm low birth weight, and cardiovascular disease. The wearable device oral cavity detection can be based on the entire open mouth measurement area or can be programmed to look for microorganisms in specific area within the oral cavity. The individual user oral cavity can be profiled and set up initially. This allows for masking the oral cavity tissues for faster detection of microorganisms. The particle detection methods are programmed to first do the comparison of detected microorganisms with commonly found microorganisms in the oral cavity. Also, based on enviro sensor parameters result, some of the microorganisms are not present in the oral cavity and can be ruled out during microorganism detection.

An organelle is a specialized structure that performs important cellular functions within a eukaryotic cell. Examples of membrane-bound organelles are nucleus, endoplasmic reticulum, Golgi apparatus, mitochondria, plastids, lysosomes, and vacuoles.

Particulate matter concentrations refer to the amount of fine particulate matter in the air. Particulates, also known as atmospheric aerosol particles, bioaerosol particles, atmospheric particulate matter, particulate matter (PM), suspended particles in the air, or suspended particulate matter (SPM)—are microscopic particles of solid or liquid matter suspended in the air. The term aerosol commonly refers to the particulate/air mixture. Particulates are the most harmful form of air pollution due to their ability to penetrate deep into the nasal cavity, lungs, blood stream, and brain, causing health problems including heart attacks, respiratory disease, and premature death. Bioaerosols (short for biological aerosols) are a subcategory of particles released from terrestrial and marine ecosystems into the atmosphere. They consist of both living and non-living components, such as prions, viruses, bacteria, fungi, protists, dust mites, and pollen.

A particulate matter sensor is an electronic component which can be used to obtain the number of suspended particles in the air, i.e., the concentration of particles, and output it in the form of a digital interface. The intended use of the particulate matter sensor is to detect, measure, and monitor the air quality index value surrounding the user, and it can be used to provide the level of health concern information. The wearable device air quality index value can be used by the user to decontaminate or use personal protective equipment based on set acceptance criteria. The air quality index value is reported in the form of a number that runs from 0 to 500. The EPA Office of Air Quality Planning and Standards (OAQPS) has set National Ambient Air Quality Standards. The particulate matter sensor sends real-time air quality information, i.e., the concentration of particles data, to the cloud server. The detected suspended particles in the air can include microorganisms, pathogens, dust, dust mites, pollens, and so on. The particulate matter sensor can use the laser scattering principle, which produces scattering by using a laser to radiate suspending particles in the air, collects scattering light in a certain degree, and finally obtains the curve of the scattering light change with time. In the end, the equivalent particle diameter, and the number of particles with different diameters per unit volume, can be calculated by a microprocessor based on the MIE theory of absorption and scattering of plane electromagnetic waves by uniform isotropic particles of the simplest form. The MIE theory is an analytical solution of Maxwell's equations for the scattering of electromagnetic radiation by particles of any size. The particulate matter sensor can distinguish types of particulate matter. PMx defines particles with a size smaller than "x" micrometers (e.g., PM2.5=particles smaller than 2.5 µm); PM.001, PM.01, PM.1, PM1, PM2.5, and PM10 in both standard and environmental units, and numbers of particles of various sizes: >0.001, >0.01, >0.1, >0.3, >0.5, >1.0, >2.5, >5, and >10 µm. The particulate matter unit of measurement is µg/m$^3$ or ng/m$^3$. The particulate matter sensor measured parameters result enables prediction of a microbial risk level. The particulate matter sensor parameter results are shown as pathogen and beneficial microorganism count, type, concentration, and biosafety level. The measured parameters result also includes pollen, type, count, and allergy level, dust mite allergen count, and a dust mite allergy level, particulate matter concentration, and air quality index. The individual parameter risks prediction can be pathogen biosafety risk level, a pollen allergy risk level, a dust mite allergy risk level, and an air quality index risk level. The particulate matter risk level is based on either individual lower or higher values of particulate matter sensor parameter result or relationship with other particulate matter sensor parameter or wearable device sensors data.

A pathogen is a prion, virus, bacterium, fungus, protist, dust mite, or other microorganism that can cause disease. Pathogens are disease-causing microorganisms and non-living things such as viruses. In total, there are approximately 1,400 known species of human pathogens that includes viruses, bacteria, and fungi. Human pathogens account for much less than 1% of the total number of microbial species on the planet. There are about 220 virus species that are known to be able to infect humans. The pathogenic viruses are known to cause disease in humans, and all can break into human cells. There are more than 900 bacteria species that are known to cause disease in humans. Pathogenic fungi are fungi that cause disease in humans or other organisms. Approximately 300 fungi are known to be pathogenic to humans.

A pathogen count is the total number of distinct prions, viruses, bacteria, fungi, protists, dust mites, or other microorganisms.

A pathogen type can be a type of prion, virus, bacterium, fungus, protist, dust mite or other microorganism. For example, a type of virus can be Influenza A/B virus, Rhinovirus, SARS-CoV-2 virus or COVID-19 virus, HIV, Smallpox, and so on. A type of bacteria can be *Legionella pneumophila, Mycobacterium tuberculosis, Staphylococcus aureus*, and so on. A type of fungus can be *Histoplasma capsulatum, Aspergillus flavus, Blastomyces dermatitidis*, and so on.

A pathogen concentration refers to the number of pathogen particulate matter in the air.

A pathogen biosafety level measurement is based on biological safety levels.

A personalized wellness program for a healthy lifestyle is based on a personalized user wellness dimension ranking which is calculated from the user smart band sensor result, user clinical laboratory test result, intelligent relationship interpretation data, and sensor data of the set of wearable electronics. The personalized user wellness dimension ranking comprises physical, environmental, occupational, financial, intellectual, emotional, social, and spiritual elements. Machine learning is used in case of missing data. There are well defined actionable personalized wellness program items for each of the wellness dimension rankings, resulting in a healthy lifestyle which is a way of living that lowers the risk of being seriously ill or dying early. World health organization published risk and data is also used as part of the program.

Photodiodes or photodetectors are used for light-based measurements. Smart band applications such as absorption, reflection, scattering, and emission spectroscopy, color measurement, gas detection, and more, all rely on photodiodes for precision light measurement. Photodiodes generate a current proportional to the light that strikes their active area. Most measurement applications involve using a transimpedance amplifier to convert the photodiode current into an output voltage.

A physician is a person qualified to practice medicine. A physician can diagnose a disease based on pathogen type and prescribe applicable medication. The physician reviews patient test results in conjunction with user smart band sensor parameters result and determines the root cause of the disorder to treat the user.

A physiological sensor is an electronic component comprising a set of biophysical sensors that is used to detect, measure, and monitor the way in which a living organism or bodily part functions using thermistor, photoconductivity, thermoelectric effects, pressure/strain, optical properties of light, and so on. The intended use of the physiological sensor is to detect, measure, and monitor noninvasively in vivo complete skin temperature, body temperature, heart rate, heart rate variability, respiratory rate, blood pressure, electrocardiogram parameters, blood oxygen, and blood carbon dioxide. The physiological sensor contains specialized probes to detect best blood vessels for accurate measurement of physiological parameters by discarding the small, hidden, or compromised blood vessels. The physiological sensor measured parameters result enables prediction of a physiological risk level. The physiological sensor parameter results are often shown as a set of numbers known as a reference range. A reference range may also be called "normal reference range" or "normal values." If the physiological sensor parameter measured results fall outside the reference range, the user or patient can have health problems. The physiological risk level is based on either individual lower or higher values of physiological parameter result or relationship with other physiological parameter or wearable device sensors data.

A picocamera is a component or device for recording visual images in the form of photographs, film, or video signals. A picocamera is a high-magnification and high-resolution camera made of picomaterials. The picomaterials optical fibers are fabricated from silica, but some other materials, such as collagen, gelatin, slik fibrion, polystyrene, as well as crystalline materials like sapphire, are used. The silicon atomic size is about 210 µm or 0.2 nm. The size of a microchip is about 2 nm. The size of a picocamera is around 0.4×0.4×0.8 mm, which is about the size of the grain of sand. The picosurface optics provide a high quality imager with a wide field of view. The picocamera has an artificial intelligence machine vision sensor with multiple functions, such as nasal cavity, oral cavity, and top of the surface recognition, line tracking, and so on. The intended use of the picocamera is to take photos and videos of the nasal cavity, oral cavity, or surface which can be used for nasal ID, open mouth ID, and surface ID recognition. The picocamera also takes images and videos of the small particles such as small molecules, proteins, microorganisms, and after image analysis identifies the microorganism type. The specialized picocamera can continually learn new surfaces such as top of the water, food, wall, table, and so on, even from different angles and in various ranges. The powerful picocamera optics can take high-magnification and high-resolution images of the microorganisms. The more it learns, the more accurate it is when it is running its neural network algorithm. The picocamera is part of the microbial biosensor and particulate matter sensor, which also includes a flash. The picocamera is made of picomaterials, nanomaterials, and MEMS. To detect microorganisms clearly, the size of the wavelength should be considerably smaller, in the picometer and nanometer range. Gamma rays and X rays cannot be used because they are hazardous to humans. The wavelength of visible light is far larger than the small molecules, lipids, proteins, and microorganisms. The picocamera working principle involves passing the light rays through picofibers or picotubes, thereby by cutting or slicing and compressing them into multiple smaller excitation quanta (MSEQ). These excitation quanta are smaller than small molecules and strike the microorganisms. A picocamera lens using picofibers and picotubes takes all the excitation quanta bouncing around from the microorganisms and uses glass to redirect them to a single point, creating an image. The visible light can also be spliced when it strikes the nano structured metallic surface at the tip of the picofibers before it hits the particle. The picocamera sends real-time photo and video data files to the mobile healthcare application and cloud server.

A platform dataset comprises a set of reference microorganism, microbiome, microbial genome, pathogen data, pollen genome, and pollen data from publicly available sources that constitutes the framework within which microorganism beneficial, pathogenic, and pollen data information is handled by the platform. The platform dataset can be derived from National Center for Biotechnology Information (NCBI), European Molecular Biology Laboratory/European Bioinformatics Institute (EMBL-EB), MicrobeNet—Centers for Disease Control and Prevention (CDC), Pathosystems Resource Integration Center (PATRIC), Virus Pathogen Resources (ViPR), Fungi Database (FungiDB), and the Ensembl genome browser, which provide access to organized information from the analysis of biological data for prions, virus, bacteria, fungi, protists, and so on, and pollen data from National Centers for Environmental Information. The actual sources, versions, genome build(s), and external links per platform dataset version are available in the mobile healthcare application user interface. The platform dataset curation can add or delete the references to a dataset. A version number is assigned to a platform dataset based on existing public database content. A new version of the platform dataset is created to incorporate new data available in the public databases. The updated data can include addition of new microorganisms and pathogens. The platform dataset version used by the mobile healthcare application can be selected by a user.

A pollen is a fine powdery substance, usually yellow, consisting of microscopic grains discharged from the male part of a flower or from a male cone. Each grain contains a male gamete that can fertilize the female ovule, to which pollen is transported by the wind, insects, or other animals. Pollen is produced by the anther of flowering plants. Each pollen grain contains a gametophyte that can produce sperm to fertilize an egg within the female part of the flower—the pistil. Pollen is a common name for the male gametophyte of seed plants. It can be all pollen or a single pollen grain. Pollen can also be a mass of microspores in a seed plant appearing usually as a fine dust.

A pollen grain is a structure that contains entire male gametes in a seed plant. A pollen grain is one of the granular microspores that occur in pollen and give rise to the male gametophyte of a seed plant. A pollen grain is a microscopic body that contains the male reproductive cell of a plant. Pollen grains are microscopic structures that carry the male reproductive cell of plants. The inside of the grain contains cytoplasm along with the tube cell (which becomes the pollen tube) and the generative cell (which releases the sperm nuclei). The outer shell is made of two layers. The inside layer intine (interior) is composed partly of cellulose, a common component in the cell walls of plant cells. The outer layer is known as the exine (exterior). This highly sophisticated and complex outer layer is rich in a compound known as sporopollenin. A pollen grain seen through a microscope displays an extremely durable body and has a tough outer coating. This hardy coat offers great protection from the harsh outdoor environment. This is important because inside this tough shell lie two cells: the tube cell, which will eventually become the pollen tube, and a generative cell, which contains the male sperm nuclei needed for fertilization. Pollen grains are microscopic particles, typically single cells, of which pollen is composed. Pollen grains have a tough coat that has a form characteristic of the pollen-producing plant. Pollen grain is a structure produced by plants containing the male haploid gamete to be used in reproduction. Each pollen grain contains vegetative (non-reproductive) cells (only a single cell in most flowering plants but several in other seed plants) and a generative (reproductive) cell. In flowering plants the vegetative tube cell produces the pollen tube, and the generative cell divides to form the two sperm nuclei. Angiosperms are flowering plants that have seeds inside a protective chamber called an ovary. Gymnosperms are plants that produces seeds that are exposed rather than seeds enclosed in fruits. Pollen grains are produced by seed plants (angiosperms and gymnosperms), and spores by fungi, bacteria, ferns, lycopods, horsetails, and mosses.

Pollination is the transfer of pollen from the male reproductive structure gametophyte to the female reproductive structure gametophyte. Most gymnosperms and some angiosperms are wind pollinated, whereas most angiosperms are pollinated by animals.

A pollen allergy is a damaging immune response by the body caused by pollen or dust in which the mucous membranes of the eyes and nose are itchy and inflamed, causing a runny nose and watery eyes. The symptoms are usually sneezing, nasal congestion, runny nose, watery eyes, itchy throat and eyes, and wheezing. The pollen allergy level is reported as very high, moderate, or very low. It can also report as low (0-2.4), low-med (2.5-4.8), medium (4.9-7.2), med-high (7.3-9.6), and high (9.7-12). The pollen allergy level can be set in the mobile healthcare application.

A pollen count is the measurement of the number of pollen grains in a cubic meter of air. High pollen counts result in increased rates of pollen allergic reaction for people with allergic disorders. The pollen count can be reported as number or qualitative value as very low, low, moderate, high, very high, extreme.

The pollen type reported can be grass, tree, and weed. Grass pollen causes a runny nose and other hay fever symptoms. In North America, grass pollen generally affects people from mid-May to July. The types of grasses that are most likely to cause allergy symptoms are Orchard, Sweet Vernal, Bermuda, Rye, and so on. Tree pollens occur during different times of the year. The trees that are most likely to cause allergy symptoms include Oak, Birch, Cedar, Willow, Ash, Aspen, Cottonwood, Mulberry, Beech, and so on. Weed pollen is most likely to cause hay fever. The following weeds most likely to cause allergy symptoms include Sagebrush, Tumbleweeds, Pigweed, Burning Bush, Russian Thistle, and so on.

A pollen database stores the pollen type, subtype, type of allergy, symptoms, medication, location, history, and pollen safety data sheet related information.

A pressure sensor is an electronic component that can be used to measure atmospheric or air pressure in environments. The intended use of the pressure sensor is to detect, measure, and monitor air pressure or simply pressure surrounding the user. The wearable device air pressure value can be used by a physician to associate a medical condition associated with pressure based on set acceptance criteria. The unit of measurement of pressure is reported in pascal units, or in short, kilopascal (kPa). It is also reported as hPa, which is the abbreviated name for hectopascal (100×1 pascal) pressure units, which are exactly equal to millibar pressure units (mb or mbar). The pressure sensor sends real-time wearable device pressure data surrounding the user to the cloud server. In older days, mercury and aneroid barometers were used to measure the pressure. The working principle of a pressure sensor can use membranes, thin plates, piezo resistive sensors, capacitive sensors, optoelectronic pressure sensors, and so on. The modern-day barometer uses MEMS technology, making it capable of measuring atmospheric pressure in a small and flexible structure. The pressure sensor sends real-time data to the cloud server. The landfill and wearable device methane and other gas emissions are strongly dependent on changes in barometric pressure; the rising barometric pressure suppresses the emission while the falling barometric pressure enhances the emission, a phenomenon called barometric pumping. Lower pressure will result in more gas seeping out from landfills and waste bins, and into the air. Microorganisms that require high atmospheric pressure for growth are called barophiles. The bacteria that live at the bottom of the ocean are able to withstand great pressures. Exposure to high pressure kills many microbes. In the food industry, high-pressure processing (also called pascalization) is used to kill bacteria, yeast, molds, parasites, and viruses in foods while maintaining food quality and extending shelf life. High pressure can be used to sterilize or kill pathogenic microorganisms in a nasal cavity, or an oral cavity, or on a surface.

Predisposition or Predisposition factor is a tendency that some disease that is likely to happen. For example, a predisposition of heart disease based on cholesterol results, a predisposition of asthma based on particulate matter sensor such as pollen count and enviro sensor results, a predisposition is being likely to have an illness that mother and father both had, a predisposition that a genetic characteristic will influence the possible phenotypic development. It also includes a range of conditions and illnesses linked to a genetic predisposition. These include certain cancers, diabetes, obesity, heart disease, asthma, celiac disease, and so on.

Prevention or Prevention factor is action taken to decrease the chance of getting a disease or condition. For example, cancer prevention includes avoiding risk factors such as smoking (lifestyle sensor parameter), obesity, lack of exercise (biokinetics sensor parameter), and radiation exposure (solar flare sensor) and increasing protective factors such as getting regular physical activity, lifestyle changes, staying at a healthy weight, and having a healthy diet.

Prognosis is likely outcome or course of a disease i.e., the chance of recovery or recurrence. Prognostic factor is a situation or condition, or a characteristic of a patient, that can be used to estimate the chance of recovery from a disease or the chance of the disease recurring or coming back. For example, a prognosis of a heart disease based on biokinetics and lifestyle sensor parameter results, a cancer prognosis depends on multiple factors, such as the type of cancer and its stage. The prognosis may vary according to injury, disease, age, sex, race, and treatment. The term prognosis and prognostic factor are used interchangeably.

A prion is a type of protein that can cause disease in humans and animals by triggering normally healthy proteins, usually in the brain, to fold abnormally. Prions are misfolded proteins with the ability to transmit their misfolded shape onto normal variants of the same protein. Prions are smaller than viruses. Prions are also unique since they do not contain nucleic acid, unlike bacteria, fungi, viruses, and other pathogens. Prion diseases include Creutzfeldt-Jakob disease (CJD) in humans, bovine spongiform encephalopathy (BSE or "mad cow" disease) in cattle, scrapie in sheep, and chronic wasting disease (CWD) in deer, elk, moose, and reindeer. Human prion diseases comprise: a) Creutzfeldt-Jakob Disease (CJD)—It is a rapidly progressive, invariably fatal neurodegenerative disorder believed to be caused by an abnormal isoform of a cellular glycoprotein known as the prion protein; b) Variant Creutzfeldt-Jakob Disease (vCJD)—It is also called human mad cow disease or human bovine spongiform encephalopathy (BSE). It is a rare, degenerative, and fatal brain disease that can occur in humans. The disease damages brain cells and the spinal cord; c) Gerstmann-Straussler-Scheinker Syndrome—It results in progressive loss of coordination; d) Fatal Familial Insomnia–a rare hereditary disorder causing difficulty sleeping; and e) Kuru, caused by eating human brain tissue contaminated with infectious prions.

A protist is any eukaryotic organism that is not an animal, plant, or fungus. Pathogenic protists are single-celled organisms that cause diseases in their hosts like human, animal, or plant. These types of protists enter a host and live within the organism. Protists, when they are inside the organism, feed, grow, and reproduce, causing harm. Pathogenic protists vary in the severity of the damage they cause, but they all have a negative impact on their host. For example, *plasmodium* species are known to infect humans, and *Plasmodium falciparum* are causative agents of malaria, African sleeping sickness, amoebic encephalitis, and waterborne gastroenteritis in humans. Trypanosomes *brucei* is a flagellated endoparasite responsible for the deadly disease nagana in cattle and horses, and for African sleeping sickness in humans. Some protist pathogens prey on plants, effecting massive destruction of food crops. The oomycete *Plasmopara viticola* parasitizes grape plants, causing a disease called downy mildew.

Program logic is instructions in a program arranged in a prescribed order to solve a problem, usually a user request through application software. Program logic can receive the sensor data from wearable devices and store it into the database of the cloud server. It can also receive data and instructions from the mobile healthcare application and laboratory information system and process them. It can send the performance data to the laboratory information system. It can branch off and execute various methods and algorithms.

A prokaryote is a single celled microorganism that lacks a nucleus. Prokaryotes have cell membranes and cytoplasm but do not contain nuclei. All bacteria are prokaryotes. Example prokaryotes are as follows: a) Most *Escherichia coli*, which live in intestines, are harmless and are an important part of a healthy human intestinal tract. However, some *Escherichia coli* are pathogenic, meaning they can cause illness, either diarrhea or illness outside of the intestinal tract; and b) *Staphylococcus aureus*, which causes skin infection.

Proteins are a very important class of molecules found in all living cells. A protein is composed of one or more long chains of amino acids, the sequence of which corresponds to the DNA sequence of the gene that encodes it. Proteins act as structural components of body tissues such as muscle, hair, collagen, etc., and as enzymes and antibodies. Proteins play a variety of roles in the cell, including structural (cytoskeleton), mechanical (muscle), biochemical (enzymes), and cell signaling (hormones). Proteins are also an essential part of diet. Microorganism protein and composition information can be used for detection.

RAM (random access memory) is the hardware in a single board computer (SBC) where the operating system (OS), application programs, and sensors data in current use are kept so they can be quickly reached by the device's processor. RAM is the main memory in a computer, and it is much faster to read from and write to than other kinds of storage such as a hard disk drive (HDD), solid-state drive (SSD), or secure digital card (SDC). The wearable device SBC uses RAM to temporarily store the operating system software and sensor data.

Radio frequency identification (RFID) is a form of wireless communication that incorporates the use of electromagnetic fields in the radio frequency portion of the electromagnetic spectrum to uniquely identify an object.

A radio frequency identification tag sensor (RFID tag sensor) is an electronic tag or identification that exchanges data with an RFID reader and writer through radio waves. An RFID tag is also known as an RFID chip. The intended use of the RFID tag sensor is to detect and send RFID digital data of the wearable device. The RFID tag sensor can be passive or active. Passive RFID tag sensors have no power of their own and are powered by the radio frequency energy transmitted from RFID readers and writer antennas. The signal sent by the reader and writer is used to power on the tag and reflect the energy back to the reader. Active RFID tag sensors use battery power that continuously broadcasts its own signal. Active tags provide a much longer read range than passive tags. Wearable devices use active RFID tag sensors. RFID tag memory is split into three: unique tag identifier (TID) memory, electronic product code (EPC) memory, and user memory. Every wearable device has a unique tag identifier. The electronic product code can be a wearable device type, content type, and so on. There can be additional writeable memory locations called the access password and kill password. The access password can be used to prevent people from reconfiguring wearable device tags. The kill password is used to disable a wearable device tag permanently and irrevocably. This can be done if a wearable device is damaged or broken.

A radio frequency identification reader and writer (RFID reader) is a device used to gather information from an RFID tag, which is used to track individual objects. The device is used to write new RFID tag information. Physicians and laboratory directors are equipped with RFID readers and writers to read the wearable device RFID tag sensor electronic data. The RFID tag with unique device identifier can be used for tracking the user device. The unique device identification (UDI) is a unique numeric or alphanumeric code related to a device. It allows for a clear and unambiguous identification of specific devices with the user and facilitates their traceability. The UDI comprises a device identifier, and a production identifier. These provide access to useful information about the device. The specificity of the UDI makes traceability of the device more efficient, allows easier recall of devices, combats counterfeiting, and improves patient safety.

Resolution is the least count or smallest detectable change in the physical quantity, property, or condition being measured.

Ribonucleic acid (RNA) is a nucleic acid present in all living cells. RNA's principal role is to act as a messenger carrying instructions from DNA for controlling the synthesis of proteins. In some viruses RNA rather than DNA carries the genetic information. The RNA is single-stranded. An RNA strand has a backbone made of alternating sugar (ribose) and phosphate groups. Attached to each sugar is one of four nitrogenous bases-adenine (A), uracil (U), cytosine (C), or guanine (G). Different types of RNA exist in the cell such as messenger RNA (mRNA), ribosomal RNA (rRNA), and transfer RNA (tRNA). The picocamera, a component of the particle imaging system, allows for high-magnification and high-resolution pictures of microorganisms and small molecules. The particle imaging system allows for detection of microorganisms based on RNA segments.

A risk level or risk priority number calculation is based on the severity ranking, probability of occurrence ranking, and detection ranking. The severity ranking is classified as: Catastrophic (death)=5, Critical (permanent impairment)=4, Serious (injury requiring medical intervention)=3, Minor (physical injury or temporary impairment not requiring medical intervention=2, and Negligible (Temporary discomfort)=1. The probability of occurrence ranking is classified as: Frequent=5, Probable=4, Occasional=3, Remote=2, and Improbable=1. The detection ranking is classified as: Remote=5, Low=4, Moderate=3, High=2, and Very High=1. The risk level is based on the equation—Risk Level=Severity Ranking×Probability of Occurrence Ranking×Detection Ranking resulting in the risk levels of Intolerable (INT)=45-125, Investigate (INV)=16-44, and Broadly Acceptable Region (BAR)=1-15. The risk level (RL) is also known as risk priority number (RPN). The INT risk level is defined as risk in this category is not acceptable. Situation can result in death or critical illness. Risk mitigation through corrective actions and preventive actions required. The INV risk level is defined as risk should be mitigated. Situation can result in serious or moderate illness. Additional mitigation should be investigated to reduce the risk through corrective actions and preventive actions to Broadly Acceptable Region. The BAR is defined as Risk is negligible compared to the risk of other health hazards. Situation may result in temporary discomfort or might not result in illness. ISO 14971 Medical devices—Application of risk management to medical devices are used to do risk assessment and determine the risk controls in the form of corrective actions and preventive actions. The Failure Mode Effect Analysis (FMEA) risk assessment consists of smart band parameter (component), parameter result value outside the normal reference range (failure mode), health hazard (failure effect) and associated severity ranking, cause and associated probability of occurrence ranking, and current controls and associated detection ranking. The risk severity ranking, probability of occurrence ranking, and detection ranking is applied to each of the microbial biosensor parameters result value, particulate matter sensor parameters result value, enviro sensor parameters result value, physiological sensor parameters result value, biofluid sensor parameters result value, biokinetics sensor parameters result value, and lifestyle sensor parameters result value. The risk levels are calculated for each of the smart band sensor parameters result value. The overall microbial risk level, particulate matter risk level, pathogen biosafety risk level, pollen allergy risk level, dust mite allergy risk level, physiological risk level, biofluid risk level, biokinetics risk level, and lifestyle risk level is based on the average of all the individual corresponding sensor parameters risk level. The Failure Mode Effect Analysis (FMEA) risk controls consists of corrective actions and preventive actions and calculation of residual risk level (RRL) or residual risk priority number (RRPN). Based on the failure mode, accurate root cause analysis is done using intelligent relationship interpretation and risk controls in the form of corrective actions and preventive actions are determined and communicated to the user in the mobile healthcare application. The corrective actions and preventive actions are the treatments, physical fitness, lifestyle changes, healthy eating, personalized wellness programs for a healthy lifestyle and so on. These corrective actions and preventive actions are also documented in pathogen and pollen safety data sheets. The risk level of Intolerable (INT) should be mitigated immediately through corrective actions and preventive actions to reduce the risk of death or serious injury/illness. The risk level of investigate (INV) which can result in serious or moderate illness requires further investigation and implementation or risk control measures in the form of corrective actions and preventive measures. The risk level of broadly acceptable region is acceptable, but a situation may result in temporary discomfort or might not result in illness, but user should still work on the corrective actions and preventive actions. The goal of the risk controls measures comprising corrective actions and preventive actions is to ensure that risk level is in the Broadly Acceptable Region (BAR) by ensuring the probability of occurrence ranking decreases (injury/illness), and the detection ranking (injury/illness) is very high. The risk level model can be based on risk severity ranking, probability ranking, and detection ranking or risk severity ranking, and probability of occurrence ranking or just risk severity ranking. The risk level ranges are based on number of rankings used. In summary the corrective actions and preventive actions reduce the health hazards and allow for a healthy lifestyle.

Screening is checking for disease when there are no symptoms. Since screening may find diseases at an early stage, there may be a better chance of curing the disease. Examples of screening tests include blood screening which used to evaluate your overall health and detect a wide range of disorders, including anemia, infection and leukemia; cholesterol tests results (biofluids sensor) enable to monitor and screen for risk of cardiovascular disease; metabolite test result (biofluid sensor) enable identifying metabolites that modulate phenotype, high readings from the cancer screening tests such as mammogram (for breast cancer), colonoscopy (for colon cancer), and the Pap test and HPV tests (for cervical cancer). Screening also includes doing a genetic test to check for a person's risk of developing an inherited disease.

A secure digital card (SDC) is a tiny flash memory card designed for high-capacity memory and various portable devices such as car navigation systems, cellular phones, e-books, PDAs, smartphones, digital cameras, music players, digital video camcorders, and single board computers. An SDC is used in a single board computer to install wearable device operating software, software compilers, utilities, and sensor software drivers. Wearable device data is stored locally in a secure digital card (SDC). The data includes a microorganism database and pollen database, allowing the wearable device to be operated without being connected to the network.

A sensor can be a module or electronic component or device that receives a stimulus or input such as quantity, property, or condition, and responds with an electrical signal. It acquires a physical quantity, property, or condition and converts it into a signal suitable for processing (e.g., optical, electrical, mechanical). The intended use of the sensor is to detect and respond to some type of stimulus or input from the physical environment or motion. The stimulus or specific input can be pathogen, particulate matter, geospatial position, temperature, humidity, pressure, air quality, smoke, gas, ambient light, motion event, RFID tag sensor, or any one of a great number of other environmental phenomena. The output is generally a signal that is converted to a human-readable display at the sensor location or transmitted electronically over a network to the cloud server for reading or further processing. A sensor in general is intended to detect, measure, and monitor input. Sensors are classified in several different ways. Sensors can be classified based on external excitation signals, or a power signal, as an active or passive sensor. Active sensors are those which require an external excitation signal or power signal. Passive sensors, on the other hand, do not require any external power signal and directly generate output responses. The next classification is based on physical principles of sensing conversion phenomena, i.e., the input and the output. Some common conversion phenomena are capacitance, magnetism, induction, resistance, photoelectric, piezoelectric effect, thermoelectric effect, sound waves, thermal properties of materials, heat transfer, electrochemical, electromagnetic, and such. Sensors can also be classified based on output signal types, namely analog or digital sensors. An analog sensor is a sensor that outputs a signal that is continuous in both magnitude and space. A digital sensor is a sensor that outputs a signal that is discrete in time and/or magnitude. Wearable devices can use any of the above sensor types, which are accurate, reliable, and robust.

A single board computer is a complete computer built on a single board with central processing unit, memory, Wi-Fi/Bluetooth, accelerometer, gyroscope, microphone, speaker, secure digital card (SDC), display DSI port, camera CSI port, general purpose input/output, ports, power supply, and other features required of a functional computer. Wearable device sensors are either built in or connected to a single board computer using general purpose input/output pins.

A skin infection or a wound infection or an infected wound is a localized defect or excavation of the skin or underlying soft tissue in which pathogens have invaded into viable tissue surrounding the wound. A wound infection occurs when germs, such as bacteria, grow within the damaged skin of a wound. Symptoms can include increasing pain, swelling, and redness. More severe infections may cause nausea, chills, or fever. Many infections will be self-contained and resolve on their own, such as a scratch or infected hair follicle. Other infections, if left untreated, can become more severe and require medical intervention. Common skin infections include cellulitis, erysipelas, impetigo, folliculitis, furuncles, and carbuncles. The most common pathogens found in wound infections are *Staphylococcus aureus*, Coagulase-negative *Staphylococci, Enterococci*, and *Escherichia coli*. A bacterial wound culture is primarily ordered to detect pathogens, and to prepare a sample for susceptibility testing where required. Currently, the doctor often orders microscopy, culture, and sensitivity testing (M/C/S) as the initial test for bacterial wound culture.

A software library is a collection of non-volatile resources used by computer programs, often for application software development. These may include configuration data, documentation, help data, message templates, pre-written code, and subroutines such as math, network, internet, and so on, classes, values, or type specifications. In single board computers, the software library can include the board configuration data, peripheral interfaces, and general purpose input/output pinout configurations.

Smoke is a visible suspension of carbon or other particles in air, typically emitted from a burning substance. Smoke is a collection of tiny solid, liquid, and gas particles. Although smoke can contain hundreds of different chemicals and fumes, visible smoke is mostly carbon (soot), tar, oils, and ash. Smoke occurs when there is incomplete combustion (not enough oxygen to burn the fuel completely). Smoke can contain carbon dioxide, carbon monoxide, nitrogen oxide, and particulate matter. Particulate matter is a complex mixture of small solid or tar (liquid) particles. The size, shape, density, and other physical properties are highly variable, but the individual particles are too small to be seen with the naked eye. Smoke contributes to modifications of the nasal, oral, lung, and gut microbiome, leading to various diseases, such as periodontitis, asthma, chronic obstructive pulmonary disease, heart disease, Crohn's disease, ulcerative colitis, and cancers.

A smoke sensor is an electronic component that can be used to detect the presence or concentration of smoke. The intended use of the smoke sensor is to detect, measure, and monitor smoke surrounding the user. A smoke sensor is usually used to detect the presence or concentration of smoke surrounding the user. The wearable device smoke value can be used by the user to take appropriate actions based on set acceptance criteria. The smoke sensor information can also be used to take appropriate preventive measures such as fire reporting and activating the fire alarm system during high temperature days. The smoke value is critical for the early detection of a fire and could mean the difference between life and death. In a fire, smoke and deadly gases tend to spread farther and faster than heat. Inhaling smoke for a short amount of time can cause immediate (acute) effects, especially during hot summer days. A wearable device can provide early warning and location of the fire. Smoke is irritating to the eyes, nose, and throat, and its odor may be nauseating. Exposure to heavy smoke causes temporary changes in lung function, which makes breathing more difficult. Real-time smoke sensing is important for fire detection and industrial production to detect problems in time and protect personnel safety. The unit of measurement of smoke is usually parts per million, which can be reported as smoke value such as 1 (white), 2 (slightly grey), 3 (grey), 4 (dark grey), and 5 (black) based on the opacity of the smoke. The smoke sensor sends real-time smoke data to the cloud server. The smoke sensor working principle can be based on any of the commonly used technologies like metal oxide semiconductor (MOS), also known as chemiresistors, optical scattering, filter/dilution tunnel, ringelmann scale, and interference from carbon monoxide, which is incompletely burned carbon, and so on.

A software driver is a type of software program that controls a hardware device. The wearable device software driver is used to control the sensor hardware through a single board computer. The software drivers tell the single board computer what type of sensor is connected, what it can do, and how to communicate with it from other software on the single board computer, including the operating system. Software drivers allow setup, control, and changing of settings of the microbial biosensor, particulate matter sensor, and enviro sensor.

The software graphical user interface is a user interface that includes graphical elements, such as windows, icons, buttons, menus, tabs, and pointers, which allow users to interact with electronic software and devices. A mobile healthcare application or laboratory information system software graphical user interface offers visual representations of the available commands and functions of an operating system or software program. The commands and functions can be methods and algorithms. These visual representations consist of elements like windows, icons, buttons, menus, tabs, and pointers.

Solar flare is a brief eruption of intense high-energy radiation from the sun's surface, associated with sunspots and causing electromagnetic disturbances on the earth, as with radio frequency communications and power line transmissions. As more energy is released by a solar flare, it can create shock waves that accelerate particles away from the sun, causing what is known as a particle storm.

Speakers are transducers that convert electromagnetic waves into sound waves. The wearable device microphone and speaker allow a person near the wearable device two-way communication with the person on the mobile device through the mobile healthcare application.

A spore is an asexual structure that can develop into an adult organism. Usually found in fungi and algae, a spore is a reproductive cell capable of developing into a new organism without fusion with another reproductive cell. Spores are produced by bacteria, fungi, algae, and plants. Spores of bacteria, fungi, algae, and protists are rarely preserved, but those of terrestrial plants are very common fossils. Terrestrial plants produce extremely resistant spores and pollen which are easily transported by wind, insects, and water. The main difference between spores and seeds as dispersal units is that spores are unicellular, the first cell of a gametophyte, while seeds contain within them a developing embryo, produced by the fusion of the male gamete of the pollen tube with the female gamete. Spores are usually 10 to 20 μm in diameter, although larger sizes also occur in some species.

A system on Chip (SoC) is an integrated circuit that integrates most of the components of the single board computer (SBC). The components include a central processing unit (CPU), graphical processing unit (GPU), memory input/output ports, and secondary storage, all on a single substrate or microchip.

A temperature sensor is an electronic component that measures the temperature of its environment and converts the input data into electronic data to record, monitor, or signal temperature change. The intended use of the temperature sensor is to detect, measure, and monitor temperature surrounding the user. The wearable device temperature value can be used by the user to take appropriate actions based on set acceptance criteria. The temperature value can also be used to take appropriate preventive measures such as cooling the environment around the user or moving to shade. Temperature units of measurement are usually Celsius and Fahrenheit. The temperature of the wearable device can be reported in the form Celsius or Fahrenheit. The temperature sensor sends real-time temperature data to the cloud server. The temperature sensor working principle can be based on any of the four commonly used temperature sensor types such as: 1) Thermocouple, which is made from two dissimilar metals that generate electrical voltage in direct proportion to changes in temperature, 2) Resistance temperature detector (RTD), which measures temperature by correlating the resistance of the RTD element with temperature, 3) Negative temperature coefficient (NTC) thermistor, consisting of a thermally sensitive resistor that exhibits a large, predictable, and precise change in resistance correlated to variations in temperature, and 4) Semiconductor-based MEMS sensors placed on integrated circuits (ICs). These sensors are effectively two identical diodes with temperature-sensitive voltage vs current characteristics that can be used to monitor changes in temperature. Microorganisms can also be classified according to the range of temperature at which they can grow. The growth rates are the highest at the optimum growth temperature for the organism. The lowest temperature at which the organism can survive and replicate is its minimum growth temperature. The highest temperature at which growth can occur is its maximum growth temperature. High temperature can result in deactivation of the microorganisms.

Treatment is an instance of treating a patient or medical condition. The treatment can include healthy food, nutritious diet, vitamins, medicines, surgical and so on. The treatment can include any or all of the following: treatment plan, treatment cycle, treatment course, treatment schedule, and treatment summary.

Treatment plan is a detailed plan with information about a patient's disease, the goal of treatment, the treatment options for the disease and possible side effects, and the expected length of treatment. A treatment plan may also include information about how much the treatment is likely to cost and about regular follow-up care after treatment ends. Treatment options can be based on medicines, therapy, surgery, nutrition, dietary supplements, healthy eating and so on.

Treatment cycle is a period of treatment followed by a period of rest (no treatment) that is repeated on a regular schedule. For example, treatment given for one week followed by three weeks of rest is one treatment cycle. When this cycle is repeated multiple times on a regular schedule, it makes up a course of treatment. Also called cycle of treatment.

Treatment course is a treatment plan made up of several cycles of treatment. For example, treatment given for one week followed by three weeks of rest (no treatment) is one treatment cycle. When a treatment cycle is repeated multiple times on a regular schedule, it makes up a treatment course. A treatment course can last for several months. Also called course of treatment.

Treatment schedule is a step-by-step plan of the treatment that a patient is going to receive. A treatment schedule includes the type of treatment that will be given (such as chemotherapy or radiation therapy), how it will be given (such as by mouth or by infusion into a vein), and how often it will be given (such as once a day or once a week). It also includes the amount of time between courses of treatment and the total length of time of treatment.

Treatment summary is a detailed summary of a patient's disease, the type of treatment the patient received, and any side effects or other problems caused by treatment. It usually includes results of laboratory tests (such as pathology reports and biomarker tests) and imaging tests (such as x-rays, CT scans, and MRIs), and whether a patient took part in a clinical trial. A treatment summary may be used to help plan follow-up care after treatment for a disease, such as cancer.

An ultraviolet light sensor intended use is to measure ultraviolet radiation. Ultraviolet radiation (UV) is present in sunlight, and constitutes about 10% of the total electromagnetic radiation output from the sun. The UV index is a measure to help determine the effects of the sun on outdoor activities. It is computed using forecast ozone levels, cloudiness, and elevation. Values are usually highest at solar noon, which is when the sun is at its highest point of the day. The UV index ranges from 1-11+ based on how the sun's UV rays affect the person. The ranges are: 1-2 (low), 3-5 (moderate), 6-7 (high), 8-10 (very high), 11+ (extreme). The UV region covers the wavelength range 100-400 nm and is divided into three bands: UV-A (315-400 nm), UV-B (280-315 nm), UV-C (100-280 nm). The ultraviolet light sensor outputs an analog voltage that is directly proportional to UV radiation incident on a planar surface. Higher ultraviolet light inhibits growth of most of the microorganisms. High ultraviolet light inactivates microorganisms by forming pyrimidine dimers in RNA and DNA, which can interfere with transcription and replication.

A unique identifier (UI) is a unique identification of a microorganism based on a biosensor transducer used to detect microorganisms. This biosensor transducer signal to detect microorganisms comprises: a) Optical—infrared spectroscopy, fluorescence imaging, particle imaging-nucleic acid sequence read, light scattering, and imaging; b) Mass based electromagnetic wave; c) Ultrasound—acoustic wave. The picocamera image detection is based on microorganism image acquisition and classification. The UI can be used to identify and characterize microorganisms for diverse goals such as beneficial microorganism and pathogen detection in the nasal cavity, in the oral cavity, or on a surface, real time monitoring of environment, medical diagnostics, biodefense, and microbial forensics. The desired microorganism and pathogen detection resolution varies based on type but could easily range from family to genus to species to strain to isolate. The UI can be an already identified value based on the biosensor transducer method or can be an artificial intelligence method based calculated predictive value using microorganism database information.

A universal serial bus (USB) is a common interface that enables communication between devices and a single board computer. A USB is a type of computer port that can be used to connect to items such as a keyboard, mouse, and camera. In the case of wearable devices, it can be used to connect to other sensors like weight, wind, and rain. There are several types of USB such as A, B, C, Mini-USB, and Micro-USB. The single board computer is compatible with various types of USB.

A user is a person who is using a wearable device with a smart band. A user is considered as patient who requests or receives health care services. The user is a patient in the context of clinical laboratory test results. The term is interchangeably used in the context of patient testing. The smart band comprises a microbial biosensor, a particulate matter sensor, an enviro sensor, a physiological sensor, a biofluid sensor, a biokinetics sensor, a lifestyle sensor, and a single board computer with associated sensor data. In addition, a user can have wearable electronics and data. The wearable device allows for continuous monitoring of user health for accurate clinical outcomes and wellness programs.

A virion is a complete, infective form of a virus outside a host cell, with a core of RNA or DNA and a capsid. It is an entire fully assembled virus particle, consisting of an outer protein shell called a capsid and an inner core of nucleic acid (either RNA or DNA) outside the cell.

A viroid is an infectious entity affecting plants, smaller than a virus and consisting only of nucleic acid without a protein coat. Viroids are plant pathogens that consist of a very short stretch of circular, single-stranded RNA that does not have a protein coat. Viroids are strands of naked RNA.

A virus is an infective agent that typically consists of a nucleic acid molecule in a protein coat, is very small to be seen by light microscopy, and can multiply only within the living cells of a host. Viruses are particles of nucleic acid, protein, and in some cases lipids that can reproduce only by infecting living cells. Viruses are made up of a piece of genetic code, such as DNA or RNA, and protected by a coating of protein. All viruses enter living cells, and once inside, use the machinery of the infected cell to produce more viruses. Viruses differ widely in terms of size, structure, and chemical composition. Most viruses have a diameter from 20 nm to 250-400 nm. The largest measure about 500 nm in diameter and are about 700-1,000 nm in length. Virus shapes are usually complex (comprising head, DNA, tail, tail fiber), helical, polyhedral, spherical, or enveloped. Viruses can affect humans, plants, and bacteria. A tobacco mosaic virus causes the leaves of tobacco plants to develop a pattern of spots called a mosaic. Most viruses have a pathogenic relationship with their hosts, but they are not all bad. Some viruses can kill bacteria, while others can fight against more dangerous viruses. Like protective bacteria (probiotics), there are protective viruses in our body. Viruses that help humans comprise: a) Bacteriophages that infect and destroy specific bacteria. Bacteriophages are found in the mucous membrane lining in the digestive, respiratory, and reproductive tracts. Bacteriophages have been used to treat dysentery, sepsis caused by *Staphylococcus aureus*, *salmonella* infections, and skin infections; b) An oncolytic virus preferentially infects and kills cancer cells. As the infected cancer cells are destroyed by oncolysis, they release new infectious virus particles or virions to help destroy the remaining tumor; c) Viruses can be used to inject genes into cells, which can reverse genetic diseases. For example, some viruses have been able to cure hemophilia, a blood disorder that prevents clotting; and d) Viral infections at a young age are important to ensure the proper development of our immune systems. The immune system can be continuously stimulated by systemic viruses at low levels sufficient to develop resistance to other infections. Viral infection can be as follows: a) COVID-19 disease. The SARS-CoV-2 virus belongs to the same large family of viruses as SARS-CoV, known as coronaviruses, and results in severe acute respiratory syndrome. This normally happens because of poor handwashing or from consuming contaminated food or water. The airborne transmission occurs through coughing, talking, and sneezing. Common symptoms include fever, dry cough, and shortness of breath, and the disease can progress to pneumonia in severe cases; b) Flu is caused by influenza viruses that infect the nose, throat, and lungs. These viruses spread when people with flu cough, sneeze, or talk, sending droplets with the virus into the air and potentially into the mouths or noses of people who are nearby; c) Dengue is a mosquito-borne viral infection causing a severe flu-like illness; d) Ebola virus causes fatigue, fever, and muscle pain; e) Rabies virus transmitted through an infected animal's saliva causes brain damage; f) HIV (human immunodeficiency virus) is a virus that attacks cells that help the body fight infection, making a person more vulnerable to other infections and disease; g) Rotavirus infection usually spreads from fecal-oral contact due to poor sanitation and causes diarrhea; and h) Marburg virus causes hemorrhagic fever, meaning that infected people develop high fevers and bleeding throughout the body that can lead to shock, organ failure, and death.

A wearable device consists of a smart band, and a display unit. The smart band consists of a microbial biosensor, a particulate matter sensor, an enviro sensor, a physiological sensor, a biofluid sensor, a biokinetics sensor, a lifestyle sensor, a single board computer, a power supply unit, a band fastener, and a set of watch adapters. The intended use of the wearable device is for detection of microorganisms, sterilization of pathogens, and environmental monitoring. A wearable device sensor can be worn on the wrist and ankle. Wearable devices can be attached on a necklace, a waistband, a belt, or a headband. Users can wear one or more wearable devices. In this case, when more than one wearable device is used, each one of them can be uniquely identified using an RFID tag sensor.

Wi-Fi is a family of wireless networking technologies, allowing computers, smartphones, or other devices to connect to the internet or communicate with one another wirelessly within a particular area. The mobile healthcare application allows users to access the wearable device data through Wi-Fi. Wi-Fi can also be used to connect to other sensor devices like external rooftop rain and wind weather stations to monitor other environmental conditions near the user.

Exemplary Systems and Methods

FIG. 1-105 illustrate an example wearable device 100, according to some embodiments.

FIG. 1 is an example perspective view of an example wearable device 100 design that can be utilized to implement various embodiments.

A wearable device 100 consists of a smart band 200 and a display unit 102.

The smart band 200 comprises a microbial biosensor 310, a particulate matter sensor 320, an enviro sensor 330, a physiological sensor 390, a biofluid sensor 392, a biokinetics sensor 396, a lifestyle sensor 398, a single board computer 350, a power supply unit 380, a band fastener 202, and a set of watch adapters 204 and 206. The smart band 200 also has set of clip adapters 208 and 210 to connect to a necklace, a waistband, a belt, a headband, and so on for discreet monitoring of a set of sensor parameters.

The band fastener 202 is a mechanism that closes or secures the smart band 200. The band fastener 202 can be a magnetic lock, clip, or any other locking mechanism which secures the two sides of the smart band 200.

The display unit 102 comprises a touchscreen 104, a display unit power button 106, a crown 108, and a set of attachment slots 110 and 112.

The power supply unit 380 comprises a wireless charging unit 382, a battery 384, a charging port 386, and a band power button 388.

The microbial biosensor 310 comprises a transmitter 312, a receiver 314, a sterilizer 316, a picocamera 318, and a microbial biosensor power button 319.

The particulate matter sensor 320 comprises a sensing cavity 322.

The enviro sensor 330 comprises a set of sensors 332-347.

The physiological sensor 390 comprises a set of sensors 390A-390H.

The biofluid sensor 392 comprises a set of sensors 392A-392B.

The biokinetics sensor 396 comprises a set of sensors 396A-396E.

The lifestyle sensor 398 comprises a set of sensors 398A-398E.

A mobile healthcare application 250 allows a user/patient 8710 to access the wearable device 100 and smart band 200 sensor data.

The smart band 200 is configured to detect a set of sensor parameters comprising: a microorganism parameter, a particulate matter parameter, an enviro parameter, a physiological parameter, a biofluid parameter, a biokinetics parameter, and a lifestyle parameter.

The microbial or microorganism parameters detected are listed in the "Microorganism data 2110" table item 6 and stored in "Microorganism database 2120".

The particulate matter parameter detected include microorganism parameters in the air, and parameters listed in the "Pollen data 3430" table item no 6 and stored in the "Pollen database 3450," particulate matter size and concentration, air quality index and so on.

The enviro parameter detected are listed in the "Enviro parameters detected 3790" table.

The physiological parameters detected are listed in the "Physiological parameters, detection sensor, and detected normal reference ranges 4200" table.

The biofluid parameters detected are listed in the "Biofluid complete blood count parameters, detection sensor, and detected normal reference ranges 5100", "Biofluid complete metabolic panel analytes, detection sensor, and detected normal reference ranges 5300", and "Biofluid lipid panel parameters, detection sensor, and detected normal reference ranges 5400".

The biokinetics parameters detected are listed in the "Biokinetics parameters, detection sensor, detected normal reference ranges 6700".

The lifestyle parameters detected are listed in the "Lifestyle parameters, detection sensor, and detected normal reference ranges 7000".

The smart band 200 set of sensor parameters result comprises: a parameter name, a result value, a flag, a unit, a normal reference range, and an intelligent relationship interpretation; and wherein the intelligent relationship interpretation comprises: a symptom, a cause, and a treatment when the set of sensor parameters result value falls outside the normal reference range and wherein the cause and the treatment are accurately determined based on a correlated smart band sensor parameter result value. Example intelligent relationship interpretation correlated parameters are listed in the FIG. 81, FIG. 82, FIG. 83, and FIG. 84. The mobile healthcare application 250 displays a set of sensor parameters results comprising: a symptom, a cause, a treatment, and an intelligent relationship interpretation when the set of sensor parameters values falls outside a normal reference range. A symptom is defined as physical or mental problem that a person experiences that may indicate a disease or condition. Symptoms usually cannot be seen and do not show up on medical tests. A cause is defined as a branch of medical science concerned with the causes and origins of diseases or abnormal condition. The treatment is the action or way of treating a patient or a condition medically or surgically. Management and care are used to prevent, cure, ameliorate, or slow progression of a medical condition. The normal reference ranges are based on the normal test results of a large group of healthy people. The smart band 200 sensor parameter results for health are used to help diagnose, screen, or monitor a specific disease or condition. Some examples of symptoms are headache, fatigue, nausea, and pain. Causes examples are anemia, leukemia, malnutrition, and so on. Treatments can be in the form of nutrients, dietary supplements, drugs, and exercise. The intelligent relationship interpretation enables the accurate cause and treatment. In many cases cause can be due to environmental, physiological, biokinetics, or lifestyle parameters and not necessarily due to biofluid parameters. The intelligent relationship interpretation allows the user 8710 to get right diagnosis and treatment saving lot of money.

For example, the red blood cells results may contain following information:

A red blood cell (RBC) count measures the number of red blood cells, also known as erythrocytes, in blood. Red blood cells carry oxygen from lungs to every cell in the body. The cells need oxygen to grow, reproduce, and stay healthy. An RBC count that is higher or lower than the normal reference range is often the first sign of an illness. So, the smart band 200 biofluid 392 allows a user 8710 to get prognostic information and treatment even before the symptoms appear. In other cases, cause and treatment can be based on other correlated smart band 200 sensor parameters.

Example below describes a Lower than normal reference range RBC count result comprising symptoms, causes, intelligent relationship interpretation, and treatments.

Symptoms: Weakness, fatigue, pale skin, rapid heartbeat

Causes: Anemia causes: Leukemia, a type of blood cancer, Malnutrition, a condition in which body does not get the calories, vitamins, and/or minerals needed for good health, Multiple myeloma, a cancer of the bone marrow. The above causes are generic in nature. Intelligent relationship interpretation provides accurate cause information about low RBC count.

Intelligent relationship interpretation: The low RBC count can be due to correlated high body temperature result value, high pollution result value, or low ambient temperature result value. For example, if the user 8710 had high body temperature result value, it can cause the low red blood count due to limiting cellular metabolism, resulting in body's efforts to reduce metabolic heat production as described in FIG. 81. If the environmental parameter of air quality index result value was high, the RBC count and size is low as described in FIG. 81. If the environmental parameter ambient temperature result value was low surrounding the user 8710 it causes the blood vessels and arteries to narrow, restricting blood flow and count and reducing oxygen to the heart as described in FIG. 83. In summary the smart band 200 sensors parameter result values correlated relationship enable accurate determination of causes.

Treatments: Food diet consisting of dark, leafy, green vegetables, such as spinach and kale, dried fruits, such as prunes and raisins, beans, legumes, egg yolks. Vitamin B12 supplement also helps increase RBC count. The treatment is generic in nature. Intelligent relationship interpretation provides accurate treatment information. If the body temperature result value was high, in that case the accurate treatment is ibuprofen, aspirin, or naproxen to ensure that user 8710 body temperature result value was in normal range. If the environmental parameter air quality index value was high in that case the accurate treatment is for the person to live and/or work in pollution free area. If the environmental parameter ambient temperature result value was low the accurate treatment is for the user 8710 to live and/or work in ambient temperature within range of 15 to 25° C. In summary the smart band 200 sensors parameter result values relationship enable accurate determination of the treatments.

Example below describes a Higher than normal reference range RBC count result comprising symptoms, causes, intelligent relationship interpretation, and treatments.

Symptoms: Headache, dizziness, vision problems

Causes: Dehydration, heart disease, polycythemia vera, a bone marrow disease that causes too many red blood cells to be made, scarring of the lungs, often due to cigarette smoking, lung disease, and kidney cancer. The above causes are generic in nature. Intelligent relationship interpretation provides accurate cause information about high RBC count.

Intelligent relationship interpretation: If the user 8710 physiological parameter heart rate result value is high, it results in increased RBC count as explained in FIG. 81. If environmental parameter location result value indicates higher altitude than there is less oxygen which results in increased RBC count because of high heart rates as explained in FIG. 83. In summary the smart band 200 sensors parameter result values correlated relationship enable accurate determination of the causes.

Treatments: Exercise to improve heart and lung function, eat less red meat and iron-rich foods, avoid iron supplements, keep body well hydrated, avoid diuretics, including coffee and caffeinated drinks, which can dehydrate the body, stop smoking, especially if a person has COPD or pulmonary fibrosis. The treatment is generic in nature. Intelligent relationship interpretation provides accurate treatment information. If the user 8710 physiological parameter heart rate result value is high the actual treatment is exercise and lose weight. If the cause is due to environmental parameter location result value indicates higher altitude, the actual treatment can be to relocate to lower altitude areas. The wearable device 100 with smart band 200 is also used as companion diagnostics. The is to a) identify, before and/or during treatment, patient 8710 who is most likely to benefit from the corresponding medicinal product; or b) identify, before and/or during treatment, patient 8710 likely to be at increased risk of serious adverse reactions because of treatment with the corresponding medicinal product. The wearable device 100 with smart band 200 is also used in screening, diagnosis, or staging of cancer. 'Cancer' is the uncontrolled growth and spread of cells. It can affect almost any part of the body. The growths often invade surrounding tissue and can metastasize to distant sites. Cancer is a generic term for a large group of diseases characterized by the growth of abnormal cells which can invade nearby tissues and may spread to other parts of the body through the blood and lymph systems. Other common terms used are malignant tumors and malignant neoplasms. The detection of abnormal cell is done by the biofluid sensor 392 as described in morphology of blood cells diagram 4960. In summary the smart band 200 sensors parameter result values correlated relationship enable accurate determination of the treatments.

A user 8710 smart band 200 sensor result comprises: a set microbial biosensor parameters result, a set of particulate matter sensor parameters result, a set of enviro sensor parameters result, a set of physiological sensor parameters result, a set of biofluid sensor parameters result, a set of biokinetics sensor parameters result, and a set of lifestyle sensor parameters result.

A user 8710 smart band 200 sensor result comprises: a set microbial biosensor 310 parameters result comprising microorganism 610 microorganism data 2110, a set of particulate matter sensor 320 parameters result comprising microorganism data 2110, pollen grain 630 pollen data 3430, dust mite allergen 640 data, and set of suspended particles in air, a set of enviro sensor 330 parameters result comprising environmental parameters detected 3790, a set of physiological sensor 390 parameters result as listed in the "Physiological parameters, detection sensor, and detected normal reference ranges 4200", a set of biofluid sensor 392 parameters result as listed in the "Biofluid complete blood count parameters, detection sensor, and detected normal reference ranges 5100", "Biofluid complete metabolic panel analytes, detection sensor, and detected normal reference ranges 5300", and "Biofluid lipid panel parameters, detection sensor, and detected normal reference ranges 5400", a set of biokinetics sensor 396 parameters result as listed in the "Biokinetics parameters, detection sensor, detected normal reference ranges 6700", and a set of lifestyle sensor 398 parameters result in the "Lifestyle parameters, detection sensor, and detected normal reference ranges 7000 and "Human wellness dimensions description 7350 values".

The user 8710 smart band 200 sensor result is configured to output a diagnosis, a monitoring, a screening, a prevention, a prediction, a predisposition, a prognosis, a treatment, or an alleviation of a disease.

The diagnosis is identification of a disease. For example, a complete blood count results using CBC sensor 392A is used to diagnose a medical condition. The cause can be abnormal levels of the blood count levels. Abnormal levels of red blood cells 5022, hemoglobin 5022H, or hematocrit 5022HCT may be a sign of anemia, and heart disease. Low white cell counts 5024 may be a sign of an autoimmune disease or disorder, bone marrow disorder, or cancer. High white cell counts 5024 may be a sign of an infection or a reaction to medicine. Wherein the diagnosis result is reported in the intelligent relationship interpretation.

The monitoring is regularly tracking and trending a user/patient 8710 condition or health parameter to see if there is any change. For example, a complete blood count results using CBC sensor 392A can be used to monitor medical treatment, if a patient/user is taking medications that may affect blood cell 5020 counts. Monitoring includes smart band 200 that records and/or displays patient or user 8710 data on mobile healthcare application 250, such as microbial biosensor 310 parameters, particulate matter sensor 320 parameters, enviro sensor 330 parameters, physiological sensor 390 parameters, biofluids sensor 392 parameters, biokinetics sensor 396 parameters, and a lifestyle sensor 398 parameter. It also includes devices used for the measurement of the analyte (measurand) levels for the purpose of adjusting treatments/interventions as required. The monitoring result is reported in the intelligent relationship interpretation.

The screening or screening factor is checking for disease when there are no symptoms. Since screening may find diseases at an early stage, there may be a better chance of curing the disease. For example, a complete blood count result using CBC sensor 392A to monitor user/patient 8710 general health and to screen for a variety of disorders, such as anemia or leukemia. The screening result is reported in the intelligent relationship interpretation.

The prevention or prevention factor is action taken to decrease the chance of getting a disease or condition. For example, cancer prevention includes avoiding risk factors such as: reducing number of smoking occurrences 7060 using lifestyle sensor, increasing exercise 6680 results using biokinetics sensor 396, and reducing solar flare radiation exposure using solar flare sensor 347-2, and increasing protective factors such as: getting and monitoring regular physical activity using the biokinetics sensor396, lifestyle changes monitoring using lifestyle sensor 398, staying at a healthy weight, and having a healthy diet. The prevention result is reported in the intelligent relationship interpretation.

The prediction or predictive factor is a condition or finding that can be used to help predict whether a user's 8710 disease such as cancer will respond to a specific treatment. For example, a heart rate 4216, a heart rate variability 4218, and a respiratory rate 4220 results from the physiological sensor 390 can provide prediction or predictive factor for a heart disease from a commonly prescribed medicines such as Benazepril (Lotensin), Captopril (Capoten), Enalapril (Vasotec), Fosinopril (Monopril), Lisinopril (Prinivil, Zestril), Moexipril (Univasc), Perindopril (Aceon), and Quinapril (Accupril). Some of the commonly prescribed medications for are Anticoagulants, Antiplatelet Agents and Dual Antiplatelet Therapy, ACE Inhibitors, Angiotensin II Receptor Blockers, Angiotensin Receptor-Neprilysin Inhibitors, Beta Blockers, Calcium Channel Blockers, Cholesterol-lowering medications, Digitalis Preparations, Diuretics, and Vasodilators. The prediction result is reported in the intelligent relationship interpretation.

The predisposition or predisposition factor is a tendency that some disease that is likely to happen. For example, a predisposition of heart disease based on cholesterol results from a BML sensor 392B, a predisposition of asthma based on the pollen type, pollen count, and the pollen allergy level results using the particulate matter sensor 320. The predisposition result is reported in the intelligent relationship interpretation.

The prognosis or prognostic factor is likely outcome or course of a disease i.e., the chance of recovery or recurrence. For example, a prognosis of a heart disease based on biokinetics sensor 396 and lifestyle sensor 398 parameter results, a cancer prognosis depends on multiple factors, such as the type of cancer and its stage. The prognosis may vary according to injury, disease, age, sex, race, and treatment. The term prognosis and prognostic factor are used interchangeably. The prognosis result is reported in the intelligent relationship interpretation.

The treatment is an instance of treating the user/patient or medical condition. The treatment can include healthy food, nutritious diet, vitamins, medicines, surgical and so on. The treatment can include any or all of the following: treatment plan, treatment cycle, treatment course, treatment schedule, and treatment summary. For example, pathogen count, a pathogen type, a pathogen concentration result from microbial biosensor 310, treatment will be antibiotics for the pathogenic bacteria 616 and will be vaccine for pathogenic virus 614. The grass and weeds pollen type, a pollen count, and a pollen allergy level from particulate matter sensor 320 can result in asthma and treatment will be from inhaled corticosteroids, or medicines such as Montelukast (Singulair), zafirlukast (Accolate), and zileuton (Zyflo).

The alleviation of a disease is easing the severity of a pain or a disease without removing the cause. It also includes making pain or suffering more bearable. For example, a medicine alleviates the symptoms, a reduced number of smoking occurrences 7060 from lifestyle sensor 398 reduces asthma symptoms and a condition involving constriction of the airways and difficulty or discomfort in breathing.

The screening or screening factor, prevention or prevention factor, prediction or predictive factor, predisposition or predisposition factor, and prognosis or prognostic factor are reported as Extremely Unlikely=1. Unlikely=2. Neutral=3, Likely=4, and Extremely Likely=5.

The user 8710 smart band 200 sensor result is configured to output a personalized daily nutritional goal comprising a nutrient, a source of goal, a personal dietary reference intake, and an intelligent nutrient required recommendation to maintain a healthy diet. An example personalized daily nutritional goal comprising nutrient and daily reference intake 10300 lists nutrients, source of goals, DRI goal, personal DRI and intelligent nutrient required recommendations based on the age, gender, body weight, height, and user smart band sensor result.

The user 8710 smart band 200 sensor result is configured to output a personalized dietary pattern comprising a food, an amount, and an intelligent food required recommendation to maintain the healthy diet. An example personalized dietary pattern comprising food and amount 10400 lists food, amount, and intelligent food required recommendation.

The mobile healthcare application 250 displays a personalized daily nutritional goal comprising a nutrient, a source of goal, a personal dietary reference intake, and an intelligent nutrient required recommendation to maintain the healthy diet.

The mobile healthcare application 250 displays a personalized dietary pattern comprising a food, an amount, and an intelligent food required recommendation to maintain the healthy diet.

The personalized daily nutritional goal comprising a nutrient, a source of goal, a personal dietary reference intake, and an intelligent nutrient required recommendation to maintain a healthy diet are calculated based on the user 8710 smart band 200 sensor parameter result values. The macronutrients and minerals personal DRI are calculated based on the user 8710 smart band 200 sensor parameter result values from biofluid sensor 392. In case of vitamins surrogate user smart band 200 parameter result are used. The user 8710 can override a personal DRI and an intelligent nutrient recommendation through the mobile healthcare application 250. If the personal DRI or personal dietary reference intake is low the intelligent nutrient required recommendation lists the dietary supplements and food required. Similarly, if the personal DRI or personal dietary reference intake is high the intelligent nutrient required recommendation lists to reduce dietary supplements and food. The nutrient examples include macronutrients, minerals, and vitamins. The National Institutes of Health (Office of Dietary Supplements) provides detailed information about the Nutrient recommended Dietary Reference Intakes (DRI) or Recommended Dietary Intake (RDI). These values, which vary by age and sex, include Recommended Dietary Allowance (RDA), Adequate Intake (AI), Estimated Average Requirement (EAR), and Tolerable Upper Intake Level (UL). The FDA 101 defines dietary supplements in part as products taken by mouth that contain a dietary ingredient. Dietary ingredients include vitamins, minerals, amino acids, probiotics, and herbs or botanicals, as well as other substances that can be used to supplement the diet. Dietary supplements come in many forms, including tablets, capsules, powders, energy bars, and liquids. The mobile healthcare application 250 interfaces with NIH Nutrient Recommendations and Databases to list daily value of nutrients associated with the sensor parameter result to maintain a healthy diet. A healthy diet is a diet that maintains or improves overall health. A healthy diet provides the body with essential nutrition: fluid, macronutrients such as protein, micronutrients such as vitamins, minerals, and food energy. In the case of an abnormal parameter result, the method auto calculates the required daily value needed to potentially address the root cause of deficiency for a disease. For Personalized dietary pattern comprising food and amount 10400, the food, amount, and intelligent food required recommendation calculation is based on the daily nutritional goals. The user 8710 can override an amount, and an intelligent food required recommendation through the mobile healthcare application 250. The personalized daily nutritional goal comprising nutrient and daily reference intake 10300, and personalized dietary pattern comprising food and amount 10400 provided to user 8710 based on the user smart band sensor result reduces the likelihood of illness or disease. In the case of illness or disease, the intelligent nutrient required recommendation, and intelligent food required recommendation is either to reduce or increase the dietary intake based on the higher, or lower than normal reference ranges.

The user 8710 smart band 200 sensor result is configured to provide information on the predisposition to a medical condition or a disease, predict a treatment response or a reaction, and to define or monitor a therapeutic measure. A predisposition to a medical condition or a disease is a special susceptibility to a disease or disorder, as by the action of direct or indirect environmental parameters, physiological parameters, biofluid parameters, genetic and so on. These include certain cancers, diabetes, obesity, heart disease, asthma, celiac disease, mental illnesses, autism, and even drug addiction. The predisposition information is either calculated using AI algorithms or in some cases part of the intelligent relationship interpretation tables listed in FIGS. 81, 82, 83, and 84. For example, high blood pressure or high cholesterol result value are overall risk or predisposition for developing cardiovascular disease (CVD). A prediction is a statement about the way things will be in the future. The smart band 200 uses the machine learning for predicting a priori whether a user/patient 8710 will benefit from a treatment or not, based on algorithms trained on user 8710 smart band 200 result. Therapeutic measure is defined based on the user 8710 smart band 200 result. Therapeutic measures are methods and techniques that pertain to interventions, treatment, or prevention of diseases, disorders, or conditions. Therapeutic drug monitoring is the practice of measuring specific drugs at designated intervals to maintain a constant concentration in a patient's bloodstream, thereby optimizing individual dosage regimen. Therapeutic drug monitoring (TDM) is testing that measures the amount of certain medicines in the blood. It is done to make sure the amount of medicine user/patient 8710 is taking is both safe and effective. Surrogate smart band 200 set of sensor parameters result value are used to define and monitor the therapeutic treatment. For example, whole blood count result used for monitoring for the development of a life threatening hematological disorder in patient/user 8710 being treated for disorders or conditions, where this risk exists e.g., monitoring of patients with a diagnosis of schizophrenia for neutropenia/agranulocytosis; bilirubin monitoring in response to treatment of neonatal jaundice; and cortisol levels monitoring e.g., for patients with cortisol insufficiency. Smart band 200 is used to assess whether a parameter or an analyte remains within physiological levels or within an established therapeutic drug range to evaluate the users 8710 current state. Smart band 200 sensor data is also used for serial measurement, whereby multiple determinations are taken over time for the detection/assessment of disease progression/regression, disease recurrence, minimum residual disease, response/resistance to therapy and/or adverse effects due to therapy to evaluate changes in the user/patient 8710 state.

The user 8710 smart band 200 sensor result is configured for a continuous monitoring of a user/patient 8710 health for an accurate clinical outcome assessment and a personalized wellness program for a healthy lifestyle. FIG. 105 lists an example personalized wellness program. FDA defines a clinical outcome assessment (COA) as a measure that describes or reflects how a patient feels, functions, or survives. Types of COAs include a) Patient-reported outcome (PRO) measures, b) Observer-reported outcome (ObsRO) measures, c) Clinician-reported outcome (ClinRO) measures, and d) Performance outcome (PerfO) measures. COA can be a well-defined and reliable assessment of patients' symptoms, overall mental state, or how they function. Smart band 200 enables automation of a) Patient-reported outcome (PRO) measures. Automation is through the microbial biosensor 310, physiological sensor 390, and biofluid sensor 392 results where measurement based on a report comes directly from the patient smart band 200 about the status of a patient's health condition without amendment or interpretation of the patient's response by a clinician. b) Observer-reported outcome (ObsRO) measures automation through the biokinetics sensor 396, and lifestyle sensor 398, where a measurement is based on a report of observable signs, events, or behaviors related to a patient's health condition by someone other than the patient or a health professional. Again, in this case smart band 200 provides that result. Thus, ObsROs reporting by a parent, caregiver, or someone who observes the patient in daily life and are particularly useful for patients who cannot report for themselves (e.g., infants or individuals who are cognitively impaired) is no longer required. c) Clinician-reported outcome (ClinRO) measures are automated measurements based on a report that comes from a trained healthcare professional after observation of a patient's health condition. Most ClinRO measures involve a clinical judgment or interpretation of the observable signs, behaviors, or other manifestations related to a disease or condition. ClinRO measures cannot directly assess symptoms that are known only to the patient. ClinRO measures include Reports of clinical findings (e.g., presence of a skin lesion or swollen lymph nodes) or clinical events (stroke, heart attack, death, hospitalization for a particular cause), which can be based on clinical observations together with biomarker data from smart band 200 microbial biosensor 310, physiological sensor 390, and biofluid sensor 392 results, such as electrocardiogram (ECG) and creatine results supporting a myocardial infarction, and d) Performance outcome (PerfO) measures automation is through biokinetics sensor 396, and lifestyle sensor 398, where a measurement based on standardized task(s) is actively undertaken by a patient according to a set of instructions. A PerfO assessment may be administered by an appropriately trained individual or completed by the patient independently using smart band 200 lifestyle sensor 392 queries. PerfO assessments include measures of gait speed (e.g., timed 25 foot walk test using a stopwatch or using sensors on ankles) (physical wellness ranking), and measures of memory (e.g., word recall test) (intellectual wellness ranking). A personalized wellness program is intended to improve and promote health and fitness. The personalized wellness program for a healthy lifestyle is based on a personalized user wellness dimension ranking which is calculated from the user smart band sensor result, user clinical laboratory test result, intelligent relationship interpretation data, and sensor data of the set of wearable electronics, and wherein the personalized user wellness dimension ranking comprises physical, environmental, occupational, financial, intellectual, emotional, social, and spiritual elements. Machine learning is used in case of missing data. The personalized user wellness dimension ranking is classified as: excellent=5, very good=4, good=3, fair=2, and poor=1 as defined in human wellness dimensions reference ranges 7420. The personalized wellness program goals are to ensure smart band 200 sensor parameters result value are within normal reference ranges. The overall user personalized wellness dimension ranking is within is in good to excellent range. The human wellness dimensions descriptions 7350 describes each of the wellness dimensions. There are well defined actionable personalized wellness program items for each of the wellness dimension rankings, resulting in a healthy lifestyle which is a way of living that lowers the risk of being seriously ill or dying early. World health organization published risk and data is also used as part of the program.

The noninvasive in vivo measurement of the smart band 200 sensor result allows for a reduced number of hospital visits, a reduced medical waste, and a reduced healthcare cost. Physiological tests require the user/patient to visit a doctor or hospital. Clinical laboratory biofluid tests require the user/patient to visit a hospital where a health care professional takes a blood sample from a vein in the user's arm, using a small needle. After the needle is inserted, a small amount of blood is collected into a test tube or vial. The noninvasive in vivo monitoring of the physiological and biofluid parameters eliminates the blood, syringe, band aid, and lab testing. The biohazardous waste generated due to lab testing, also called medical or infectious waste (such as blood, body fluids, and human cell lines), is contaminated with potentially infectious agents or other materials that are deemed a threat to public health, or the environment and is eliminated. The cost associated with blood draw, sample transportation, laboratory testing, and results transmission is also eliminated. Cost of the blood testing varies and is dependent on the insurance coverage and without insurance. The present average cost of physical test at doctor's office is $200, laboratory CBC test is $150, laboratory metabolic panel test is $500, and laboratory lipid panel test is $300 with a total laboratory test cost of approximately $1150 per user 8710. If on an average 100 million user 8710 in US takes clinical laboratory tests once every year, the total cost of laboratory tests is around $115 billion. The wearable device 100 with smart band 200 eliminates the laboratory tests costs.

Figure 2:
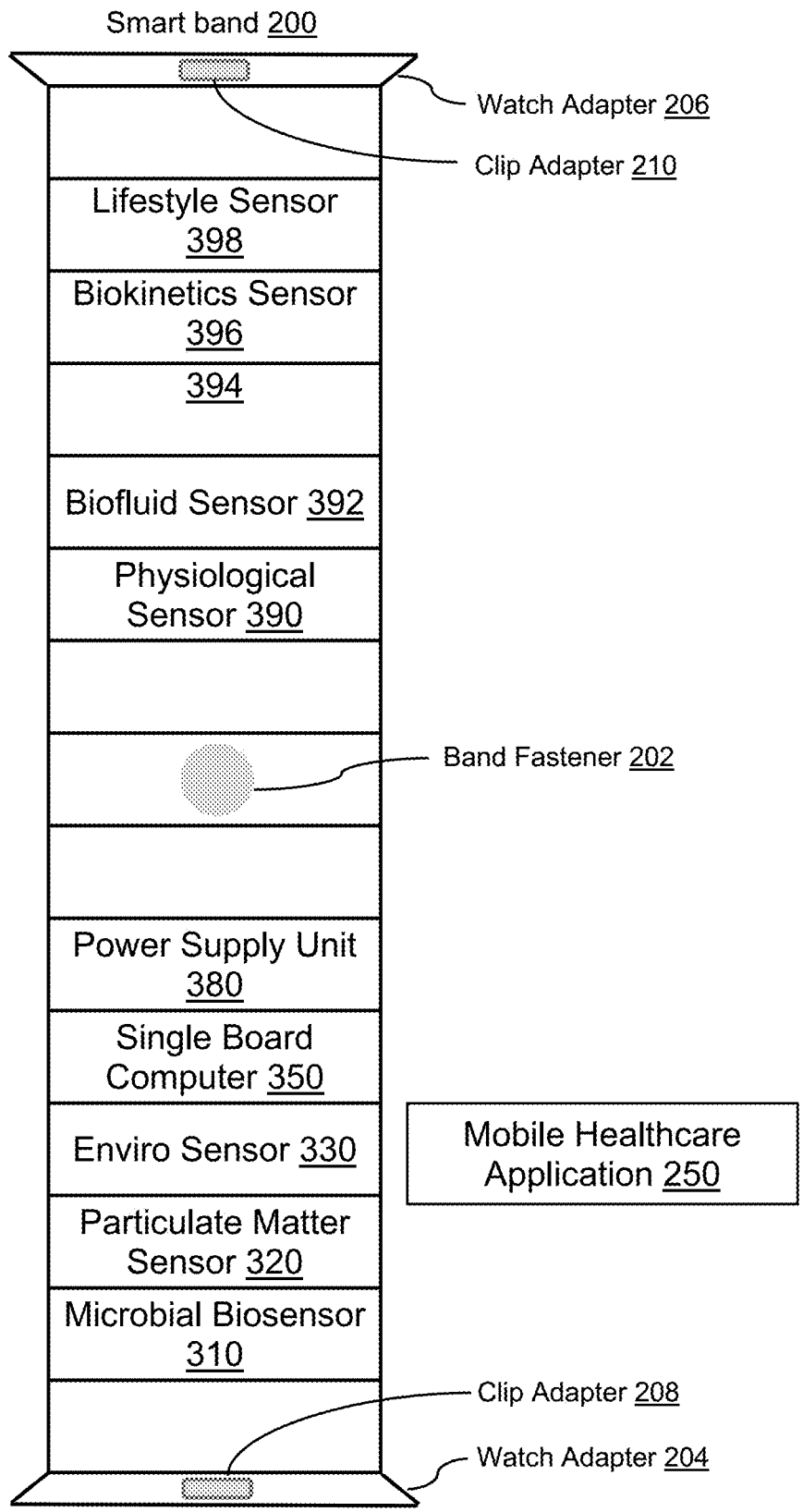
FIG. 2 is an example smart band design that can be utilized to implement various embodiments.

FIG. 2 is an example smart band 200 design that can be utilized to implement various embodiments.

The smart band 200 comprises a microbial biosensor 310, a particulate matter sensor 320, an enviro sensor 330, a physiological sensor 390, a biofluid sensor 392, a biokinetics sensor 396, a lifestyle sensor 398, a single board computer 350, a power supply unit 380, a band fastener 202, a set of watch adapters 204 and 206, and a set of clip adapters 208 and 210. The watch adapters 204 and 206 allow the smart band 200 to be connected to any watch. The set of clip adapters 208 and 210 allow it to be attached to a necklace, a waistband, a belt, a headband, and so on for discreet monitoring. The software consists of mobile healthcare application 250 which is preinstalled in the wearable device 100 and displays the sensor data on the display unit. The mobile healthcare application 250 can also be installed on the smartwatch and mobile devices.

FIG. 3 is an example smart band circuit block diagram 300, according to some embodiments.

The wearable device circuit block diagram 300 of the smart band 200 consists of the microbial biosensor 310, particulate matter sensor 320, enviro sensor 330, physiological sensor 390, biofluid sensor 392, biokinetics sensor 396, lifestyle sensor 398, and a power supply unit 380 connected to the single board computer 350 through GPIO pinout 370.

The microbial biosensor 310 comprises a transmitter 312, a receiver 314, a sterilizer 316, a picocamera 318, and a microbial biosensor power button 319.

The particulate matter sensor 320 comprises a sensing cavity 322 enabling detection of the microorganism 600, a pollen grain 630, a dust mite allergen 640, and a particulate matter.

The enviro sensor 330 comprises a set of sensors 332-346 and 347-1 to 347-4. The set of sensors are an RFID tag sensor 332, location sensor 334, ambient light sensor 336, gas sensor 338, smoke sensor 340, temperature, humidity, and pressure sensor 342, sound sensor 344, ultraviolet light sensor 346, cosmic ray sensor 347-1, solar flare sensor 347-2, ozone sensor 347-3, and climate change sensor 347-4. The enviro pinout cable 348 is connected to the single board computer 350 general purpose input/output (GPIO) pinout 370. The sensors 332-347 are made up of space saving rugged micro-electromechanical system (MEMS) and picomaterial components.

The single board computer 350 comprises a system on chip (SOC) 352, RAM 354, accelerometer 356, gyroscope 358, secure digital card (SDC) 360, display DSI port 362, Wi-Fi Bluetooth 364, microphone and speaker 366, camera CSI port 368, and general purpose input/output (GPIO) pinout 370.

The power supply unit 380 comprises a wireless charging unit 382, a battery 384, a charging port 386, and a band power button 388.

A mobile healthcare application 250 allows a user to access the wearable device 100 with smart band 200 sensor data.

The physiological sensor 390 comprises a set of sensors comprising skin temperature sensor 390A, cardiac photoplethysmography (PPG) sensor 390B, ECG sensor 390C, blood pressure sensor 390D, blood oxygen sensors LEDs element 390E1 and PDs element 390E2, blood carbon dioxide sensor 390F, EEG sensor 390G, and EMG sensor 390H.

The biofluid sensor 392 comprises a set of sensors comprising CBC sensor 392A, and BML sensor 392B.

The biokinetics sensor 396 comprises a set of sensors comprising BK accelerometer sensor 396A, BK gyroscope sensor 396B, BK ultrasound sensor 396C, BK magnetometer 396D, and BK piezoelectric 396E.

The lifestyle sensor 398 comprises a set of sensors comprising breath analyzer sensor 398A, LS gyroscope 398B, picocamera element 398C1, LS smoke sensor 398D, and LS sound sensor 398E.

The element 394 can be a cavity sensor or biological sensor configured to output set of sensor parameters comprising: a microorganism parameter, and a biofluid parameter in an ear, an eye, a vaginal cavity, an anus, an annual canal, or an anal cavity; wherein element 394 comprises microbial biosensors, and biofluid sensors. The ear infection is usually due to virus 614 or bacteria 616 infection. An eye infection is any disease of the eyes caused by a harmful microorganism, such as a virus 614, bacteria 616, or fungus 618. A vaginal infection is due to an imbalance of yeast (fungus 618) and bacteria 616 that normally live in the vagina. A vaginal yeast infection is at the opening of the vagina (vulva) caused by the fungus *candida* 618. An anus infection is a collection of pus in the tissue around the anus and rectum. The pus usually is composed of pathogenic bacteria 616.

FIG. 4 is an example schematic representation of a single board computer general purpose input output pin numbering diagram 410, and a general purpose input output pinout function 450 that can be utilized to implement various embodiments.

The general purpose input output pin numbering diagram 410 shows the layout of pins 1-42 of GPIO pinout 370. The light gray pinout is either a 3V3-volt (3.3-volt) or 5-volt power supply. The black pinout is represented as Ground or GND.

The remaining GPIO pins are uncommitted digital signal pins on an integrated circuit or electronic circuit board of the single board computer 350 whose behavior—including whether they act as input or output—is controllable by the user at run time. Sensor software drivers are used to map the GPIO pinout 370 to the sensor pinout of microbial biosensor 310, particulate matter sensor 320, enviro sensor 330, and power supply unit 380.

The general purpose input output pinout function 450 shows pins 1-42 of GPIO pinout 370 functions.

FIG. 5 is an example single board computer 350 general purpose input output pinout function description table 500 that can be utilized to implement various embodiments.

The voltage 502 describes the ground and power functions.

The inputs 504 describe how the GPIO pin is assigned an input pin through single board computer 350 software settings.

The outputs 506 describe how the GPIO pin is assigned an output pin through single board computer 350 software settings.

The pulse-width modulation (PWM) 508 is a technique for getting analog results with digital means. Digital control is used to create a square wave, a signal switched between on and off. This on-off pattern can simulate voltages in between full on (5 volts) and off (0 volts) by changing the portion of the time the signal spends on versus the time that the signal spends off. The duration of "on time" is called the pulse width. To get varying analog values, one can change, or modulate, that pulse width. If this on-off pattern is repeated fast enough with an LED, for example, the result is as if the signal is a steady voltage between 0 and 5 V, controlling the brightness of the LED of the flash.

The serial peripheral interface (SPI) 510 is a synchronous serial communication interface specification used for a short distance communication. The serial peripheral interface (SPI) is an interface bus commonly used to send data between the single board computer 350 and small peripherals such as shift registers, microbial biosensor 310, particulate matter sensor 320, enviro sensor 330, physiological sensor 390, biofluid sensor 392, biokinetics sensor 396, lifestyle sensor 398, and a secure digital card 360. It uses separate clock and data lines, along with a select line to connect to the sensor component. SPI allows attachment of multiple compatible microbial biosensor 310, particulate matter sensor 320, and enviro sensor 330, physiological sensor 390, biofluid sensor 392, biokinetics sensor 396, lifestyle sensor 398 to a single set of pins by assigning them different chip-select pins. SPI is another type of communication protocol for communicating between sensors. It also uses a master/slave setup but is primarily used in short distances between a main (master) controller and peripheral devices (slaves) such as sensors. SPI typically uses three wires to communicate with the single board computer 800: SCLK, MOSI, and MISO. SPI needs to be enabled within the single board computer 350 configuration menu before it can be used. There are two types of SPI modes as below:

Standard mode—In standard SPI master mode, the peripheral implements the standard 3-wire serial protocol (SCLK, MOSI, and MISO).

Bidirectional mode—In bidirectional SPI master mode, the same SPI standard is implemented, except that a single wire is used for data (MOMI) instead of the two used in standard mode (MISO and MOSI). In this mode, the MOSI pin serves as MOMI pin.

Either of the two SPI modes can be used by the microbial biosensor 310, particulate matter sensor 320, and enviro sensor 330 based on the sensor pinout connection requirements.

The inter-integrated circuit (I2C) 512 protocol is a synchronous protocol intended to allow multiple "slave" digital integrated circuits ("chips") to communicate with one or more "master" chips. It is widely used for attaching lower-speed peripheral ICs to processors and the single board computer 350 in short-distance, intra-board communication. It only requires two signal wires to exchange information. This is a common type of communication between the single board computer 350 and microbial biosensor 310, particulate matter sensor 320, and enviro sensor 330, physiological sensor 390, biofluid sensor 392, biokinetics sensor 396, lifestyle sensor 398. It works by having a master and a slave. The master in this case is the single board computer 350, and the slave devices are hardware peripherals like microbial biosensor 310, particulate matter sensor 320, and enviro sensor 330, physiological sensor 390, biofluid sensor 392, biokinetics sensor 396, lifestyle sensor 398 that would normally extend the functionality of the device. The advantage of I2C is that one can connect hundreds of sensors up to the same master using the same two-wire interface, providing that each device has a different I2C address. This is very useful in the case of a wearable device 100 containing many sensors.

In serial interface 514, a serial pin TX is used to transmit, and a serial pin RX is used to receive the data. In telecommunication and data transmission, serial communication is the process of sending data one bit at a time, sequentially, over a communication channel or computer bus. This contrasts with parallel communication, when several bits are sent as a whole, on a link with several parallel channels. Sensors like GPS are connected to GPIO TX and RX pins.

FIG. 6 illustrates an example set of microorganisms 610, pollen grain 630, dust mite allergen 640, and relative size of particles 650 that can be utilized to implement various embodiments.

The set of microorganisms 610 can be a prion or prions 612, virus or viruses 614, bacterium or bacteria 616, a fungi or fungus 618, a protist or protists 620, and a dust mite or dust mites 622.

The prions 612 are found in diseased meat, skin, brain, and so on. The prions are also found in leaves, at levels that should be able to infect an animal.

The most common microorganisms 610 found in the nasal cavity 2840 and oral cavity 2890 comprise:

Virus 614 comprising SARS-CoV-2, Dengue, Ebola, Hepatitis A, Norovirus, Rotavirus, Adenoviruses, Astroviruses, and so on;

Bacteria 616 comprising *Salmonella, Escherichia coli, Streptococcus, Shigella, Pseudomonas aeruginosa, mycobacterium, Giardia Lamblia, Yersinia, Klebsiella*, and so on; and Fungi 618 comprising Ringworm, Dermatophytes, Yeast *candida*, and so on.

Most protists 620 are aquatic organisms. Protists 620 need a moist environment to survive. As such they are found mainly in contaminated water, damp soil, marshes, puddles, lakes, and the ocean. Protists are found on the surfaces of an object.

The dust mites 622 are found in bedding, mattresses, upholstered furniture, carpets, or curtains in your home. They feed on dead human skin cells and hair cells. There are two main types of house dust mites in North America. The American Dust Mite is known as *Dermatophagoides farinae*, and the European Dust Mite is known as *Dermatophagoides pteronyssinus*. Dust mites 622 do not bite humans or animals. House dust mite 622 excrements are considered the main source of allergy. The dust mite 622 excrement or droppings are the major source of allergens and a major contributor to allergic diseases such as asthma, rhinitis, and atopic dermatitis.

Pollen grains 630 are microscopic structures that carry the male reproductive cell of plants. Pollen grains 630 have many different kinds of shapes and usually identified by shape and number of apertures.

The dust mite allergens 640 are dust mite excrements 1818 found in the environment air.

The relative size of particles 650 provides insight into various sizes of particles like atoms, small molecules, lipids, proteins, prions, viruses, bacteria, organelles, fungi, protists, eukaryotic cells (depicted bigger than actual size), pollen, and dust mites. The relative size of particles 650 provides visual correspondence to the size of the microorganisms 610.

In addition, there are many allergens, including different types of mites, molds, animal dander, weeds, grasses, insects, trees, and shrubs which can be detected by the particulate matter sensor 320 in the form of particulate matter concentration and associated information about particulate matter type, concentration, and size.

The smallest particle is the atom, which is 100 picometers (pm), and dust mites are 0.2-0.3 mm (millimeters) long. The eye can see particles of sizes up to 0.1 mm. Light microscopes allow seeing of particle sizes as small as about 500 nanometers (nm). The electron microscope allows seeing of particle sizes less than 1 nm and about 100 micrometers (µm). Light microscope and electron microscope disadvantages are cost, size, maintenance, training, and image artifacts resulting from specimen preparation. They are large, cumbersome, expensive pieces of equipment, extremely sensitive to vibration and external magnetic fields. The electromagnetic spectrum 2300 used by electron microscopes falls in the region of ionizing radiation and is hazardous to humans. The picocamera 318 and particle imaging 2530 detection method allow seeing of particle sizes less than 1 nm and about 1 mm using visible, near infrared and infrared light.

FIG. 7 is an example prion structure and components diagram 710, a prion structure components, function, and chemical composition list 730, a prion disease, status, and source list 750, and a prion attributes and biosensor detector list 790, according to some embodiments.

The prion structure and components diagram 710 shows how normal prion protein 712 amino acids in alpha helix 716 form transform to misfolded prion protein 712 amino acids in beta helix 718 form and cause disease.

The prion structure components, function, and chemical composition list 730 lists the amino acids in alpha helix 716 form and amino acids in beta helix 718 form primary function and shape and chemical composition.

The prion disease, status, and source list 750 describes the prion disease, its contagious or noncontagious status, and source.

The prion attributes and biosensor detector list 790 describes the prion attributes.

The above structure, components, and chemical composition information for each prion 612 is used by the microbial biosensor 310 and particulate matter sensor 320 to detect it. The particle detection methods 2500 of particle imaging 2530, and light scattering and imaging 2570, are more suitable to detect prions 612.

FIG. 8 is an example virus structure and components diagram 810, a virus structure components, function, and chemical composition list 830, and a percent chemical composition of a virus list 850, according to some embodiments.

The virus structure and components diagram 810 shows the various components and their shapes of an exemplary SARS-CoV-2 virus.

The virus structure components, function, and chemical composition list 830 describes the component name, its primary function, and predominant chemical composition.

The percent chemical composition of a virus list 850 describes primary constituents and corresponding percent of dry weight.

The above structure, components, and chemical composition information for each virus 614 is used by the microbial biosensor 310 and particulate matter sensor 320 to detect it. The particle detection methods 2500 of particle imaging 2530, nucleic acid sequence identification 2540, and light scattering and imaging 2570 are more suitable to detect virus 614.

Figure 9:
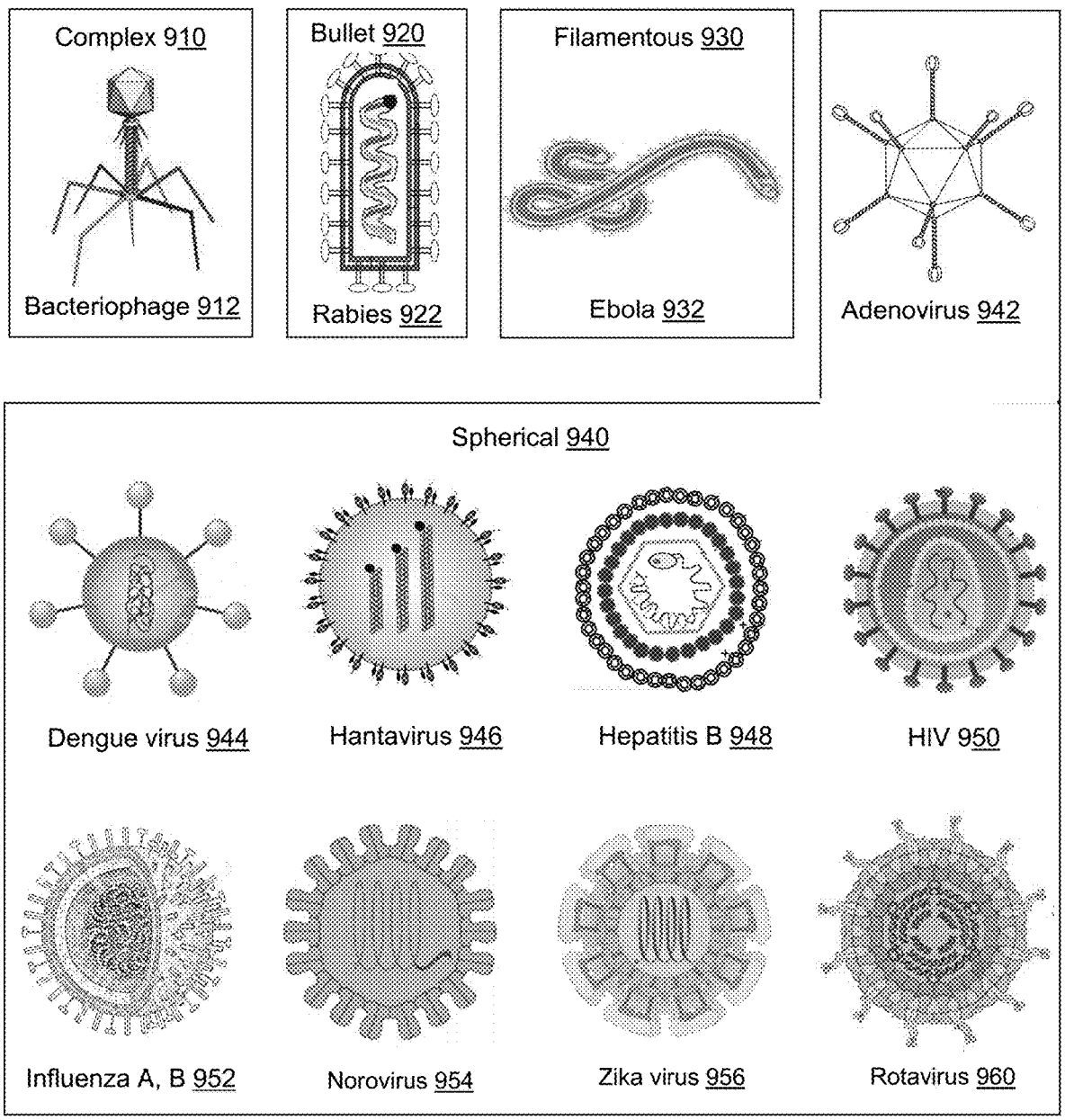
FIG. 9 is an example virus shapes diagram, according to some embodiments.

FIG. 9 is an example virus shapes diagram 900, according to some embodiments.

The virus 614 shapes can be a Complex 910, a Bullet 920, a Filamentous 930, and a Spherical 940.

The example viruses 614 for each shape are listed below:
Complex 910 e.g., Bacteriophage 912
Bullet 920 e.g., Rabies 922
Filamentous 930 e.g., Ebola 932 and Marburg
Spherical 940 e.g., Adenovirus 942, Dengue virus 944, Hantavirus 946, Hepatitis B 948, HIV 950, Influenza A, B 952, Norovirus 954, Zika virus 956, Rotavirus 960.

The above virus shape attribute information for each virus 614 is used by the microbial biosensor 310 and particulate matter sensor 320 to detect it.

FIG. 10 is an example virus name, disease, status, source, shape, size, and nucleic acid list 1000, and a virus attributes and biosensor detector list 1090, according to some embodiments.

The virus name, disease, status, source, shape, size, and nucleic acid list 1000 and a virus attributes and biosensor detector list 1090 are used by the microbial biosensor 310 and particulate matter sensor 320 to detect it. The virus 614 pathogen safety data sheet of FIG. 96, FIG. 97, and FIG. 98 information is derived from this data.

FIG. 11 is an example bacteria cell structure and components diagram 1110, a bacteria cell structure components, function, and chemical composition list 1130, and a percent chemical composition of a bacteria list 1150, according to some embodiments.

The bacteria cell structure and components diagram 1110 shows the various components and their shapes of an exemplary *Escherichia coli* bacteria.

The bacteria cell structure components, function, and chemical composition list 1130 describes the component name, its primary function, and predominant chemical composition.

The percent chemical composition of a bacteria list 1150 describes primary constituents and corresponding percent of dry weight.

The above structure, components, and chemical composition information for each bacterium 616 is used by the microbial biosensor 310 and particulate matter sensor 320 to detect it. The particle detection methods 2500 of infrared spectroscopy 2510, fluorescence imaging 2520, particle imaging 2530, nucleic acid sequence identification 2540, ultrasound waves 2560, and light scattering and imaging 2570 are more suitable to detect bacteria 616.

FIG. 12 is an example bacterial cell shapes diagram 1200, according to some embodiments.

The bacteria 616 shapes can be Spherical 1210, Spiral 1220, Rod 1230, Comma 1250, Box 1260, Appendaged 1270, and Pleomorphic 1280.

The example bacteria 616 for each shape are listed below:

Spherical (Cocci) 1210 e.g., *Streptococcus pneumoniae* 1212, *Staphylococcus aureus* 1214

Spiral 1220 e.g., *Treponema pallidum* 1222

Rod (*Bacillus*) 1230 e.g., *Legionella pneumophila* 1232, *Clostridium botulinum* 1234, *Streptobacillus moniliformis* 1236, *Salmonella typhi* 1238, *Helicobacter pylori* 1240

Comma 1250 e.g., *Vibrio cholerae* 1252

Box 1260 e.g., Halophilic 1262

Appendaged 1270 e.g., *Hyphomicrobium* 1272

Pleomorphic 1280 e.g., *Corynebacterium diphtheria* 1282

The above bacteria cell shapes 1200 information for each bacterium 616 is used by the microbial biosensor 310 and particulate matter sensor 320 to detect it.

FIG. 13 is an example bacteria name, disease, status, source, shape, size, and nucleic acid list 1300, and a bacteria attributes and biosensor detector list 1390, according to some embodiments.

The bacteria name, disease, status, source, shape, size, and nucleic acid list 1300 and bacteria attributes and biosensor detector list 1390 are used by the microbial biosensor 310 and particulate matter sensor 320 to detect it. The bacteria 616 pathogen safety data sheet information is derived from this data.

FIG. 14 is an example fungi cell structure and components diagram 1410, a fungi cell structure components, function, and chemical composition list 1440, and a percent chemical composition of a fungi list 1450, according to some embodiments.

The fungi cell structure and components diagram 1410 shows the various components and their shapes of an exemplary yeast fungi.

The fungi cell structure components, function, and chemical composition list 1440 describes the component name, its primary function, and predominant chemical composition.

The percent chemical composition of a fungi list 1450 describes primary constituents and corresponding percent of dry weight.

The above structure, components, chemical composition information for each fungus 618 is used by the microbial biosensor 310 and particulate matter sensor 320 to detect it. The particle detection methods 2500 of infrared spectroscopy 2510, fluorescence imaging 2520, particle imaging 2530, nucleic acid sequence identification 2540, ultrasound waves 2560, and light scattering and imaging 2570 are more suitable to detect fungi 618.

FIG. 15 illustrates a fungi cell shapes diagram 1510, and a fungi cell shape in environment and shape shift in host diagram 1520, according to some embodiments.

The fungi 618 shapes can be a Yeast cell 1512, Septate hyphae 1514, and Coenocytic hyphae 1516.

The yeast cell 1512 is described in fungi cell structure and components diagram 1410.

Septate hyphae 1514 have dividers between the cells, called septa (singular septum). The septa have openings called pores between the cells, to allow the flow of nutrients, cytoplasm, ribosomes, mitochondria, and sometimes nuclei to flow among cells and throughout the mycelium.

Coenocytic hyphae 1516 are nonseptate, meaning they are one long cell that is not divided into compartments. Coenocytic hyphae are big, multinucleated cells. The branches are hyphae, or filaments, of a mold called *Penicillium*. A mycelium may range in size from microscopic to very large. One of the largest living organisms on Earth is the mycelium of a single fungus 618.

The fungi cell shape in environment and shape shift in host diagram 1520 describes the shape of fungi 618 in the environment 1522 to shape shift in host 1524 as follows:

*Aspergillus fumigatus* 1530 shape shift in host 1524 is to Conidia to hyphae 1532

*Coccidioides immitis* 1540 shape shift in host 1524 is to Arthrosporic to sphere 1542

*Blastomyces dermatitidis* 1550 shape shift in host 1524 is to Spores to yeast cell 1552 in lungs and blood stream

*Candida albicans* 1560 shape shift in host 1524 is to Hyphae to Pseudo hyphae 1562

*Histoplasma capsulatum* 1570 shape shift in host 1524 is to Conidia to budding 1572

The above fungi cell shape in environment and shape shift in host diagram 1520 for each fungus 618 is used by the microbial biosensor 310 and particulate matter sensor 320 to detect it. The microbial biosensor 310 uses the data associated with shape shift in host 1524, whereas the particulate matter sensor 320 uses data associated with the shape in the environment 1522 to detect fungi 618.

FIG. 16 is an example fungi name, disease, status, source, shape, size, and nucleic acid list 1600, and a fungi attributes and biosensor detector list 1690, according to some embodiments.

The fungi name, disease, status, source, shape, size, and nucleic acid list 1600, and a fungi attributes and biosensor detector list 1690 are used by the microbial biosensor 310 and particulate matter sensor 320 to detect it. The fungi 618 pathogen safety data sheet information is derived from this data.

FIG. 17 is an example protist cell structure and components diagram 1710, a protist cell components, function, chemical composition list 1750, and a protist attributes, protists disease, source, shape, size, and nucleic acid list 1780, and protist attributes and biosensor detector list 1790, according to some embodiments.

The protist cell structure and components diagram 1710 shows an example Paramecia protist. Paramecia are single-celled protists that are naturally found in aquatic habitats. They are typically oblong or slipper-shaped and are covered with short hairy structures called cilia as shown in the diagram. The protist 620 can be found in the mouth after drinking contaminated water.

The protist cell structure and components diagram 1710, protist cell components, function, chemical composition list 1750, and protist attributes, protists disease, source, shape, size, and nucleic acid list 1780, and protist attributes and biosensor detector list 1790 information for each protist 620 is used by the microbial biosensor 310 and particulate matter sensor 320 to detect it. The particle detection methods 2500 of infrared spectroscopy 2510, fluorescence imaging 2520, particle imaging 2530, nucleic acid sequence identification 2540, ultrasound waves 2560, and light scattering and imaging 2570 are more suitable to detect protists 620.

FIG. 18 is an example dust mite structure and components diagram 1810, a dust mite structure components, function and chemical composition list 1850, and a dust mite attributes and biosensor detector list 1890, according to some embodiments.

The dust mite structure and components diagram 1810, dust mite structure components, function and chemical composition list 1850, and dust mite attributes and biosensor detector list 1890 information for each dust mite 622 is used by the microbial biosensor 310 and particulate matter sensor 320 to detect it. The particulate matter sensor 320 also detects the dust mite allergens 640 which are excrements 1818 found in the environment air. Dust mite allergens 640 are Peptidase 1 enzymes found in the fecal pellets of mites. Enzymes structures are made up of a amino acids which are linked together via amide (peptide) bonds in a linear chain. This is the primary structure. The resulting amino acid chain is called a polypeptide or protein and is used to detect the dust mite allergen 640.

The particle detection methods 2500 of infrared spectroscopy 2510, fluorescence imaging 2520, particle imaging 2530, nucleic acid sequence identification 2540, electromagnetic waves 2550, ultrasound waves 2560, and light scattering and imaging 2570 are more suitable to detect dust mites 622.

FIG. 19 is an example virus, bacteria, and fungi attributes comparison list 1900, according to some embodiments.

The comparison attributes allow the initial sorting of data based on size, shape, color, cell membrane, genetic material, and so on. This reduces the amount of time it takes to detect the virus 614, bacteria 616, and fungi 618 in the nasal cavity 2840, or in the oral cavity 2890, or on the surface 3050.

FIG. 20 is an example platform dataset 2010, and a microorganism taxonomy 2050, according to some embodiments.

The platform dataset 2010 comprises information from important open-source resources such as NCBI, EMBL-EB, CDC MicrobeNet, and prion, virus, bacteria, fungi, protist, dust mite, and pollen databases. The data is further augmented with annotated information associated with attributes and unique identifiers based on biosensor detector and particle detection methods 2500.

The microorganism taxonomy 2050 allows for classifying new organisms or reclassifying existing ones. Microorganisms are scientifically recognized using a binomial nomenclature using two words that refer to the genus and the species. The names assigned to microorganisms are in Latin. This includes variants associated with same microorganism based on structure component and/or DNA/RNA sequence. Taxonomy is the science of naming, describing, and classifying organisms and includes all plants, animals, and microorganisms of the world. Biological classification uses taxonomic ranks such as Domain, Kingdom, Phylum, Class, Order, Family, Genus, Species, and Strain. Currently there is no prion taxonomy. Prions have not been classified in the same way as viruses, thus there are no families, genera, or species. They first are identified by their host species, and associated clinical disease, and then characterized further by their molecular and biological properties. The microorganism taxonomy 2050 lists consist of examples associated with virus taxonomy, bacteria taxonomy, fungi taxonomy, protist taxonomy, and dust mite taxonomy.

FIG. 21 is an example microorganism data 2110, and a microorganism database 2120, according to some embodiments.

The microorganism data 2110 contains genomic information derived from platform datasets, annotation information, pathogen safety data sheets, attributes, and unique identifiers based on the particle detection methods 2500 used.

The microorganism database 2120 comprises the following important tables:

Prions Table 2130 which comprises: Prions Platform Dataset Table 2132, Prions, Genome, Annotation, Pathogen Safety Data Sheet Table 2134, Prions Attributes and Unique Identifiers 2136;

Virus Table 2140 which comprises: Virus Platform Dataset Table 2142, Virus Taxonomy, Genome, Annotation, Pathogen Safety Data Sheet Table 2144, Virus Attributes and Unique Identifiers 2146;

Bacteria Table 2150 which comprises: Bacteria Platform Dataset Table 2152, Bacteria Taxonomy, Genome, Annotation, Pathogen Safety Data Sheet Table 2154, Bacteria Attributes and Unique Identifiers 2156;

Fungi Table 2160 which comprises: Fungi Platform Dataset Table 2162, Fungi Taxonomy, Genome, Annotation, Pathogen Safety Data Sheet Table 2164, Fungi Attributes and Unique Identifiers 2166;

Protists Table 2170 which comprises: Protists Platform Dataset Table 2172, Protists Taxonomy, Genome, Annotation, Pathogen Safety Data Sheet Table 2174, Protists Attributes and Unique Identifiers 2176;

Dust Mites Table 2180 which comprises: Dust Mites Platform Dataset Table 2182, Dust Mites Taxonomy, Genome, Annotation, Pathogen Safety Data Sheet Table 2184, Dust Mites Attributes and Unique Identifiers 2186;

The curated microorganism database 2120 containing the unique identifiers associated with particle detection methods 2500 allows for fast detection, and reporting a given microorganism for a given type of biosensors 2202.

The microorganism database 2120 contains publicly available as well as curated information such as taxonomy, morphology, organelles, physiology, cultivation, geographic origin, application, interaction or sequences for genomes, and images. Apart from images taken by wearable device 100 microbial biosensor 310 and particulate matter sensor 320, the microorganism database 2120 also contains the images and other identification information obtained from other orthogonal or comparator detection methods such as electron microscope images, scanning probe microscope, surface enhanced Raman spectroscopy, surface plasmon resonance, and so on. This comparator detection methods information increases the accuracy of microorganisms 610 detection.

Figure 22:
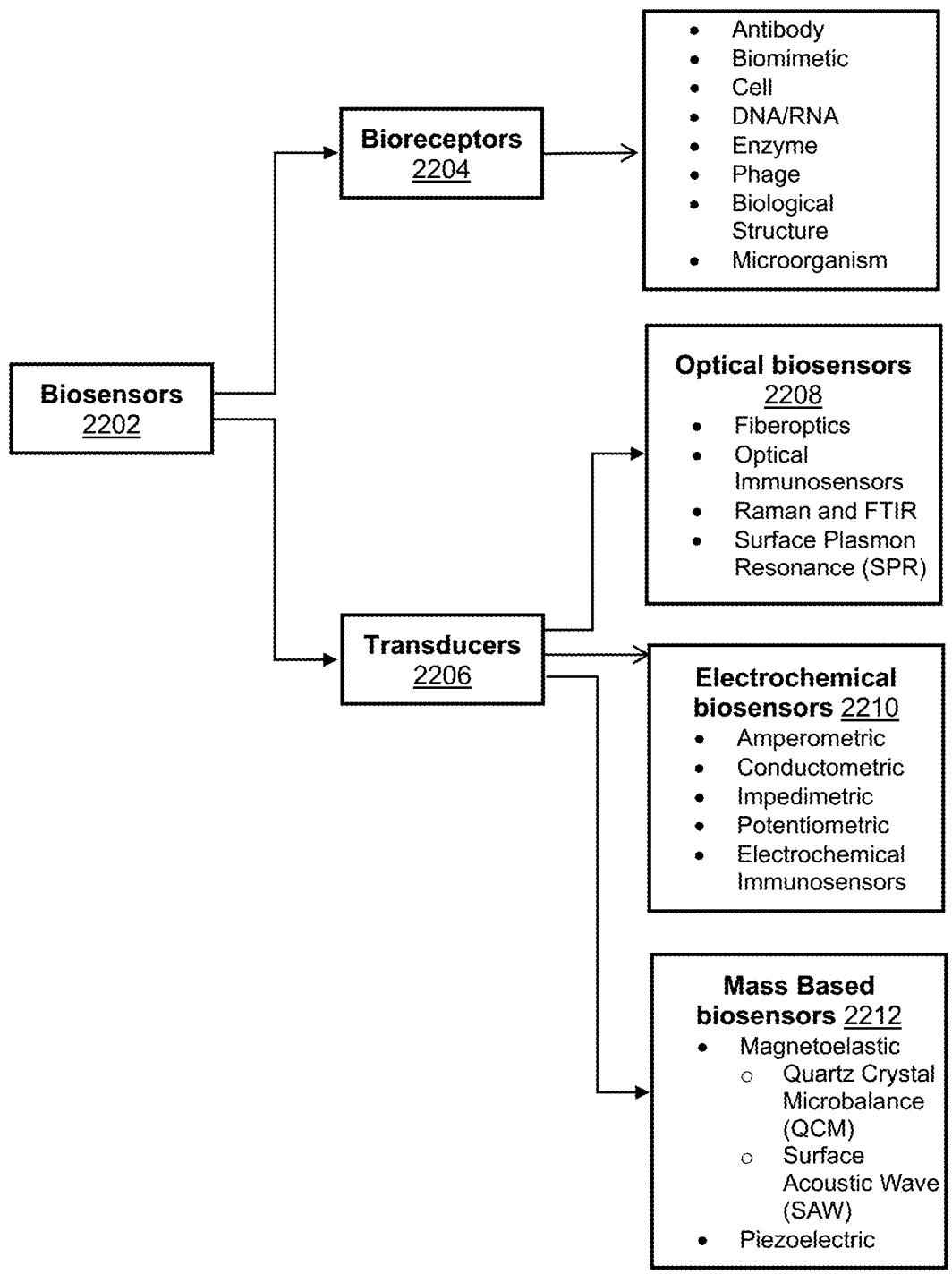
FIG. 22 illustrates a biosensor's classification based on bioreceptors and transducers, according to some embodiments.
Figure 26:
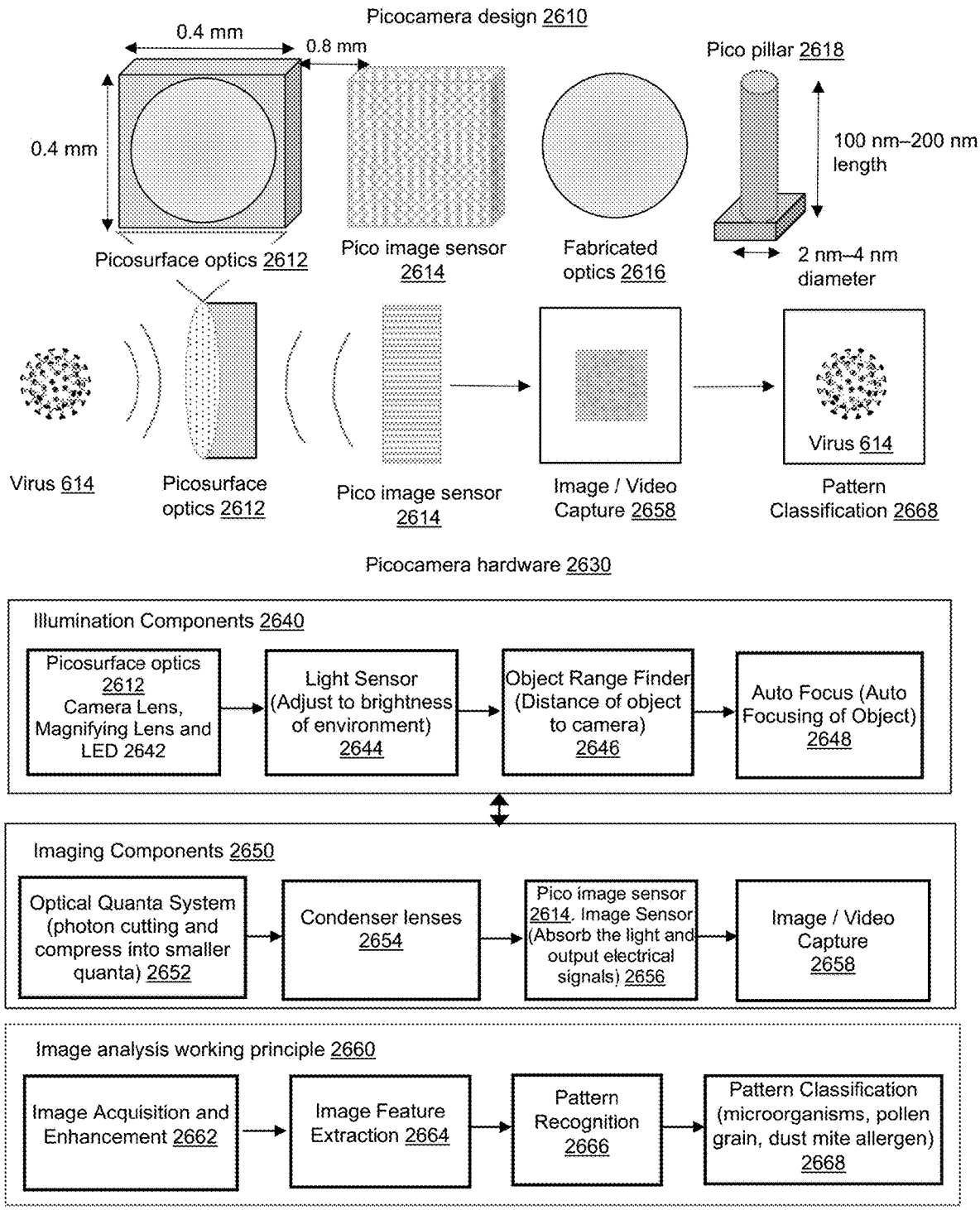
FIG. 26 illustrates an example picocamera design, picocamera hardware comprising illumination components and imaging components, and an image analysis working principle that can be utilized to implement various embodiments.
Figure 37:
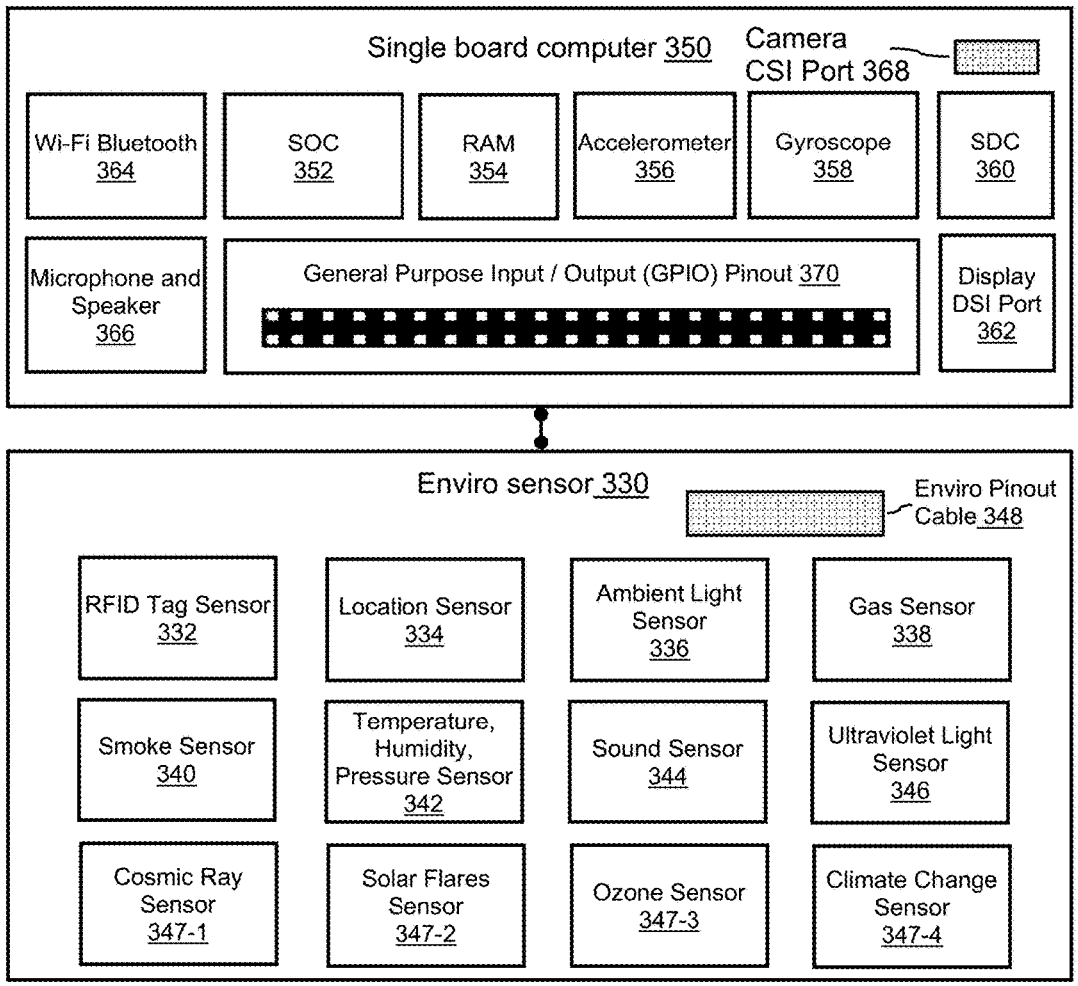
FIG. 37 is an example single board computer and enviro sensor circuit block diagram, enviro sensor wiring table, and enviro parameters detected, according to some embodiments.

FIG. 22 illustrates biosensors classification based on bioreceptors and transducers 2200, according to some embodiments.

Biosensors 2202 are devices used to detect the presence or concentration of bioreceptors 2204. The bioreceptors 2204 or biological analyte or element comprises antibody, biomimetic, cell, DNA/RNA, enzyme, phage, a biological structure, a microorganism comprising a prion 612, a virus 614, a bacterium 616, a fungus 618, a protist 620, a dust mite 622, a tissue, and so on. It has a sensor that integrates a biological element with a physiochemical transducer to produce an electronic signal proportional to an analyte, which is then conveyed to a detector. The process of signal generation (in the form of light, heat, pH, charge, or mass change, etc.) upon interaction of the bioreceptor with the analyte is termed biorecognition. Biosensors consist of three parts: a component that recognizes the analyte and produces a signal, a signal transducer with an amplifier, and a reader device. The transducers 2206 are elements that convert one form of energy into another. In a biosensor the role of the transducers 2206 is to convert the biorecognition event into a measurable signal. Most transducers 2206 produce either optical or electrical signals that are usually proportional to the amount of analyte-bioreceptor interactions.

The biosensors 2202 are classified based on the biological analyte used in the analysis or the method of transduction implemented. The most common classification of biosensors 2202 is based on the type of transducers 2206 or transduction used in the sensor, i.e., type of physiochemical resulting from the sensing event. The biosensor types are:

1) Optical biosensors 2208 are most common type of biosensor. They can be label-free or label-based. Optical biosensors 2208 measure the interaction of an optical field with a biorecognition sensing element. They include infrared light sensor, fluorescence, and surface enhanced Raman spectroscopy (SERS). Detection can be colorimetric, which measures changes in light adsorption, or photometric, which measures light intensity. The method used can be fiber optics, Raman and Fourier transform infrared spectrometer (FTIR), and surface plasmon resonance (SPR). Optical immunosensors are affinity ligand-based biosensor solid-state devices in which the immunochemical reaction is coupled to a transducer. This sensor is based on an immunochemical reaction comprised of an antigen or antibody as the biorecognition element that is immobilized on a transducer surface. The wearable device 100 uses optical methods of infrared spectroscopy 2510, fluorescence imaging 2520, particle imaging 2530, nucleic acid sequence identification 2540, and light scattering and imaging 2570;

2) Electrochemical biosensors 2210 can be classed as amperometric, potentiometric, conductometric, or impedimetric depending on the signal type. Electrochemical biosensors 2210 react with an analyte of interest to produce an electrical signal proportional to the analyte concentration. Electrochemical biosensors 2210 can be Amperometric, which measures current due to the reduction or oxidation of electroactive species, Conductometric, which is based on measurement of electrical conductivity in a sample solution between two electrodes because of the biochemical reaction, Impedimetric, which measures the variation in resistance, or Potentiometric, which measures variations in open circuit potential, converting the chemical information into a measurable electrical signal. Electrochemical immunosensors rely on the measurements of an electrical signal recorded by an electrochemical transducer. Thermometric biosensors' biological reactions are associated with the release of heat. Thermometric biosensors measure the temperature change of the solution containing the analyte caused by these enzymatic reactions. The wearable device 100 can use thermometric biosensors which release heat when light of certain wavelengths strikes the microorganisms 610.

3) Mass based biosensors 2212 such as acoustic biosensors or piezoelectric biosensors measure the change in the physical properties of an acoustic wave or in the case of magnetic biosensors, measure changes in magnetic properties or magnetically induced effects. They also include quartz crystal microbalance (QCM) and surface acoustic wave (SAW). The wearable device 100 can use electromagnetic waves-based impedance spectroscopy by varying radio wave frequencies, so that changes in microorganism 610 response can be determined.

There are a few other biosensors 2202 like:

4) Ultrasound sensors are for directing sound waves toward a surface and measuring the reflected echoes. Echoes are different depending on the density of the microorganism 610 that the ultrasound waves hit. There have been experiments with acoustic reporter genes to scatter sound waves coupled with cell structure high resolution imaging techniques that can also be used to detect microorganism 610. Listening to the unique sound of one microorganism is possible through the picotube 2454 microphone. There are four types of ultrasonic sensors, classified by frequency and shape: the drip-proof type (for outdoor use), high-frequency type (double feed detection), and open structure type lead type (distance detection/moving object detection), and standardized mean difference—SMD type (distance detection and object detection).

FIG. 23 illustrates an electromagnetic spectrum 2300, and a spectrum of sound 2350, according to some embodiments.

The electromagnetic spectrum 2300 is classified as being either ionizing or non-ionizing. Ionizing radiation is of shorter wavelength/high frequency with high energy. Non-ionizing radiation is longer wavelength/lower frequency with lower energy. The ionizing radiation is usually harmful to humans. The electromagnetic spectrum 2300 consists of Gamma rays, X rays, Ultraviolet, Laser, Visible light, Infrared, Microwave, Radio waves, and corresponding applications such as a scintigraphy, a dental/chest, scopes like microscope, thermal imaging, cancer, electro surgery, and MRI (magnetic resonance imaging). The gamma ray's wavelength is shortest and radio wave the longest. The diagram also describes the sizes of elements like atomic nuclei, atoms, microorganisms 610, cells, molecules, pinpoints, bee, humans, and a building. The particle detection methods 2500 use electromagnetic spectrum 2300, which is not harmful to humans or the surface 3050. The regions are ultraviolet, laser, infrared, and part of micro and radio waves.

The spectrum of sound 2350 consists of inaudible sounds (20 Hz), audible sounds (200 Hz to 20 kHz), and inaudible sounds which are greater than 200 MHz. The use of picomaterials 2450 allows for ultrasound echo, images, and listening to sound of microorganisms 610.

FIG. 24 illustrates a noninvasive biosensors for particle detection and sterilization list 2410, picomaterials 2450, and particle detection methods working principle list 2490, according to some embodiments.

The noninvasive biosensors for particle detection and sterilization list 2410 describes in detail the microorganisms 610 detected, biosensor detector used, type of biosensor/transducer, measurement condition, and microorganism detection method.

The microbial biosensor 310 sterilizer 316 allows for sterilization using heat, ultraviolet light, wavelengths of certain type, and acoustic waves to lyse and kill microorganisms 610.

The picomaterials 2450 consists of picoparticle 2452, picotube 2454, picofiber 2456, and picorod 2458. Picomaterials 2450 have diameters below the wavelength of the guided light. The material size can be in pico, nano, and micrometer. These tiny fibers offer engineerable waveguiding properties including optical confinement, fractional evanescent fields, and surface intensity for optical sensing on the pico/nano/micro scale. The material used for manufacturing the microbial biosensor 310, particulate matter sensor 320, and enviro sensor 330 contain picomaterials 2450. The microbial biosensor 310, transmitter 312, receiver 314, sterilizer 316, and picocamera 318 are built using picomaterials 2450.

The particle detection methods working principle list 2490 describes the microorganism detection method corresponding to microorganisms' attributes based unique identifiers. The unique identifiers are predetermined and available in the microorganism database 2120. The artificial intelligence methods allow for calculating the unique identifiers for a new microorganism 610 or new variant/strain based on existing microorganism data 2110.

FIG. 25 illustrates particle detection methods 2500, according to some embodiments.

The method comprises the step of detecting the pathogen and beneficial microorganisms inside the nasal cavity 2840, oral cavity 2890, or on the surface 3050 with the microbial biosensor 310 and particulate matter sensor 320 comprising: particle detection methods 2500 of infrared spectroscopy 2510, fluorescence imaging 2520, particle imaging 2530, nucleic acid sequence identification 2540, electromagnetic waves 2550, ultrasound waves 2560, and light scattering and imaging 2570.

The microbial biosensor 310 and particulate matter sensor 320 use particle detection methods 2500 to detect microorganisms 610, pollen grains 630, and dust mite allergens 640.

The microbial biosensor 310 based methods use a transmitter 312, receiver 314, sterilizer 316, and a picocamera 318. The receiver 314 is programmed to function as transmitter 312 and vice-versa for fluorescence imaging 2520, particle imaging 2530, and nucleic acid sequence identification 2540 detection methods.

The object 2502 can be a nasal cavity 2840, an oral cavity 2890, or on a surface 3050.

The particle detection methods 2500 comprises:

1. Infrared spectroscopy 2510 (IR spectroscopy) which is the measurement of the interaction of infrared radiation with matter by absorption, transmission, or reflection. Infrared spectroscopy 2510 is used to identify chemical composition and substances or functional groups in microorganisms 610. The infrared spectroscopy 2510 is spectra of intact microorganisms' 610 cells with highly specific fingerprint-like signatures which are used to differentiate, classify, and identify diverse microorganism 610 species and strains. The infrared portion of the electromagnetic spectrum 2300 is usually divided into three regions; the near-, mid-, and far-infrared, named for their relation to the visible light. The infrared radiation in the wavelength near- and mid-infrared region of 305-3,000 nm is used so that a user 8710 measurement area can be exposed without adverse health effects. The method can use Fourier Transform IR (FT-IR) spectroscopy. IR spectroscopy exploits the fact that molecules 3814 absorb specific frequencies that are characteristic of their structure. Microorganisms' 610 IR spectra are also useful to detect intracellular structures, components, and chemical composition. The fingerprint-like patterns generated by the absorption or transmission of IR light by cell structure components and chemical composition are highly specific and are used to classify microorganisms according to their phenotype. Identification of microorganisms 610 at the species level is done by comparison of detected spectra to the reference spectra in the microorganism database 2120. The steps to detect microorganisms 610 using the infrared spectroscopy 2510 method are as follows:
   a. Throw a beam of infrared light 2512 on an object 2502. The object 2502 can be a nasal cavity 2840, an oral cavity 2890, or on a surface 3050.
   b. Some of the IR light is absorbed, some IR light is transmitted 2516, and the remaining IR light reflected 2514 is received by the receiver 314.
   c. The % transmittance (T), % reflectance (R), and % absorbance (A) are recorded in the digital format. These numbers are unique to microorganisms 610 based on their chemical composition. The infrared spectrum of a microorganism 610 can be visualized in a graph 2518 of infrared light as % transmittance (T), % reflectance (R), and % absorbance (A), on the vertical Y-axis. The X-axis of an IR spectrum is labeled as "Wavelength" and provides the absorption number.

2. Fluorescence imaging 2520 is a type of noninvasive imaging technique that allows detection of biological molecular structures in a microorganism 610. Fluorescence measurement can be based on variety of methods such as imaging using picocamera 318, and spectroscopy. Fluorescence imaging 2520 can use particle imaging 2530 detection methods to analyze images. Fluorescence imaging 2520 involves taking pictures of the radiation emitted by the microorganisms 610 using picocamera 318 and analyzing it. Fluorescence is a specific radiation emitted by the microorganisms 610 because of incident radiation of a certain wavelength. Fluorescence is a form of luminescence. The emitted light usually has a longer wavelength, and lower energy, than the absorbed radiation. Fluorescence spectroscopy is like infrared spectroscopy 2510. Fluorescence in several wavelengths such as interval from 10 to 200 nm in the ultraviolet region can be detected by an array detector made of picomaterials 2450. The receiver 314 is configured to act as transmitter 312 in this mode. The steps to detect microorganisms 610 using a fluorescence imaging 2520 method are as follows:
   a. Irradiate a beam of excitation light 2522 and 2524 on an object 2502 with a desired and specific band of wavelengths using transmitter 312 and receiver 314.
   b. Separate the much weaker emitted fluorescence from the excitation light 2522 and 2524.
   c. Take an image and videos of the object 2502 using picocamera 318. The image and videos are analyzed using image analysis working principle 2660, and microorganisms 610 are detected. The microorganisms 610 image taken by picocamera 318 also allows for detection of cells and subcellular structures. The image 2528 is an example rod shaped bacteria 614 identified using fluorescence imaging.

3. Particle imaging 2530 is the process of making a digital representation of microorganisms 610 by taking a picture or photo with a picocamera 318. The receiver 314 is configured to act as transmitter 312 in this mode. Photons are too large to see individual atoms, molecules, proteins, and microorganisms 610, pollen grains 630, and dust mite allergens 640. In the particle imaging 2530 method, photons are passed through and aimed at the end of picotubes 2454 and picofibers 2456, the photon is compressed to a much smaller dimension than usual size, and photon quarks strike the nasal cavity 2840, or oral cavity 2890, or surface 3050 and are absorbed and re-emitted. This allows individual atoms to be seen. The light in this case is shrunk or compressed. The picotubes 2454 and picofibers 2456 can also contain a silver or gold needle or other material at the tip to compress the photon. The steps to detect microorganisms 610 using microbial biosensor 310 using a particle imaging 2530 method are as follows:
   a. Irradiate a beam of excitation light 2532 and 2534 on an object 2502 with a desired and specific band of wavelengths using transmitter 312 and receiver 314.
   b. Take multiple high-magnification images of microorganisms 610 using picocamera 318.
   c. Analyze images and videos using image analysis working principle 2660, and microorganisms 610, pollen grains 630, and dust mite allergens 640 are detected. During image analysis the nasal cavity 2840 tissues, oral cavity 2890 tissues, and surface 3050 features are masked out for accurate determination of microorganisms 610. To speed up the detection, a user 8710 can set up and record the nasal cavity and oral cavity images to mask out the tissues. The image 2538 is an example colony of cocci shaped bacteria 614 identified by the particle imaging 2530 method.

4. Nucleic acid sequence identification 2540 is noninvasive identification of a succession of bases signified by a series of a set of five different letters that indicate the order of nucleotides forming alleles within a DNA (using GACT) or RNA (GACU) molecule. The process involves taking high-resolution images at multiple magnification using a particle imaging 2530 technique and picocamera 318 as follows:
  a. Irradiate a beam of excitation light 2542 and 2544 on an object 2502 with a desired and specific band of wavelengths using transmitter 312 and receiver 314.
  b. Take multiple high-magnification images of microorganisms 610 using picocamera 318.
  c. Analyze images and videos using image analysis working principle 2660, and microorganisms 610 are detected. Classify microorganisms 610 at a high level based on shape, size, and other structural components attributes.
  d. Analyze the next higher magnification images and find the presence of DNA/RNA area, chromatin, and nucleus area within images.
  e. Analyze the next higher magnification images of DNA/RNA and tag them as ATGCU based on structural bond.
  f. Create a nucleotide sequence, align the sequence in microorganism database 2120, and identify the microorganism at genus and species levels. The sequence 2546 is an example segment of a SARS-CoV-2 virus sequence.

5. Electromagnetic waves 2550 is based on the principle of a Hall effect sensor. As described in FIGS. 8, 11, 14, and 17, chemical composition and elements in some microorganisms 610 are ferromagnetic. The electromagnetic waves 2550 method uses transmitter 312 designed like a solenoid coil made of picofibers 2456 to generate a magnetic field or flux 2552 which strikes the nasal cavity 2840, or oral cavity 2890, or surface 3050. The magnitude of the magnetic field changes if the microorganism 610 contains ferromagnetic material. A Hall sensor array at the receiver 314 detects the presence and magnitude of a magnetic field 2554 using the Hall effect.

The steps to detect microorganisms 610 using the electromagnetic waves 2550 method are as follows:

a. Direct electromagnetic waves 2552 toward a surface of an object 2502. The magnitude of the intensity changes if microorganisms 610 contains ferromagnetic material.
b. The Hall sensor array at the receiver 314 detects the presence and magnitude of a magnetic field 2554 using the Hall effect.
c. Measure the magnitude of a magnetic field 2554 using the Hall effect. The magnitude of the magnetic field 2554 is different depending on microorganisms' 610 ferromagnetic composition.

The electromagnetic waves 2550 method is more suitable for microorganisms 610 containing ferromagnetic materials.

6. Ultrasound waves 2560 involve directing sound waves toward a surface of an object 2502 and measuring the reflected echoes. Echoes are different depending on the density of the microorganisms 610 that the ultrasound waves hit. In certain cases, microorganisms 610 can also contain acoustic reporter genes to scatter sound waves, coupled with imaging the cell structure in a high-resolution imaging technique to detect it. The other technique used is to listen to the unique sound of one microorganism 610 through picotube 2454 microphone.

The steps to detect microorganisms 610 using the ultrasound waves 2560 method are as follows:

a. Direct sound waves 2562 toward a surface of an object 2502. The objects 2502 are usually hard surfaces.
b. Some of the sound waves reflected 2564 are received by the receiver 314.
c. Measure the reflected echoes. Echoes are different depending on the density of the microorganism that the ultrasound waves hit.

The ultrasound waves 2560 method is more suitable for a hard surface than a nasal cavity 2840 or oral cavity 2890.

7. Light scattering and imaging 2570 is analysis of reflection patterns of incident laser light from the outer surface of microorganisms 610, pollen grains 630, and dust mite allergens 640.

The steps to detect microorganisms 610 using light scattering and imaging 2570 are as follows:

a. Laser 2572 beam radiates suspended particles 2576 in the air entering through an air channel.
b. Collect scattering light through detector 2574 in a certain degree θ and obtain the curve of scattering light change with time. The raw electric signal is amplified. Equivalent particle diameter and the number of particles with different diameters per unit volume are calculated based on the MIE theory of absorption and scattering of plane electromagnetic waves by uniform isotropic particles of the simplest form.
c. Record the particle size number in the digital format. These numbers are unique to microorganisms 610 based on the size. Light scattering of a microorganism 610 can also be visualized in a graph 2580 of scattering of reflectance, on the vertical Y-axis. The X-axis is labeled as "Particle size" and provides the particle size number.

The imaging system uses the microbial biosensor 310 hardware. The steps of imaging using particle imaging 2530 detection method principles are as follows:

a. Irradiate a beam of excitation light 2578 and 2580 on the particle 2576 with a desired and specific band of wavelengths.
b. Take multiple high-magnification images of particles 2576 when they are in front of a special darkfield photographic plate 2582 using picocamera 318.
c. Analyze images and videos using image analysis working principle 2660, and detect microorganisms 610, pollen grains 630, and dust mite allergens 640. During image analysis the nasal cavity 2840 tissues, oral cavity 2890 tissues, and surface 3050 features are masked out for accurate determination of microorganisms 610. To speed up the detection, a user 8710 can set up and record the nasal cavity and oral cavity images to mask out the tissues. The example image 2590 contains an influenza virus, cocci bacteria, and fungi identified using high resolution imaging.

The microbial biosensor 310 and particulate matter sensor 320 particle comprising detection methods 2500 of infrared spectroscopy 2510, fluorescence imaging 2520, particle imaging 2530, nucleic acid sequence identification 2540, electromagnetic waves 2550, ultrasound waves 2560, and light scattering and imaging 2570 also allow detection of particles like small molecules, lipids, proteins and so on.

FIG. 26 illustrates an example picocamera design 2610, picocamera hardware 2630 comprising illumination components 2640, imaging components 2650, and an image analysis working principle 2660, and a picocamera hardware schematic that can be utilized to implement various embodiments.

The intended use of the picocamera 318 is to take photos and videos of the nasal cavity 2840, an oral cavity 2890, or surface 3050 which can be used for nasal ID, open mouth ID, and surface ID recognition. The particle detection methods 2500 use picocamera 318 and take the small particles such as small molecule, protein, microorganism 610, and pollen grain image pictures and videos, and after image analysis identify microorganism 618 type, pollen grain 630, and dust mite allergen 640. Picocamera 318 can be operated in both normal mode and high magnification mode. The picocamera 318 picofibers 2456 scan the nasal cavity 2840, the oral cavity 2890, or the surface 3050 to create a set of super high-resolution images, enhance images, extract features, perform pattern matching, and using applicable fluorescence imaging 2520, particle imaging 2530, nucleic acid sequence identification 2540, and light scattering and imaging 2570 methods, detect the following:

the pathogen count, the pathogen type, the pathogen concentration, and the pathogen biosafety level;
the beneficial microorganism count, the beneficial microorganism type, and the beneficial microorganism concentration;
a pollen type, a pollen count, and a pollen allergy level;
a dust mite allergen count, and dust mite allergy level;

The picocamera design 2610 illustrates design of the picocamera 318. The picocamera design 318 comprises picosurface optics 2612 of diameter and thickness of about 0.4 mm allowing design of an ultra-miniature camera with pico image sensor 2614. The fabricated optics 2616 consists of many pico pillars 2618 of size 100-2000 nm length to 2-4 nm diameter. The picosurface optic 2612 is about the size of grain of sand. The picocamera 318 consists of picosurface optics 2612 and pico image sensor 2614 with a size of 0.4×0.4×0.8 mm. The virus 614 image is received by the picosurface optics 2612 and sensed by pico image sensor 2614. The image/video capture 2658 is further processed through the image feature extraction 2664 algorithm followed by the pattern classification 2668 as virus 614. In the traditional camera, plastic lenses are used to bend incoming light rays into focus on a digital image sensor. In the case of picocamera design 2610, the pico pillar 2618 interacts with the incoming light rays and signal processing algorithms then interpret the image. The picosurface optics 2612 consist of around 2 million pico pillars 2618. The picocamera 318 can use either picosurface optics 2612 or traditional miniaturized plastic camera lens, magnifying lens and LED depending on the type of sensing required for a microbial biosensor 310, a particulate matter sensor 320, a physiological sensor 390, a biofluid sensor 392, and a lifestyle sensor 398.

The picocamera 318 illumination components 2640 comprise: picosurface optics 2612, camera lens, magnifying lens, and LED 2642, light sensor 2644 to adjust to brightness of the environment, object range finder 2646, which allows finding of the distance of the object to picocamera 318 (in this case, the distance of wearable device 100 to the nasal cavity 2840, oral cavity 2890, and surface 3050), and finally auto focus 2648, which allows for auto focusing of objects.

The picocamera 318 imaging components 2650 comprise: optical quanta system 2652 responsible for photon cutting or slicing and compressing it into smaller quanta using picomaterials 2450 such as picotube 2454, picofiber 2456, and picorod 2458; condenser lenses 2654 to gather the quanta or sub photon based on resolution required in pm, nm, or mm in size of the first crossover image and focus them onto a nasal cavity 2840, an oral cavity 2890, or on a surface 3050 to illuminate only the area being examined. A condenser is a lens that concentrates the light on a measurement area and increases the resolution and reduces aberrations. Condenser lenses 2654 are not required for a picosurface optics 2612 based design. A pico image sensor 2614 or an image sensor 2656 absorbs the light and output electrical signals; and image/video capture 2658 stores the digital image and video.

The image analysis working principle 2660 comprises: image acquisition and enhancement 2662, image feature extraction 2664, pattern recognition 2666, and particle pattern classification 2668. The image analysis working principle 2660 includes taking microorganism 610, pollen grain 630, dust mite allergen 640, and surface 3050 photos and classification of the microorganisms 610, pollen grains 630, and surfaces 3050 based on machine learning algorithms. In the processing step image acquisition and enhancement 2662, photos are taken, and an algorithm converts the photo into a digital format. In the case of videos, a video image processing system is used to process frames of the video clip. In processing step image feature extraction 2664, an initial set of the raw photo data and video frames is divided and reduced to more manageable groups. The input photo image and video frames are transformed into a reduced set of features. The processing step pattern recognition 2666 is the process of recognizing patterns by using a machine learning algorithm. The image pattern recognition involves classification of feature extracted data in recognizing the microorganisms 610, pollen grains 630, and dust mites' allergens 640 types. In the processing step pattern classification 2668, particle detection methods 2500 detect the following:

the pathogen count, the pathogen type, the pathogen concentration, and the pathogen biosafety level;
the beneficial microorganism count, the beneficial microorganism type, and the beneficial microorganism concentration;
a pollen type, a pollen count, and a pollen allergy level;
a dust mite allergen count, and dust mite allergy level;

The videos are used to increase the sensitivity of the results using video processing, using images as the data format to store the video frames. This is very helpful in case the photo images taken are blurry.

FIGS. 27, 28, 29, and 30 illustrate example wearable device 100 microbial biosensor 310 implementation and working.

FIG. 27 illustrates an example microbial biosensor pinout 2710 and a microbial biosensor wiring table 2750 describing the hardware wiring connection steps of a microbial biosensor pinout 2710 connected to the single board computer general purpose input output pinout 370 that can be utilized to implement various embodiments.

1. Log in to the single board computer 350 operating software and access general purpose input output pinout 370 settings. Assign and map the general purpose input output pinout 370 to be connected to a microbial biosensor pinout 2710. Save general purpose input output pinout 370 settings.

2. Connect the microbial biosensor pinout 2710 to a single board computer 350 assigned general purpose input output pinout 370 as listed in the microbial biosensor wiring table 2750. The hardware implementation of the microbial biosensor 310 is complete after the pathogen biosensor pinout 2710 is connected to a single board computer 350 general purpose input output pinout 370.

3. Prepare the single board computer 350 operating software to communicate with the microbial biosensor 310 by loading the general purpose input output pinout 370 software library and installing the microbial biosensor 310 software driver.

4. Program, install, execute, and run the microbial biosensor 310 software on the single board computer 350 operating software.

The microbial biosensor 310 software is part of microbiome application software 250.

The microbial biosensor 310 has seven dedicated channels for detecting microorganisms 610, pollen grains 630, and dust mite allergens 640 as follows:

PRI OUT 2714—Output channel for prions 612
VIR OUT 2716—Output channel for viruses 614
BAC OUT 2718—Output channel for bacteria 616
FUN OUT 2720—Output channel for fungi 618
PRO OUT 2722—Output channel for protists 620
DUS OUT 2724—Output channel for dust mites 622
POL OUT 2726—Output channel for pollen grains 630 and dust mite allergens 640

The individual dedicated channel for each microorganism 610, pollen grain 630 and dust mite allergen 640 allows for fast high throughput multiplexed detection. Each output channel 2714 to 2726 is dedicated to use the best particle detection methods 2500 based on microorganism 610 types, and pollen grain 630. The microorganisms 610 limit of detection (LOD) is based on the measurement resolution. Particle detection methods 2500 with higher resolution images like particle imaging 2530 and light scattering and imaging 2570 allow for detection of very low number of microorganisms. The microbial biosensor 310 methods allow for faster detection of microorganism 610 clusters, pollen grain 630 clusters, and dust mites allergen 640 clusters.

The processing units 2742 are used for dedicated calculations of microorganism 610 count and concentration.

The microbial biosensor 310 uses particle detection methods 2500 to detect microorganisms 610 comprised as follows:

The microbial biosensor 310 detects, measures, and monitors a pathogen count, a pathogen type, a pathogen concentration, and a pathogen biosafety level in a nasal cavity 2840, an oral cavity 2890, or on a surface 3050;

The wearable device 100 smart band 200 microbial biosensor 310 is configured to detect, measure, and monitor microorganism parameters comprising:

A pathogen count, a pathogen type, a pathogen concentration, and a pathogen biosafety level in a nasal cavity 2840, an oral cavity 2890, or on a surface 3050; and wherein a set of pathogen attributes comprising: a shape, a size, a source, a cell structure, a cell component, and a chemical composition are configured for a rapid identification of an antigen to develop a vaccine and an antipathogen drug for a De Novo pathogen type. This is very useful for De Novo pathogens where timely vaccine, and/or drugs could avoid pandemics. The creation of a vaccine involves scientists, clinicians, and medical experts from around the world, and it usually requires around 10 years of research before the vaccine is made available to the public. A vaccine usually contains a part of a germ (bacteria or virus) that is called an antigen. The antigen has already been killed or disabled or multiplies without causing any harm such as mRNA before it's used to make the vaccine, so it can't make you sick. Antigens are substances, often a protein, that stimulate the body to produce an immune response to protect itself against attacks from future actual disease exposure. For example, using an mRNA blueprint, cells produce the viral protein. As part of a normal immune response, the immune system recognizes that the protein is foreign and produces specialized proteins called antibodies. In addition, vaccines contain other ingredients that make them safer and more effective, including preservatives, adjuvants, additives, and residuals of the vaccine production process. The vaccine development uses the complete pathogenic microorganism 610 information comprising microorganism data 2110 and microorganism database 2120 to make vaccine using a) Weaken the pathogen—The artificial intelligence simulation allows for candidate weakened pathogen, so they develop poorly once inside the body. The vaccine viruses replicate well enough to induce "memory B cells" and increase IgG and IgM antibodies that protect against infection in the future; b) Inactivate the pathogen—The artificial intelligence simulation uses chemicals that can be used to inactive the pathogen. The pathogen is completely inactivated (or killed) with a chemical so that it cannot reproduce itself or cause disease, but the pathogen is still "seen" by the body, cells of the immune system that protect against disease are generated; c) Use part of the pathogen— The artificial intelligence simulation determines the one part of the pathogen that should be removed and used as a vaccine; and d) mRNA vaccines— The artificial intelligence simulation determines the mRNA code or blue print for the spike protein of the pathogen. Once the immune system realizes this protein is "foreign," it creates an immune response against it, including immunologic memory, so the next time, the person is exposed to the pathogen, the immune system is ready to respond rapidly. Once the candidate vaccines are short listed the animal and human clinical trials are started resulting in accelerated development of vaccine.

The specific vaccine or drug ingredients can be like pathogen cell ingredients. The development of antipathogen drug therapies requires a fundamental understanding of the chemical biology of the virus and in particular its interaction with the host cell. As obligate parasites, all viruses are dependent on the cellular processes of their host cells and as such, share the basic features of their infectious lifecycle. The availability of complete pathogen structure and chemical composition information through microbial biosensor 310, and particulate matter sensor 320 accelerates the development of a drug to inactivate a pathogen. The vaccine and drug development also uses the existing databases for example, vaccine databases are DNAVaxDB and VaximmutorDB. The drug databases are sites where information about drugs and medications are stored, and one of the largest and most used drug databases is compiled by the Food & Drug Administration (FDA). The other commonly used databases are ChEMBL, ADME, and so on. The candidate pathogen drugs are in the form of tablets, capsules, liquids, creams, and ointments. The artificial intelligence simulation finds the best drug form containing active pharmaceutical ingredients that can kill the pathogen by attacking the wall or coating surrounding the pathogen, interfering with pathogen reproduction, or blocking protein production in pathogen. Candidate simulated drugs ingredients are made through a series of artificial chemical reactions that produce the substance used in the medication to treat pathogen infection. For example, common antibiotic drugs like amoxicillin and penicillin come from fungus, others have active ingredients as bacitracin, neomycin, or polymyxin and so on. Again, just like vaccine development, once the candidate drugs are short listed, animal, and human clinical trials are started resulting in accelerated development of drug.

The microbial biosensor 310 is also configured to detect, measure, and monitor a set of microorganism parameters comprising a beneficial microorganism count, a beneficial microorganism type, and a beneficial microorganism concentration in the nasal cavity 2840, oral cavity 2890, or on the surface 3050 which are configured to output a probiotic intake. The beneficial microorganism plays a very important role in health by helping control digestion and benefiting the immune system and many other aspects of health. An imbalance of unhealthy microorganisms in the intestines may contribute to weight gain, high blood sugar, high cholesterol, and other disorders. The beneficial microorganism stimulates the immune system, breaks down potentially toxic food compounds, and synthesizes certain vitamins and amino acids. Probiotics are microorganisms introduced into the body for their beneficial qualities. Probiotics are a combination of beneficial bacteria and/or yeasts that naturally live in the human body. Probiotics can help prevent or treat diarrhea caused by infections or antibiotics, probiotics can improve symptoms of irritable bowel syndrome, probiotics can boost the immune system, and probiotics can reduce inflammation and allergies. The intake can be in the form of amount of food, air, or another substance taken into the body. The microbial biosensor 310, particulate matter sensor 320, and lifestyle sensor 396 parameter results value are used to calculate the probiotic intake required. In addition, gut bacteria clinical result information is used if it is available as part of input calculation. Probiotic intake is calculated and expressed in colony-forming units (C.F.U.s). This allows user 8710 to know microorganism strain ingredients, daily value intake already taken, and associated benefits in the form of healthy digestive balance, nutrient absorption, reduce allergies, prevent diarrhea, ease vaginal infections, prevent autoimmune diseases, ease skin ailments, fend off urinary infections, and so on.

The microbial biosensor 310 comprises a transmitter 312, a receiver 314, a sterilizer 316, a picocamera 318, and a microbial biosensor power button 319. The microbial biosensor 310 uses particle detection methods 2500 to detect microorganisms 610.

The sterilizer 316 is configured to kill the pathogen type or pathogenic microorganism 610 enabling faster recovery from a disease to prevent spread of the pathogen type. The method used to kill or sterilize the microorganisms 610 can be heat, radiation, acoustic waves, ultrasound, ultraviolet light, infrared light, wavelength of specific frequency, and so on. The method used can also be cell lysis which involves breaking down of the membrane of a cell. Lysis is disintegration of a cell by rupture of the cell wall or membrane.

The set of microbial biosensor 310 parameters result comprises: a parameter name, a result value, a flag, a unit, a normal reference range, and an intelligent relationship interpretation; and wherein the intelligent relationship interpretation comprises: a symptom, a cause, and a treatment and wherein the cause and the treatment are accurately determined based on a correlated smart band sensor parameter result value when the set of microbial biosensor parameters result value falls outside the normal reference range as described in FIG. 89-94, FIG. 101, and FIG. 102. The microorganisms 610 can also be reported as positive or negative. The detailed information is also provided in the form of a pathogen safety data sheet as described in FIG. 96-99. The microorganism data 2110 and microorganism database 2120 has list of microorganism parameters detected. For example, the intelligent relationship interpretation determines the physiological sensor parameter respiratory rate 4220 irregularity accurate cause is due to correlated microbial biosensor parameter pathogenic virus 614 or correlated biokinetics sensor parameter heavy exercise 6680 result value outside of normal reference range and provide accurate treatment information in the form of antiviral drug/vaccines or slowing down the heavy exercise 6680 activity.

The set of microbial biosensor 310 parameters result is configured to predict a microbial risk level. Each microbial biosensor 310 parameter risk level is calculated based on the severity ranking, probability of occurrence ranking, and detection ranking using the parameter result value as described in risk level definition and in an example smart band sensor risk level and corrective action and preventive action table 9520. Overall microbial risk level is an average of all the individual microbial biosensor 310 parameters risk level.

A microbial risk alert is sent to the mobile healthcare application 250 of the user 8710 when the microbial risk level is above a predetermined threshold level as shown in an example smart band alert 9510. A microbial biosensor 310 parameter risk alert is also sent to the mobile healthcare application 250 of the user 8710 when the microbial biosensor 310 parameter result value is outside the normal reference range.

The microbial risk level assessment is configured to output a corrective action and a preventive action to ensure the set of microbial biosensor parameters result value as listed in the microorganism data 2110 are within normal reference range to prevent exposure and spread of the pathogen type as described in an example smart band sensor risk level and corrective action and preventive action table 9520.

A user 8710 positive result for a pandemic pathogen microorganism 610 is configured for an auto upload to a local, a state, or a national health information system for a real time tracking of a set of positive results to isolate or quarantine an infected user and allow contact tracing preventing further spread of the pandemic pathogen. The pandemic pathogen data comprises number of positive cases, deaths, and hospitalization. If the pandemic pathogen vaccine is available, the vaccination data uploaded is also tracked. The pandemic pathogen data is used for tracking and trending of a) cases, deaths, and testing; b) case and death demographic trends; c) vaccination distribution and coverage; d) vaccine effectiveness and breakthrough surveillance, e) people at increased risk; and f) variants and genomic surveillance. Contact tracing involves identifying user/people who have recently been in contact with someone diagnosed with an infectious disease especially to treat or quarantine them. When the smart band 200 microbial biosensor 310 detects pathogen, it continuously transmits the RFID data and location information of the infected user to the cloud server 8740, wherein when another user/person is close to the infected user it receives the text alert on its mobile device 8720.

The conditions that mean someone is a high-risk close contact are:

A person with pandemic pathogen in an enclosed space, such as a house, classroom, waiting room, or office.

A person in an airplane and sitting near someone with pandemic pathogen.

A healthcare worker or a person providing care to pandemic pathogen patients.

A healthcare worker coming into regular contact with pandemic pathogen specimens or samples without using personal protective equipment.

A student in proximity with other student in the class.

Pandemic pathogens (PPPs) are bacteria, viruses and other microorganisms that are likely highly transmissible and capable of wide, uncontrollable spread in human populations and highly virulent, making them likely to cause significant morbidity and/or mortality in humans. For example, SARS-CoV-2, Ebola, Nipah, Zika and so on viruses are pandemic pathogens. Currently the clinical testing laboratory must upload the positive diagnostic and screening results for pandemic pathogen SARS-CoV-2. In US Center for Disease Control and Prevention (CDC) provides guidance on uploading the laboratory data. This is very cumbersome and time consuming process. The data is not available in real time to take proactive measure to control the spread of the virus. The wearable device 100 smart band 200 has application programmer interface which enables it to connect to the health information system setup by the government and regulatory agencies. The health information system are electronic gateways with complete information regarding uploading the patient pandemic pathogen positive results. Some of the user positive report data uploaded consists of Test Result date, Device RFID Identifier, Test result for pandemic pathogen, Patient age, Patient race, Patient ethnicity, Patient sex, Patient residence zip code, Patient residence county, Date tested positive, Date tested negative. Wearable device 100 smart band 200 can be setup to send the test results at certain frequency after testing positive for pandemic pathogen for the first time or send test results when the user tests positive for the first time and when the user tests negative.

The wearable device 100 with smart band 200 microbial biosensor 310 is also intended to be used for the detection of the presence of, or exposure to, a transmissible agent that causes a life threatening disease with a high or suspected high risk of propagation. There are several factors that contribute to the risk of propagation of a pathogen within a population, namely: the direct or in-direct transmissibility (i.e., the probability of infection when there is contact between a susceptible and an infected individual). This example infectious dose and route of transmission includes aerosol, zoonosis, vector-mediated; the contact rate of infected and susceptible individuals (i.e., the number of contacts per time); and the duration of infectiousness. The example pathogens are listed in virus name, disease, status, shape, size, and nucleic acid list 1000, and bacteria name, disease, status, source, shape, size, and nucleic acid list 1300 and so on. The wearable device 100 with smart band 200 microbial biosensor 310 is also intended to be used for determining the infectious load of a life-threatening disease where monitoring is critical in the process of patient management. The wearable device 100 with smart band 200 microbial biosensor 310 is intended for detecting the presence of, or exposure to, a sexually transmitted agent (pathogen). This is done by detecting the sexually transmitted infections through vaginal, and anal cavities. The example detection includes *Chlamydia trachomatis, Haemophilus ducreyi*, Herpes simplex virus 1&2, Human papilloma virus (HPV), *Neisseria gonorrhoeae, Mycoplasma hominis, Mycoplasma genitalium, Trichomonas vaginalis, Treponema pallidum*, and *Ureaplasma urealyticum*. The wearable device 100 with smart band 200 microbial biosensor 310 is intended for detecting the presence of an infectious agent or microorganisms 610 (either the agent itself or component thereof) e.g., a prion 612, a virus 614, a bacterium 616, a fungus 618, a protist 620, protozoal infectious agents, specifically in specimens derived from cerebrospinal fluid or blood. The cerebrospinal fluid or blood specimen is smeared on top of the glass slide. The microorganism 610 is detected on top of the cerebrospinal fluid or blood specimen surface smeared on the glass slide. The microbial biosensor 310 can also be used for other openings or cavities like ear, and eyes to detect microorganisms 610 directly or taking a sample swab with smear on top of a glass slide.

FIG. 28 illustrates an example microbial biosensor infrared spectroscopy sensing working principle diagram 2810 and a microbial biosensor particle imaging working principle diagram 2850 that can be utilized to implement various embodiments.

A microbial biosensor 310 is a device that detects microorganisms 610. Microorganisms detected include both beneficial microorganisms and pathogenic microorganisms, also known as pathogens. A microbial biosensor 310 is an electronic component that utilizes optical, mass based, and acoustic sensors to detect microorganisms 610 and kill pathogens. The intended use of the microbial biosensor 310 is to detect, measure, and monitor pathogen types, concentrations, and biosafety levels, and kill pathogens in a nasal cavity 2840, an oral cavity 2890, or on a surface 3050 of the object. The microbial biosensor 310 also detects, measures, and monitors a beneficial microorganism count, a beneficial microorganism type, and a beneficial microorganism concentration in a nasal cavity 2840, an oral cavity 2890, or on a surface 3050 of the object. The microorganisms 610 detected can be prions, viruses, bacteria, fungi, protists, dust mites, and so on. The microbial biosensor 310 consists of a transmitter 312, a receiver 314, and a sterilizer 316. The transmitter 312 can transmit light energy as well as ultrasound signals. The receiver 314 can receive the reflected light and reflected ultrasound signals. The sterilizer 316 can transmit antipathogen ultraviolet energy 2818, antipathogen ultrasound energy 2858, and heat.

The microbial biosensor infrared spectroscopy working principle diagram 2810 illustrates the detection of microorganisms 610 using infrared spectroscopy 2510 and sterilization of pathogens using antipathogen ultraviolet energy 2818. The steps to detect microorganisms 610 using the infrared spectroscopy 2510 method are as follows:

a. Throw a beam of transmitted infrared light 2812 on a nasal cavity 2840.
b. Some of the infrared light is absorbed, some infrared light is transmitted in the form of transmission/absorption 2814 and remaining reflected infrared light 2816 is received by the receiver 314.
c. The % transmittance (T), % reflectance (R), and % absorbance (A) are recorded in the digital format. These numbers are unique and allow for detection of microorganisms 610 based on their chemical composition.

The pathogens or pathogenic microorganisms 610 are killed or sterilized by the safe antimicrobial sterilizer 316 of the microbial biosensor 310. The antipathogen ultraviolet energy 2818 is focused toward the area of nasal cavity 2840 where there are pathogenic microorganisms 610. The antipathogen ultraviolet energy 2818 destroys the pathogens' cell covering, protein, or nucleic acids by killing or inactivating the microorganisms 610.

The microbial biosensor particle imaging working principle diagram 2850 illustrates the detection of microorganisms 610 using particle imaging 2530 and sterilization of pathogens using antipathogen ultrasound energy 2858. The receiver 314 is configured to act as transmitter 312 in this mode. The steps to detect microorganisms 610 using the particle imaging 2530 method are as follows:

a. Irradiate a beam of transmitted excitation light 2852 and 2854 on an oral cavity 2890 with a desired and specific band of wavelengths using transmitter 312 and receiver 314.
b. Take multiple high-magnification images of microorganisms 610 using picocamera 318.
c. Analyze image and videos using image analysis working principle 2660, and microorganisms 610, pollen grains 630, and dust mite allergens 640 are detected.

The microorganisms 610 are killed or sterilized by the sterilizer 316 of the microbial biosensor 310. The high frequency antipathogen ultrasound energy 2858 is suitable for sterilization and is used for cell disruption to kill pathogenic microorganisms 610.

The microbial biosensor 310 infrared spectroscopy 2510 and particle imaging 2530 allow easy-to-use, rapid, portable, multiplexed, and cost-effective detection of microorganisms 610.

The wearable device 100 sends a pathogen biosafety alert to the mobile healthcare application 250 of the user 8710 when the pathogen biosafety level is above the predetermined threshold level in the nasal cavity 2840, oral cavity 2890, surface 3050, or in the air surrounding the user 8710.

The microbial biosensor 310 sterilizer 316 kills pathogens. When the biosafety level is still above the predetermined threshold level in the wearable device 100, the user 8710 can select appropriate sterilization methods.

FIG. 29 and FIG. 30 illustrate a microbial biosensor 310 nasal cavity test method, oral cavity test method, and a surface test method and sterilization diagrams.

FIG. 29 illustrates a microbial biosensor nasal cavity test method diagram 2910 and microbial biosensor oral cavity test method diagram 2950 that can be utilized to implement various embodiments.

A method comprising a wearable device 100 consisting of a smart band 200 and a display unit 102.

The smart band 200 comprises a microbial biosensor 310, a particulate matter sensor 320, an enviro sensor 330, a physiological sensor 390, a biofluid sensor 392, a biokinetics sensor 396, a lifestyle sensor 398, a single board computer 350, a power supply unit 380, a band fastener 202, and a set of watch adapters 204 and 206. The smart band 200 also has set of clip adapters 208 and 210 to connect to a necklace, a waistband, a belt, a headband, and so on for discreet monitoring of a set of sensor parameters.

The band fastener 202 is a mechanism that closes or secures the smart band 200. The band fastener 202 can be a magnetic lock, clip, or any other locking mechanism which secures the two sides of the smart band 200.

The display unit 102 comprises a touchscreen 104, a display unit power button 106, a crown 108, and a set of attachment slots 110 and 112.

The microbial biosensor 310 comprises a transmitter 312, a receiver 314, a sterilizer 316, a picocamera 318, and a microbial biosensor power button 319. The microbial biosensor 310 is configured to detect, measure, and monitor a pathogen count, a pathogen type, a pathogen concentration, and a pathogen biosafety level in a nasal cavity 2840, an oral cavity 2890, or on a surface 3050. The microbial biosensor 310 is also configured to detect, measure, and monitor a beneficial microorganism count, a beneficial microorganism type, and a beneficial microorganism concentration in the nasal cavity 2840, the oral cavity 2890, or on the surface 3050. The microbial biosensor 310 sterilizer 316 is configured to kill the pathogen type.

The particulate matter sensor 320 comprises a sensing cavity 322. The sensing cavity 322 is configured to detect suspended particles of picometer, nanometer, and micrometer sizes and is configured to differentiate and identify the suspended particles in the air. The particulate matter sensor 320 is configured to detect, measure, and monitor a set of particulate matter parameters in a surrounding air comprising: microorganism parameters comprising: a pathogen count, a pathogen type, a pathogen concentration, and a pathogen biosafety level; and a beneficial microorganism count, a beneficial microorganism type, and a beneficial microorganism; a pollen type, a pollen count, and a pollen allergy level; a dust mite allergen count and a dust mite allergy level; a particulate matter concentration; and an air quality index.

The enviro sensor 330 comprises a set of sensors 332-346.

The power supply unit 380 comprises a wireless charging unit 382, a battery 384, a charging port 386, and a band power button 388.

A mobile healthcare application 250 allows user to access the wearable device 100 sensor data.

The wearable device comprises a microbial biosensor nasal cavity test method, a microbial biosensor oral cavity test method, a microbial biosensor surface test method, and a particulate matter sensor test method.

The method of operating a wearable device 100 microbial biosensor nasal cavity test method diagram 2910 comprises the following steps:

1. Strap the wearable device 100 around the user wrist 2912;
2. Power on the wearable device 100 by pressing the band power button 388;
3. Power on the microbial biosensor 310 by pressing the microbial biosensor power button 319;
4. Face the microbial biosensor 310 to a nasal cavity 2840 of the user 8710;
5. Auto verify the identity of the nasal cavity 2840 of the user 8710 utilizing the picocamera of the user of the wearable device;
6. Detect a pathogen inside the nasal cavity 2840 of the user 8710 with the microbial biosensor 310;
7. Display a pathogen count, a pathogen type, a pathogen concentration, and a pathogen biosafety level on the mobile healthcare application 250;
8. Detect a beneficial microorganism inside the nasal cavity 2840 of the user 8710 with the microbial biosensor 310;
9. Display a beneficial microorganism count, a beneficial microorganism type, and a beneficial microorganism concentration on the mobile healthcare application 250;
10. Sterilize the pathogen type found by pressing and holding the microbial biosensor power button 319; and
11. Power off the microbial biosensor 310 by pressing the microbial biosensor power button 319.

The exemplary microbial biosensor nasal cavity test method diagram 2910 shows detection of microorganisms 610 in a nasal cavity 2840 using infrared spectroscopy 2510 and particle imaging 2530 methods.

The method of operating the wearable device 100 microbial biosensor oral cavity test method diagram 2950 comprises the following steps:

1. Strap the wearable device 100 around the user wrist 2912;
2. Power on the wearable device 100 by pressing the band power button 388;
3. Power on the microbial biosensor 310 by pressing the microbial biosensor power button 319;
4. Face the microbial biosensor 310 to an oral cavity 2890 of the user 8710;
5. Auto verify the identity of the oral cavity 2890 of the user 8710 utilizing the picocamera of the user of the wearable device;
6. Detect the pathogen inside the oral cavity 2890 of the user 8710 with the microbial biosensor 310;
7. Display the pathogen count, the pathogen type, the pathogen concentration, and the pathogen biosafety level on the mobile healthcare application 250;

8. Detect the beneficial microorganism inside the oral cavity 2890 of the user 8710 with the microbial biosensor 310;
9. Display a beneficial microorganism count, a beneficial microorganism type, and a beneficial microorganism concentration on the mobile healthcare application 250;
10. Sterilize the pathogen type found by pressing and holding the microbial biosensor power button 319; and
11. Power off the microbial biosensor 310 by pressing the microbial biosensor power button 319.

The exemplary microbial biosensor oral cavity test method diagram 2950 shows detection of microorganisms 610 in an oral cavity 2890 using infrared spectroscopy 2510 and particle imaging 2530 methods.

FIG. 30 illustrates a microbial biosensor surface test method diagram 3010, and surface 3050 types that can be utilized to implement various embodiments.

The method of further operating the wearable device 100 smart band 200 microbial biosensor surface test method comprises the following steps:
1. Strap the wearable device 100 around the user wrist 2912;
2. Power on the wearable device 100 by pressing the band power button 388;
3. Power on the microbial biosensor 310 by pressing the microbial biosensor power button 319;
4. Face the microbial biosensor 310 to a surface 3050;
5. Auto verify the identity of the surface 3050 utilizing the picocamera of the user of the wearable device;
6. Detect the pathogen on the surface 3050 with the microbial biosensor 310;
7. Display the pathogen count, the pathogen type, the pathogen concentration, and the pathogen biosafety level on the mobile healthcare application 250;
8. Detect the beneficial microorganism on the surface 3050 with the microbial biosensor;
9. Display the beneficial microorganism count, the beneficial microorganism type, and the beneficial microorganism concentration on the mobile healthcare application 250;
10. Sterilize the pathogen type found by pressing and holding the microbial biosensor power button 319; and
11. Power off the microbial biosensor 310 by pressing the microbial biosensor power button 319.

The example microbial biosensor surface test method diagram 3010 shows detection of microorganisms 610 on a surface 3050 using infrared spectroscopy 2510 and particle imaging 2530 methods.

The example surface 3050 types illustrate the detection of microorganisms 610 on top of the drinks 3052, food 3054, furniture 3056, clothes 3058, dining table 3060, and skin infection 3062 surfaces.

The skin infection 3062 or wound infection can be cellulitis, erysipelas, impetigo, folliculitis, furuncles, and carbuncles. The most common pathogenic microorganisms 610 found by microbial biosensor 310 in wound infections are *Staphylococcus aureus*, Coagulase-negative *Staphylococci, Enterococci*, and *Escherichia coli*. The microbial biosensor 310 also detects microorganisms 610, and particles such as small molecules, lipids, and proteins in a user 8710 sample on top of a glass slide. The user 8710 sample can be blood, urine, tissue, serum, plasma, spinal fluid, cell free DNA, and so on smeared on top of the glass slide. In this case the mobile healthcare application 250 database 8746 contains the dataset and information about particles such as small molecules, lipids, and proteins. Wearable device 100 smart band 200 is also used for the detection of the presence of, or exposure to, a transmissible agent in blood, blood components, cells, tissues, or organs, or in any of their derivatives by preparing the sample on top of the glass slide, in order to assess their suitability for transfusion, transplantation or cell administration. For example, the transmissible agent can be Hepatitis B (HBs-Ag), Hepatitis C (Anti-HCV), Human Immunodeficiency Virus 1/2 (Anti-HIV 1).

FIG. 31 is an example pollen grain diagram 3110, a pollen grain structure and components diagram 3150, a pollen structure components, function, and chemical composition list 3170, and a percent chemical composition of an air-dried pollen list 3190, according to some embodiments.

The pollen grain diagram 3110, and a pollen grain structure and components diagram 3150 show the various components and their shapes of an exemplary common ragweed pollen.

The pollen structure components, function, and chemical composition list 3170 describes the component name, its primary function, and predominant chemical composition.

The percent chemical composition of an air-dried pollen list 3190 describes primary constituents and corresponding percent of dry weight. The size of the same pollen is different with and without moisture. The pollen database 3450 has the information for the same pollen with moisture and air-dried. This allows detection of the pollen correctly.

The above structure, components, chemical composition information for each pollen grain 630 is used by the microbial biosensor 310 and particulate matter sensor 320 to detect it. Pollen grains 630 can be found on the surface of the object. The particle detection methods 2500 of particle imaging 2530, and light scattering and imaging 2570, are more suitable to detect pollen grains 630.

The existing methods of pollen grain collection and counting are cumbersome. The major types of sampling devices used for outdoor monitoring of airborne particles and aeroallergens are passive gravity slides, rotary impact, and slit suction type-volumetric spore traps. Many methods are utilized to count pollen. They fall into three major categories: counting with the human eye, electronic or laser-based particle counters, and image processing algorithms. The disadvantages are collection and counting using specialized collection devices and use of time-consuming instruments.

FIG. 32 illustrates pollen grain shapes diagram 3200, according to some embodiments.

The morphological characteristics of pollen grains are categorized into different groups such as pollen units, polarity, symmetry, shape, size, number of apertures and form, and exine stratification to allow for easy detection.

The pollen grain units can be as follows:
1. Monad 3210: The pollen grains do not remain united at maturity and are dissociated into a single pollen grain called a monad.
2. Dyad 3212: Pollen grains which are united in pairs and shed from the anthers as doubles are called dyads.
3. Tetrad 3214: Four pollen grains are united to form a tetrad. Tetrads are further categorized into different types based on their arrangement. In this case it is a Tetrahedral tetrad, where pollen grains are arranged in two different planes where three grains are in one plane, and one lies centrally over the other three, e.g., Drymis (Winteraceae), Drosera (Droseraceae), and *Rhododendron* Ericaceae).
3a. Tetragonal tetrad 3214-1: All four pollen grains are arranged in one plane, e.g., *Typha latifolia* (Typhaceae) and *Hedycaria arborea* (Monimiaceae).

3b. Decussate tetrad 3124-2: Pairwise, the pollen grains are at right angles to each other, e.g., *Magnolia grandiflora* (Magnoliaceae).

3c. Rhombohedral tetrad 3214-3: All pollen grains are arranged in one plane forming a rhomboidal shape, e.g., *Annona muricata* (Annonaceae).

3d. T-shaped tetrad 3214-4: The first division of the pollen mother cell is transverse to form a dyad. The upper or lower cell of the dyad undergoes a vertical or longitudinal division instead of transverse, yielding either a straight or inverted T-shaped configuration, e.g., *Aristolochia* sp. (Aristolochiaceae), and *Polyanthes* sp. (Amaryllidaceae).

3e. Linear tetrad 3214-5: The first division of the pollen mother cell is transverse, and a dyad is formed. Each cell of the dyad again divides transversely to form a linear tetrad, e.g., *Mimosa pudica*.

3f. Crypto tetrad 3214-6: Tetrads are formed without partition walls between the four compartments. One out of the four nuclei develops normally and the other three obliterate, e.g., Cyperaceae.

4. Polyads 3216: Each of the tetrad cells divides once or twice or more, yielding a group of 8 to 64 cells which remain together after maturity. These compound grains are usually held together in small units and are called polyads, e.g., *Acacia auriculiformis, Adenanthera pavonina, Calliandra hematocephalla, Samania saman*, and *Albizzia lebbeck*.

5. Pollinia 3218: The whole contents of an anther or anther locule which shed as one united mass of pollen are called Pollinia, e.g., *Calotropis* sp., *Daemia* sp., etc., of the Asclepiadaceae and majority of the family Orchidaceae.

One of the other distinguishing characteristics of pollen grains is number of apertures. It can be single grains without apertures 3230, single grains with furrows 3240, or single grains with apertures 3250. There can be one to many apertures in case of single grains with apertures 3250.

The above pollen unit and number of apertures information is stored in the pollen database 3450 and allows for correct pollen detection.

FIG. 33 is an example pollen type source, name, disease, shape, and size list 3300, and a pollen attributes and biosensor detector list 3390, according to some embodiments.

The pollen type source, name, disease, shape, and size list 3300, and the pollen attributes and biosensor detector list 3390 are used by the microbial biosensor 310 and particulate matter sensor 320 to detect pollen. The pollen safety data sheet in FIG. 99 information is derived from this data.

FIG. 34 is an example pollen tree taxonomy 3410, pollen data 3430, and a pollen database 3450, according to some embodiments.

The pollen tree taxonomy 3410 allows for classifying new pollen trees or reclassifying existing ones.

Palynology is study of pollen grains and other spores, especially as found in archaeological or geological deposits. It can be used to reconstruct past vegetation (land plants) and marine and freshwater phytoplankton communities.

The pollen data 3430 consists of allergens of pollen, pollen allergy, pollen grain and associated allergies, pollen safety data sheet, attributes, and unique identifiers information.

The pollen database 3450 comprises Pollen Table 3452, Pollen Platform Dataset Table 3454, Pollen Tree Taxonomy, Pollen Allergy, Annotation, Pollen Safety Data Sheet Table 3456, and Pollen Attributes and Unique Identifiers 3458.

The wearable device 100 uses the data in the pollen database 3450 to display pollen type and associated information.

FIG. 35 and FIG. 36 illustrate how an example particulate matter sensor 320 operates, detects, measures, and monitors a set of suspended particles in the surrounding air near the user 8710.

FIG. 35 illustrates an example particulate matter sensor pinout 3510 and a particulate matter sensor wiring table 3550 describing the hardware wiring connection steps of a particulate matter sensor pinout 3510 connected to the single board computer 350 general purpose input output pinout 370 that can be utilized to implement various embodiments.

The particulate matter sensor 320 implements, operates, detects, measures, and monitors a set of suspended particles in the surrounding air per the following procedure:

1. Log in to the single board computer 350 operating software and access general purpose input output pinout 370 settings. Assign and map the general purpose input output pinout 370 to be connected to a particulate matter sensor pinout 3510. Save general purpose input output pinout 370 settings.
2. Connect the particulate matter sensor pinout 3510 to a single board computer 350 assigned general purpose input output pinout 370 as listed in the particulate matter sensor wiring table 3550. The hardware implementation of the particulate matter sensor 320 is complete after the particulate matter sensor pinout 3510 is connected to a single board computer 350 general purpose input output pinout 370.
3. Prepare the single board computer 350 operating software to communicate with the particulate matter sensor 320 by loading the general purpose input output pinout 370 software library and installing the particulate matter sensor 320 software driver.
4. Program, install, execute, and run the particulate matter sensor 320 software on the single board computer 350 operating software.

The wearable device 100 particulate matter sensor 320 is configured to detect, measure, and monitor a set of suspended particulate matter parameters using light scattering and imaging 2570 method in a surrounding air comprising:

A microorganism parameters comprising: a pathogen count, a pathogen type, a pathogen concentration, and a pathogen biosafety level; and wherein a set of pathogen attributes comprises: a shape, a size, a source, a cell structure, a cell component, a chemical composition are configured for a rapid identification of the antigen to develop a vaccine, and an antipathogen drug for the de novo pathogen type; and a beneficial microorganism count, a beneficial microorganism type, and a beneficial microorganism concentration is configured to output the probiotic intake. The beneficial microorganism in the surrounding air is inhaled through the nasal cavity 2840 and the oral cavity 2890. Since the microorganisms are in the air, the particulate matter sensor 320 beneficial microorganism parameters result is correlated microbial biosensor 320 beneficial microorganism parameters result to calculate the probiotic intake and expressed in colony-forming units (C.F.U.s). This allows user 8710 to know microorganism strain ingredients, daily value intake already taken, and associated benefits. The detailed information is also provided in the form of pathogen safety data sheet as described in FIG. 96-99.

A pollen type, a pollen count, and a pollen allergy level for a given pollen grain 630;

A dust mite allergen count and a dust mite allergy level for dust mite allergen 640;

A particulate matter concentration. The particulate matter can contain many allergens, including different types of mites, molds, animal dander, weeds, grasses, insects, trees, and shrubs which can be detected by the particulate matter sensor 320 in the form of particulate matter concentration and associated information about particulate matter type, concentration, size, and shape;

An air quality index for reporting air quality. The Air Quality Index is used to provide information about how polluted the air currently is or how polluted it is forecasted to become. The AQI measurement runs from 0 to 500 specified in the form of daily color, levels of concern, and values of index with green as satisfactory and maroon as hazardous;

Wherein the particulate matter sensor 320 comprises a sensing cavity 322 is configured to detect suspended particles of picometer, nanometer, and micrometer sizes and is configured to differentiate and identify the suspended particles in the air;

Wherein the set of particulate matter sensor 320 parameters result comprises: a parameter name, a result value, a flag, a unit, a normal reference range, and a intelligent relationship interpretation; and wherein the intelligent relationship interpretation comprises: a symptom, a cause, and a treatment when a set of particulate matter sensor parameters result value falls outside the normal reference range; For example, the intelligent relationship interpretation determines if the physiological sensor parameter respiratory rate 4220 irregularity accurate cause is due to related particulate matter sensor parameter pollen grain 630, or correlated particulate matter sensor parameter dust mite allergen 640 result value outside normal reference range and provide accurate treatment information in the form of antihistamine medications/nasal sprays for pollen or minimizing exposure to dust mites/Corticosteroids;

Wherein the set of particulate matter sensor 320 parameters result is configured to predict a set of airborne particle risk levels comprising: a pathogen biosafety risk level, a pollen allergy risk level, a dust mite allergy risk level, and a particulate matter risk level. Each particulate matter sensor 320 parameter risk level is calculated based on the severity ranking, probability of occurrence ranking, and detection ranking using the parameter result value as described in risk level definition and in an example smart band sensor risk level and corrective action and preventive action table 9520. Overall particulate matter risk level is an average of all the individual particulate matter sensor 320 parameters risk level;

Wherein the set of airborne particle risk alerts above a predetermined threshold level is configured to send a set of airborne particle risk alerts to the mobile healthcare application 250 of the user 8710 as shown in an example smart band alert 9510. A particulate matter sensor 320 parameter risk alert is also sent to the mobile healthcare application 250 of the user 8710 when the particulate matter sensor 320 parameter result value is outside the normal reference range;

Wherein the set of airborne particles risk level assessment are configured to output a corrective action and a preventive action to ensure the set of particulate matter sensor parameters result value as listed in the microorganism data 2110, pollen data 3430, dust mite allergen 640, particulate matter and so on are within normal reference range to prevent exposure to a set of harmful suspended particles in the surrounding air as described in an example smart band sensor risk level and corrective action and preventive action table 9520;

When the pathogen biosafety level is above a predetermined threshold level in the surrounding air for the pandemic pathogen is configured to send a neighborhood public biosafety alert to a set of resident mobile devices within a specified distance of the wearable device 100 of the user 8710 to avoid a location wherein the pandemic pathogen was detected to prevent aerosol transmission and spread of the pandemic pathogen. The alert can be in the form of the text, email, recorded audio message or video message. Usually, the predetermined threshold is greater than 2 because the pandemic pathogen in the BSL-3 and BSL-4 category are highly transmissible. The residents receiving the neighborhood public biosafety alert can avoid visiting the geographic location which contains very large cluster of pandemic pathogens preventing spread of the pandemic pathogen.

FIG. 36 illustrates an example particulate matter sensor working principle block diagram 3610 and an air quality index level of concern table 3680 that can be utilized to implement various embodiments.

The particulate matter sensor 320 uses a light scattering and imaging 2570 detection method. The working principle functioning is as follows:

The intended use of the particulate matter sensor 320 is to detect, measure, and monitor the air quality index value surrounding the user 8710 and can be used to provide level of health concern information to the user 8710. The particulate matter sensor working principle block diagram 3610 uses a laser scattering principle which is part of sensing cavity 322. The laser scattering principle used for such sensor produces scattering by using a laser source 3612 to produce a laser beam 3614 to radiate suspending particles in the air 3616 entering through an air channel 3618, passing through the light scattering measuring cavity 3620, and then collecting scattering light in a certain degree, and finally obtaining the curve of scattering light change with time. The raw electric signal 3622 is amplified when it passes through a filter amplifier circuit 3624. In the end, the filtered electric signal 3626 is processed by an on-chip microprocessor 3628. Equivalent particle diameter and the number of particles with different diameters per unit volume can be calculated by the on-chip microprocessor 3628 based on the MIE theory of absorption and scattering of plane electromagnetic waves by uniform isotropic particles of the simplest form. MIE theory is an analytical solution of Maxwell's equations for the scattering of electromagnetic radiation by particles of any size. The output digital signal 3630 is the quality and number of each particle with different size per unit volume. The unit volume of the particle number is 0.1 L, and the unit of mass concentration is $\mu g/m^3$. The sensing cavity 322 can detect picometer, nanometer, and micrometer particle size and ensures the differentiation and identification of the suspended particles in the air in terms of pathogens, beneficial microorganisms, pollen, dust mite allergen, dust, and so on.

The particulate matter sensor 320 sensing cavity 322 can detect and differentiate the microorganisms 610. The imaging system 3660 uses the microbial biosensor 310 hardware. The step of imaging uses particle imaging 2530 detection method principles. The imaging system 3660 consists of light scattering and imaging 2570 system components such as microbial biosensor 310 and picocamera 318. The imaging system 3660 is responsible for taking images and videos of the particles 3650 passing through the imaging cavity 3662 when they are in front of special darkfield photographic plate. The microorganisms 610 are classified based on cell structure, cell wall, or on differences in cell components such as DNA, RNA, fatty acids, pigments, antigens, and quinones, and classifies pollen grains 630 and dust mite allergens 640 using image analysis working principle 2660. This particulate matter sensor 320 detects the pathogen count, the pathogen type, the pathogen concentration, and the pathogen biosafety level. The particulate matter sensor 320 also detects, measures, and monitors the beneficial microorganisms count, beneficial microorganism type, and beneficial microorganism concentration in the surrounding air. The wearable device 100 is programmed and contains microorganism database 2120 which includes microorganisms' 610 unique identifiers associated with particulate matter sensor 320 particle detection methods 2500 of light scattering and imaging 2570.

An air quality index (AQI) is used by government agencies to communicate to the public how polluted the air currently is or how polluted it is forecast to become. Public health risks increase as the AQI rises. The air quality index level of concern table 2450 lists the AQI color, levels of concern, values of the index, and corresponding different level of health concern. The description of the air quality also provides information about what kind of personal protective equipment (PPE) is required while handling waste. The air quality index data obtained through the particulate matter sensor 320 can be further augmented by the Environmental Protection Agency AirNow Application Program Interface (API), which allows for access to real-time data and forecasts.

The neighborhood public biosafety alert can also be a text alert sent to a nearby user's 8710 mobile healthcare application 250 when the biosafety level, for instance, is equal to 3 and above, indicating that there is pathogenic air nearby which can result in disease outbreak. These pathogens may spread through a person, or the air breathed can be loaded with pathogens. The text alert can recommend user 8710 evacuate or stay indoors, and so on. Common pathogenic bacteria found in the air in and around the home are *Staphylococcus, Pseudomonas*, Parasitic *Bacillus*, and *Francisella tularensis*, a naturally occurring bacterium that causes tularemia, also known as rabbit fever, in harmful amounts. Many common viral infections can spread by airborne transmission at least in some cases, including but not limited to COVID-19, Measles Morbillivirus, Chickenpox Virus, *Mycobacterium Tuberculosis*, Influenza Virus, Enterovirus, and Norovirus. Airborne fungi are also responsible for many fungal infections in humans. Some of the infectious fungi are *Aspergillus fumigatus, Blastomyces dermatitidis, Cryptococcus neoformans, Histoplasma capsulatum*, and so on.

It is possible to integrate the neighborhood public biosafety alert and have a neighborhood public biosafety alert sent to mobile devices of all nearby residents in the form of public safety alerts to alert the nearby residents quickly and effectively to critical and serious emergencies.

The particulate matter sensor 320 parameters result is displayed on the mobile healthcare application 250 as shown in the figures FIG. 89, FIG. 90, FIG. 91, and FIG. 92.

A particulate matter sensor test method comprises the following steps:

1. Air 3616 enters the air channel part of a sensing cavity 322;
2. A laser source 3612 containing a laser beam 3614 radiates particles in the air 3616 entering through an air channel 3618, passing through a light scattering measuring cavity 3620;
3. Calculate a particle diameter and a number of particles with different diameters per unit volume;
4. Air 3616 then flows through an imaging cavity 3662;
5. An imaging system 3660 captures images and videos of the particles passing through the imaging cavity 3662;
6. Differentiate and identify air particles using an image analysis working principle 2660;
7. Detect a pathogen count, a pathogen type, a pathogen concentration, and a pathogen biosafety level;
8. Detect a beneficial microorganism count, a beneficial microorganism type, and a beneficial microorganism concentration;
9. Detect a pollen type, a pollen count, and a pollen allergy level;
10. Detect a dust mite allergen count and a dust mite allergy level;
11. Detect a particulate matter concentration;
12. Calculate an air quality index; AQI is calculated by taking either the 24-hour concentration average from midnight to midnight and converting to AQI or a real time value. It is user configurable. It can be either based on standard Environmental Protection Agency (EPA) such as ozone, PM2.5, PM10, CO, NO2, and SO2 or can include pathogen, smoke, gas, and so on.
13. Display the pathogen count, the pathogen type, the pathogen concentration, and the pathogen biosafety level on the mobile healthcare application;
14. Display the beneficial microorganism count, the beneficial microorganism type, and the beneficial microorganism concentration on the mobile healthcare application;
15. Display the pollen type, the pollen count, and the pollen allergy level on the mobile healthcare application;
16. Display the dust mite allergen count and the dust mite allergy level on the mobile healthcare application;
17. Auto sterilize the pathogen type in the air after it passes through the imaging cavity 3662; The serialization is achieved by the MEMS miniature PMS sterilizer 3664 using heat, ultraviolet light, wavelengths of certain type, and acoustic waves to lyse and kill pathogenic microorganisms 610. The method used to kill or sterilize the microorganisms 610 can be heat, radiation, acoustic waves, ultrasound, ultraviolet light, infrared light, wavelength of specific frequency, and so on. The method used can also be cell lysis which involves breaking down of the membrane of a cell. Lysis is disintegration of a cell by rupture of the cell wall or membrane.
18. Send a neighborhood public biosafety alert 4310 to the wearable device 100 when the pathogen biosafety level is above a predetermined threshold level, indicating that there is a pathogen in the surrounding air at a location which can result in disease outbreak; and
19. Display a corrective and a preventive measure on the mobile healthcare application 250 to reduce exposure to the pathogen type. The corrective action can be in the form of wearing cotton mask, cloth mask, N95 mask, and PPE. The preventive actions can be to avoid going to the location containing pathogenic microorganisms 610.

FIG. 37 is an example single board computer 350 and enviro sensor circuit block diagram 3710, enviro sensor wiring table 3750, and enviro parameters detected 3790, according to some embodiments.

The enviro sensor 330 implements, operates, detects, measures, and monitors and measures environmental conditions surrounding the user 8710 as per the following procedure:

1. Log in to the single board computer 350 operating software and access general purpose input output pinout 370 settings. Assign and map the general purpose input output pinout 370 to be connected to an enviro pinout cable 348. Save general purpose input output pinout 370 settings.
2. Connect the enviro pinout cable 348 to a single board computer 350 assigned general purpose input output pinout 370 as listed in the enviro sensor wiring table 3750. The hardware implementation of the enviro sensor 330 is complete after the enviro pinout cable 348 is connected to a single board computer 350 general purpose input output pinout 370.
3. Prepare the single board computer 350 operating software to communicate with the enviro sensor 330 by loading the general purpose input output pinout 370 software library and installing the enviro sensor 330 software driver.
4. Program, install, execute, and run the enviro sensor 330 software on the single board computer 350 operating software.

The wearable device 100 smart band 200 enviro sensor 330 is configured to detect, monitor, and measure surrounding environmental conditions, comprising:

An RFID tag sensor 332 configured to detect, measure, and monitor RFID tag digital data;
A location sensor 334 configured to detect, measure, and monitor a geospatial position and an altitude;
An ambient light sensor 336 configured to detect, measure, and monitor an ambient light level;
A gas sensor 338 configured to detect, measure, and monitor a gas type;
A smoke sensor 340 configured to detect, measure, and monitor a smoke level;
A temperature, humidity, and pressure sensor 342 configured to detect, measure, and monitor a temperature, a humidity, and a pressure;
A sound sensor 344 configured to detect, measure, and monitor a sound level;
An ultraviolet light sensor 346 configured to detect, measure, and monitor an ultraviolet index;
A cosmic ray sensor 347-1 configured to detect, measure, and monitor a cosmic particle;
A solar flare sensor 347-2 configured to detect, measure, and monitor a solar electromagnetic radiation;
An ozone sensor 347-3 configured to detect, measure, and monitor an ozone concentration;
A climate change sensor 347-4 configured to detect, measure, and monitor a climate change index; and wherein the climate change index is configured for detection of an effect of an extreme weather event and a preventive measure to reduce a set of greenhouse gases and use of renewable energy; The set of greenhouse gases are carbon dioxide ($CO_2$), methane ($CH_4$), nitrous oxide ($NO_2$), and industrial gases like Hydrofluorocarbons (HFCs) Perfluorocarbons (PFCs) Sulfur hexafluoride ($SF_6$) Nitrogen trifluoride ($NF_3$), Chrolofluorocarbon-12 and so on. The other preventive is putting a price on carbon emissions, end to fossil fuel subsidies, increase energy efficiency and use of renewable energy, implement climate-smart agriculture and nurture forest landscapes. The list of renewable energy is solar energy, wind energy, hydropower energy, geothermal energy, and bioenergy or biomass energy.

Wherein the set of enviro sensor 330 parameters result comprises: a parameter name, a result value, a flag, a unit, a normal reference range, and a intelligent relationship interpretation; and wherein the intelligent relationship interpretation comprises: a symptom, a cause, and a treatment when a set of enviro sensor parameters result value falls outside a normal reference range; and wherein the cause and the treatment are accurately determined based on the correlated smart band sensor parameter result value;

Wherein an enviro sensor 330 parameter intelligent relationship interpretation is associated with the microorganism parameter, the particulate matter parameter, the physiological parameter, the biofluid parameter, the biokinetics parameter, and the lifestyle parameter; For example, the intelligent relationship interpretation determines accurate cause of the biofluid sensor parameter low platelet 5026 count is due to correlated enviro sensor parameter low ambient temperature or related enviro sensor parameter high altitude result value outside of normal reference range and provide accurate treatment information in the form of moving to comfortable 15 to 25 degree C. or moving to low altitude to ensure that platelet 5026 count is in the normal reference range;

Wherein the set of enviro sensor 330 parameters result is configured to predict an enviro risk level. Each enviro sensor 330 parameter risk level is calculated based on the severity ranking, probability of occurrence ranking, and detection ranking using the parameter result value as described in risk level definition and in an example smart band sensor risk level and corrective action and preventive action table 9520. Overall enviro risk level is an average of all the individual enviro sensor 330 parameters risk level;

Wherein an enviro risk level above a predetermined threshold level is configured to send an enviro risk alert to the mobile healthcare application 250 of the user 8710 as shown in an example smart band alert 9510; and Wherein the enviro risk level assessment is configured to output a corrective action and a preventive action to ensure the set of enviro sensor parameters result value as listed in enviro parameters detected 3790 are within normal reference range to prevent exposure to an environmental parameter that affect health, and to improve an environmental wellness dimension ranking as described in an example smart band sensor risk level and corrective action and preventive action table 9520.

The artificial intelligence algorithms are used to predict and forecast risks. The input data used is hourly, daily, monthly, and yearly microbial biosensor 310, particulate matter sensor 320, and enviro sensor 330 parameters result.

The wearable device 100 single board computer 350 comprises:
an accelerometer 356 sensor to detect, measure, and monitor a tilt position;
a gyroscope 358 sensor intended to detect an orientation;
The tilt position and the orientation enable the microbial biosensor 310 to face and align to the nasal cavity 2840, oral cavity 2890, or surface 3050.

The detailed implementation, operation, detection, measurement, and monitoring, and working principle for each of the sensors is as follows:

The RFID tag sensor 332 working principle functioning is as follows:

The intended use of the RFID tag sensor 332 is to detect and send an RFID tag digital data value of the wearable device 100. An RFID or radio frequency identification system consists of two main components, an RFID tag attached to an object to be identified, and a transceiver, also known as reader and writer. A reader and writer consist of a radio frequency module and an antenna which generates a high frequency electromagnetic field. On the other hand, the RFID tag is usually a passive device, meaning it does not contain a battery. Instead, it contains a microchip that stores and processes information, and an antenna to receive and transmit a signal. To read the information encoded on the RFID tag, it is placed near the reader and writer but does not need to be within direct line-of-sight of the reader and writer. A reader generates an electromagnetic field original radio signal which causes electrons to move through the RFID tag's antenna and subsequently power the chip. The powered chip inside the RFID tag then responds by sending its stored RFID tag digital data value information back to the reader and writer in the form of another reflected radio signal. This is called backscatter. The backscatter, or change in the electromagnetic radio frequency wave, is detected, and interpreted by the reader and writer, which then sends the RFID tag digital data value out to the mobile healthcare application 250 and cloud server 8740.

The RFID tag sensor 332 operation involves reading digital data of the wearable device 100 RFID tag. The wearable device 100 also contains Universal Device Identifier (UDI) information. The wearable device's 100 information is read by the reader and writer. The RFID tag digital data value is stored in the secure digital card 360 of the single board computer 350.

The ambient light sensor 336 working principle functioning is as follows:

The intended use of the ambient light sensor 336 is to detect, measure, and monitor ambient light surrounding the user 8710 to reduce power consumption and increase wearable device 100 battery life. Ambient light sensors are silicon monolithic circuits with an integrated light-sensitive semiconductor photodiode—a PN junction which converts light into an electrical signal. Light is necessary for the sense of sight. Light is a form of electromagnetic radiation. It carries energy in the form of small energy packets called photons. The energy in the photon is transferred to the objects when they come into contact with it. This characteristic of light is used in designing sensors that can detect light. These sensors, known as ambient light sensors, absorb the energy from light and change it into electricity with the help of the photoelectric effect. The electricity produced will be proportional to the intensity of light which falls on the sensor and sensor material.

Ambient light sensor ICs have an output current proportional to light (current sourcing) and can have a measurement range of 0 to ~65,535 lux. The ambient light sensor classification range is 0-100 (dark), 101-1,000 (dim), 1,001-10,000 (overcast), 10,001-25,000 (daylight), and 25,001-65,535 (sunlight).

The wearable device 100 is in an inactive energy saving mode if the ambient light level value 620 based on illuminance surrounding the user 8710 is dim or dark.

Ambient light sensor 336 information is used to conserve the battery during the night and/or other period of inactive use of the wearable device 100. For example, wearable device 100 sensor arrangements and the single board computer 350 can be set in a low-energy sleep mode during the night using the ambient light sensor 336.

The location sensor 334 GPS operating principle functioning is as follows:

The intended use of the location sensor 334 is to determine the geospatial location and altitude of the wearable device 100 and can provide internet access to the wearable device 100. The location sensor 334 consists of two components, a GPS receiver and cellular adapter.

The GPS receiver operating principle is based on the global positioning system. The global positioning system is a satellite navigation system that provides location and time information in all climate conditions to the user.

GPS consists of three segments, the GPS satellites space segment, control segment, and user segment.

The GPS space segment consists of at least 24 satellites circling the Earth every 12 hours at about 12,000 miles in altitude. The GPS space segment is formed by a satellite constellation with at least four simultaneous satellites in view from any point on the Earth's surface at any time.

The GPS control segment includes a master control station, an alternate master control station, 12 command and control antennas, and 16 monitor stations outfitted with atomic clocks that are spread around the globe to correct any abnormalities and send back to the GPS satellites through ground antennas.

The GPS user segment comprises the GPS receiver, which receives the signals from the GPS satellites and detects how far away they are from each satellite.

The temperature, humidity, and pressure sensor 342 operating principle functioning is as follows:

The temperature, humidity, and pressure sensor 342 consists of three components: a temperature sensing element, a humidity sensing element, and a pressure sensing element.

The intended use of the temperature sensor is to detect, measure, and monitor temperature value surrounding the user 8710. The temperature sensing element working principle is based on using a diode as a temperature sensor. The functioning consists of a constant current/applied across the junction of the diode, and output voltage V is proportional to the temperature. The voltage V change across a diode or PN junction can be used with a lookup table or an equation to calculate a temperature for any given diode voltage. The MEMS semiconductor temperature sensors are based on these fundamental temperature and current characteristics of the bipolar transistor or diode. The sensor has high degree of linearity and simple calibration.

Microorganisms 610 can also be classified according to the range of temperature at which they can grow. The growth rates are the highest at the optimum growth temperature for the microorganism 610. The lowest temperature at which the organism can survive and replicate is its minimum growth temperature. The highest temperature at which growth can occur is its maximum growth temperature. High temperature can also result in deactivation of certain microorganisms 610. Temperature of 60 degree Celsius and above kills most of the microorganisms 610. Bacteria 616 thrive in the temperature range of 4 degrees Celsius to 20 degrees Celsius. Dust mites 622 thrive in temperatures of 20 to 25 degrees Celsius. The temperature of 54 degrees Celsius and above kills dust mites 622. Pollen size and shape is different based on the amount of moisture. Higher temperature results in dried pollen. Particulate matter sensor 320 uses this information to compare the pollen size based on temperature and amount of humidity in the air. The surrounding air temperature data is used by the microbial biosensor 310, and particulate matter sensor 320 to rule out sets of microorganisms 610 which might not exist based on their temperature profile, resulting in deactivating detection of certain microorganisms 610. Microbial biosensor 310 and particulate matter sensor 320 use microorganisms' 610 temperature profile attribute information to activate or deactivate certain particle detection methods 2500.

The intended use of the humidity sensor is to detect, measure, and monitor the humidity value surrounding the user 8710. The humidity sensing element working principle is based on using a differential capacitance as a humidity sensor. The MEMS humidity sensor is a differential capacitance type that consists of a humidity sensitive polymer layer sensitive to the water vapor that is sandwiched between two electrodes and that acts as capacitor plates. The upper water vapor permeability electrode consists of a grid that allows water vapor to pass into the humidity sensitive polymer layer below, which is a backplate electrode, thus altering the capacitance between the two electrodes. The capacitance of the humidity sensing element is proportional to humidity. Many microorganisms 610 require relative humidity (RH) of 60 percent or more, though some can survive and multiply in relative humidity of >20 percent. Thus, decreasing temperature and moisture (relative humidity), creates a less hospitable environment for microorganisms to grow. Viruses 614 and bacteria 616 die off faster in higher relative humidity. In the surrounding air when the humidity is high, the viral and bacterial particles decay faster, and less viral and bacterial material remains suspended in the air, leading to reduced risk of infection. Dust mites 622 like humidity levels of 70 to 80 percent. Dust mites 622 cannot live in environments where humidity levels are below 50%. Pollen moisture content is directly proportional to the humidity in the air. Decreasing temperature and moisture (relative humidity), create a less hospitable environment for microorganisms 610 to grow. Microbial biosensor 310 and particulate matter sensor 320 use microorganisms' 610 humidity profile attribute information to activate or deactivate certain particle detection methods 2500.

The pressure sensor use is to detect, measure, and monitor a pressure value surrounding the user 8710. The pressure sensing element working principle is based on using a change in capacitance as a pressure sensor. The MEMS technology allows a small and flexible structure in the form of a capacitive sensor. It contains an original diaphragm that is formed through one capacitive plate that is in contact with the atmosphere with respect to the reference backplate. The atmospheric pressure is detected through how much the original diaphragm is deformed due to resulting pressure. The higher the atmospheric pressure, the more the deformed diaphragm moves, which results in a higher barometer reading. The deformation of the diaphragm changes the spacing between the conductors and hence changes the capacitance. The deflection in the diaphragm due to change in pressure produces a change in capacitance. The capacitance change can be measured by including the sensor in a tuned circuit, which changes its frequency with changing pressure. Microorganisms 610 are killed by high hydrostatic pressure. This pressure-induced inactivation is strongly dependent on the amount of applied pressure, the temperature, and the medium. Microbial biosensor 310 and particulate matter sensor 320 use microorganisms' 610 pressure profile attribute information to activate or deactivate certain particle detection methods 2500.

The gas sensor 338 working principle functioning is as follows:

The intended use of the gas sensor 338 is to detect, measure, and monitor the gas type surrounding the user 8710. The basic principle behind metal oxide gas sensors is that the resistance of the detecting layer in the sensor changes in the presence of the target gases Reducing (RED), Oxidizing (OX), and Ammonia (NH3). The reducing and ammonia gases such as carbon monoxide or volatile organic compounds (VOC) remove some of the "insulative" oxygen species at the grain boundaries, thus causing the overall resistance to go down. Alternatively, oxidizing gases such as nitrogen dioxide add to the insulative oxygen species, causing the resistance to increase. The MEMS silicon metal oxide gas sensor is based on changes to the electrical resistance for different concentrations of varied gases.

The change in resistance is directly proportional to analog voltage. The analog voltage readings that the sensor produces are read by an analog to digital converter (ADC) and then converted into resistances.

The value of Ro is the value of resistance in clean air (or the air being compared), and the value of Rs is the value of resistance of the sensor exposed to gases. The sensor should be calibrated first by finding the value of Ro in fresh air and then using that value to find Rs using the mathematical formula:

$$\text{Resistance of sensor } (Rs)=(Vcc/VRL-1)\times RL$$

Where Vcc is the positive power supply, VRL is the output voltage of RED OUT, OX OUT, and NH3 OUT corresponding to RL variable resistance R1, R2, and R3, respectively.

Once Rs and Ro are calculated, the ratio is determined, and then using the RED sensor graph, OX sensor graph, and NH3 sensor graph, the equivalent value of parts per million (PPM) for RED, OX, and NH3 gas is calculated.

The detected gases are comprised as follows:

A reducing gas, wherein the reducing gas comprises: a carbon monoxide, an ammonia, an ethanol, a hydrogen, a methane, a propane, and an isobutane.

An oxidizing gas, wherein the oxidizing gas comprises: a nitrogen dioxide, a nitrogen oxide, and a hydrogen.

An ammonia, wherein the ammonia comprises: a hydrogen, an ethanol, an ammonia, a propane, and an isobutane.

Microbial biosensor 310 and particulate matter sensor 320 use microorganisms' 610 gas profile attribute information to activate or deactivate certain particle detection methods 2500.

The smoke sensor 340 working principle functioning is as follows:

The intended use of the smoke sensor 340 is to detect, measure, and monitor smoke surrounding the user 8710. The output voltage changes provided by the sensor changes in proportion to the concentration of smoke. The greater the smoke concentration, the higher is the output voltage, while lesser smoke concentration results in low output voltage. The smoke concentration parts per million (PPM) can be determined using the Rs/Ro V/S PPM smoke sensor graph. The value of Ro is the value of resistance in fresh or clean air (or the air which is being compared), and the value of Rs is the value of resistance of the sensor exposed to gases. The sensor should be calibrated by finding the value of Ro in clean air and then using that value to find Rs using the mathematical formula:

$$\text{Resistance of sensor}(Rs)=(Vcc/VRL-1)\times RL$$

Where Vcc is the positive power supply, VRL is the output voltage, and RL is variable resistance.

Once Rs and Ro are calculated, the ratio Rs/Ro can be determined, and using the smoke sensor graph, the corresponding equivalent value of PPM for the smoke can be calculated.

Smoke contributes to modifications of the nasal, oral, lung, and gut microbiome, leading to various diseases, such as periodontitis, asthma, chronic obstructive pulmonary disease, Crohn's disease, ulcerative colitis, and cancers. Smoke kills off the beneficial bacteria in the mouth, allowing disease-causing bacteria to flourish, resulting in a greater risk for both gum disease and tooth decay. Microbial biosensor 310 and particulate matter sensor 320 use microorganisms' 610 smoke profile attribute information to activate or deactivate certain particle detection methods 2500.

The sound sensor 344 working principle functioning is as follows:

A sound sensor is defined as a module that detects sound waves through its intensity and converts them to electrical signals. A sound sensor can be used to receive acoustic waves and display the vibration image of sound. The microphone is sensitive to sound. The microphone vibrates with the acoustic wave, resulting in the change of capacitance and the subsequent micro voltage. It responds to sound loudness the same way the human ear does. It can measure sound level along a range from 45 to 110 dB. It is ideal for measuring environmental noises and room acoustics near the user. Some audible sound frequencies, and high-power ultrasound, cause cell disruption, and particle size reduction kills microorganisms 610. The microbial biosensor 310 and particulate matter sensor 320 use microorganisms' 610 audible sound profile attribute information to activate or deactivate certain particle detection methods 2500.

The ultraviolet light sensor 346 working principle functioning is as follows:

UV radiation is present in sunlight and constitutes about 10% of the total electromagnetic radiation output from the sun. The UV region covers the wavelength range 100-400 nm and is divided into three bands: UV-A (315-400 nm), UV-B (280-315 nm), and UV-C (100-280 nm). The ultraviolet light sensor 346 outputs an analog voltage that is directly proportional to UV radiation incident on a planar surface. Not all ultraviolet light spectra kill microorganisms 610. UV-C, also known as germicidal UV, of wavelengths from 200 to 280 nm, is used to disinfect water, air, and surfaces 3050. UV-C is effective at destroying and deactivating all kinds of pathogens like viruses 614, bacteria 614, and fungus 616. Microbial biosensor 310 and particulate matter sensor 320 use microorganisms 610 ultraviolet profile attribute information to activate or deactivate certain particle detection methods 2500.

The cosmic ray sensor 347-1 working principle functioning is as follows:

A cosmic ray sensor detects high-energy-particles coming from space called cosmic rays. This typically includes photons (high-energy light), electrons, protons, and some heavier nuclei, as well as antimatter particles. A cosmic ray sensor consists of a scintillation detector, made from a scintillator material that produces a flash of light upon incident radiation, which is then observed by a light detector. Silicon photomultiplier (SiPM) is used to measure the light generated by the scintillator material. The cosmic ray sensor detects these muons. The energy of cosmic rays is usually measured in units of MeV, for mega-electron volts, or GeV, for giga-electron volts. The Earth's atmosphere and magnetic shield protect us from cosmic radiation. Earth's magnetic shield protects us from the cosmic radiation and is strongest at the equator and weakest near the poles. Cosmic rays place people near the poles, in the airplanes, and astronauts at significant risk for radiation sickness, and increased lifetime risk for cancer, alter cardiovascular system, eliminate some of the cell's linings of the blood vessels, central nervous system effects, and degenerative diseases.

The solar flare sensor 347-2 working principle functioning is as follows:

A solar flare sensor detects brief eruption of intense high-energy radiation from the sun's surface, associated with sunspots and causing electromagnetic disturbances on the earth, as with radio frequency communications and power line transmissions. Solar flares consists of MEMS magnetometers to measure the magnetic perturbations caused by coronal mass ejection (CME). Solar flares are usually not harmful to humans on the ground but do affect people flying on planes and unshielded astronauts. Solar flares classes have names: A, B, C, M, and X, with A being the tiniest and X being the largest, and the overall scale is logarithmic. Each category has nine subdivisions ranging from, e.g., C1 to C9, M1 to M9, and X1 to X9. An X-class flare is 10 times stronger than an M class and 100 times stronger than a C.

The ozone sensor 347-3 working principle functioning is as follows:

An ozone sensor 347-3 detects Ozone (O3) a highly reactive gas composed of three oxygen atoms. Ozone's unit of measurement is Dobson unit (DU). Ozone sensor 347-3 is an electrochemical (EC) sensor, where ozone gas diffuses across a porous membrane into a cell containing electrolyte and electrodes. When ozone meets the electrolyte, a change in electrochemical potential occurs between the electrodes, causing electrons to flow, which is proportional to concentration of ozone. It is both a natural and a man-made product that occurs in the Earth's upper atmosphere as well as in a localized environment, especially for users 8710 living near the poles. Ozone has two properties of interest to human health. First, it absorbs UV light, reducing human exposure to harmful UV radiation that causes skin cancer and cataracts. Second, when inhaled, it reacts chemically with many biological molecules 3814 in the respiratory tract, leading to several adverse health effects. Ozone can damage the tissues of the respiratory tract, causing inflammation and irritation, and result in symptoms such as coughing, sore or scratchy throat, chest tightness and worsening of asthma symptoms, emphysema, and chronic bronchitis. Ozone makes it more difficult to breathe deeply and vigorously and causes pain when taking a deep breath.

The climate change sensor 347-4 working principle functioning is as follows:

A climate change sensor 347-4 detects the extreme short term changes in weather patterns during a day surrounding the user 8710. Climate change sensor347-4 detects heat index and does multivariate analysis of data consisting of particulate matter sensor 320 parameters result, and enviro sensor 330 parameters result and reports out the value in the form of climate change index. In the case of user 8710 doing outdoor work, in addition, the data is augmented by temperature, sunshine hours, wind, precipitation, cyclones, hurricane, and volcanic eruptions information available from weather APIs such as OpenWeatherMap API, AccuWeather API, Dark Sky API, Air Quality API, and so on. In one of the embodiments the climate change sensor for outdoor use can measure the precipitation, and snow. Usually, the climate change refers to long-term shifts in temperatures and weather patterns. Now due to global warming, deforestation, and other factors there are extreme changes in the weather within a given day. Climate change sensor 347-4 allows for climate change during a set duration and is reported as an index in the range of 1-5. The climate change index is classified as Catastrophic=5, Critical=4, Serious=3, Minor=2, and Negligible=1.

The accelerometer 356 sensor working principle functioning is as follows:

The intended use of the accelerometer 356 sensor is to measure the movement of the wearable device 100 when the wearable device 100 is moved and can be used to set the waste fill level status to zero.

The wearable device 100 accelerometer 356 sensor measures the movement of the wearable device 100, and when the wearable device 100 is faced in front of nasal cavity 2840, oral cavity 2890, or surface 3050, the inclination angle can be used to center it and check for nose ID, face ID, and surface ID.

An example schematic representation of a single board computer 350 containing hardware, peripheral interfaces, and general purpose input output pinout 370 layouts can be utilized to connect to sensors and power supply unit 380.

The example wearable device 100 single board computer 350 computing system can be configured to perform any one of the processes provided herein. In this context, the wearable device 100 single board computer 350 or SBC 350 may include, for example, a system on chip (SOC) 352 consisting of a central processing unit (CPU)/graphical processing unit (GPU), a random-access memory (RAM) 354, an accelerometer 356 sensor, a gyroscope 358, a secure digital card 360, a display DSI port 362, a Wi-Fi Bluetooth 364, a microphone and speaker 366, and a camera CSI port 368. It can also contain a universal serial bus, an audio port, and a high-definition multimedia interface. It contains a general purpose input output pinout 370 or GPIO pinout 370. The system on chip (SOC) 352, random access memory (RAM) 354, and secure digital card 360 are used to implement various microbial biosensor 310, particulate matter sensor 320, and enviro sensor 330 algorithms and methods and store data locally. General purpose input output pinout 370 or GPIO pinout 370 and other ports are used to connect to the microbial biosensor 310, particulate matter sensor 320, enviro sensor 330, power supply unit 380, and display unit 102. The display DSI port 362 can be used to connect a capacitive touchscreen to the wearable device 100 to display all the sensor data, which is usually in the form of connectors or ribbon cables. The camera CSI port 368 is used to connect to a picocamera 318 and screen for testing of the wearable device 100. The wearable device 100 single board computer 350 may include circuitry or other specialized hardware for carrying out some or all aspects of the processes. In some operational settings, a wearable device 100 single board computer 350 may be configured as a system that includes one or more subcomponents, each of which is configured to carry out some aspects of the processes either in software, hardware, or some combination thereof.

The wearable device 100 single board computer 350 can communicate with other computing devices based on various computer communication protocols such a Wi-Fi, a Bluetooth (and/or other standards for exchanging data over short distances including those using short-wavelength radio transmissions), a USB, an ethernet, a cellular network, an ultrasonic local area communication protocol, and so on.

Figure 38:
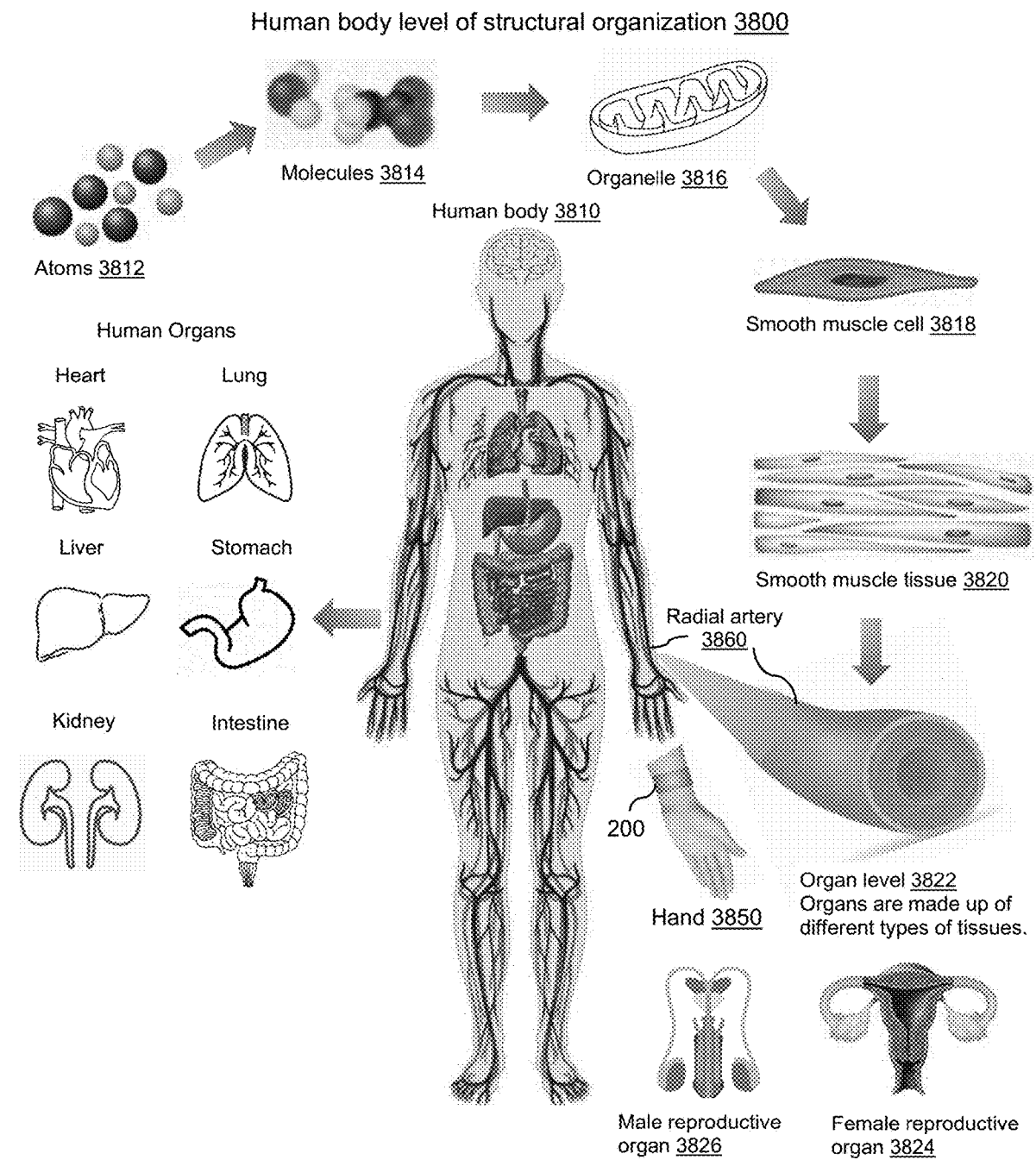
FIG. 38 illustrates a human body level of structural organization according to some embodiments.

FIG. 38 illustrates a human body level of structural organization 3800, according to some embodiments.

The human body has many levels of structural organization. The basic and simplest level of structural hierarchy is the chemical level. At this level atoms 3812, tiny building blocks of matter, combine to form molecules 3814 such as water, serum, metabolites, and proteins. Molecules 3814, in turn, associate in specific ways to form organelles 3816 that are the basic components of cells. Cells are the smallest units of living things. All cells share some common functions, but individual cells vary widely in size, shape, structure, and content, reflecting their unique functions in the human body 3810. The cells can be red blood cells, white blood cells, muscle cells, skin cells, and so on. The simplest living creatures are single cells, but in complex organisms such as human body 3810, the hierarchy continues to the tissue level such as smooth muscle tissue 3820. Tissues are groups of similar cells such as smooth muscle cell 3818 that have a common function. Human body 3810 has four basic tissue types, namely epithelial tissue, muscle tissue, connective tissue 3948, and nervous tissue. An organ level 3822 is a discrete structure composed of at least two tissue types, but four is more common, that perform a specific function for the human body 3810. The list of important human body 3810 organs is brain, lungs, liver, bladder, kidneys, heart, stomach, intestines, male reproductive organ 3826, and female reproductive organ 3824. At the organ level 3822, extremely complex functions become possible. Medical tests and clinical laboratory test results can help detect a condition, determine a diagnosis, plan treatment, check to see if treatment is working, or monitor the condition over time. The test can be based on finding a parameter or analyte at molecules 3014 level, and organ level 3822. A physician or doctor may order these tests as part of a routine checkup, to check for certain diseases and disorders, or to monitor health. Regular checkups can help find potential health issues before they become a problem. When a doctor sees a patient regularly, they can detect health conditions or diseases early. Early detection gives the user/patient the best chance for getting the right treatment quickly, avoiding any complications. This requires a doctor's or hospital visit and clinical laboratory test results using samples such as blood, saliva, urine, stool, and so on. There is time and cost associated with the physical examination and clinical laboratory testing at molecules 3814, and organ level 3822. The smart band 200 is used to monitor the microbial biosensor 310 parameters, particulate matter sensor 320 parameters, enviro sensor 330 parameters, physiological sensor 390 parameters, biofluid sensor 392 parameters, biokinetics sensor 396 parameters, and lifestyle sensor 398 parameters. These sensor parameters allow for a cost effective way of continuously monitoring of user/patient 8710 health.

FIG. 39 illustrates anatomy of the skin 3910, and light penetration into skin 3970, according to some embodiments.

The anatomy of the skin 3910 figure illustrates the different layers of skin. The skin is primarily made up of three layers. The upper layer is the epidermis 3920, the layer below is the dermis 3930, and the third and deepest layer is the fat layer 3940 or subcutaneous tissue. The epidermis 3920, the outermost layer of skin surface 3924, provides a waterproof barrier and contributes to skin tone. The hair 3932 and sweat 3926 come out of skin surface 3924. The skin has two types of sweat glands 3946: eccrine and apocrine. Eccrine glands occur over most of the body and open directly onto the skin surface 3924. Apocrine glands open into the hair follicle, leading to the skin surface 3924. The epidermis 3920 is the thin outer layer of the skin. It consists of 3 types of cells: a) Squamous cells: The outermost layer is continuously shed and is called the stratum corneum 3922; b)Basal cells: Basal cells are found just under the squamous cells, at the base of the epidermis 3920; c) Melanocytes 3928: Melanocytes 3928 are also found at the base of the epidermis 3920 and make melanin 3929. Melanin 3929 is a pigment that gives the skin its color. The dermis 3930 is the middle layer of the skin. The dermis 3930 contains capillaries 3942, blood vessels 3950, lymph vessels, hair follicles, sweat glands 3946, collagen bundles, fibroblasts, nerves 3944, sebaceous glands, connective tissue 3948. The dermis 3930 is held together by a protein called collagen 3934. The collagen 3934 is a protein layer that gives skin flexibility and strength. The dermis 3930 also contains pain and touch receptors. The subcutaneous fat layer 3940 is the deepest layer of skin. It consists of a network of fat cells. It helps conserve the body's heat and protects the body from injury by acting as a shock absorber.

The light penetration into the skin 3970 figure illustrates the thickness of the epidermis 3920 which is 0.1-0.3 mm, dermis 3930 which is 1-2 mm, and fat layer 3940 subcutaneous adipocytes which is 2-4 mm. The UV C, B, and A 3972 wavelength range is around 200-400 nm, visible light 3974 wavelength range is approximately 400-700 nm, and near infrared light 3976 wavelength range is around 700-2,500 nm The longer the wavelength of light, the deeper the penetration of the light into the skin. The red and near infrared (NIR) light do not cause harm to the user. One of the main properties of red and near infrared (NIR) light (between 600 nm and 900 nm) is its unique ability to penetrate through the skin farther than any other wavelengths on the "light" spectrum (from UV to Far-Infrared). The red-light (600-650) penetration ranges from 1-2 mm. The deep red to NIR (650-950) penetration ranges from 2-3 mm, and NIR (950-2,400) penetration range is more than 4 mm. The NIR light can easily reach dermis 3930 which contains capillaries 3942 and blood vessels 3950. Continuous long-term exposure to NIR can exert some biologic effects on human skin such as collagen degradation. In order to zero out any effect on the human skin and underlying tissue, the smart band 200 NIR light is targeted to detect the sensor parameters from different healthy blood vessels 3950. The sensors detection sampling time is dynamic based on the demographic information. Healthy user 8710 usually does not need continuous monitoring of the sensor parameters.

FIG. 40 illustrates an optical path of light into skin 4010, blood vessel expansion 4050, and blood vessel cross section 4070.

The optical path of light into skin 4010 figure illustrates behavior of incident light element 4012 at different layers of skin based on the thickness. Incident light element 4012 on the stratum corneum 3922 results in reflection element 4014. Part of the incident light passes through the epidermis 3920 and results in epidermal scattering element 4016, epidermal reflection element 4018, and epidermal absorption element 4020. The incident light element 4012 that reaches the blood vessels 3950 in dermis 3930 results in dermal scattering element 4022, dermal reflection element 4024, and dermal absorption element 4026, and is used to detect the physiological parameters, biofluid parameters, and so on. The optical characteristics of the stratum corneum 3922 are mainly defined by its rough surface which results in non-specular (diffuse) reflection. The scattering characteristics of the epidermis 3920 follow from interactions with large melanin 3929 aggregates. Scattering in the dermal layers results from collagen fibrils and bundles that create a combination of Mie and Rayleigh scattering. Overall scattering of the skin is dominated by the dermis 3930 because of its thickness (~4 mm). The optical noise sources such as environmental noise and motion artifacts can cause interference in detecting the smart band 200 sensor parameters. The environmental noise can be due to ambient and natural light such as variations in day or room light or high frequency noise such as pulse width or fluorescent artificial light sources. These environmental noise sources are less significant due to the high absorption of the skin and covering of the sensing area with an opaque material of the smart band 200. Motion artifacts are induced by relative motion to the sensor, is the primary source of noise. The motion artifacts are eliminated by picoprobes and the picocamera, which enables location of a healthy blood vessel 3950 for physiological parameters measurement.

Blood vessel expansion 4050 figure illustrates flow of blood direction and corresponding expansion. When the blood flows in the direction of element 4052 through the blood vessels 3950, it results in blood vessels expansion 4050 in the outward direction as shown in the element 4054 and element 4056. This results in widening of blood vessels 3950 and is called vasodilation. It results from relaxation of smooth muscle cells within the vessel walls, in the blood vessels 3950. The process is the opposite of vasoconstriction, which results in the narrowing of blood vessels 3950. The phenomenon is used to detect the blood pressure.

Blood vessel cross section 4070 illustrates components of the blood such as blood cells 5020, metabolites 5040, and lipids 5080. The blood cells 5020 further comprise RBC 5022, WBC 5024, and Platelets 5026. Smart band 200 physiological sensor 390, and biofluid sensor 392 detect these parameters. Blood vessels 3950 are channels that carry blood throughout user 8710 body. Blood vessels 3950 form a closed loop, like a circuit, that begins and ends at the user 8710 heart. Together, the heart vessels and blood vessels 3950 form the circulatory system. There are three main types of blood vessels 3950 as follows:

Arteries carry oxygen rich blood away from the user 8710 heart

Veins carry deoxygenated blood back toward the user 8710 heart

Capillaries 3942, the smallest blood vessels 3950, connect arteries and veins. Capillaries 3942 have thin walls that allow oxygen, nutrients, carbon dioxide, and waste products to pass through, to and from the tissue cells.

Blood vessels 3950 have a tube-like shape, but they rarely run in a straight line. Some like veins can be seen inside the arm, under the wrist, legs, and so on.

Blood vessels 3950 sizes diameter vary. The normal aorta in the abdomen is about 2 cm wide whereas blood vessels, such as capillaries 3942, are extremely small. Capillaries 3942 size range from 2 to 12 micrometers, which is less than the diameter of a human hair. The mean internal diameter of radial artery of an adult is around 2.3±0.4 mm. The mean internal diameter of ulnar artery of an adult is around 2.4±0.4 mm. The blood vessels 3950 size varies based on gender, age, diabetic and nondiabetic patients.

Blood vessels 3950 are made of three layers of tissue 1) Tunica intima: The inner layer surrounds the blood and keeps the blood flowing smoothly, 2) Media: The middle layer contains elastic fibers that keep user blood flowing in one direction. The media also helps vessels expand and contract, and 3) Adventitia: The outer layer contains nerves and tiny vessels that deliver oxygen and nutrients from blood to cells and helps remove waste. It also gives blood vessels 3950 their structure and support.

All the above factors are considered to find healthy blood vessels 3950 for accurate measurement of the blood parameters.

FIG. 41 illustrates an example physiological sensor pinout 4110, and a physiological sensor wiring table 4150 describing the hardware wiring connection steps of a physiological sensor pinout 4110 connected to the single board computer general purpose input output pinout 370 that can be utilized to implement various embodiments. The physiological sensors diagram 4170 illustrates different components of the physiological sensor 390.

The physiological sensor 390 operating steps are as follows:

1. Log in to the single board computer 350 operating software and access general purpose input output pinout 370 settings. Assign and map the general purpose input output pinout 370 to be connected to a physiological sensor pinout 4110. Save general purpose input output pinout 370 settings.

2. Connect the physiological sensor pinout 4110 to a single board computer 350 assigned general purpose input output pinout 370 as listed in the physiological sensor 390 wiring table 4150. The hardware implementation of the physiological sensor 390 is complete after the physiological sensor pinout 4110 is connected to a single board computer 350 general purpose input output pinout 370.

3. Prepare the single board computer 350 operating software to communicate with the physiological sensor 390 by loading the general purpose input output pinout 370 software library and installing the physiological sensor 390 software driver.

4. Program, install, execute, and run the physiological sensor 390 software on the single board computer 350 operating software. The physiological sensor 390 software is part of mobile healthcare application 250.

The physiological sensor 390 has five dedicated output channels as follows:

TMP OUT 4114—Output channel for skin temperature 4212, and body temperature 4214. The body temperature 4214 value is mathematically calculated based on skin temperature 4812.

CRD OUT 4116—Output channel for heart rate 4216, heart rate variability 4218, and respiratory rate 4220.

ECG OUT 4118—Output channel for electrocardiogram (ECG) 4222.

BP OUT 4120—Output channel for blood pressure 4224.

BGS OUT 4122—Output channel for blood gases 5010 comprising blood oxygen 5012, and blood carbon dioxide 5014.

EEG OUT 4124—Output channel for Electroencephalogram EEG 4230.

EMG OUT 4126—Output channel for elbow electromyogram (EEMG) 4232 and knee electromyogram (KEMG) 4234.

The individual dedicated channel allows for fast high throughput multiplexed detection of physiological parameters.

The physiological sensors diagram 4170 of physiological sensor 390 comprises skin temperature sensor 390A, cardiac photoplethysmography (PPG) sensor 390B, ECG sensor 390C, blood pressure sensor 390D, blood oxygen sensor 390E, and blood carbon dioxide sensor 390F.

The wearable device 100 smart band 200 physiological sensor 390 is configured to detect, measure, and monitor physiological parameters of the user 8710 and comprises:

A skin temperature sensor 390A configured to detect, measure, and monitor a skin temperature 4212, and a body temperature 4214;

A cardiac photoplethysmography (PPG) sensor 390B configured to detect, measure, and monitor a heart rate 4216, a heart rate variability 4218, and a respiratory rate 4220;

An ECG sensor 390C configured to detect, measure, and monitor a set of electrocardiogram (ECG) 4222 parameters;

A blood pressure sensor 390D configured to detect, measure, and monitor a systolic pressure 4224SP level, and a diastolic pressure 4224DP level;

A blood oxygen sensor 390E configured to detect, measure, and monitor a blood oxygen 5012 saturation level;

A blood carbon dioxide sensor 390F configured to detect, measure, and monitor a blood carbon dioxide 5014 level;

An EEG sensor 390G configured to detect, measure, and monitor a set of electroencephalogram 4230 parameters;

An EMG sensor 390H configured to detect, measure, and monitor a set of elbow electromyogram 4232 parameters, and a set of knee electromyogram 4234 parameters;

Wherein a set of picoprobes element 390BPT-390BPR and a picocamera element 390BPC is configured to output a location of a healthy blood vessel 3950 for a noninvasive in vivo measurement of the physiological parameter;

Wherein a set of physiological sensor 390 parameters result comprises: a parameter name, a result value, a flag, a unit, a normal reference range, and a intelligent relationship interpretation; and wherein an intelligent relationship interpretation comprises: a symptom, a cause, and a treatment when a set of physiological sensor parameters result value falls outside a normal reference range; and wherein a cause and a treatment are accurately determined based on a correlated smart band sensor parameter result value; For example, the intelligent relationship interpretation determines the accurate cause of the physiological sensor parameter high heart rate is due to related biofluid sensor parameter elevated WBC count or related physiological sensor parameter high blood pressure result value outside normal reference range and provide accurate treatment information in the form of hydroxyurea/anti-inflammatory medications or control high blood pressure by eating healthy, maintaining weight, and Angiotensin-converting enzyme (ACE) inhibitors.

Wherein the set of physiological sensor 390 parameters result is configured to predict a physiological risk level. Each physiological sensor 390 parameter risk level is calculated based on the severity ranking, probability of occurrence ranking, and detection ranking using the parameter result value as described in risk level definition and in an example smart band sensor risk level and corrective action and preventive action table 9520. Overall physiological risk level is an average of all the individual physiological sensor 390 parameters risk level.

Wherein a physiological risk alert above a predetermined threshold level is configured to send a physiological risk alert to the mobile healthcare application 250 of the user 8710 as shown in an example smart band alert 9510; and Wherein a physiological risk level assessment is configured to output a corrective action and a preventive action to ensure the set of physiological sensor 390 parameters result value as described in FIG. 42 are within normal reference range for a disease reduction or elimination and to improve physical wellness dimension ranking as described in an example smart band sensor risk level and corrective action and preventive action table 9520.

FIG. 42 lists physiological parameters, detection sensor, and detected normal reference ranges 4200, according to some embodiments.

The table lists physiological parameter, human anatomy, detection sensor, and normal reference ranges. The physiological parameters are used to assess the health of organs. Measurement of many of these parameters requires invasive monitoring techniques. Smart band 200 physiological sensors 390 allow for noninvasive in vivo detection. The physiological sensor 390 detected parameters comprise a skin temperature 4212, a body temperature 4214, a heart rate 4216, a heart rate variability 4218, a respiratory rate 4220, an electrocardiogram (ECG) 4222, a blood pressure 4224, blood oxygen 5012, and a blood carbon dioxide 5014. The blood pressure 4224 measurement consists of systolic blood pressure 4224SBP, and diastolic blood pressure 4224DBP.

The table lists the physiological parameter detected, human anatomy relationship, detection sensor, and normal reference ranges. The normal reference ranges listed are typical values. The normal reference ranges help describe what is typical for a particular group of people based on age, sex, and other characteristics. The normal reference ranges are automatically set based on the smart band 200 user 8710 demographics information. Smart band 200 physiological sensor 390 detects these physiological parameters.

Figure 43:
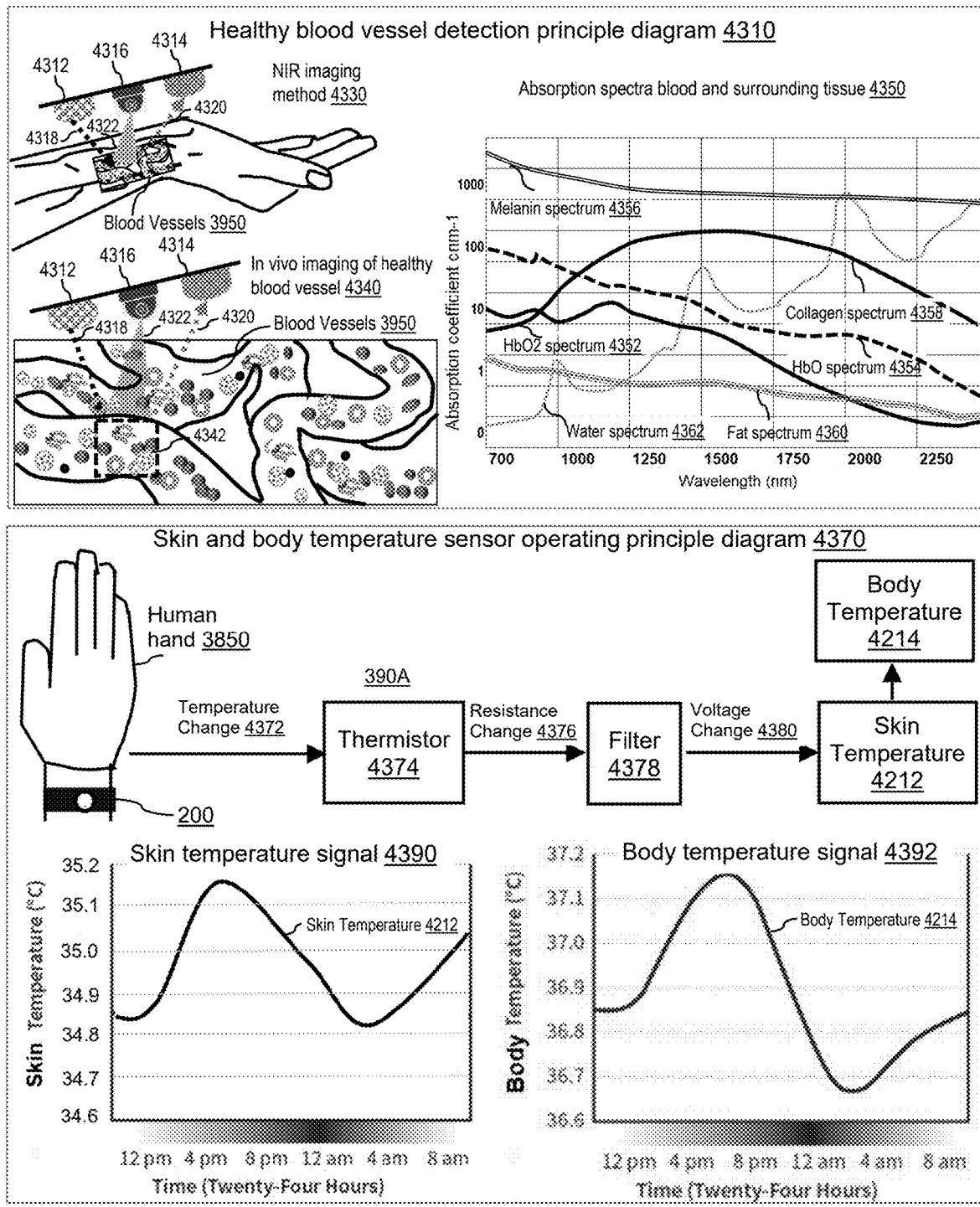
FIG. 43 illustrates a healthy blood vessel detection principle diagram, a skin and body temperature sensor operating principle diagram, skin temperature signal, and body temperature signal, according to some embodiments.

FIG. 43 illustrates a healthy blood vessel detection principle diagram 4310, a skin and body temperature sensor operating principle diagram 4370, skin temperature signal 4390, and body temperature signal 4392, according to some embodiments.

A skin temperature sensor 390A is used to detect, measure, and monitor a skin temperature 4212, and a body temperature 4214.

The healthy blood vessel detection principle diagram 4310 illustrates the detection of healthy blood vessels 3950.

The NIR imaging method 4330 illustrates a diffused reflection detection method for obtaining structural information about blood vessels 3950. The healthy blood vessel 3950 detection is based on light scattering and absorption differences between red blood cells (erythrocytes) and surrounding tissues. The difference makes it possible to visualize blood vessels 3950 under the skin using the NIR range of around 700-2500 nm. The NIR wavelengths penetration depth for melanin 3929 in epidermis 3920, collagen 3934 in dermis 3930, and fat in the fat layer 3940 is calculated based on their NIR spectrum. This allows location of the blood vessels 3950 in dermis 3930 region based on HbO2 and HbO spectrum. The method to detect the healthy blood vessel 3950 is as follows:

1) The incident light element 4318 is delivered to the tissue through picoprobe element 4312 in contact with the skin surface 3924.
2) The reflected light element 4320 from the dermal region is received by the picoprobe element 4314. The absorption spectrum of the HbO2 spectrum 4352, HbO spectrum 4354, melanin spectrum 4356, collagen spectrum 4358, fat spectrum 4360, and water spectrum 4362 are calculated. The HbO2 (oxyhemoglobin) and HbO (deoxyhemoglobin) are present in red blood cells 5022. The NIR wavelengths penetration depths of the melanin spectrum 4356, collagen spectrum 4358, fat spectrum 4360, HbO2 spectrum 4352, HbO spectrum 4354 in red blood cells 5022, and water spectrum 4362 enable exact location of the healthy blood vessels 3950. The water spectrum 4362 is also important in locating blood vessel 3950, since 55% of the whole blood contains water.
3) If the spectrum match is found, the picocamera element 4316 in NIR mode captures backscattered reflection element 4322 and image of healthy blood vessels 3950 at a calculated penetration depth. The computational algorithms allow determination of the image boundaries 4342 of healthy blood vessels 3950.

The in vivo imaging of healthy blood vessel 4340 figure illustrates the detection and imaging of the healthy blood vessels 3950. The picoprobe element 4312 transmits incident light element 4318 which moves through skin surface 3924, stratum corneum 3922, epidermis 3920, and to the blood vessels 3950 in the dermis 3930. The picoprobe element 4314 receives reflected light element 4320. Once the spectrum match is found, the picocamera element 4316 in NIR mode captures backscattered reflection element 4322 and image of blood vessels 3950. This image allows determining of the actual healthy blood vessels 3950 image boundaries 4342 for detecting physiological, biofluid, and other sensors parameters.

The smart band 200 physiological sensor 390 enables accurate detection of healthy blood vessels compared to existing smart watches, bands, and wearable devices because they do not have specialized state of art hardware and associated deep learning adaptive algorithms dedicated to detecting the healthy blood vessels 3950 for accurate measurement. There are several factors that can cause blood vessels 3950 to degrade such as age, medical condition, dry skin, and so on. Some users are genetically predisposed to having problematic blood vessels 3950, or their age causes the veins to be smaller or hidden.

A wide range of problems can affect the blood vessels 3950 as below:

Aneurysm, a bulge in a weak or damaged portion of an artery. If they rupture (break open), they may cause life-threatening internal bleeding.

Arterial diseases, including coronary artery disease, carotid artery disease, and peripheral artery disease (PAD). These diseases cause arteries to narrow, usually due to atherosclerosis.

Atherosclerosis, which is the buildup of plaque (cholesterol, fat, and other substances) inside arteries. It can also lead to a heart attack or stroke.

Blood clots, or clumps of blood that form inside veins or arteries. Clots block blood flow and can lead to deep vein thrombosis (DVT), pulmonary embolism, stroke, or occlusion of an artery.

High blood pressure, or hypertension, occurs when there's too much force against the walls of arteries.

Raynaud's disease, which causes arteries that supply blood to skin to get very narrow in response to cold temperatures.

Vascular malformations, which are abnormal clusters or connections between blood vessels. Conditions such as arteriovenous malformations are often congenital (present at birth).

Vasculitis, which is blood vessel 3950 inflammation. Blood vessel 3950 walls can thicken and narrow, which prevents blood from flowing freely In many cases it can be matter of the user 8710 being dehydrated. Smart band 200 has dedicated hardware and a deep learning algorithm to detect healthy blood vessels 3950 for accurate measurement of microbial, physiological, biofluid parameters, and so on.

The skin and body temperature sensor operating principle diagram 4370 illustrates its functioning as follows:

The user 8710 wears smart band 200 on the wrist of the human hand 3850. The temperature changes 4372 is measured by the thermistor 4374. The physiological sensor 390 consists of skin temperature sensor 390A and associated circuitry which is used to measure the skin temperature 4212 using a thermistor 4374. The thermistor 4374 is a resistance thermometer, or a resistor whose resistance is dependent on skin surface 3724 temperature. The term is a combination of "thermal" and "resistor." It is made of metallic oxides, pressed into a bead, disk, or cylindrical shape and then encapsulated with an impermeable material such as epoxy or glass. The intended use of the skin temperature sensor 390A thermistors 4374 is to detect, measure, and monitor skin temperature 4212 and body temperature 4214 of the user 8710. The resistance of the thermistor 4364 varies depending on the skin temperature 4212. The temperature of the skin is derived by measuring the thermistor 4374 resistance change 4376 in contact with the skin. A filter element 4378 is a circuit that passes (or amplifies) certain resistance change 4376 signals while attenuating other signals. The voltage changes 4380 is directly proportional to the skin temperature 4212. The resistance change 4376 in the skin temperature sensor 390A contains multiple thermistors 4374 to increase the skin temperature 4212 measurement accuracy. Wrist-wearable device 100 using smart band 200 measures skin temperature 4212, which is a few ° C. less than the body temperature 4214. In addition, skin temperature 4212 shows oscillations depending on environmental temperature and humidity. The body temperature 4214 usually varies less than 1° C. throughout the day. Skin temperature 4212 wrist measurement along with environmental parameters such as temperature and humidity are used to calculate the estimated body temperature. Alan C. Burton proposed that mean-body temperature (MBT) could be calculated from a formula: MBT=a. TCore+(1−a). TSkin. The general form of the equation was based on the logic that core tissues are relatively homogeneous, whereas tissue temperature in the peripheral decreases parabolically from core temperature to skin temperature 4212. The resulting value of the coefficient alpha was 0.64, thus giving the formula: MBT=0.64. TCore+0.36. TSkin.

The improved and accurate mathematical formula for estimated body temperature 4214 is as follows:

$$Tb = MBT + c1*Te + c2*He$$

where "Tb" is body temperature 4214, "Te" is temperature of the surrounding air in the environment, and "He" is humidity of the surrounding air. The correction coefficient values c1, and c2 are dynamic and based on the surrounding air temperature and humidity. Body temperature 4214 together with other measurements is also used to measure stress and detect emotions. The body temperature 4214 is negatively correlated with stress. The body temperature 4214 increases when stress levels decrease.

The skin temperature signal 4390 graph shows the skin temperature 4212 values (y-axis) detected over period of twenty-four hours (x-axis). The body temperature signal 4392 graph shows the calculated body temperature 4214 values (y-axis) over period of twenty-four hours (x-axis).

FIG. 44 illustrates a cardiac photoplethysmography (PPG) sensor operating principle diagram 4410, a pulse waveform PPG signal AC part 4430, a heart rate PPG signal 4440, a respiratory rate PPG signal 4450, and a heart rate variability PPG signal 4460, according to some embodiments.

A cardiac photoplethysmography (PPG) sensor 390B is used to detect, measure, and monitor a heart rate 4216, a heart rate variability 4218, and a respiratory rate 4220. The in vivo imaging of healthy blood vessel 4340 allows detection of the healthy blood vessels 3950. The picoprobe element 390BPT transmits incident light element 4412 which moves through skin surface 3924, stratum corneum 3922, epidermis 3920, and to the blood vessels 3950 in the dermis 3930. The picoprobe element 390BPR receives reflected light element 4414. Once the spectrum match is found, the picocamera element 390BPC in NIR mode captures backscattered reflection element 4416 and image of blood vessels 3950.

The cardiac photoplethysmography (PPG) sensor operating principle diagram 4410 detects, measures, and monitors a heart rate 4216, a heart rate variability 4218, and a respiratory rate 4220. Photoplethysmography (PPG) is an optical technique that is used to detect blood volume changes in the microvascular bed of tissue. It is used non-invasively to make in vivo measurements at the skin surface 3924. The intended use of PPG is to detect the heart rate 4216, heart rate variability 4218, and respiratory rate 4220. The in vivo imaging of healthy blood vessel 4340 method using picoprobe element 390BPT, picoprobe element 390BPR, and picocamera element 390BPC is used to locate the healthy blood vessels 3950. The healthy blood vessels 3950 is used by PPG to detect the heart rate 4216, heart rate variability 4218, and respiratory rate 4220. The NIR incident light element 4418 from LEDs element 390BL reaches the healthy blood vessel 3950, and the reflected light element 4420 PPG signal element 4422 is received by the photodiodes (PDs) element 390BD. The AC and DC components of PPG signal element 4422 are composed of a pulsatile component (AC) and nonpulsatile component (DC). AC is synchronized with the heart and related to arterial pulsation with systolic peak, and diastolic peak, while DC is related to light absorption in the tissue, vein, blood vessels 3950, and diastolic arterial blood volume.

The pulse waveform PPG signal AC part 4430 illustrates physiological waveform attributed to cardiac synchronous changes in the blood volume with each heartbeat. The cardiac photoplethysmography (PPG) sensor 390B also uses near infrared light to increase the accuracy of the results. The PPG sensing circuit is primarily composed of photodiodes (PDs) element 390BD, a transimpedance amplifier and two sets of cascaded active filters. Each set of filters is specifically tuned for monitoring heart rate, which has a frequency range of 0.33 Hz to 3.66 Hz corresponding to 20 beats per minute (BPM) to 220 BPM, and respiratory rate, which has a frequency range of 0.2 Hz to 0.5 Hz corresponding to 12 breaths per minute (BrthPM) to 30 BrthPM, in a healthy human adult. The transimpedance amplifier converts the current produced by the photodiodes (PDs) element 390BD to a voltage. This voltage is then sent into each respective set of active filters tuned for heart and respiratory rate monitoring respectively. The outputs of PPG sensing circuits are sensed by a microcontroller with analog to-digital converter. The heart rate circuit is sampled at 11.9 Hz, while the respiration circuit is sampled at 4.0 Hz. The signal from the photodiode varies with several physiological factors such as skin tone, thickness and so on. To avoid any noise or interferences the circuit employs dynamic amplifiers to compensate for it.

Heart rate 4216 is derived measures of blood volume pulse by measuring the interbeat interval and then transforming this information into beats per minute. For example, in 60 seconds, the interbeat interval of 0.80 seconds is equal to a heart rate of 60/0.80=75 beats per minute, whereas in 60 seconds, the interbeat interval of 0.90 seconds is equal to a heart rate of 60/0.90=66. The accuracy of the heart rate obtained with PPG sensing from a wrist 2912 is improved using signal processing techniques.

The heart rate PPG signal 4440 shows the graph of the relative amplitude (y-axis) over time (x-axis). Heart rate 4216 (HR) or pulse is the frequency of cardiac cycles and is expressed as beats per minute (bpm). The cardiac photoplethysmography (PPG) sensor 390B is based on photoplethysmography (PPG). The color of blood is red because it reflects red light and absorbs green light. The LEDs element 390BL with green light of wavelength 550 nm along with photodiodes (PDs) element 390BD is used to detect the amount of blood flowing through the user's wrist 2912 at any given moment. When the user's heart beats, the blood flows in the user 8710 wrist 2912 resulting in green light absorption, which is greater. Between the heart beats the blood is less, resulting in less absorption of green light. The LEDs element 390BL with green light of wavelength 550 nm is flashed onto the wrist 2912 many times per second, then measuring light absorption with photodiodes (PDs) element 390BD. The working principle is based on blood absorbing flashing green LEDs element 390BL, and each pulse brings a spike in blood flow, determining heart rate 4216 is measuring the changes in green light absorption by photodiodes (PDs) element 390BD. The changes in the absorption results in PPG signal element 4422.

Respiratory rate 4220 is also derived from PPG signals. The respiratory rate PPG signal 4450 shows the relative amplitude (y-axis) over time (x-axis).

The heart rate variability PPG signal 4460 is also used to calculate the heart rate variability 4218 and walking average. Heart rate variability 4218 is the measure of the variation in time between heartbeats. Unlike basic heart rate (HR) that counts the number of beats per minute, smart band 200 PPG sensors use an optical technique that detects blood volume changes under the skin surface 3924 to calculate an HRV score for the exact changes in time between successive beats. PPG (photoplethysmography) measures interbeat intervals or IBIs. This marks the time from the steepest increase in signal prior to the completion of the ventricular contraction (heartbeat). PPG determines the timing of cardiac cycles via continuous monitoring of changes in blood volume in a portion of the peripheral microvasculature. The heart rate variability PPG signal 4460 shows the graph of relative amplitude (y-axis) over time (x-axis).

FIG. 45 illustrates an ECG sensor operating principle diagram 4510, and ECG signal 4550, according to some embodiments.

An ECG sensor 390C is used to detect, measure, and monitor a set of electrocardiogram (ECG) 4222 parameters.

An electrocardiogram 4222 (also called an ECG or EKG) is a test that records the timing and strength of the electrical signals that make the heart beat. An ECG signal 4550 allows a doctor to gain insights about user 8710 heart rhythm and look for irregularities. The mobile healthcare application 250 records user 8710 heart beat and rhythm using the ECG sensor 390C on the smart band 200 and then checks the recording for normal heart rhythm, atrial fibrillation (A Fib), a form of irregular rhythm, and other heart problems.

The steps to detect the ECG signal 4550 consist of following:
1. Wear the smart band 200 on the the user wrist 2912 as shown in ECG sensor operation 4520 diagram and ECG and heart rhythm 4530 diagram.
2. Open the mobile healthcare application 250 on the wearable device 100 or mobile device.
3. With the hand opposite to user 8710 wearable device 100, hold a finger on metallic portion element 390C1 of the ECG sensor 390C. Wait for 10 seconds recording. At the end of the recording, user 8710 receives ECG signal 4550.

A hospital-grade ECG device generally consists of 10 electrodes placed on different parts of the user 8710 body. This requires electrodes (small, plastic patches that stick to the skin) be placed at certain spots on the chest, arms, and legs of the user 8710. The electrodes are connected to an ECG machine by lead wires. The electrical activity of the heart is then measured, interpreted, and printed out. The entire ECG signal recording process usually requires a visit to hospital or doctor's clinic, time and measurement done by a trained professional. The smart band 200 has 2 leads: 1 electrode on the smart band 200 consisting of band fastener 202, and one electrode on the metallic portion element 390C1 of the ECG sensor 390C.

The ECG signal 4550 is an electrical activity of the heart on the vertical y-axis against time on the horizontal x-axis. The P wave in an ECG complex indicates atrial depolarization 4532. The PR interval represents the time between atrial depolarization 4532 and ventricular depolarization 4534. Abnormalities in the timing of the PR interval of under 120 milliseconds (ms) may indicate that electrical impulses are traveling between the atria and ventricles too quickly. The QRS is responsible for ventricular depolarization 4534 and the T wave is ventricular repolarization 4536. RR interval is the time elapsed between two successive R-waves of the QRS signal on the electrocardiogram (and its reciprocal, the HR) and is a function of intrinsic properties of the sinus node. The ST interval represents the initial, slow phase of ventricular repolarization 4536. The Q-T interval is the section on the electrocardiogram (ECG) representing the time it takes for the electrical system to fire an impulse through the ventricles and then recharge. The ECG signal 4550 accuracy is improved by applying the Arterial Blood Pressure (ABP) obtained using blood pressure sensor 390D, and PPG signal from cardiac photoplethysmography (PPG) sensor 390B. Heart disease can be determined through the presence of abnormalities in PQRST interval on ECG signals 4550. It allows for preliminary diagnosis of heart health and to prevent or decrease the mortality rate due to heart attack. Normal ranges of most ECG parameters vary according to age and sex, and the ECG diagnostic criteria are specified in the database for these demographic measures.

FIG. 46 illustrates a blood pressure sensor operating principle diagram 4600, according to some embodiments.

A blood pressure sensor 390D is used to detect, measure, and monitor a systolic pressure 4224SBP level, and a diastolic pressure 4224DBP level.

Blood pressure 4224 (BP) represents the pressure of the blood against the inner walls of the blood vessels due to blood circulation. The blood pressure 4224 is measured as two numbers: Systolic blood pressure 4224SBP (the first and higher number) measures pressure inside arteries when the heart beats. Diastolic blood pressure 4224DBP (the second and lower number) measures the pressure inside the artery when the heart rests between beats. The gold standard method to continuously measure blood pressure 4224 is by using arterial cannula, in which a catheter is inserted into the blood vessel. The standard method is invasive and can cause pain and discomfort. The auscultatory or oscillometric method is commonly used to monitor BP at regular intervals but is discontinuous and causes discomfort, due to repeated cuff inflations. Smart band 200 uses a cuffless blood pressure method which uses blood pressure pulse wave (PW). The in vivo imaging of healthy blood vessel 4340 method using picoprobe element 390BPT, picoprobe element 390BPR, and picocamera element 390BPC is used to locate the healthy blood vessels 3950. Periodic relaxation and contraction of the heart creates rhythmic intermittent blood ejection, which leads to pulsation changes in the pressure of the artery, and then causes action-reaction processes such as vibrations of the skin surface 3924 in many areas of the body including the wrist 2912. The blood pressure sensor 390D consists of piezoelectric sensor element 390D1 and Hall effect sensor element 390D2. The blood pressure sensor 390D is in direct contact with the wrist skin surface 3924 to measure artery pulses by generating voltage in response to changes in the pressure. The wrist 2912 pulsation changes are recorded by a pressure sensor such as capacitive, piezoelectric sensor element 390D1, and Hall effect sensor element 390D2. Smart band 200 blood pressure sensor 390D uses piezoelectric sensor element 390D1 and Hall effect sensor element 390D2 simultaneously for accurate blood pressure measurement. Systolic blood pressure 4224SBP and diastolic blood pressure 4224DBP results are reported when the correlation between the piezoelectric sensor element 390D1 and Hall effect sensor element 390D2 are within 0.05 range. There is no calibration required since the blood pressure sensor 390D is precalibrated to pulse pressure waveform for the blood pressure 4224 normal reference ranges based on the age, sex, skin type and so on.

The piezoelectric sensor element 390D1 blood pressure 4624 measurement method is as follows:

The dilation 4620 and coarctation 4630 diagrams illustrate the piezoelectric sensor element 390D1 and Hall effect sensor element 390D2 pressure sensing technique which measures a pressure pulse wave (PPW) that reflects the pressure changes within the radial artery or ulnar artery. The piezoelectric sensor element 390D1 has a diaphragm structure for measuring fluctuating input pressure signals. The dilation 4620 diagram depicts the pressure wave element 4622 due to the widening of the radial artery 3860. This is systolic peak element SBP 4682 point and corresponding systolic element SBP 4692 results. The coarctation 4630 diagram depicts the pressure wave element 4632 due to the narrowing of the radial artery 3860. This is diastolic low element DBP 4684 point and corresponding diastolic element DBP 4694 results.

Piezoelectric sensor pressure conversion to an electric signal 4640 circuit diagram illustrates converting sensed measurements into electric results. A pressure sensitive transistor is used for blood pressure wave measurement. These pressure sensors are in the form of capacitors with positive and negative charges. The capacitors use compressible dielectric which induce a change in capacitance or a piezoelectric due to pressure to induce a voltage Vp 4646 across the device. The output voltage Vp 4646 is proportional to systolic blood pressure 4224SBP results during dilation 4620 and diastolic blood pressure 4224DBP during coarctation 4630 cycle. The piezoelectric sensor element 390D1 output voltage is amplified through an amplification circuit consisting of resistive element 4642 and amplifier element 4644 since the result of the background pressure is substantially larger due to motion artifacts than the pulse pressure. In addition, Hall effect sensor element 390D2 also detects the blood pressure 4224 based on minute changes in the magnetic field of a permanent magnet.

The Hall effect sensor element 390D2 blood pressure 4624 measurement method is as follows:

The dilation 4620 diagram depicts the magnetic wave element 4624 due to the widening of the radial artery 3860. This is systolic peak element SBP 4686 point and corresponding systolic element SBP 4696 results. The coarctation 4630 diagram depicts the magnetic wave element 4634 due to the narrowing of the radial artery 3860. This is diastolic low element DBP 4688 point and corresponding diastolic element DBP 4698 results.

Hall effect sensor conversion to an electric signal 4660 circuit diagram illustrates converting sensed measurements into electric results. The sensing part is comprised of multiple Hall devices and detects the pulse. The permanent magnets are in contact with the user's 8710 skin. The pulse in the user 8710 is measured based on the force of the pulsatory motion; the period of the pulsatory motion; the speed of expansion and contraction of the pulse; and the depth, width, and length of the pulse during palpitation. The output Hall voltage $V_H$4666 of the basic Hall element is directly proportional to the strength of the magnetic field passing through the semiconductor material. This output Hall voltage $V_H$ 4666 can be quite small, only a few microvolts, even when having strong magnetic fields. As such it has built-in DC amplifiers, logic switching circuits, and voltage regulators to improve the sensor's sensitivity, hysteresis, and output Hall voltage $V_H$ 4666. This also allows the Hall effect sensor element 390D2 to operate over a wider range of power supplies and magnetic field conditions. The output Hall voltage $V_H$4666 is proportional to systolic blood pressure 4224SBP and diastolic blood pressure 4224DBP results during dilation 4620 and coarctation 4630 cycle. The Hall effect sensor element 390D2 output voltage is amplified through an amplification circuit consisting of resistive element 4662 and amplifier element 4664 since the result of the background pressure is substantially larger due to motion artifacts than the pulse pressure.

The blood pressure signal 4680 graph has two waveforms with time (sec) as x-axis and amplitude as y-axis. The solid waveform is the output of piezoelectric sensor element 390D1 measurement. The broken waveform is the output of Hall effect sensor element 390D2. The systolic and diastolic blood pressure 4690 graphs have two lines with time (sec) as x-axis and blood pressure mmHg as y-axis. The solid line is the output of piezoelectric sensor element 390D1 measurement. The broken line is the output of Hall effect sensor element 390D2.

FIG. 47 illustrates a red blood cell containing hemoglobin 4710, blood oxygen sensor operating principle diagram 4720, blood carbon dioxide sensor operating principle diagram 4750, brain EEG operating principle diagram 4770, elbow EMG operating principle diagram 4780, and knee EMG operating principle diagram 4790, according to some embodiments.

The red blood cell containing hemoglobin 4710 diagram shows the hemoglobin 5022H and blood oxygen 5012. Red blood cells 5022 contain a protein called hemoglobin 5022H, which carries blood oxygen 5012 from the lungs to all parts of the body.

A blood oxygen sensor 390E is used to detect, measure, and monitor a blood oxygen 5012 saturation level.

The blood gas test consists of blood oxygen saturation ($O_2$Sat) and the partial pressure of blood carbon dioxide ($PaCO_2$). The blood oxygen saturation ($O_2$Sat) measures the amount of hemoglobin 5022H in the user 8710 blood. Hemoglobin 5022H is a protein in the user 8710 red blood cells 5022 that carries oxygen from user lungs to the rest of the body. Partial pressure of blood carbon dioxide ($PaCO_2$) measures the amount of carbon dioxide in the blood. Blood oxygen 5012 saturation or oxygenation is the concentration of oxyhemoglobin in the blood divided by the sum of the concentration of oxy- and deoxyhemoglobin 5022H in the blood. Oxygen is extracted from the air that fills users' 8710 lungs during inhalation. It is mixed into user's 8710 blood supply and pushed throughout the body with each heartbeat.

A blood oxygen sensor 390E comprising LEDs element 390E1 and photodetector PDs element 390E2 measures how much oxygen (compared to maximum capacity) is in user 8710 bloodstream as it travels around the body. This value should be 95% or higher in most settings, but this value can be influenced by altitude, activity, and an individual's health. The blood oxygen 5012 saturation numbers below 90% are considered low. The reflectance-based technique is used for noninvasively monitoring the blood oxygen 5012 saturation. The picoprobe element 390BPT, picoprobe element 390BPR, and picocamera element 390PBC use in vivo imaging of healthy blood vessel 4340 method to locate the healthy blood vessels 3950.

The reflectance-based blood oxygen sensor operating principle 4720 consist of an incident light element 4722 from red LEDs emitter element 390E-RED and incident light element 4724 from infrared LEDs emitter element 390E-IR, which are passed through the skin surface 3924 and reflected off the oxygenated and deoxygenated RBC 5022 in the healthy blood vessels 3950. The blood oxygen sensor LEDs element 390E1 sensor is made up of two LEDs, a red LEDs emitter element 390E-RED, with a peak emission wavelength of 660 nm, and an infrared LEDs emitter element 390E-IR with a peak emission wavelength of 940 nm. These two LEDs are positioned next to each other. The photodetectors (PDs) element 390E2 are connected in photovoltaic mode to produce a voltage output. The reflected light element 4724 from the red and reflected light element 4726 from the infrared are received by the PDs element 390E2 and converted to voltage. The voltage output is low and operational amplifiers are utilized to amplify the photodiode output. The amplified red and infrared PPG signals obtained from the photodetectors are sent through two sample-and-hold circuits to separate the signals into their respective alternating current (AC) and direct current (DC) components for further filtering and amplification. Blood oxygen 5012 is calculated by obtaining the ratio of the AC and DC components of the red PPG and dividing that by the ratio of the AC and DC components of the infrared PPG. To calculate heart rate, the frequency of the infrared AC signal is measured using frequency measurement parameters and then multiplied by 60 to display heart rate in beats per minute (bpm). The heart rate calculated is compared with heart rate detected using the cardiac photoplethysmography sensor to increase the accuracy.

A blood carbon dioxide sensor 390F is used to detect, measure, and monitor a blood carbon dioxide 5014 level.

The blood carbon dioxide sensor operating principle 4750 figure illustrates blood carbon dioxide 5014 measurement. The blood carbon dioxide sensor 390F can use nondispersive infrared (NDIR), resistive, piezoelectric devices, electrochemical sensor mechanism, and so on. An example nondispersive infrared (NDIR) is described. The blood carbon dioxide 5014 is measured using monitoring of transcutaneous $CO_2$ using nondispersive infrared (NDIR) blood carbon dioxide sensor 390F. Correction is applied to transcutaneous measurement of $CO_2$ to calculate the blood carbon dioxide 5014. Carbon dioxide ($CO_2$) is an odorless and colorless gas. It is a waste product made by the user 8710 body. The blood carries carbon dioxide to user 8710 lungs. The user 8710 breathes out carbon dioxide and breathes in oxygen all day, every day for proper functioning of the body. A blood carbon dioxide 5014 test measures the amount of $CO_2$ in user 8710 blood. Too much or too little carbon dioxide in the blood can indicate a health problem. Most of the $CO_2$ in the blood is present as bicarbonate ion, a minor portion is bound to the hemoglobin 5022H as carbonate compounds. The remaining $CO_2$ exists as dissolved gas that diffuses across the blood vessels 3950 and capillaries 3942. Transcutaneous measurement makes use of the fact that $CO_2$ gas diffuses through body tissue and skin and can be detected by the blood carbon dioxide sensor 390F at the skin surface 3924. The $CO_2$ gas gets released through the sweat 3926. Correction is applied to the transcutaneous measurement of $CO_2$ value to calculate blood carbon dioxide 5014. The blood carbon dioxide sensor 390F is placed over the skin surface 3924 to capture the transcutaneous $CO_2$ gas for measurement. The blood carbon dioxide sensor 390F consists of an O-ring 390F1 placed over the NDIR sensor 390F2. The O-ring 390F1 provides an airtight seal with the skin surface 3924 to avoid any gas leakage from the surrounding air. The hollow opening of the sensor is exposed to the skin, allowing transcutaneous $CO_2$ gas to diffuse directly into it. The Beer-Lambert's law, which establishes relationship between the concentration and the absorption of a given analyte, is used for determining the $CO_2$ concentration in NDIR sensor 390F2. The NDIR sensor 390F2 uses the 4.26-micron band of the infrared spectrum since $CO_2$ has one of its highest absorptions at this wavelength. The NDIR sensor 390F2 is in an enclosed chamber for transcutaneous $CO_2$ sensing. The opening of NDIR sensor 390F2 is exposed to the skin, allowing the transcutaneous $CO_2$ to diffuse directly into it. An O-ring placed over the NDIR sensor 390F2 acts as a cushion between the smart band 200 and the skin surface 3924, and provides air-tight sealing to avoid any gas leakage from surrounding air.

An EEG sensor 390G detects, measures, and monitor a set of electroencephalogram parameters.

The brain EEG operating principle diagram 4770 illustrates smart band 200 EEG sensor 390G on the user 8710 head at four different positions 4772 for 5 seconds each. An EEG sensor 390G uses the principle of differential amplification or recording voltage differences between different points using a pair of electrodes that compares one active exploring electrode site with another neighboring or distant reference electrode. Currently the 10-20 system of electrode placement method is used to describe the location of scalp electrodes. These scalp electrodes are used to record the electroencephalogram (EEG) using a machine called an electroencephalograph. The EEG is a record of brain activity. The physiological sensor 390 has innovative EEG sensor 390G design with array of electrodes enabling dry electrode EEG recording. The procedure to record EEG consists of placing the EEG sensor 390G on the user 8710 head in four different positions for 5 seconds each. The 4 different positions are nasion, inion, and 2 positions above the ear. The electrodes noninvasively detect brainwaves from the user 8710. EEG sensor 390G can record up to several thousands of snapshots of the electrical activity generated in the brain within a single second. The data from 4 different positions for 5 seconds enables an EEG to calculate changes in brain activity that are useful in diagnosing brain disorders, especially epilepsy or another seizure disorder. An EEG might also be helpful for diagnosing or treating brain tumors and brain damage from head injury. The unit of measurement is normalized to range of 1-5 Absolute Unit (AU) where the muscle signal range or brain activity is classified as excellent=5, very good=4, good=3, fair=2, and poor=1. In one of the embodiments the EEG sensor 390G is designed and placed on top of the band fastener 202 facing user 8710 for easy access and placement on top of the brain.

An EMG sensor 390H intended use is to measure the Electromyogram (EMG). An EMG sensor 390H is used to detect, measure, and monitor a set of elbow and knee electromyogram parameters. A surface EMG technique is used in which electrodes are placed on the skin overlying a muscle to detect the electrical activity of the muscle. Surface EMG (SEMG) does not involve piercing the skin and does not hurt.

An EMG sensor 390H intended use is to measure the Electromyogram (EMG) to assess the health of muscles and the nerve cells that control them (motor neurons). EMG results can reveal nerve dysfunction, muscle dysfunction, or problems with nerve-to-muscle signal transmission. Motor neurons transmit electrical signals that cause muscles to contract. An EMG uses tiny devices called electrodes to translate these signals into graphs, sounds, or numerical values that are then interpreted by a specialist.

The figure elbow EMG operating principle diagram 4780 illustrates smart band 200 EMG sensor 390H placement on top of the biceps muscles 4782, or triceps muscles 4784 for elbow muscle EMG measurement. The procedure to record elbow EMG of the user 8710 consists of placing the hand with smart band 200 EMG sensor 390H over the elbow biceps or triceps muscle for 10 seconds. The unit of measurement is normalized to a range of 1-5 Absolute Unit (AU) where the muscle signal range or health of elbow muscles is classified as excellent=5, very good=4, good=3, fair=2, and poor=1.

The knee EEG operating principle diagram 4790 illustrates smart band 200 EMG sensor 390H placement on top of the quadriceps muscles 4792 or hamstring muscles 4794 for knee muscle EMG measurement. The procedure to record a knee EMG of the user 8710 consists of placing the hand with smart band 200 EMG sensor 390H over the knee quadriceps 4792 tendon right above the patella or hamstring muscle 4794 for 10 seconds each. The unit of measurement is normalized to a range of 1-5 Absolute Unit (AU) where the muscle signal range or health of knee muscles is classified as excellent=5, very good=4, good=3, fair=2, and poor=1. In one of the embodiments the EMG sensor 390H is designed and placed on the top of the band fastener 202 facing user 8710 for easy access and placement on top of the muscles.

Figure 48:
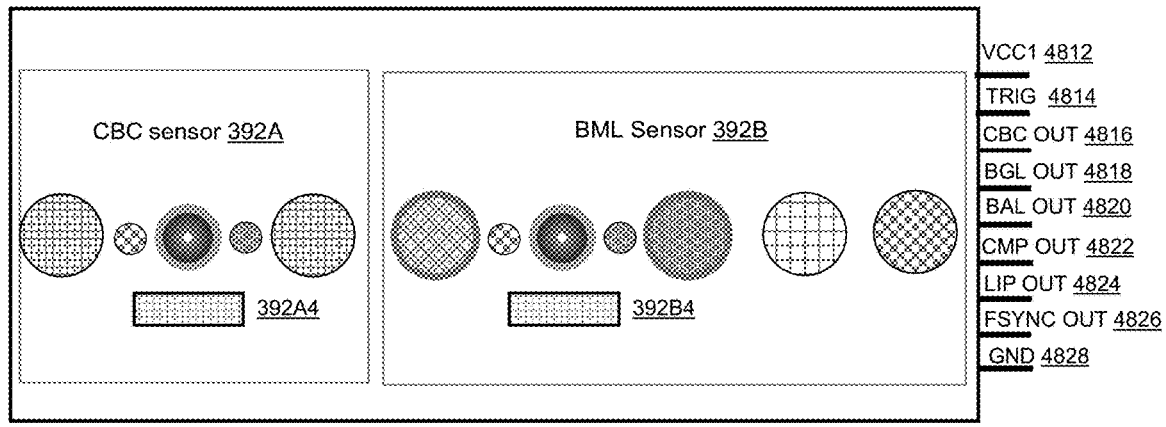
FIG. 48 illustrates an example biofluid sensor pinout, and a biofluid sensor wiring table describing the hardware wiring connection steps of a biofluid sensor pinout connected to the single board computer general purpose input output pinout that can be utilized to implement various embodiments.

FIG. 48 illustrates an example biofluid sensor pinout 4810, and a biofluid sensor wiring table 4850 describing the hardware wiring connection steps of a biofluid sensor pinout 4810 connected to the single board computer general purpose input output pinout 370 that can be utilized to implement various embodiments.

1. Log in to the single board computer 350 operating software and access general purpose input output pinout 370 settings. Assign and map the general purpose input output pinout 370 to be connected to a biofluid sensor pinout 4810. Save general purpose input output pinout 370 settings.

2. Connect the biofluid sensor pinout 4810 to a single board computer 350 assigned general purpose input output pinout 370 as listed in the biofluid sensor 392 wiring table 4850. The hardware implementation of the biofluid sensor 392 is complete after the biofluid sensor pinout 4810 is connected to a single board computer 350 general purpose input output pinout 370.

3. Prepare the single board computer 350 operating software to communicate with the biofluid sensor 392 by loading the general purpose input output pinout 370 software library and installing the biofluid sensor 392 software driver.

4. Program, install, execute, and run the biofluid sensor 392 software on the single board computer 350 operating software.

The biofluid sensor 392 software is part of mobile healthcare application 250.

The biofluid sensor 392 has five dedicated channels for detecting complete blood count, blood glucose 5046, blood alcohol 5048, complete metabolite panel, and lipid panel as follows:

TRIG 4814 pin produces a pulse when reflected light is received.

CBC OUT 4816—Output channel for complete blood count parameters.

BGL OUT 4818—Output channel for blood glucose 5046.

BAL OUT 4820—Output channel for blood alcohol 5048.

CMP OUT 4822—Output channel for metabolites 5040 except for blood glucose 5046 and blood alcohol 5048.

LIP OUT 4824—Output channel for lipids 5080.

The FSYNC OUT 4826 is for picocamera element 392A3 and picocamera element 392B3 image stabilization and elimination of user 8710 movement artifacts interferences.

The individual dedicated channel allows for complete blood count, blood glucose 5046, blood alcohol 5048, complete metabolite panel, and lipid panel fast high throughput multiplexed detection. Each output channel 4816 to 4824 is dedicated to use the biofluid parameter detection methods based on the parameter to be detected.

The biofluid sensor 392 consists of a CBC sensor 392A to detect blood cells 5020 and BML sensor 392B to detect metabolites 5040 and lipids 5080. The detection method used are flow cytometry imaging, hyperspectral imaging, and autofluorescence, diffuse reflectance spectrum, and absorption line spectrum.

The wearable device 100 smart band 200 biofluid sensor 392 is configured to detect, measure, and monitor biofluid parameters of the user 8710 and comprises:

A CBC sensor 392A configured to detect, measure, and monitor complete blood count comprising: a red blood cell (RBC) 5022, a hemoglobin level 5022Hb, a hematocrit level 5022HCT, a mean corpuscular volume (MCV) 5022MCV, a mean corpuscular hemoglobin (MCH) 5022MCH, a mean corpuscular hemoglobin concentration (MCHC) 5022MCHC, a white blood cell (WBC) 5024, a white blood cell differential 5024D, and a platelet 5026; wherein the white blood cell differential 5024D detected comprises: a monocyte 5024M, a lymphocyte 5024L, a neutrophil 5024N, an eosinophil 5024E, and a basophil 5024B; and wherein a blood cell morphology as specified in the morphology of blood cells diagram 4960 comprises associated disease states and conditions;

A BML sensor 392B configured to detect, measure, and monitor a set of panels comprising:

A comprehensive metabolic panel comprising: an albumin 5042, a bilirubin 5044, a blood glucose 5046, a blood alcohol 5048, a blood urea nitrogen (BUN) 5050, a cortisol 5052, a creatinine 5054, a calcium 5056Ca, a chloride 5056Cl, a magnesium 5056Mg, a phosphorus 5056P, a potassium 5056K, a sodium 5056Na, an alkaline phosphatase (ALP) 5060, an alanine aminotransferase (ALT) 5062, and an aspartate aminotransferase (AST) 5064; and A lipid panel comprising: an HDL cholesterol 5082, an LDL cholesterol 5084, a triglycerides 5086, and a total cholesterol 5080T;

Wherein the set of picoprobes element 392A5, 392A6, 392B5, 392B6 and the picocamera element 392A3, 392B3 are configured to output a location of a healthy blood vessel 3950 for a noninvasive in vivo measurement of the biofluid parameter;

Wherein the set of biofluid sensor 392 parameters result comprises: a parameter name, a result value, a flag, a unit, a normal reference range, and an intelligent relationship interpretation; and wherein the intelligent relationship interpretation comprises: a symptom, a cause, and a treatment when the set of biofluid sensor parameters result value falls outside a normal reference range; and wherein the cause and the treatment are accurately determined based on the related smart band sensor parameter result value; For example, the intelligent relationship interpretation determines the changes in the biofluid sensor parameter sodium 5056Na levels accurate cause is due to correlated particulate matter sensor parameter high pollution/air quality index value or correlated enviro sensor parameter altitude result value outside the normal reference range and provide accurate treatment information in the form of reduce salt intake to reduce the biofluid sensor parameter sodium 5056Na;

Wherein the set of biofluid sensor 392 parameters result is configured to predict a biofluid risk level. Each biofluid sensor 392 parameter risk level is calculated based on the severity ranking, probability of occurrence ranking, and detection ranking using the parameter result value as described in risk level definition and in an example smart band sensor risk level and corrective action and preventive action table 9520. Overall biofluid risk level is an average of all the individual biofluid sensor 3920 parameters risk level.

Wherein a biofluid risk level above a predetermined threshold level is configured to send a biofluid risk alert to the mobile healthcare application 250 of the user 8710 as shown in an example smart band alert 9510; and Wherein a biofluid risk level assessment is configured to output a corrective action and a preventive action to ensure the set of biofluid sensor parameters result value as described in FIG. 49, FIG. 50, FIG. 51, FIG. 53, and FIG. 54 are within the normal reference range for a disease reduction or elimination, a healthy blood formation, to improve a physical wellness dimension ranking, and to improve an emotional wellness dimension ranking as described in an example smart band sensor risk level and corrective action and preventive action table 9520. The healthy blood formation includes composition, and function of the blood cells.

FIG. 49 illustrates a biofluid sensors diagram 4910, schematic structure of pixelated LEDs array 4930, a single pixelated LED 4940, a single pixelated photodetector (PDs) 4950, and a morphology of blood cells diagram 4960 that can be utilized to implement various embodiments.

The complete blood count CBC sensor 392A comprises LEDs element 392A1, LEDs element 392A2, picocamera element 392A3, camera CSI port element 392A4, picoprobe element 392A5, and picoprobe element 392A6. The camera CSI port element 392A4 is connected to the SBC Camera CSI port 368. The element 392A2 acts as transmitter (LEDs) and receiver (PDs) based on detection method.

The BML sensor 392B LEDs element 392B1, PDs element 392B2, picocamera element 392B3, camera CSI port element 392B4, picoprobe element 392B5, and picoprobe element 392B6 are dedicated for detecting metabolites 5040. The LEDs element 392B8, and photodiodes PDs 392B9 are for detecting lipids 5080.

The schematic structure of pixelated LEDs array 4930 consists of pico, nano, and micro-LEDs. The LEDs are made of semiconductor materials. The LEDs have a unique structure that consists of picodisks 4942 sandwiched between two layers of nanorods respectively. The high efficiency pixelated LEDs array offer wide variety of wavelength, low power consumption, long lifetime, and wide spectral regions. The single pixelated LEDs 4940 are embedded in substrate to provide the active-matrix addressable signals to each LED. This allows the LEDs to emit wavelengths in any of the regions of UVA, visible, near infrared, and infrared region. Each of the LEDs can be programmed to emit different wavelength. The LEDs array can be segmented into different areas with each area emitting programmed wavelengths. The LED can perform double duty of emitting and detecting light in the same circuit without changing its physical or electrical connections. This is achieved by using two I/O pins on the microcontroller and an LED. The dedicated photodiodes or photodetectors are also made of pico materials. The single photodiodes 4950 are embedded in substrate to provide the active-matrix addressable signals to each photodiode. Like LEDs, photodiodes have a unique structure that consists of picodisks element 4952 sandwiched between two layers of nanorods respectively. Photodetectors are sensors of light or other electromagnetic radiation that converts light photons into current. This is converted to a voltage that encodes the information. Photodetectors are also made from pico, nano, and micro semiconductor materials such as silicon and are used widely in detecting light in the UVA, visible, and infrared region by the smart band 200. The structure of these photo sensors is made of metal picoparticles that are in the range of 5-20 μm and placed on a silicon substrate.

The morphology of blood cells diagram 4960 illustrates RBC morphology, WBC morphology, and platelet morphology. The morphological information is stored in the biofluid platform dataset. The red blood cell morphology is evaluated in terms of size, shape, color, red cell distribution, and intracytoplasmic inclusions. The red cells have a uniform variation in size, with a red cell distribution width of 11-15% in normal individuals. The WBC morphology includes normal and abnormal WBC differentials. The WBCs are irregular in shape, with oval or clefted (kidney-shaped) nucleus and fine, delicate chromatin. Cytoplasm is abundant. After migration to the tissues from blood, they are called as macrophages. Coarse granules present in the cytoplasm of neutrophils are seen in severe bacterial infections. Presence of vacuoles in neutrophils indicate a condition called phagocytosis. The premature leukocytes are another example of an abnormal morphology of the WBC. The platelet morphology includes normal and abnormal platelets. Platelets have a round or oval shape.

FIG. 50 illustrates biofluid analyte detected structure 5000, according to some embodiments.

The biofluid analytes detected structure comprises blood gases 5010, blood cells 5020, metabolites 5040, and lipids 5080. The terms biofluid analyte or biofluid parameter are interchangeably used. The term analyte is more prevalent and often used in the context of clinical laboratory test results terminology. The parameter or analyte is defined as a substance or material; something that identifies or that is used to identify; a factor that establishes the nature of an entity or event; constituent of a sample with a measurable property.

The blood gases 5010 detected are a blood oxygen 5012, and a blood carbon dioxide 5014.

The blood cells 5020 detected comprise a red blood cell (RBC) 5022, a hemoglobin 5022H, a white blood cell (WBC) 5024, and a platelet 5026. The white blood cell (WBC) 5024 consists of monocyte 5024M, lymphocyte 5024L, neutrophil 5024N, eosinophil 5024E, and basophil 5024B. The detection of hemotocrit (HCT) 5022HCT, mean corpuscular volume (MCV) 5022MCV, mean corpuscular hemoglobin (MCH) 5022MCH, and mean corpuscular hemoglobin concentration (MCHC) 5022MCHC can be through sensors and/or mathematically calculated.

The metabolites 5040 detected comprise an albumin 5042, a bilirubin 5044, a blood glucose 5046, a blood alcohol 5048, a blood urea nitrogen (BUN) 5050, a cortisol 5052, a creatinine 5054, electrolytes 5056, an alkaline phosphatase (ALP) 5060, an alanine aminotransferase (ALT) 5062, and an aspartate aminotransferase (AST) 5064. The electrolytes 5056 detected comprise of a calcium 5056Ca, a chloride 5056Cl, a magnesium 5056Mg, a phosphorus 5056P, a potassium 5056K, and a sodium 5056Na.

The lipids 5080 detected consist of a high density lipoprotein (HDL) 5082, a low density lipoprotein (LDL) 5084, and a triglyceride 5086. The total cholesterol 5080T can be detected either through a sensor or mathematically calculated. Smart band 200 physiological sensor 390 detects blood gases 5010, and biofluid sensor 392 detects blood cells 5020, metabolites 5040, and lipids 5080.

FIG. 51 lists biofluid complete blood count parameters, detection sensor, and detected normal reference ranges 5100.

The table list comprises biofluid parameters, human anatomy, detection sensor, and normal reference ranges. The biofluid parameters detected comprise a red blood cell 5022 count, a hemoglobin 5022H level, a hematocrit (HCT) 5022HCT level, a mean corpuscular volume (MCV) 5022MCV, a mean corpuscular hemoglobin (MCH) 5022MCH, a mean corpuscular hemoglobin concentration (MCHC) 5022MCHC, a white blood cell (WBC) 5024 count, a white blood cell (WBC) 5024 differential, and a platelet 5026 count. The WBC 5024 differential comprises monocyte 5024M, lymphocyte 5024L, neutrophil 5024N, eosinophil 5024E, and basophil 5024B. The hematocrit (HCT) 5022HCT, Mean Corpuscular Volume (MCV) 5022MCV Mean Corpuscular Hemoglobin (MCH) 5022MCH, and Mean Corpuscular Hemoglobin Concentration (MCHC) 5022MCHC can also be mathematically calculated as per the formulae in FIG. 51 table. Smart band 200 biofluid sensor 392 detects these parameters. The normal reference ranges help describe what is typical for a particular group of people based on age, sex, and other characteristics. The normal reference ranges are automatically set based on the smart band 200 user 8710 demographics information and smart band 200 sensor result.

FIG. 52 lists blood cell components 5200 comprising a red blood cell (RBC) 5022, a white blood cell (WBC) 5024, and a platelet 5026.

The table lists features comprise scientific name, detection method, appearance, size, production location, production number, formation process, motility, percentage in blood, types, life span, constitution, color, function, circulation, low count effect, and high count effect. The features such as detection method specify the smart band 200 sensor detection methods. The features such as function, circulation, low count effect, and high count effect are displayed as part of the result annotations associated with RBC 5022, WBC 5024, and platelet 5026 results in mobile healthcare application 250. Remaining features are used by the CBC sensor 392A methods as described in spectrally encoded flow cytometry (SEFC) imaging of blood cells operating principle diagram 5530 and NIR hyperspectral (HS) imaging of blood cells operating principle diagram 5550 to detect the RBC 5022, WBC 5024, and platelet 5026.

FIG. 53 lists biofluid complete metabolic panel analytes, detection sensor, and detected normal reference ranges 5300.

The list comprises biofluid parameter, human anatomy, detection sensor, and normal reference ranges information. The biofluid parameters detected are an albumin 5042, a bilirubin 5044, a blood glucose 5046 level, a blood alcohol 5048 concentration level, a blood urea nitrogen (BUN) 5050, a cortisol 5052, a creatinine 5054, a calcium 5056Ca, a chloride 5056Cl, a magnesium 5056Mg, a phosphorus 5056P, a potassium 5056K, a sodium 5056Na, an alkaline phosphatase (ALP) 5060, an alanine aminotransferase (ALT) 5062, and an aspartate aminotransferase (AST) 5064. Smart band 200 biofluid sensor 392 detects these parameters. The normal reference ranges help describe what is typical for a particular group of people based on age, sex, and other characteristics. The normal reference ranges are automatically set based on the smart band 200 user 8710 demographics information and smart band 200 sensor result.

FIG. 54 lists biofluid lipid panel parameters, detection sensor, and detected normal reference ranges 5400.

The table list comprises biofluid parameter, human anatomy, detection sensor, and normal reference ranges. The biofluid parameters detected comprise a high density lipoprotein (HDL) 5082, a low density lipoprotein (LDL) 5084, a triglyceride 5086, and total cholesterol 5080T. Smart band 200 biofluid sensor 392 detects these parameters. Total cholesterol 5080T can also be mathematically calculated. The HDL, and LDL diameter, % of total content, and % of total lipid content are used in differentiating the HDL and LDL. The % of total lipid content of triacylglycerols, cholesteryl esters, and phospholipids is used to refine the results. The normal reference ranges help describe what is typical for a particular group of people based on age, sex, and other characteristics. The normal reference ranges are automatically set based on the smart band 200 user 8710 demographics information and smart band 200 sensor result.

FIG. 55 illustrates an in vivo noninvasive imaging of blood flow in a single vessel diagram 5510, spectrally encoded flow cytometry (SEFC) imaging of blood cells operating principle diagram 5530, and NIR hyperspectral (HS) imaging of blood cells operating principle diagram 5550, according to some embodiments.

The CBC parameter measurement is based on noninvasive in vivo blood cell measurements by imaging of the microcirculation in the blood vessels 3950 using CBC sensor 392A.

The principle of in vivo noninvasive imaging of blood flow in a single vessel diagram 5510 involves in vivo image capture using picocamera element 392A3 to quantify CBC count. CBC sensor 392A is used to detect, measure, and monitor complete blood count comprising: a red blood cell 5022, a hemoglobin 5022Hb level, a hematocrit 5022HCT level, a mean corpuscular volume (MCV) 5022MCV, a mean corpuscular hemoglobin (MCH) 5022MCH, a mean corpuscular hemoglobin concentration (MCHC) 5022MCHC, a white blood cell 5024, a white blood cell differential 5024D, and a platelet 5026. The white blood cell differential comprises neutrophils 5024N, lymphocytes 5024L, monocytes 5024M, eosinophils 5024E, and basophils 5024B. The raw images are acquired using SEFC and HS imaging methods. The figure element 5512 is raw image with magnification of 10× acquired during the flow, element 5514 is magnification of the image by 50×, and element 5516 is magnification of the image by 100×. The acquired images are processed through filters and converted into same format as blood smear slide images, enabling the use of existing digital image processing algorithms for digital blood cell count. The blood cells are clearly visible and are easily identified as red blood cells 5022, white blood cells 5024, and platelets 5026. The information is processed by blood cells spectral encoded flow cytometry and NIR hyperspectral imaging method 5660, and blood cell count using digital image processing method 5670. The smart band 200 provides blood cell histograms by plotting the sizes of different blood cells on the X-axis and their relative number on the Y-axis. The RBC histogram 5520 is a graphic representation of a collection of data based on cell size and/or cell number depicting variations in the process. It enables one to visualize, analyze, and interpret data that displays morphological changes graphically as points, and peaks or valleys. It provides invaluable information regarding a) reliability of smart band 200 results, b) information about certain conditions such as presence of fragmented red cells or red cell agglutination. The RBC histogram 5520 in various hematological conditions also provides information about normal histogram, iron deficiency anemia, microcytosis, macrocytosis with normal RDW, macrocytosis, megaloblastic anemia, cold agglutination, sideroblastic anemia, beta thalassemia major, pyro poikilocytosis, reticulocytotosis, and post-iron therapy. The WBC histogram 5522 provides information about the normal and abnormal WBC differential cell distribution. The PLT histogram 5524 provides information about the normal distribution with information such as a sharp increase to a peak and tapers downward as cell size increases. This indicates that most platelets are smaller in size, with fewer large sized platelets.

Spectrally encoded flow cytometry (SEFC) imaging of blood cells operating principle 5530 steps used to detect the CBC count are as follows:

1. Find the healthy blood vessel 3950 under the wrist skin surface 3924 in the dermis 3930 using picoprobe element 392A5, picoprobe element 392A6 and picocamera element 392A3 with in vivo imaging of healthy blood vessel 4340 method. The incident light element 5532 and reflected light element 553 are used to detect the healthy blood vessel 3950.
2. Irradiate a beam of incident light element 5536 and incident light element 5538 using LEDs element 392A1 and LEDs element 392A2 on a healthy blood vessel 3950 in dermis 3930 with a desired and specific band of wavelengths.
3. A single line within a blood vessel 3950 is imaged with different wavelength of light element 5540 that encodes lateral position as shown in figure SEFC image acquisition 5542. This produces a two-dimensional image with one axis encoded by wavelength and the other by time as shown in single cell crossing spectral line 5544 figure. The image is captured as per blood cells spectral encoded flow cytometry and NIR hyperspectral imaging method 5660.
4. Analyze the images with blood cell count using digital image processing method 5670. The images/videos are fed into a computerized image analysis system capable of identifying numerous individual cells simultaneously and analyzing them in real time.

The NIR hyperspectral imaging (HS) of blood cells operating principle diagram 5550 figure illustrates NIR hyperspectral imaging and identification of complete blood cell counts. HS imaging measures reflected light that interacts with blood, containing information about structural and spectral features. When the light meets blood, there are complicated light blood interactions, such as absorption, scattering, or transmission as described in optical path of light into skin 4010. Biomolecules show distinct absorption properties, which means spectrally resolved imaging methods could predict biochemical features by measuring the amount of attenuated light signal as a function of wavelength. The fundamental working principle of NIR hyperspectral imaging is to measure an image as a function of wavelength using spectroscopic techniques. The HS method used is a snapshot imaging method. The snapshot method acquires spatial and spectral information in a single measurement. Multiple filter arrays are placed in front of the camera sensor to measure both spatial and spectral information. This allows fast imaging and easy implementation of the spectral imaging method. As each camera pixel measures spectral information with a different wavelength, the demosaicing is done to obtain structural images that correspond to spectral channels.

Hyperspectral (HS) imaging of blood cells operating principle 5550 steps to detect the CBC count are as follows:

1. Find the healthy blood vessel 3950 under the wrist skin surface 3924 in the dermis 3930 using picoprobe element 392A5, picoprobe element 392A6, and picocamera element 392A3 with in vivo imaging of healthy blood vessel 4340 method to locate the healthy blood vessels 3950. The incident light element 5552, and reflection light element 5554 are used to detect the healthy blood vessel 3950.
2. Irradiate a beam of incident light element 5556-5558 using LEDs element 392A1-392A2 on a healthy blood vessel 3950 in dermis 3930 with a desired and multiple bands of wavelengths element. The blood cells are imaged using backscattered light element 5560.
3. A snapshot imaging method 5562 is used to acquire the flowing blood cell image.
4. Acquire several images of healthy blood vessel 3950 of the microcirculation using picocamera element 392A3. The picocamera element 392A3 allows magnification that is several times greater than with a conventional camera. Perform demosaicing of the images.
5. Analyze the images with blood cell count using digital image processing method 5670. The images/videos are fed into a computerized image analysis system capable of identifying numerous individual cells simultaneously and analyzing them in real time.

Figure 56:
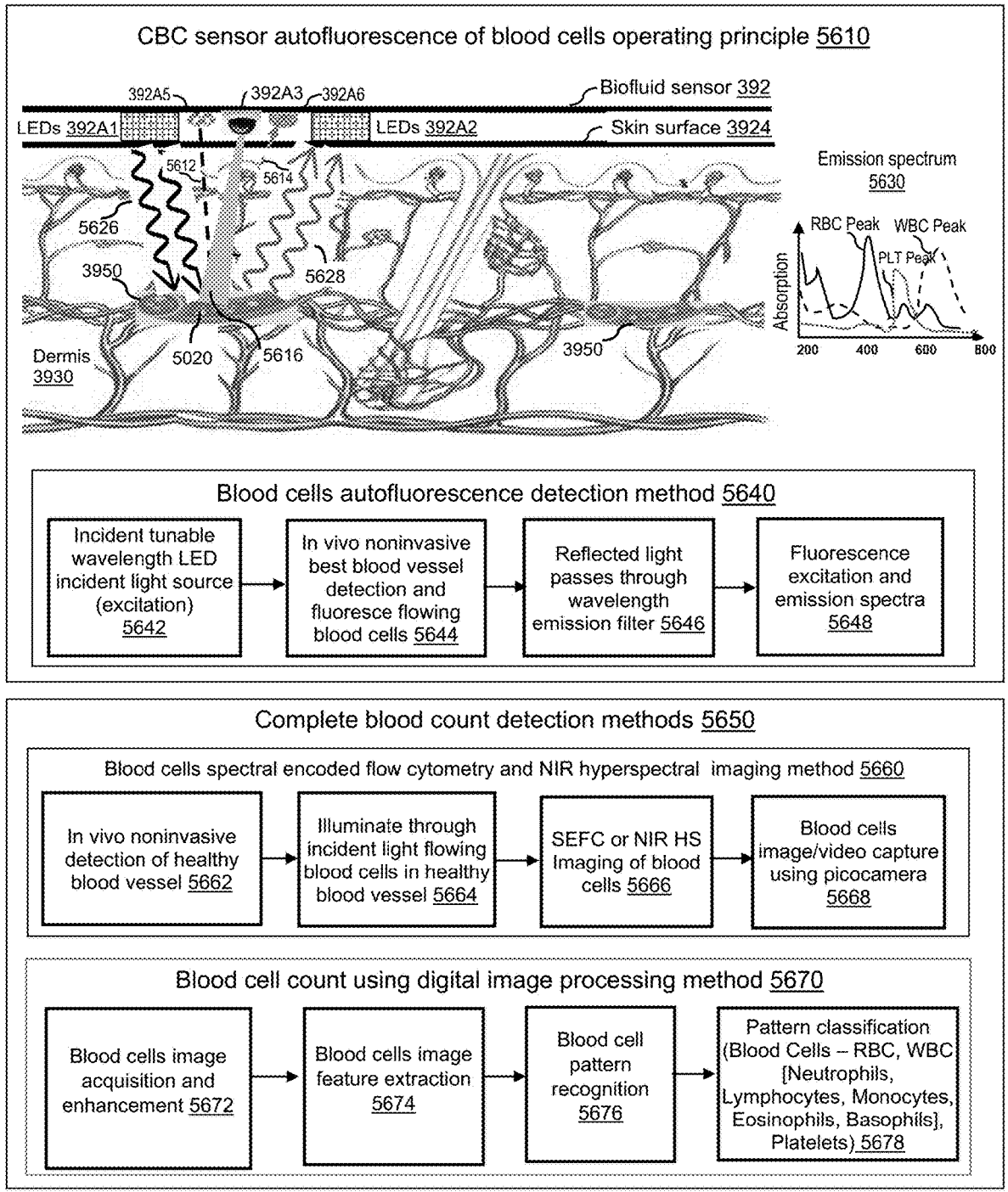
FIG. 56 illustrates Complete Blood Count (CBC) sensor autofluorescence of blood cells operating principle, and complete blood count detection methods, according to some embodiments.

FIG. 56 illustrates a CBC sensor autofluorescence of blood cells operating principle 5610, and complete blood count detection methods 5650, according to some embodiments. Autofluorescence is natural emission of light by blood cells which become fluorescent when excited by radiation of suitable wavelength. This fluorescence emission arises from endogenous fluorophores.

The CBC sensor autofluorescence of blood cells operating principle 5610 comprises following processing steps:

1. Find the healthy blood vessel 3950 under the wrist skin surface 3924 in the dermis 3930 using picoprobe element 392A5, picoprobe element 392A6 and picocamera element 392A3 with in vivo imaging of healthy blood vessel 4340 method by imaging backscattered reflection element 5616 at a calculated penetration depth. The incident light element 5612 and reflected light element 5614 are used to detect the healthy blood vessel 3950.
2. Irradiate a beam of incident light element 5626 using LEDs element 392A1 on a healthy blood vessel 3950 in dermis 3930 with a desired and specific band of wavelengths and receive emission light element 5628 using PDs element 392A2.
3. Detect blood cells 5020 as per blood cells autofluorescence detection method 5640 using NIR wavelength embedding method 6230. The RBC autofluorescence excitation wavelength is 405 nm and emission spectral range 425 nm to 790 nm, WBC excitation wavelength is 405/488 nm and emission wavelength is 450/525 nm, and platelet excitation wavelength is 350-370 nm and emission spectra peak at 360 nm.
4. Analyze the excitation and emission spectrum to determine the complete blood count as shown in example of emission spectrum 5630.

The blood cells autofluorescence detection method 5640 processing steps are as follows:

1. Incident tunable wavelength LED incident light source (excitation) 5642
2. In vivo noninvasive best blood vessel detection and fluoresce flowing blood cells 5644

3. Reflected light passes through wavelength emission filter 5646
4. Fluorescence excitation and emission spectra 5648

The complete blood count detection methods 5650 comprise blood cells spectral encoded flow cytometry and NIR hyperspectral imaging method 5660, and blood cell count using digital image processing method 5670.

The blood cells spectral encoded flow cytometry and NIR hyperspectral imaging method 5660 processing steps are as follows:
1. In vivo noninvasive detection of healthy blood vessel 5662
2. Illuminate through incident light flowing blood cells in healthy blood vessel 5664
3. SEFC or HS imaging of blood cells 5656
4. Blood cells image/video capture using picocamera 5668

After the blood cells image/video is acquired, it is further processed to detect the 5022, WBC 5024, and platelet 5026. The blood cell count using digital image processing method 5670 comprises following processing steps:
1. Blood cells image acquisition and enhancement 5672
2. Blood cells image feature extraction 5674
3. Blood cell pattern recognition 5676
4. Pattern classification (Blood Cells— RBC, WBC [Neutrophils, Lymphocytes, Monocytes, Eosinophils, Basophils], Platelets) 5678

The process includes conversion of the acquired images to standard blood smear slide images format. This allows counting of RBCs based on Gray Threshold, ABCCS method, Circular Hough Transform and thresholding, and so on. The five types of white blood cells are recognized based on image processing algorithms based on K-means clustering, Gram-Schmidt orthogonalization, snake algorithm, and so on, to segment the nucleus and cytoplasm of the cells. The result consists of complete blood count including morphology of blood cells 4960.

FIG. 57 illustrates NIR spectroscopy fundamental equations 5710, a vibration of a diatomic molecule 5740, and vibrations of polyatomic molecules (AX2 group) 5760 to detect metabolites, according to some embodiments.

The principal of molecular spectroscopy is based on the electromagnetic radiation to determine molecule structure. It is based on energy of photons, Planck's equation 5712. A molecule absorbs electromagnetic radiation when the energy of the photon corresponds to the difference in energy between the ground state and excited state.
1. Infrared spectroscopy (IR)—IR spectroscopy works on the principle that molecules 3814 absorb specific frequencies that are characteristic of their structure. It is based on triggering molecular vibrations through irradiation with infrared light which provides information about the presence or absence of certain functional groups. NIR is part of the IR spectroscopy.
2. Near infrared (NIR) spectroscopy is a type of vibrational spectroscopy based on the absorption and reflection of electromagnetic (EM) radiation at wavelengths in the range of 700 nm to 2,500 nm (wavenumbers: 13,300 to 4,000 cm$^{-1}$). Near-IR spectroscopy is characterized by low molar absorptivity and high scattering efficiency. NIR spectra contain information about the major X—H chemical bonds, i.e., C—H, O—H, and N—H. Metabolites 5040 and lipids 5080 molecules containing hydrogen have a measurable NIR spectrum, resulting in a large range of organic materials to be suitable for NIR analysis.
3. Ultraviolet visible spectroscopy (UV-S)—The principle of UV-visible spectroscopy is based on the absorption of ultraviolet light or visible light by chemical compounds, which results in the production of distinct spectra. It is based on promotion of electrons to higher energy levels through irradiation of the molecule with ultraviolet light. It provides mostly information about the presence of conjugated $\pi$ systems and the presence of double and triple bonds.
4. Mass spectrometry—The basic principle of mass spectrometry (MS) is to generate ions from either inorganic or organic compounds by any suitable method, to separate these ions by their mass-to-charge ratio (m/z) and to detect them qualitatively and quantitatively by their respective m/z and abundance. It is based on bombardment of the sample with electrons and detection of resulting molecular fragments. It provides information about molecular mass and atom connectivity. Mass (MS) spectrometry is not really spectroscopy. In summary, mass spectrometry gives the mass to charge ratio.
5. Nuclear magnetic resonance (NMR)—The principle behind NMR is that many nuclei have spin, and all nuclei are electrically charged. If an external magnetic field is applied, an energy transfer is possible between the base energy to a higher energy level. It involves excitation of the nucleus of atoms through radiofrequency irradiation. NMR provides extensive information about molecular structure and atom connectivity. It usually involves study of molecules 3814 by recording the interaction of radiofrequency (Rf) electromagnetic radiations with the nuclei of molecules 3814 placed in a strong magnetic field.

The near infrared spectroscopy is most suitable because it can penetrate the skin and reach blood vessels 3950 and generally does not cause harm to humans. Compared to other spectroscopic methods the NIR spectroscopy conserves time and materials for the following reasons:
1. In-vivo noninvasive and nondestructive analysis of metabolites in blood vessels 3950
2. NIR provides molecular structural information of the metabolites.
3. Metabolites detection limits can be very low.
4. Faster analysis of metabolites detection times under one second.
5. Simultaneous multi metabolites analysis.
6. Physical properties and clinical biological effects can be calculated from spectra of samples.
7. Automated correction of background and interferences due to water, and other molecules 3814 is performed by means of computer algorithms.

The NIR spectroscopy for metabolites detection is governed by NIR spectroscopy fundamental equations 5710. The NIR spectroscopy fundamental equations 5710 consist of Planck's equation 5712, travelling wave equation 5714, speed of light 5716, wavenumber equation 5718, absorbance 5720, reflectance 5722, Kubelka-Munk Function 5726, and energy conservation equation 5728.

The Planck's equation 5712 $E=hf$ states that the energy of a particle of light (E), called a photon, is proportional to its frequency (f), by a constant factor (h). The travelling wave equation 5714 $v=f\lambda$ is the speed of the wave (v) which is equal to the product of frequency multiplied by wavelength ($\lambda\cdot$). The speed of light 5716 equation is (c) is equal to product of frequency (f) multiplied wavelength ($\lambda\cdot$). The speed of light (c) is 299,792,458 m/s. The wavenumber equation 5718 $w=1/\lambda$ states that wavenumber (w) is inverse of frequency $(1/\lambda)$.

The absorbance 5270 is governed by Beer-Lambert law. It can be expressed in multiple ways. Absorbance (A) is the flip side of transmittance and states how much of the light the metabolites or sample has absorbed. It is also referred to as optical density (OD). Absorbance is calculated as a logarithmic function of Transmission (T) as shown in equation $A_\lambda = -\log 10(T_\lambda)$. Transmission $(T_\lambda)$ is defined as the ratio of the transmitted light intensity to the incident light intensity, $I/I_O$. It is also expressed as logarithm ratio of intensity of light "I" that reaches smart band 200 detector to the incident light intensity "$I_O$". There is a linear relationship between absorbance and metabolite concentration. It is expressed as $A=\varepsilon cl$, where the variables are absorbance (A), concentration (c), sample path length (l). The molar absorptivity (extinction coefficient) ($\varepsilon$) is a proportionality constant for a specific absorbance of a substance. The Beer's law is valid for only transparent samples.

The reflectance 5722 $R=-\log_{10}(I_R/I_{RO})$ equation allows calculation of the reflectance. The variable $I_R$ is the intensity of light reflected by the sample and $I_{RO}$ is the light reflected by a non-absorbing material.

The diffuse reflectance Kubelka-Munk equation $f(C)=(1-R)^2/2R$ establishes a linear relationship between the concentration (C) and the diffuse reflectance (R). The reflectance as stated above is obtained by $R=I_R/I_{RO}$.

The energy conservation equation $A+R+T+S=1$ states that absorbance (A), Reflectance (R), Transmission (T), and scattering (5) is equal to 1. The formulae allow conversion between A, R, T and S.

At normal temperature most of the molecules 3814 are in their fundamental vibrational energy levels which is equilibrium 5742 state. Molecules of atoms 3812 participating in chemical bonds are displaced if radiation energy is transferred to them as shown in stretched 5744. The radiation is largely thermal energy which induces stronger molecular vibrations in covalent bonds, which can be viewed as springs holding together two masses, or atoms.

The infrared spectroscopy is due to radiation causing changes in molecular vibrations. The vibrations of polyatomic molecules (Ax2 group) 5760 is due to symmetric stretch 5762, asymmetric stretch 5764, rocking 5766, scissoring 5768, wagging 5770, and twisting 5772. All these phenomena are used to determine the metabolites 5040 and lipids 5080.

The metabolites 5040 and lipids 5080 diffuse reflectance spectroscopy identification and classification are based on both supervised and unsupervised methods. For supervised methods class variability is supplied to mobile healthcare software 250 in the training set with spectra from a representative number of samples of the same class and providing all possible spectral variability, due to physical, chemical, and sample presentations.

The first step in the analysis of near infrared (NIR) data is the evaluation of the spectra that are obtained by scanning over the range of NIR wavelengths. The absorbance and/or diffuse reflectance spectrum obtained for a pure compound with molecular formula and chemical structure like biofluid analyte exhibits multiple peaks and troughs corresponding to maximum and minimum absorbance and/or diffuse reflectance over a range of wavelengths. The dependence of peak height on the biofluid analytes is then used to measure the substance of interest. However, the identification of peaks, particularly in complex mixtures such as blood, is often very difficult. Calculation of the first or second derivative of the absorbance and/or diffuse reflectance with respect to wavelength allows for more accurate identification of a peak and the measurement of peak heights for a particular biofluid analyte. This includes FTIR analysis, partial least squares (PLS) analysis, and multivariate analysis.

FIG. 58 lists principal types of NIR absorption bands and their locations 5810, and biofluid chemical NIR vibrational mode list 5850, according to some embodiments.

The principal types of NIR absorption bands and their locations 5810 shows listing of wavelengths (nm), frequency, wavenumber, and corresponding vibrational bonds. In the NIR region metabolites 5040 and lipids 5080, absorption bands come from overtones, combinations of overtones, and combinations of fundamental vibrational motions. The overtone bands and combination bands are much less intense and are broader than the corresponding fundamental absorption bands. The overtone bands are principally the O—H, N—H, and C—H stretching modes. The diffuse reflectance spectra allow detection of the metabolites 5040 and lipids 5080.

The biofluid chemical NIR vibrational mode list 5850 lists approximate wavenumber in nm and vibrational mode. The vibrational mode peaks and overtones based on the bond enable the detection of metabolites 5040 and lipids 5080.

FIG. 59 shows a metabolites molecular formula and chemical structure 5900 for albumin MF 5912, bilirubin MF 5914, blood glucose MF 5916, blood alcohol MF 5918, blood urea nitrogen MF 5920, cortisol MF 5922, creatinine MF 5924, and electrolyte MF 5926. The molecular formula and chemical structure allow identification of the expected diffuse reflectance bands based on vibration bonds.

FIG. 60 shows a metabolites and lipids molecular formula and chemical structure 6000 for ALP MF 6012, ALT MF 6014, AST MF 6016, cholesterol MF 6018, cholesteryl ester MF 6020, phospholipids MF 6022, and triglycerides MF 6024. The molecular formula and chemical structure allow identification of the expected diffuse reflectance bands based on vibration bonds. As listed in biofluid lipid panel parameters, detection sensor, and detected normal reference ranges 5400 table, the HDL 5082, LDL 5084 have well defined percentages of cholesteryl ester and phospholipids, with molecular formulae enabling their detection.

FIG. 61 illustrates a BML sensor diffuse reflectance spectroscopy working principle diagram 6110, BML sensor NIR diffuse reflectance spectroscopy operating principle diagram 6150, and diffuse reflectance detection method 6180, according to some embodiments.

The BML sensor diffuse reflectance spectroscopy working principle diagram 6110 is based on that not only does light reflected from the sample come from the surface as specular reflected light element 6116, but some is reflected internally as diffuse reflected light 6114. The incident light from NIR LEDs 6112 reaches the skin surface 3924 and reaches the blood vessel 3950 in the dermis 3930. It strikes the healthy blood vessel 3950 and biofluid. The diffuse reflected light 6114 is the reflection of light or other waves or particles from the blood gases 5010, blood cells 5020, metabolites 5040, and lipids 5080 such that a ray incident on the surface is scattered at many angles rather than at just one angle as in the case of specular reflected light 6116. Diffuse reflected light 6114 is more suitable for detection of blood metabolites 5040 and lipids 5080. The diffuse reflected light 6114, scattering and absorbance by metabolites 5040 and lipids 5080 contribute to change in the signal intensity. The metabolites 5040 or lipids 5080 concentration is calculated from the signal obtained in this type of measurement by Kubelka-Munk function 5726 or through non-linear equation of (C)=log (1/R) where $I_R$ is the intensity of radiation reflected by the metabolites 5040 or lipids 5080 and $I_{RO}$ the same quantity reflected by a non-absorbing metabolite 5040 or lipids 5080 over the whole spectral range of measurement. The measurement of $I_R$ and $I_{RO}$ requires the collection of the scattered radiation by a spherical photodetector element 6120.

The BML sensor NIR diffuse reflectance spectroscopy operating principle diagram 6150 comprises following processing steps:

1. Find the healthy blood vessel 3950 under the wrist skin surface 3924 in the dermis 3930 using picoprobe element 392B5, picoprobe element 392B6, and picocamera element 392B3. The incident light element 6152 and reflected light element 6154 are used to detect the healthy blood vessel 3950.
2. Irradiate a beam of incident NIR light element 6162 using LEDs element 392B1 on a healthy blood vessel 3950 in dermis 3930 with a desired and specific band of wavelengths. The incident light element 6164 continues to travel through dermis 3930. The reflected light element 6166 is detected by PDs element 392B2.
3. Detect the metabolite 5040 or lipids 5080 as per diffuse reflectance detection method 6180.
4. Analyze the diffuse reflectance spectra fingerprint to determine the complete metabolites 5040 and lipids 5080 molecules.

The diffuse reflectance detection method 6180 processing steps are as follows:

1. Irradiation with NIR light source of metabolites, and lipid molecules 6182
2. Excitation of metabolites and lipid components 6184
3. Certain bonds respond by vibrating faster. Photodetector and signal conditioning 6186
4. Calculate and record diffuse reflectance spectra fingerprint 6188

The example spectra are as shown in albumin, bilirubin, BUN, cortisol, creatinine diffuse reflectance spectra 6210; ALP ZnMg surrogate absorption line spectrum 6310; ALT NH2 and AST NH3 surrogate diffuse reflectance spectra 6320; and lipids diffuse reflectance spectra 6330.

FIG. 62 shows albumin, bilirubin, BUN, cortisol, creatinine diffuse reflectance spectra 6210, NIR wavelength embedding method 6230, electrolyte absorption line spectrum 6240, and electrolytes absorption line wavelength locations 6260, according to some embodiments.

The albumin, bilirubin, BUN, cortisol, creatinine diffuse reflectance spectra 6210 figure shows exemplary diffuse reflectance spectra signature of albumin spectrum 6212, bilirubin spectrum 6214, blood urea nitrogen spectrum 6216, cortisol spectrum 6218, and creatinine spectrum 6220 detected using diffuse reflection detection method 6180.

The NIR wavelength embedding method 6230 is used to detect the electrolytes 5056 in blood vessels 3950 using both NIR and visible light. The NIR wavelength allows for in vivo penetration under the skin surface 3924, and the visible portion is used for the absorption line spectrum to detect the electrolytes 5056. For example, the input NIR wavelengths $N\lambda_1$, $V\lambda_2$, $N\lambda_3$, and $V\lambda_4$ are segmented in the wavelength segmentation 6232 processing step. The segmented waves NIR $N\lambda_1$ is combined with visible $V\lambda_2$, and NIR $N\lambda_3$ is combined with visible $V\lambda_4$ in the processing step wavelength embedding 6234. NIR light waves segments are bigger than visible light. This allows the visible light of a given wavelength to hitch a ride in the NIR light to reach blood vessels 3950. In the processing step MUX, different near infrared and visible light wavelengths combinations are multiplexed and are incident on electrolytes 5056 in the blood vessels 3950. The reflected received light is demultiplexed in the DEMUX processing step where it separates a multiplex signal into its component parts. In the processing step wavelength division 6236 the different near infrared and visible light combination wavelengths are separated. In the processing step wavelength restore 6238, the reflected received light is further processed and combined light wave is reconstructed into separate NIR and visible light wavelengths. The visible light $V\lambda_2$ was absorbed by the electrolytes 5056 as such portion of it was not reflected. The absorption line spectrum is primarily determined by the atomic and molecular composition of the electrolytes 5056. For example, if $V\lambda_2$ wavelength of 422.7 is absorbed, it signifies the presence of calcium 5056Ca in the blood. The near infrared light is also combined with infrared light to detect the ALT and AST because their vibrational wavelength range is between 3,030 nm and 2,850 nm.

The electrolyte absorption line spectrum 6240 figure shows exemplary absorption line spectrum of calcium ASL 6242, chloride ASL1 6244-1, chloride ASL2 6244-2, magnesium ASL1 6246-1, magnesium ASL2 6246-2, phosphorus ASL 6248, potassium ASL 6250, and sodium ASL 6252.

The electrolytes absorption line wavelength locations 6260 table lists the electrolyte element and corresponding absorption line wavelengths.

FIG. 63 illustrates an ALP ZnMg surrogate absorption line spectrum 6310, ALT NH2 and AST NH3 surrogate diffuse reflectance spectra 6320, and lipids diffuse reflectance spectra 6330, according to some embodiments. The Y axis is shown in the form of Absorbance=1−(DR−T−S), where DR is Diffuse Reflectance, T is Transmission and S is Scattering values based on energy conservation equation 5728.

Alkaline phosphatase (ALP) is a protein found in all body tissues and blood. Tissues with higher amounts of ALP include the liver, bile ducts, and bone. High levels of ALP can indicate liver disease or bone disorders. Currently a blood test is done to measure the level of ALP. The measurement of ALP level in physiological fluids such as plasma or serum is generally accomplished using spectrometric, spectrophotometric, or electrochemical detection techniques. The current commonly used clinical method of quantifying ALP is the spectrophotometric method based on a procedure published by McComb et al. The ALP is a homodimeric protein enzyme. It is found throughout the body. As shown in part of ALP MF 6012 chemical structure, each monomer contains five cysteine residues, two zinc (Zn1, Zn2) atoms and one magnesium (Mg) atom crucial to its catalytic function. Due to ALP composition and ALP MF 6012 chemical structure, it is challenging to detect through diffuse reflectance spectroscopy. A surrogate method is used since ALP of interest cannot be easily measured or computed. Combined absorption line spectrum of two zinc (Zn1, Zn2) atoms at wavelength (481, 589 nm) and close by magnesium (Mg) atoms at wavelength (383.8, 518.4 nm) is used to detect ALP using NIR wavelength embedding method 6230.

Alanine aminotransferase (ALT) is an enzyme found primarily in the liver and kidney. The alanine aminotransferase (ALT) results are used to check for liver damage. ALT results enable finding out if a disease, drug, or injury has damaged the liver. The liver makes a fluid called bile that helps the body digest food. The spectrophotometric detection is the widely adopted clinical standard method in the determining the plasma or serum concentration of ALT. In this detection method, the measurement of the absorbance change of nicotinamide adenine dinucleotide (NADH) concentration at 340 nm UV light is used based on the pyruvate reaction with lactate dehydrogenase (LDH). The activity of ALT is calculated by measuring the increase of fluorescence value at the excitation wavelength of 535 nm and the emission wavelength of 590 nm. In the reaction, the AST catalyzes the reversible transamination of L-aspartate and α-ketoglutarate to oxaloacetate and L-glutamate. The oxaloacetate is then reduced to malate in the presence of malate dehydrogenase with the concurrent oxidation of NADH to NAD. ALT MF 6014 shows presence of NH2 amine functional group. It consists of stretching vibration with assignment of scissoring and wagging.

The aspartate aminotransferase (AST) result checks for liver damage. Aspartate aminotransferase is a pyridoxal phosphate-dependent transaminase enzyme. NH3 has a rich spectrum in the near infrared region, in the spectral range from 1450 nm to 1560 nm.

The lipids diffuse reflectance spectra 6330 illustrates finger spectrum of HDL spectrum 6332, LDL spectrum 6334, triglycerides spectrum 6336, total cholesterol spectrum 6338, and water spectrum 6340 detected using diffuse reflection detection method 6180. The water spectrum 6340 is important and very close to peaks of other spectrum. Fourier transform infrared (FTIR) spectroscopy analysis permits fine discrimination between like lipids and water.

FIG. 64 illustrates a blood glucose and alcohol sensor diffuse reflectance operating principle diagram 6410, blood glucose diffuse reflectance spectrum 6450, blood glucose level 6460, blood alcohol diffuse reflectance spectrum 6470, and blood alcohol level 6480, according to some embodiments.

Noninvasive in vivo optical blood glucose and alcohol detection methods include near-infrared reflectance spectroscopy (NIRS), fluorescence, polarized optical rotation, and so on. Blood glucose and alcohol require continuous monitoring, and as such dedicated sensors LEDs element 392B8 and PDs element 392B9 are used.

The blood glucose and alcohol sensor operating principle 6410 comprises following processing steps:
1. Find the healthy blood vessel 3950 under the wrist skin surface 3924 in the dermis 3930 using picoprobe element 392B5, picoprobe element 392B6, and picocamera element 392B3. The incident light element 6412, and reflection light element 6414, and captured backscattered reflection element 6416 and image of healthy blood vessels 3950 at a calculated penetration depth using picocamera 392B3 are used to detect the healthy blood vessel 3950.
2. Irradiate a beam of incident light element 6422 using LEDs element 392B8 on a healthy blood vessel 3950 in dermis 3930 with a desired and specific band of wavelengths. The reflected light element 6424 is detected by PDs element 392B9.
3. The blood glucose and blood alcohol detection are as per BML sensor diffuse reflectance spectroscopy working principle diagram 6110.
4. Analyze the blood glucose diffuse reflectance spectrum 6450 to determine the blood glucose level 6460 over a period. For example, the blood glucose 5046 value at 12 μm was around 105 mg/dL.
5. Analyze the blood alcohol diffuse reflectance spectrum 6470 to determine the blood alcohol level 6480. For example, the blood alcohol 5048 concentration at 11 μm was 0.12 percent.

FIG. 65 illustrates an example biokinetics sensor pinout 6510, and a biokinetics sensor wiring table 6550 describing the hardware wiring connection steps of a biokinetics sensor pinout 6510 connected to the single board computer general purpose input output pinout 370 that can be utilized to implement various embodiments.
1. Log in to the single board computer 350 operating software and access general purpose input output pinout 370 settings. Assign and map the general purpose input output pinout 370 to be connected to a biokinetics sensor pinout 6510. Save general purpose input output pinout 370 settings.
2. Connect the biokinetics sensor pinout 6510 to a single board computer 350 assigned general purpose input output pinout 370 as listed in the biokinetics sensor 396 wiring table 6550. The hardware implementation of the biokinetics sensor 310 is complete after the biokinetics sensor pinout 6510 is connected to a single board computer 350 general purpose input output pinout 370.
3. Prepare the single board computer 350 operating software to communicate with the biokinetics sensor 396 by loading the general purpose input output pinout 370 software library and installing the biokinetics sensor 396 software drivers.
4. Program, install, execute, and run the biokinetics sensor 396 software on the single board computer 350 operating software.

The biokinetics sensor 396 software is part of mobile healthcare application 250.

The biokinetics sensor 396 has SCL OUT 6516, SDA OUT 6518, INTR OUT 6520, DRDY OUT 6522, POS+ OUT 6524 and NEG− OUT 6526 outputs for detecting biokinetics positions. The outputs are from the sensor components BK accelerometer sensor 396A, BK gyroscope sensor 396B, BK ultrasound sensor 396C, BK magnetometer sensor 396D, and BK piezoelectric sensor 396E.

The wearable device 100 smart band 200 biokinetics sensor 396 is configured to detect, measure, and monitor biokinetics parameters of the user 8710 comprising:
Walking 6662; Standing 6664; Sitting 6666; Running 6668; Yoga 6670; Hiking 6672; Cycling 6674; Swimming 6676; Movement 6678; Exercise 6680; Sleep 6682; Stress 6684; Fall 6686; and Proximity to an object 6688;

Wherein the set microbial biosensor 310 parameters result, the set of particulate matter sensor 320 parameters result, the set of enviro sensor 330 parameters result, the set of physiological sensor 390 parameters result, and the set of biofluid sensor 392 parameters result are configured to predict to predict a set of biokinetics sensor 396 parameters normal reference range as listed in biokinetics parameters, detection sensor, detected normal reference ranges 6700; and wherein the cause and the treatment are accurately determined based on the correlated smart band sensor parameter result value;

Wherein the set of biokinetics sensor parameters result comprises: a parameter name, a result value, a flag, a unit, a normal reference range, and a intelligent relationship interpretation; and wherein the intelligent relationship interpretation comprises: a symptom, a cause, and a treatment when the set of biokinetics sensor parameters result value falls outside a normal reference range; and wherein the cause and the treatment are accurately determined based on the related smart band sensor parameter result value; For example, the intelligent relationship interpretation determines the accurate cause of physiological sensor parameter high heart rate 4216 is due tachycardia or related biokinetics sensor parameter excessive running 6668 value outside the normal reference range and provide accurate treatment information in the form of beta blockers drug or slowing down the intense running 6668 activity;

Wherein the set of biokinetics sensor 396 parameters result is configured to predict a biokinetics risk level. The biokinetics sensor 396 parameter risk level is calculated based on the severity ranking, probability of occurrence ranking, and detection ranking using the parameter result value as described in risk level definition and in an example smart band sensor risk level and corrective action and preventive action table 9520. Overall biokinetics risk level is an average of all the individual biokinetics sensor 396 parameters risk level;

Wherein the biokinetics risk level above a predetermined threshold level is configured to send a biokinetics risk alert to the mobile healthcare application 250 as shown in an example smart band alert 9510; and Wherein a biokinetics risk level assessment is configured to output a corrective action and a preventive action to ensure the set of biokinetics sensor parameters result value are within normal reference range as described in FIG. 66 and FIG. 67 to improve physical wellness dimension ranking, and an occupational wellness dimension ranking as described in an example smart band sensor risk level and corrective action and preventive action table 9520.

FIG. 66 illustrates a human musculoskeletal system diagram 6610, and biokinetics position diagram 6660, according to some embodiments.

Human musculoskeletal system diagram 6610 is composed of two main body systems which are the muscular system and skeletal system, that work together to perform the different processes. The figure woman muscles 6612 and man muscles 6614 illustrate different type of muscles responsible for body movements. The important muscles include neck 6822, arm 6624, thigh 6626, leg 6628, pivot joint 6632, hinge joint 6634, ball and socket joint 6636, wrist joint 6638, condyloid joint 6640, knee joint 6642, and gliding joint 6644. The biokinetics sensors comprising accelerometer sensor 396A, gyroscope sensor 396B, ultrasound sensor 396C, magnetometer sensor 396D, and piezoelectric sensor 396E allow monitoring of the musculoskeletal and muscle system. This biokinetics parameters monitoring allow for eating a healthy diet which is good for joints, because it helps build strong bones and muscles. The biofluid parameter calcium 5056Ca results also provide recommendations for eating foods such as milk, yogurt, broccoli, kale, figs, and fortified foods like soy or almond milk for proper functioning of joints.

The biokinetics position diagram 6660 comprises walking 6662; standing 6664; sitting 6666; running 6668; yoga 6670; hiking 6672; cycling 6674; swimming 6676; movement 6678; exercise 6680; sleep 6682; stress 6684; fall 6686; and proximity to an object 6688.

FIG. 67 lists biokinetics parameters detected normal reference ranges 6700.

The table list comprises biokinetics parameter, human anatomy, detection sensor, and normal reference ranges. The biokinetics parameters detected comprise walking 6662; standing 6664; sitting 6666; running 6668; yoga 6670; hiking 6672; cycling 6674; swimming 6676; movement 6678; exercise 6680; sleep 6682; stress 6684; fall 6686; and proximity to an object 6668. The sleep 6682 recommended ranges are calculated based on physiological and AGMP sensors. The stress 6684 results are based on cortisol, physiological sensor, and AGMP sensors results. The normal reference ranges are automatically set based on the smart band 200 user 8710 demographics information and a microbial biosensor, a particulate matter sensor, an enviro sensor, a physiological sensor, a biofluid sensor, a biokinetics sensor, and a lifestyle sensor parameters result. Smart band 200 biokinetics sensor 396 detects these parameters. The biokinetics parameter normal reference ranges are user configurable for a day, week, or month to monitor overall exercise and physical activities.

FIG. 68 illustrates biokinetics parameters detection methods, according to some embodiments.

The biokinetics parameters detection methods 6800 comprises:

BK accelerometer sensor operating diagram 6810 illustrates the movement of an object in x, y, and z direction. An accelerometer sensor element 396A is used to measure the acceleration or deceleration of forces exerted upon the sensor. The intended use of the accelerometer sensor element 396A is to measure the various movements of the user 8710 body such as walking motion 6812.

BK gyroscope sensor operating diagram 6830 illustrates measuring or maintaining the orientation and angular velocity of the wearable device using the gyroscope sensor element 396B. The spin axis 6832 is the axis that the gyro rotor is rotating. The input axis 6836 is the axis about which the spin axis 6832 rotation of the gyro causes a maximum output axis 6834. The intended use of the gyroscope sensor element 396A is to measure the various movements of the user 8710 body.

BK ultrasound sensor operating diagram 6850 illustrates the ultrasound sensor element 396C consisting of a transmitter and receiver to measure the distance to a wide range of objects regardless of shape, color, or surface texture. It is used to detect proximity to an object. The ultrasound sensor element 396C provides alerts to the person walking 6852 when it they are closer to an object such as room wall 6854.

BK magnetometer sensor operating diagram 6860 illustrates working of a magnetometer sensor element 396D to sense smart band 200 orientation in space to determine user 8710 location with respect to magnetic north (or south). A magnetometer measures magnetic field or magnetic dipole moment. Magnetometer sensor element 396D works on the principle of Hall effect, as shown in directions 6864, if a current carrying conductor is placed in the magnetic field, a voltage (V) is generated which is perpendicular to both current (I) and magnetic field (B). The intended use of magnetometer sensor element 396D is to monitor orientation.

BK piezoelectric sensor operating diagram 6880 illustrates working of piezoelectric sensor element 396E. Piezoelectricity is the charge created across certain materials when a force is applied resulting in the voltage across a piezoelectric element generated by the applied force. Surface electromyography is used to detect musculoskeletal movements and activities which are controlled via nerves emitting signals which can be measured at the wrist skin's surface. The piezoelectric sensor element 396E is used to detect hand gestures. Since the palm side of the wrist deflects noticeably during finger flexion gestures, the deflections can be measured using an array of piezoelectric sensor elements 396E. The accelerometer sensor element 396A, gyroscope sensor element 396B, magnetometer sensor element 396D, and piezoelectric sensor element 396E are the four main sensors we use for detecting motion and orientation.

FIG. 69 illustrates an example lifestyle sensor pinout 6910, and a lifestyle sensor wiring table 6950 describing the hardware wiring connection steps of a lifestyle sensor pinout 6910 connected to the single board computer general purpose input output pinout 370 that can be utilized to implement various embodiments.

1. Log in to the single board computer 350 operating software and access general purpose input output pinout 370 settings. Assign and map the general purpose input output pinout 370 to be connected to a lifestyle sensor pinout 6910. Save general purpose input output pinout 370 settings.
2. Connect the lifestyle sensor pinout 6910 to a single board computer 350 assigned general purpose input output pinout 370 as listed in the lifestyle sensor 398 wiring table 6950. The hardware implementation of the lifestyle sensor 398 is complete after the lifestyle sensor pinout 6910 is connected to a single board computer 350 general purpose input output pinout 370.
3. Prepare the single board computer 350 operating software to communicate with the lifestyle sensor 398 by loading the general purpose input output pinout 370 software library and installing the lifestyle sensor 398 software driver.
4. Program, install, execute, and run the lifestyle sensor 398 software on the single board computer 350 operating software.

The lifestyle sensor 398 software is part of mobile healthcare application 250.

The lifestyle sensor 398 has the following output channels:

1. BTA OUT 6916 is the output pin for breath sample output from the breath analyzer sensor 398A.
2. SCL OUT 6918, and SDA OUT 6920 are output pins for wrist 2912 movement from the LS gyroscope 398B, and picocamera element 398C1 and 318 to record number of meals, drinks, number of bathroom visits, and so on.
3. FSYNC OUT 6922 is the output pin connected to picocamera element 398C1 image stabilization system.
4. INTR OUT 6924 is the output pin for interrupts. This is used to generate an interrupt when there is no activity and puts the lifestyle sensor 398 to sleep mode.
5. SMK OUT 6926 is the output pin for detecting the number of smoking occurrences. The type of smoking recorded is cigarettes, marijuana, cigar, etc. with the help of hand gesture and pictures from picocamera element 398C1 and 318 when the resulting smoke is orally inhaled.
6. AUD OUT 6928 is the output pin for detecting the various type of sounds such as number of occupational interactions 7064, number of financial interactions 7066, number of intellectual interactions 7068, number of emotional interactions 7070, number of social interactions 7072, and number of spiritual interactions 7074. The user 8710 voice input is transcribed and converted into different interaction types using artificial intelligence algorithms. For privacy reasons, no voice or transcription recording is stored in the system.

The lifestyle results are from the breath analyzer sensor 398A, LS gyroscope 398B, picocamera element 398C1 and 318, LS smoke sensor 398D, and LS sound sensor 398E.

The wearable device 100 smart band 200 lifestyle sensor 398 is configured to detect, measure, and monitor lifestyle parameters of the user 8710 comprising:

A breath analyzer sensor 398A configured to detect, measure, and monitor a breath sample comprising: an alcohol 7012, an amphetamine 7014, a benzoylecgonine 7016, a cocaine 7018, a heroin (6-acetylmorphine) 7020, a marijuana (tetrahydrocannabinol) 7022, a methamphetamine 7024, and a morphine 7026. The result can be programmed to be displayed as positive/negative or based on cutoff value. The cutoff can be screen cutoff or confirmation cutoff value. Cut ff levels are used to determine whether to report out a negative test result. The confirmation test is then the definitive testing for a positive result. Lifestyle parameters, detection sensor, and detected normal reference ranges 7000 table lists example cutoff values. The breath alcohol level can also be displayed in standard color coded format as 1 green band means that the blood-alcohol level is 0.05% or lower, 2 green bands mean a level between 0.05% and 0.10%, 3 green bands mean a level between 0.10% and 0.15% and so on;

A number of meals 7050; a set of food types 7052;
A number of drinks 7054; a set of drink types 7056;
A number of bathroom visits 7058;
A number of smoking occurrences 7060;
A number of occupational interactions 7062;
A number of financial interactions 7064;
A number of intellectual interactions 7066;
A number of emotional interactions 7068;
A number of social interactions 7070;
A number of spiritual interactions 7072;

Wherein the set microbial biosensor parameters result, the set of particulate matter sensor parameters result, the set of enviro sensor parameters result, the set of physiological sensor parameters result, the set of biofluid sensor parameters result, and the set of biokinetics sensor parameters result enable prediction of a set of lifestyle sensor parameters normal reference range;

Wherein the set of lifestyle sensor parameters result comprises: a parameter name, a result value, a flag, a unit, a normal reference range, and an intelligent relationship interpretation; and wherein the intelligent relationship interpretation comprises: a symptom, a cause, and a treatment when the set of lifestyle sensor parameters result value falls outside the normal reference range; and wherein the cause and the treatment are accurately determined based on the correlated smart band sensor parameter result value; For example, the intelligent relationship interpretation determines the physiological sensor parameter respiratory rate 4220 irregularity accurate cause is due to related microbial biosensor parameter pathogenic virus 614 or related lifestyle sensor parameter number of smoking occurrence 7060 outside normal reference range and provide accurate treatment information in the form of controlling exposure to pathogenic virus 614 or decrease or quit smoking/tobacco intake.

Wherein the set of lifestyle sensor 398 parameters result is configured to predict a lifestyle risk level. Each lifestyle sensor 398 parameter risk level is calculated based on the severity ranking, probability of occurrence ranking, and detection ranking using the parameter result value as described in the risk level definition and in an example smart band sensor risk level and corrective action and preventive action table 9520. Overall lifestyle risk level is an average of all the individual microbial biosensor 310 parameters risk level.

Wherein the lifestyle risk level above a predetermined threshold level is configured to send a lifestyle risk alert to the mobile healthcare application 250 of the user 8710 as shown in an example smart band alert 9510; and Wherein a lifestyle risk level assessment is configured to output a corrective action and a preventive action to ensure the set of lifestyle sensor parameters result value as described in FIG. 70, FIG. 73, and FIG. 74 are within normal reference range to improve an occupational wellness dimension ranking, a financial wellness dimension ranking, an intellectual wellness dimension ranking, an emotional wellness dimension ranking, a social wellness dimension ranking, and a spiritual wellness dimension ranking as described in an example smart band sensor risk level and corrective action and preventive action table 9520.

FIG. 70 lists lifestyle parameters, detection sensor, and detected normal reference ranges.

The table list comprises lifestyle parameter, human anatomy, detection sensor, and normal reference ranges. The normal reference ranges help describe what is typical for a particular group of people based on age, sex, and other characteristics. The normal reference ranges are automatically set based on the smart band 200 user 8710 demographics information and a microbial biosensor, a particulate matter sensor, an enviro sensor, a physiological sensor, a biofluid sensor, a biokinetics sensor, a lifestyle sensor parameters result. The lifestyle parameter normal reference ranges are user 8710 configurable for a day, week, or month to monitor and track overall exercise and physical activities.

FIG. 71 illustrates a breath analyzer sensor working principle 7110, and breath analyzer sensor test method 7150, according to some embodiments.

The breath analyzer sensor working principle 7110 illustrates the design of breath analyzer sensor 398A and chemiresistor sensor operating principle 7130.

The breath analyzer sensor 398A consists of materials that changes its electrical resistance in response to changes in the nearby chemical environment such as breath sample 7132. The breath analyzer sensor 398A consists of spherical substrate 7122, chemiresistive sensing material layer 7124, and set of 4 chemiresistive sensing material controls 7128. The chemiresistive sensing material layer 7124 consists of many pillars. Each pillar consists of 8 different chemiresistive sensing material chips for each of the 8-breath sample parameter or analytes to be detected. This allows increase of the uniformity and sensitivity of the breath sample 7132 results. The chemiresistive sensing material layer 7124 is made of metal-oxide semiconductors, conductive polymers, and nanomaterials like graphene, carbon nanotubes, and nanoparticles that have chemiresistor properties. The sensing is based on chemical interaction between chemiresistive sensing material and chemical structure of alcohol 7012, amphetamine 7014, benzoylecgonine 7016, cocaine 7018, heroin (6-acetylmorphine) 7020, marijuana (tetrahydrocannabinol) 7022, methamphetamine 7024, and morphine 7026. The normal exhaled breath sample 7132 is predominantly composed of 79% nitrogen, 13.6-16.0% oxygen, 4.0-5.3% carbon dioxide, as well as water vapor. The set of 4 chemiresistive sensing material controls 7128 is used to detect the nitrogen, oxygen, and carbon dioxide. A breath sample 7132 results are valid if set of 4 chemiresistive sensing material controls 7128 readings for nitrogen, oxygen, and carbon dioxide are within 5%.

The method of operating the wearable device 100 breath analyzer sensor test method 7150 comprises the following steps:
1. Strap the wearable device 100 around the wrist 2912 of the user 8710;
2. Power on the wearable device 100 with smart band 200 by pressing the band power button 388;
3. Face the breath analyzer sensor 398A to an oral cavity 2890 of the user 8710;
4. Auto verify the identity of the oral cavity 2890 of the user 8710;
5. Exhale breath sample 7132 for 3 times with a gap of 5 seconds between each exhale;
6. Detect the breath analytes of the user 8710 with the breath analyzer sensor 398A;
7. Display the breath analytes or parameters results on the mobile healthcare application 250.

FIG. 72 illustrates various lifestyle parameters detection methods 7200, according to some embodiments.

The LS gyroscope 398B and picocamera element 398B and 318 allow for recognizing an eating activity and inferring what and how much the user eats. The dietary habits have been studied by health researchers and it is well-understood that diet plays a critical role in overall human health. To map the diet and disease, doctors usually rely on verbal conversation or food frequency questionnaires. There are neck collars for swallow detection, or ear microphones for chewing. The form factor and placement make the automated food intake monitoring difficult. The smart band 200 LS gyroscope 398B senses the eating gestures, and picocamera element 398C1 records the type of food that was eaten.

LS gyroscope operating diagram 7210 illustrates recognizing eating activities as part of automated food intake monitoring. This is done using LS gyroscope 398B and picocamera element 398C1 and picocamera 318. The inferring eating moments are based on 3-axis accelerometry collected through LS gyroscope 398B. The example gestures illustrate the grabbing 7212, holding 7214, twist 7216, roll 7217, and eating 7220 of an apple. The picocamera element 398C1 and picocamera 318 capture items eaten and their composition.

The LS camera operating diagram 7230 illustrates automated food and drinks 7232 intake monitoring in the oral cavity 2890. The LS gyroscope 398B and picocamera element 398C1 along with picocamera 318 allow for recognizing an eating activity and inferring what and how much the user 8710 eats and drinks.

The LS smoke sensor operating diagram 7240 shows the man smoking 7244 events detected by the smoke sensing element schematic circuit 7242 of LS smoke sensor 398D. The types of smoking event recorded are cigarettes, cigars, marijuana, and so on.

The LS sound sensor operating diagram 7260 sound sensor unit 7262 consists of LS sound sensor 398E which detects the sound waves 7264 and monitors various interactions such as occupational, financial, intellectual, emotional, social, spiritual interactions 7266, and noise pollution 7268. The user 8710 voice input is transcribed and converted into different interaction types using artificial intelligence algorithms.

FIG. 73 illustrates a human wellness dimensions wheel 7310, and a human wellness dimensions description 7350.

The human wellness dimensions wheel 7310 comprises a physical 7312, an environmental 7314, an occupational 7316, a financial 7318, an intellectual 7320, an emotional 7322, a social 7324, and a spiritual 7326.

The human wellness dimensions description 7350 table contains detailed description of each of the wellness dimension.

FIG. 74 lists a human wellness dimensions database 7410, human wellness dimensions reference ranges 7420, human wellness dimensions detection methods 7450, and example personalized wellness programs, according to some embodiments.

The human wellness dimension database 7410 comprises query, quiz, test, worksheets, and so on. The wellness ranking is scored based on the interactive quiz on the mobile healthcare application 250 configured to provide a plurality of web pages and a plurality of wellness programs. A survey that has wellness dimension is delivered to the user via the plurality of web pages. The user provides a response to the survey that has a plurality of numerical scores for each of the wellness dimensions. Each of the wellness dimensions are configured to improve the health and wellness of the user. Each of the wellness dimensions have a predefined numerical equation for health and wellness categories to calculate numerical scores. The wellness dimension score is further refined using wellness dimension specific databases such as Nutrition.gov, FoodData Central, Health.gov, CDC, meeting invite planners, credit card company ratings, and so on. The database information is also used to annotate the scoring results to calculate the wellness dimension ranking.

The human wellness dimensions reference ranges 7420 lists wellness dimension ranking, definition, and description. The wellness dimension ranking is classified as excellent=5, very good=4, good=3, fair=2, and poor=1.

The human wellness dimensions detection methods 7450 comprises following steps:
1. User 8710 submits wellness dimensions mobile healthcare application quiz and worksheet 7452
2. Calculate and rank wellness dimension ranking results using sensor data 7454
3. Acquire user wellness dimension data from the internet 7456
4. Normalize and calculate the wellness dimension ranking 7458

The annotation data provides guidance on how to improve the wellness dimension ranking. The wellness dimension ranking contributes to sense of wellness or quality of life, and each affect and overlaps the others. There is no particular order and at times one may be more prominent than others, but neglect of any one dimension for any length of time has adverse effects on overall health. The automated monitoring of wellness dimension ranking allows user 8710 to focus on improving the health and quality of life. The example personalized wellness programs 7490 describes each wellness dimension based programs.

Figure 75:
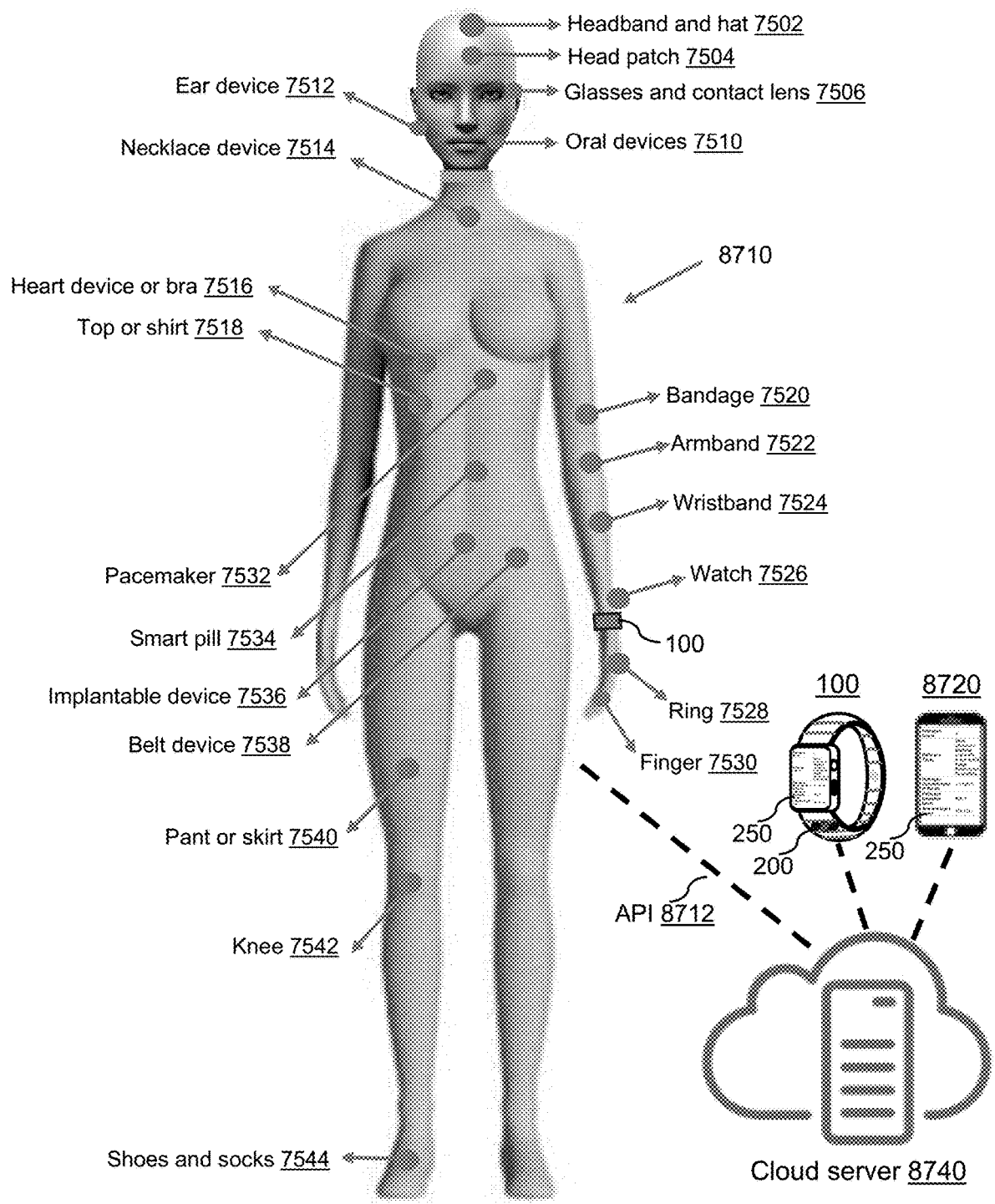
FIG. 75 illustrates a human wearable electronics application diagram, according to some embodiments.

FIG. 75 illustrates a human wearable sensors application diagram 7500, according to some embodiments.

The wearable electronics has revolutionized the way various parameters are sensed, detected, and monitored. In recent years, advances in flexible and stretchable hybrid electronics have enhanced the compliance of devices to our skin, and inside the body. Some of the wearable electronics sensors comprise headband and hat 7502, head patch 7504, glasses and contact lens 7506, oral devices 7510, ear device 7512, necklace device 7514, heart device or bra 7516, top or shirt 7518, bandage 7520, armband 7522, wristband 7524, watch 7526, ring 7528, finger 7530, pacemaker 7532, implantable device 7536, belt device 7538, pant or skirt 7540, knee 7542, shoes and socks 7544, and so on. All these wearable electronics sensors can send the data to cloud server 8740. The wearable electronics sensor data is accessed by the mobile healthcare application 250 installed on the smart band 200 or mobile devices 8720 using application programming interface (API) 8712. The wearable electronics sensors data is used to further refine the results from microbial biosensor 310, particulate matter sensor 320, enviro sensor 330, physiological sensor 390, biofluid sensor 392, biokinetics sensor 396, and lifestyle sensor 398 using novel AI algorithms and methods 8748.

Figure 76:
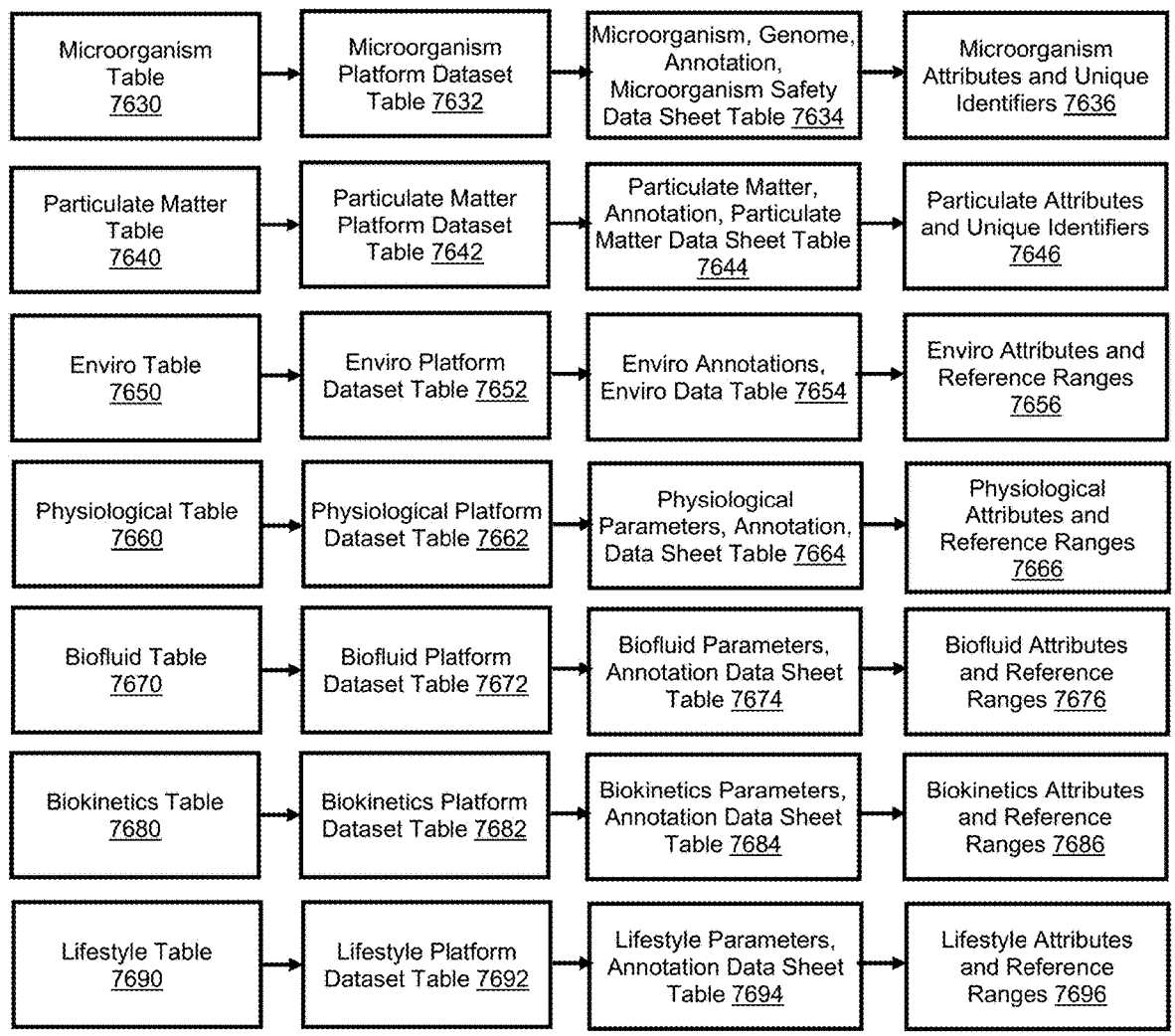
FIG. 76 lists smart band data sets and smart band sensor type database, according to some embodiments.

FIG. 76 lists smart band data sets 7610 and smart band sensor type database 7620. The smart band datasets 7610 consist of sensor specific platform datasets from variety of sources, annotations, attributes, and unique identifiers as listed in the table. The smart band sensor type database 7620 consists of microorganism, a particulate matter, an enviro, a physiological, a biofluid, a biokinetics, a lifestyle specific dataset, annotation, data sheet, attributes, and unique identifiers. The smart band sensor type database 7620 schema shows the structure of the individual database and relations between database objects. The unique identifiers are used by the microbial biosensor, a particulate matter sensor, an enviro sensor, a physiological sensor, a biofluid sensor, a biokinetics sensor, and a lifestyle sensor to detect, measure, and monitor the sensor specific parameters.

FIG. 77 clinical laboratory test discipline and test methods list 1 7700 is a table listing medical discipline, subdiscipline, and clinical laboratory test methods description. The table lists discipline anatomic pathology, chemistry and toxicology, clinical biochemical genetics, cytogenetics, forensic drug testing, hematology, and coagulation and corresponding subdiscipline and clinical laboratory test methods description. These tests are part of clinical laboratory tests that are ordered by the physician for the patient. The patient clinical laboratory test results accuracy is increased by adding additional sensor parameter results with explanation of the way in which they are connected. The explanation or description is based on the scientific validity of the relationship between a clinical laboratory test result and sensor parameter result.

FIG. 78 clinical laboratory test discipline and test methods list 2 7800 is a table listing medical discipline, subdiscipline and clinical laboratory test methods description. The table lists discipline immunology, microbiology, molecular pathology, point-of-care testing (poc), and urinalysis and corresponding subdiscipline and clinical laboratory test methods description. These tests are part of clinical laboratory tests that are ordered by the physician for the patient.

FIG. 79 commonly ordered clinical laboratory tests 7900 is a table listing human anatomy, sample type, and commonly ordered clinical laboratory tests description. The table lists human anatomy areas of complete blood test (hematology), complete metabolic panel (e.g., kidney, liver, pancreas), cholesterol test (cardiovascular system), drugs and toxins, endocrinology system, gastroenterology, oncology, immunology, musculoskeletal system, nephrology/kidney/renal system, nervous system, reproductive system, respiratory system, vitamins, and trace elements, and corresponding sample type required and commonly ordered clinical laboratory tests. These commonly ordered clinical laboratory tests are requested by the physician to test for functioning of the patient human anatomy area.

FIG. 80 endocrinology ordered clinical laboratory tests 8000 is a table listing endocrinology system, human anatomy area, and commonly ordered clinical laboratory tests description. The table lists endocrinology which is a branch of physiology and medicine concerned with endocrine glands and hormones, human anatomy area, and commonly ordered clinical laboratory tests. These commonly ordered clinical laboratory tests are requested by the physician to test for functioning of the patient endocrinology system.

For FIG. 77-80 the accuracy of the patient clinical laboratory test results performed using clinical laboratory test methods is increased by adding sensor parameter results with explanation of the way in which they are connected. The explanation or description is based on the scientific validity of the relationship between a clinical laboratory test result and sensor parameter result.

FIG. 81-84 tables list the intelligent relationship interpretation between clinical laboratory test results and sensor parameters.

FIG. 81 is an example intelligent relationship interpretation table 1 between sensor parameters 8100. The table first column lists the blood glucose level, RBC count, hemoglobin, WBC count, platelet count, and blood oxygen saturation with normal reference ranges. The next columns list corresponding sensor parameters such as body temperature, heart rate, and blood pressure normal reference ranges.

FIG. 82 is an example intelligent relationship interpretation table 2 between sensor parameters 8200. The table first column lists the carbon dioxide, calcium, phosphorous, potassium, and sodium normal reference ranges. The next columns list corresponding sensor parameters such as body temperature, heart rate, and blood pressure normal reference ranges.

FIG. 83 is an example intelligent relationship interpretation table 3 between sensor parameters 8300. The table first column lists the blood glucose level, RBC count, hemoglobin, WBC count, platelet count, and blood oxygen saturation normal reference ranges. The next columns list corresponding sensor parameters such as pollution, altitude, and ambient temperature normal reference ranges.

FIG. 84 is an example intelligent relationship interpretation table 4 between sensor parameters 8400. The table first column lists the carbon dioxide, calcium, phosphorous, potassium, and sodium normal reference ranges. The next columns list corresponding sensor parameters such as pollution, altitude, and ambient temperature normal reference ranges.

The intelligent relationship interpretation description in FIG. 81-84 contains detailed information about relationship between the smart band 200 sensor parameters. The intelligent relationship interpretation holds true in case of parameters result value is detected through clinical laboratory test results, clinical devices, other smart watches, wearable electronics and so on. For example, the biofluid parameters comprising complete blood count, complete metabolic panel, and lipid panels can be clinical laboratory tests result. The accuracy of patient smart band 200 sensor parameters and/or clinical laboratory test results is increased by providing the intelligent relationship interpretation when the clinical laboratory test results are abnormal. Results that lie outside the normal reference ranges are abnormal. These can be values which are below the lower limit or above the higher limit or in the case of an infectious disease, a positive result.

FIG. 85 is an example clinical laboratory test critical results range 8500. The laboratories commonly refer to critical values as results requiring immediate notification to the physician or caregiver for necessary patient evaluation or treatment to avert significant patient morbidity or mortality. The clinical laboratory test results that lie outside the normal reference ranges are abnormal. These can be values which are below the lower limit or above the higher limit. The critical results are usually values which are beyond the abnormal lower and upper limits or in the case of an infectious disease a positive result. The example table lists the chemistry, toxicology, hematology, arterial blood gases test, virology test, and coagulation test biomarker or analyte critical values. For example, the WBC count normal reference range for male is 3.9-11.7×10E3/μL, and for female is 4.0-11.6×10E3/μL. In the case of WBC count the critical results are a value of ≤2.0 or value of ≥40×10E3/μL. These values are beyond the abnormal lower and upper limits. In addition, for some infectious diseases, the critical results are usually positive results. For example, positive detection of SARS-CoV-2 virus is a critical result which should be immediately reported to the physician and regulatory authorities.

Figure 86:
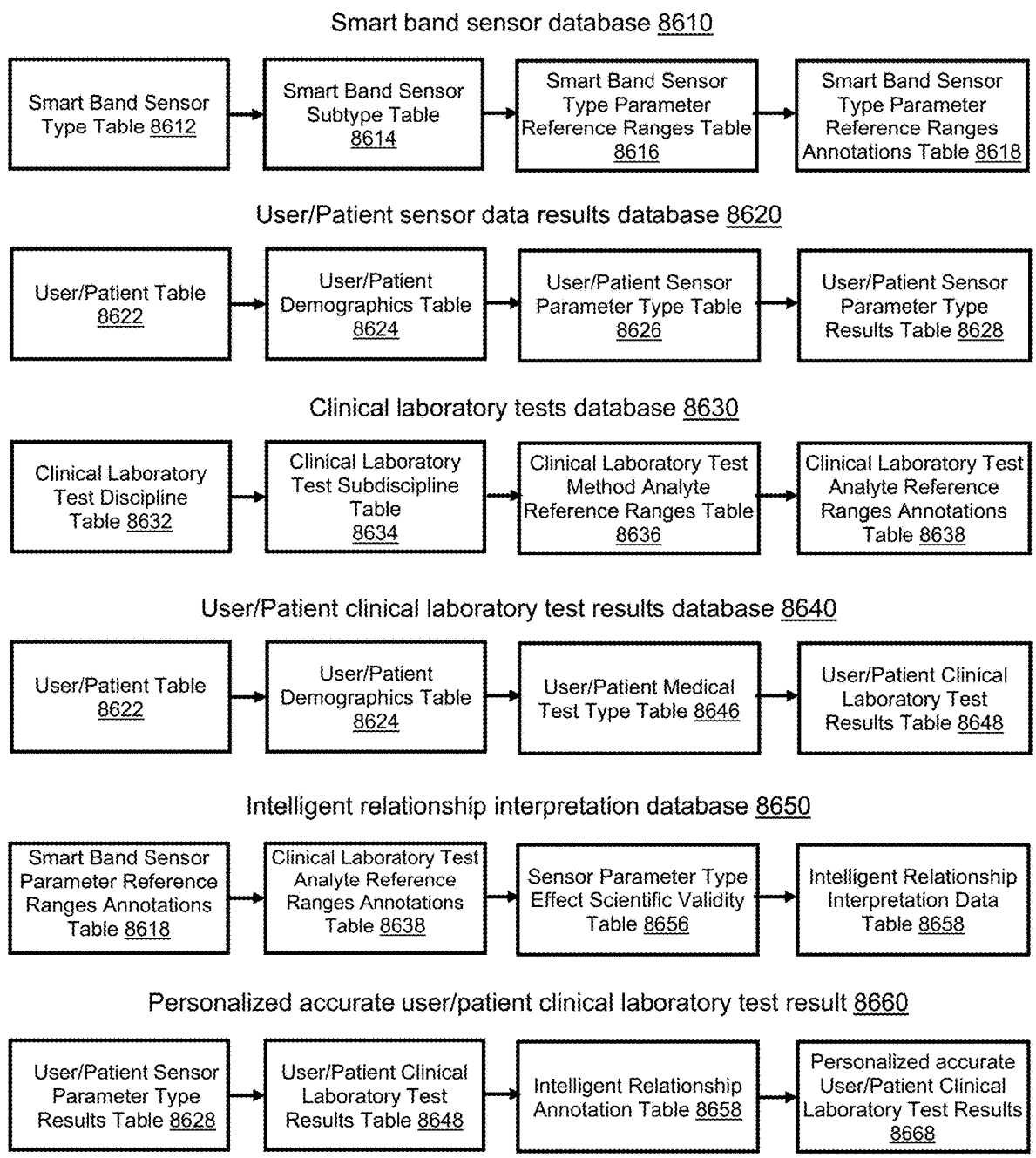
FIG. 86 is an example list of databases, according to some embodiments.

FIG. 86 is an example list of databases. The list of databases is smart band sensor database 8610, user/patient sensor data results database 8620, clinical laboratory tests database 8630, user/patient clinical laboratory test results database 8640, intelligent relationship interpretation database 8650, and personalized accurate user/patient clinical laboratory test result 8660. The FIG. 86 database schema shows the structure of the individual database and relations between database objects. The smart band sensor type table 8612 contains information about the smart band sensor type database 7620. The user/patient sensor data results database 8620 comprises user/patient demographic data such as name, age, gender, weight, and so on including user/patient sensor parameters results from the smart band 200. The clinical laboratory tests database 8630 contains information about the medical test discipline, subdiscipline, clinical laboratory test method analyte reference ranges of FIG. 77-80, and annotations about what the abnormal results mean. The user/patient clinical laboratory test results database 8640 consists of user/patient demographic and user/patient clinical laboratory test results. The results are annotated for abnormal value. The intelligent relationship interpretation database 8650 comprises the relationship tables of FIG. 81-84. The personalized accurate patient/user clinical laboratory test result 8660 is the curated results from user/patient sensor parameters and clinical laboratory test results with intelligent relationship interpretation.

Figure 87:
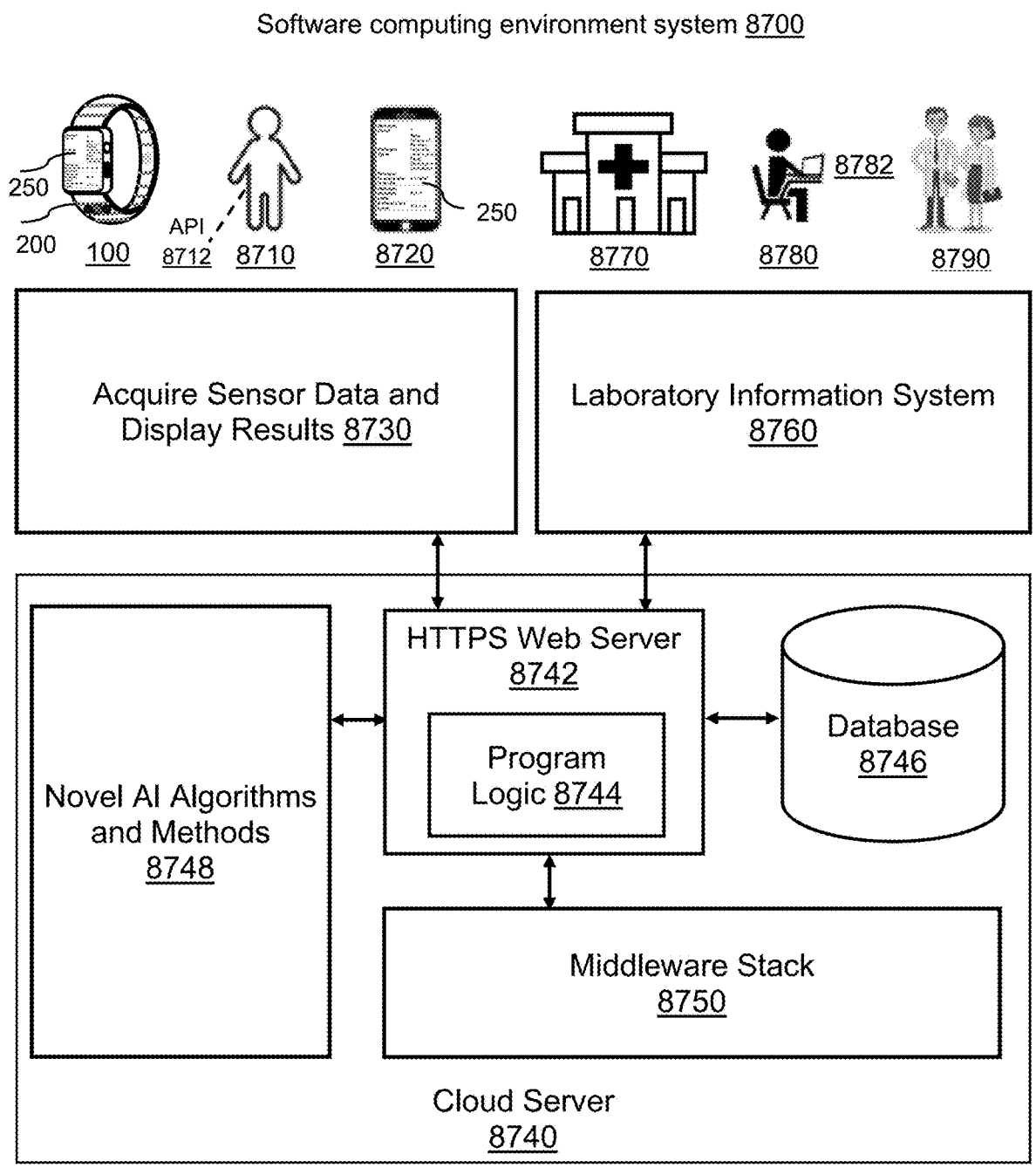
FIG. 87 illustrates an example system computing environment system that can be utilized to implement various embodiments.

FIG. 87 illustrates an example software computing environment system 8700, which can be utilized to implement various embodiments.

A system comprising:

A wearable device 100 consisting of a smart band 200 and a display unit 102. The smart band 200 comprises a microbial biosensor 310, a particulate matter sensor 320, an enviro sensor 330, physiological sensor 390, biofluid sensor 392, biokinetics sensor 396, lifestyle sensor 398, a single board computer 350, a power supply unit 380, a band fastener 202, and a set of watch adapters 204 and 206. The watch adapters 204 and 206 allow smart band 200 to be connected to any watch;

A display unit 102 comprises a touchscreen 104, a display unit power button 106, a crown 108, and a set of attachment slots 110 and 112;

A power supply unit 380 comprises a wireless charging unit 382, a battery 384, a charging port 386, and a band power button 388;

A mobile healthcare application 250 allows a user to access the smart band sensor data;

A mobile device 8720;

A cloud server 8740;

A laboratory testing facility 8770;

A laboratory computer 8782;

A laboratory information system 8760;

An intelligent relationship interpretation data;

A user clinical laboratory test result;

An application programming interface;

Wherein the smart band 200 is configured to detect a set of sensor parameters comprising: a microorganism parameter, a particulate matter parameter, an enviro parameter, a physiological parameter, a biofluid parameter, a biokinetics parameter, and a lifestyle parameter;

Wherein the smart band 200 set of sensor parameters result comprises: a parameter name, a result value, a flag, a unit, a normal reference range, and an intelligent relationship interpretation; and wherein the intelligent relationship interpretation comprises: a symptom, a cause, and a treatment when the set of sensor parameters result value falls outside the normal reference range;

Wherein a user 8710 smart band 200 sensor result comprises: a set of microbial biosensor parameters result, a set of particulate matter sensor parameters result, a set of enviro sensor parameters result, a set of physiological sensor parameters result, a set of biofluid sensor parameters result, a set of biokinetics sensor parameters result, and a set of lifestyle sensor parameters result;

Wherein the user 8710 smart band 200 sensor result is configured to output a diagnosis, a monitoring, a screening, a prevention, a prediction, a predisposition, a prognosis, a treatment, or an alleviation of a disease;

Wherein the user 8710 smart band 200 sensor result is configured to output a personalized daily nutritional goal comprising nutrient, and a daily reference intake required to maintain a healthy diet;

Wherein the user 8710 smart band 200 sensor result is configured to output a a personalized dietary pattern comprising food, and an amount required to maintain the healthy diet;

Wherein the user 8710 smart band 200 sensor result is configured to output a personalized daily nutritional goal comprising a nutrient, a source of goal, a personal dietary reference intake, and an intelligent nutrient required recommendation to maintain a healthy diet. An example personalized daily nutritional goal comprising nutrient and daily reference intake 10300 lists nutrients, source of goals, DRI goal, personal DRI and intelligent nutrient required recommendations based on the age, gender, body weight, height, and user smart band sensor result;

Wherein the user 8710 smart band 200 sensor result is configured to output a personalized dietary pattern comprising a food, an amount, and an intelligent food required recommendation to maintain the healthy diet. An example personalized dietary pattern comprising food and amount 10400 lists food, amount, and intelligent food required recommendation;

Wherein the user 8710 smart band 200 sensor result is configured for continuous monitoring of a user health for an accurate clinical outcome assessment and a personalized wellness program for a healthy lifestyle; FIG. 105 lists an example personalized wellness program;

Wherein noninvasive in vivo measurement of the user smart band sensor result allows for a reduced number of hospital visits, a reduced medical waste, and a reduced healthcare cost;

Wherein the user clinical laboratory test result comprises: allergy; body scan; anesthesiology; cardiovascular; chemistry; dental; ear, nose, and throat; gastroenterology and urology; general and plastic surgery; genetics; hematology; immunology; infectious disease; microbiology; neurology; obstetrical and gynecological; ophthalmic; orthopedic; pathology; physical medicine; radiology; and toxicology;

Wherein the application programming interface comprises a set of functions enabling a cloud application to access a set of wearable electronics sensor data;

Wherein a set of personalized user wellness dimensions comprises: physical, environmental, occupational, financial, intellectual, emotional, social, and spiritual;

Wherein a personalized user wellness dimension ranking is classified as: excellent=5, very good=4, good=3, fair=2, and poor=1; and The smart band sends and receives a set of sensor signals through a wireless network to the mobile healthcare application 250 installed on the mobile device 8720, and to the cloud server 8740.

The software computing environment system 8700 illustrates the operation steps as follows:

The processing step acquire sensor data and display results 8730 is responsible for collecting and sending the wearable device 100 smart band 200 data to the cloud server 8740. The data from set of wearable electronics is acquired through the API 8712. The data is also locally stored in the secure digital card 360 for standalone processing of the data. The data collected is from microbial biosensor 310, particulate matter sensor 320, enviro sensor 330, physiological sensor 390, biofluid sensor 392, biokinetics sensor 396, and lifestyle sensor 398. The wearable device 100 smart band 200 data values results can be displayed on the mobile healthcare application 250.

The processing step HTTPS web server 8742 is used for secure communication over a computer network between a client and server. The program logic 8744 performs decision making based on sensor data and allows branching to different parts of the mobile healthcare application 250 and laboratory information system 8760. The program logic 8744 is responsible for sending the information about novel AI algorithms and methods 8748 to be executed based on the user 8710 request. The middleware stack 8750 acts as a bridge between the operating system, database 8746, and the application software like the mobile healthcare application 250 and laboratory information system 8760 to display the data rapidly. The database 8746 contains smart band database 8610, user/patient sensor data results database 8620, clinical laboratory tests database 8630, user/patient clinical laboratory test results database 8640, intelligent relationship interpretation database 8650, and personalized accurate patient/user clinical laboratory test result 8660, and so on.

In processing step novel AI algorithms and methods 8748, the sensor data is processed through the system cloud server 8740 and sent to the database 8746 system to be stored. The novel AI algorithms and methods 8748 are responsible for following activities:

1. Perform the wearable device 100 smart band 200 microbial biosensor 310 data, a particulate matter sensor 320 data, an enviro sensor 330 data, physiological sensor 390 data, biofluid sensor 392 data, biokinetics sensor 396 data, and lifestyle sensor 398 data analysis and evaluation using corresponding methods. The De Novo AI-based "Artificial Intelligence based Clinically Accurate Result (AICAR) algorithm" does big data analytics using inputs comprising patient clinical laboratory test results, user 8710 smart band data, and set of human wearable electronics application diagram 7500 data to report out accurate patient clinical laboratory test results with intelligent relationship interpretation.
2. Display the microbial biosensor 310, particulate matter sensor 320, enviro sensor 330, physiological sensor 390, biofluid sensor 392, biokinetics sensor 396, and lifestyle sensor 398 results on mobile healthcare application 250.
3. Analyze the wearable device 100 microbial biosensor 310 data comprising a particulate matter sensor 320 data, an enviro sensor 330 data, physiological sensor 390 data, biofluid sensor 392 data, biokinetics sensor 396 data, and lifestyle sensor 398 data clusters to predict the microbial risk level, pathogen biosafety risk level, a pollen allergy risk level, a dust mite allergy risk level, particulate matter risk level, enviro risk level, physiological risk level, biofluid risk level, biokinetics risk level, and lifestyle risk level. If any of the risk levels are above the predetermined threshold level, an alert is sent to the mobile healthcare application 250.

4. Make real-time updates to the wearable device 100 data.

In processing step laboratory information system 8760 in the laboratory testing facility 8770, a laboratory director 8780 using a laboratory computer 8782 is responsible for the review and routing the user/patient 8710 results to the physician 8790. The laboratory testing facility can be College of American Pathologist (CAP), Clinical Laboratory Improvement Amendments (CLIA), or ISO 15189 medical laboratories certified.

The software computing environment system 8700 wearable device 100 sends the microbial biosensor 310 parameters result, a particulate matter sensor 320 parameters result, enviro sensor 330 parameters result, physiological sensor 390 parameters result, biofluid sensor 392 parameters result, biokinetics sensor 396 parameters result, and lifestyle sensor 398 parameters result to the cloud sever. The laboratory director 8780 reviews the results and determines the cause of disorders and reports out a user/patient 8710 test results. The physician 8790 reviews user/patient 8710 clinical laboratory test results in conjunction with the sensor data and determines the root cause of the disorder to treat the user 8710.

Microorganisms 610, pollen grains 630, and dust mite allergens 640 can all cause sinusitis and lung disorders. The microbial biosensor 310 parameters result, the particulate matter sensor 320 parameters result, and the enviro sensor 330 parameters result of user 8710 test results allow for accurate determination of nasal and lung related disorders. The precise root cause allows the physician 8790 to provide the right treatment to the user/patient 8710.

The mobile healthcare application 250 comprises a set of functionalities to set up, control, and display data results of the wearable device 100. The setup functionality allows mobile healthcare application 250 to send and receive the data from wearable device 100. The control functionality allows sensor settings. The configurable display data results functionality allows the user/patient 8710 to change the look and feel of the results displayed on the mobile healthcare application 250.

A laboratory information system 8760 comprises a set of functionalities to monitor user 8710 test results, microbial biosensor 310 results, particulate matter sensor 320 results, enviro sensor 330 results, physiological sensor 390 results, biofluid sensor 392 results, biokinetics sensor 396 results, and lifestyle sensor 398 results. The wearable device 100 real time data view allows laboratory director 8780 and physician 8790 to take appropriate measures in case of critical value results wherein the variance with normal is life-threatening if therapy is not instituted immediately.

The cloud server 8740 comprises a cloud sever memory, wherein the cloud server memory comprises a wearable device 100 model, wherein the wearable device 100 model comprises a set of wearable device attributes. The set of wearable device attributes comprises a wearable device unique device identifier (UDI), a name, an RFID tag, a geospatial position, an altitude, an ambient light level, a gas type, a smoke level, a temperature, a humidity, a pressure, a sound level, an ultraviolet light index, an air quality index, and so on.

The system 8700 further comprises a method of operating the cloud server 8740, wherein the method includes following steps:
1. Strap the wearable device 100 around a user wrist 2912;
2. Power on the wearable device 100 by pressing the band power button 388;
3. Receive the user smart band 200 sensor result by the cloud server 8740;
4. Receive the user clinical laboratory test result from the laboratory information system 8760;
5. Receive the set of wearable electronics sensor data;
6. Calculate the set of personalized user wellness dimensions ranking from the user smart band sensor result, the user clinical laboratory test result, the intelligent relationship interpretation data, and the set of wearable electronics sensor data;
7. Calculate an accurate personalized wellness program for the healthy lifestyle from the set of personalized user wellness dimensions ranking; and
9. Send the set of personalized user wellness dimensions ranking and the accurate personalized wellness program to the user mobile healthcare application 250.

A personalized user wellness dimension ranking is classified as: excellent=5, very good=4, good=3, fair=2, and poor=1; and wherein the personalized user wellness dimension ranking presents the user with a personalized wellness program for a healthy lifestyle as described in Human wellness dimensions reference ranges 7420.

FIG. 88 illustrates a personalized accurate user/patient clinical laboratory test results method 8810, and personalized accurate user/patient clinical laboratory test critical results method 8850, according to some embodiments.

The system 8700 comprises a method of operating the cloud server 8740, wherein the method includes following steps:
1. Strap the wearable device 100 around the user wrist 2912
2. Power on the wearable device 100 by pressing the band power button 388;
3. Receive the user smart band sensor result by the cloud server 8740;
4. Receive the user clinical laboratory test result from the laboratory information system 8760;
5. Receive the set of wearable electronics sensor data;
6. Calculate a personalized user clinical laboratory test result for an accurate clinical outcome assessment from the user smart band sensor result, user clinical laboratory test result, intelligent relationship interpretation data, and the set of wearable electronics sensor data;
7. Send the personalized user clinical laboratory test result to the laboratory information system 8760;
8. Auto review and report out the personalized user clinical laboratory test result in the laboratory information system 8760 to a physician mobile healthcare application 250 installed on the mobile device 8720;
9. Automatically communicate a critical test result notification by the laboratory information system 8760 to the mobile healthcare application 250 installed on the mobile device 8720 of a physician 8790 responsible for the user's 8710 care; wherein the personalized user clinical laboratory test result exceeds an established critical test value that is important for prompt patient management decisions; and wherein the critical test result is an imminently life-threatening personalized user clinical laboratory test result requiring rapid clinical attention to avert significant patient morbidity or mortality;

10. Auto review the personalized user clinical laboratory test result by the physician 8790 or auto verification of the results by the laboratory information system 8760 to determine the root cause of a disorder to treat the disease for user 8710; and wherein the personalized user clinical laboratory test result enables the physician 8790 to review and make assessment of the critical value in context of the user smart band sensor result for an accurate clinical outcome assessment;

11. Prompt by critical test result notification confirmation of a receipt by the physician 8790 mobile healthcare application 250; and record the confirmation of receipt of the critical test result notification by the physician 8790 mobile healthcare application 250 in the laboratory information system 8760, comprising:

a date of communication;
a time of communication;
a responsible laboratory individual full name;
a notified physician full name; and
a user critical test result.

The steps to create a personalized accurate user/patient clinical laboratory test results method 8810 are as follows:

1a. Acquire and store patient/user sensor parameters result, patient/user clinical laboratory test results big data 8812.
2a. Execute Artificial Intelligence (AICAR) algorithm big data analytics using intelligent relationship interpretation table 8814.
3a. Create personalized user/patient clinical laboratory test results for accurate diagnosis and treatment 8816.
4a. Send personalized user/patient clinical laboratory test results to LIS, physician, and mobile healthcare application 8818.

Steps to create a personalized accurate user/patient clinical laboratory test critical results method 8850 are as follows:

Execute steps above 1a to 3a.
4b. Send personalized user/patient clinical laboratory critical test results to LIS, and mobile healthcare application 8858.
5b. Physician 8790 reviews and makes assessment of the critical value in context of the user smart band sensor result 8860.
6b. Critical result notification prompts confirmation of receipt by the physician 8790.
7b. Confirmation of receipt of the critical result notification by the physician 8790 is recorded in the laboratory information system 8760.
8b. Follow-up by the laboratory director 8780.

FIG. 89 illustrates a mobile healthcare application displaying sensor settings interface 8910, and a mobile healthcare application displaying smart band sensor result 8950, according to some embodiments.

The wearable device 100 has the mobile healthcare application 250 installed on the single board computer.

The mobile healthcare application 250 is configured to be installed on a mobile device 8720 wherein the smart band sends and receives signals through a wireless network to the mobile healthcare application installed on the mobile device.

The mobile healthcare application 250 sensor setting functionality allows the user 8710 to configure a smart band sensor setting comprising: a smart band on/off functionality, a sensor on/off functionality, a reportable range, an alert threshold, and a parameter result unit.

The mobile healthcare application 250 displays the set microbial biosensor 310 parameters result, the set particulate matter sensor 320 parameters result, the set enviro sensor 330 parameters result, the set physiological sensor 390 parameters result, the set biofluid sensor 392 parameters result, the set biokinetics sensor 396 parameters result, and the set lifestyle sensor 398 parameters result. The set biofluid sensor 392 parameters result consists of CBC sensor parameters result and BMC sensor parameters result. The set of lifestyle sensor parameters result consists of daily lifestyle sensor result, breath analyzer sensor result, and wellness activity result.

The mobile healthcare application 250 displays an intelligent relationship interpretation, a risk alert, a risk level, a safety data sheet, a corrective action, and a preventive action.

The mobile healthcare application 250 enables continuous monitoring of a user 8710 health and a wellness program for a healthy lifestyle.

The example mobile healthcare application displaying sensor settings interface 8910 consists of sensor settings 8912 comprising microbial biosensor settings, particulate matter sensor settings, enviro sensor settings, physiological sensor settings, biofluid sensor settings, biokinetics sensor settings, lifestyle sensor settings, and other wearable sensor settings 8914. Clicking on any settings link displays a settings window. The settings window allows the user 8710 to change the default normal reference range of the sensor parameter. The settings window allows enabling any of the sensors to an on state or an off state. In the off state the sensor does not detect any parameters. The settings window also allows user 8710 to turn on or off individual sensor parameters to be detected.

The example mobile healthcare application displaying smart band sensor data results 8950 comprises sensor results 8952, clinical laboratory test results 8954, wearable electronics sensor data 8956, and smart band alerts 9500. The sensor results 8952 comprises Microbial biosensor parameters result, particulate matter sensor parameters result, enviro sensor parameters result, physiological sensor parameters result, biofluid sensor parameters result, biokinetics sensor parameters result, lifestyle sensor parameters result, and wellness dimension parameters result. The biofluid sensor parameters result consists of CBC sensor parameters result, and BML sensor parameters result. The lifestyle sensor parameters result comprises daily lifestyle sensor parameters result, breath analyzer sensor parameters result, and wellness activity parameters result. Clicking on any sensor data link displays the detail results of all the sensor parameters. Clicking on any of the smart band alerts 9500 links displays a window with details for pathogen biosafety alert, pollen allergy alert, dust mite allergy alert, air quality alert, microbial risk alert, particulate matter risk alert, enviro risk alert, physiological risk alert, biofluid risk alert, biokinetics risk alert, lifestyle risk alert, and wellness dimension risk alert. The data results are customizable and displayed as per the user 8710 configured look and feel.

The functionality of the mobile healthcare application 250 installed on the native wearable device 100 or smartwatch or mobile device 8720 is the same.

The mobile healthcare application 250 displays the set microbial biosensor 310 parameters result, the set of particulate matter sensor 320 parameters result, the set of enviro sensor 330 parameters result, the set of physiological sensor 390 parameters result, the set of biofluid sensor 392 parameters result, the set of biokinetics sensor 396 parameters result, and the set of lifestyle sensor 398 parameters result on the touchscreen 104 or mobile device screen.

The display unit 102 is powered to an on-state or to an off-state by pressing the display unit power button 106. The data displayed on the touchscreen 104 is scrolled by rotating the crown or can be scrolled by moving the finger up or down on the touchscreen 104. There is an audio alert when the crown 108 is pressed. The audio alert can be used in case user 8710 needs some help. Selecting the pathogen type virus influenza A displays a pathogen safety data sheet of FIGS. 96, 97, and 98. Selecting the pollen type ragweed displays a pollen safety data sheet of FIG. 99.

The wearable device 100 mobile healthcare application 250 is enabled to be installed on a smartwatch, or a mobile device 8720.

The smart band 200 in this case sends and receives signals through a wireless network to the mobile healthcare application 250 installed on the smartwatch, or the mobile device 8720.

The wearable device 100 display unit 102 is removed from the smart band 200 by sliding the set of watch adapters 204 and 206 from the set of attachment slots 110 and 112, and the smartwatch is connected to the set of watch adapters 204 and 206.

The smart band 200 sends and receives signals through the wireless network to the mobile healthcare application 250 installed on smartwatch. In this case the smartwatch displays the microbial biosensor 310 parameters result, the particulate matter sensor 320 parameters result, and the enviro sensor 330 parameters result, the physiological sensor 390 parameters result, the biofluid sensor 392 parameters result, the biokinetics sensor 396 parameters result, and the lifestyle sensor 398 parameters result.

FIG. 90 illustrates an example mobile healthcare application displaying microbial biosensor nasal cavity parameters result 9010, and a mobile healthcare application displaying microbial biosensor oral cavity parameters result 9050, according to some embodiments.

The example mobile healthcare application displaying microbial biosensor nasal cavity parameters result 9010 element 9012 displays pathogen types of Virus SARS-CoV-2, Bacteria *Staphylococcus aureus*, and Fungi Saprophytic Fungus, and element 9014 displays a pathogen biosafety level of BSL-2.

The example mobile healthcare application displaying microbial biosensor oral cavity parameters result 9050 element 9052 displays pathogen types of Virus SARS-Cov-2, Bacteria *Legionella pneumophila*, and Fungi *Candida albicans*, and element 9054 displays a pathogen biosafety level of BSL-2. The element 9056 displays Intelligent relationship interpretation for blood oxygen=94.5%, and irregular respiratory rate=13-17 is due to pathogen infection.

Figure 91:
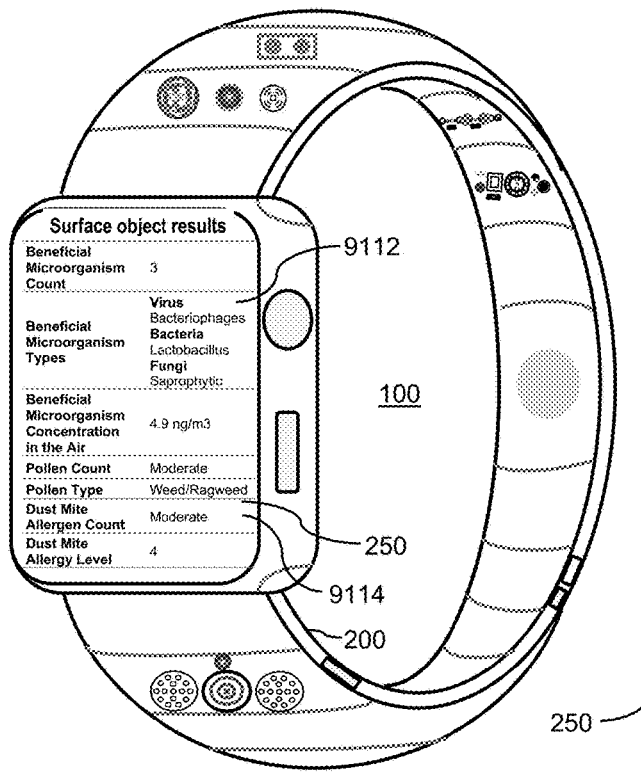
FIG. 91 illustrates an example mobile healthcare application displaying microbial biosensor surface object parameters result, and a mobile healthcare application displaying enviro sensor parameters result and particulate matter sensor parameters result, according to some embodiments.

FIG. 91 illustrates an example mobile healthcare application displaying microbial biosensor surface object parameters result 9110, and a mobile healthcare application displaying enviro sensor parameters results and particulate matter sensor parameters result 9150, according to some embodiments.

The example mobile healthcare application displaying microbial biosensor surface object parameters result 9110 element 9112 displays beneficial microorganism types of virus Bacteriophages, Bacteria *Lactobacillus*, and Fungi Saprophylic, and element 9114 displays a dust mite allergen count of moderate.

The example mobile healthcare application displaying enviro sensor parameters result and particulate matter sensor parameters result 9150 element 9152 displays pathogen types of Virus Influenza A, Bacteria *Staphylococcus*, and Fungi Aspergillosis, and element 9154 displays a beneficial microorganism type Bacteria *micrococcus*. The element 9156 displays intelligent relationship interpretation physiological sensor parameter result: Respirator Rate=18-21 due to pollen and dust mite allergen.

FIG. 92 illustrates an example mobile healthcare application displaying physiological sensor parameters result 9210, and a mobile healthcare application displaying biofluid sensor parameters CBC result 9250, according to some embodiments. The CBC result is part of the biofluid sensor parameters result.

The example mobile healthcare application displaying physiological sensor parameters result 9210 consists of physiological parameter results element 9212 for skin and body temperature, heart rate, heart rate variability, respiratory rate, blood pressure, electrocardiogram, blood oxygen saturation, blood carbon dioxide, and physiological risk level. The respiratory rate results above the normal range are shown in bold. This can be due to presence of SARS-CoV-2 in the nasal cavity. The intelligent relationship interpretation element 9214 shows the presence of microbial biosensor parameter result pathogen=SARS-CoV-2 in the nasal cavity.

The example mobile healthcare application displaying biofluid sensor parameters CBC result 9250 consists of complete blood count results element 9252, a red blood cell (RBC) count, a hemoglobin level, a hematocrit level, a mean corpuscular volume (MCV), a mean corpuscular hemoglobin (MCH), a mean corpuscular hemoglobin concentration (MCHC), a white blood cell (WBC) count, a white blood cell (WBC) differential, a platelet count, and biofluid risk level. The intelligent relationship interpretation element 9254 shows the presence of enviro sensor parameter altitude with a value of 6500 ft. The high WBC count and low platelet count values in bold can be due to user 8710 living at the high altitude of 6500 ft.

FIG. 93 illustrates an example mobile healthcare application displaying complete metabolic panel parameters result 9310, and a mobile healthcare application displaying biokinetics sensor parameters result 9350, according to some embodiments. The complete metabolic panel parameters result 9310 is part of the biofluid sensor parameters result. It also consists of complete cholesterol panel parameters result.

The example mobile healthcare application displays complete metabolic panel parameters result 9310. The complete metabolic panel results element 9312 comprises an albumin 5042, a bilirubin 5044, a blood glucose 5046 level, a blood alcohol 5048 level, a blood urea nitrogen (BUN) 5050, a cortisol 5052, a creatinine 5054, a calcium 5056Ca, a chloride 5056Cl, a magnesium 5056Mg, a phosphorus 5056P, a potassium 5056K, a sodium 5056Na, an alkaline phosphatase (ALP) 5060, an alanine aminotransferase (ALT) 5062, and an aspartate aminotransferase (AST) 5064. The cholesterol panel comprises an HDL cholesterol level, an LDL cholesterol level, a triglyceride level, and a total cholesterol level. The overall biofluid risk level is 2. The intelligent relationship interpretation element 9314 shows the presence of particulate matter sensor result: AQI=149 which means pollution could be the reason for the high blood glucose level.

The mobile healthcare application displaying biokinetics sensor parameters result 9350 shows the biokinetics parameter results element 9352 comprises walking 6662; standing 6664; sitting 6666; running 6668; yoga 6670; hiking 6672; cycling 6674; swimming 6676; movement 6678; exercise 6680; sleep 6682; stress 6684; fall 6686; and proximity to an object 6688. The intelligent relationship interpretation element 9354 shows that physiological sensor parameter result: high blood pressure=135/90 mmHg and biofluid sensor parameter: high cortisol=35 mg/dL results might be due to lower sleep value of 4.5 hours.

FIG. 94 illustrates an example mobile healthcare application displaying lifestyle sensor parameters result 9410, and a mobile healthcare application displaying wellness dimension parameters result 9450, according to some embodiments.

The example mobile healthcare application displaying lifestyle sensor parameters result 9410 comprises lifestyle parameter results element 9412 comprising breath parameters: an alcohol 7012, an amphetamine 7014, a benzoylecgonine 7016, a cocaine 7018, a heroin (6-acetylmorphine) 7020, a marijuana (tetrahydrocannabinol) 7022, a methamphetamine 7024, and a morphine 7026 if they are positive;

A number of meals 7050; a set of food types 7052;
A number of drinks 7054; a set of drink types 7056;
A number of bathroom visits 7058;
A number of smoking occurrences 7060;
A number of occupational interactions 7062;
A number of financial interactions 7064;
A number of intellectual interactions 7066;
A number of emotional interactions 7068;
A number of social interactions 7070;
A number of spiritual interactions 7072;

Wherein the microbial biosensor 310 parameters result, particulate matter sensor 320 parameters result, enviro sensor 330 parameters result, physiological sensor 390 parameters result, biofluid sensor 392 parameters result, and biokinetics sensor 396 parameters result enable prediction of a set of user lifestyle parameters normal reference ranges as listed in the lifestyle parameters, detection sensor, and detected normal reference ranges 7000;

The intelligent relationship interpretation element 9414 lists particulate matter sensor parameters result indicating that the quality of air is too poor. It is also very hot and humid.

The example mobile healthcare application displaying wellness dimension parameters result 9450 comprises demographic element 9452 containing user 8710 information and wellness dimension results 9454 comprising physical, environmental, occupational, financial, intellectual, emotional, social, and spiritual. In addition, it displays overall average total score and lifestyle risk level. The intelligent relationship interpretation element 9454 shows that apart from physiological sensor parameter result: Heart Rate=100, number of smoking occurrences=12, the AQI=135 might be resulting in the lower score for the environment dimension.

FIG. 95 illustrates an example smart band alert 9510, and smart band sensor risk level and corrective action and preventive action 9520, according to some embodiments.

The smart band 200 risk level comprises a microbial risk level, pathogen biosafety risk level, a pollen allergy risk level, a dust mite allergy risk level, particulate matter risk level, enviro risk level, physiological risk level, biofluid risk level, biokinetics risk level, and lifestyle risk level. If any of the risk levels are above a predetermined threshold level, a risk alert is sent to the mobile healthcare application 250. The smart band alert contains the detailed information about the corresponding sensor data value, risk level, date, and location.

The smart band alert 9510 illustrates example overall sensor based risk alert 9512, and parameter based risk alert 9514. Clicking on the risk alert provides details about risk level, parameter results, and the corrective actions and preventive actions.

The smart band risk level and corrective action and preventive action table 9520 lists risk level, health hazard, and example microbial biosensor risk, biofluid sensor risk, physiological sensor risk, particulate matter sensor risk, biokinetics sensor risk, and lifestyle sensor risk.

FIGS. 96, 97, and 98 illustrate an example pathogen safety data sheet.

FIG. 96 is an example page 1 of a pathogen safety data sheet, according to some embodiments. The mobile healthcare application 250 displays the pathogen type and data. In the example use case, SARS-CoV-2 virus was detected in the nasal cavity 2840, oral cavity 2890, on a surface 3050, or in the air, and displayed. Selecting the pathogen type SARS-CoV-2 virus hyperlink page 1 in the mobile healthcare application 250 displays the pathogen safety data sheet for SARS-CoV-2 virus. It contains information like infectious agent, hazard identification information, and dissemination/transmission. This information enables the user 8710 to take appropriate actions in case they have the SARS-CoV-2 virus.

FIG. 97 is an example page 2 of a pathogen safety data sheet, according to some embodiments. The mobile healthcare application 250 displays the pathogen type and data. In the example use case, SARS-CoV-2 virus was detected in the nasal cavity 2840, oral cavity 2890, on a surface 3050, or in the air, and displayed. Selecting the pathogen type SARS-CoV-2 virus page 2 hyperlink in the mobile healthcare application 250 displays the pathogen safety data sheet for SARS-CoV-2 virus. It contains information like stability and viability, first aid/medical, and laboratory hazards. This information enables the user 8710 to take appropriate actions in case they have the SARS-CoV-2 virus.

FIG. 98 is an example page 3 of a pathogen safety data sheet, according to some embodiments. The mobile healthcare application 250 displays the pathogen type and data. In the example use case, SARS-CoV-2 virus was detected in the nasal cavity 2840, oral cavity 2890, on a surface 3050, or in the air and displayed. Selecting the pathogen type SARS-CoV-2 virus page 3 hyperlink in the mobile healthcare application 250 displays the pathogen safety data sheet for SARS-CoV-2 virus. It contains information like exposure controls/personal protection, handling and storage, and regulatory and other information. This information enables the user 8710 to take appropriate actions in case they have the SARS-CoV-2 virus.

FIG. 99 is an example page 1 of a pollen safety data sheet, according to some embodiments. The mobile healthcare application 250 displays the pollen type and data. In the example use case, ragweed pollen was detected in the air surrounding the user 8710 and displayed. Selecting the pollen type ragweed hyperlink in the mobile healthcare application 250 displays the pollen safety data sheet for ragweed. It contains information like pollen type, allergy identification, diagnosis, first aid/medical, and regulatory. This information enables the user 8710 to take appropriate actions in case they have the ragweed allergy. The mobile healthcare application 250 can also display an entire pollen safety data sheet. In this case, the user 8710 must scroll down to view the information.

FIG. 100 illustrates an exemplary predicted surrogate user CBC test result from the user smart band sensor result 10010, and method to predict a surrogate user CBC test result 10050, according to some embodiments.

The exemplary predicted surrogate user CBC test result from the user smart band sensor result 10010 table lists predicted surrogate calculation from the physiological parameter. In the simplified example the multivariate analysis using physiological parameter normal reference ranges based on age is used to predict normal reference ranges for the surrogate blood cells RBC 5022, and WBC 5024, and Platelet 5026 values. In big data multivariate analysis, multiple user 8710 attributes such as age, gender, weight, and other factors are used. The calculation is based on a statistical model where the probability of one event taking place such as predicting a surrogate RBC value by having the log-odds for the event be a linear combination of one or more independent variables which includes physiological parameters, age, sex, weight, and so on.

The method to predict a surrogate user CBC test result 10050 consists of following steps:
1. Acquire and store user smart band sensor result 10052.
2. Execute CBC multivariate algorithm data analytics on user smart band sensor result 10054. The multivariate analysis consists of statistical analysis of the multiple parameters results of the smart band sensor data where the relationships among multivariate and their structure are used to predict biofluid parameter normal reference ranges.
3. Refine the surrogate user CBC test result based on intelligent relationship interpretation data 10056.
4. Predict a surrogate user CBC test result from the user smart band sensor result 10058.

The system 8700 further comprises a method of operating the cloud server 8740, wherein the method includes following steps:
1. Strap the wearable device 100 with smart band 200 around the user wrist 2912;
2. Power on the wearable device 100 by pressing the band power button 388;
3. Receive the user smart band sensor result, wherein the user smart band sensor result comprises a CBC sensor test result;
4. Receive the user clinical laboratory test result from the laboratory information system, wherein the user clinical laboratory test result comprises a user CBC clinical laboratory test result;
5. Predict a surrogate user CBC test result from the user smart band sensor result;
6. Calculate a first correlation coefficient between the user CBC sensor test result and the user CBC clinical laboratory test result;
7. Calculate a second correlation coefficient between the user CBC sensor test result and the surrogate user CBC test result;
8. Calculate an error correlation coefficient between first correlation coefficient and second correlation coefficient;
9. Send an error correlation alert to the user 8710 mobile healthcare application 250 when the error correlation coefficient is greater than or equal to 0.05; wherein the error correlation alert displays the clinical laboratory test result parameter/analyte error; and Wherein the surrogate user CBC test result is configured for a noninvasive measurement of a complete blood count for the user wrist with a vascular disease;

In summary, in the case of user 8710 with compromised blood vessels, the surrogate user CBC test results can be predicted.

FIG. 101 is an example personalized accurate user/patient clinical laboratory test results report 1 10101. The report contains patient details, health care physician, and the tests/analyte tested and patient results. The reported flag value is tagged as low or high compared to the normal reference range based on the patient demographics. For the low or high value of the flag, the clinical laboratory tests results comprise additional intelligent relationship interpretation element 10110 of physiological sensor parameter result: blood pressure 10112, particulate matter sensor parameter result: AQI 10114, enviro sensor parameter: altitude 10116, microbial biosensor parameter result: pathogen type virus 10118, and biokinetics sensor parameter result: exercise 10120 from the user/patient smart band sensor result. This information allows the physician 8790 to make accurate diagnosis, better treatment outcomes of the user/patient 8710, and eliminates unnecessary clinical testing and reduces the number of doctors and hospital visits by the user/patient 8710.

FIG. 102 is an example personalized accurate user/patient clinical laboratory test results report 2 10200. The report contains patient details, health care physician, and the tests/analyte tested and patient results. The reported flag value is tagged as low or high compared to normal reference range based on the patient demographics. For the low or high value of the flag, the clinical laboratory tests results comprise additional intelligent relationship interpretation element 10210 of physiological sensor parameter result: body temperature 10212, enviro sensor parameter: humidity 10214, lifestyle sensor parameter result: number of smoking occurrences 10216, physiological sensor parameter result: body temperature 10218, physiological sensor parameter result: blood pressure 10220, physiological sensor parameter result: body temperature 10222, and physiological sensor parameter result: blood pressure 10224 from the user/patient smart band sensor result. This information allows the physician 8790 to make accurate diagnosis, better treatment outcomes of the user/patient 8710, and eliminates unnecessary clinical testing and reduces the number of doctors and hospital visits by the user/patient 8710.

FIG. 103 is an example personalized daily nutritional goal comprising nutrient and daily reference intake, according to some embodiments.

The daily nutritional goals report comprises a nutrient, a source of goal, a DRI goal, a your DRI, and an intelligent nutrient recommendation. The intelligent nutrient recommendation list DRI to be increased in case of nutrient deficiency or decreased in case of excessive DRI in the form of dietary supplements or foods to maintain a healthy diet. The user smart band sensor result parameters are used to calculate the DRI based age, gender, body weight, and physical activity. The source of goal, DRI goal, and estimated calories needs per day are as per U.S. Department of Agriculture and U.S. Department of Health and Human Services. Dietary Guidelines for Americans, 2020-2025.

FIG. 104 is an example personalized dietary pattern comprising food and amount, according to some embodiments.

The personalized dietary patterns report comprises a food, an amount, and an intelligent food recommendation. The intelligent food recommendation list type of foods such as vegetables, fruits, grains, dairy, protein foods, and oils needed to maintain a healthy diet based on personal preference. The food types with examples, and amount required are per U.S. Department of Agriculture and U.S. Department of Health and Human Services. Dietary Guidelines for Americans, 2020-2025.

FIG. 105 is an example personalized wellness program, according to some embodiments.

The personalized wellness program report comprises wellness dimension, program activity, and current ranking.

The goal of the personalized wellness program activity is to ensure that a wellness dimension ranking is around 4 (very good) or 5 (excellent).

CONCLUSION

A wearable device consists of a smart band and a display unit. The smart band comprises a microbial biosensor, a particulate matter sensor, an enviro sensor, a physiology sensor, a biokinetics sensor, a lifestyle sensor, a single board computer, a power supply unit, a band fastener, and a set of watch adapters. The microbial biosensor detects, measures, and monitors beneficial microorganisms and pathogens in a nasal cavity, an oral cavity, or on a surface. The microbial biosensor sterilizer kills pathogens. The particulate matter sensor detects, measures, and monitors a set of suspended particles in the surrounding air comprising beneficial microorganisms, pathogens, pollen grains, dust mite allergens, and an air quality index. The enviro sensor detects, monitors, and measures environmental conditions surrounding the user. The physiological sensor detects, measures, and monitors functioning of the user's physiological parameters. The biofluid sensor detects, measures, and monitors biological fluid parameters of the user. The biokinetics sensor detects, measures, and monitors physical activities of the user. The lifestyle sensor detects, measures, and monitors healthy way of living activities of the user in a day. A computing system comprises a wearable device, a mobile healthcare application, a patient/user, a mobile device, a cloud server, a laboratory testing facility, a laboratory computer, a laboratory information system, a laboratory director, a physician, an application programming interface, a user smart band sensor result, a user clinical laboratory test result.

The application programming interface comprises a set of functions enabling a cloud application to access the sensor data of a set of wearable electronics. The user smart band sensor result comprises a microbial biosensor result, a particulate matter sensor result, an enviro sensor result, a physiological sensor result, a biofluid sensor result, a biokinetics sensor result, and a lifestyle sensor result. The clinical laboratory test result are from various medical test disciplines.

The smart band sends and receives signals through a wireless network to the mobile healthcare application installed on the mobile device, and to the cloud server.

The wearable device allows for continuous monitoring of user health for accurate clinical outcomes and wellness programs.

The wearable device eliminates sample collection, transportation, laboratory testing, reporting of results, and associated biohazardous medical waste. The analytical and clinical performance of the wearable device is very high because of confirmation of results by multiple particle detection methods.

The COVID-19 pandemic and local, state, and governmental policies to contain the spread of the virus have generated an enormous amount of biohazardous waste or medical waste. The medical waste composition is greatly influenced by disposable plastic-based personal protective equipment (PPE), COVID-19 test kits, hand sanitizer containers, and single-use plastics. The use of PPE, COVID-19 test kits, hand sanitizer containers, and single-use plastics during the pandemic not only increases the quantity of medical waste but also alters the average density of the medical waste. The current rapid surge in healthcare waste due to the COVID-19 pandemic is further exacerbating the problem, and there is an immediate threat that the impacts of unsafe disposal of healthcare waste will spill over into a crisis of environmental pollution. Unsafe disposal of healthcare waste not only pollutes the environment but also is conducive to the spread of infectious diseases such as COVID-19, hepatitis, HIV/AIDS, cholera, typhoid, and respiratory complications. The present invention reduces the environmental pollution and spread of infectious diseases by sterilizing the waste in the wearable device using a sterilizer to kill pathogens.

The increasing prevalence of growing population in the world, climate change, aging, and rise of chronic diseases is increasing healthcare costs. The healthcare system is undergoing a vital transformation from the traditional hospital-centered system to an individual-centered personalized system. The present invention of a wearable device with smart band allows continuous monitoring of a user's health, empowering continuous measurement of critical biomarkers for monitoring of the diseased condition and health, medical diagnostics, and evaluation in biological fluids like nasal swab cell samples, blood, and sweat. The smart band is used for the continuous monitoring of health, exercise activity, assessing wellness performance, and other monitoring activities. With real-time information, the wearable device with smart band allows individuals to change their lifestyle, optimize exercises or training, prevent hazards, and optimize sleep patterns, among other use cases.

Although the present embodiments have been described about specific example embodiments, different modifications can be made to these without changing or taking away from the broader objective of the design. For example, additional sensors, devices, modules, microorganism detection methods, or alterations in the software can be operated to improve the system.

The wearable device can also be used to detect set of sensor parameters comprising: a microorganism parameter, a physiological, and a biofluid parameter in an ear, an eye, a vaginal cavity, an anus, or an anal cavity.

The wearable device can also be used to detect set of sensor parameters comprising: a microorganism parameter, a particulate matter parameter, an enviro parameter, a physiological parameter, a biofluid parameter, a biokinetics parameter, and a lifestyle parameter in an animal.

In addition, it can be appreciated that the various operations, processes, and methods disclosed herein can be embodied in a machine readable medium and/or a machine accessible medium compatible with a data processing system and can be performed in any order. Accordingly, the specifications and drawings are to be regarded in an illustrative rather than a restrictive sense. In some embodiments, the machine-readable medium can be a non-transitory form of machine-readable medium.

The invention claimed is:
1. A wearable device comprising:
a smart band, wherein the smart band comprises a microbial biosensor, a particulate matter sensor, an enviro sensor, a physiological sensor, a biofluid sensor, a biokinetics sensor, a lifestyle sensor, a single board computer, a power supply unit, a band fastener, and a set of watch adapters;
a display unit, wherein the display unit comprises a touchscreen, a display unit power button, a crown, and a set of attachment slots;
wherein the power supply unit comprises a wireless charging unit, a battery, a charging port, and a band power button;

a mobile healthcare application comprising a set of computer executable instructions stored on a non-transitory computer readable storage medium;

wherein the microbial biosensor is configured to detect a microorganism parameter result;

wherein the particulate matter biosensor is configured to detect a particulate matter parameter result;

wherein the enviro sensor is configured to detect an enviro sensor parameter result;

wherein the physiological sensor is configured to detect a physiological parameter result;

wherein the biofluid sensor is configured to detect a biofluid parameter result;

wherein the biokinetics sensor is configured to detect a biokinetics parameter result;

wherein the lifestyle sensor is configured to detect a lifestyle parameter result;

the wearable device is configured to analyze and correlate the plurality of sensor parameter results for an intelligent relationship interpretation, the intelligent relationship interpretation comprises: identify a symptom and determining the cause of the symptom and recommend a treatment;

the mobile healthcare application is configured to output:
a diagnosis, a monitoring, a screening, a prevention, a prediction, a predisposition, a prognosis, a treatment, or an alleviation of a disease;
a personalized daily nutritional goal comprising a nutrient, a source of goal, a personal dietary reference intake, and an nutrient recommendation to maintain a healthy diet;
a personalized dietary pattern comprising a food, an amount, and an food recommendation to maintain the healthy diet; and
a continuous monitoring of user health for a clinical outcome assessment and a personalized wellness program for a healthy lifestyle.

2. The wearable device of claim 1, wherein the microbial bio sensor is configured to detect, measure, and monitor a set of microorganism parameters comprising:
a pathogen count, a pathogen type, a pathogen concentration, and a pathogen biosafety level in a nasal cavity, an oral cavity, or on a surface; and wherein a set of pathogen attributes comprising: a shape, a size, a source, a cell structure, a cell component, and a chemical composition are configured for a rapid identification of an antigen to develop a vaccine and an antipathogen drug for a de novo pathogen type; and
a beneficial microorganism count, a beneficial microorganism type, a beneficial microorganism concentration in the nasal cavity, oral cavity, or on the surface, and a probiotic intake;
wherein the microbial biosensor comprises a transmitter, a receiver, a sterilizer, a picocamera, and a microbial biosensor power button;
wherein the sterilizer is configured to kill the pathogen type for a fast recovery from a disease and to prevent spread of the pathogen type;
wherein the microorganism parameters result comprises a microbial risk level;
wherein when the microbial risk level above a predetermined threshold level, a microbial risk alert is sent to the mobile healthcare application;
wherein a microbial risk level assessment is configured to output a corrective action and a preventive action to bring the set of microbial bio sensor parameters result value to be within a normal reference range to prevent exposure and spread of the pathogen type; and
wherein when a user positive result for a pandemic pathogen is configured for an auto upload to a local, a state, or a national health information system for a real time tracking of a set of user positive results to isolate or quarantine and allow contact tracing to prevent further spread of the pandemic pathogen.

3. The wearable device of claim 2, wherein the particulate matter sensor is configured to detect, measure, and monitor a set of particulate matter parameters in a surrounding air comprising:
microorganism parameters comprising:
the pathogen count, the pathogen type, the pathogen concentration, and the pathogen biosafety level; and wherein the shape, the size, the source, the cell structure, the cell component, and the chemical composition are configured for the rapid identification of the antigen to develop the vaccine and the antipathogen drug for the de novo pathogen type; and
the beneficial microorganism count, the beneficial microorganism type, the beneficial microorganism concentration, and the probiotic intake;
a pollen type, a pollen count, and a pollen allergy level;
a dust mite allergen count and a dust mite allergy level;
a particulate matter concentration;
an air quality index;
wherein the particulate matter sensor comprises a sensing cavity configured to detect suspended particles of picometer, nanometer, and micrometer sizes and is configured to differentiate and identify the suspended particles in the air;
wherein the particulate matter parameters result comprises a set of airborne particle risk levels comprising: a pathogen biosafety risk level, a pollen allergy risk level, a dust mite allergy risk level, and a particulate matter risk level;
wherein when the set of airborne particle risk levels above a predetermined threshold level, a set of airborne particle risk alerts are sent to the mobile healthcare application;
wherein a set of airborne particle risk levels assessment are configured to output a corrective action and a preventive action to bring the set of particulate matter sensor parameters result value to be within a normal reference range to prevent exposure to a set of harmful suspended particles in the surrounding air; and
wherein when the pathogen biosafety level is above a predetermined threshold level in the surrounding air for a pandemic pathogen, a neighborhood public biosafety alert is sent to a set of resident mobile devices within a specified distance of the wearable device to avoid a location wherein the pandemic pathogen was detected to prevent aerosol transmission and spread of the pandemic pathogen.

4. The wearable device of claim 3, wherein the enviro sensor is configured to detect, measure, and monitor enviro parameters in the surrounding air comprising:
an RFID tag sensor configured to detect, measure, and monitor an RFID tag digital data;
a location sensor configured to detect, measure, and monitor a geospatial position and an altitude;
an ambient light sensor configured to detect, measure, and monitor an ambient light level;
a gas sensor configured to detect, measure, and monitor a gas type;

a smoke sensor configured to detect, measure, and monitor a smoke level;

a temperature, humidity, and pressure sensor configured to detect, measure, and monitor a temperature, a humidity, and a pressure;

a sound sensor configured to detect, measure, and monitor a sound level;

an ultraviolet sensor configured to detect, measure, and monitor an ultraviolet index;

a cosmic ray sensor configured to detect, measure, and monitor a cosmic particle;

a solar flare sensor configured to detect, measure, and monitor a solar electromagnetic radiation;

an ozone sensor configured to detect, measure, and monitor an ozone concentration;

a climate change sensor configured to detect, measure, and monitor a climate change index;

wherein the enviro parameter result comprises an enviro risk level;

wherein when the enviro risk level is above an predetermined threshold level, an enviro risk alert is sent to the mobile healthcare application; and wherein an enviro risk level assessment comprises a corrective action and a preventive action to bring the set of enviro sensor parameters result value to be within a normal reference range to prevent exposure to an environmental parameter that affects health, and to improve an environmental wellness dimension ranking.

5. The wearable device of claim 4, wherein the physiological sensor is configured to detect, measure, and monitor physiological parameters and comprises:

a skin temperature sensor configured to detect, measure, and monitor a skin temperature and a body temperature;

a cardiac photoplethysmography (PPG) sensor configured to detect, measure, and monitor a heart rate, a heart rate variability, and a respiratory rate;

an ECG sensor configured to detect, measure, and monitor a set of electrocardiogram parameters;

a blood pressure sensor configured to detect, measure, and monitor a systolic pressure level and a diastolic pressure level;

a blood oxygen sensor configured to detect, measure, and monitor a blood oxygen saturation level;

a blood carbon dioxide sensor configured to detect, measure, and monitor a blood carbon dioxide level;

an EEG sensor configured to detect, measure, and monitor a set of electroencephalogram parameters;

an EMG sensor configured to detect, measure, and monitor a set of elbow electromyogram parameters and a set of knee electromyogram parameters;

wherein a set of picoprobes and a picocamera is configured to output a location of a healthy blood vessel for a noninvasive in vivo measurement of the physiological parameter;

wherein the physiological parameters result comprises a physiological risk level;

wherein when the physiological risk level above a predetermined threshold level, a physiological risk alert is sent to the mobile healthcare application; and wherein a physiological risk level assessment comprises a corrective action and a preventive action to bring the set of physiological sensor parameters result value to be within a normal reference range for a disease reduction or elimination and to improve a physical wellness dimension ranking.

6. The wearable device of claim 5, wherein the biofluid sensor is configured to detect, measure, and monitor biofluid parameters and comprises:

a complete blood count (CBC) sensor configured to detect, measure, and monitor a complete blood count comprising: a red blood cell, a hemoglobin level, a hematocrit level, a mean corpuscular volume (MCV), a mean corpuscular hemoglobin (MCH), a mean corpuscular hemoglobin concentration (MCHC), a white blood cell, a white blood cell differential, and a platelet;

wherein the white blood cell differential detected comprises: a monocyte, a lymphocyte, a neutrophil, an eosinophil, and a basophil; and wherein a blood cell morphology comprises a disease state and a condition;

a blood metabolites and lipid panels (BML) sensor configured to detect, measure, and monitor a set of panels comprising:

a comprehensive metabolic panel comprising: an albumin, a bilirubin, a blood glucose, a blood alcohol, a blood urea nitrogen (BUN), a cortisol, a creatinine, a calcium, a chloride, a magnesium, a phosphorus, a potassium, a sodium, an alkaline phosphatase (ALP), an alanine aminotransferase (ALT), and an aspartate aminotransferase (AST); and a lipid panel comprising: an HDL cholesterol, an LDL cholesterol, a triglyceride, and a total cholesterol;

wherein the set of picoprobes and the picocamera are configured to output the location of the healthy blood vessel for the noninvasive in vivo measurement of the biofluid parameter;

wherein the biofluid parameters result comprises a biofluid risk level;

wherein when the biofluid risk level is above a predetermined threshold level, a biofluid risk alert is sent to the mobile healthcare application; and wherein a biofluid risk level assessment comprises a corrective action and a preventive action to bring the set of biofluid sensor parameters result value to be within a normal reference range for the disease reduction or elimination, a healthy blood formation, to improve the physical wellness dimension ranking, and to improve an emotional wellness dimension ranking.

7. The wearable device of claim 6, wherein the biokinetics sensor is configured to detect, measure, and monitor biokinetics parameters comprising: walking; standing; sitting; running; yoga; hiking; cycling; swimming; movement; exercise; sleep; stress; fall; and proximity to an object;

wherein the biokinetics parameters result comprises a biokinetics risk level;

wherein when the biokinetics risk level above a predetermined threshold level, a biokinetics risk alert is sent to the mobile healthcare application; and wherein a biokinetics risk level assessment comprises a corrective action and a preventive action to bring the set of biokinetics sensor parameters result value to be within a normal reference range to improve the physical wellness dimension ranking and an occupational wellness dimension ranking.

8. The wearable device of claim 7, wherein the lifestyle sensor is configured to detect, measure, and monitor lifestyle parameters comprising:

a breath analyzer sensor configured to detect, measure, and monitor a breath sample comprising: an alcohol, an amphetamine, a benzoylecgonine, a cocaine, a heroin (6-acetylmorphine), a marijuana (tetrahydrocannabinol), a methamphetamine, and a morphine;

a number of meals; a set of food types;
a number of drinks; a set of drink types;
a number of bathroom visits;
a number of smoking occurrences;
a number of occupational interactions;
a number of financial interactions;
a number of intellectual interactions;
a number of emotional interactions;
a number of social interactions;
a number of spiritual interactions;
wherein the lifestyle parameters result comprises a lifestyle risk level;
wherein when the lifestyle risk level is above a predetermined threshold, a lifestyle risk alert is sent to the mobile healthcare application; and
wherein a lifestyle risk level assessment comprises a corrective action and a preventive action to bring the set of lifestyle sensor parameters result value to be within a normal reference range to improve the occupational wellness dimension ranking, a financial wellness dimension ranking, an intellectual wellness dimension ranking, the emotional wellness dimension ranking, a social wellness dimension ranking, and a spiritual wellness dimension ranking.

9. The wearable device of claim 8, wherein the mobile healthcare application is installed on the single board computer;
wherein the mobile healthcare application is further configured to be installed on a mobile device;
wherein the smart band is configured to send and receive signals through a wireless network to the mobile healthcare application installed on the mobile device;
wherein a mobile healthcare application sensor setting functionality for smart band sensor setting comprising: a smart band on/off functionality, a sensor on/off functionality, a reportable range, an alert threshold, and a parameter result unit;
wherein the mobile healthcare application is configured to display the set of microbial biosensor parameters result, the set of particulate matter sensor parameters result, the set of enviro sensor parameters result, the set of physiological sensor parameters result, the set of biofluid sensor parameters result, the set of biokinetics sensor parameters result, and the set of lifestyle sensor parameters result;
wherein the mobile healthcare application is configured to display the intelligent relationship interpretation, risk alert, risk level, a safety data sheet, the plurality of corrective actions, and the plurality of preventive actions; and
wherein the mobile healthcare application is configured for the continuous monitoring of the user health and the personalized wellness program for the healthy lifestyle.

10. A method for sterilizing comprising:
providing a wearable device comprising:
a smart band, wherein the smart band comprises a microbial biosensor, a particulate matter sensor, an enviro sensor, a physiological sensor, a biofluid sensor, a biokinetics sensor, a lifestyle sensor, a single board computer, a power supply unit, a band fastener, and a set of watch adapters;
a display unit, wherein the display unit comprises a touchscreen, a display unit power button, a crown, and a set of attachment slots;
wherein the power supply unit comprises a wireless charging unit, a battery, a charging port, and a band power button;
wherein the microbial biosensor comprises a transmitter, a receiver, a sterilizer, a picocamera, and a microbial biosensor power button;
wherein the microbial biosensor is configured to detect, measure, and monitor a pathogen count, a pathogen type, a pathogen concentration, and a pathogen biosafety level in a nasal cavity, an oral cavity, or on a surface utilizing the picocamera;
wherein the microbial biosensor is further configured to detect, measure, and monitor a beneficial microorganism count, a beneficial microorganism type, and a beneficial microorganism concentration in the nasal cavity, the oral cavity, or on the surface utilizing the picocamera;
wherein the sterilizer is configured to kill the pathogen type;
wherein the particulate matter sensor comprises a sensing cavity;
wherein the sensing cavity is configured to detect suspended particles of picometer, nanometer, and micrometer sizes and is configured to differentiate and identify the suspended particles in the air;
wherein the particulate matter sensor is configured to detect, measure, and monitor passing through the sensing cavity a set of particulate matter parameters in a surrounding air comprising microorganism parameters consisting of:
the pathogen count, the pathogen type, the pathogen concentration, and the pathogen biosafety level; and
the beneficial microorganism count, the beneficial microorganism type, and the beneficial microorganism;
a pollen type, a pollen count, and a pollen allergy level;
a dust mite allergen count and a dust mite allergy level;
a particulate matter concentration; and3n air quality index;
wherein the microbial bio sensor is configured to detect a microorganism parameter result;
wherein the particulate matter bio sensor is configured to detect a particulate matter parameter result;
wherein the enviro sensor is configured to detect an enviro sensor parameter result;
wherein the physiological sensor is configured to detect a physiological parameter result;
wherein the biofluid sensor is configured to detect a biofluid parameter result;
wherein the biokinetics sensor is configured to detect a biokinetics parameter result;
wherein the lifestyle sensor is configured to detect a lifestyle parameter result; and
providing a mobile healthcare application comprising a set of computer executable instructions stored on a non-transitory computer readable storage medium on the wearable device.

11. The method of claim 10, wherein the microbial bio sensor performs the following:
strap the wearable device around a user wrist;
power on the wearable device by pressing the band power button;
power on the microbial biosensor by pressing the microbial biosensor power button;
face the microbial biosensor to a nasal cavity;
auto verify an identity of the nasal cavity of the user of the wearable device utilizing the picocamera;
detect a pathogen inside the nasal cavity with the microbial biosensor;

display a pathogen count, a pathogen type, a pathogen concentration, and a pathogen biosafety level on the mobile healthcare application;
detect a beneficial microorganism inside the nasal cavity with the microbial bio sensor;
display a beneficial microorganism count, a beneficial microorganism type, and a beneficial microorganism concentration on the mobile healthcare application;
sterilize the pathogen type found inside the nasal cavity by pressing and holding the microbial biosensor power button; and
power off the microbial biosensor by pressing the microbial biosensor power button.

12. The method of claim 11, wherein the microbial biosensor performs the following steps:
strap the wearable device around the user wrist;
power on the wearable device by pressing the band power button;
power on the microbial biosensor by pressing the microbial biosensor power button;
face the microbial biosensor to an oral cavity;
auto verify an identity of the oral cavity of the user of the wearable device utilizing the picocamera;
detect a pathogen inside the oral cavity with the microbial biosensor;
display a pathogen count, a pathogen type, a pathogen concentration, and a pathogen biosafety level on the mobile healthcare application;
detect a beneficial microorganism inside the oral cavity with the microbial biosensor;
display a beneficial microorganism count, a beneficial microorganism type, and a beneficial microorganism concentration on the mobile healthcare application;
sterilize the pathogen type found inside the oral cavity by pressing and holding the microbial biosensor power button; and
power off the microbial biosensor by pressing the microbial biosensor power button.

13. The method of claim 12, wherein the microbial biosensor performs the following:
strap the wearable device around the user wrist;
power on the wearable device by pressing the band power button;
power on the microbial biosensor by pressing the microbial biosensor power button;
face the microbial biosensor to a surface;
auto verify an identity of the surface of the user of the wearable device utilizing the picocamera;
detect a pathogen on the surface with the microbial biosensor;
display a pathogen count, a pathogen type, a pathogen concentration, and a pathogen biosafety level on the mobile healthcare application;
detect a beneficial microorganism on the surface with the microbial biosensor;
display a beneficial microorganism count, a beneficial microorganism type, and a beneficial microorganism concentration on the mobile healthcare application;
sterilize the pathogen type found on the surface by pressing and holding the microbial biosensor power button; and
power off the microbial biosensor by pressing the microbial biosensor power button.

14. The method of claim 13, wherein the particulate matter sensor performs the following:
air enters an air channel part of the sensing cavity of the particulate matter sensor;
a laser source containing a laser beam radiates particles in the air entering through the air channel, passing through a light scattering measuring cavity;
calculate a particle diameter and a number of particles with different diameters per unit volume;
air then flows through an imaging cavity;
an imaging system within the imaging cavity captures images and videos of the particles in the air passing through the imaging cavity;
differentiate and identify the particles using by image analysis;
detect a pathogen count, a pathogen type, a pathogen concentration, and a pathogen biosafety level;
detect a beneficial microorganism count, a beneficial microorganism type, and a beneficial microorganism concentration;
detect a pollen type, a pollen count, and a pollen allergy level;
detect a dust mite allergen count and a dust mite allergy level;
detect a particulate matter concentration;
calculate an air quality index;
display the pathogen count, the pathogen type, the pathogen concentration, and the pathogen biosafety level on the mobile healthcare application;
display the beneficial microorganism count, the beneficial microorganism type, and the beneficial microorganism concentration on the mobile healthcare application;
display the pollen type, the pollen count, and the pollen allergy level on the mobile healthcare application;
display the dust mite allergen count and the dust mite allergy level on the mobile healthcare application;
auto sterilize the pathogen type in the air after it passes through the imaging cavity;
send a neighborhood public biosafety alert to the wearable device when the pathogen biosafety level is above a predetermined threshold level, indicating that there is a pathogen in the surrounding air at a location which can result in disease outbreak;
and display a corrective and a preventive measure on the mobile healthcare application to reduce exposure to the pathogen type.

15. A system for monitoring and analyzing user health data comprising:
a wearable device comprising: a smart band, wherein the smart band comprises a microbial biosensor, a particulate matter sensor, an enviro sensor, a physiological sensor, a biofluid sensor, a biokinetics sensor, a lifestyle sensor, a single board computer, a power supply unit, a band fastener, and a set of watch adapters;
a display unit, wherein the display unit comprises a touchscreen, a display unit power button, a crown, and a set of attachment slots;
wherein the power supply unit comprises a wireless charging unit, a battery, a charging port, and a band power button;
wherein the microbial biosensor is configured to detect a microorganism parameter result;
wherein the particulate matter biosensor is configured to detect a particulate matter parameter result;
wherein the enviro sensor is configured to detect an enviro sensor parameter result;
wherein the physiological sensor is configured to detect a physiological parameter result;
wherein the biofluid sensor is configured to detect a biofluid parameter result;

wherein the biokinetics sensor is configured to detect a biokinetics parameter result;
wherein the lifestyle sensor is configured to detect a lifestyle parameter result;
a mobile healthcare application comprising a set of computer executable instructions stored on a non-transitory computer readable storage medium;
a mobile device;
a cloud server;
a laboratory information system;
an intelligent relationship interpretation data;
a user clinical laboratory test result;
an application programming interface;
the wearable device is configured to analyze and correlate the plurality of sensor parameter results for an intelligent relationship interpretation, the intelligent relationship interpretation comprises: identify a symptom and determining the cause of the symptom and recommend a treatment;
the mobile healthcare application is configured to output a diagnosis, a monitoring, a screening, a prevention, a prediction, a predisposition, a prognosis, a treatment, or an alleviation of a disease;
a personalized daily nutritional goal comprising a nutrient, a source of goal, a personal dietary reference intake, and an intelligent nutrient required recommendation to maintain a healthy diet;
a personalized dietary pattern comprising a food, an amount, and an intelligent food required recommendation to maintain the healthy diet; and
a continuous monitoring of user health for a clinical outcome assessment and a personalized wellness program for a healthy lifestyle;
wherein the user clinical laboratory test result comprises: allergy; body scan; anesthesiology; cardiovascular; chemistry; dental; ear, nose, and throat; gastroenterology and urology; general and plastic surgery; genetics; hematology; immunology; infectious disease; microbiology; neurology; obstetrical and gynecological; ophthalmic; orthopedic; pathology; physical medicine; radiology; and toxicology;
wherein the application programming interface comprises a set of functions enabling a cloud application to access a set of wearable electronics sensor data;
wherein a set of personalized user wellness dimensions comprises: physical, environmental, occupational, financial, intellectual, emotional, social, and spiritual;
wherein a personalized user wellness dimension ranking is classified as: excellent=5, very good=4, good=3, fair=2, and poor=1; and
wherein the smart band sends and receives a set of sensor signals through a wireless network to the mobile healthcare application installed on the mobile device, and to the cloud server.

16. The system of claim 15, wherein the cloud server, is configured to perform the following:
receive the user smart band sensor result;
receive the user clinical laboratory test result from the laboratory information system;
receive the set of wearable electronics sensor data;
calculate the set of personalized user wellness dimensions ranking from the user smart band sensor result, the user clinical laboratory test result, the intelligent relationship interpretation data, and the set of wearable electronics sensor data;
calculate a personalized wellness program for the healthy lifestyle from the set of personalized user wellness dimensions ranking; and
send the set of personalized user wellness dimensions ranking and the accurate personalized wellness program to the user mobile healthcare application.

17. The system of claim 16, wherein the cloud server is further configured to perform the following:
auto review and report out the personalized user clinical laboratory test result in the laboratory information system to a physician mobile healthcare application installed on the mobile device;
automatically communicate a critical test result notification by the laboratory information system to the mobile healthcare application installed on the physician mobile device responsible for the user's care;
wherein the personalized user clinical laboratory test result exceeds an established critical test value that is important for prompt patient management decisions; and
wherein the critical test result is an imminently life-threatening personalized user clinical laboratory test result requiring rapid clinical attention to avert significant patient morbidity or mortality;
auto review the personalized user clinical laboratory test result to determine a root cause of a disorder to treat a disease; wherein the personalized user clinical laboratory test result is configured to output an assessment of the critical value in context of the user smart band sensor result for a clinical outcome assessment; and prompt by a critical test result notification confirmation of a receipt by the physician mobile healthcare application; and record the confirmation of receipt of the critical test result notification in the laboratory information system, comprising:
a date of communication; a time of communication; a responsible laboratory individual full name; a notified physician full name; and a user critical test result.

18. The system of claim 17, wherein the cloud server is further configured to perform performs the following:
receive the user smart band sensor result comprises a complete blood count (CBC) sensor test result;
receive the user clinical laboratory test result from the laboratory information system, wherein the user clinical laboratory test result comprises a user CBC clinical laboratory test result;
predict a surrogate user CBC test result from the user smart band sensor result;
calculate a first correlation coefficient between the user CBC sensor test result and the user CBC clinical laboratory test result;
calculate a second correlation coefficient between the user CBC sensor test result and the surrogate user CBC test result;
calculate an error correlation coefficient between first correlation coefficient and second correlation coefficient;
send an error correlation alert to the user mobile healthcare application when the error correlation coefficient is greater than or equal to 0.05;
wherein the error correlation alert displays the clinical laboratory test result parameter/analyte error; and
wherein the surrogate user CBC test result is configured for a noninvasive measurement of a complete blood count for the user wrist with a vascular disease.

* * * * *